US007223759B2

(12) United States Patent
Zhou et al.

(10) Patent No.: US 7,223,759 B2
(45) Date of Patent: May 29, 2007

(54) ANTIBACTERIAL 3,5-DIAMINOPIPERIDINE-SUBSTITUTED AROMATIC AND HETEROAROMATIC COMPOUNDS

(75) Inventors: Yuefen Zhou, San Diego, CA (US); Dionisios Vourloumis, San Diego, CA (US); Vlad E. Gregor, Del Mar, CA (US); Geoffrey C. Winters, Coquitlam (CA); Thomas Hermann, Cardiff By The Sea, CA (US); Benjamin Ayida, Spring Valley, CA (US); Zhongxiang Sun, San Diego, CA (US); Douglas Murphy, San Diego, CA (US); Klaus B. Simonsen, Frederiksberg (DK)

(73) Assignee: Anadys Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 10/940,615

(22) Filed: Sep. 15, 2004

(65) Prior Publication Data
US 2005/0239827 A1    Oct. 27, 2005

Related U.S. Application Data

(60) Provisional application No. 60/548,852, filed on Mar. 2, 2004, provisional application No. 60/502,612, filed on Sep. 15, 2003.

(51) Int. Cl.
*A61K 31/53* (2006.01)
(52) U.S. Cl. ............ 514/245; 514/313; 514/314; 514/315; 514/316; 514/318; 514/248; 514/256; 546/184; 546/187; 546/159; 546/152; 546/170; 546/192; 544/182; 544/194; 544/198; 544/238; 544/242; 544/256; 544/297; 544/322
(58) Field of Classification Search ............ 514/245, 514/313, 248, 314, 316, 315, 318, 256; 546/187, 546/184, 192, 159, 152, 170; 544/198, 194, 544/182, 238, 242, 322, 297, 256
See application file for complete search history.

(56) References Cited

U.S. PATENT DOCUMENTS

| 3,879,790 | A | * | 4/1975 | Girard | 15/104.061 |
| 4,522,643 | A | * | 6/1985 | Quinlan | 504/155 |
| 5,238,936 | A | | 8/1993 | Regnier et al. | |
| 5,300,643 | A | | 4/1994 | Grohe et al. | |
| 5,574,055 | A | | 11/1996 | Borgulya et al. | |
| 5,852,019 | A | | 12/1998 | Ejima et al. | |
| 6,248,306 | B1 | | 6/2001 | Schmitt-Willich et al. | |
| 6,514,977 | B1 | | 2/2003 | Anantanarayan et al. | |
| 2003/0106169 | A1 | | 6/2003 | Vidal et al. | |

FOREIGN PATENT DOCUMENTS

| JP | 2002338537 | 11/2002 |
| WO | WO-96/04914 | 2/1996 |
| WO | WO-96/28164 | 9/1996 |
| WO | WO-96/32945 | 10/1996 |
| WO | WO-97/18220 | 5/1997 |
| WO | WO-00/056729 | 9/2000 |
| WO | WO-01/10834 | 2/2001 |
| WO | WO-01/023386 | 4/2001 |
| WO | WO-01/023390 | 4/2001 |
| WO | WO-02/056882 | 7/2002 |
| WO | WO-02/060877 | 8/2002 |
| WO | WO-02/078659 | 10/2002 |
| WO | WO-03/059894 | 7/2003 |
| WO | WO-03/101980 | 12/2003 |
| WO | WO-04/002948 | 1/2004 |

OTHER PUBLICATIONS

Ames and Ward, "[1,4] Benzodioxinopyridazines," *J. Chem. Soc.*, 6, 534-538 (1975).
Breshears et al., "The Aminolysis of Certain Chlorosubstituted Purines," *J. Am. Chem. Soc.*, 81, 3789-3792 (1959).
Elsager et al., "Folate Antagonists, 3. 2,4-Diamino-6-(heterocyclic)quinazolines, a Novel Class of Antimetabolites with Potent Antimalarial and Antibacterial Activity," *J. Med. Chem.*, 15(8), 827-836 (1972).
Grasa and Nolan, "Palladium/Imidazolium Salt Catalyzed Coupling of Aryl Halides with Hypervalent Organostannates," *Org. Lett.*, 3(1), 119-122 (2001).
Gujadhur et al., "Formation of Aryl—Nitrogen Bonds Using a Soluble Copper(I) Catalyst," *Tet. Lett.*, 42, 4791-4793 (2001).
Ji et al., "Selective Amination of Polyhalopyridines Catalyzed by a Palladium-Xantphos Comples," *Organic Letters*, 5(24), 4611-4614 (2003).
La Brecque et al., "Substituted Melamines as Chemosterilants of House Flies," *J. Economic Entomology*, 61(6), 1621-1632 (1968).
Lebreton et al., "Antibacterial single-bead screening," *Tetrahedron*, 59, 10213-10222 (2003).
Littke and Fu, "Palladium-Catalyzed Coupling Reactions of Aryl Chlorides," *Angew. Chem. Int. Ed.*, 41, 4176-4211 (2000).
Menicagli et al., "in Vitro Cytotoxic Activities of 2-Alkyl-4,6-diheteroalkyl-1,3,5-triazines: New Molecules in Anticancer Research," *J. Med. Chem.*, 47, 4649-4652 (2004).
Menichincheri et al., "Parallel Synthesis of 4-Amino-2,6-Dialkylamino-Pyridines," *Tet. Lett.*, 44, 519-522 (2003).

* cited by examiner

*Primary Examiner*—Amelia A. Owens
(74) *Attorney, Agent, or Firm*—Connolly Bove Lodge & Hutz LLP

(57) ABSTRACT

The invention relates to antibacterial 3,5-diaminopiperidine-substituted aromatic and heteroaromatic compounds and pharmaceutical compositions thereof. This invention also relates to a method of using such compounds in the treatment of bacterial infections in mammals, especially humans.

11 Claims, No Drawings

ANTIBACTERIAL 3,5-DIAMINOPIPERIDINE-SUBSTITUTED AROMATIC AND HETEROAROMATIC COMPOUNDS

CROSS REFERENCE TO RELATED APPLICATIONS

The present application claims priority to U.S. Provisional Application No. 60/502,612 now abandoned filed Sep. 15, 2003 and U.S. Provisional Application No. 60/548,852 filed Mar. 2, 2004 the contents of each are incorporated herein by reference in their entireties.

This invention was made possible by Grant Number 1R43 AI151104-01 from the National Institute of Allergy and Infectious Diseases. The United States Government may have certain rights in the invention.

1. FIELD OF THE INVENTION

The invention relates to 3,5-diaminopiperidine-substituted aromatic and heteroaromatic compounds and pharmaceutical compositions thereof. The compounds of the invention are useful as antibacterial agents. This invention also relates to a method of using such compounds in the treatment of bacterial infections in mammals, especially humans.

2. BACKGROUND OF THE INVENTION

An "antibiotic" is broadly defined as a chemical compound that inhibits the growth of microorganism. Antibiotics can act on organisms by inhibiting cell wall synthesis, increasing cell membrane permeability, interfering with protein synthesis, or interfering with nucleic acid metabolism. In general, bacterial pathogens may be classified as either Gram-positive or Gram-negative. Antibiotic compounds with activity against both Gram-positive and Gram-negative pathogens are generally regarded as having broad spectrum activity.

When the first therapeutic antibiotic, penicillin, was introduced in the early 1940's, many believed that the threat from infectious diseases was over. However, in the past 25 years, through the abuse and misuse of antibiotics, many bacteria have developed resistance to these antibiotics. The most frequent misuse is probably in the treatment of fevers that are not caused by bacterial infections. Other common misuses and errors include choosing an ineffective antibiotic, giving inadequate or excessive doses, treating non-bacterial infections such as uncomplicated viral disease, using an improper route of administration, continuing use after bacterial resistance has developed, continuing in the presence of a serious toxic or allergic reaction, prematurely stopping therapy, using improper combinations of chemotherapeutic drugs, and relying on chemotherapy or prophylaxis to the exclusion of surgical intervention (e.g., drainage of localized infection and removal of a foreign body).

Today, there are strains of virtually every major bacterial human pathogen that are resistant to some of the most effective antibiotics. These strains include pathogens that can cause diarrhea, urinary tract infections, otitis media, meningitis, tuberculosis, gonorrhea, pneumonia, dysentery, wound infections, septicemia, bacteremia and surgical infections.

Whereas in the first decades of antibiotics discovery, development of novel antibacterial therapeutics has kept pace with the occurrence of drug-resistant bacterial strains, the widespread and sometimes indiscriminate use of antibiotics has accelerated the emergence of resistance, often against multiple drugs simultaneously and in pathogenic bacteria that cause life-threatening infections. Not only is antibiotic resistance escalating in agents of infectious diseases, but also normally nonpathogenic bacteria are acquiring resistance, and acting as opportunistic pathogens, increasingly threatening patients with weakened immune defense.

The problem of antibiotic resistance is particularly severe because examples of most antibacterial drug classes used today have been in the clinic for more than 30 years. The initial broad stream of novel antibiotics discovered from both natural and synthetic sources, has narrowed down to a trickle. Novel and potent antibiotics are required to replace the currently used drugs, which are increasingly compromised by development of resistance. Thus, there is a crucial need for novel antibacterial agents that work by novel mechanisms and effectively inhibit the growth of bacteria.

3. SUMMARY OF THE INVENTION

The present invention has addressed this need by the discovery of 3,5-diaminopiperidine-substituted aromatic and heteroaromatic compounds and pharmaceutically acceptable salts thereof, which have antibacterial activity against Gram-positive and Gram-negative bacteria.

In a general aspect, the invention relates to compounds of Formula I

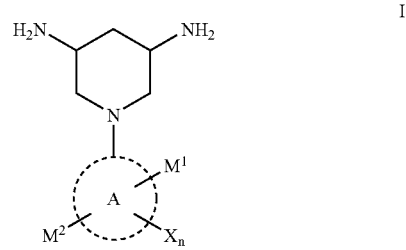

wherein:

Ring A is a 5 or 6-membered mono- or bicyclic aryl or heteroaryl;

$M^1$ and $M^2$ are independently —H, halo, $CF_3$, —CN, —$NO_2$, —$CONH_2$, —COOH, —OH, or $NHNH_2$, or an unsubstituted or substituted —($C_1$–$C_6$)alkyl, aryl, heteroaryl, —$(CH_2)_n$-aryl, —$(CH_2)_n$-heteroaryl, —$(CH_2)_n$-heterocycloalkyl, —$(CH=CH)_n$-aryl, —$(CH=CH)_n$-heteroaryl, —($C_2$–$C_6$)alkenyl-aryl, —($C_2$–$C_6$)alkenyl-heteroaryl, —$(C≡C)_n$-aryl, —$(C≡C)_n$-heteroaryl, —O—($C_1$–$C_6$)alkyl, —O-aryl, —O-heteroaryl, —O-cycloalkyl, —O-heterocycloalkyl, —S—($C_1$–$C_6$)alkyl, —S-aryl, S-heteroaryl, S-cycloalkyl, S-heterocycloalkyl, —(C=O)($C_1$–$C_6$)alkyl, —(C=O)aryl, —(C=O)heterocycloalkyl, —O(C=O)—($C_1$–$C_6$)alkyl, —(C=O)O—($C_1$–$C_6$)alkyl, —(S=O)aryl, —(S=O)heterocycloalkyl, —$S(O)_2$aryl, —$S(O)_2$heterocycloalkyl, NHC(NH)-aryl, NHNH-aryl, —NNNHC(O)-aryl, —NHNH-cycloheteroalkyl, —$NHNHS(O)_2$-aryl, —NHOH, —NHO—($C_1$–$C_6$)alkyl, —N(OH)—($C_1$–$C_6$)alkyl, —N(($C_1$–$C_6$)alkyl)O—($C_1$–$C_6$)alkyl, —NHNHC(S)NH—($C_1$–$C_6$)alkyl, NHNH-heteroaryl, or $N(R^1)R^2$, wherein $R^1$ and $R^2$ are independently selected from —H, a substituted or unsubstituted alkyl, aryl, heteroaryl, cycloalkyl, or heterocycloalkyl, or $R^1$ and $R^2$ together with the N atom form a 4-, 5-, or 6-membered substituted or unsubstituted heterocycloalkyl, wherein n is 1–4; and In one embodiment, $X_n$ is independently selected from —H, halo, —CF$_3$, —CN, —COOH, —OH, —NH$_2$, —NO$_2$, —C(O)N(R$^3$)R$^4$ wherein R$^3$ and R$^4$ are independently —(C$_1$–C$_6$)alkyl or —H, and optionally substituted —O—(C$_1$–C$_6$)alkyl or —(C$_1$–C$_6$)alkyl, wherein n is 1–3.

In one embodiment of the invention, ring A is selected from:

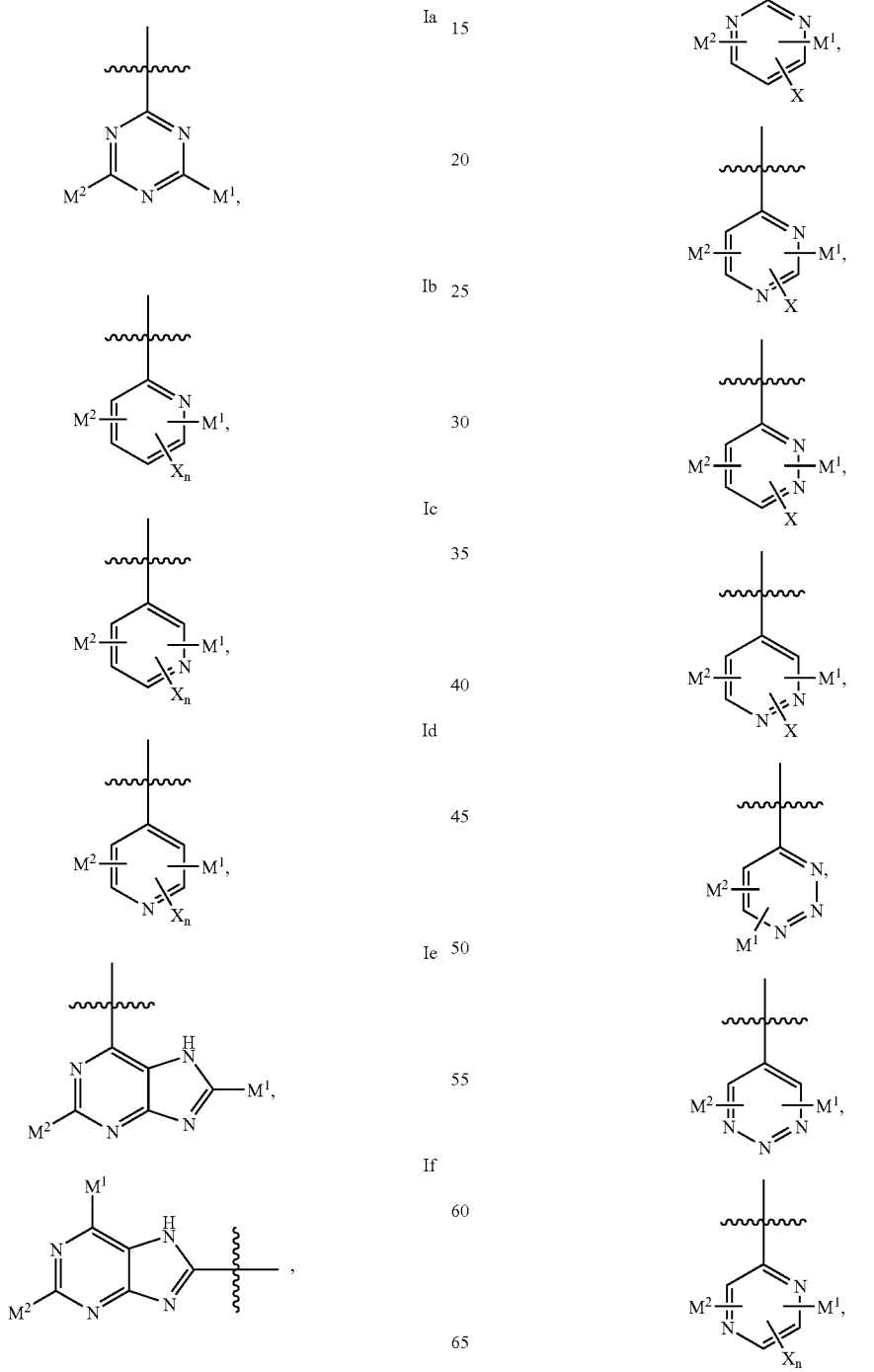

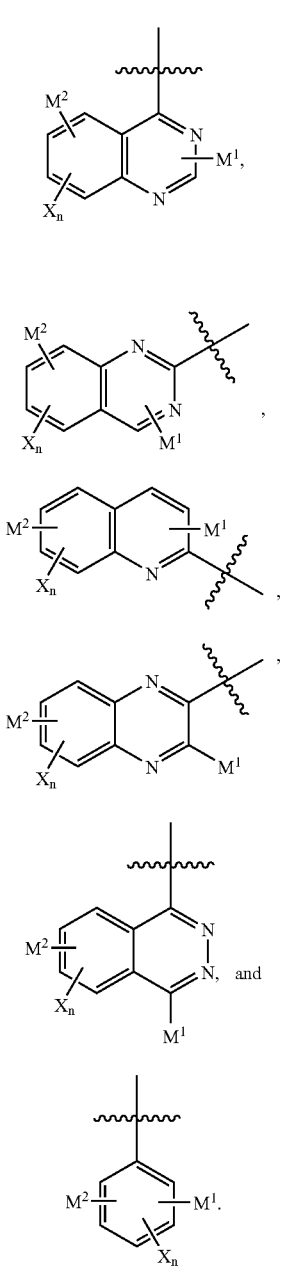

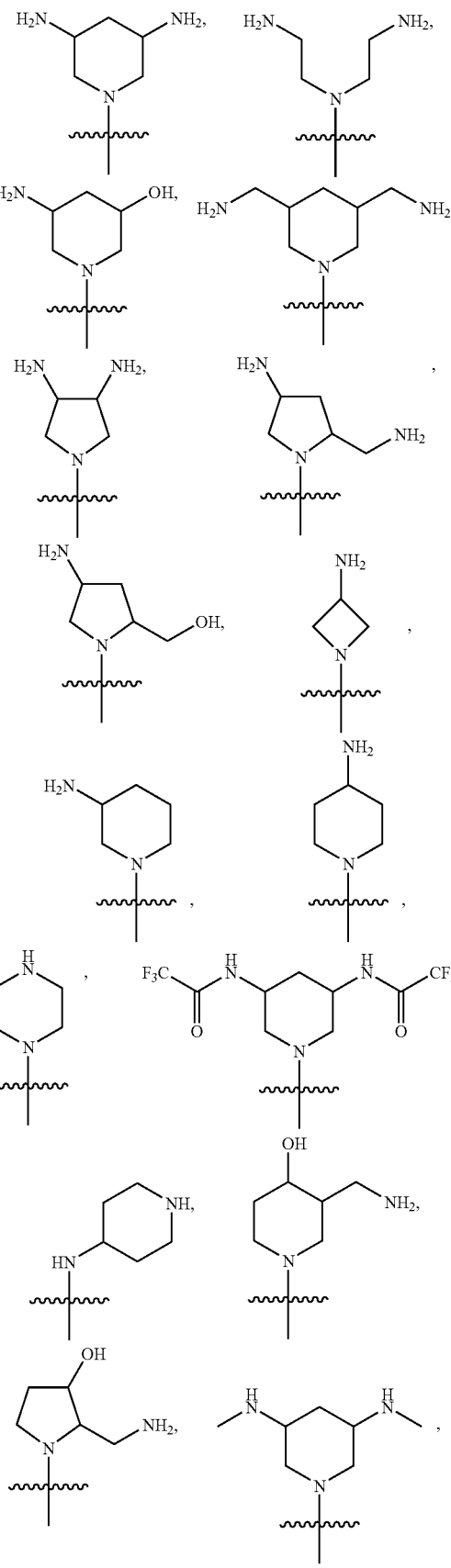

In another embodiment, the invention relates to compounds of Formula I wherein $M^1$ and $M^2$ are selected from $N(R^1)R^2$, wherein $R^1$ and $R^2$ are independently selected from —H, a substituted or unsubstituted alkyl, aryl, heteroaryl, cycloalkyl, or heterocycloalkyl, or $R^1$ and $R^2$ together with the N atom form a 4-, 5-, or 6-membered substituted or unsubstituted heterocycloalkyl.

In another preferred embodiment, the invention relates to compounds of Formula I wherein $M^1$ and $M^2$ are independently selected from $N(R^1)R^2$, wherein $R^1$ and $R^2$ are independently selected from —H, a substituted or unsubstituted aryl or heteroaryl, or $R^1$ and $R^2$ together with the N atom form a 4-, 5-, or 6-membered heterocycloalkyl or bis-amino alkyl amino group selected from the following:

-continued

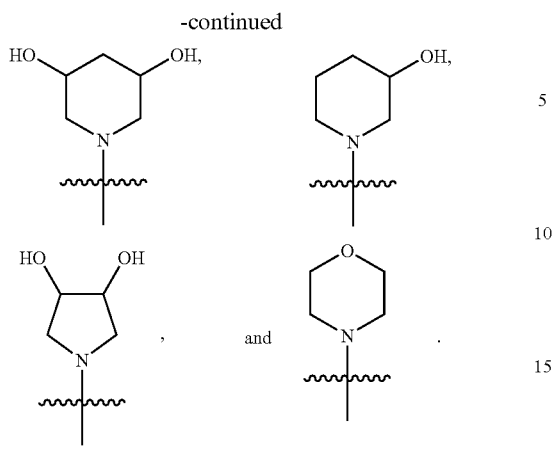

In another preferred embodiment, the invention relates to compounds of Formula Iu:

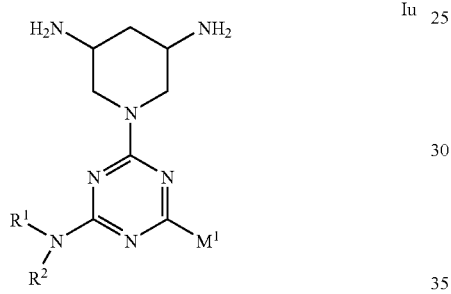

wherein $M^1$ is H or halo, or an unsubstituted or substituted —($C_1$–$C_6$)alkyl, —O—($C_1$–$C_6$)alkyl, —O-heterocycloalkyl, aryl, heteroaryl, —(CH$_2$)$_n$-aryl, —(CH$_2$)$_n$-heteroaryl, —(CH$_2$)$_n$-heterocycloalkyl, —(CH=CH)$_n$-aryl, —(CH=CH)$_n$-heteroaryl, —(C≡C)$_n$-aryl, —(C≡C)$_n$-heteroaryl, or N($R^1$)$R^2$, wherein $R^1$ and $R^2$ are independently selected from —H, a substituted or unsubstituted alkyl, aryl, heteroaryl, cycloalkyl, or heterocycloalkyl, or $R^1$ and $R^2$ together with the N atom form a 4-, 5-, or 6-membered substituted or unsubstituted heterocycloalkyl, and wherein n is 1–4.

In another preferred embodiment of the invention, $X_n$ if present is independently selected from —H, —OH, halo, and optionally substituted —($C_1$–$C_6$)alkyl and —O—($C_1$–$C_6$)alkyl, wherein n is 1 or 2.

In a more preferred embodiment, the invention relates to compounds of Formula I wherein ring A is selected from:

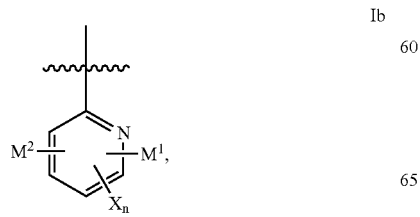

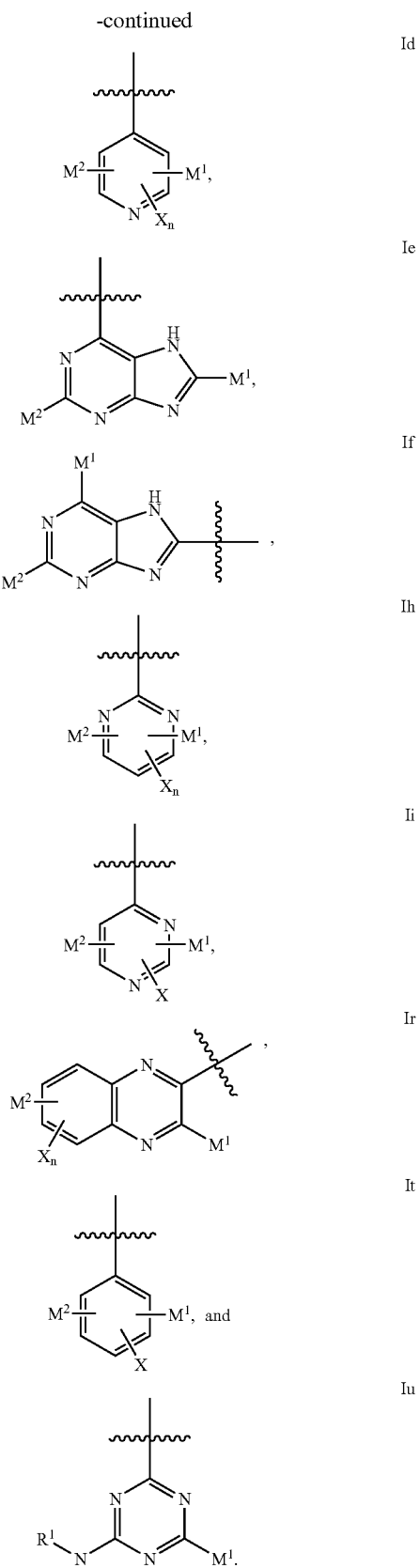

In another more preferred embodiment, $M^1$ and $M^2$ are independently selected from:
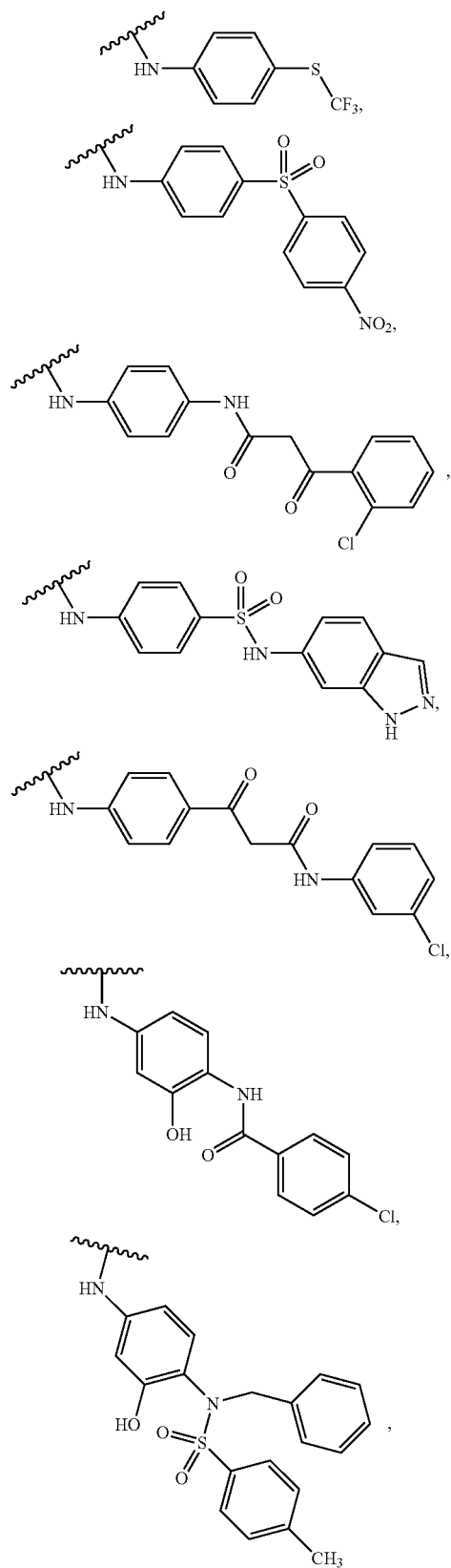
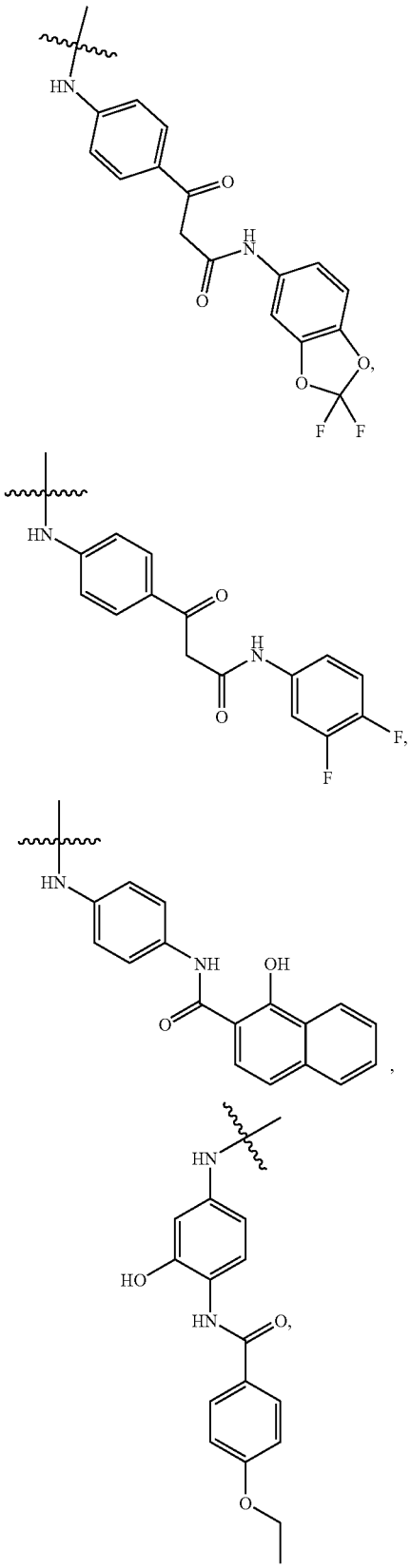

-continued
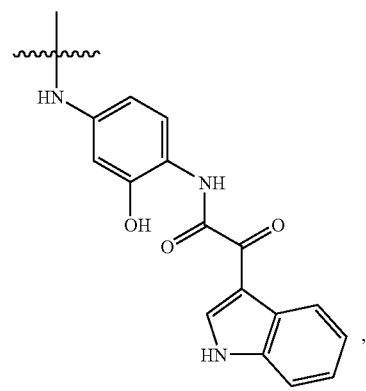
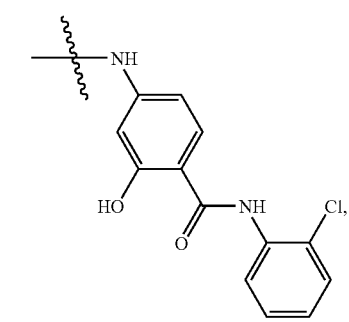
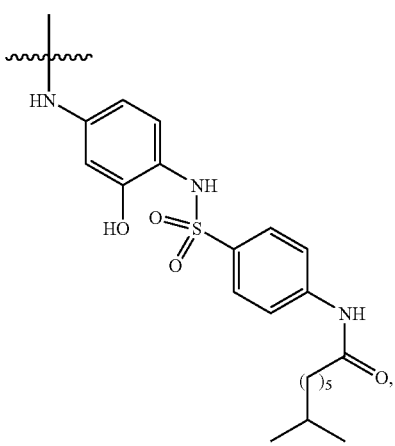
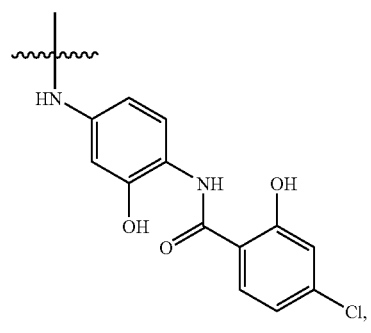
-continued
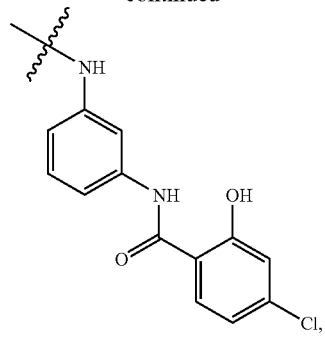
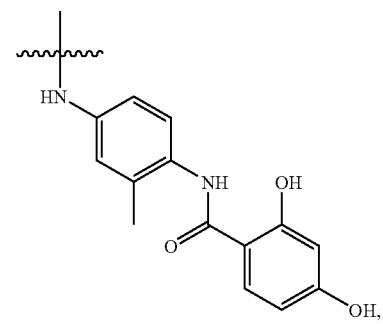
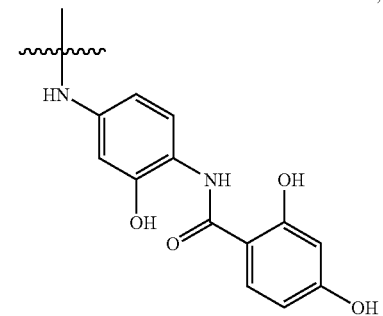
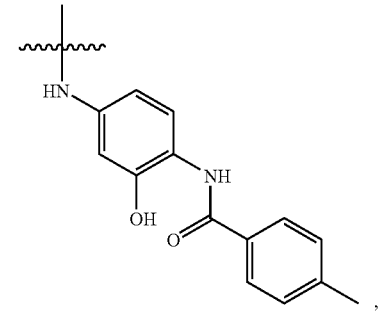
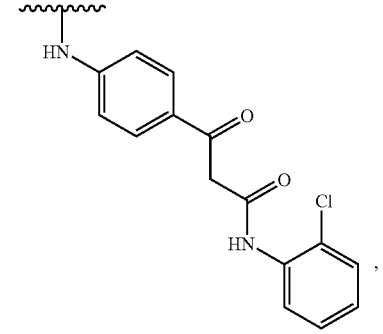

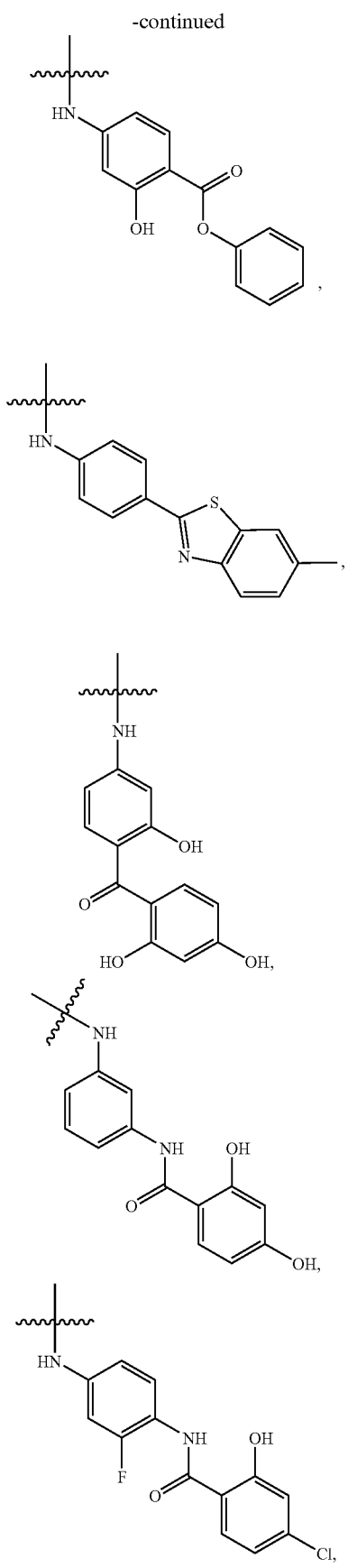
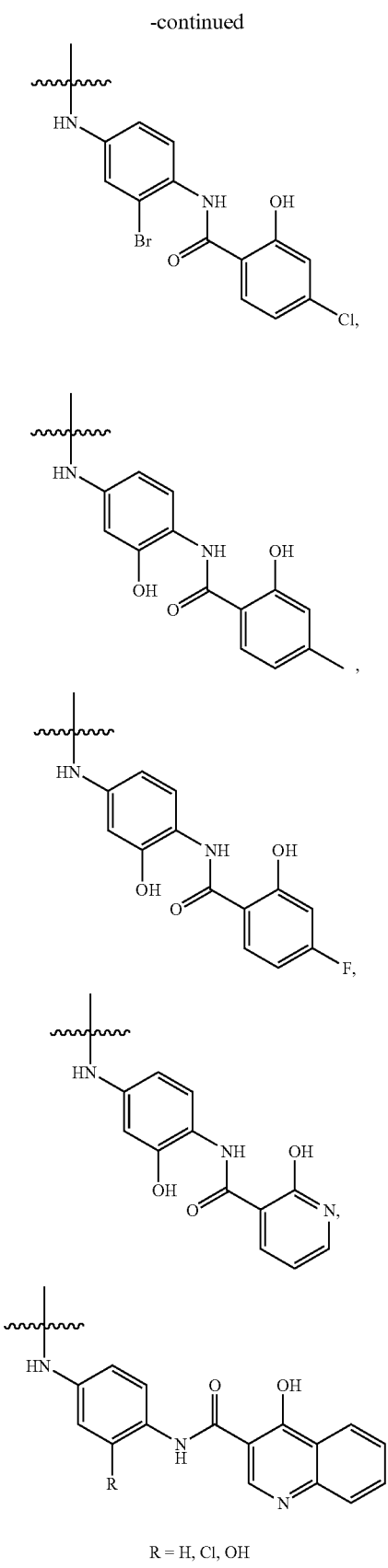
R = H, Cl, OH

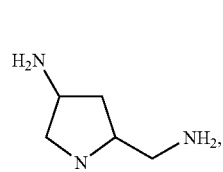
In a most preferred embodiment, the invention relates to compounds of Formula I wherein ring A is selected from Formulas Ia, Ib, Id, Ie, If, Ih, Ii, Ir, and It; X is —H or —(C$_1$–C$_6$)alkyl; and M$^1$ and M$^2$ are independently selected from:
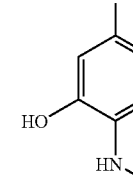

-continued
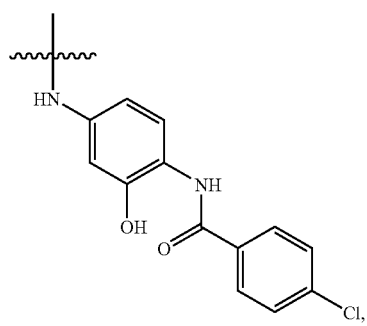
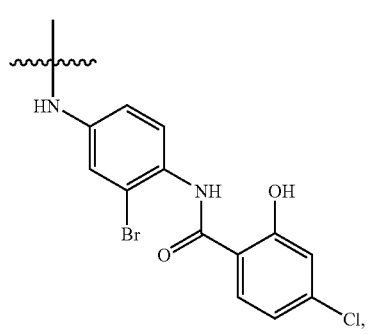
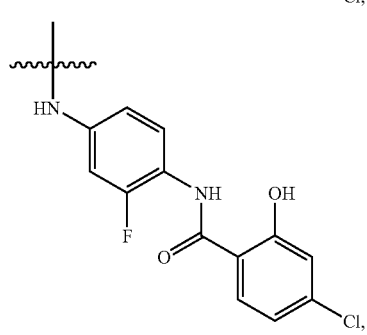
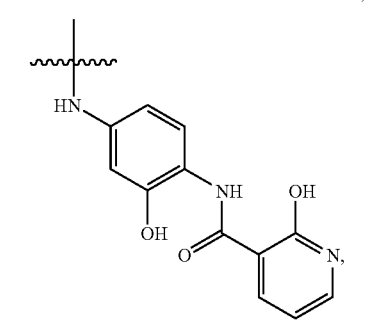
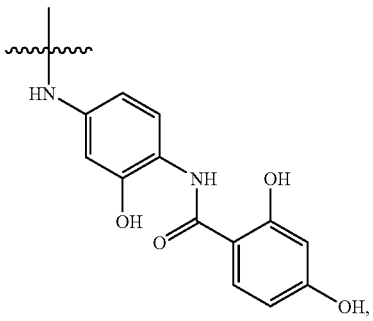
-continued
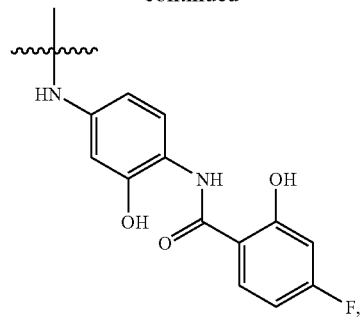
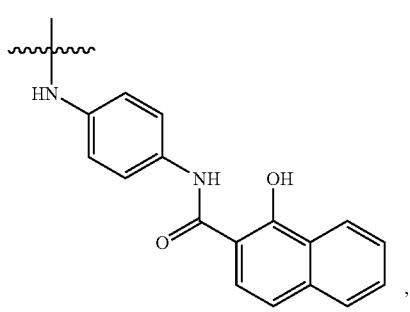
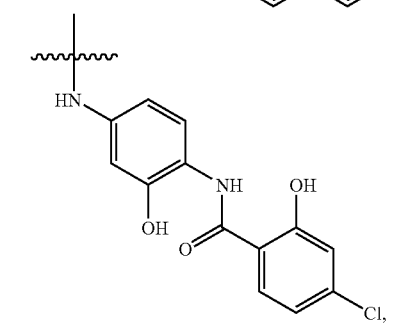
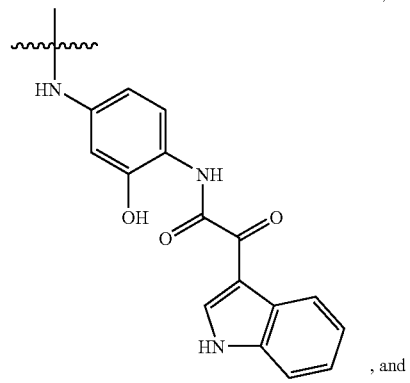, and
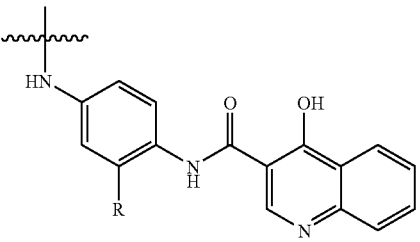
R = H, Cl, OH In another embodiment, the invention relates to compounds or salts thereof individually selected from Table 1. For example the compound can be selected from the group consisting of a compound selected from the group consisting of:

N-[4-(2,2-difluoro-benzo[1,3]dioxol-5-ylcarbamoyl)-3-hydroxy-phenyl]-4,6-Bis-((3R,5S)-3,5-diamino-piperidin-1-yl)-[1,3,5]triazine-2-amine;

N-[4-(4-chloro-2,5-dimethoxy-phenylcarbamoyl)-3-hydroxy-phenyl]-4,5-Bis-((3R,5S)-3,5-diamino-piperidin-1-yl)-[1,3,5]triazine-2-amine;

N-[4-(2,4-dichloro-phenylcarbamoyl)-3-hydroxy-phenyl]-4,6-Bis-((3R,5S)-3,5-diamino-piperidin-1-yl)-[1,3,5]triazine-2-amine;

N-[4-(3-chloro-phenylcarbamoyl)-3-hydroxy-phenyl]-4,6-Bis-((3R,5S)-3,5-diamino-piperidin-1-yl)-[1,3,5]triazine-2-amine;

N-[4-(4-fluoro-phenylcarbamoyl)-3-hydroxy-phenyl]-4,6-Bis-((3R,5S)-3,5-diamino-piperidin-1-yl)-[1,3,5]triazine-2-amine;

N-[4-(2,5-dimethoxy-phenylcarbamoyl)-3-hydroxy-phenyl]-4,6-Bis-((3R,5S)-3,5-diamino-piperidin-1-yl)-[1,3,5]triazine-2-amine;

N-[4-(3-chloro-4-fluoro-phenylcarbamoyl)-3-hydroxy-phenyl]-4,6-Bis-((3R,5S)-3,5-diamino-piperidin-1-yl)-[1,3,5]triazine-2-amine;

N-[3-hydroxy-4-(3-trifluoromethoxy-phenylcarbamoyl)-phenyl]-4,6-Bis-((3R,5S)-3,5-diamino-piperidin-1-yl)-[1,3,5]triazine-2-amine;

N-[4-(3,4-difluoro-phenylcarbamoyl)-3-hydroxy-phenyl]-4,6-Bis-((3R,5S)-3,5-diamino-piperidin-1-yl)-[1,3,5]triazine-2-amine;

N-[4-(4-chloro-2-fluoro-phenylcarbamoyl)-3-hydroxy-phenyl]-4,6-Bis-((3R,5S)-3,5-diamino-piperidin-1-yl)-[1,3,5]triazine-2-amine;

N-[4-(benzo[1,3]dioxol-5-ylcarbamoyl)-3-hydroxy-phenyl]-4,6-Bis-((3R,5S)-3,5-diamino-piperidin-1-yl)-[1,3,5]triazine-2-amine;

N-[3-hydroxy-4-(3-trifluoromethylsulfanyl-phenylcarbamoyl)-phenyl]-4,6-Bis-((3R,5S)-3,5-diamino-piperidin-1-yl)-[1,3,5]triazine-2-amine;

N-[3-hydroxy-4-(3-trifluoromethyl-phenylcarbamoyl)-phenyl]-4,6-Bis-((3R,5S)-3,5-diamino-piperidin-1-yl)-[1,3,5]triazine-2-amine;

N-[4-(3,4-dichloro-phenylcarbamoyl)-3-hydroxy-phenyl]-4,6-Bis-((3R,5S)-3,5-diamino-piperidin-1-yl)-[1,3,5]triazine-2-amine;

N-[3-hydroxy-4-(4-hydroxy-phenylcarbamoyl)-phenyl]-4,6-Bis-((3R,5S)-3,5-diamino-piperidin-1-yl)-[1,3,5]triazine-2-amine;

N-[4-(1H-benzoimidazol-5-ylcarbamoyl)-3-hydroxy-phenyl]-4,6-Bis-((3R,5S)-3,5-diamino-piperidin-1-yl)-[1,3,5]triazine-2-amine;

1-Hydroxy-naphthalene-2-carboxylic acid {4-[4-[bis-(2-amino-ethyl)-amino]-6-((3R,5S)-3,5-diamino-piperidin-1-yl)-[1,3,5]triazin-2-ylamino]-phenyl}-amide;

N-{4-[2-(2-chloro-phenylcarbamoyl)-acetyl]-phenyl}-4,6-Bis-((3R,5S)-3,5-diamino-piperidin-1-yl)-[1,3,5]triazine-2-amine;

3-{4-[4-((3S,5R)-3-Amino-5-hydroxy-piperidin-1-yl)-6-((3S,5R)-3,5-diamino-piperidin-1-yl)-[1,3,5]triazin-2-ylamino]-phenyl}-N-(2-chloro-phenyl)-3-oxo-propionamide;

1-Hydroxy-naphthalene-2-carboxylic acid {4-[4-((3S,5R)-3-amino-5-hydroxy-piperidin-1-yl)-6-((3S,5R)-3,5-diamino-piperidin-1-yl)-[1,3,5]triazin-2-ylamino]-phenyl}-amide;

3-[4-((3S,5R)-3-Amino-5-hydroxy-piperidin-1-yl)-6-((3S,5R)-3,5-diamino-piperidin-1-yl)-[1,3,5]triazin-2-ylamino]-fluoren-9-one;

4-[4-((3S,5R)-3-Amino-5-hydroxy-piperidin-1-yl)-6-((3S,5R)-3,5-diamino-piperidin-1-yl)-[1,3,5]triazin-2-ylamino]-2-hydroxy-benzoic acid phenyl ester;

N-{4-[4-((3S,5R)-3-Amino-5-hydroxy-piperidin-1-yl)-6-((3S,5R)-3,5-diamino-piperidin-1-yl)-[1,3,5]triazin-2-ylamino]-2-hydroxy-phenyl}-4-chloro-benzamide;

N-Benzyl-N-{4-[4-((3R,5S)-3,5-diamino-piperidin-1-yl)-6-((3R,4S)-3,4-diamino-pyrrolidin-1-yl)-[1,3,5]triazin-2-ylamino]-2-hydroxy-phenyl}-4-methyl-benzenesulfonamide;

1-Hydroxy-naphthalene-2-carboxylic acid {4-[4-((3R,5S)-3,5-diamino-piperidin-1-yl)-6-((3R,4S)-3,4-diamino-pyrrolidin-1-yl)-[1,3,5]triazin-2-ylamino]-phenyl}-amide;

N-[4-(3,5-dichloro-2-hydroxy-benzenesulfonylamino)-3-hydroxy-phenyl]-4,6-Bis-((3R,5S)-3,5-diamino-piperidin-1-yl)-[1,3,5]triazine-2-amine;

N-[4-(4-ethoxy-benzoylamino)-3-hydroxy-phenyl]-4,6-Bis-((3R,5S)-3,5-diamino-piperidin-1-yl)-[1,3,5]triazine-2-amine;

N-{4-[4-((3R,5S)-3,5-Bis-(aminomethyl)-piperidin-1-yl)-6-((3R,5S)-3,5-diamino-piperidin-1-yl)-[1,3,5]triazin-2-ylamino]-2-hydroxy-phenyl}-4-chloro-benzamide;

1-Hydroxy-naphthalene-2-carboxylic acid {4-[4-((3R,5S)-3,5-bis-(aminomethyl)-piperidin-1-yl)-6-((3R,5S)-3,5-diamino-piperidin-1-yl)-[1,3,5]triazin-2-ylamino]-phenyl}-amide;

N-{4-[2-(3,4-difluoro-phenylcarbamoyl)-acetyl]-phenyl}-4,6-Bis-((3R,5S)-3,5-diamino-piperidin-1-yl)-[1,3,5]triazine-2-amine;

N-{4-[2-(2,2-difluoro-benzo[1,3]dioxol-5-ylcarbamoyl)-acetyl]-phenyl}-4,6-Bis-((3R,5S)-3,5-diamino-piperidin-1-yl)-[1,3,5]triazine-2-amine;

N-[4-(3-bromo-benzoylamino)-3-hydroxy-phenyl]-4,6-Bis-((3R,5S)-3,5-diamino-piperidin-1-yl)-[1,3,5]triazine-2-amine;

N-[3-hydroxy-4-(3-phenyl-acryloylamino)-phenyl]-4,6-Bis-((3R,5S)-3,5-diamino-piperidin-1-yl)-[1,3,5]triazine-2-amine;

1-Hydroxy-naphthalene-2-carboxylic acid {4-[4-((2S,4S)-4-amino-2-aminomethyl-pyrrolidin-1-yl)-6-((3R,5S)-3,5-diamino-piperidin-1-yl)-[1,3,5]triazin-2-ylamino]-phenyl}-amide;

3-{4-[4-((2S,4S)-4-Amino-2-aminomethyl-pyrrolidin-1-yl)-6-((3R,5S)-3,5-diamino-piperidin-1-yl)-[1,3,5]triazin-2-ylamino]-phenyl}-3-oxo-N-(4-trifluoromethylsulfanyl-phenyl)-propionamide;

4-[4-((2S,4S)-4-Amino-2-aminomethyl-pyrrolidin-1-yl)-6-((3R,5S)-3,5-diamino-piperidin-1-yl)-[1,3,5]triazin-2-ylamino]-2-hydroxy-benzoic acid phenyl ester;

N-{4-[4-((2S,4S)-4-Amino-2-aminomethyl-pyrrolidin-1-yl)-6-((3R,5S)-3,5-diamino-piperidin-1-yl)-[1,3,5]triazin-2-ylamino]-2-hydroxy-phenyl}-4-chloro-benzamide;

3-{4-[4-((2S,4S)-4-Amino-2-aminomethyl-pyrrolidin-1-yl)-6-((3R,5S)-3,5-diamino-piperidin-1-yl)-[1,3,5]triazin-2-ylamino]-phenyl}-N-(2,2-difluoro-benzo[1,3]dioxol-5-yl)-3-oxo-propionamide;

1-Hydroxy-naphthalene-2-carboxylic acid {4-[4-((2S,4S)-4-amino-2-hydroxymethyl-pyrrolidin-1-yl)-6-((3R,5S)-3,5-diamino-piperidin-1-yl)-[1,3,5]triazin-2-ylamino]-phenyl}-amide;

3-{4-[4-((2S,4S)-4-Amino-2-hydroxymethyl-pyrrolidin-1-yl)-6-((3R,5S)-3,5-diamino-piperidin-1-yl)-[1,3,5]triazin-2-ylamino]-phenyl}-3-oxo-N-(4-trifluoromethylsulfanyl-phenyl)-propionamide;

3-{4-[4-((2S,4S)-4-Amino-2-hydroxymethyl-pyrrolidin-1-yl)-6-((3R,5S)-3,5-diamino-piperidin-1-yl)-[1,3,5]triazin-2-ylamino]-phenyl}-N-(2,2-difluoro-benzo[1,3]dioxol-5-yl)-3-oxo-propionamide;

N-(2-Chloro-phenyl)-3-{4-[4-((3R,5S)-3,5-diamino-piperidin-1-yl)-6-methoxy-[1,3,5]triazin-2-ylamino]-phenyl}-3-oxo-propionamide;

N-Benzyl-N-{4-[4-((3R,5S)-3,5-diamino-piperidin-1-yl)-6-methoxy-[1,3,5]triazin-2-ylamino]-2-hydroxy-phenyl}-4-methyl-benzenesulfonamide;

1-Hydroxy-naphthalene-2-carboxylic acid {4-[4-((3R,5S)-3,5-diamino-piperidin-1-yl)-6-methoxy-[1,3,5]triazin-2-ylamino]-phenyl}-amide;

3-{4-[4-((3R,5S)-3,5-Diamino-piperidin-1-yl)-6-methoxy-[1,3,5]triazin-2-ylamino]-phenyl}-3-oxo-N-(4-trifluoromethylsulfanyl-phenyl)-propionamide;

4-[4-((3R,5S)-3,5-Diamino-piperidin-1-yl)-6-methoxy-[1,3,5]triazin-2-ylamino]-2-hydroxy-benzoic acid phenyl ester;

4-Chloro-N-{4-[4-((3R,5S)-3,5-diamino-piperidin-1-yl)-6-methoxy-[1,3,5]triazin-2-ylamino]-2-hydroxy-phenyl}-benzamide;

3-{4-[4-((3R,5S)-3,5-Diamino-piperidin-1-yl)-6-methoxy-[1,3,5]triazin-2-ylamino]-phenyl}-N-(3,4-difluoro-phenyl)-3-oxo-propionamide;

3-{4-[4-((3R,5S)-3,5-Diamino-piperidin-1-yl)-6-methoxy-[1,3,5]triazin-2-ylamino]-phenyl}-N-(2,2-difluoro-benzo[1,3]dioxol-5-yl)-3-oxo-propionamide;

N-{4-[(adamantane-1-carbonyl)-amino]-3-hydroxy-phenyl}-4,6-Bis-((3R,5S)-3,5-diamino-piperidin-1-yl)-[1,3,5]triazine-2-amine;

N-[4-(3-chloro-benzoylamino)-3-hydroxy-phenyl]-4,6-Bis-((3R,5S)-3,5-diamino-piperidin-1-yl)-[1,3,5]triazine-2-amine;

1-Hydroxy-naphthalene-2-carboxylic acid {4-[4-((3R,4S)-3-aminomethyl-4-hydroxy-piperidin-1-yl)-6-((3R,5S)-3,5-diamino-piperidin-1-yl)-[1,3,5]triazin-2-ylamino]-phenyl}-amide;

1-Hydroxy-naphthalene-2-carboxylic acid {4-[4-((2S,3S)-2-aminomethyl-3-hydroxy-pyrrolidin-1-yl)-6-((3R,5S)-3,5-diamino-piperidin-1-yl)-[1,3,5]triazin-2-ylamino]-phenyl}-amide;

N-{4-[4-((2S,3S)-2-Aminomethyl-3-hydroxy-pyrrolidin-1-yl)-6-((3R,5S)-3,5-diamino-piperidin-1-yl)-[1,3,5]triazin-2-ylamino]-2-hydroxy-phenyl}-4-methyl-benzamide;

N-{3-hydroxy-4-[2-(1H-indol-3-yl)-2-oxo-acetylamino]-phenyl}-4,6-Bis-((3R,5S)-3,5-diamino-piperidin-1-yl)-[1,3,5]triazine-2-amine;

N-{3-hydroxy-4-[3-phenyl-2-(toluene-4-sulfonylamino)-propionylamino]-phenyl}-4,6-Bis-((3R,5S)-3,5-diamino-piperidin-1-yl)-[1,3,5]triazine-2-amine;

N-[4-(3-oxo-3-phenyl-propionylamino)-phenyl]-4,6-Bis-((3R,5S)-3,5-diamino-piperidin-1-yl)-[1,3,5]triazine-2-amine;

N-[3-hydroxy-4-(4-methoxy-benzoylamino)-phenyl]-4,6-Bis-((3R,5S)-3,5-diamino-piperidin-1-yl)-[1,3,5]triazine-2-amine;

N-[4-(2,4-dimethoxy-benzoylamino)-3-hydroxy-phenyl]-4,6-Bis-((3R,5S)-3,5-diamino-piperidin-1-yl)-[1,3,5]triazine-2-amine;

N-[3-hydroxy-4-(2-methoxy-benzoylamino)-phenyl]-4,6-Bis-((3R,5S)-3,5-diamino-piperidin-1-yl)-[1,3,5]triazine-2-amine;

N-Benzyl-N-{4-[4-((3R,5S)-3,5-diamino-piperidin-1-yl)-6-(4-pyridin-4-yl-piperazin-1-yl)-[1,3,5]triazin-2-ylamino]-2-hydroxy-phenyl}-4-methyl-benzenesulfonamide;

4-Chloro-N-{4-[4-((3S,5R)-3,5-diamino-piperidin-1-yl)-6-piperazin-1-yl-[1,3,5]triazin-2-ylamino]-2-hydroxy-phenyl}-benzamide;

N-{4-[4-((3R,5S)-3,5-Diamino-piperidin-1-yl)-6-(piperidin-4-ylamino)-[1,3,5]triazin-2-ylamino]-2-hydroxy-phenyl}-4-methyl-benzamide;

4-Chloro-N-{4-[4-((3S,5R)-3,5-diamino-piperidin-1-yl)-6-(piperidin-4-ylamino)-[1,3,5]triazin-2-ylamino]-2-hydroxy-phenyl}-benzamide;

4-Chloro-N-{4-[4-((3S,5R)-3,5-diamino-piperidin-1-yl)-6-(piperidin-3-ylamino)-[1,3,5]triazin-2-ylamino]-2-hydroxy-phenyl}-benzamide;

N-{4-[(1-hydroxy-naphthalene-2-carbonyl)-amino]-phenyl}-4,6-Bis-((3R,5S)-3,5-diamino-piperidin-1-yl)-[1,3,5]triazine-2-amine;

N-[3-hydroxy-4-(4-methyl-benzoylamino)-phenyl]-4,6-Bis-((3R,5S)-3,5-diamino-piperidin-1-yl)-[1,3,5]triazine-2-amine;

4-[4,6-Bis-((3R,5S)-3,5-diamino-piperidin-1-yl)-[1,3,5]triazin-2-ylamino]-2-hydroxy-benzoic acid phenyl ester;

N-(9H-fluoren-2-yl)-4,6-Bis-((3R,5S)-3,5-diamino-piperidin-1-yl)-[1,3,5]triazine-2-amine;

N-{4-[4-(3-Amino-azetidin-1-yl)-6-((3R,5S)-3,5-diamino-piperidin-1-yl)-[1,3,5]triazin-2-ylamino]-2-hydroxy-phenyl}-4-chloro-benzamide;

N-pyren-1-yl-4,6-Bis-((3R,5S)-3,5-diamino-piperidin-1-yl)-[1,3,5]triazine-2-amine;

N-(4-methyl-2-oxo-2H-chromen-7-yl)-4,6-Bis-((3R,5S)-3,5-diamino-piperidin-1-yl)-[1,3,5]triazine-2-amine;

N-(9-oxo-9H-fluoren-3-yl)-4,6-Bis-((3R,5S)-3,5-diamino-piperidin-1-yl)-[1,3,5]triazine-2-amine;

N-(4-phenylazo-phenyl)-4,6-Bis-((3R,5S)-3,5-diamino-piperidin-1-yl)-[1,3,5]triazine-2-amine;

N-[4-(6-methyl-benzothiazol-2-yl)-phenyl]-4,6-Bis-((3R,5S)-3,5-diamino-piperidin-1-yl)-[1,3,5]triazine-2-amine;

3-{4-[4-((2S,4R)-2-Aminomethyl-4-hydroxy-pyrrolidin-1-yl)-6-((3R,5S)-3,5-diamino-piperidin-1-yl)-[1,3,5]triazin-2-ylamino]-phenyl}-3-oxo-N-(4-trifluoromethylsulfanyl-phenyl)-propionamide;

3-{4-[4-((2S,4R)-2-Aminomethyl-4-hydroxy-pyrrolidin-1-yl)-6-((3R,5S)-3,5-diamino-piperidin-1-yl)-[1,3,5]triazin-2-ylamino]-phenyl}-N-(2,2-difluoro-benzo[1,3]dioxol-5-yl)-3-oxo-propionamide;

1-Hydroxy-naphthalene-2-carboxylic acid {4-[4-(2-amino-ethylamino)-6-((3R,5S)-3,5-diamino-piperidin-1-yl)-[1,3,5]triazin-2-ylamino]-phenyl}-amide;

N-[3-(2-hydroxy-3-methyl-benzoylamino)-phenyl]-4,6-Bis-((3R,5S)-3,5-diamino-piperidin-1-yl)-[1,3,5]triazine-2-amine;

N-[3-hydroxy-4-(2-hydroxy-3-methyl-benzoylamino)-phenyl]-4,6-Bis-((3R,5S)-3,5-diamino-piperidin-1-yl)-[1,3,5]triazine-2-amine;

N-[4-(2,3-dihydroxy-benzoylamino)-phenyl]-4,6-Bis-((3R,5S)-3,5-diamino-piperidin-1-yl)-[1,3,5]triazine-2-amine;

N-[3-(2,3-dihydroxy-benzoylamino)-phenyl]-4,6-Bis-((3R,5S)-3,5-diamino-piperidin-1-yl)-[1,3,5]triazine-2-amine;

N-[4-(2,3-dihydroxy-benzoylamino)-3-methyl-phenyl]-4,6-Bis-((3R,5S)-3,5-diamino-piperidin-1-yl)-[1,3,5]triazine-2-amine;

N-[4-(2,3-dihydroxy-benzoylamino)-3-hydroxy-phenyl]-4,6-Bis-((3R,5S)-3,5-diamino-piperidin-1-yl)-[1,3,5]triazine-2-amine;

N-[4-(2-hydroxy-4-methyl-benzoylamino)-phenyl]-4,6-Bis-((3R,5S)-3,5-diamino-piperidin-1-yl)-[1,3,5]triazine-2-amine;

N-[3-hydroxy-4-(2-hydroxy-4-methyl-benzoylamino)-phenyl]-4,6-Bis-((3R,5S)-3,5-diamino-piperidin-1-yl)-[1,3,5]triazine-2-amine;

N-{4-[2-(3-chloro-phenylcarbamoyl)-acetyl]-phenyl}-4,6-Bis-((3R,5S)-3,5-diamino-piperidin-1-yl)-[1,3,5]triazine-2-amine;

N-[4-(2-phenylcarbamoyl-acetyl)-phenyl]-4,6-Bis-((3R,5S)-3,5-diamino-piperidin-1-yl)-[1,3,5]triazine-2-amine;

N-{4-[2-(4-trifluoromethylsulfanyl-phenylcarbamoyl)-acetyl]-phenyl}-4,6-Bis-((3R,5S)-3,5-diamino-piperidin-1-yl)-[1,3,5]triazine-2-amine;

N-{4-[2-(3-trifluoromethylsulfanyl-phenylcarbamoyl)-acetyl]-phenyl}-4,6-Bis-((3R,5S)-3,5-diamino-piperidin-1-yl)-[1,3,5]triazine-2-amine;

N-{4-[2-(4-chloro-phenylcarbamoyl)-acetyl]-phenyl}-4,6-Bis-((3R,5S)-3,5-diamino-piperidin-1-yl)-[1,3,5]triazine-2-amine;

N-[4-(4-chloro-benzoylamino)-3-hydroxy-phenyl]-4,6-Bis-((3R,5S)-3,5-diamino-piperidin-1-yl)-[1,3,5]triazine-2-amine;

N-[3-(2-hydroxy-3-nitro-benzoylamino)-phenyl]-4,6-Bis-((3R,5S)-3,5-diamino-piperidin-1-yl)-[1,3,5]triazine-2-amine;

N-[4-(2,4-dihydroxy-benzoylamino)-phenyl]-4,6-Bis-((3R,5S)-3,5-diamino-piperidin-1-yl)-[1,3,5]triazine-2-amine;

N-[4-(2,4-dihydroxy-benzoylamino)-3-methyl-phenyl]-4,6-Bis-((3R,5S)-3,5-diamino-piperidin-1-yl)-[1,3,5]triazine-2-amine;

1-Hydroxy-naphthalene-2-carboxylicacid {4-[3-((3R,5S)-3,5-diamino-piperidin-1-yl)-5-((3S,5R)-3,5-diamino-piperidin-1-yl)-phenylamino]-phenyl}-amide;

N-{4-[4-((2S,4S)-4-Amino-2-aminomethyl-pyrrolidin-1-yl)-6-((3R,5S)-3,5-diamino-piperidin-1-yl)-[1,3,5]triazin-2-ylamino]-2-hydroxy-phenyl}-2-(1H-indol-3-yl)-2-oxo-acetamide;

1-Benzyloxy-naphthalene-2-carboxylicacid {4-[3-((3R,5S)-3,5-diamino-piperidin-1-yl)-5-((3S,5R)-3,5-diamino-piperidin-1-yl)-phenylamino]-phenyl}-amide;

1-Hydroxy-naphthalene-2-carboxylic acid {4-[4,6-bis-((2S,4S)-4-amino-2-aminomethyl-pyrrolidin-1-yl)-[1,3,5]triazin-2-ylamino]-phenyl}-amide;

N-(4-hexanoylamino-3-hydroxy-phenyl)-4,6-Bis-((3R,5S)-3,5-diamino-piperidin-1-yl)-[1,3,5]triazine-2-amine;

N-[3-hydroxy-4-(7-methyl-octanoylamino)-phenyl]-4,6-Bis-((3R,5S)-3,5-diamino-piperidin-1-yl)-[1,3,5]triazine-2-amine;

N-[4-(2-ethyl-heptanoylamino)-3-hydroxy-phenyl]-4,6-Bis-((3R,5S)-3,5-diamino-piperidin-1-yl)-[1,3,5]triazine-2-amine;

N-(4-decanoylamino-3-hydroxy-phenyl)-4,6-Bis-((3R,5S)-3,5-diamino-piperidin-1-yl)-[1,3,5]triazine-2-amine;

N-(4-benzoylamino-3-hydroxy-phenyl)-4,6-Bis-((3R,5S)-3,5-diamino-piperidin-1-yl)-[1,3,5]triazine-2-amine;

N-{4-[4-(2-ethyl-heptanoylamino)-benzene sulfonylamino]-3-hydroxy-phenyl}-4,6-Bis-((3R,5S)-3,5-diamino-piperidin-1-yl)-[1,3,5]triazine-2-amine;

N-[4-(4-decanoylamino-benzenesulfonylamino)-3-hydroxy-phenyl]-4,6-Bis-((3R,5S)-3,5-diamino-piperidin-1-yl)-[1,3,5]triazine-2-amine;

N-{3-hydroxy-4-[4-(3-methyl-butyrylamino)-benzene sulfonylamino]-phenyl}-4,6-Bis-((3R,5S)-3,5-diamino-piperidin-1-yl)-[1,3,5]triazine-2-amine;

1-Hydroxy-naphthalene-2-carboxylicacid {4-[4-((3S,5R)-3,5-diamino-piperidin-1-yl)-[1,3,5]triazin-2-ylamino]-phenyl}-amide;

N-{4-[4-[Bis-(2-amino-ethyl)-amino]-6-((3R,5S)-3,5-diamino-piperidin-1-yl)-[1,3,5]triazin-2-ylamino]-2-hydroxy-phenyl}-2-(1H-indol-3-yl)-2-oxo-acetamide;

N-{4-[(1-hydroxy-naphthalene-2-carbonyl)-amino]-phenyl}-4,6-Bis-((3R,5S)-3,5-diamino-piperidin-1-yl)-[1,3,5]triazine-2-amine;

N-[4-(4-chloro-2-hydroxy-benzoylamino)-phenyl]-4,6-Bis-((3R,5S)-3,5-diamino-piperidin-1-yl)-[1,3,5]triazine-2-amine;

N-[4-(4-chloro-2-hydroxy-benzoylamino)-3-methyl-phenyl]-4,6-Bis-((3R,5S)-3,5-diamino-piperidin-1-yl)-[1,3,5]triazine-2-amine;

N-[3-chloro-4-(4-chloro-2-hydroxy-benzoylamino)-phenyl]-4,6-Bis-((3R,5S)-3,5-diamino-piperidin-1-yl)-[1,3,5]triazine-2-amine;

N-[3,5-dichloro-4-(4-chloro-2-hydroxy-benzoylamino)-phenyl]-4,6-Bis-((3R,5S)-3,5-diamino-piperidin-1-yl)-[1,3,5]triazine-2-amine;

N-[3-bromo-4-(4-chloro-2-hydroxy-benzoylamino)-phenyl]-4,6-Bis-((3R,5S)-3,5-diamino-piperidin-1-yl)-[1,3,5]triazine-2-amine;

N-[4-(4-chloro-2-hydroxy-benzoylamino)-3-fluoro-phenyl]-4,6-Bis-((3R,5S)-3,5-diamino-piperidin-1-yl)-[1,3,5]triazine-2-amine;

N-(8-hydroxy-quinolin-5-yl)-4,6-Bis-((3R,5S)-3,5-diamino-piperidin-1-yl)-[1,3,5]triazine-2-amine;

N-[4-(4-chloro-2-hydroxy-benzoylamino)-3-trifluoromethyl-phenyl]-4,6-Bis-((3R,5S)-3,5-diamino-piperidin-1-yl)-[1,3,5]triazine-2-amine;

N-[4-(4-chloro-2-hydroxy-benzoylamino)-3-phenylcarbamoyl-phenyl]-4,6-Bis-((3R,5S)-3,5-diamino-piperidin-1-yl)-[1,3,5]triazine-2-amine;

N-[4-(4-chloro-2-hydroxy-benzoylamino)-3-methoxy-phenyl]-4,6-Bis-((3R,5S)-3,5-diamino-piperidin-1-yl)-[1,3,5]triazine-2-amine;

N-{4-[(1-hydroxy-naphthalene-2-carbonyl)-amino]-phenyl}-4,6-Bis-((3R,5S)-3,5-diamino-piperidin-1-yl)-[1,3,5]triazine-2-amine;

N-[3-chloro-4-(4-chloro-2-hydroxy-benzoylamino)-5-methyl-phenyl]-4,6-Bis-((3R,5S)-3,5-diamino-piperidin-1-yl)-[1,3,5]triazine-2-amine;

N-[4-(4-fluoro-2-hydroxy-benzoylamino)-3-hydroxy-phenyl]-4,6-Bis-((3R,5S)-3,5-diamino-piperidin-1-yl)-[1,3,5]triazine-2-amine;

N-[3-hydroxy-4-(2-hydroxy-5-trifluoromethoxy-benzoylamino)-phenyl]-4,6-Bis-((3R,5S)-3,5-diamino-piperidin-1-yl)-[1,3,5]triazine-2-amine;

N-[3-chloro-4-(3,4-difluoro-2-hydroxy-benzoylamino)-phenyl]-4,6-Bis-((3R,5S)-3,5-diamino-piperidin-1-yl)-[1,3,5]triazine-2-amine;

N-{3-chloro-4-[4-(1,3-dihydro-isoindol-2-yl)-2-hydroxy-benzoylamino]-phenyl}-4,6-Bis-((3R,5S)-3,5-diamino-piperidin-1-yl)-[1,3,5]triazine-2-amine;

N-{3-chloro-4-[(2-hydroxy-naphthalene-1-carbonyl)-amino]-phenyl}-4,6-Bis-((3R,5S)-3,5-diamino-piperidin-1-yl)-[1,3,5]triazine-2-amine;

N-{3-chloro-4-[(2-hydroxy-6-trifluoromethyl-pyridine-3-carbonyl)-amino]-phenyl}-4,6-Bis-((3R,5S)-3,5-diamino-piperidin-1-yl)-[1,3,5]triazine-2-amine;

N-{3-hydroxy-4-[4-(7-methyl-octanoylamino)-benzene sulfonylamino]-phenyl}-4,6-Bis-((3R,5S)-3,5-diamino-piperidin-1-yl)-[1,3,5]triazine-2-amine;

N-[4-(4-fluoro-2-hydroxy-benzoylamino)-phenyl]-4,6-Bis-((3R,5S)-3,5-diamino-piperidin-1-yl)-[1,3,5]triazine-2-amine;

N-(3-chloro-4-nitro-phenyl)-4,6-Bis-((3R,5S)-3,5-diamino-piperidin-1-yl)-[1,3,5]triazine-2-amine;

N-{4-[4-(1,3-dihydro-isoindol-2-yl)-2-hydroxy-benzoylamino]-phenyl}-4,6-Bis-((3R,5S)-3,5-diamino-piperidin-1-yl)-[1,3,5]triazine-2-amine;

N-{4-[(2-hydroxy-6-trifluoromethyl-pyridine-3-carbonyl)-amino]-phenyl}-4,6-Bis-((3R,5S)-3,5-diamino-piperidin-1-yl)-[1,3,5]triazine-2-amine;

N-(6-nitro-benzothiazol-2-yl)-4,6-Bis-((3R,5S)-3,5-diamino-piperidin-1-yl)-[1,3,5]triazine-2-amine;

N-[4-(2-hydroxy-3,5-diisopropyl-benzoylamino)-phenyl]-4,6-Bis-((3R,5S)-3,5-diamino-piperidin-1-yl)-[1,3,5]triazine-2-amine;

N-[4-(4-dimethylamino-2-hydroxy-benzoylamino)-phenyl]-4,6-Bis-((3R,5S)-3,5-diamino-piperidin-1-yl)-[1,3,5]triazine-2-amine;

N-[4-(5-bromo-2-hydroxy-benzoylamino)-3-hydroxy-phenyl]-4,6-Bis-((3R,5S)-3,5-diamino-piperidin-1-yl)-[1,3,5]triazine-2-amine;

N-[3-hydroxy-4-(2-hydroxy-3,5-diisopropyl-benzoylamino)-phenyl]-4,6-Bis-((3R,5S)-3,5-diamino-piperidin-1-yl)-[1,3,5]triazine-2-amine;

N-[4-(4-dimethylamino-2-hydroxy-benzoylamino)-3-hydroxy-phenyl]-4,6-Bis-((3R,5S)-3,5-diamino-piperidin-1-yl)-[1,3,5]triazine-2-amine;

N-[4-(5-chloro-2-hydroxy-benzoylamino)-phenyl]-4,6-Bis-((3R,5S)-3,5-diamino-piperidin-1-yl)-[1,3,5]triazine-2-amine;

N-[4-(5-bromo-2-hydroxy-benzoylamino)-phenyl]-4,6-Bis-((3R,5S)-3,5-diamino-piperidin-1-yl)-[1,3,5]triazine-2-amine;

N-(4-hydroxy-naphthalen-1-yl)-4,6-Bis-((3R,5S)-3,5-diamino-piperidin-1-yl)-[1,3,5]triazine-2-amine;

N-[3-hydroxy-4-(2-hydroxy-4-methoxy-benzoylamino)-phenyl]-4,6-Bis-((3R,5S)-3,5-diamino-piperidin-1-yl)-[1,3,5]triazine-2-amine;

N-[3-hydroxy-4-(2-hydroxy-5-methoxy-benzoylamino)-phenyl]-4,6-Bis-((3R,5S)-3,5-diamino-piperidin-1-yl)-[1,3,5]triazine-2-amine;

N-[3-hydroxy-4-(2-hydroxy-4-methyl-benzoylamino)-phenyl]-4,6-Bis-((3R,5S)-3,5-diamino-piperidin-1-yl)-[1,3,5]triazine-2-amine;

N-[4-(4-chloro-2-hydroxy-benzoylamino)-3-hydroxy-phenyl]-4,6-Bis-((3R,5S)-3,5-diamino-piperidin-1-yl)-[1,3,5]triazine-2-amine;

N-{4-[4-((2S,4S)-4-Amino-2-aminomethyl-pyrrolidin-1-yl)-6-((3R,5S)-3,5-diamino-piperidin-1-yl)-[1,3,5]triazin-2-ylamino]-2-hydroxy-phenyl}-4-chloro-2-hydroxy-benzamide;

N-[3-(4-chloro-2-hydroxy-benzoylamino)-phenyl]-4,6-Bis-((3R,5S)-3,5-diamino-piperidin-1-yl)-[1,3,5]triazine-2-amine;

1-Hydroxy-naphthalene-2-carboxylic acid [4-(3,5-dichloro-2,6-Bis-((3R,5S)-3,5-diamino-piperidin-1-yl)-pyridin-4-ylamino)-phenyl]-amide;

N-[3-(2,4-dihydroxy-benzoylamino)-phenyl]-4,6-Bis-((3R,5S)-3,5-diamino-piperidin-1-yl)-[1,3,5]triazine-2-amine;

N-[4-(2,4-dihydroxy-benzoylamino)-3-methyl-phenyl]-4,6-Bis-((3R,5S)-3,5-diamino-piperidin-1-yl)-[1,3,5]triazine-2-amine;

N-[4-(2,4-dihydroxy-benzoylamino)-3-hydroxy-phenyl]-4,6-Bis-((3R,5S)-3,5-diamino-piperidin-1-yl)-[1,3,5]triazine-2-amine;

1-Hydroxy-naphthalene-2-carboxylicacid {4-[6-((3R,5S)-3,5-diamino-piperidin-1-yl)-8-((3S,5R)-3,5-diamino-piperidin-1-yl)-7H-purin-2-ylamino]-phenyl}-amide;

1-Hydroxy-naphthalene-2-carboxylicacid {4-[2-((3R,5S)-3,5-diamino-piperidin-1-yl)-6-((3S,5R)-3,5-diamino-piperidin-1-yl)-pyrimidin-4-ylamino]-phenyl}-amide;

N-{3-hydroxy-4-[(2-hydroxy-naphthalene-1-carbonyl)-amino]-phenyl}-4,6-Bis-((3R,5S)-3,5-diamino-piperidin-1-yl)-[1,3,5]triazine-2-amine;

N-{4-[(2-hydroxy-naphthalene-1-carbonyl)-amino]-phenyl}-4,6-Bis-((3R,5S)-3,5-diamino-piperidin-1-yl)-[1,3,5]triazine-2-amine;

1-Hydroxy-naphthalene-2-carboxylic acid [4-(2,6-Bis-((3R,5S)-3,5-diamino-piperidin-1-yl)-pyridin-4-ylamino)-phenyl]-amide;

N-{4-[2-(4-methoxy-phenylcarbamoyl)-acetyl]-phenyl}-4,6-Bis-((3R,5S)-3,5-diamino-piperidin-1-yl)-[1,3,5]triazine-2-amine;

1-Hydroxy-naphthalene-2-carboxylic acid [4-(4,6-Bis-((3R,5S)-3,5-diamino-piperidin-1-yl)-pyridin-2-ylamino)-phenyl]-amide;

N-{4-[2-(3-bromo-phenylcarbamoyl)-acetyl]-phenyl}-4,6-Bis-((3R,5S)-3,5-diamino-piperidin-1-yl)-[1,3,5]triazine-2-amine;

N-{4-[2-(biphenyl-4-ylcarbamoyl)-acetyl]-phenyl}-4,6-Bis-((3R,5S)-3,5-diamino-piperidin-1-yl)-[1,3,5]triazine-2-amine;

N-{4-[2-(2-chloro-5-trifluoromethyl-phenylcarbamoyl)-acetyl]-phenyl}-4,6-Bis-((3R,5S)-3,5-diamino-piperidin-1-yl)-[1,3,5]triazine-2-amine;

N-{4-[2-(4-chloro-2,5-dimethoxy-phenylcarbamoyl)-acetyl]-phenyl}-4,6-Bis-((3R,5S)-3,5-diamino-piperidin-1-yl)-[1,3,5]triazine-2-amine;

N-{4-[2-(4-fluoro-phenylcarbamoyl)-acetyl]-phenyl}-4,6-Bis-((3R,5S)-3,5-diamino-piperidin-1-yl)-[1,3,5]triazine-2-amine;

N-{4-[2-(3-trifluoromethyl-phenylcarbamoyl)-acetyl]-phenyl}-4,6-Bis-((3R,5S)-3,5-diamino-piperidin-1-yl)-[1,3,5]triazine-2-amine;

N-{4-[2-(4-chloro-2-fluoro-phenylcarbamoyl)-acetyl]-phenyl}-4,6-Bis-((3R,5S)-3,5-diamino-piperidin-1-yl)-[1,3,5]triazine-2-amine;

N-{3-hydroxy-4-[(2-hydroxy-pyridine-3-carbonyl)-amino]-phenyl}-4,6-Bis-((3R,5S)-3,5-diamino-piperidin-1-yl)-[1,3,5]triazine-2-amine;

N-{4-[4-((2S,4S)-4-Amino-2-aminomethyl-pyrrolidin-1-yl)-6-((3R,5S)-3,5-diamino-piperidin-1-yl)-[1,3,5]triazin-2-ylamino]-2-hydroxy-phenyl}-2,4-dihydroxy-benzamide;

N-(4-{4-[benzyl-(toluene-4-sulfonyl)-amino]-3-hydroxy-phenylcarbamoyl}-3-hydroxy-phenyl)-4,6-Bis-((3R,5S)-3,5-diamino-piperidin-1-yl)-[1,3,5]triazine-2-amine;

N-[3-hydroxy-4-(4-methyl-2-oxo-2H-chromen-7-ylcarbamoyl)-phenyl]-4,6-Bis-((3R,5S)-3,5-diamino-piperidin-1-yl)-[1,3,5]triazine-2-amine;

N-[4-(5-bromo-2,3-dihydro-indole-1-carbonyl)-3-hydroxy-phenyl]-4,6-Bis-((3R,5S)-3,5-diamino-piperidin-1-yl)-[1,3,5]triazine-2-amine; and N-[4-(biphenyl-4-ylcarbamoyl)-3-hydroxy-phenyl]-4,6-Bis-((3R,5S)-3,5-diamino-piperidin-1-yl)-[1,3,5]triazine-2-amine.

The invention is also directed to pharmaceutically acceptable prodrugs, pharmaceutically active metabolites, pharmaceutically acceptable solvates, and pharmaceutically acceptable salts of the compounds, prodrugs, metabolites or solvates of Formula I. Advantageous methods of making the compounds of Formula I are also described.

In another aspect, the invention relates to a method for the treatment of bacterial infection in a mammal, including a human, comprising administering to said mammal an amount of a compound of the Formula I as defined above, or a pharmaceutically acceptable prodrug, pharmaceutically active metabolite, pharmaceutically acceptable solvate, or pharmaceutically acceptable salt, that is effective in reducing the bacterial infection. The compounds of the present invention inhibit the bacterial growth of both Gram-positive and Gram-negative strains.

In another aspect, Formula I compounds or pharmaceutically acceptable compositions thereof are utilized in a method for inhibiting the bacterial growth of both Gram-positive and Gram-negative strains at MIC (minimum inhibitory concentrations) of better than 32 µg/ml. The compounds are bactericidal at these concentrations and they retain potency in common antibiotics-resistant strains.

In another aspect, the invention comprises a process of synthesizing compounds of formula I. In one embodiment, the process comprises selectively synthesizing a cis isomer of the Formula I compound.

4. DETAILED DESCRIPTION OF THE INVENTION

4.1 Definitions

Where the following terms are used in this specification, they are used as defined below:

The terms "comprising" and "including" are used herein in their open, non-limiting sense.

The term "alkyl" as used herein refers to a straight- or branched-chain alkyl group having one to twelve carbon atoms. Exemplary alkyl groups include methyl (Me, which also may be structurally depicted by "/"), ethyl (Et), n-propyl, isopropyl, butyl, isobutyl, sec-butyl, tert-butyl (tBu), pentyl, isopentyl, tert-pentyl, hexyl, isohexyl, and the like. The term "lower alkyl" designates an alkyl having from 1 to 6 carbon atoms (a $(C_1-C_6)$alkyl).

The term "alkoxy" refers to —O-alkyl. Illustrative examples include methoxy, ethoxy, propoxy, and the like.

The term "alkenyl" represents alkyl moieties having at least one carbon-carbon double bond wherein alkyl is as defined above and including E and Z isomers of said alkenyl moiety.

The term "alkynyl" represents alkyl moieties having at least one carbon-carbon triple bond wherein alkyl is as defined above.

The term "halogen" represents chlorine, fluorine, bromine or iodine. The term "halo" represents chloro, fluoro, bromo or iodo.

The term "cycloalkyl" refers to a saturated or partially saturated, monocyclic or fused or spiro polycyclic, carbocycle having from three to twelve ring atoms per ring and up to twenty ring atoms in total. Illustrative examples of cycloalkyl groups include the following moieties:

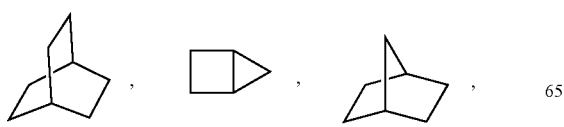

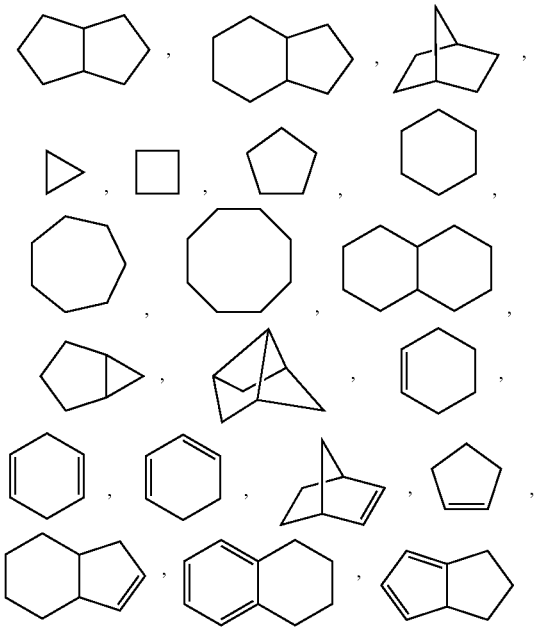

and the like.

A "heterocycloalkyl" refers to a monocyclic, or fused or spiro polycyclic, ring structure that is saturated or partially saturated and has from three to twelve ring atoms per ring selected from C atoms and N, O, and S heteroatoms and up to twenty ring atoms in total. A heterocycloalkyl has at least one ring heteroatom. Illustrative examples of heterocycloalkyl groups include:

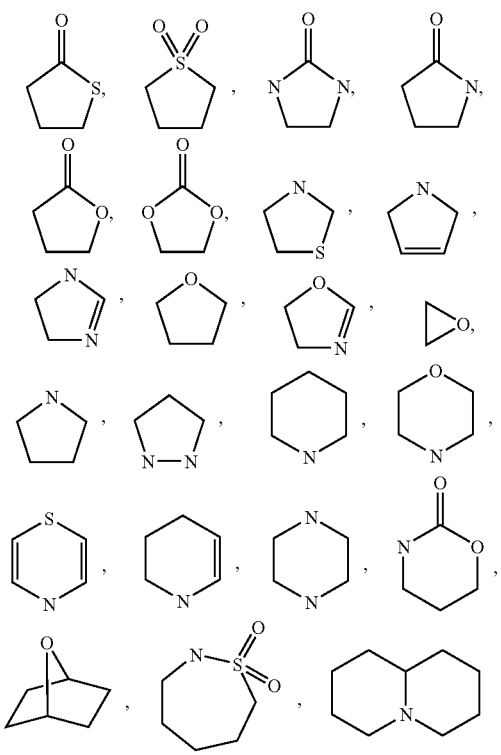

-continued

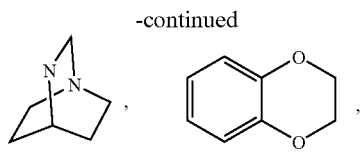

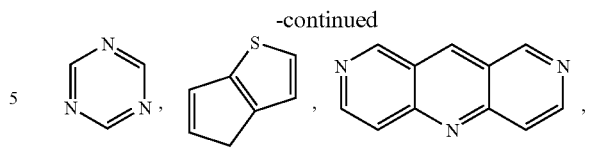

and the like.

The term "aryl" (Ar) refers to a monocyclic, or fused or spiro polycyclic, aromatic carbocycle (ring structure having ring atoms that are all carbon) having from three to twelve ring atoms per ring and up to twenty total ring atoms. Illustrative examples of aryl groups include the following moieties:

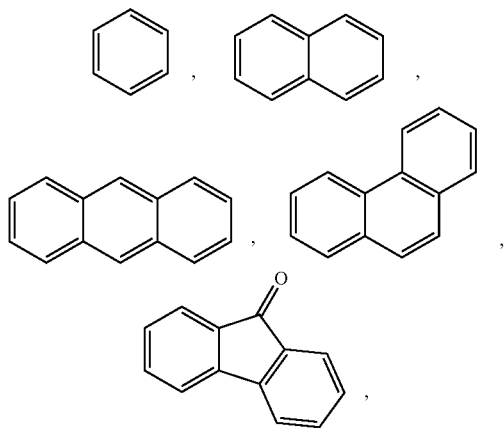

and the like.

The term "heteroaryl" (heteroAr) refers to a monocyclic, or fused or spiro polycyclic, aromatic heterocycle (ring structure having ring atoms selected from carbon atoms as well as nitrogen, oxygen, and sulfur heteroatoms) having from three to twelve ring atoms per ring and up to twenty total ring atoms. In a heteroaryl, at least one ring atom is a heteroatom. Illustrative examples of heteroaryl groups include the following moieties:

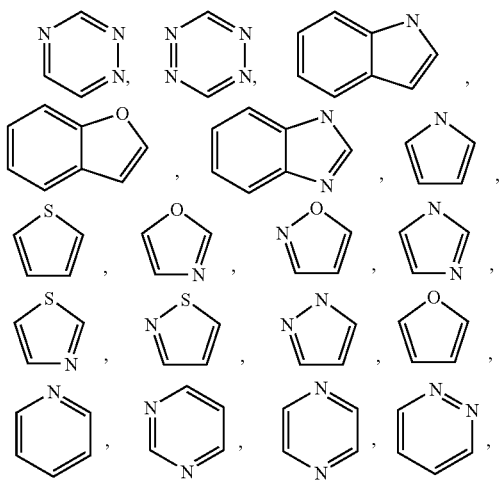

and the like.

The term "substituted" means that the specified group or moiety bears one or more substituents. The term "unsubstituted" means that the specified group bears no substituents. "Substituted" can mean that the specified group or moiety bears substituents that differ from each other.

Thus, the terms "substituted alkyl," "substituted alkoxy," "substituted alkenyl," "substituted alkynl," "substituted cycloalkyl," "substituted heterocycloalkyl," "substituted aryl," or "substituted heteroaryl" refer to that particular group, which is substituted with one or more substituents independently selected from the group consisting of: halogens; =O; =S; —CN; and —NO$_2$; and alkyl, alkenyl, heteroalkyl, haloalkyl, alkynyl, aryl, cycloalkyl, heterocycloalkyl, heteroaryl, —(CH$_2$)$_z$CN where z is an integer from 0 to 4, =NH, —NHOH, —OH, —C(O)H, —OC(O)H, —C(O)OH, —OC(O)OH, —OC(O)OC(O)H, —OOH, —C(NH)NH$_2$, —NHC(NH)NH$_2$, —C(S)NH$_2$, —NHC(S) NH$_2$, —NHC(O)NH$_2$, —S(O$_2$)H, —S(O)H, —NH$_2$, —C(O)NH$_2$, —OC(O)NH$_2$, —NHC(O)H, —NHC(O)OH, —C(O)NHC(O)H, —OS(O$_2$)H, —OS(O)H, —OSH, —SC(O)H, —S(O)C(O)OH, —SO$_2$C(O)OH, —NHSH, —NHS(O)H, —NHSO$_2$H, —C(O)SH, —C(O)S(O)H, —C(O)S(O$_2$)H, —C(S)H, —C(S)OH, —C(SO)OH, —C(SO$_2$)OH, —NHC(S)H, —OC(S)H, —OC(S)OH, —OC(SO$_2$)H, —S(O$_2$)NH$_2$, —S(O)NH$_2$, —SNH$_2$, —NHCS(O$_2$)H, —NHC(SO)H, —NHC(S)H, and —SH groups unsubstituted or substituted with one or more substituents independently selected from the group consisting of halogens, =O, —NO$_2$, —CN, —(CH$_2$)$_z$—CN where z is an integer from 0 to 4, —OR$^c$, —NR$^c$OR$^c$, —N(R$^c$)R$^c$, —C(O)NR$^c$, —C(O)OR$^c$, —C(O)R$^c$, —N(R$^c$)C(O)N(R$^c$)R$^c$, —NR$^c$C(O)R$^c$, —OC(O)OR$^c$, —OC(O)N(R$^c$)R$^c$, —SR$^c$, unsubstituted alkyls, unsubstituted alkenyls, unsubstituted alkynyls, unsubstituted aryls, unsubstituted cycloalkyls, unsubstituted heterocycloalkyls, and unsubstituted heteroaryls, where R$^c$ is hydrogen, unsubstituted alkyl, unsubstituted alkenyl, unsubstituted alkynyl, unsubstituted aryl, unsubstituted cycloalkyl, unsubstituted heterocycloalkyl, or unsubstituted heteroaryl, or two or more R$^c$ groups together cyclize to form part of a heteroaryl or heterocycloalkyl group unsubstituted or substituted with an unsubstituted alkyl group.

In accordance with a convention used in the art,

are used in structural formulae herein to depict the bond that is the point of attachment of the moiety or substituent to the core or backbone structure. Moreover,

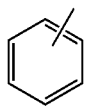

and

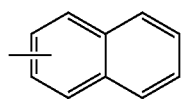

are used in structural formulae herein to depict that the point of attachment of the moiety or substituent to the core of the backbone aryl structure is unspecified.

The term "preventing" refers to the ability of a compound or composition of the invention to prevent a disease identified herein in patients diagnosed as having the disease or who are at risk of developing such disease. The term also encompasses preventing further progression of the disease in patients who are already suffering from or have symptoms of such disease.

The term "treating" refers to:

(i) preventing a disease, disorder, or condition from occurring in an animal or human that may be predisposed to the disease, disorder and/or condition, but has not yet been diagnosed as having it;

(ii) inhibiting the disease, disorder, or condition, i.e., arresting its development; and (iii) relieving the disease, disorder, or condition, i.e., causing regression of the disease, disorder, and/or condition.

The term "treatment" refers to the act of treating as "treating" is defined immediately above.

One of the compounds of the invention is (3R,5S)-3,5-bis(tert-butoxycarbonylamino)-piperidine, which is a meso compound that is identical to (3S,5R)-3,5-bis(tert-butoxycarbonylamino)-piperidine. This compound can also be termed cis-3,5-bis(tert-butoxycarbonylamino)-piperidine. For purposes of this application, all these terms are understood to refer to the same compound.

The 3,5-bis(tert-butoxycarbonylamino)-piperidine compound can also exist in the trans configuration. The trans compound, and derivatives thereof, are also within the scope of the invention.

The compounds of the invention may also exhibit the phenomenon of tautomerism. While Formula I (including Formulas Ia through Iu and $M^1$, $M^2$, and X substituents) cannot expressly depict all possible tautomeric forms, it is to be understood that Formula I is intended to represent any tautomeric form of the depicted compound and are not to be limited merely to a specific compound form depicted by the formula drawings.

The present invention also includes isotopically-labelled compounds, which are identical to those recited in Formula I but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, $^{36}Cl$, $^{125}I$, and $^{131}I$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of Formula I of this invention and prodrugs thereof can generally be prepared by carrying out the procedures disclosed in the Schemes and/or in the Examples and Preparations below, by substituting a readily available isotopically labelled reagent for a non-isotopically labelled reagent.

The inventive compounds of Formula I may exist as single stereoisomers (i.e., essentially free of other stereoisomers), racemates, and/or mixtures of enantiomers and/or diastereomers. All such single stereoisomers, racemates and mixtures thereof are intended to be within the scope of the present invention. Preferably, the inventive compounds that are optically active are used in optically pure form. The structures as depicted in the application include both cis and trans configurations, unless a specific configuration is depicted. The compounds of the invention may also exist as particular configurations. Preferably, the compounds of the invention exist in a cis configuration.

As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure. Preferably, the compounds of the present invention are used in a form that is at least 90% optically pure, that is, a form that contains at least 90% of a single isomer (80% enantiomeric excess ("e.e.") or diastereomeric excess ("d.e.")), more preferably at least 95% (90% e.e. or d.e.), even more preferably at least 97.5% (95% e.e. or d.e.), and most preferably at least 99% (98% e.e. or d.e.).

Additionally, Formula I are intended to cover solvated as well as unsolvated forms of the identified structures. For example, Formula I includes compounds of the indicated structure in both hydrated and non-hydrated forms. Other examples of solvates include the structures in combination with isopropanol, ethanol, methanol, DMSO, ethyl acetate, acetic acid, or ethanolamine.

In addition to compounds of Formula I, the invention includes pharmaceutically acceptable prodrugs, pharmaceutically active metabolites, and pharmaceutically acceptable salts of such compounds and metabolites.

The compounds of the Formula I may be administered in the form of a pro-drug which is broken down in the human or animal body to give a compound of the Formula I. A prodrug may be used to alter or improve the physical and/or pharmacokinetic profile of the parent compound and can be formed when the parent compound contains a suitable group or substituent which can be derivatised to form a prodrug. Examples of pro-drugs include in-vivo hydrolysable esters of a compound of the Formula I or a pharmaceutically-acceptable salt thereof. Various forms of prodrugs are known in the art, for examples see: a) Design of Prodrugs, edited by H. Bundgaard, (Elsevier, 1985) and Methods in Enzymology, Vol. 42, p. 309–396, edited by K. Widder, et al. (Academic Press, 1985); b) A Textbook of Drug Design and Development, edited by Krogsgaard-Larsen and H. Bundgaard, Chapter 5 "Design and Application of Prodrugs", by H. Bundgaard p. 113–191 (1991); c) H. Bundgaard, Advanced Drug Delivery Reviews, 8, 1–38 (1992); d) H. Bundgaard, et al., Journal of Pharmaceutical Sciences, 77, 285 (1988); and e) N. Kakeya, et al., Chem Pharm Bull, 32, 692 (1984).

An in vivo hydrolysable ester of a compound of the Formula I or a pharmaceutically-acceptable salt thereof containing carboxy or hydroxy group is, for example, a pharmaceutically-acceptable ester which is hydrolyzed in the human or animal body to produce the parent acid or alcohol. Suitable pharmaceutically-acceptable esters for carboxy include $(C_1-C_6)$alkoxymethyl esters for example methoxymethyl, $(C_1-C_6)$alkanoyloxymethyl esters for example pivaloyloxymethyl, phthalidyl esters, $(C_3-C_6)$cycloalkoxycarbonyloxy$(C_1-C_6)$alkyl esters for example 1-cyclohexylcarbonyloxyethyl; 1,3-dioxolan-2-onylmethyl esters for example 5-methyl-1,3-dioxolan-2-ylmethyl; and $(C_1-C_6)$alkoxycarbonyloxyethyl esters for example 1-methoxycarbonyloxyethyl and may be formed at any carboxy group in the compounds of this invention.

"A pharmaceutically active metabolite" is intended to mean a pharmacologically active product produced through metabolism in the body of a specified compound or salt thereof. After entry into the body, most drugs are substrates for chemical reactions that may change their physical properties and biologic effects. These metabolic conversions, which usually affect the polarity of the Formula I compounds, alter the way in which drugs are distributed in and excreted from the body. However, in some cases, metabolism of a drug is required for therapeutic effect. For example, anticancer drugs of the anti-metabolite class must be converted to their active forms after they have been transported into a cancer cell.

Since most drugs undergo metabolic transformation of some kind, the biochemical reactions that play a role in drug metabolism may be numerous and diverse. The main site of drug metabolism is the liver, although other tissues may also participate.

A feature characteristic of many of these transformations is that the metabolic products, or "metabolites," are more polar than the parent drugs, although a polar drug does sometime yield a less polar product. Substances with high lipid/water partition coefficients, which pass easily across membranes, also diffuse back readily from tubular urine through the renal tubular cells into the plasma. Thus, such substances tend to have a low renal clearance and a long persistence in the body. If a drug is metabolized to a more polar compound, one with a lower partition coefficient, its tubular reabsorption will be greatly reduced. Moreover, the specific secretory mechanisms for anions and cations in the proximal renal tubules and in the parenchymal liver cells operate upon highly polar substances.

As a specific example, phenacetin (acetophenetidin) and acetanilide are both mild analgesic and antipyretic agents, but are transformed within the body to a more polar and more effective metabolite, p-hydroxyacetanilid (acetaminophen), which is widely used today. When a dose of acetanilide is given to a person, the levels of successive metabolites reach a peak and then decay in the plasma sequentially. During the first hour, acetanilide is the principal plasma component. In the second hour, as the acetanilide level falls, the metabolite acetaminophen concentration reaches a peak. Finally, after a few hours, the principal plasma component is a further metabolite that is inert and can be excreted from the body. Thus, the plasma concentrations of one or more metabolites, as well as the drug itself, can be pharmacologically important.

"A pharmaceutically acceptable salt" is intended to mean a salt that retains the biological effectiveness of the free acids and bases of the specified compound and that is not biologically or otherwise undesirable. A compound of the invention may possess a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of the compounds of the present invention with a mineral or organic acid or an inorganic base, such as salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds and salts may exist in different crystal or polymorphic forms, all of which are intended to be within the scope of the present invention and specified formulas.

A further aspect of the present invention is directed to a pharmaceutical composition comprising a pharmaceutically acceptable carrier or a diluent and a therapeutically effective amount of a Formula I compound, a pharmaceutically acceptable salt, hydrate, ester, solvate, prodrug, metabolite, or stereoisomer.

Formula I compounds are useful in the manufacture of pharmaceutical formulations comprising an effective amount thereof in conjunction with or as an admixture with excipients or carriers suitable for either enteral or parenteral application. As such, formulations of the present invention suitable for oral administration may be in the form of discrete units such as capsules, cachets, tablets, troche or lozenges, each containing a predetermined amount of the active ingredient; in the form of a powder or granules; in the form of a solution or a suspension in an aqueous liquid or nonaqueous liquid; or in the form of an oil-in-water emulsion or a water-in-oil emulsion. The active ingredient may also be in the form of a bolus, electuary, or paste.

The composition will usually be formulated into a unit dosage form, such as a tablet, capsule, aqueous suspension or solution. Such formulations typically include a solid, semisolid, or liquid carrier. Exemplary carriers include lactose, dextrose, sucrose, sorbitol, mannitol, starches, gum acacia, calcium phosphate, mineral oil, cocoa butter, oil of theobroma, alginates, tragacanth, gelatin, syrup, methyl cellulose, polyoxyethylene sorbitan monolaurate, methyl hydroxybenzoate, propyl hydroxybenzoate, talc, magnesium stearate, and the like.

Particularly preferred formulations include tablets and gelatin capsules comprising the active ingredient together with (a) diluents, such as lactose, dextrose, sucrose, mannitol, sorbitol, cellulose, dried corn starch, and glycine; and/or (b) lubricants, such as silica, talcum, stearic acid, its magnesium or calcium salt, and polyethylene glycol.

Tablets may also contain binders, such as magnesium aluminum silicate, starch paste, gelatin, tragacanth, methylcellulose, sodium carbosymethylcellulose and polyvinylpyrrolidone; carriers, such as lactose and corn starch; disintegrants, such as starches, agar, alginic acid or its sodium salt, and effervescent mixtures; and/or absorbents, colorants, flavors, and sweeteners. The compositions of the invention may be sterilized and/or contain adjuvants, such as preserving, stabilizing, swelling or emulsifying agents, solution promoters, salts for regulating osmotic pressure, and/or buffers. In addition, the composition may also contain other therapeutically valuable substances. Aqueous suspensions may contain emulsifying and suspending agents combined with the active ingredient. All oral dosage forms may further contain sweetening and/or flavoring and/or coloring agents.

These compositions are prepared according to conventional mixing, granulating, or coating methods, respectively, and contain about 0.1 to 75% of the active ingredient, preferably about 1 to 50% of the same. A tablet may be made by compressing or molding the active ingredient optionally with one or more accessory ingredients. Compressed tablets may be prepared by compressing, in a suitable machine, the active ingredient in a free-flowing form such as a powder or granules, optionally mixed with a binder, lubricant, inert diluent, surface active, or dispersing agent. Molded tablets may be made by molding, in a suitable machine, a mixture of the powdered active ingredient and a suitable carrier moistened with an inert liquid diluent.

When administered parenterally, the composition will normally be in a unit dosage, sterile injectable form (aqueous isotonic solution, suspension, or emulsion) with a pharmaceutically acceptable carrier. Such carriers are preferably non-toxic, parenterally-acceptable and contain non-therapeutic diluents or solvents. Examples of such carriers include water; aqueous solutions, such as saline (isotonic sodium chloride solution), Ringer's solution, dextrose solution, and Hanks' solution; and nonaqueous carriers, such as 1,3-butanediol, fixed oils (e.g., corn, cottonseed, peanut, sesame oil, and synthetic mono- or di-glyceride), ethyl oleate, and isopropyl myristate.

Oleaginous suspensions can be formulated according to techniques known in the art using suitable dispersing or wetting agents and suspending agents. Among the acceptable solvents or suspending mediums are sterile fixed oils. For this purpose, any bland fixed oil may be used. Fatty acids, such as oleic acid and its glyceride derivatives, including olive oil and castor oil, especially in their polyoxyethylated forms, are also useful in the preparation of injectables. These oil solutions or suspensions may also contain long-chain alcohol diluents or dispersants.

Sterile saline is a preferred carrier, and the compounds are often sufficiently water soluble to be made up as a solution for all foreseeable needs. The carrier may contain minor amounts of additives, such as substances that enhance solubility, isotonicity, and chemical stability, e.g., anti-oxidants, buffers and preservatives.

When administered rectally, the composition will usually be formulated into a unit dosage form such as a suppository or cachet. These compositions can be prepared by mixing the compound with suitable non-irritating excipients that are solid at room temperature, but liquid at rectal temperature, such that they will melt in the rectum to release the compound. Common excipients include cocoa butter, beeswax and polyethylene glycols or other fatty emulsions or suspensions.

Formulations suitable for nasal or buccal administration (such as self-propelling powder dispensing formulations), may comprise about 0.1% to about 5% w/w of the active ingredient or, for example, about 1% w/w of the same. In addition, some formulations can be compounded into a sublingual troche or lozenge.

Moreover, the compounds may be administered topically, especially when the conditions addressed for treatment involve areas or organs readily accessible by topical application, including disorders of the eye, the skin or the lower intestinal tract.

For topical application to the eye, or ophthalmic use, the compounds can be formulated as micronized suspensions in isotonic, pH-adjusted sterile saline or, preferably, as a solution in isotonic, pH-adjusted sterile saline, either with or without a preservative such as benzylalkonium chloride. Alternatively, the compounds may be formulated into ointments, such as petrolatum.

For topical application to the skin, the compounds can be formulated into suitable ointments containing the compounds suspended or dissolved, for example, mixtures with one or more of the following: mineral oil, liquid petrolatum, white petrolatum, propylene glycol, polyoxyethylene compound, polyoxypropylene compound, emulsifying wax and water. Alternatively, the compounds can be formulated into suitable lotions or creams containing the active compound suspended or dissolved in, for example, a mixture of one or more of the following: mineral oil, sorbitan monostearate, polysorbate 60, cetyl ester wax, cetearyl alcohol, 2-octyldodecanol, benzyl alcohol and water.

Topical application to the lower intestinal tract can be effected in rectal suppository formulations (see above) or in suitable enema formulations.

The formulations may conveniently be presented in unit dosage form and may be prepared by any of the methods well known in the art of pharmacy. All methods include the step of bringing the active ingredient into association with the carrier, which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

The pharmaceutical composition of the present invention is used in amount that are therapeutically effective and the amounts used may depend upon the desire release profile, the concentration of the pharmaceutical composition required for the sensitizing effect, and the length of time that the pharmaceutical composition has to be released for treatment.

Formula I compounds of the invention are preferably administered as a capsule or tablet containing a single or divided dose of the compound, or as a sterile solution, suspension, or emulsion, for parenteral administration in a single or divided dose.

The compounds of the invention are used in the composition in amounts that are therapeutically effective. While the effective amount of the Formula I compounds will depend upon the particular compound being used, amounts of these compounds varying from about 1% to about 65% have been easily incorporated into liquid or solid carrier delivery systems.

For medical use, the amount required of a Formula I compound to achieve a therapeutic effect will vary according to the particular compound administered, the route of administration, the mammal under treatment, and the particular disorder in disease concerned. A suitable systemic dose of a Formula I compound for a mammal suffering from, or likely to suffer from, any condition as described herein is typically in the range of about 0.1 to about 100 mg of base per kilogram of body weight. It is understood that the ordinarily skilled physician or veterinarian will readily be able to determine and prescribe the amount of the compound effective for the desired prophylactic or therapeutic treatment.

In so proceeding, the physician or veterinarian may employ an intravenous bolus followed by an intravenous infusion and repeated administrations, as considered appropriate. In the methods of the present invention, the compounds may be administered, for example, orally, parentally, in inhalation spray, topically, rectally, nasally, buccally, sublingually, vaginally, intraventricularly, or via an implanted reservoir in dosage formulations containing conventional non-toxic pharmaceutically-acceptable carriers, adjuvants and vehicles.

Parenteral includes, but is not limited to, the following examples of administration: intravenous, subcutaneous, intramuscular, intraspinal, intraosseous, intraperitoneal, intrathecal, intraventricular, intrasternal or intracranial injection and infusion techniques, such as by subdural pump. Invasive techniques are preferred, particularly direct administration to damaged neuronal tissue. While it is possible for the Formula I compounds to be administered alone, it is preferable to provide it as part of a pharmaceutical formulation.

To be effective therapeutically as central nervous system targets, the compounds used in the methods of the present invention should readily penetrate the blood-brain barrier when peripherally administered. Compounds that cannot penetrate the blood-brain barrier, however, can still be effectively administered by an intraventricular route.

The compounds used in the methods of the present invention may be administered by a single dose, multiple discrete doses or continuous infusion. Since the compounds are small, easily diffusible and relatively stable, they are well suited to continuous infusion. Pump means, particularly subcutaneous or subdural pump means, are preferred for continuous infusion.

For the methods of the present invention, any effective administration regimen regulating the timing and sequence of doses may be used. Doses of the compounds preferably include pharmaceutical dosage units comprising an efficacious quantity of active compound. By an efficacious quantity is meant a quantity sufficient to provide immune enhancing response and/or derive the desired beneficial effects through administration of one or more of the pharmaceutical dosage units.

An exemplary daily dosage unit for a vertebrate host comprises an amount of from about 0.001 mg/kg to about 50 mg/kg. Typically, dosage levels on the order of about 0.1 mg to about 10,000 mg of the active ingredient compound are useful in the treatment of the above conditions, with preferred levels being about 0.5 mg to about 2,000 mg. The specific dose level for any particular patient will vary depending upon a variety of factors, including the activity of the specific compound employed; the age, body weight, general health, sex, and diet of the patient; the time of administration; the rate of excretion, any combination of the compound with other drugs; the severity of the particular disease being treated; and the form and route of administration. Typically, in vitro dosage-effect results provide useful guidance on the proper doses for patient administration. Studies in animal models can also be helpful. The considerations for determining the proper dose levels are well known in the art.

The compounds and compositions can be co-administered with one or more therapeutic agents either (i) together in a single formation, or (ii) separately in individual formulations designed for optimal release rates of their respective active agent. Each formulation may contain from about 0.01% to about 99.99% by weight, preferably from about 3.5% to about 60% by weight, of the compound of the invention, as well as one or more pharmaceutical excipients, such as wetting, emulsifying and pH buffering agents. When the compounds used in the methods of the invention are administered in combination with one or more other therapeutic agents, specific dose levels for those agents will depend upon considerations such as those identified above for compositions and methods of the invention in general.

For the methods of the present invention, any administration regimen regulating the timing and sequence of delivery of the compound can be used and repeated as necessary to effect treatment. Such regimen may include pretreatment and/or co-administration with additional therapeutic agents.

The inventive agents may be prepared using the reaction routes and synthesis schemes as described below, employing the general techniques known in the art using starting materials that are readily available. A particularly useful compilation of synthetic methods which may be applicable to the synthesis of compounds of the present invention may be found in Comprehensive Organic Transformations, Larock, R. C., VCH: New York, 1989. The synthesis of non-exemplified compounds according to the invention may be successfully performed by modifications apparent to those skilled in the art, e.g., by appropriately protecting interfering groups, by changing to other suitable reagents known in the art, or by making routine modifications of reaction conditions. A compendium of protecting groups which may be useful, together with reaction conditions for their introduction and removal may be found in Protective Groups in Organic Synthesis, Second Edition; Greene, T.

W.; Wuts, P. G. M., Wiley: New York 1991. Alternatively, other reactions disclosed herein or generally known in the art will be recognized as having applicability for preparing other compounds of the invention.

4.2 Preparation of Compounds

In the synthetic schemes described below, unless otherwise indicated all temperatures are set forth in degrees Celsius. Reagents were purchased from commercial suppliers such as Aldrich Chemical Company or Lancaster Synthesis Ltd. and were used without further purification unless otherwise indicated. Tetrahydrofuran (THF) and N,N-dimethylformamide (DMF) were purchased from Aldrich in Sure Seal bottles and used as received. THF, $Et_2O$, $CH_2Cl_2$, MeCN, MeOH, PhMe, EtOAc, diisopropylethylamine, pyridine and $Et_3N$ were used as received.

The reactions set forth below were done in anhydrous solvents generally either in flasks or vials. Glassware was oven dried and/or heat dried and vials (8 mL and 40 mL) were used as received. The reactions were monitored by thin layer chromatography (TLC) and/or LC-MS and terminated as judged by the consumption of starting material. Analytical TLC was performed on silica gel 60 $F_{254}$ 0.25 mm plates (Merck), and visualized with UV light (254 nm). Preparative TLC was performed on Merck 1.0 mm silica gel 60 $F_{254}$ plates and visualized with UV light (254 nm).

Work-ups were typically done by evaporation of the solvents under reduced pressure on a rotary evaporator or in a Savant SpeedVac followed by liquid-liquid extraction between $CHCl_3$ or EtOAc and $H_2O$ layers. The product solution was then concentrated in vacuo. Column chromatography was completed under positive pressure using 230–400 mesh silica gel. Hydrogenation was done at the pressure indicated in the examples.

Both $^1H$-NMR and $^{13}C$-NMR spectra were recorded on a Varian Mercury-VX400 instrument operating at 400 MHz. NMR spectra were reported in ppm using reference standard such as $CDCl_3$ (7.27 ppm and 77.00 ppm), $CD_3OD$ (3.4 and 4.8 ppm and 49.3 ppm), DMSO-$d_6$, or internally tetramethylsilane (0.0 ppm) when appropriate. Other NMR solvents were used as needed. When peak multiplicities are reported, the following abbreviations are used: s (singlet), d (doublet), t (triplet), q (quartet), m (multiplet), br (broadened), dd (doublet of doublets), dt (doublet of triplets). Coupling constants, when given, are reported in Hertz (Hz).

Mass spectra reported are ES or APCI LC/MS conducted by the Analytical Chemistry Department of Anadys Pharmaceuticals, Inc. Elemental analyses were conducted by the Atlantic Microlab, Inc. in Norcross, Ga. or by Numega, Inc., in San Diego, Calif.

The described synthetic pathways and experimental procedures utilize many common chemical abbreviations, THF (tetrahydrofuran), DMF (N,N-dimethylformamide), EtOAc (ethyl acetate), DMSO (di-methyl sulfoxide), DMAP (4-dimethylaminopyridine), DBU (1,8-diazacyclo[5.4.0]undec-7-ene), TFA (trifluoroacetic acid), $^iPr_2NEt$ (diisopropylethylamine), HOBt (1-hydroxybenzotriazole hydrate), EDCI (1-[3-(Dimethylamino)propyl]-3-ethylcarbodiimide hydrochloride), NMP (N-methylpyrrolidinone), DME (ethylene glycol dimethyl ether), DMA (N,N-dimethylacetamide), HMPA (hexamethylphosphoramide), ELSD (evaporative light scattering detector), ESI (electrospray ionization), APCI (atmospheric pressure chemical ionization), $Pd_2(dba)_3$ (tris(dibenzylideneacetone)dipalladium(0)), Xantphos (9,9-dimethyl-4,5-bis(diphenylphosphino)xanthene), BINAP (2,2'-bis(diphenylphosphino)-1,1'-binaphthyl), Boc (N-tert-butoxycarbonyl), DBN (1,5-diazabicyclo[4,3,0]non-5-ene), DABCO (1,4-diazabicyclo[2,2,2]octane), ACN (acetonitrile) and the like.

4.3 General Method of Synthesis of Formula Ia Compounds

Scheme 1 describes a general synthetic procedure for preparing compound (4) and (7) of Formula Ia.

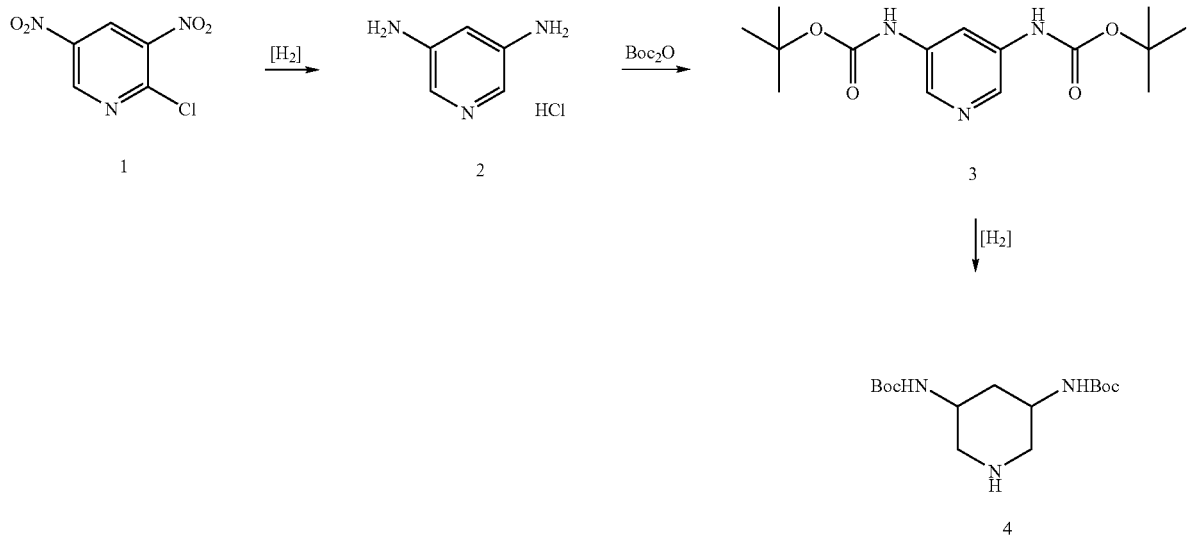

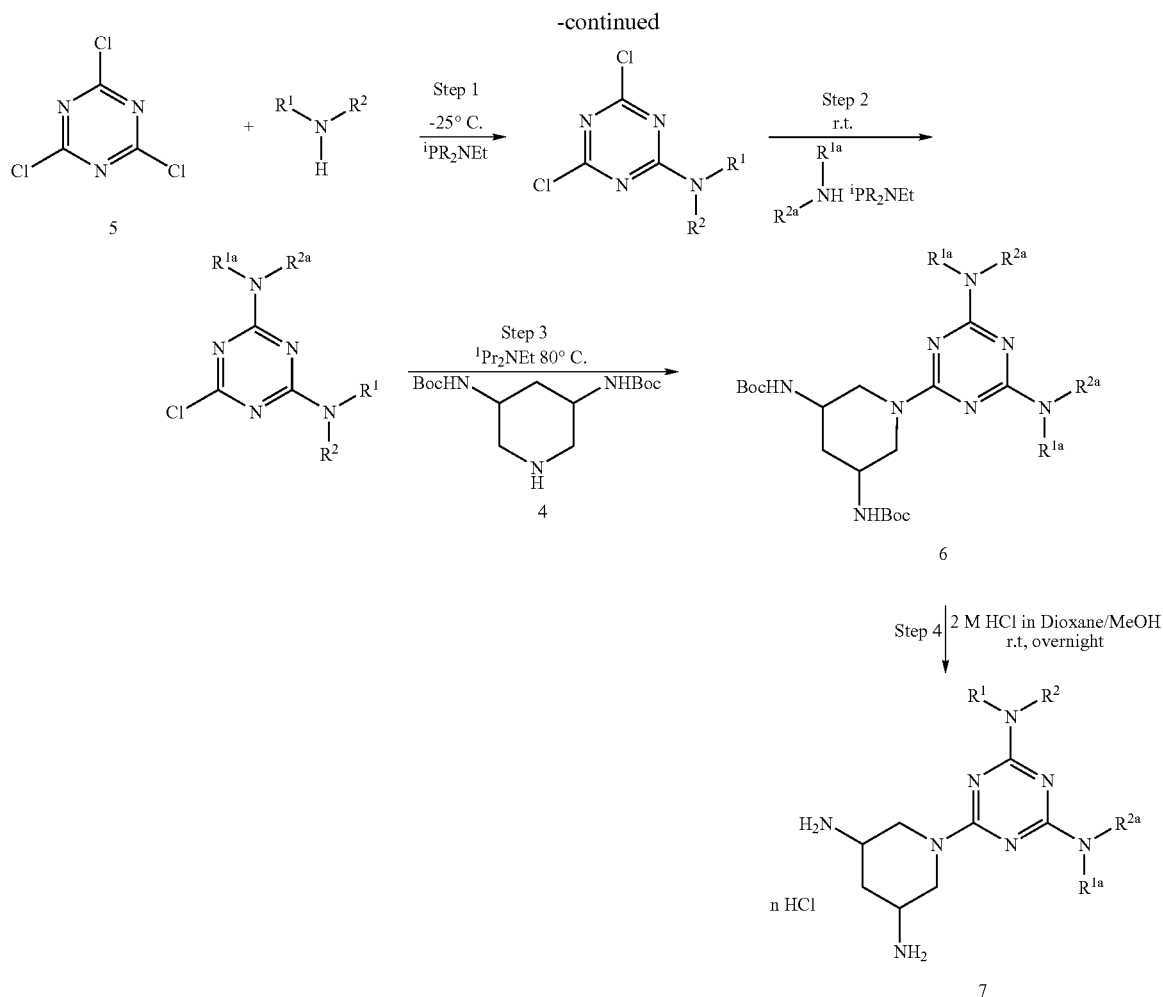

$R^{1a}$ and $R^{2a}$ are independently defined as $R^1$ and $R^2$.

In this general method of producing compounds of Formula Ia, the 2-chloro-3,5-dinitropyridine 1 was hydrogenated to 3,5-diaminopyridine 2, followed by protecting the amino-groups as the di-BOC derivative 3. This was subsequently hydrogenated to the piperidine derivative 4.

Cyanuric chloride (5) was treated sequentially by three different amines at increasing temperatures. Preferably the less reactive amines, such as aromatic or heteroaromatic amines were used first to displace the most reactive Cl, followed by reactive amines to displace the second Cl and finally (3R,5S)-3,5-bis-(tert-butoxycarbonylamino)-piperidine (4) was used to displace the third Cl to give compound 6. Deprotection of the BOC of compound 6 with HCl in dioxane furnished the targets of compound 7.

This methodology is useful for the production of various derivatives represented by Formula Ia. Other variations of this methodology would be apparent to those skilled in the art. This methodology and variants thereof are collectively termed triazine chemistry.

4.3.1 Synthesis of 3,5-diaminopyridine hydrochloride (2)

2-chloro-3,5-dinitro-pyridine (27.36 g, 1) was divided into two equal portions and added into two 2 L round bottomed flasks. Methanol (700 mL) was then added to each flask. Nitrogen gas was bubbled through the solution while stirring and 7.15 g of 10% palladium on carbon was divided into two equal portions and added to each flask portion-wise under nitrogen. The solutions were cooled down under $N_2$ to 0° C. using an ice-water bath. The $N_2$ inlets were then replaced by hydrogen balloons. After evacuation, the solutions were exposed to $H_2$ gas at slightly positive pressure. This vacuum-hydrogen exchange was done at least 5 times. The reactions were stirred under slight positive pressure of $H_2$ for 2 days. Then the solutions were filtered with suction through Celite to remove the catalyst. The filtrate was concentrated down in vacuo. The crude product (24.27 g, >100% crude yield) was obtained as a dark green solid that was immediately used directly in the next step without further purification. The identity of the product (2) was confirmed by LC-MS.

4.3.2 Synthesis of di-BOC-protected 3,5-diamino-pyridine (3)

The crude 3,5-diaminopyridine hydrochloride (19.56 g, 0.1344 mol, 2) was dissolved in 150 mL of methanol in a 2 L reaction vessel. Nitrogen was used to purge the flask. The reaction solution was then cooled to 0° C. A solution of 58.67 g (0.2688 mol) of di-tert-butyldicarbonate in 85 mL of methanol was added dropwise. 18.9 mL of triethylamine (0.1344 mol) was diluted with 20 ml of methanol and added dropwise. Then another 58.67 g of di-tert-butyldicarbonate dissolved in 85 mL of methanol was added dropwise. After that another 29.34 g of di-tert-butyldicarbonate, dissolved in 40 mL of methanol was added dropwise.

The reaction mixture was allowed to warm up to room temperature (r.t.) and was stirred overnight. TLC analysis showed that no starting material and very little mono-BOC-protected diaminopyridine remained. The methanol was removed in vacuo. The resulting solid was dissolved in ethyl acetate and was extracted with brine. The aqueous layer was extracted three times with ethyl acetate. The organic layers were combined and washed with brine. The organic layer was dried with $MgSO_4$ and passed through a layer of silica gel (135 cm×3 cm) constructed in a fritted funnel. The silica was thoroughly washed with ethyl acetate. The ethyl acetate solution was concentrated in vacuo and the resulting solid was dissolved in a minimal amount of refluxing methylene chloride. It was allowed to cool down to room temperature naturally.

The crystallized solid was filtered with suction and washed with a very small amount of $CH_2Cl_2$ and hexane and was dried in a vacuum oven at 50–60° C. The first crop of crystals weighed 18.12 g. Using the same method a second crop of crystals was obtained, which weighed 5.02 g, a third crop of the crystals weighed 3.85 g and the fourth crop of crystals (from methanol) weighed 3.59 g. Total 30.58 g of the desired product (3) was obtained (73.6% isolated yield). $^1$H NMR (CDCl$_3$): δ 8.23 ppm (s, 2H), 8.18 (s, 2H), 6.68 (s, 2H, NH), 1.54 (s, 18H, BOC).

4.3.3 Synthesis of (3R,5S)-3,5-bis-(tert-butoxycarbonylamino)-piperidine (4)

The 3,5-di-BOC diamino-pyridine (3) (10 g, 32.34 mmol) was dissolved in 350 mL of methanol. Glacial acetic acid (1.85 mL, 32.34 mmol) was added, followed by 5% Rh—C (wet, 6.66 g, 5 mol %), purged with $N_2$ and transferred to a high-pressure hydrogenator. The vessel was flushed with $H_2$ twice at 500 psi of $H_2$ gas, the $H_2$ pressure was increased to 1000 psi and heated to 110° C. Then the $H_2$ pressure was increased to 2200 psi and the mixture was stirred for 28 hours. The reaction mixture was cooled to room temperature.

The catalyst was filtered off through Celite with suction. The filtrate was then concentrated in vacuo to remove methanol. $Na_2CO_3$ (3.43 g, 32.34 mmol) in 100 mL of $H_2O$ was added followed by 100 mL of EtOAc. After stirring for 90 minutes, a thick white precipitate formed. The mixture was then suction filtered and the solid was washed with EtOAc, dried in a vacuum oven at 60° C. overnight. The desired product (3R,5S)-3,5-bis-(tert-butoxycarbonylamino)-piperidine (4) (5.6 g) was obtained as an off-white solid that was confirmed by LC-MS and $^1$H NMR. MS m/e 316 [M+1] (exact MS: 315). $^1$H NMR (DMSO-d$_6$): δ 6.71 (br, 2H, NH), 3.16–3.30 (br, 2H), 2.78–2.81 (m, 2H), 1.99 (t, 2H, J=11.2 Hz), 1.855 (br, 1H), 1.59 (s, 1H), 1.09 (q, 1H, J=11.6 Hz). The above process produces the cis isomer in high purity.

This compound [(3R,5S)-3,5-bis-(tert-butoxycarbonylamino)-piperidine] is identical to (3S,5R)-3,5-bis-(tert-butoxycarbonylamino)-piperidine.

The trans-3,5-bis-(tert-butoxycarbonylamino)-piperidine can be made in a way similar to that described in WO 00/056729 (Published Sept. 28, 2000). In the WO 00/056729 patent application, the synthesis of a mixture of the cis- and trans-3,5-bis(ethoxycarbonylamino)piperidine was described with a trans/cis ratio of 80/20.

3.3.4 EXAMPLE 1

Synthesis of Formula Ia Compound 8

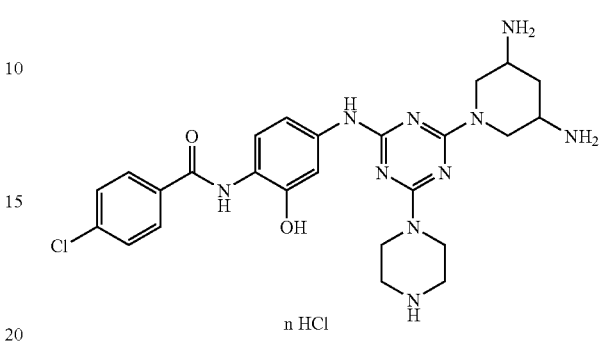

Cyanuric chloride (400 μL of 0.25 M, 5) in anhydrous THF was cooled to −25° C. for about 0.5 hours. N-(4-Amino-2-hydroxy-phenyl)-4-chloro-benzamide (400 μL of 0.25 M) in anhydrous THF containing 100 μmol of $^i$Pr$_2$NEt was then injected into the above cooled cyanuric chloride solution. The reaction mixture was vortexed and immediately put back in a freezer at −25° C. overnight.

The reaction mixture was then warmed up to room temperature with shaking. A solution of 4-N-BOC protected piperazine (400 μL of 0.25 M) in anhydrous THF containing 100 μmol of iPr$_2$NEt was then added into the above solution. The resulting reaction mixture was shaken at room temperature for 24 hours. A slurry of (3R,5S)-3,5-bis-(tert-butoxycarbonylamino)-piperidine (4) (100 μmol) in THF (0.125 M) was added, followed by 100 μL of 1.0 M $^i$Pr$_2$NEt in THF. The reaction mixture was shaken at 80° C. for 48 h. Then the reaction mixture was dried under vacuum with slight heating. The product was first pre-purified by liquid-liquid extraction using CHCl$_3$ and H$_2$O. The organic layer was washed with H$_2$O three times and was then analyzed by LC-MS (after further dilution by CH$_3$CN) to confirm the identity of the desired product. The organic layer was then concentrated under vacuum. The crude product was further purified by reverse-phase HPLC purification using a mixture of ACN and water to give a (3R,5S)-3,5-bis-(tert-butoxycarbonylamino)-piperidine-substituted-3-hydroxy-4-(4'-chlorobenzeneamide)aniline substituted triazine intermediate.

The resulting above purified tri-BOC-intermediate was then dissolved in MeOH (2 mL) and treated with 2 mL of 4.0 M HCl in 1,4-dioxane. After shaking at room temperature overnight, the solvent and excess HCl was evaporated under vacuum with heating (40–60° C.). 2 mL of MeOH was added to dissolve the crude product and the resulting solution was concentrated under vacuum to small volume. The solid was then filtered under vacuum and washed with small amount of MeOH, dried in vacuo for 2 hours. LC-MS, NMR and elemental analysis were used to confirm the identity of the desired product (8) as an HCl salt. LC-MS (exact MS: 538.23): MS m/e 539.3 [M+1]; $^1$H NMR (DMSO-d$_6$): δ 9.80 (br, 1H), 9.47 (s, 1H), 9.38 (br, 2H, CNH$_2$$^+$), 9.21 (s, 1H), 8.59 (br, 6H, 2NH$_3$$^+$), 7.95 (d, 2H, J=8.4 Hz), 7.56 (d, 2H J=8.4 Hz), 7.5 (d, 1H), 7.41 (s, 1H), 7.06 (d, 1H), 5.05 (br, 2H), 4.0 (br, 4H), 3.12 ((br, 6H), 2.78 (m, 3H), 1.76 (q, 1H).

4.3.5 EXAMPLE 2

Synthesis of Compound 11 of Formula Ia (Scheme 2)

In this example, a modification of the 3,5-diaminopiperidine was made on the final product instead of making the 3,5-diaminopiperadine derivative first and then attaching the triazine.

of MeOH and 2 mL of 4.0 M HCl in dioxane was then added and the mixture was shaken at room temperature overnight. The mixture was concentrated under reduced pressure and the residue was purified by reverse-phase HPLC to give 2.8 mg of final product (11) with HPLC purity of 100% by ELSD. LC-MS: m/e 481.1 [M+1]$^+$.

Each of the Formula Ia compounds shown in Table 1 were prepared in a manner similar to one of the protocols exemplified above.

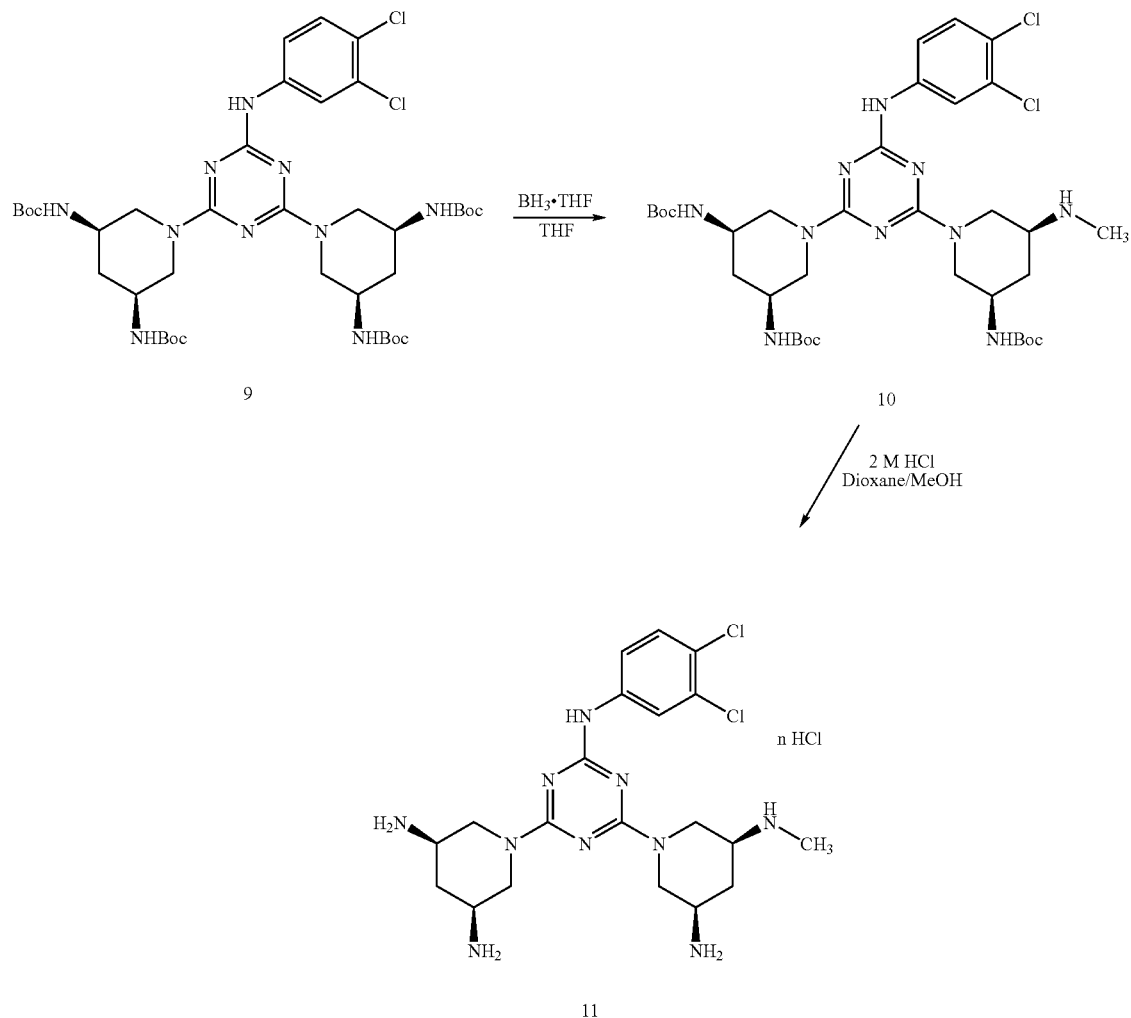

Scheme 2

Into 40 mg of compound 9 (made in the same way as compound 6 using the procedure described in Scheme 1), 2 mL of BH$_3$.THF (1.0 M) was added and the mixture was stirred at room temperature for 15 hours. The LC-MS result indicated that the reaction was incomplete. An additional amount of BH$_3$.THF (1.0 M, 1 mL) in THF was added and the mixture was shaken at room temperature overnight. LC-MS indicated no further improvement in the reaction progress. The reaction mixture was then concentrated under reduced pressure and the crude product (10) was purified by MS-triggered HPLC. Compound 10 was dissolved in 2 mL

4.4 General Method of Synthesis of Compounds of Formula Ia Having a Second 3,5-diaminopiperidine Group Scheme 3 describes a general synthetic procedure for preparing compound (10) of Formula Ia.

Scheme 3

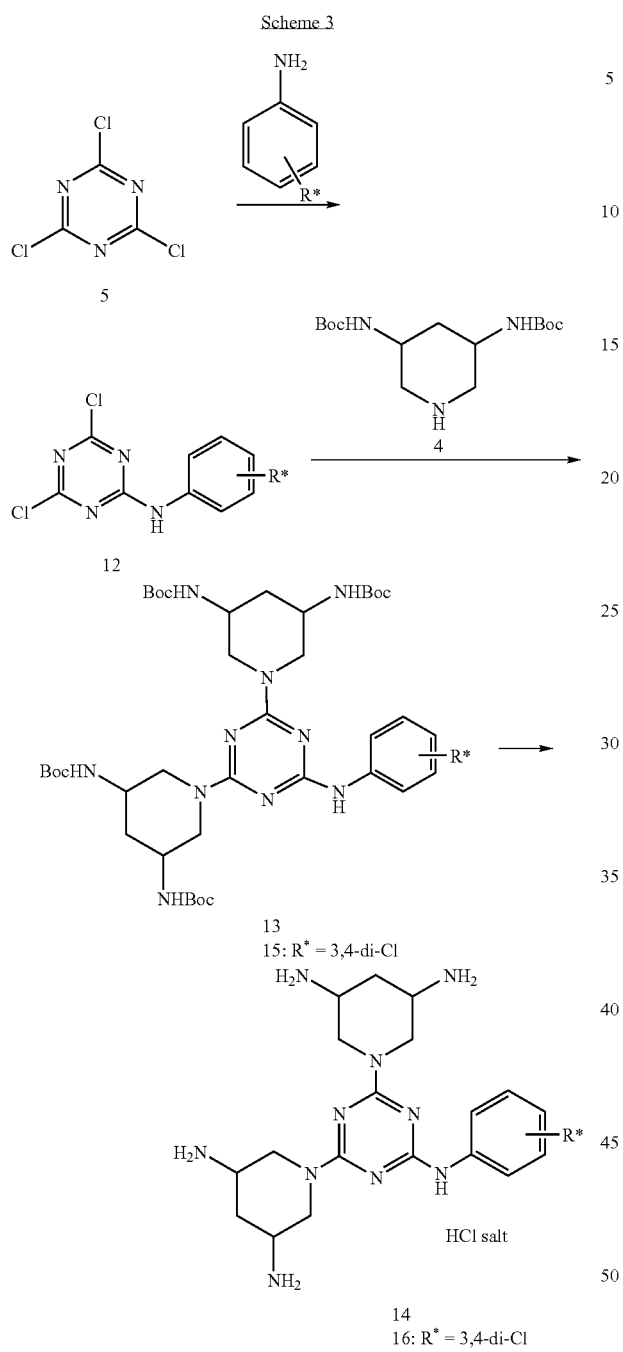

R* refers to the substituents defined above for a "substituted aryl" group.

In this general method of producing Formula Ia compounds, cyanuric chloride (5) was treated with an aromatic amine at a low temperature, followed by treatment with 4 to give the trisubstituted 1,3,5-triazine derivative 13. Deprotection (removal of the BOC protecting groups by HCl in dioxane) gave the target compound 14. In a specific example the aromatic amine was 3,4-dichloroaniline, which gave the triazine derivative 15. In the case of the 3,4-dichlorophenylamino substitution, the target compound was 16. This methodology is useful for the production of various derivatives represented by Formula Ia having a second 3,5-di- amino piperidine moiety. Other variations of this methodology would be apparent to those skilled in the art.

4.4.1 General Procedure for the Synthesis of 1,3,5-triazine Compounds Substituted with Two (3R,5S)-3,5-bis-(tert-butoxycarbonylamino)-piperidine Groups (13)

Cyanuric chloride (5) (400 μL of 0.25 M) in anhydrous THF was cooled to −25° C. for about 0.5 hours. 400 μL of 0.25 M of an aniline in anhydrous THF (or DMF) containing 100 μmol of $^i$Pr$_2$NEt was then injected into the above cooled cyanuric chloride solution. The reaction mixture was briefly vortexed and immediately put back in freezer at −25° C. overnight.

The reaction mixture was then warmed up to room temperature with shaking. A slurry of (3R,5S)-3,5-bis-(tert-butoxycarbonylamino)-piperidine (4) (100 μmol) in THF (0.125M) was added, followed by 100 μL of 1 M iPr$_2$NEt in THF. The reaction mixture was shaken at 80° C. for 48 h. The reaction mixture was dried under vacuum with slight heating. The product was first pre-purified by liquid-liquid extraction using CHCl$_3$ and H$_2$O. The organic layer was washed with H$_2$O twice and was then analyzed by LC-MS (after further dilution by CH$_3$CN) to confirm the identity of the desired product. The organic layer was then concentrated under vacuum. The crude product was further purified by flash column chromatography or HPLC to get the desired product (13).

4.4.2 General Procedure for the Synthesis of 1,3,5-triazine Compounds Substituted with Two 3,5-diaminopiperidine Groups (14)

The resulting above purified intermediate (13) was then dissolved in a mixture of MeOH and dioxane (1:1, 2 mL) and treated with 2 mL of 4 M HCl in dioxane. After shaking at room temperature overnight, the solvent and excess HCl was evaporated under vacuum with heating (40–60° C.). NMR, LC-MS, or both, were used to confirm the identity of the desired product (14).

4.4.3 EXAMPLE 3

2-(3,4-dichlorophenylamino)-4,6-bis(3,5-diaminopiperidinyl)-1,3,5-triazine (16)

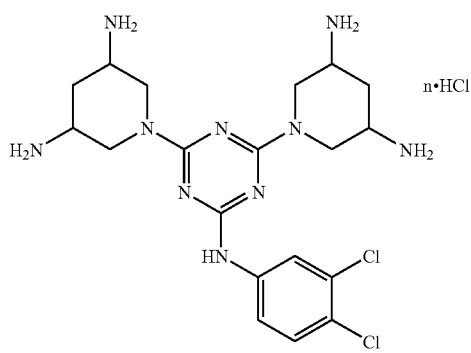

Cyanuric chloride (400 μL of 0.25 M, 5) in anhydrous THF was cooled to −25° C. for about 0.5 hours. 3,4-dichloroaniline (400 μL of 0.25 M) in anhydrous THF containing 100 μmol of $^i$Pr$_2$NEt was then injected into the above cooled cyanuric chloride solution. The reaction mixture was vortexed and immediately put back in freezer at −25° C. overnight.

The reaction mixture was then warmed up to room temperature with shaking. A slurry of 3,5-di-BOC-protected diaminopiperidine (200 µmol) in THF (0.125 M) was added, followed by 200 µL of 1.0 M $^i$Pr$_2$NEt in THF. The reaction mixture was shaken at 80° C. for 48 h. Then the reaction mixture was dried under vacuum with slight heating. The product was first pre-purified by liquid-liquid extraction using CHCl$_3$ and H$_2$O. The organic layer was washed with H$_2$O three times and was then analyzed by LC-MS (after further dilution by CH$_3$CN) to confirm the identity of the desired product. The organic layer was then concentrated under vacuum. The crude product was further purified by flash chromatography using a mixture of solvents of hexane, ethyl acetate and methylene chloride to give two (3R,5S)-3,5-bis-(tert-butoxycarbonylamino)-piperidine substituted and 3,4-di-chloroaniline substituted triazine (15). This product was confirmed by LC-MS. LC-MS (exact MS: 866.4; MW: 867.86): a single HPLC peak (both ELSD and UV-254) with MS (m/e) of 867.5 [M+1] and 869.5 [M+3] was found as expected.

The intermediate (15), purified as above, was dissolved in MeOH (2 mL) and treated with 2 mL of 4.0 M HCl in 1,4-dioxane. After shaking at room temperature overnight, the solvent and excess HCl was evaporated under vacuum with heating (40–60° C.). 2 mL of MeOH was added to dissolve the crude product and the resulting solution was concentrated under vacuum to a small volume. The solid was then filtered under vacuum and washed with small amount of MeOH, dried over oil vacuum pump for 2 hours. LC-MS, NMR and elementary analysis were used to confirm the identity of the desired product (16) as an HCl salt. LC-MS (exact MS: 466.19; MW: 467.4): MS m/e 467.1 [M+1] and 469.1 [M+3] were found; $^1$H NMR (DMSO-d$_6$): δ 9.46 (br, 1H), 8.66 and 8.61 (12H, 4 NH$_3^+$), 8.03 (br, 1H), 7.64–7.69 (m, 2H), 5.36 (d, 2H), 4.70–4.90 (m, 2H), 3.05–3.30 (m, 4H), 2.87 (t, 2H, J=12 Hz), 2.71 (t, 2H, J=11.6 Hz), 1.77 (q, 2H, J=11.6 Hz); Elemental analysis calculated (calcd) (%) for C$_{19}$H$_{28}$Cl$_2$N$_{10}$.4.5 HCl.1.8 H$_2$O: C, 34.36; H, 5.44; N, 21.10; Cl, 34.77; and O, 4.34. found C, 34.53; H, 5.59; N, 20.82; Cl, 34.90; and O, 4.28.

4.5 Synthesis of Salicylic Acid Derivative 17 of Formula Ia and Related Compounds

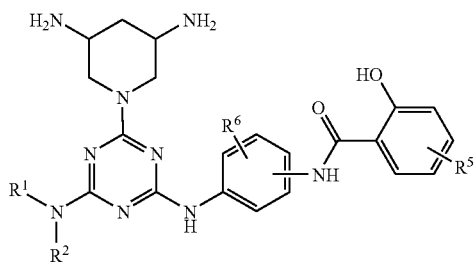

R, R$^5$ and R$^6$ refer to substituents as defined for substituted aryls.

Two methods (Method A and Method B) were used for synthesis of the compounds represented by 17.

R$^1$ and R$^2$ refer to the substituents as defined on p. 3.

4.5.1 Method A: Synthesis of Salicylic Amide Substituted Aniline Followed by Attachment of the Triazine Ring Scheme 4 describes the general procedure for preparing salicylic acid derivative of Formula Ia using method A.

Scheme 4

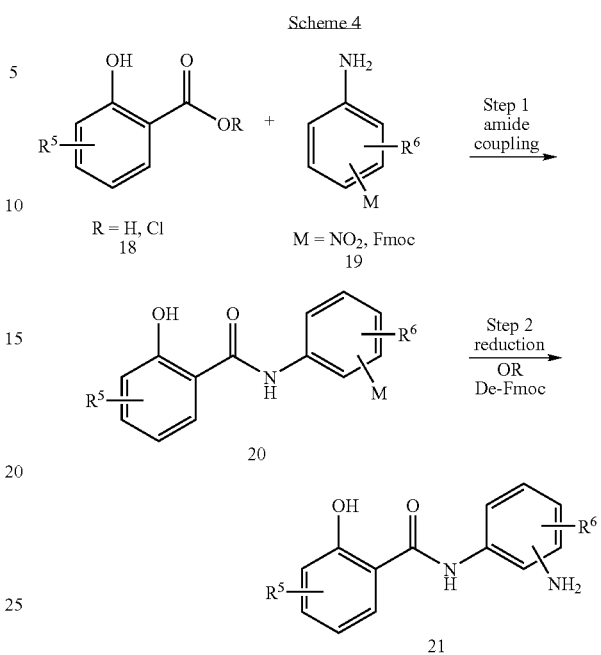

Step 3: Triazine Chemistry

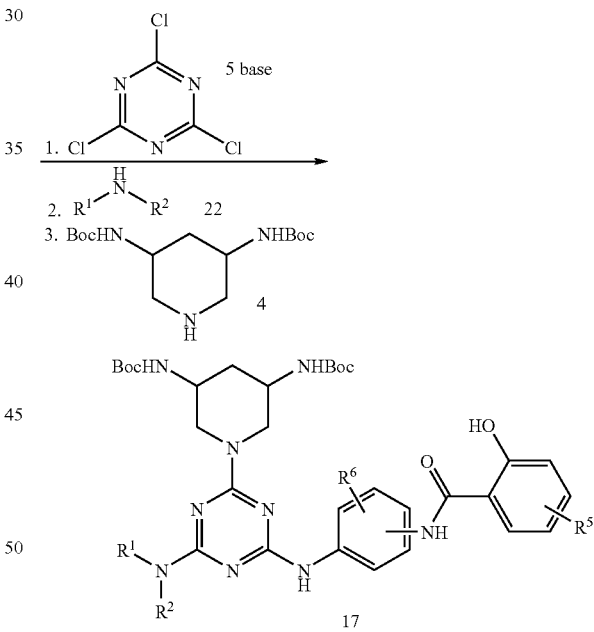

R$^1$ and R$^2$ refer to substituents as defined on p. 3.

R$^5$ and R$^6$ refer to substituents as defined for substituted aryls.

In this general method, salicylic acid (18) was first coupled with nitro-substituted or Fmoc-substituted aniline (19) followed by the reduction of the nitro-group or deprotection of the Fmoc group to give the salicylic amide substituted aniline 21. The key intermediate 21 was allowed to react with cyanuric chloride 5 first, followed by treating with amine 22, and then 4 at different temperatures in the presence of base to give the desired product 17.

4.5.2 General Methods of Deprotection (1) Simultaneous Removal of Boc and Benzyl-ether Protecting Groups (Scheme 5):

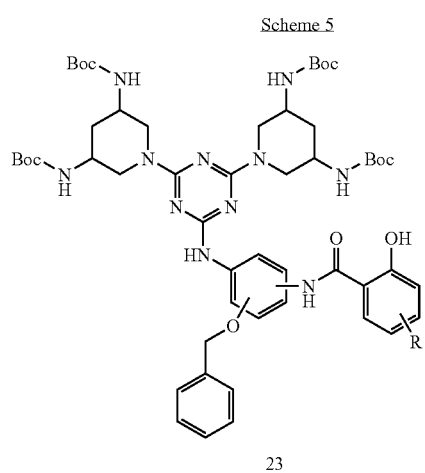

23

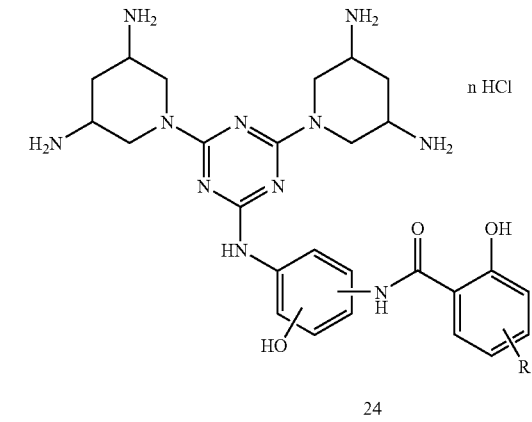

24

R refers to substituents defined for substituted aryls.

The Boc/benzyl protected compound (23) was dissolved in a mixture of thioanisole and TFA (1:4, 0.1 M) and shaken in a Teflon septum capped vial for 3 h. LC-MS typically indicated complete reaction at this point. The mixture was concentrated to an oil, dissolved in aqueous 1.0 M HCl and washed with a mixture of hexanes/EtOAc (4:1, 5 times). The aqueous phase was concentrated to dryness under reduced pressure. Purification by reverse phase HPLC followed by lyophilization twice from aqueous 0.25 M HCl gave the desired product (24) as the HCl salt in moderate to high yield.

(2) Removal of Boc Protecting Groups (Scheme 6):

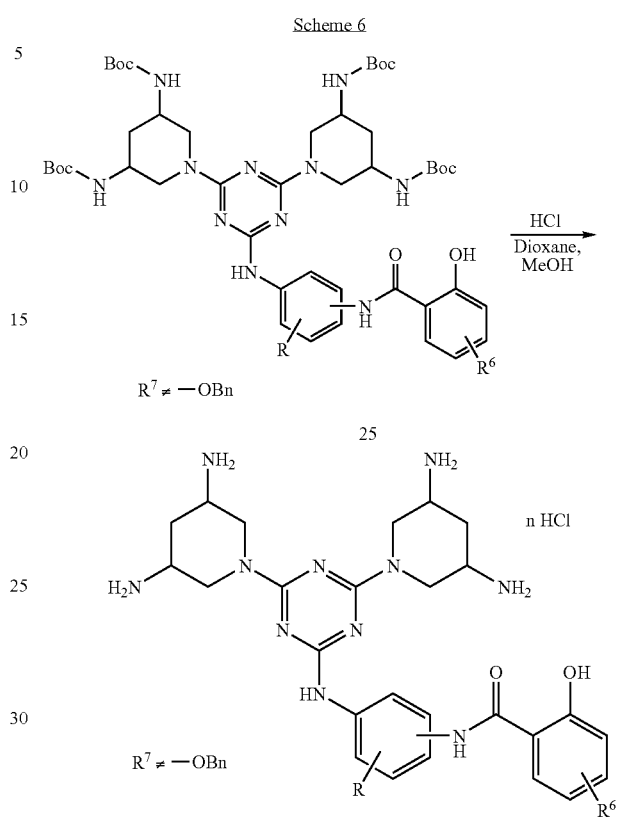

$R^6$ and $R^7$ refer to substituents as defined for substituted aryls with the proviso that $R^7$ is not —O-benzyl.

The Boc protected compound (25) was dissolved in a mixture of MeOH (0.1 M) and 4 M HCl in dioxane (0.1 M). The mixture was shaken in a Teflon septum capped vial for 16 h at room temperature. A white precipitate was typically observed. LC-MS typically indicated complete reaction at this point. The mixture was concentrated to dryness under reduced pressure. Purification by reverse phase HPLC followed by lyophilization twice from aqueous 0.25 M HCl gave the desired product (26) as the HCl salt in moderate to high yield.

4.5.3 Method A-1: Amide Coupling of Salicylic Acid Chloride with Nitroaniline in the Presence of $K_2CO_3$ or $NaHCO_3$ (Scheme 7)

Scheme 7 describes the general procedure for preparing salicylic acid derivative 34 of Formula Ia using method A-1.

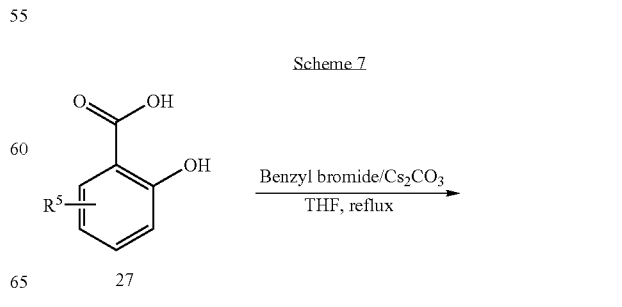

27

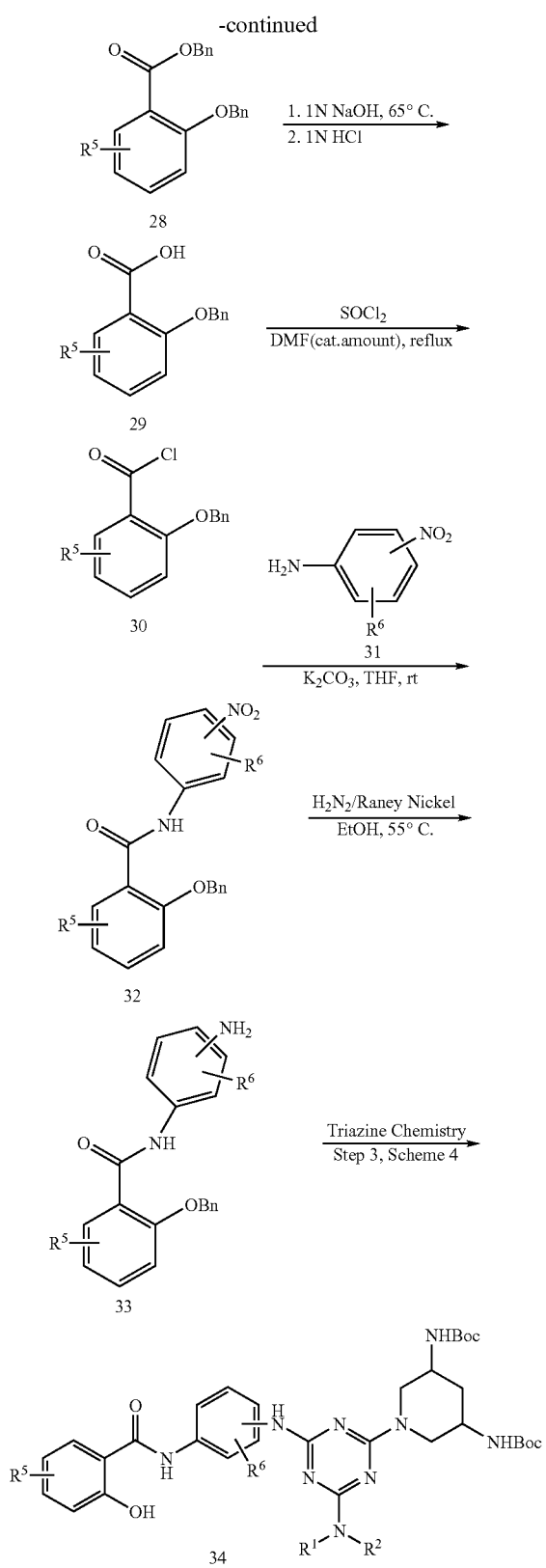

R[1] and R[2] refer to substituents as defined on p. 3.
R[5] and R[6] refer to substituents as defined for substituted aryls.

Into a salicylic acid (27) is added THF followed by cesium carbonate (3 equiv.) and benzyl bromide (2 equiv.). The reaction mixture is heated to reflux for 2–16 h. After cooling to room temperature, cesium carbonate is filtered off through Celite and the filtrate is dried under vacuum. The crude product is dissolved in $CHCl_3$ and washed twice with $H_2O$ via extraction. The organic layer is dried over $MgSO_4$, filtered and dried under reduced pressure to give product 28. In some cases, flash chromatography purification might be needed.

Compound 28 is dissolved in MeOH. NaOH (1.0 M) is added into the reaction mixture. The reaction mixture was then heated to 65° C. with stirring for 4 h. After the reaction was complete, the mixture was cooled to room temperature and 1.0 N HCl was added to neutralize the reaction mixture. The reaction mixture is dried under vacuum and dissolved in $CHCl_3$ and washed with $H_2O$ via extraction. The organic layer is dried over $MgSO_4$, filtered and dried under vacuum again to give product 29.

Compound 29 is put into a round-bottom flask. Thionyl chloride (20 equiv.) is added into the flask as a solvent followed by 3 drops of DMF. The reaction mixture is heated to reflux for 3 h under $N_2$ atmosphere. The reaction mixture is concentrated under reduced pressure. Toluene is added into the reaction vessel and the solution is concentrated down again to help remove residual thionyl chloride. This process is repeated once more. The crude product is further dried on oil pump vacuum for half an hour to give product 30. Compound 30 is immediately used in the next step.

Compound 30 is dissolved in THF. $K_2CO_3$ (10 equiv.) is added followed by nitroaniline 31 (1.5 equiv). The reaction mixture is stirred at room temperature for 2 h. $K_2CO_3$ is filtered off through Celite and the filtrate is concentrated under vacuum. The residue is dissolved in $CHCl_3$, and then washed with $H_2O$ for extraction of salts. The organic layer is dried and purified by flash chromatography to give product 32.

Compound 32 is dissolved in ethanol and is shaken at 80° C. for 5–15 minutes (if not soluble, DMF is added) in an opened vial. In the meantime the heating plate is heated to 55° C. The sample vial is then placed on the heating plate at 55° C. without cap. $NH_2NH_2$ (excess) is added and immediately followed by Raney Nickel (a catalytic amount, 50% slurry in water). The vial is let sit on the heating plate at 55° C. for 15–20 minutes until bubbling stops. After filtering off the solid through a plug of Celite and washing with MeOH, the filtrate is dried under vacuum until very dry to give the product 33. Compound 33 is immediately used in the next step in triazine chemistry as shown in step 3 of scheme 4. In some cases, purification by flash chromatography is needed.

At the end of synthesis of the final product and prior to biological testing, the benzyl group is removed by the treatment with thioanisole (10 equiv), methanesulfonic acid (16 equiv) and TFA (as a solvent) in an ice-water bath for 1 h to give compound 34. After completion of the reaction, the solvent is evaporated in vacuo and the resulting residue is purified by HPLC to give the final product for biological testing. The Boc groups are also removed under this condition.

4.5.4 EXAMPLE 4

Synthesis of Salicylic Acid Derivative 44 Using Method A-1 where K$_2$CO$_3$ was Used During the Salicylic Amide Formation (Scheme 8)

Scheme 8

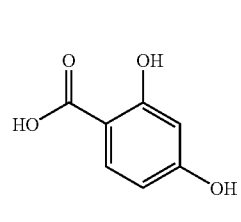

35

Step 1
Benzyl bromide
Cs$_2$CO$_3$
———————→
THF, 80° C., o.n.

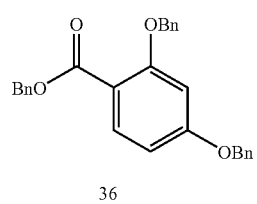

36

Step 2
NaOH/H$_2$O
———————→
MeOH, 65° C., o.n.

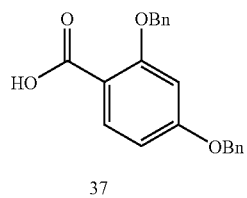

37

Step 3
Thionyl chloride
———————→
DMF (cat.), reflux, 3 h

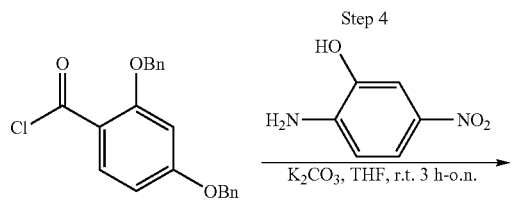

38

Step 4
K$_2$CO$_3$, THF, r.t. 3 h-o.n.
———————→

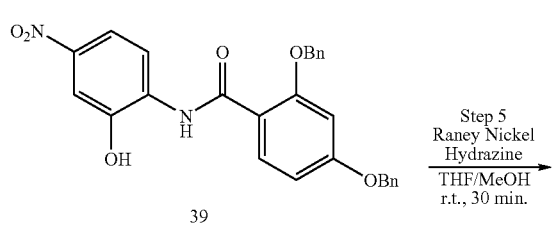

39

Step 5
Raney Nickel
Hydrazine
———————→
THF/MeOH
r.t., 30 min.

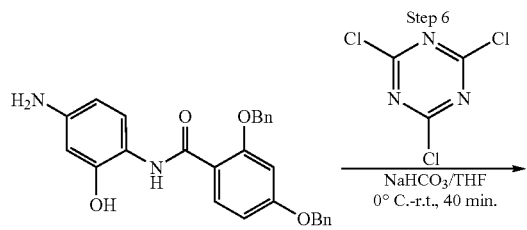

40

Step 6
NaHCO$_3$/THF
0° C.-r.t., 40 min.
———————→

-continued

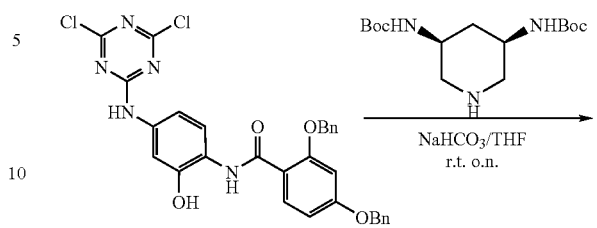

41

Step 7
NaHCO$_3$/THF
r.t. o.n.
———————→

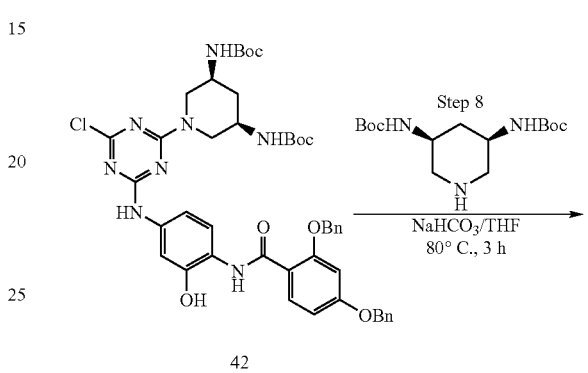

42

Step 8
NaHCO$_3$/THF
80° C., 3 h
———————→

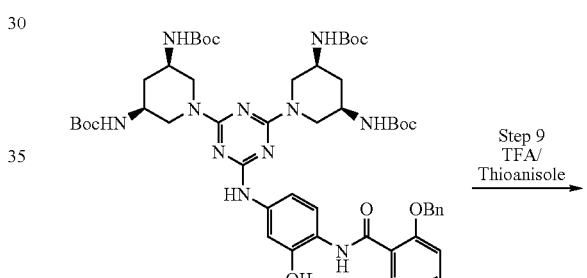

43

Step 9
TFA/
Thioanisole
———————→

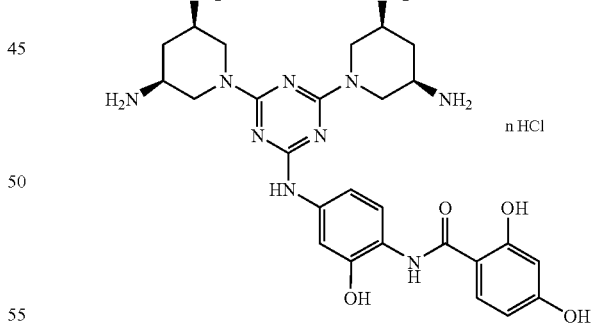

44

Step 1: 2,4-Bis-benzyloxy-benzoic acid benzyl ester (36)

2,4-dihydroxy-benzoic acid (35) (2 g, 13 mmol) in THF (250 mL) was mixed with cesium carbonate (16.9 g, 52 mmol) and benzyl bromide (6.2 mL, 52 mmol). The reaction mixture was refluxed overnight and then cooled down to room temperature. Cesium carbonate was filtered off through filter paper. The solvent was removed under reduced pressure. Liquid-liquid extraction was performed using 200 mL of CHCl$_3$ and H$_2$O (100 mL×3). The organic layer was dried over MgSO$_4$. After filtering off the MgSO$_4$, the organic layer was concentrated to give compound 36 (4.3 g) as a solid. LC-MS (ESI): m/e=425.2 [M+1]$^+$ Step 2: 2,4-Bis-benzyloxy-benzoic acid (37)

NaOH (1 N) (150 mL) was added to compound 36 (4.3 g) in MeOH (50 mL). The reaction mixture was heated to 65° C. with stirring for 48 h. After the reaction mixture was cooled down to room temperature, 1.0 M HCl (200 mL) was added to neutralize the reaction mixture. The solvent was concentrated under reduced pressure. The residue was extracted with CHCl$_3$ and H$_2$O. The combined organic layer was dried over MgSO$_4$. After the MgSO$_4$ was filtered off, the solvent was removed under reduced pressure. The residue was purified by flash chromatography to give the compound 37 (1.3 g) as a solid with total yield of 38.92% for 2 steps. LC-MS (ESI): m/e=335.2 [M+1]$^+$ Step 3: 2,4-Bis-benzyloxy-benzoyl chloride (38)

Compound 37 (1 g, 3 mmol) was mixed with thionyl chloride (7.2 g, 60 mmol) and 3 drops of DMF. The reaction mixture was refluxed for 3 h under nitrogen. After cooling down to room temperature, thionyl chloride was removed under reduced pressure. Toluene (5 mL) was then added, and the mixture was dried under reduced pressure again. This process was repeated twice to ensure all the excess of thionyl chloride was removed. The compound 38 was further dried under high vacuum for half an hour and was used directly in the next step without purification.

Step 4: 2,4-Bis-benzyloxy-N-(2-hydroxy-4-nitro-phenyl)-benzamide (39)

Compound 37 (1 g, 3 mmol) was dissolved in THF (100 mL). K$_2$CO$_3$ (2 g, 15 mmol) was added followed by 2-amino-5-nitro-phenol (693 mg, 4.5 mmol). The reaction mixture was allowed to stir at room temperature overnight. K$_2$CO$_3$ was filtered off though filter paper. The solvent was removed under reduced pressure. Liquid-liquid extraction was performed using CHCl$_3$ (100 mL) and H$_2$O (50 mL). The organic layer was dried over MgSO$_4$. After MgSO$_4$ was filtered off, the solvent was removed under reduced pressure. The residue was purified by flash chromatography to give compound 39 (786 mg, 55.7% isolated yield). LC-MS (ESI): m/e=471.1 [M+1]$^+$ Step 5: N-(4-Amino-2-hydroxy-phenyl)-2,4-bis-benzyloxy-benzamide (40)

Compound 39 (470 mg, 1 mmol) was dissolved in MeOH (15 mL) and THF (15 mL). Raney Nickel (50% slurry in water) (2 mL) was added to the reaction mixture followed by anhydrous hydrazine (1 mL). The reaction mixture was stirred at room temperature for 30 minutes until the bubbling was stopped. The solid was filtered off through Celite under reduced pressure and washed with MeOH. The solvent was removed under reduced pressure. Liquid-liquid extraction was performed using CHCl$_3$ (15 mL) and H$_2$O (8 mL×2). The organic layer was dried over MgSO$_4$, filtered and concentrated to give the compound 40 (263.8 mg, 59.9% crude yield) LC-MS (ESI): m/e=441.1 [M+1]$^+$ Step 6: 2,4-Bis-benzyloxy-N-[4-(4,6-dichloro-[1,3,5]triazin-2-ylamino)-2-hydroxy-phenyl]-benzamide (41)

NaHCO$_3$ (300 mg, 3.58 mmol) was added to a solution of compound 40 (263.8 mg, 598 µmol) in THF (5 mL). Cyanuric chloride (110 mg, 598 µmol) in THF (3 mL) was added to the reaction mixture in an ice water bath. The reaction mixture was stirred from 0° C. to room temperature for 30 minutes. The reaction progress was monitored by TLC and LC-MS. The reaction mixture was directly used in the next step. LC-MS (ESI): m/e=588.2 [M+H]$^+$ Step 7: (1-{4-[4-(2,4-Bis-benzyloxy-benzoylamino)-3-hydroxy-phenylamino]-6-chloro-[1,3,5]triazin-2-yl}-5-tert-butoxycarbonylamino-piperidin-3-yl)-carbamic acid tert-butyl ester (42)

(3R,5S)-3,5-bis-(tert-butoxycarbonylamino)-piperidine (190 mg, 598 µmol) was added into the above reaction mixture. The reaction mixture was stirred at room temperature for about five hours. The reaction progress was monitored by TLC and LC-MS. The reaction mixture was used directly in the next step without workup. LC-MS (ESI): m/e=867.5 [M+H]$^+$ Step 8: (3R,5S)-3,5-bis-(tert-butoxycarbonylamino)-piperidine (190 mg, 598 µmol) was added into the reaction mixture from the previous step. The mixture was heated at 80° C. overnight. The solvent was removed under reduced pressure. Liquid-liquid extraction was performed using CHCl$_3$ and H$_2$O. The organic layer was dried over MgSO$_4$. After filtration, the solvent was removed under reduced pressure. The resulting solid was purified by flash chromatography to give the intermediate 43 (263.6 mg, 33.6% isolated yield for 3 steps) as a solid. LC-MS (ESI): m/e=1146.7 [M+H]$^+$ Step 9: N-{4-[4,6-Bis-(3,5-diamino-piperidin-1-yl)-[1,3,5]triazin-2-ylamino]-2-hydroxy-phenyl}-2,4-dihydroxy-benzamide (44)

Compound 43 (263.6 mg, 230 µmol) was dissolved in TFA (2 mL). Thioanisole (291 mg, 2.3 mmol) was then added. The mixture was shaken at room temperature for 2 h. The solvent was removed under reduced pressure. The crude was then purified by HPLC purification to give the desired compound 44 (40.6 mg, 18.7% isolated yield). LC-MS (ESI): m/e=566.5 [M+H]$^+$. $^1$H NMR (400 MHz, DMSO-d$_6$): δ=1.82 (q, 2H, J=11.2 Hz), 2.74 (t, 2H, J=10.8 Hz), 2.88 (s, br, 2H), 3.26 (m, 4H), 4.96 (s, br, 2H), 5.40 (s, 2H), 6.41 (m, 2H), 7.04 (d, 1H, J=8.8 Hz), 7.57 (d, 1H, J=2.4), 7.87 (d, 1H, J=8.4 Hz), 8.15 (d, 1H, J=8.4 Hz), 8.71 (d, 10H, J=43.2 Hz), 9.08 (s, 1H), 10.04 (s, 2H), 10.36 (s, 1H); Elemental analysis calculated (%) for C$_{26}$H$_{35}$N$_{11}$O$_4$.7H$_2$O.7 HCl: C, 32.98; H, 5.96; N, 16.27. found: C, 33.36; H, 5.95; N, 16.11.

4.5.5 EXAMPLE 5

Synthesis of Keto Acid Derivative 49 Using Method A-1 where NaHCO$_3$ was Used in the Amide Formation

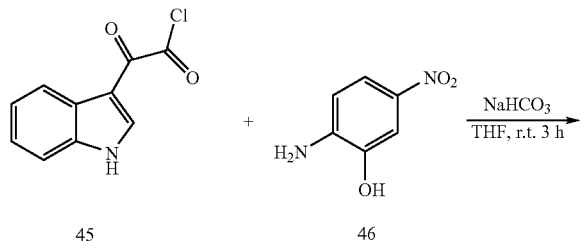

Scheme 9

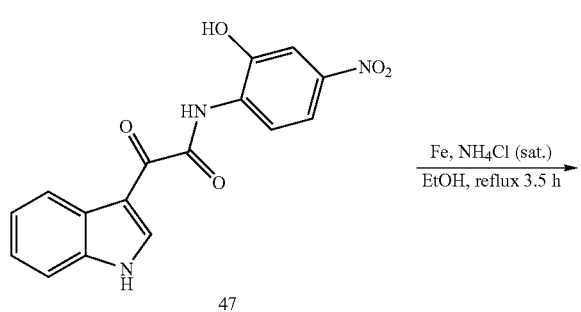

47

Fe, NH₄Cl (sat.)
EtOH, reflux 3.5 h

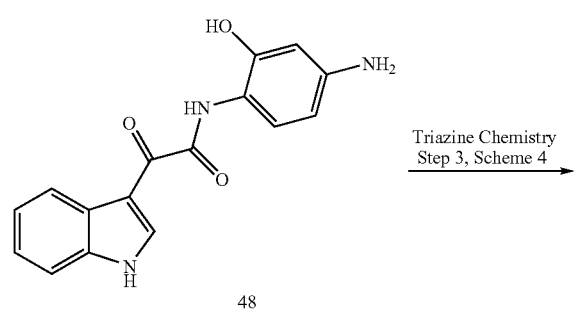

48

Triazine Chemistry
Step 3, Scheme 4

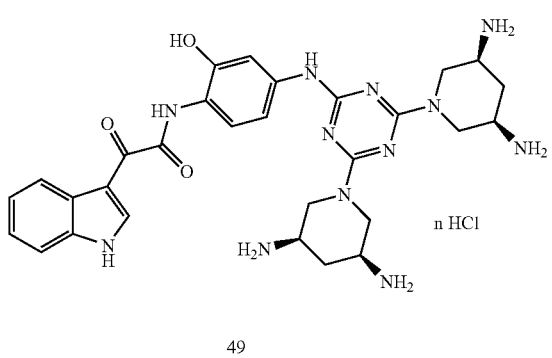

49

The α-keto acid chloride (45) (673.5 mg, 3.24 mmol), 2-hydroxy-4-nitro-aniline (46) (0.5 g, 3.24 mmol), NaHCO₃ (1.36 g, 16.22 mmol) and 10 μL of THF were mixed and the mixture was stirred at room temperature for 2 hours. The additional α-keto acid chloride (45) (100 mg, 0.48 mmol) was added. After stirring for 1 hour at room temperature, the TLC result confirmed the completion of the reaction. EtOAc (30 mL) and H₂O (20 mL) were added. After liquid-liquid extraction, the two layers were separated. HCl (1.0 M, 13 mL) was then added into the aqueous layer to neutralize it. The product in the aqueous layer was extracted out by EtOAc (50 mL×3) via liquid-liquid extraction. The organic layers were combined, dried over anhydrous Na₂SO₄ overnight. After filtration, the solvent was concentrated under reduced pressure to give a yellow solid. After recrystalization in MeOH, 957 mg of the pure desired product (47) was obtained in 91.1% isolated yield. Multiple batches of this reaction had been run. $^1$H NMR (400 MHz, DMSO-$d_6$): δ=12.40 (s, 1H), 11.50 (1, s, br, 1H), 10.08 (s, 1H), 8.97 (d, J=3.2 Hz, 1H), 8.49 (d, J=8.8 Hz, 1H), 8.22–8.28 (m, 1H), 7.83 (dd, $J_1$=8.8 Hz, $J_2$=2.6 Hz, 1H), 7.73 (d, J=2.8 Hz, 1H), 7.53–7.58 (m, 1H), 7.26–7.31 (m, 2H).

Compound 47 (1.36 g, 4.18 mmol), Fe powder (702.2 mg, 12.54 mmol), 25 mL of EtOH and saturated NH₄Cl (15 mL) were mixed. The mixture was refluxed for 3.5 hours. TLC result confirmed the completion of the reaction. The reaction mixture was concentrated on a rotary evaporator without filtering off the iron powder. The residue was directly added on a silica gel column and was purified by flash chromatography using 100% EtOAc as eluting solvent to give 1.065 g (86.6% isolated yield) desired product (48) as a yellow solid with HPLC purity of 100% by ELSD. LC-MS: m/e 296.3 [M+1]⁺ (expect ms: 295.1). $^1$H NMR (400 MHz, DMSO-$d_6$): δ=12.26 (s, br, 1H), 9.77 (s, br, 1H), 9.57 (s, 1H), 8.98 (s, 1H), 8.22–8.27 (m, 1H), 7.80 (d, J=8.8 Hz, 1H), 7.50–7.56 (m, 1H), 7.22–7.29 (m, 2H), 6.20 (d, J=2.4 Hz, 1H), 6.05 (dd, $J_1$=8.6 Hz, $J_2$=2.2 Hz, 1H), 4.98 (s, 2H).

Aniline 48 underwent the triazine chemistry using the same method as described in step 3 in Scheme 800, where NH(R³)R⁴ is (3R,5S)-3,5-bis-(tert-butoxycarbonylamino)-piperidine, with $^i$Pr₂NEt as the base. The final product (49) was obtained as the HCl salt in 41.9% yield (from compound 48 to compound 49, calculated based on the molecular weight of the HCl salt obtained by elemental analysis). Elemental analysis calculated (%) for C₂₉H₃₆N₁₂O₃·5HCl·4H₂O: C, 40.74; H, 5.78; N, 19.66. found: C, 41.08; H, 5.40; N, 19.57. LC-MS: m/e 601.4 [M+1]⁺ (expect ms: 600.30). $^{13}$C NMR (500 MHz, D₂O): δ=177.652, 157.063, 144.909, 138.602, 134.505, 134.215, 125.041, 122.906, 122.055, 120.294, 118.989, 118.641, 111.240, 110.694, 109.491, 104.716, 44.006, 43.504 and 31.446. $^1$H NMR (400 MHz, DMSO-$d_6$): δ=12.39 (d, J=2.8 Hz, 1H), 10.35 (s, br, 1H), 9.74 (s, 1H), 9.15 (s, br, 1H), 8.98 (d, J=3.2 Hz, 1H), 8.44–8.74 (m, 12H), 8.22–8.28 (m, 1H), 8.13 (d, J=8.8 Hz, 1H), 7.60 (d, J=2 Hz, 1H), 7.52–7.57 (m, 1H), 7.24–7.30 (m, 2H), 7.07 (d, J=8 Hz, 1H). 5.30–5.43 (m, 2H), 4.90 (s, br, 2H), 3.06–3.30 (m, 4H), 2.78–2.92 (m, 2H), 2.62–2.78 (m, 2H), 2.40–2.54 (m, 2H), 1.76 (q, J=11.6 Hz, 2H).

4.5.6 Method A-2: Amide Coupling of Salicylic Acid with Nitroaniline Using PBr₃ Reagent Scheme 10 describes the general procedure of synthesis of compound 53 of Formula Ia using method A-2.

Scheme 10

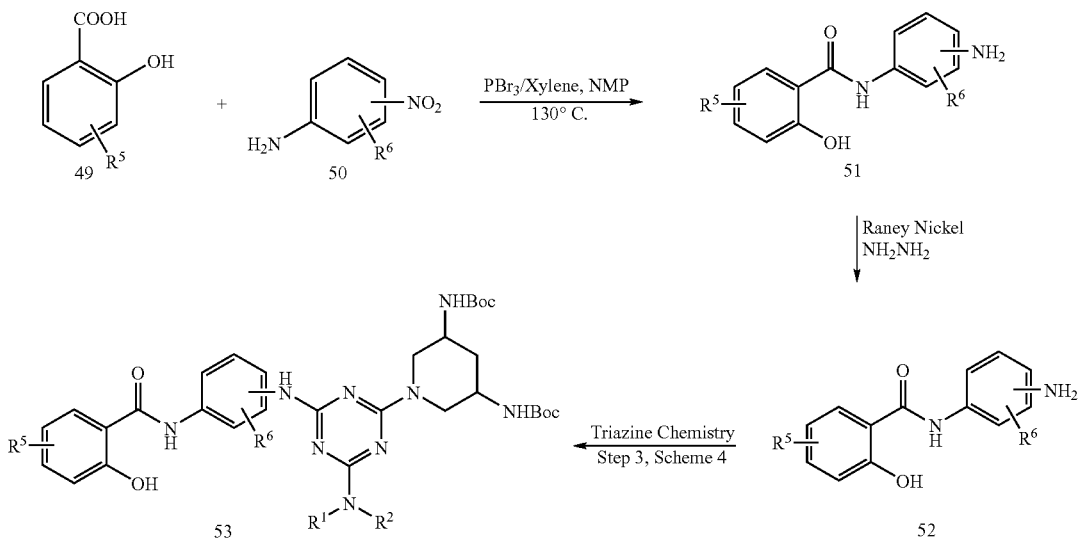

R[1] and R[2] are substituents as defined on p. 3.

R[5] and R[6] are substituents as defined for substituted aryls.

The following reactions were run in either direct fashion or parallel fashion. In case of the parallel synthesis, some reactions were run on the MiniBlock™ XT system (supplied from Mettler-Toledo AutoChem, Inc) and some reactions were run in a silicon oil bath.

Equivalent amounts of compound 49 and compound 50 in 0.1 M xylene or a mixture of xylene and NMP were mixed and placed in test tubes that were placed on the MiniBlock™ XT system and were heated to 130° C. A fresh made solution of $PBr_3$ (0.4 equivalent) was added at 130° C. and the mixture was continued to heat at 130° C. for 0.5–4 hours. After cooling, the reaction mixture was dried under reduced pressure. The residue was purified by liquid-liquid extraction ($CHCl_3$/aqueous saturated $NaHCO_3$, brine). The LC-MS result confirmed that the organic layer contained the desired product. The organic layer was then dried under reduced pressure to give the desired product 51.

Compound 51 was dissolved in THF and MeOH and the mixture was heated to 50° C. Excess of 98% $NH_2NH_2$ (120 μL for 600 μmol reaction scale) and excess of Raney Nickel (50% slurry in $H_2O$) (400 μL for 600 μmol reaction scale) was added and the mixture was let sit at 50° C. for 15–30 minutes. Upon the completion of the nitro-reduction reaction confirmed by LC-MS, the reaction mixture was cooled and the inorganic solid was filtered off through a plug of silica gel and Celite. The filtrate was concentrated under reduced pressure and was further purified by flash chromatography on silica gel using a gradient of hexane and EtOAc to give the pure desired aniline 52.

Aniline (52) was used in the triazine chemistry as shown in the step 3 of Scheme 4 to give the desired product 53.

4.5.7 EXAMPLE 6

Synthesis of Salicylic Acid Derivative 61 Using Method A-2 (Scheme 11)

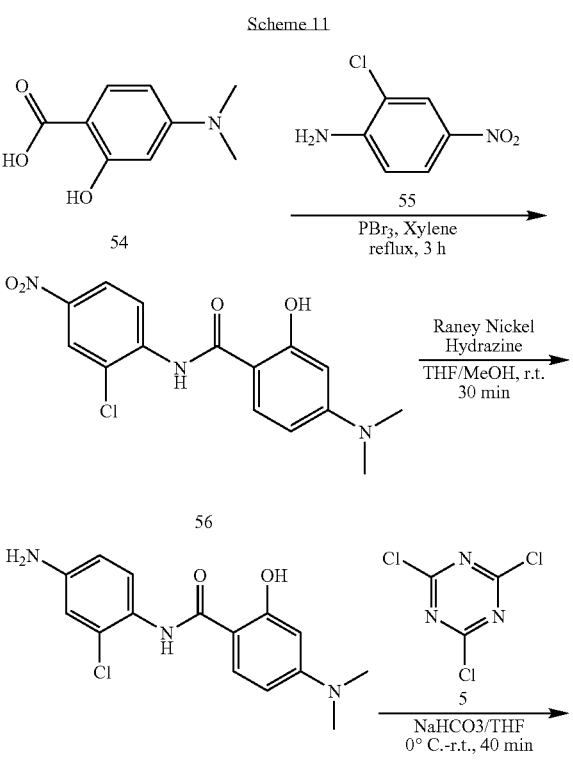

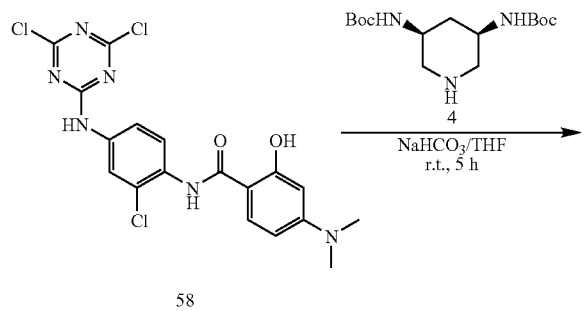

58

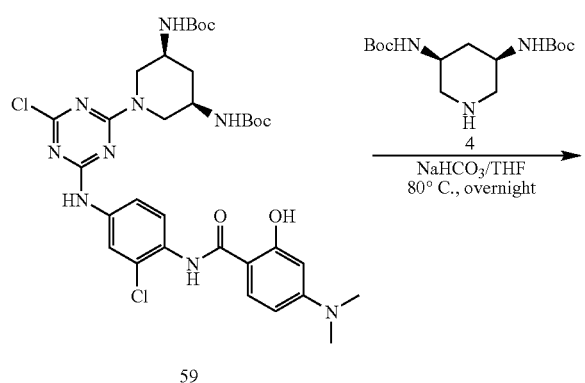

59

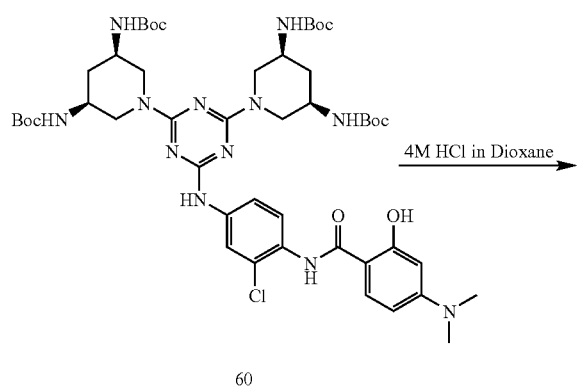

60

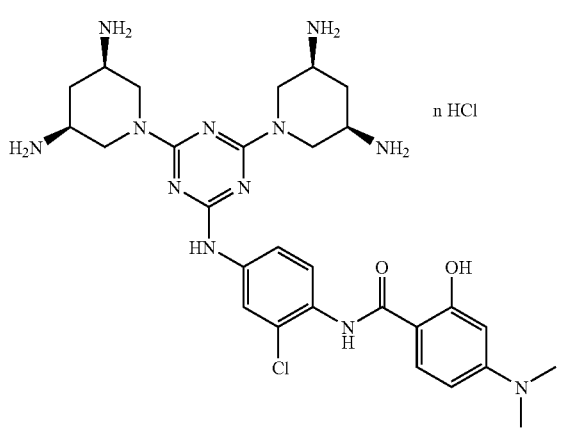

61

4-Dimethylamino-2-hydroxy-benzoic acid (54) (55 mg, 300 μmol) and 2-chloro-4-nitro-aniline (55) in xylene (4 mL) were heated to reflux. PBr$_3$ (12 μL, 120 μmol) was added drop wise. The reaction mixture was refluxed for another 3 h and then cooled down to room temperature. The solvent was removed under reduced pressure. Liquid-liquid extraction with CHCl$_3$ (4 mL) and H$_2$O (2 mL×3) followed by flash chromatography purification gave the compound 56 (71 mg, 70.6%) as a solid. LC-MS (ESI): m/z=336.2 [M+1]$^+$ Compound 56 (71 mg, 212 μmol) was dissolved in MeOH (2 mL) and THF (2 mL). Raney Nickel (50% slurry in water) (500 μL) was added to the reaction mixture followed by anhydrous hydrazine (30 μL, 848 μmol). The reaction mixture was stirred for 15–20 minutes until the bubbling stopped. The solid was filtered off celite under nitrogen and washed with MeOH. The solvent was removed under reduced pressure. The solid was extracted with CHCl$_3$ (3 mL) and H$_2$O (1.5 mL×2). The organic layer was dried over MgSO$_4$. After filtration, the solvent was evaporated under vacuum to give 57 (24 mg, 37%) as a solid. LC-MS (ESI): m/z=306.2 [M+1]$^+$ NaHCO$_3$ (40 mg, 468 μmol) was added into a solution of compound 57 (24 mg, 78 μmol) in THF (3 mL). Cyanuric chloride (5) (16 mg, 78 μmol) in THF (1 ml) was added into the reaction mixture under water-ice bath. The reaction mixture was stirred from 0° C. to room temperature for 40 minutes. The reaction was monitored by TLC and LC-MS. The reaction mixture containing 58 was directly used in next step.

(3R,5S)-3,5-bis-(tert-butoxycarbonylamino)-piperidine (4) (25 mg, 78 μmol) was added into the above reaction mixture. The reaction mixture was stirred at room temperature for 5 hours. The reaction was monitored by TLC and LC-MS and the desired product 59 was confirmed by LC-MS. The reaction mixture was directly used in next step.

The reaction mixture from the previous step was treated with (3R,5S)-3,5-bis-(tert-butoxycarbonylamino)-piperidine (4) (25 mg, 78 μmol) and heated at 80° C. overnight. The solvent was removed under reduced pressure. Liquid-liquid extraction was performed using CHCl$_3$ (4 mL) and H$_2$O (2 mL×2). The organic layer was dried over MgSO$_4$, filtered. The solvent was removed under reduced pressure. The resulting solid was purified by flash chromatography to give the compound 60 as a solid. LC-MS (ESI): m/e=1011.4 [M+1]$^+$ A solution of compound 60 in MeOH (2 mL) was treated with 4 M HCl in dioxane (3 mL) to give the final product 61 (10.4 mg, 16.7%, 13 μmol) (4 steps) that was purified by HPLC. LC-MS (ESI): m/z=611.4 [M+1]$^+$; $^1$H NMR (400 MHz, D$_2$O): 1.72 (q, 2H, J=12.4 Hz), 2.50 (s, br, 2H), 2.83 (t, 4H, J=12 Hz), 3.05 (s, 6H), 3.34 (s, br, 4H), 4.89 (s, br, 4H), 6.69 (s, 1H), 6.80 (m, 1H), 7.465 (s, 2H), 7.65 (m, 1H), 7.81(m,1H)

4.5.8 Method A-3: Amide Coupling of Salicylic Acid with NHBoc-substituted Aniline Using HOBt/EDCI (Scheme 12)

Scheme 12 describes a general procedure to synthesis of salicylic acid derivative 5 of Formula Ia using method A-3.

Scheme 12

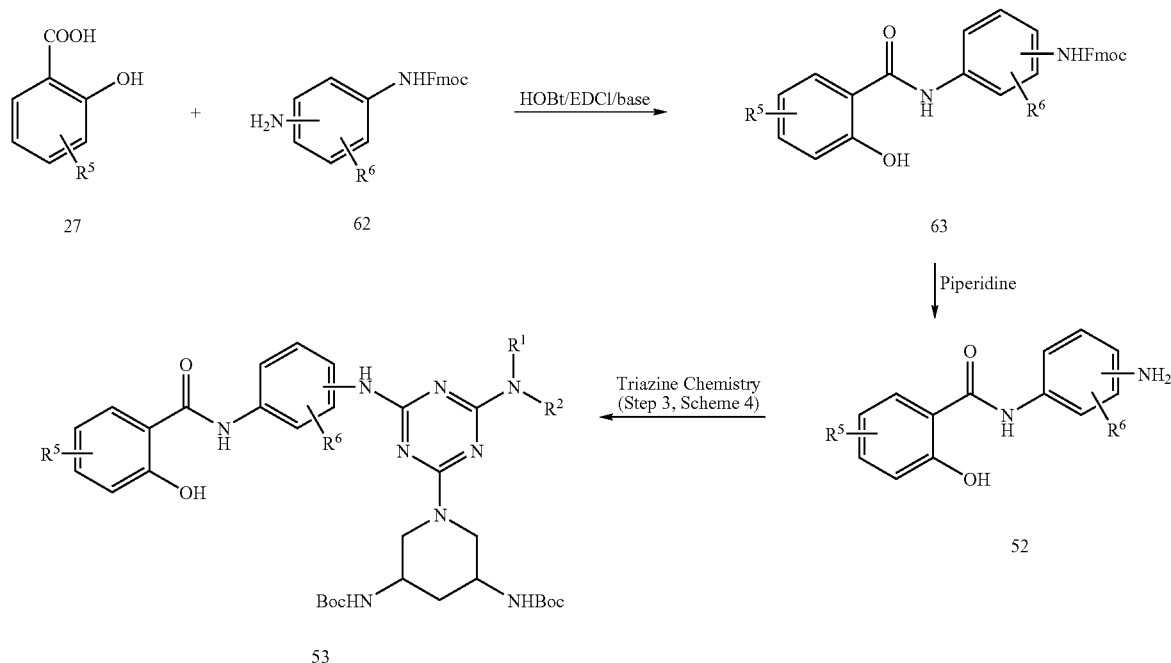

R[1] and R[2] are substituents as defined on p. 3.
R[5] and R[6] are substituents as defined for substituted aryls.
In this general method, the salicylic acid (27) was coupled with the NHFmoc-substituted aniline (62) using HOBt/EDCI in the presence of base to form the salicylic amide 63. De-protecting the Fmoc-group using piperidine gave the key salicylic amide substituted aniline 52 that underwent the same triazine chemistry as that described in step 3 of Scheme 4 to give the desired product 53.

4.5.9 EXAMPLE 7

Synthesis of Salicylic Acid Derivative 73 of Formula Ia Using Method A-3 (Scheme 13)

Scheme 13

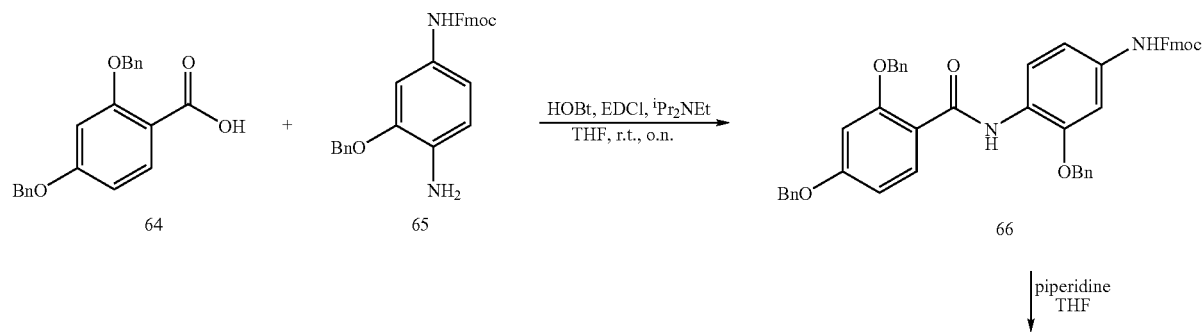

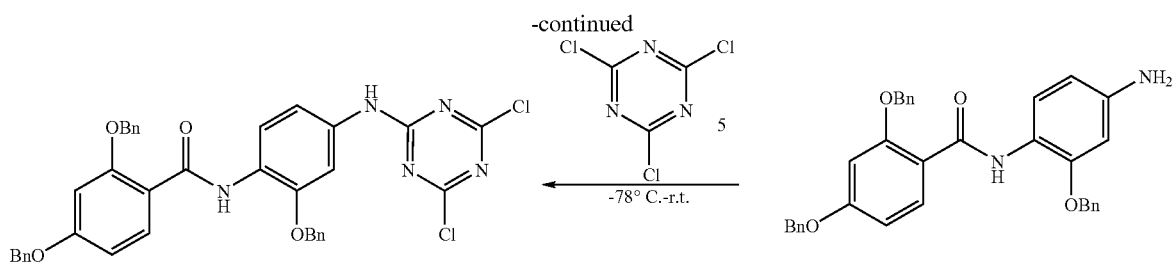

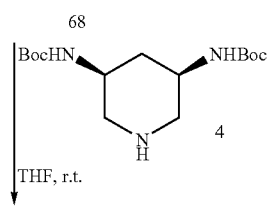

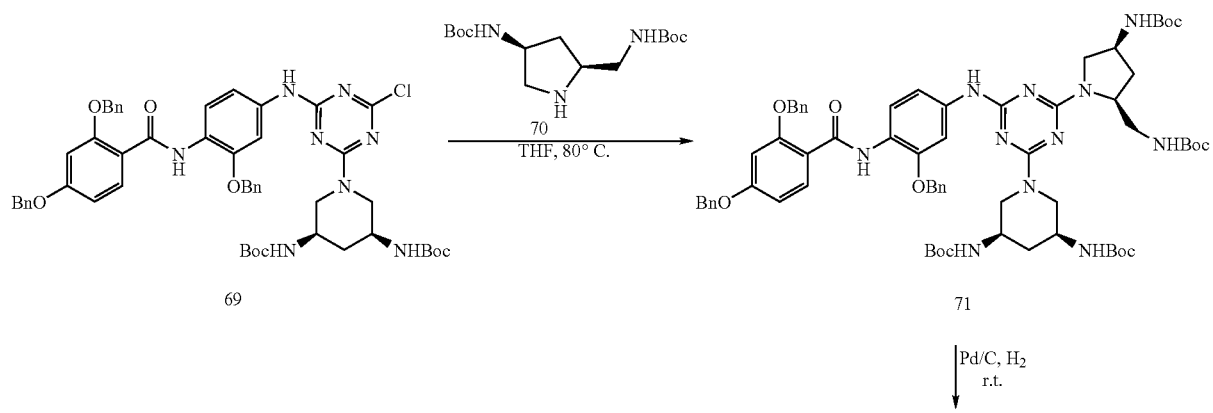

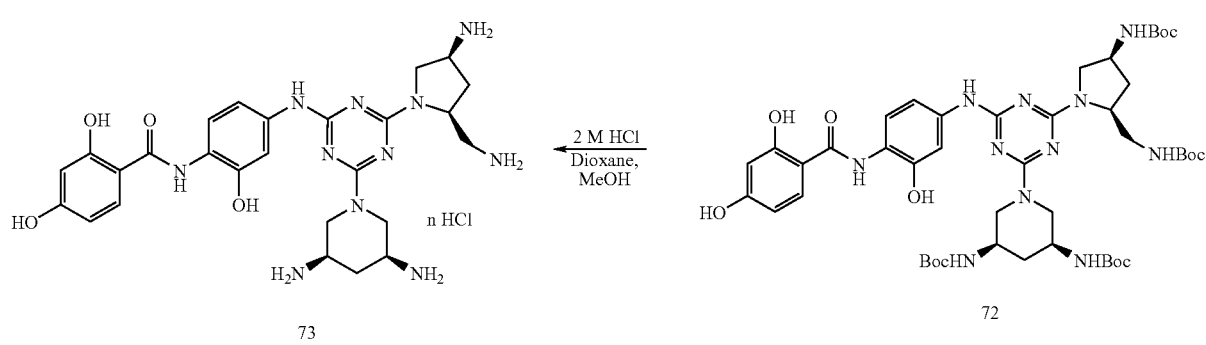

Compound 64 (101.6 mg, 304.2 μmol), compound 65 (133 mg, 304.2 μmol) and 1.0 M of $^iPr_2NEt$ in THF were mixed. HOBt (93.2 mg, 608.4 μmol) in 1.2 mL of THF was added and the resulting mixture was shaken at room temperature for 5 minutes. EDCI (117 mg, 608.4 μmol) in 2.4 mL of $CH_2Cl_2$ was then added and the mixture was shaken at room temperature for 16 hours. LC-MS result confirmed the completion of the reaction. The mixture was concentrated on a rotary evaporator and the residue was purified by liquid-liquid extraction using $CHCl_3$ (6 mL), 15% aqueous $NaHCO_3$ (3 mL) and $H_2O$ (3 mL) to give 253.5 mg of the desired product (66) as a brown puffy solid. LC-MS: m/e 753.4 [M+1]$^+$.

The compound 66 was dissolved in 2.5 mL of THF. Piperidine (1 mL, 10.1 mmol), was added, and the mixture was shaken at room temperature for 3.5 hours. LC-MS result confirmed the completion of the reaction. The mixture was concentrated under reduced pressure and the residue was purified by flash chromatography using a gradient of hexane and EtOAc to give 95.4 mg (179.8 μmol) of the desired product 67 as a gray solid in 59.1% isolated yield for 2 steps. LC-MS: m/e 531.3 [M+1]$^+$.

Compound 67 (95.4 mg, 179.8 μmol) was dissolved in 3 mL of THF. NaHCO$_3$ (91 mg, 1.08 mmol) was added followed by 4 drops of water. The mixture was cooled to −78° C. using a dry ice-acetone bath. A solution of cyanuric chloride (5) (33.2 mg, 180 μmol) in 800 μL of THF was added with stirring. The reaction mixture was stirred at −78° C. to room temperature overnight. LC-MS result confirmed the completion of the reaction and the identity of the desired product 68 with the HPLC purity of 100% by ELSD. LC-MS: m/e 678.2 [M+1]$^+$.

A slurry of amine 4 (57 mg, 180.7 μL) in 800 μL of THF was added into the above reaction mixture containing compound 68. The resulting mixture was stirred at room temperature for 4.5 hours. LC-MS confirmed the completion of the reaction and the identity of the desired product 69. LC-MS: m/e 957.6 [M+1]$^+$ (expect ms: 956.4).

A mixture of amine 70 (85 mg, 269.5 μmol) in 1.0 mL of THF was added. The reaction mixture was heated at 80° C. with stirring overnight. The solvent was removed under reduced pressure and the residue was purified by liquid-liquid extraction using CH$_2$Cl$_2$ (4 mL) and H$_2$O (2 mL×2). The organic layer was concentrated under reduced pressure and the residue was purified by flash column on silica gel using a gradient of hexane and EtOAc to give 142.1 mg (115 μmol) of the desired product 71 as a pale pink solid in 90.4% isolated yield for 2 steps (after considering 35.6 mg of the starting material 69 recovered during the purification).

Compound 71 (142.1 mg, 115 μmol) was dissolved in 12 mL of methanol. The solution was degassed by alternately connecting the system with vacuum, then N$_2$ for three times. Pd/C (dry, 10 wt %, 300 mg) was added under N$_2$ atmosphere. A balloon containing H$_2$ was then attached to the reaction system. The reaction mixture was stirred at room temperature for 3 hours under slightly positive pressure of H$_2$. The LC-MS result of the reaction mixture confirmed the identity of the desired product (72). MeOH (10 mL) was added to dilute the reaction mixture, and the inorganic solid was filtered off through Celite twice. The solvent was evaporated under reduced pressure to give 75.9 mg (78.6 μmol, 68.4% isolated yield) of the desired product 72 as a dark gray solid with HPLC purity of 100% by ELSD.

Compound 72 (75.9 mg, 78.6 μmol) was dissolved in 3 mL of MeOH. HCl (4.0 M in dioxane, 3 mL) was added and the reaction mixture was shaken at room temperature overnight. The solvent was evaporated under reduced pressure to give 62.4 mg of crude product 73 as a pale gray solid. The crude product was purified by reverse-phase HPLC using a gradient of CH$_3$CN and H$_2$O to give 38.7 mg (44.3 μmol, 56.3% yield based on the molecular weight determined by elemental analysis) of the desired pure product 73 as the HCl salt as a very pale yellow solid. LC-MS: m/e 566.3 [M+1]$^+$ (expect ms: 565.29). Elemental analysis calculated (%) for C$_{26}$H$_{35}$N$_{11}$O$_4$·5.5HCl·6H$_2$O (874.25): C, 35.72; H, 6.05; N, 17.62. found: C, 35.93; H, 5.74, 17.39. $^1$H NMR (400 MHz, DMSO-d$_6$): δ=10.39 (s, 1H), 10.00–10.28 (m, 3H), 8.48–8.80 (m, 12H, 4 NH$_3^+$), 8.10–8.22 (m, 1H), 7.85 (d, 1H), 7.20–7.50 (m, 1H), 7.00 (s, br, 1H), 6.40 (s, 1H), 6.36 (d, 1H), 5.20–5.40 (m, 1H), 4.85–5.05 (m, 1H), 3.20–3.60 (m, 8H), 2.70–2.95 (m, 2H), 2.40–2.65 (m, 1H), 1.70–2.00 (m, 3H).

4.5.10 Method A-4: Amide Coupling of Salicylic Acid with NHBoc-substituted Aniline Using 2-(1H-Benzotriazol-1-yl)-1,1,3,3-Tetramethyl-uronium Hexafluorophosphate (HBTU) (Scheme 13a)

Scheme 13a describes the general procedure for preparing salicylic acid derivative 53 of Formula Ia using method A-4.

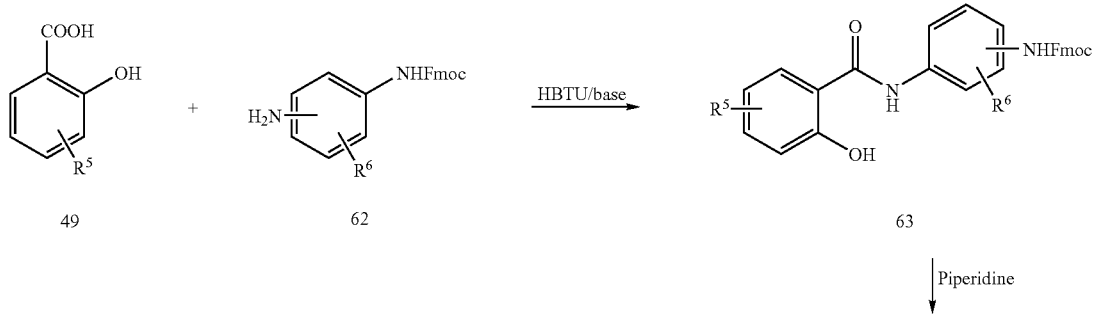

Scheme 13a

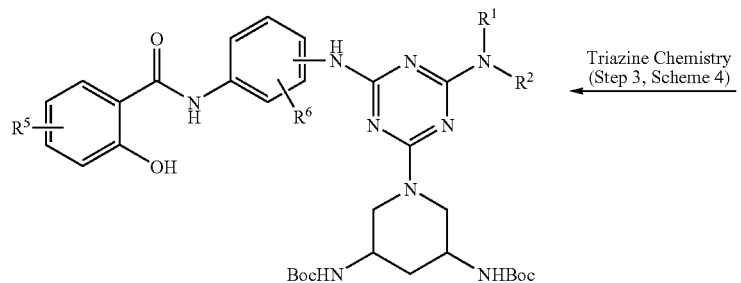
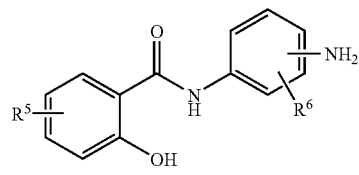
$R^1$ and $R^2$ are substituents as defined on p. 3.
$R^5$ and $R^6$ are substituents as defined for substituted aryls.
In this general method, HBTU was used as the coupling reagent in the first step, whereas other steps are the same as that in Scheme 12.
4.5.11 EXAMPLE 8
Synthesis of the Salicylic Acid Derivative (79) of Formula Ia Using Method A-4 (Scheme 14)
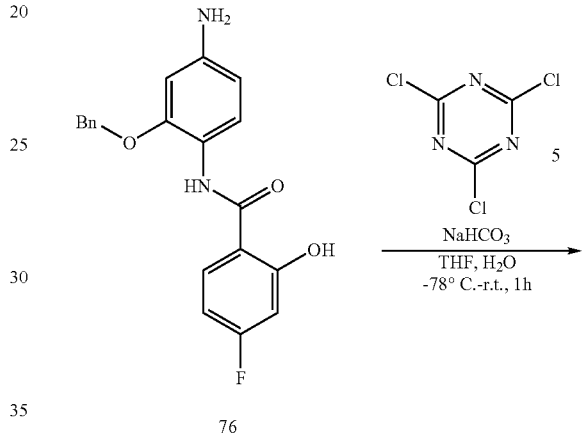
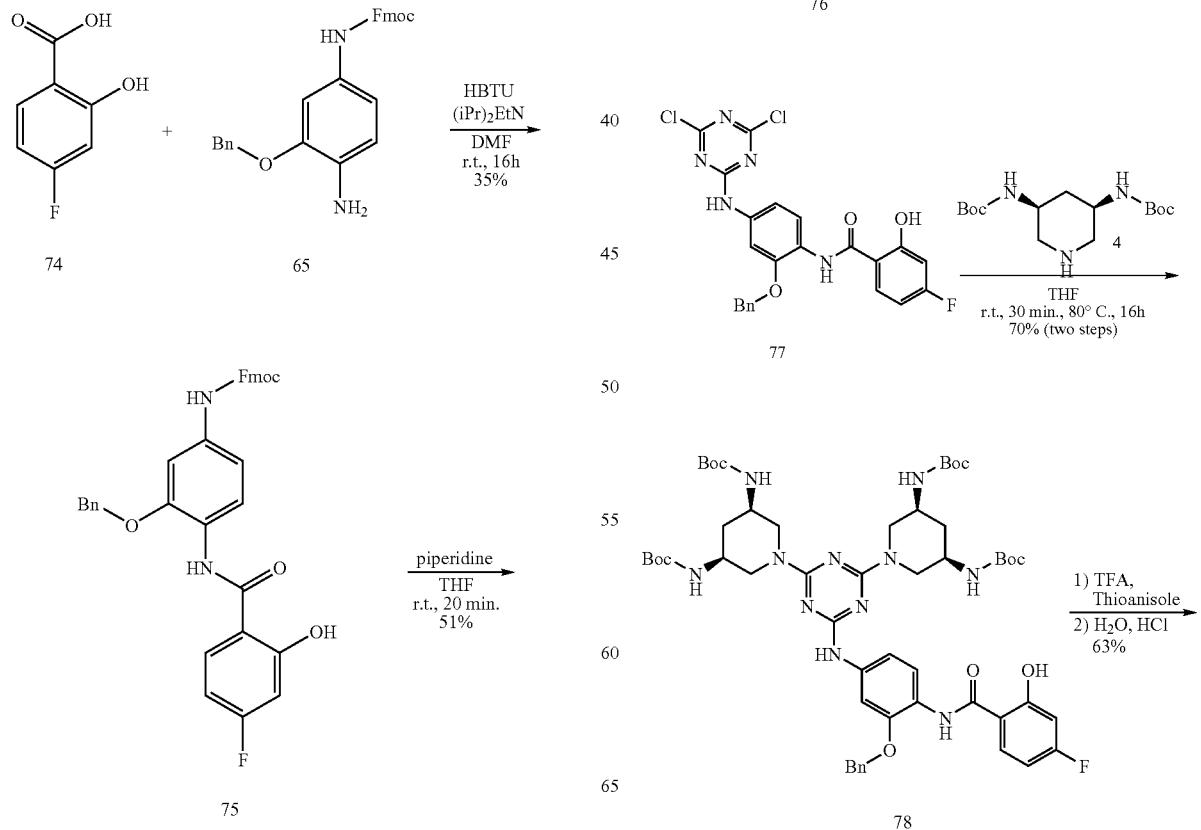

-continued

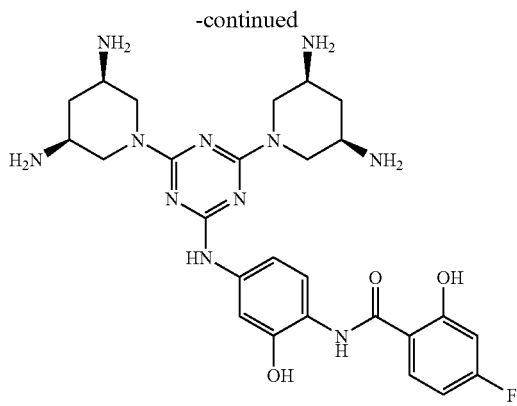

79

[3-Benzyloxy-4-(4-fluoro-2-hydroxy-benzoylamino)-phenyl]-carbamic acid 9H-fluoren-9-ylmethyl ester (75)

4-Fluoro-2-hydroxy-benzoic acid (74) (0.15 g, 0.961 mmol) was dissolved in DMF (6 mL), 2-(1H-benzotriazol-1-yl)-1,1,3,3-tetramethyl-uronium hexafluorophosphate (HBTU) (0.382 g, 1.01 mmol) was added followed by $^{i}Pr_2EtN$ (0.167 mL, 0.961 mmol) and the mixture was shaken in a Teflon septum capped 40 mL I-Chem vial at room temperature for 25 minutes. (4-Amino-3-benzyloxyphenyl)-carbamic acid 9H-fluoren-9-ylmethyl ester (0.419 g, 0.961 mmol) was added and the mixture was shaken at room temperature for 16 h. LC-MS indicated complete coupling at this point. The mixture was diluted with EtOAc (50 mL), washed with water (25 mL), aqueous saturated NaHCO$_3$ (25 mL) and brine (25 mL) via extraction, dried over MgSO$_4$. The organic layer was concentrated to give a yellow oil. Purification by flash chromatography using a gradient of hexane and EtOAc (eluding with 15–100% EtOAc in hexane in 30 minutes) gave the desired product (75) upon concentration (0.192 g, 0.334 mmol, 35% yield). LC-MS (ESI): (exact mass: 574.19) m/e=575.2 [M+1]$^+$ (100%), 1149.5 [2M+1]$^+$ (25%).

N-(4-Amino-2-benzyloxy-phenyl)-4-fluoro-2-hydroxy-benzamide (76)

[3-Benzyloxy-4-(4-fluoro-2-hydroxy-benzoylamino)-phenyl]-carbamic acid 9H-fluoren-9-yl-methyl ester (75) (0.192 g, 0.334 mmol) was dissolved in a mixture of THF (3 mL) and DMF (1 mL). Piperidine (0.57 g, 6.68 mmol) was added. The mixture was shaken at room temperature in a Teflon septum capped vial for 20 minutes. TLC indicated complete de-protection at this point. The mixture was concentrated to give an oil. Purification by flash chromatography using a gradient of hexane and EtOAc (5–100% EtOAc in hexane for 25 minutes followed by 100% EtOAc for 5 minutes) gave the desired product (76) upon concentration (0.060 g, 0.170 mmol, 51% yield). LC-MS (ESI): (exact mass: 352.12) m/e=353.3 [M+1]$^+$ (100%), 705.3 [2M+1]$^+$ (5%).

N-[2-Benzyloxy-4-(4,6-dichloro-[1,3,5]triazin-2-ylamino)-phenyl]-4-fluoro-2-hydroxy-benzamide (77)

N-(4-Amino-2-benzyloxy-phenyl)-4-fluoro-2-hydroxy-benzamide (76) (0.060 g, 0.170 mmol) was dissolved in THF (3.4 mL), NaHCO$_3$ (0.086 g, 1.02 mmol) was added and the mixture was chilled on a dry-ice/acetone bath. Cyanuric chloride (5) (0.032 g, 0.184 mmol) was dissolved in THF (2 mL) and added directly to the chilled solution while stirring. The ice bath was removed and the mixture continued to stir while warming to room temperature for 1 h. TLC (R$_f$: 0.8 compared to R$_f$: 0.35 for compound 76 in 1:1 hexane/EtOAc, single spot) indicated complete reaction at this point. The reaction mixture was used immediately in the next step without purification or characterization.

N-[2-Benzyloxy-4-(4,6-bis-((3R,5S)-3,5-bis-(tert-Butoxycarbonylamino)-piperidin-1-yl)-[1,3,5]triazin-2-ylamino)-phenyl]-4-fluoro-2-hydroxy-benzamide (78)

(3R,5S)-3,5-bis-(tert-Butoxycarbonylamino)-piperidine (4) (0.107 g, 0.34 mmol) was suspended in DMF (2 mL), sonicated for 2 minutes and added to the crude reaction mixture containing N-[2-Benzyloxy-4-(4,6-dichloro-[1,3,5]-triazin-2-ylamino)-phenyl]-4-fluoro-2-hydroxy-benzamide (77). The mixture was heated to 80° C. for 16 h. LC-MS and TLC (R$_f$: 0.4 compared to R$_f$: 0.8 for compound 77 in 1:1 hexane/EtOAc, single spot) indicated complete reaction at this point. The mixture was diluted with EtOAc (50 mL), washed with aqueous saturated NaHCO$_3$ (25 mL), water (25 mL) and brine (25 mL) via extraction, dried over MgSO$_4$ and concentrated to give a brown oil. Purification by flash chromatography on silica gel using a gradient of hexane and EtOAc (15–100% EtOAc in hexane) gave the desired product (78) upon concentration (0.126 g, 0.119 mmol, 70% total yield for two steps). LC-MS (ESI): (exact mass: 1057.54) m/e=1058.8 [M+1]$^+$ (100%).

N-[4-(4-fluoro-2-hydroxy-benzoylamino)-3-hydroxy-phenyl]-4,6-Bis-((3R,5S)-3,5-diamino-piperidin-1-yl)-[1,3,5]triazine-2-amine (79)

N-[2-Benzyloxy-4-(4,6-bis-((3R,5S)-3,5-bis-(tert-butoxycarbonylamino)-piperidin-1-yl)-[1,3,5]triazin-2-ylamino)-phenyl]-4-fluoro-2-hydroxy-benzamide (78) (0.126 g, 0.119 mmol) was dissolved in a mixture of thioanisole and TFA (1:4, 5 mL) and shaken in a Teflon septum vial for 2.5 h. LC-MS indicated complete reaction at this point. The mixture was concentrated (to about 1 mL), dissolved in aqueous 1.0 M HCl (15 mL) and washed with a mixture of hexane/EtOAc (4:1, 5×5 mL). The aqueous phase was concentrated to give a beige powder. Purification by reverse phase HPLC followed by lyophilization twice from aqueous 0.25 M HCl gave the desired product (79) as a white powder as the HCl salt [0.063 g, 075 mmol (calculated based on the molecular weigh of the HCl salt determined by elemental analysis), 63% yield, 7.8% total yield for 5 steps]. LC-MS (ESI): (exact mass: 567.28) m/e=568.3 [M+1]$^+$. $^1$H NMR (400 MHz, DMSO-d$_6$): δ 1.78 (q, 2H, J=12 Hz), 2.71 (t, 2H, J=11.2 Hz), 2.86 (t, 2H, J=11.2 Hz), 3.18 (m, 4H), 4.91 (s, br, 2H), 5.36 (s, br, 2H), 6.76–6.85 (m, 2H), 6.96 (d, 1H, J=8.4 Hz), 7.59 (s, 1H), 8.05 (t, 1H, J=8 Hz), 8.15 (d, 1H, J=9.2 Hz), 8.60 (s, br, 7H), 8.69 (s, br, 7H), 9.13 (s, 1H), 10.51 (s, 1H). Elemental analysis calculated (%) for $C_{26}H_{34}FN_{11}O_3 \cdot 7H_2O \cdot 4$ HCl: C, 37.20; H, 6.24; N, 18.35. found: C, 36.87; H, 6.36; N, 18.45.

4.5.12 Method B: To Make the Triazine Substituted Aniline Intermediate First Followed by the Amide Coupling with Salicylic Acid or Activated Salicylic Acid (Scheme 15)

Scheme 15 describes the general procedure for preparing salicylic acid derivative 3 of Formula Ia using method B.

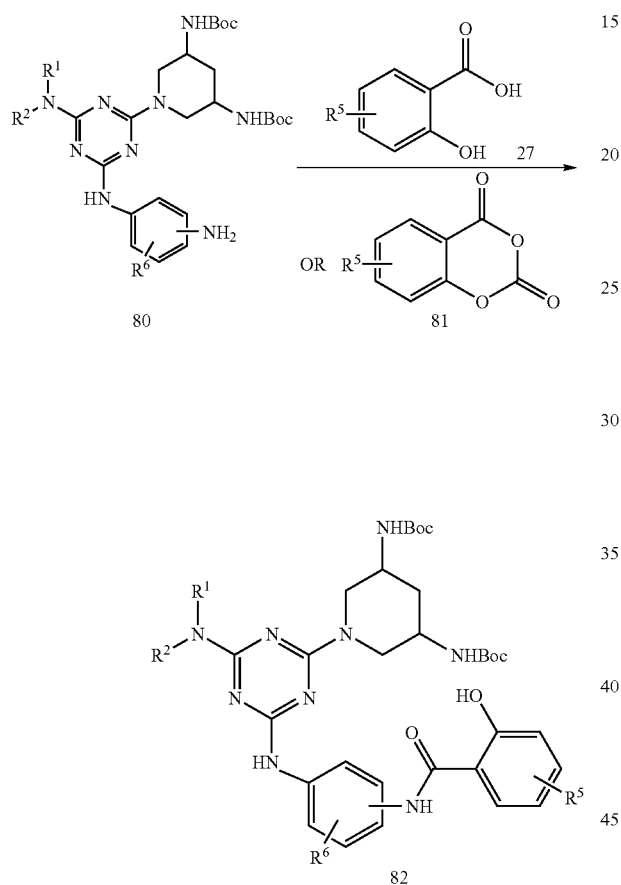

$R^1$ and $R^2$ are substituents as defined on p. 3.

$R^5$ and $R^6$ are substituents as defined for substituted aryls.

In this general method, the triazine-substituted aniline (80) is coupled with the salicylic acid (27) or activated salicylic acid (81) to give the desired compound 53. Removing the protecting groups in compound 53 (as shown in Scheme 5 & 6) gives the final products as the HCl salt.

4.5.13 Method B-1: Amide Coupling Using HOBt/EDCI (Scheme 16)

Scheme 16 describes the general procedure for preparing salicylic acid derivative 82 of Formula Ia using method B-1.

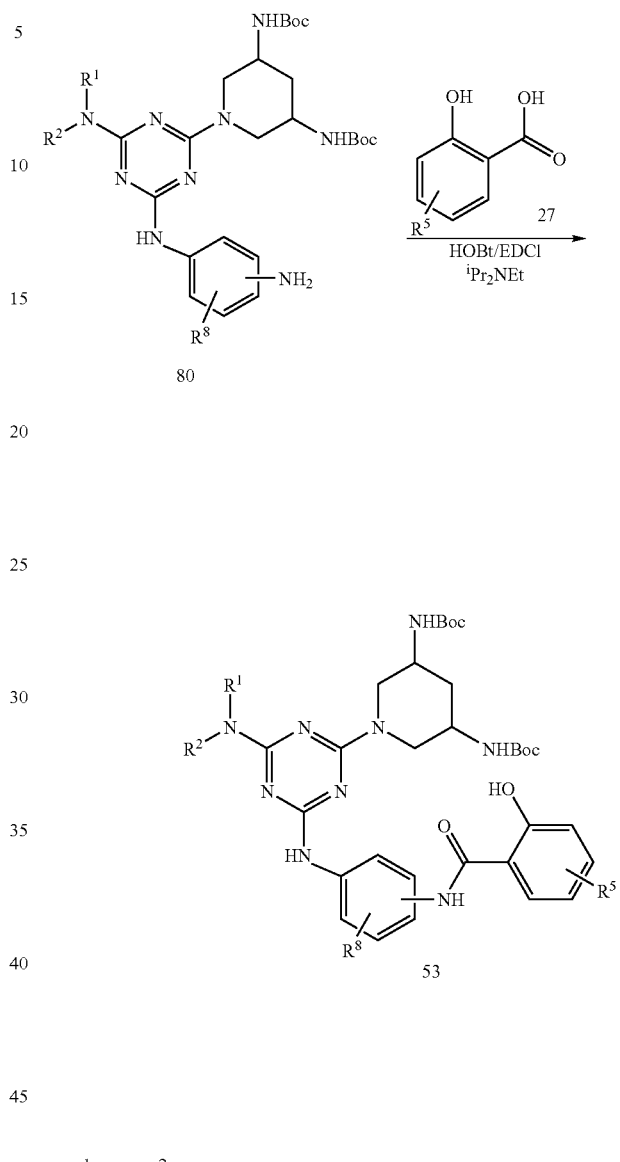

$R^1$ and $R^2$ refer to substituents defined on p. 3.

$R^5$ and $R^8$ refer to substituents as defined for substituted aryls with the proviso that $R^8$ does not include strong e-withdrawing groups such as the $NO_2$ group.

In this general method, a solution of 4 equivalents of $^iPr_2NEt$ in THF was added to a mixture of 1 equivalent of salicylic acid (27) and 1 equivalent of aniline (80) in THF followed by 4 equivalent of HOBt in THF. After shaking 5 minutes, 4 equivalent of EDCI in $CH_2Cl_2$ was added. The reaction mixture was shaken at room temperature for 4 h. Another equivalent of salicylic acid was then added. The reaction mixture was allowed to shake at room temperature overnight. The solvent was removed under reduced pressure. The residue was dissolved in $CHCl_3$. The organic solvent was washed with 10% $NaHCO_3$ and $H_2O$ via extraction, dried over $MgSO_4$, filtered and concentrated under reduced pressure. After flash chromatography purification, compound 53 was obtained.

4.5.14 EXAMPLE 9

Synthesis of Salicylic Acid Derivative Using Method B-1 (Scheme 17)

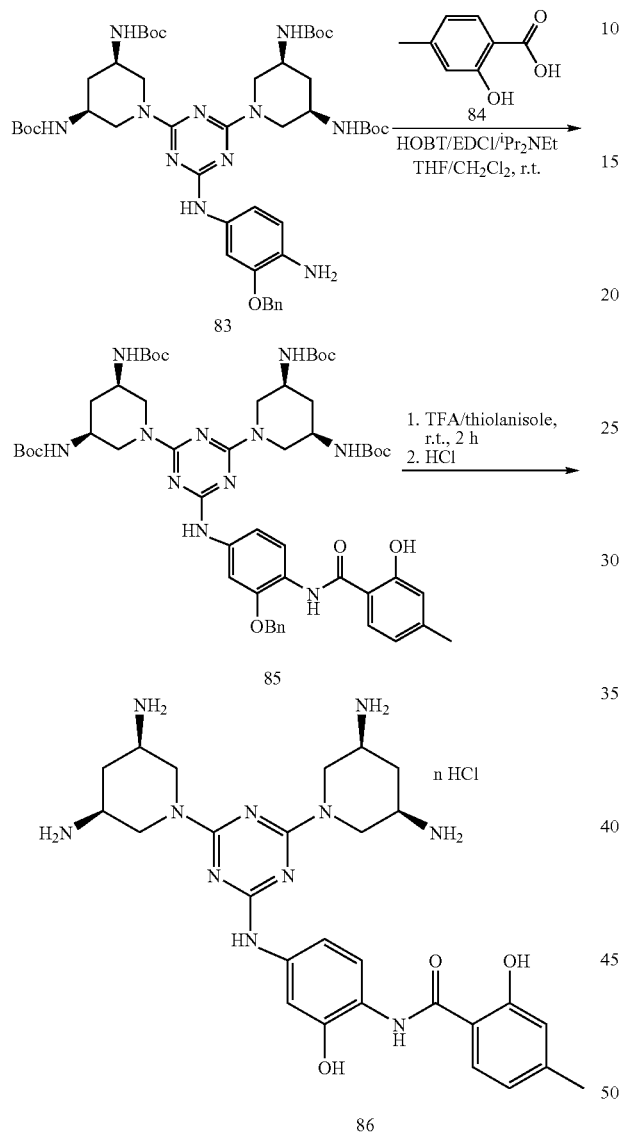

$^i$Pr$_2$NEt (115 μL, 652 μmol) in THF (1 mL) was added to a mixture of 4-methylsalicylic acid (84) (24.8 mg, 163 μmol) and aniline (83) (150 mg, 163 μmol) in THF (2 mL) followed by HOBT (99.85 mg, 652 μmol) in THF (2 mL). After stirring for 5 minutes, EDCI (124.99 mg, 652 μmol) in CH$_2$Cl$_2$ (2 mL) was then added. The reaction mixture was shaken at room temperature for 4 hours. Another 2 equivalents of 4-methylsalicylic acid (84) (49.6 mg, 326 μmol) was added. The reaction mixture was allowed to shake at room temperature overnight. The solvent was removed under reduced pressure. The solid was dissolved in CHCl$_3$ (4 mL). The organic solvent was washed with 10% aqueous NaHCO$_3$ (2 ml) and H$_2$O (2 mL×2). The organic layer was dried over MgSO$_4$, filtered and the solvent was removed under reduced pressure. After flash chromatography purification, compound 85 (140 mg, 81.5% isolated yield) was obtained as a solid. LC-MS (ESI): m/e=1054.5 [M+1]$^+$ N-{4-[4,6-Bis-(3,5-diamino-piperidin-1-yl)-[1,3,5] triazin-2-ylamino]-2-hydroxy-phenyl}-2-hydroxy-4-methyl-benzamide (86)

Compound 85 (140 mg, 132 μmol) was dissolved in TFA (2 mL). Thioanisole (165 mg, 1.32 mmol) was then added. The mixture was shaken at room temperature for 2 h. The solvent was removed under the reduced pressure. The solid was then purified by HPLC purification and converted to HCl salt by treating with HCl to give the desired product 86 (31.6 mg, 28.63%). LC-MS (ESI): m/e=564.5 [M+1]$^+$; $^1$H NMR (400 MHz, DMSO-d$_6$): δ=1.82 (q, J=12.4 Hz, 2H), 2.32 (S, 3H), 2.74 (t, J=10.4 Hz, 2H), 2.88 (t, J=10.4 Hz, 2H), 3.26 (m, 4H), 4.96 (s, br, 2H), 5.43 (d, J=10.8 Hz, 2H), 6.81 (t, J=8.8 Hz, 2H), 7.06 (d, J=8.8 Hz, 1H), 7.58 (d, J=2.4 Hz, 1H), 7.93 (d, J=7.6 Hz, 1H), 8.22 (d, J=8.8 Hz, 1H) 8.45–8.80 (m,12H), 9.10 (s, 1H), 10.11 (s, 1H), 10.58 (s, 1H), 11.63 (s, 1H). Elemental analysis calculated (%) for C$_{27}$H$_{37}$N$_{11}$O$_3$.5H$_2$O.5HCl: C, 38.79; H, 6.27; N, 18.43. found: C, 39.00; H, 5.95; N, 18.03.

4.5.15 Method B-2: Amide Coupling Using HBTU (Scheme 17a)

Scheme 17a describes the general procedure for preparing salicylic acid derivative of Formula Ia using method B-2.

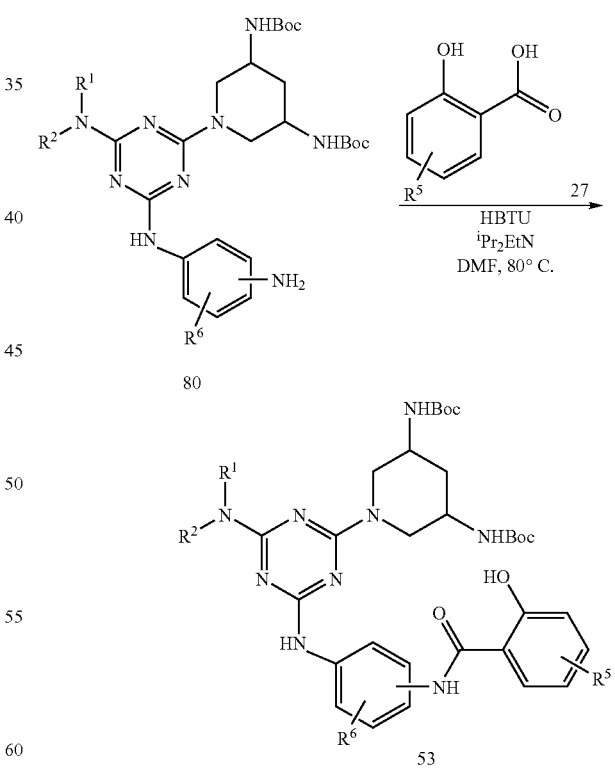

R$^1$ and R$^2$ are substituents as defined on p. 3.
R$^5$ and R$^6$ are substituents as defined for substituted aryls.
The salicylic acid (27) (1 equiv.), $^i$Pr$_2$EtN (1.1 equiv.) and HBTU (1.1 equiv.) were dissolved in DMF (0.2 M) and shaken in a Teflon septum-capped vial for 25 minutes. The aniline (80) (1 equiv.) was added and the mixture was heated to 80° C. for 3–16 h. Upon completion of the reaction, the mixture was concentrated under reduced pressure and the crude product was dissolved in CHCl₃, washed with aqueous saturated NaHCO₃ and water via extraction. The organic layer was concentrated to dryness in vacuo. Purification by flash chromatography on silica gel gave the desired product (53). When $R^6$ was ortho-Cl, the reaction time was as long as 16 h.

4.5.16 EXAMPLE 10

Synthesis of Salicylic Acid Derivative 89 Using Method B-2 (Scheme 18)

Scheme 18

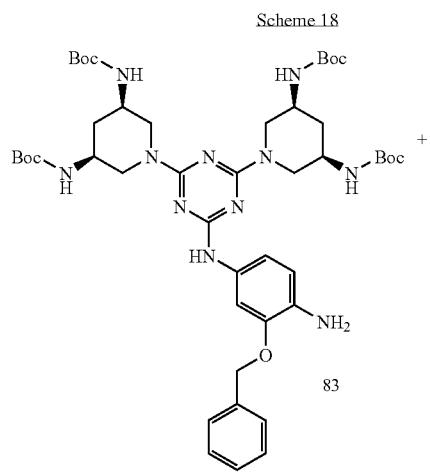

83

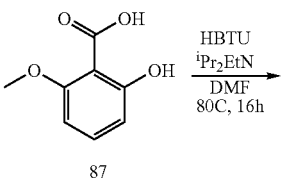

87

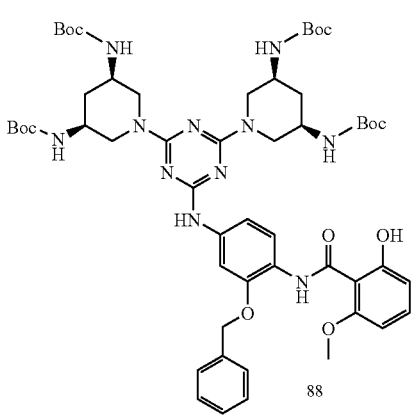

88

1. TFA, Thioanisole
2. HCl

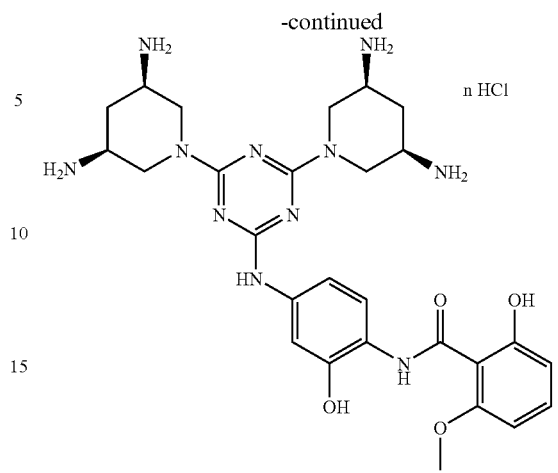

89

N-[2-Benzyloxy-4-(4,6-bis-((3R,5S)-3,5-bis-(tert-Butoxycarbonylamino)-piperidin-1-yl)-[1,3,5]triazin-2-ylamino)-phenyl]-2-hydroxy-6-methoxy-benzamide (88)

2-Hydroxy-6-methoxy-benzoic acid (87) (0.067 g=0.4 mmol), iPr₂EtN (0.6 mmol) and HBTU (0.44 mmol) were dissolved in DMF (2 mL) and shaken in a sealed vial for 25 min. 2-Benzyloxy-N4-(4,6-bis-((3R,5S)-3,5-bis-(tert-butoxycarbonylamino)-piperidin-1-yl)-[1,3,5]triazin-2-yl)-benzene-1,4-diamine (83) (0.184 g, 0.2 mmol) was added and the mixture was heated to 80° C. for 3 h. LC-MS indicated complete coupling at this point. Upon concentrating, the crude product was dissolved in CHCl₃ (4 mL), washed with aqueous sat. NaHCO₃ (2×2 mL), water (2×2 mL) and concentrated to dryness. Purification by ISCO (15–100% EtOAc/hexanes) gave the desired product (88) (0.073 g, 0.069 mmol, 34.5% yield). LC-MS (ESI): (exact mass: 1069.56) m/e=1070.9 [M+1]⁺ (100%).

N-[4-(4,6-Bis-((3R,5S)-3,5-diamino-piperidin-1-yl)-[1,3,5]triazin-2-ylamino)-2-hydroxy-phenyl]-2-hydroxy-6-methoxy-benzamide (89)

N-[2-Benzyloxy-4-(4,6-bis-((3R,5S)-3,5-bis-(tert-butoxycarbonylamino)-piperidin-1-yl)-[1,3,5]triazin-2-ylamino)-phenyl]-2-hydroxy-6-methoxy-benzamide (88) (0.073 g, 0.069 mmol) was dissolved in a mixture of thioanisole and TFA (1:4, 0.1 M) and shaken in a sealed vial for 3 h. LC-MS indicated complete reaction at this point. The mixture was concentrated to an oil, dissolved in aqueous 1.0 M HCl and washed with a mixture of hexane/EtOAc (4:1, 5 times). The aqueous phase was concentrated to dryness. Purification by reverse phase HPLC followed by lyophilization twice from aqueous 0.25 M HCl gave the desired product (89) as the HCl salt (0.028 mg, 0.0386 mmol, 56% yield). LC-MS (ESD): (exact mass: 579.30) m/e=580.3 [M+H⁺] (100%).

4.5.17 Method B-3: Amide Coupling with Benzo-Dioxine-Diones (Scheme 19)

Scheme 19 describes the general procedure for preparing salicylic acid derivative 82 of Formula Ia using method B-3.

4.5.18 EXAMPLE 11

Synthesis of the Salicylic Acid Derivative (93) of Formula Ia Using Method B-3 (Scheme 20)

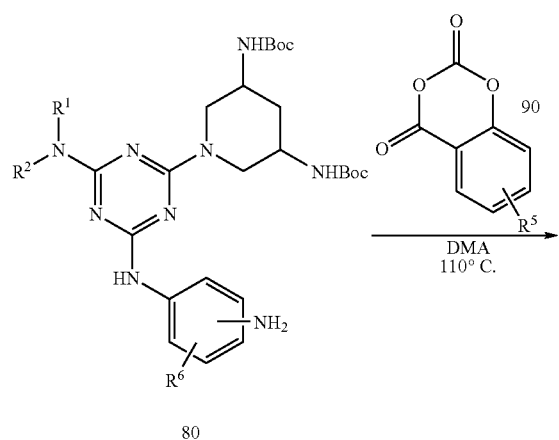

80

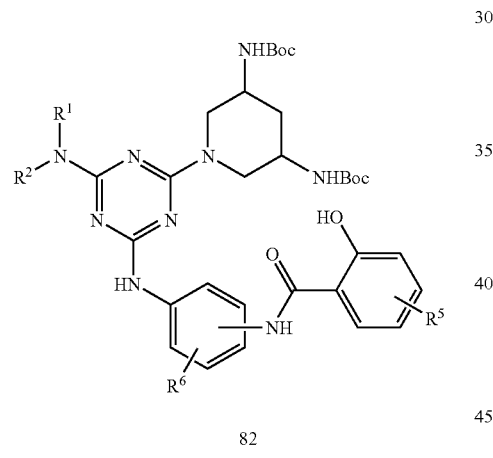

82

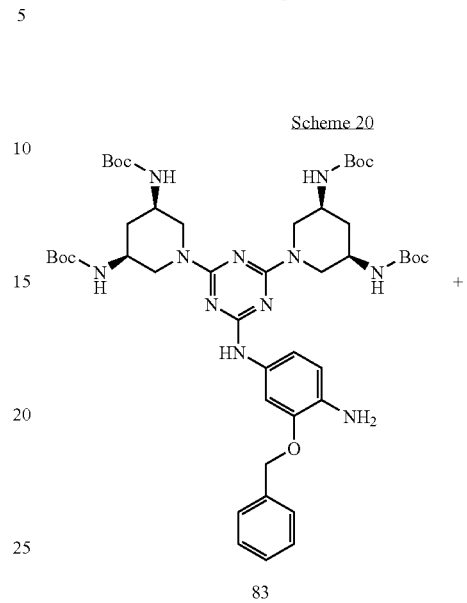

83

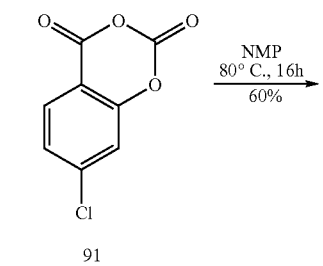

91

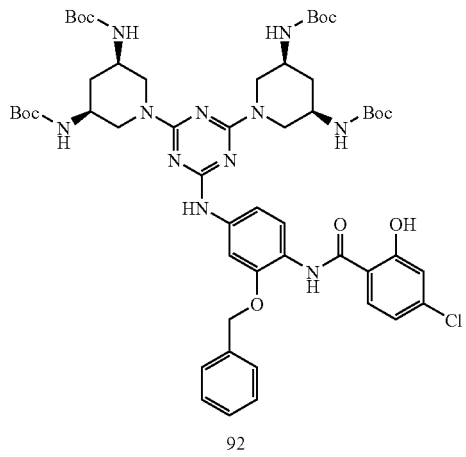

92

1. TFA, Thioanisole
2. H$_2$O, HCl 34.9%
(13.5% overall for 5 steps)

R$^1$ and R$^2$ are substituents as defined on p. 3.

R$^5$ and R$^6$ are substituents as defined for substituted aryls.

The triazine-substituted aniline (80) (1 equiv.) and the benzo-dioxine-dione (90) (3 equiv.) were combined and dissolved in NMP (0.4 M). The mixture was heated to 110° C. for 24 h. The mixture was diluted with EtOAc, washed with water, saturated aqueous NaHCO$_3$ and water via extraction, dried over MgSO$_4$, concentrated under reduced pressure. Purification by flash chromatography on silica gel gave the desired product (82) in low to moderate yield. When R$^5$ is an e-donating group, longer reaction times may be necessary. This reaction is suitable for R$^5$=OH.

-continued

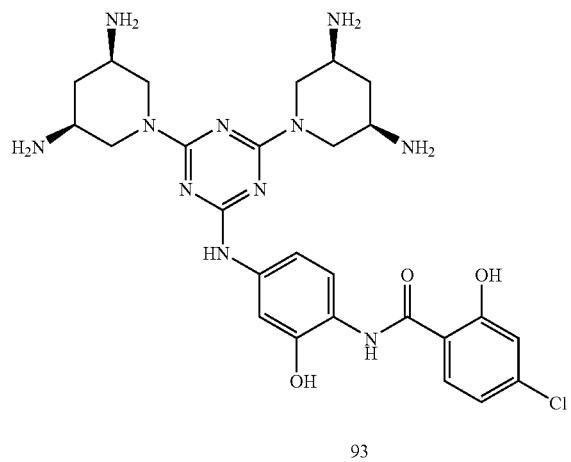

93

N-[2-Benzyloxy-4-(4,6-bis-((3R,5S)-3,5-bis-(tert-Butoxycarbonylamino)-piperidin-1-yl)-[1,3,5]triazin-2-ylamino)-phenyl]-4-chloro-2-hydroxy-benzamide (92)

2-Benzyloxy-N4-(4,6-bis-((3R,5S)-3,5-bis-(tert-butoxycarbonylamino)-piperidin-1-yl)-[1,3,5]triazin-2-yl)-benzene-1,4-diamine (83) (0.16 g, 0.174 mmol) and 7-chloro-benzo[1,3]dioxine-2,4-dione (91) (0.2 g, 1.0 mmol) were combined and dissolved in NMP (8 mL). The mixture was heated to 80° C. for 16 h. LC-MS indicated complete reaction at this point. The mixture was diluted with EtOAc (30 mL), washed with water (2×15 mL), saturated aqueous NaHCO$_3$ (2×15 mL) and brine (2×15 mL) via extraction, dried over MgSO$_4$ and concentrated to give a brown oil. Purification by flash chromatography on silica gel using a gradient of hexane and EtOAc (15–100% EtOAc in hexane) gave the desired product (92) as a yellow powder upon concentration (0.111 g, 0.103 mmol, 60% yield). LC-MS (ESI): (exact mass: 1073.51) m/e=1074.6 [M+1]$^+$ (100%).

N-[4-(4-chloro-2-hydroxy-benzoylamino)-3-hydroxy-phenyl]-4,6-Bis-((3R,5S)-3,5-diamino-piperidin-1-yl)-[1,3,5]triazine-2-amine (93)

N-[2-Benzyloxy-4-(4,6-bis-((3R,5S)-3,5-bis-(tert-butoxycarbonylamino)-piperidin-1-yl)-[1,3,5]triazin-2-ylamino)-phenyl]-4-chloro-2-hydroxy-benzamide (92) (0.111 g, 0.103 mmol) was dissolved in a mixture of thioanisole and TFA (1:4, 1.5 mL) and shaken in a sealed vial for 90 minutes. LC-MS indicated complete reaction at this point. The mixture was concentrated, dissolved in aqueous 1.0 M HCl (15 mL) and washed with a mixture of hexanes/EtOAc (4:1, 5×5 mL) via extraction. The aqueous phase was concentrated to give a yellow powder. Purification by reverse phase HPLC followed by lyophilization twice from aqueous 0.25 M HCl gave the desired product (93) as a yellow powder as the HCl salt [0.0295 g, 0.036 mmol (based on 4 HCl+5 H$_2$O salt form), 34.9% yield, 13.5% total yield for 5 steps). LC-MS (ESI): (exact mass: 583.25) m/e=584.3 [M+1]$^+$. $^1$H NMR (400 MHz, DMSO-d$_6$): δ 1.23 (s, 2H), 1.77 (q, 2H, J=11.2 Hz), 2.70 (t, 2H, J=10.4 Hz), 2.84 (t, 2H, J=10.4 Hz), 3.18 (m, 4H), 4.91 (s, br, 2H), 5.31 (m, 2H), 7.01 (t, 2H, J=8.4 Hz), 7.08 (s, 1H), 8.00 (d, 1H, J=8.4 Hz), 8.19 (d, 1H, J=8.8 Hz), 8.56 (s, br, 6H), 8.66 (s, br, 6H), 9.09 (s, 1H), 10.15 (s, 1H), 10.57 (s, 1H), 12.27 (s, 1H). Elemental analysis calculated (%) for C$_{26}$H$_{34}$ClN$_{11}$O$_3$.5H$_2$O.4 HCl: C, 38.08; H, 5.9; N, 18.79. found: C, 37.96; H, 5.91; N, 18.64.

4.5.19 Method B-4: Amide Coupling of Salicylic Acid Chloride Using K$_2$CO$_3$ (Scheme 21)

Scheme 21 describes the synthetic procedure for preparing compound of Formula Ia using method B-4.

Scheme 21

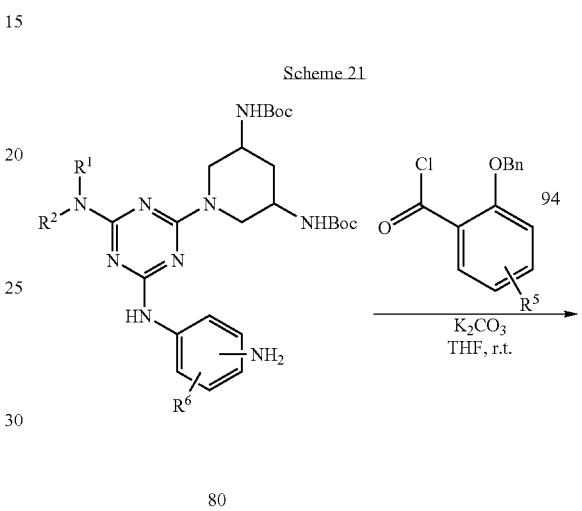

80

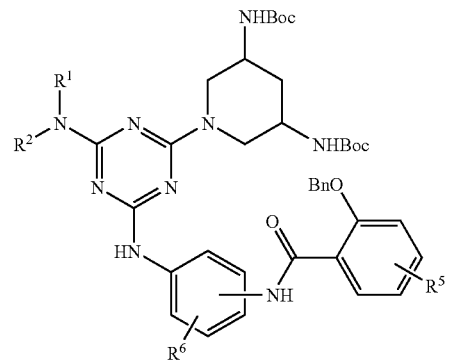

95

R$^1$ and R$^2$ are substituents as defined on p. 3.

R$^5$ and R$^6$ are substituents as defined for substituted aryls.

In this general method, the triazine substituted aniline (80) (1 equiv.), acid chloride (94) (1 equiv.), K$_2$CO$_3$ (10 equiv.) and THF was mixed. The mixture was shaken at room temperature overnight. The inorganic solid was filtered off and the filtrate was concentrated under reduced pressure. The residue was first purified by liquid-liquid extraction (CH$_2$Cl$_2$/sat'd NH$_4$Cl/H$_2$O) and then purified by flash chromatography on silica gel using a gradient of hexane and EtOAc to give the desired product (95).

4.5.20 EXAMPLE 12

Synthesis of Salicylic Acid Derivative of Formula Ia Using Method B-4 (Scheme 21a)

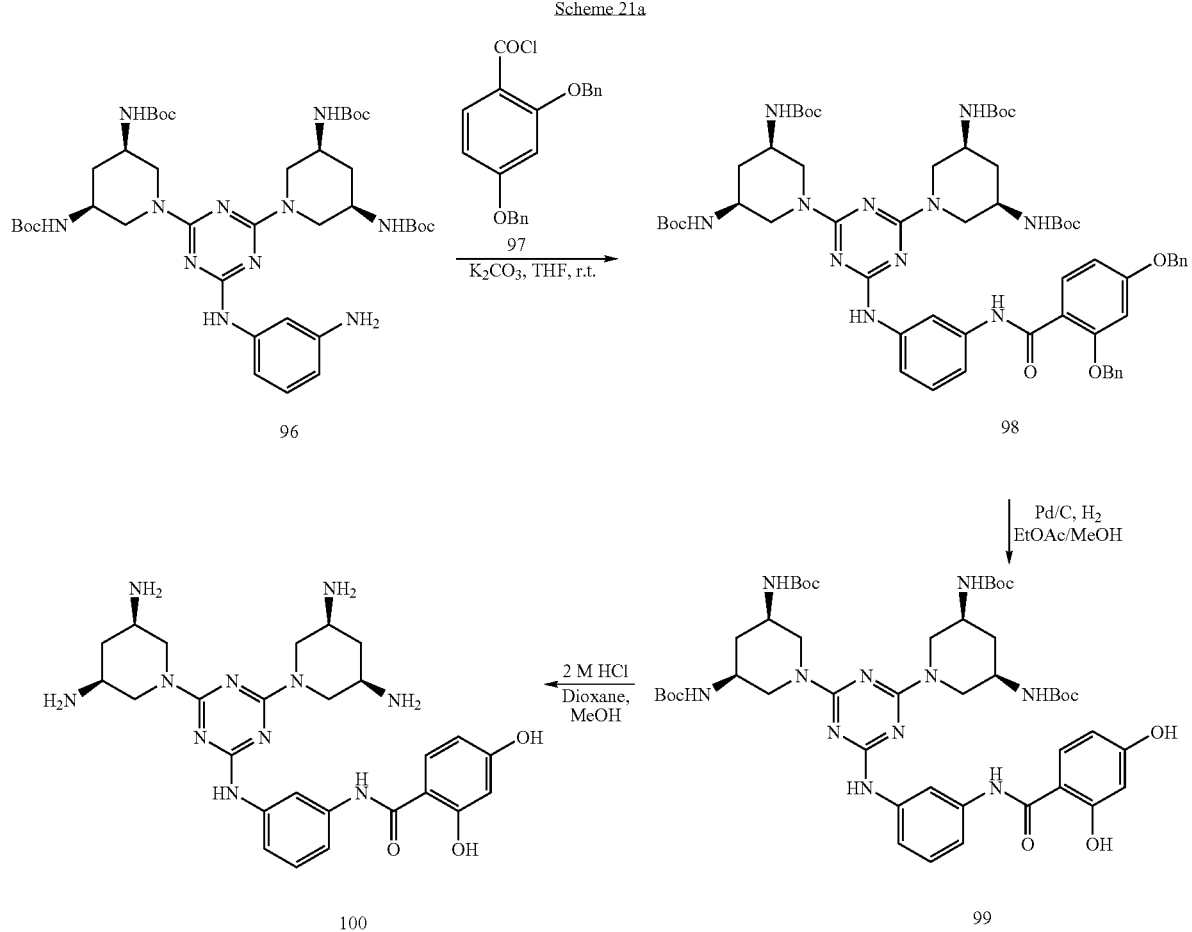

The triazine substituted aniline (96) (174.8 mg, 214.9 μmol), acid chloride 97 (0.25 M in THF, 214.9 μmol), $K_2CO_3$ (300 mg, 2.17 mmol) and 3 mL of THF was mixed. The mixture was shaken at r.t. overnight. The inorganic solid was filtered off and the filtrate was concentrated down under reduced pressure. The residue was first purified by liquid-liquid extraction ($CH_2Cl_2$sat'd $NH_4Cl/H_2O$) and then purified by flash chromatography on silica gel using a gradient of hexane and EtOAc to give the desired product (98) as a white solid. LC-MS: m/e 1130.7 $[M+1]^+$ (exact ms: 1129.60).

Compound 98 was dissolved in 20 mL of methanol and 20 mL of EtOAc. The solution was purged with $N_2$ and Pd/C (10 wt %, dry, 350 mg) was added under $N_2$ atmosphere. The solution was degassed by alternately connecting the system to vacuum, and then to $N_2$ for three times. A balloon containing $H_2$ was then attached to the reaction system. The mixture was stirred at room temperature overnight under slightly positive pressure of $H_2$. LC-MS confirmed the completion of the reaction. Methanol (5 mL) and EtOAc (5 mL) was added to dilute the reaction mixture and the inorganic solid was filtered off through the Celite under reduced pressure. The filtrate was concentrated under reduced pressure to give desired product 99 (157.9 mg, 166 μmol, 77.3% isolated yield for 2 steps) as an off-white solid. LC-MS: m/e 950.8 $[M+1]^+$ (exact ms: 949.50).

Compound 99 (157.9 mg, 166 μmol) was dissolved in 3 mL of methanol. HCl (4.0 M in dioxane, 3 mL) was added and the mixture was shaken at room temperature for 6.5 hours. LC-MS confirmed the completion of the reaction. The solvent was evaporated under reduced pressure to give the desired product (76.4 mg) as a white solid. This crude product was purified by reverse-phase HPLC using a gradient of $CH_3CN$ and $H_2O$ to give the pure desired product 100 (37.6 mg, 46.77 μmol, 28.2% isolated yield calculated based on the molecular weigh of the HCl salt determined by elemental analysis) as the HCl salt. LC-MS: m/e 550.3 $[M+1]^+$ (exact ms: 549.29). Elemental analysis calculated (%) for $C_{26}H_{35}N_{11}O_3$.5HCl.4$H_2O$ (803.99): C, 38.84; H, 6.02; N, 19.16. found: C, 38.56; H, 6.16; N, 19.11. $^1$H NMR (400 MHz, DMSO-$d_6$): δ=10.22 (s, 1H), 9.20–9.30 (m, 1H), 8.44–8.78 (m, 12H), 8.22–8.34 (m, 1H), 7.81 (d, J=8 Hz, 1H), 7.32 (d, J=8 Hz, 1H), 7.25 (t, J=8 Hz, 1H), 7.12–7.18 (m, 1H), 6.45 (d, J=2 Hz, 1H), 6.36 (dd, $J_1$=9.0 Hz, $J_2$=2.2 Hz, 1H), 5.30–5.42 (m, 2H), 4.82–5.02 (m, 2H), 3.06–3.28 (m, 4H), 2.88 (t, J=11.6 Hz, 2H), 2.72 (t, J=11.4 Hz, 2H), 2.42–2.56 (m, 2H), 1.78 (q, J=11.3 Hz, 1H).

4.6 General Method of Synthesis of Formula Ia Compounds

Scheme 22 describes a general synthetic procedure for preparing compounds 17 and 18 of Formula Ia.

This methodology is useful for the production of various derivatives represented by Formula Ia. Other variations of this methodology would be apparent to those skilled in the art. See, e.g., WO 03/101980A1, and the references therein.

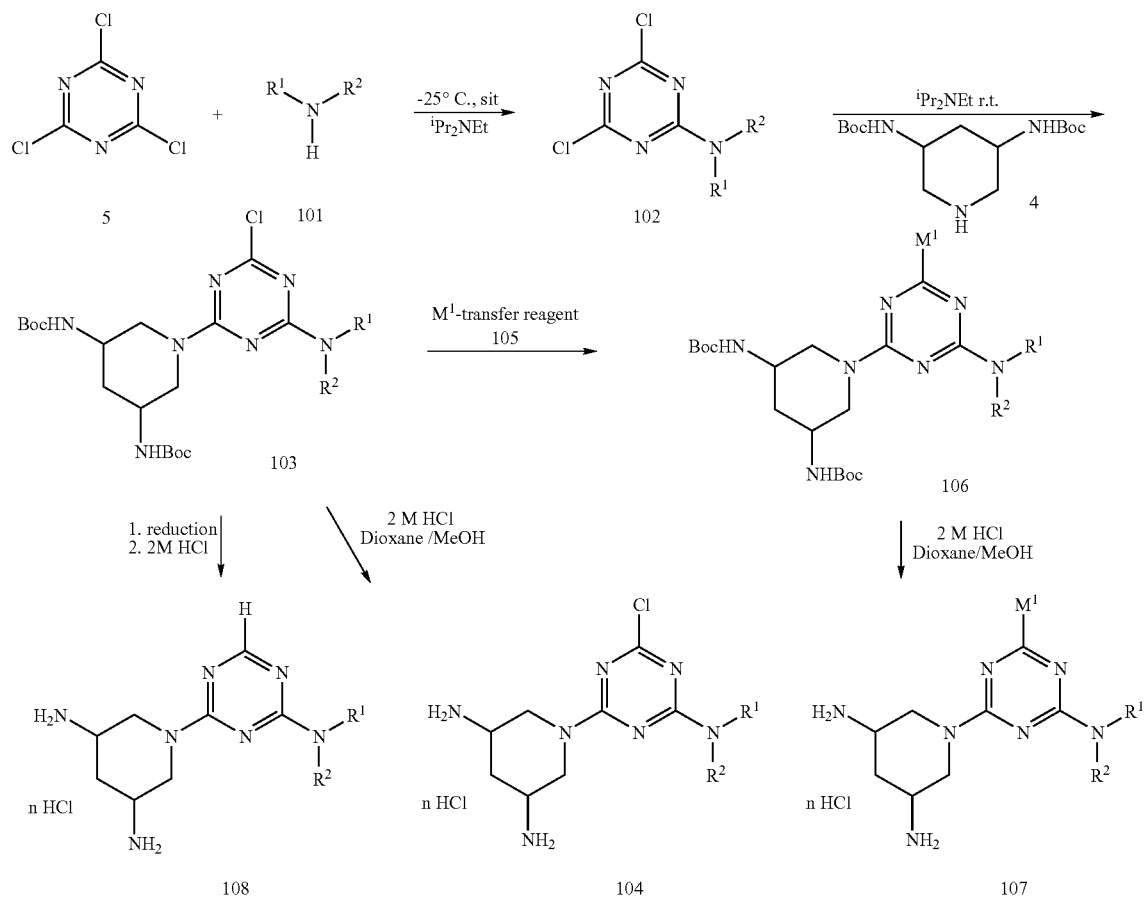

Scheme 22

In this general method, cyanuric chloride, (5) (or any other tri-halogenated (homo or mixed) triazine can be used) is treated sequentially by different nucleophile reagents at increasing temperatures. Preferably the less reactive amines (101), such as aromatic or heteroaromatic amines are used first to displace the most reactive chloride, followed by reactive amines to displace the second chloride and finally replace the last chloride by the nucleophile to form compound 106. The (3R,5S)-3,5-bis(tert-butoxycarbonylamino)-piperidine (4) is used to displace the second chloride atom to give compound 103. Compound 103 can either directly undergo de-protection to give product 104 or continue to react with $M^1$-transfer reagent (wherein the transfer reagent is, e.g., MeOH, $Ph_4Sn$ and the like) (105) to give compound 106. Deprotection of the BOC and other groups of compound 106 furnish the targets of compound 107. Compound 103 can undergo the reduction reaction either by using Raney Nickel and hydrazine or by hydrogenation catalyzed by Pd/C to remove the chloride group followed by the deprotection of the Boc group to give the desired product 108.

4.6.1 EXAMPLE 13

Synthesis of Formula Ia Compound 110 (Scheme 4)

Scheme 23

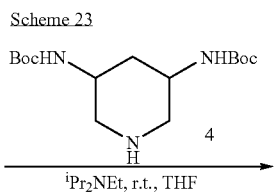

-continued

109

2 M HCl/ Dioxane + MeOH
r.t. overnight

110

A solution of cyanuric chloride, (5) (100 μmol) in 400 uL of THF was mixed with (3R,5S)-3,5-bis(tert-butoxycarbonylamino)-piperidine (4) (63.1 mg, 200 μmol) in 1.6 mL of THF and 200 uL of 1 M $^{i}Pr_2NEt$ in THF (200 μmol). The mixture was shaken at room temperature overnight. LC-MS results confirmed the completion of the reaction. The reaction mixture was dried and worked up by liquid-liquid extraction between $CHCl_3$ and $H_2O$ layers. The organic layer was dried to give crude product 109 with HPLC purity of 100% (ELSD). LC-MS: m/e 742.5 $[M+1]^+$.

Compound 109 was dissolved in 2 mL of MeOH. 2 mL of 4 M of HCl in dioxane was then added at room temperature and the resulting mixture was shaken at room temperature overnight. The mixture was dried and gave 42.9 mg of the desired product 110 as the HCl salt with a purity by HPLC of 100% (ELSD) in 88% yield. LC-MS: m/e 342.3 $[M+1]^+$, 344.3.

4.6.2 EXAMPLE 14

Synthesis of Formula Ia Compound 115 (Scheme 24)

Scheme 24

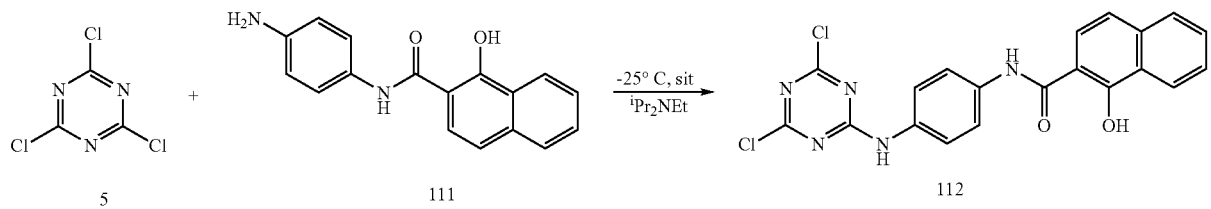

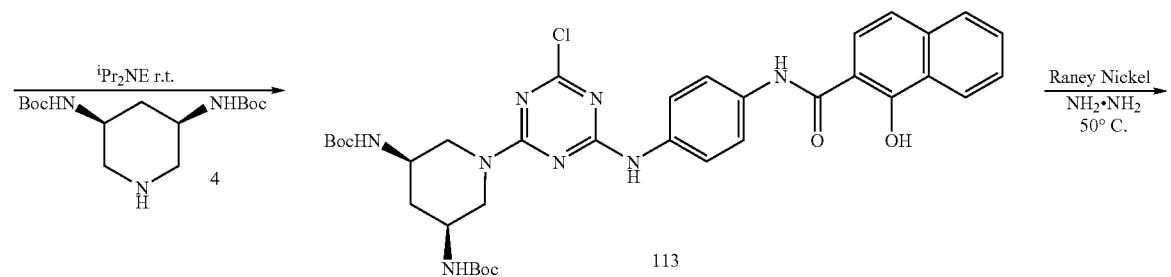

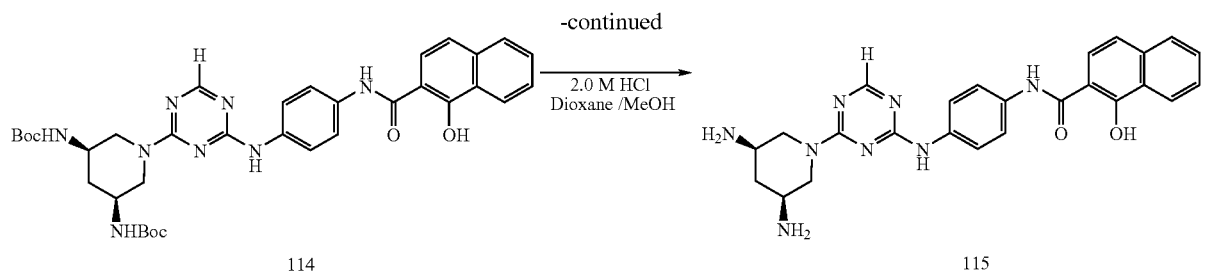

114 → 115

Compound 111 (56 mg, 200 μmol) in 500 μL of THF and 200 μL of $^i$Pr$_2$NEt in 1.0 M THF was combined and cooled at −25° C. for 13 minutes. Cyanuric chloride, compound 5 (37 mg, 200 μmol) was dissolved in 500 μL of THF and first cooled to −25° C. for 15 minutes and then added into above solution. After vortexing, the mixture was let sit at −25° C. overnight.

A slurry of 63 mg of compound 4 in 500 uL of THF and 500 μL of DMF along with $^i$Pr$_2$NEt (200 μL Of 1.0 M in THF) was added into the reaction mixture. The mixture was shaken at room temperature for 19 hours. The LC-MS result indicated the completion of the reaction. The mixture was dried under reduced pressure and the crude product (113) was directly used in the next step.

The above crude product (113) was dissolved in 2 mL of THF and heated at 50° C. Hydrazine (98%, 200 μL) was added followed by 400 μL of Raney Nickel (50% slurry in water). The mixture was heated at 50° C. without cap for 20 minutes. The reaction was cooled and concentrated under reduced pressure to give the crude product (114) as a grey solid. The crude was purified by flash chromatography on silica gel using a gradient of hexane and EtOAc to give the desired product (114). LC-MS: m/e 671.5 [M+1]$^+$.

Compound 114 was dissolved in 1 mL of MeOH and 1 mL of 4.0 M HCl in dioxane was added and the mixture was shaken at room temperature overnight. The mixture was dried to give final product (115) (5.17 mg). LC-MS m/e 471.2 [M+1]$^+$.

4.7 General Method for Synthesis of O-Attached Triazines of Formula Ia (Scheme 25)

Scheme 25 describes a general method for synthesis of O-attached triazines of Formula Ia.

Scheme 25

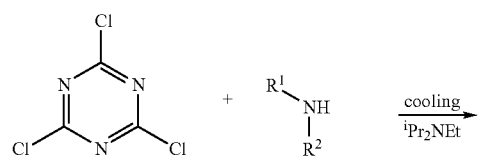

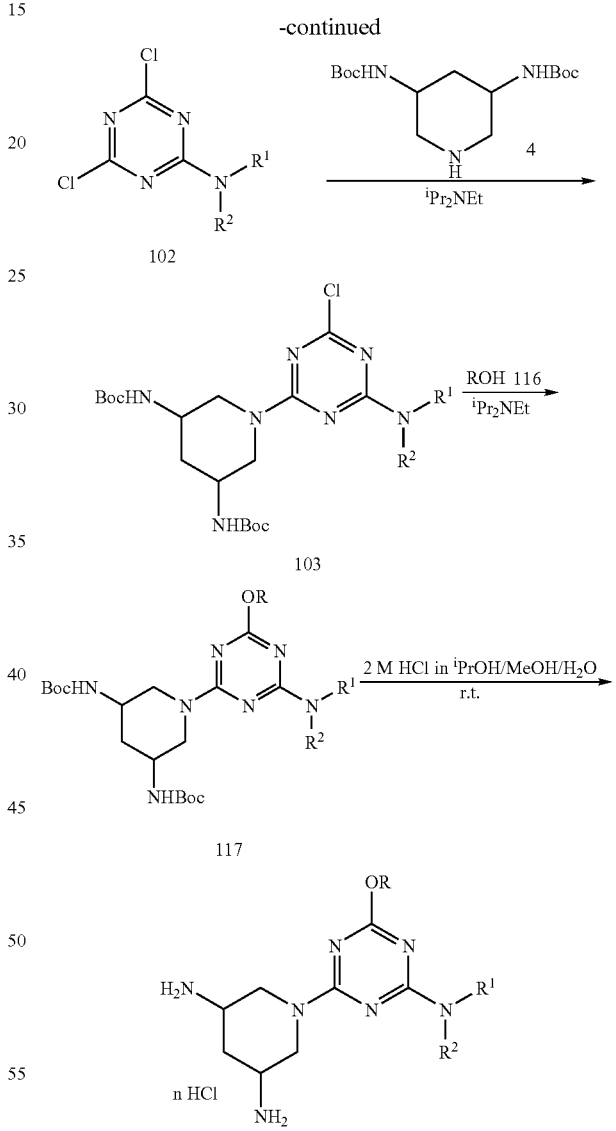

R = optionally substituted (C$_1$–C$_6$)alkyl, aryl, heteroaryl, —(CH$_2$)$_n$—aryl, —(CH$_2$)$_n$—heteroaryl,—(C$_1$–C$_6$) heteroalkyl, cycloalkyl, heterocycloalkyl, —(CH$_2$)$_n$—cycloalkyl, and —(CH$_2$)$_n$—heterocycloalkyl, wherein n is 1–3.

R$^1$ and R$^2$ refer to substituents as defined on page 5.

In this general method, to a cooled (−20° C.) solution of cyanuric chloride (5) (100 μmol) in dry THF (1.5 mL) in an 8 mL vial is added a cooled (−20° C.) solution of the desired aniline (101) (100 mmol) and iPr₂NEt (100 μmol) in dry THF (2 mL). The solution is allowed to stand in a −20° C. freezer for 16 h at which point the progress of the reaction is assessed via TLC (R_f dependent on aniline used) to give compound 102. The solution containing compound 102 is allowed to warm to 5° C. and a suspension of (3R,5S)-3,5-bis(tert-butoxycarbonylamino)-piperidine (4) (100 μmol) in THF (1 mL) and N,N-di-isopropyl-ethylamine (100 μmol) is added with agitation. After 1 h at 5° C., the solution (of 103) is allowed to warm to room temperature and ROH (116) (500 μmol) and ⁱPr₂NEt (500 μmol) in THF is added with agitation. The vial is then capped and placed on a heated shaker at 20° C. to 100° C., preferably from 20° C. to 80° C. for 18 h to 24 h at which point the progress of the reaction is assessed either by TLC or LC-MS.

The solution is diluted (CHCl₃, 50 mL), transferred to a separatory funnel and washed with H₂O (50 mL), saturated NaHCO₃ (50 mL), brine (50 mL), dried (MgSO₄) and concentrated to give a material that is purified either by flash chromatography (0–5% MeOH in CHCl₃) or HPLC to give compound 117. This material is dissolved in MeOH (2 mL) and 5 M HCl (in 2-propanol; 2 mL) is added with agitation. This solution is allowed to stand overnight for 16 h at which point H₂O (1 mL) is added with agitation and allowed to stand for 2 h. The solution is then concentrated to dryness and the solid is purified by HPLC to give the compound 118 as an HCl salt.

Other alkoxy, aryloxy, heteroaryloxy, arylalkoxy, heteroarylalkoxy or hydroxy substituted diaminotriazines were prepared in a similar manner to the protocol exemplified above.

4.7.1 EXAMPLE 15

Synthesis of Formula Ia Compound 123

Scheme 25a describes the synthesis of methoxy-diamino substituted triazine (123).

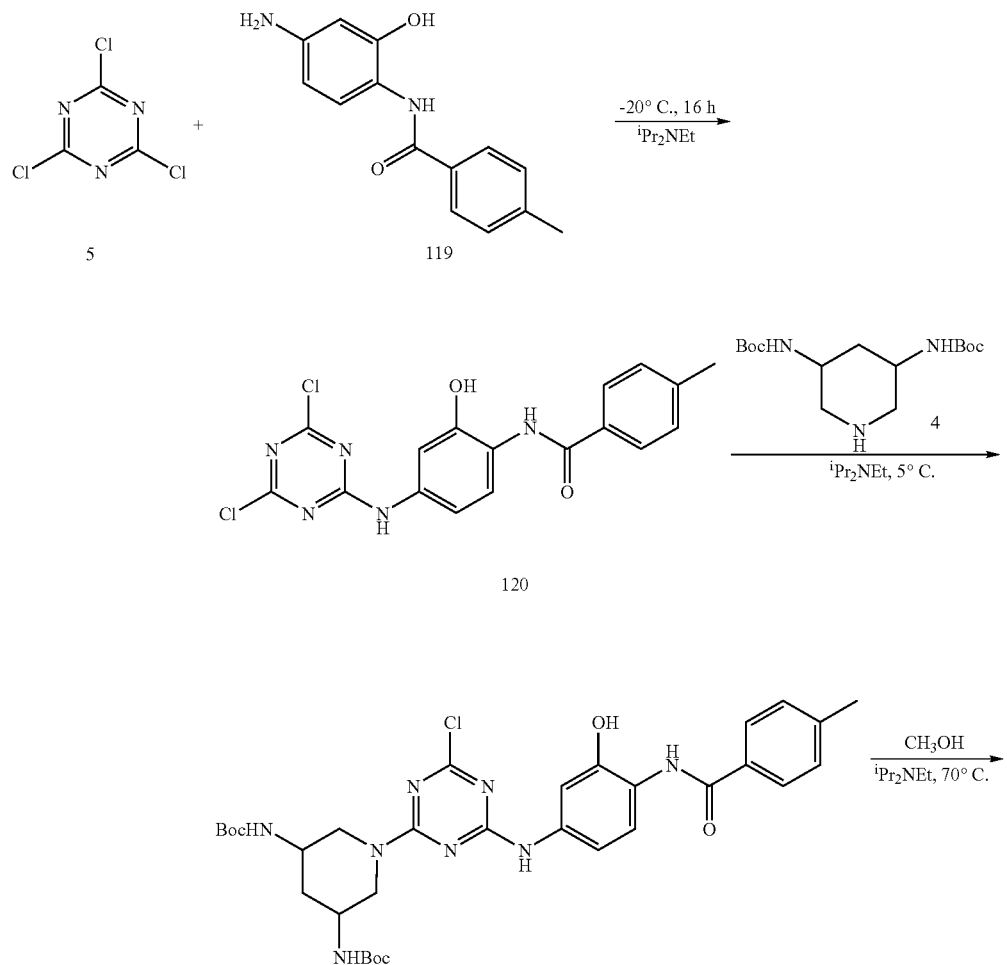

-continued

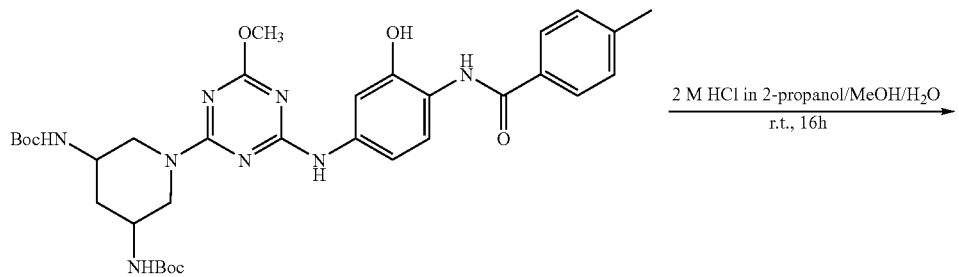

122

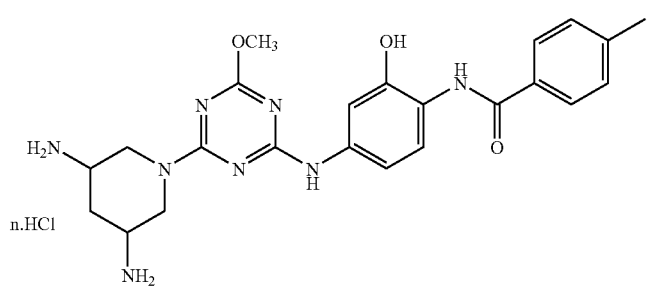

123

To a cooled (−20° C.) solution of cyanuric chloride (5) (100 μmol) in dry THF (1.5 mL) in an 8 mL vial was added a cooled (−20° C.) solution of the desired aniline (119) (100 mmol) and N,N-di-isopropyl-ethylamine (100 μmol) in dry THF (2 mL). The solution was allowed to stand in a −20° C. freezer for 16 h at which point the progress of the reaction was assessed via TLC ($R_f$ dependent on aniline used) to give compound 120. The solution containing compound 120 was allowed to warm to 5° C. and a suspension of (3R,5S)-3,5-bis(tert-butoxycarbonylamino)-piperidine (4) (100 μmol) in THF (1 mL) and iPr$_2$NEt (100 μmol) was added with agitation. After 1 h at 5° C., the solution (of 121) was allowed to warm to room temperature and MeOH (500 mmol) and iPr$_2$NEt (500 μmol) in THF was added with agitation. The vial was then capped and placed on a heated shaker at 70° C. for 18 h at which point the progress of the reaction was assessed either by TLC or LC-MS.

The solution was diluted (CHCl$_3$, 50 mL), transferred to a separatory funnel and washed with H$_2$O (50 mL), saturated NaHCO$_3$ (50 mL), brine (50 mL), dried (MgSO$_4$) and concentrated to give a material that was purified either by flash chromatography (0–5% MeOH in CHCl$_3$) or HPLC to give compound 122. This material was dissolved in MeOH (2 mL) and 5 M HCl (in 2-propanol; 2 mL) was added with agitation. This solution was allowed to stand overnight for 16 h at which point H$_2$O (1 mL) was added with agitation and allowed to stand for 2 h. The solution was then concentrated to dryness and the solid was purified by HPLC to give the compound 123. $^1$H NMR (400 MHz, D$_2$O) δ=1.77 ppm (m, 1H), 2.25 (s, 3H), 2.49–2.59 (m, 1H), 2.87 (m, 2H), 3.26–3.42 (m, 2H), 3.86 (s, 3H), 4.76–4.93 (m, 2H), 6.80–6.93 (m, 1H), 6.98 (br s, 1H), 7.13–7.21 (m, 2H), 7.29 (br d, 1H, J=8 Hz), 7.52–7.62 (m, 2H). LC-MS: m/e 465.0 [M+1]$^+$.

Other methoxy diamino triazines of the Formula Ia compounds shown in Table 1 were prepared in a similar manner to the protocol exemplified above.

4.8 General Methods of Synthesis of Formula Ia Compounds with C-Attachment

Schemes 26 and 27 describe the general procedure for synthesis of the C-attached triazines (129). These methods can also be applied to other cores described in Formula I.

Scheme 26

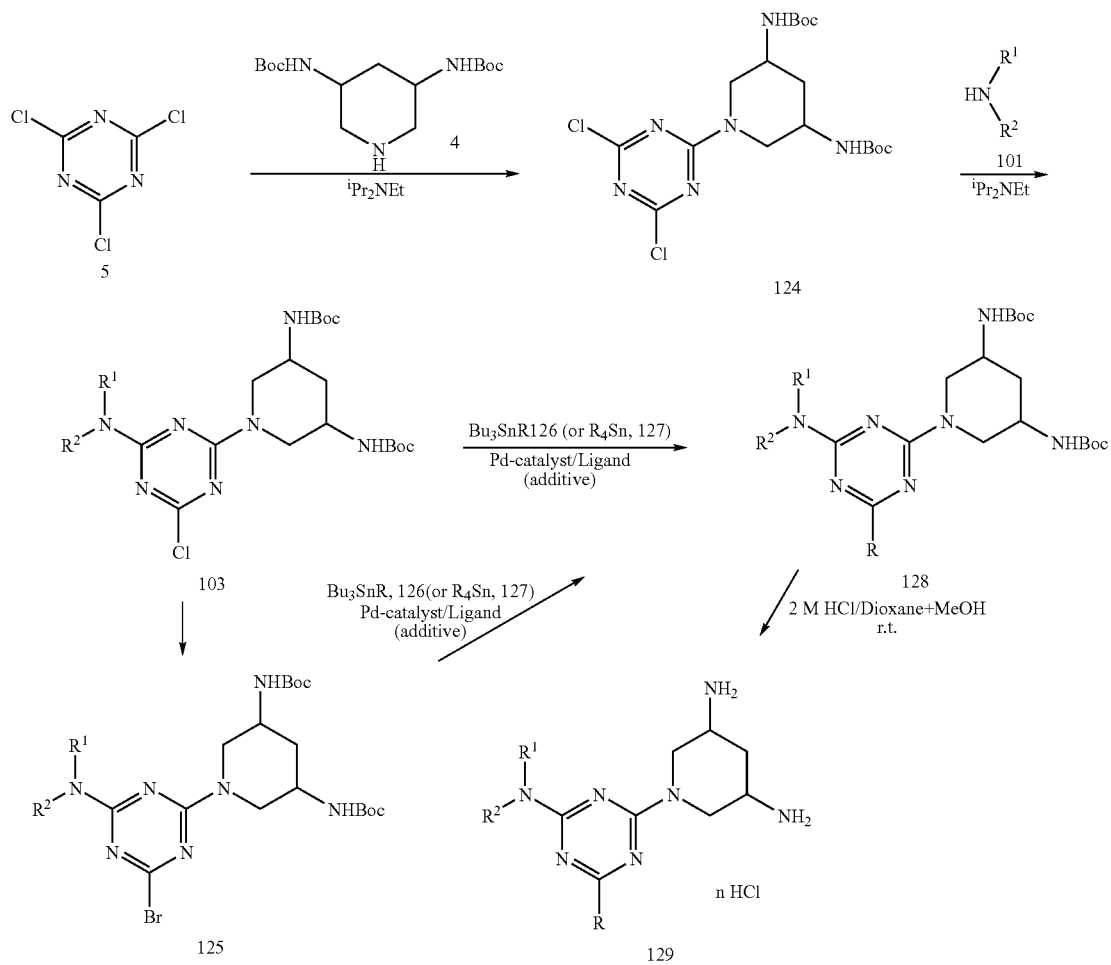

R = optionally substituted —(C$_1$–C$_6$)alkyl, aryl, heteroaryl, heterocycloalkyl, —(CH$_2$)$_n$—heterocycloalkyl, —(CH$_2$)$_n$—aryl, (CH$_2$)$_n$—heteroaryl, —(CH═CH)$_n$—aryl, —(CH═CH)$_n$—heteroaryl, —(C≡C)$_n$-aryl, and —(C≡C)$_n$-heteroaryl.

$R^1$ and $R^2$ refer to substituents as defined on page 5.

In this general method, cyanuric chloride (5) reacts with (3R,5S)-3,5-bis(tert-butoxycarbonylamino)-piperidine (4) in the presence of $^i$Pr$_2$NEt at −25° C. to give compound 124 that further reacts with amine 101 at room temperature in the presence of $^i$Pr$_2$NEt to give compound 103.

Compound 103 can be optionally converted to the corresponding bromo-derivative (125) by the treatment with alkali metal or alkaline earth bromide selected from LiBr, NaBr, MgBr$_2$ in a solvent selected from THF, DMF, Dioxane, HMPA, NMP, toluene and/or a mixture thereof.

Compound 103 (or 125) can react with Bu$_3$SnR (126) or optionally R$_4$Sn (127) in the presence of Pd-catalyst selected from PdCl$_2$(PPh$_3$)$_2$, Pd(PPh$_3$)$_4$, Pd(OAc)$_2$, Pd$_2$(dba)$_3$, PdCl$_2$ and Pd(P($^t$Bu$_3$)$_2$), PdCl$_2$(PCy$_3$)$_2$, PdCl$_2$[P($^t$Bu)$_2$OH] with or without ligand selected from Xantphos, P($^t$Bu)$_3$, BINAP, 2-(dicyclohexylphosphino)biphenyl, 2-(Di-t-butylphosphino)biphenyl, 2-Dicyclohexylphosphino-2'-(N,N-dimethylamino)biphenyl and (R)-(+)-2,2'-Bis(dicyclohexylphosphino)-1,1'-Binaphthyl and with or without an additive selected from Et$_4$NCl, CsF and the imidazolium salt IPr.HCl (IPr=1,3-bis(2,6-diisopropylphenyl)imidazol-2-ylidene) in combination with TBAF ("Bu$_4$NF) as reported in Grasa G. A. and Nolan P., Org. Lett., 3 (1), 119–122, 2001, in a solvent selected from PhMe, DME, xylenes, dioxane, MeCN, DMF, benzene, THF and HMTA at a temperature from 20° C. to 140° C. preferentially between 20–120° C. for 16–72 hours under N$_2$ atmosphere.

The reaction is checked for progress by TLC or LC-MS and upon completion the mixture is diluted with chloroform or other suitable solvent, extracted with water, dried with magnesium or sodium sulfate and concentrated in vacuo. The residue is purified by column chromatography on a silica gel column using a gradient of chloroform-ethyl acetate or chloroform-methanol to give the desired product 29. A related synthesis is described in Littke A. F. and Fu G. C., Angew. Chem. Int. Ed. 2000, 41, 4176–4211.

Treatment of 128 with an excess of 2 M HCl in dioxane and methanol at room temperature, followed by evaporation under reduced pressure provides the target 129.

4.8.1 Another General Method of Synthesis of Formula Ia Compounds with C-attachment.

Scheme 28 describes another general procedure for synthesis of the C-attached triazines as an example. This method can be applied to other cores described in Formula I.

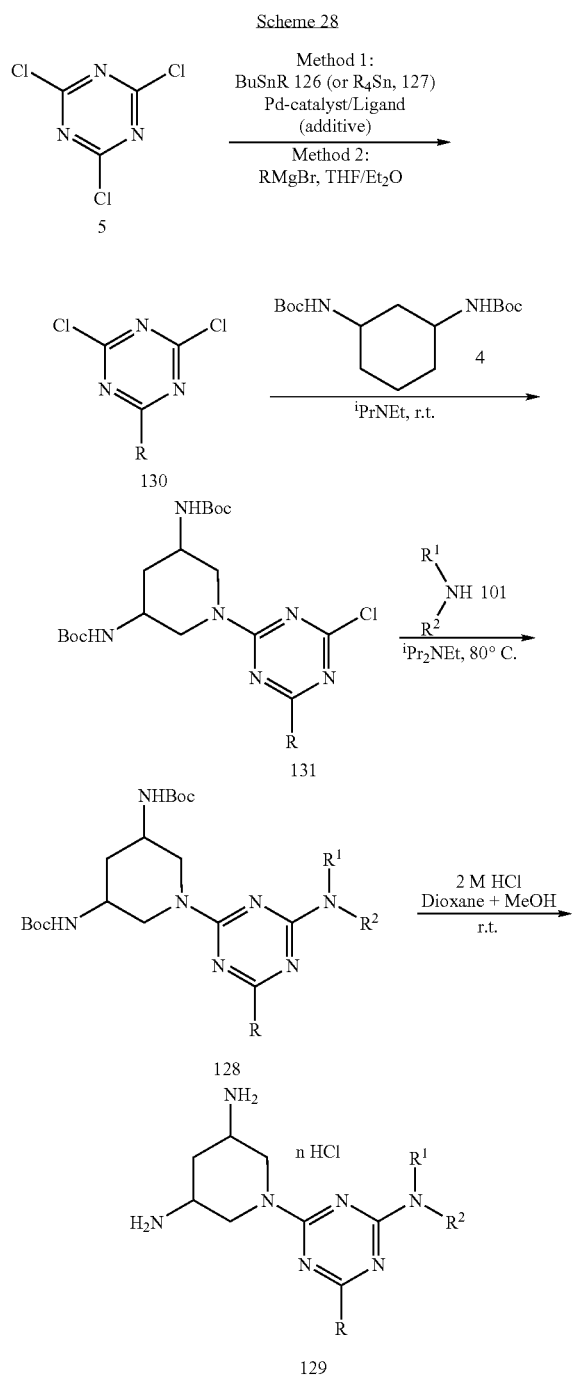

R = optionally substituted —($C_1$–$C_6$) alkyl, aryl, heteroaryl, —$(CH_2)_n$—aryl, —$(CH_2)_n$—heteroaryl, —$(CH=CH)_n$—aryl, —$(CH=CH)_n$—heteroaryl, —$(C≡C)_n$—aryl, and —$(C≡C)_n$—heteroaryl, wherein n is 1–3.

$R^1$ and $R^2$ refer to substituents as defined on page 5.

In this general method 1, cyanuric chloride (5) can react with $Bu_3SnR$ (126) or optionally $R_4Sn$ (127) in the presence of Pd-catalyst selected from $PdCl_2(PPh_3)_2$, $Pd(PPh_3)_4$, $Pd(OAc)_2$, $Pd_2(dba)_3$, $PdCl_2$ and $Pd(P(^tBu_3)_2)$, $PdCl_2(PCy_3)_2$, $PdCl_2[P(^tBu)_2OH]$ with or without ligand selected from Xantphos, $P(^tBu)_3$, BINAP, 2-(dicyclohexylphosphino)biphenyl, 2-(di-t-butylphosphino)biphenyl, 2-Dicyclohexylphosphino-2'-(N,N-dimethylamino)biphenyl and (R)-(+)-2,2'-Bis(dicyclohexylphosphino)-1,1'-Binaphthyl and with or without additive selected from $Et_4NCl$, CsF and the imidazolium salt IPr.HCl (IPr=1,3-bis(2,6-diisopropylphenyl) imidazol-2-ylidene) in combination with TBAF ("$Bu_4NF$) as reported in Grasa G. A. and Nolan P., *Org. Lett.*, 3 (1), 119–122, 2001, in a solvent selected from PhMe, DME, O-xylene, Dioxane, MeCN, DMF, benzene, THF and HMPA at a temperature from 20° C. to 140° C. preferentially between 20–120° C. for 16–72 hours under $N_2$ atmosphere. The reaction is checked for progress by TLC or LC-MS and upon completion the mixture (130) is directly used in the next step. A related synthesis is described in Littke A. F. and Fu G. C., *Angew. Chem. Int. Ed.* 2000, 41, 4176–4211.

In another alternative general method 2, a cooled (−20° C.) THF solution of cyanuric chloride is treated with an ethereal THF solution ($Et_2O$:THF 2:3 v/v) of RMgBr ([cyanuric chloride]/[RMgBr]=1/1 molar ratio). The temperature is raised to 5° C. and the mixture is stirred until the complete conversion of cyanuric chloride into the intermediate 130 is observed (TLC, LC-MS). The mixture is directly used in the next step. A related synthesis is described in Rita Menicagli, Simona Samaritani, Giovanni Signore, Francesca Vaglin and Lisa Dalla Via, *J. Med. Chem.* 2004, 47, 4649–4652.

Compound 130 is treated with slight excess of (3R,5S)-3,5-bis-(tert-butoxycarbonylamino)-piperidine (4) in the presence of $^iPr_2NEt$ at room temperature. The reaction is checked for progress by TLC or LC-MS and upon completion the resulting mixture (131) is treated with amine 101 in the presence of $^iPr_2NEt$ and is heated at 80° C. for 16–72 hours. The reaction is checked for progress by TLC or LC-MS and upon completion the mixture is diluted with chloroform or other suitable solvent, extracted with water, dried with magnesium or sodium sulfate and concentrated in vacuo. The residue is purified by column chromatography on a silica gel column using a gradient of hexane-ethyl acetate to give the desired product 128.

Treatment of 128 with excess of 2.0 M HCl in dioxane and methanol at room temperature, followed by evaporation under reduced pressure provides the target 129.

4.9 General Method of Synthesis of Formula Ib Compounds (135)

Scheme 29 describes a general synthetic procedure for preparing compound of Formula Ib.

Scheme 29

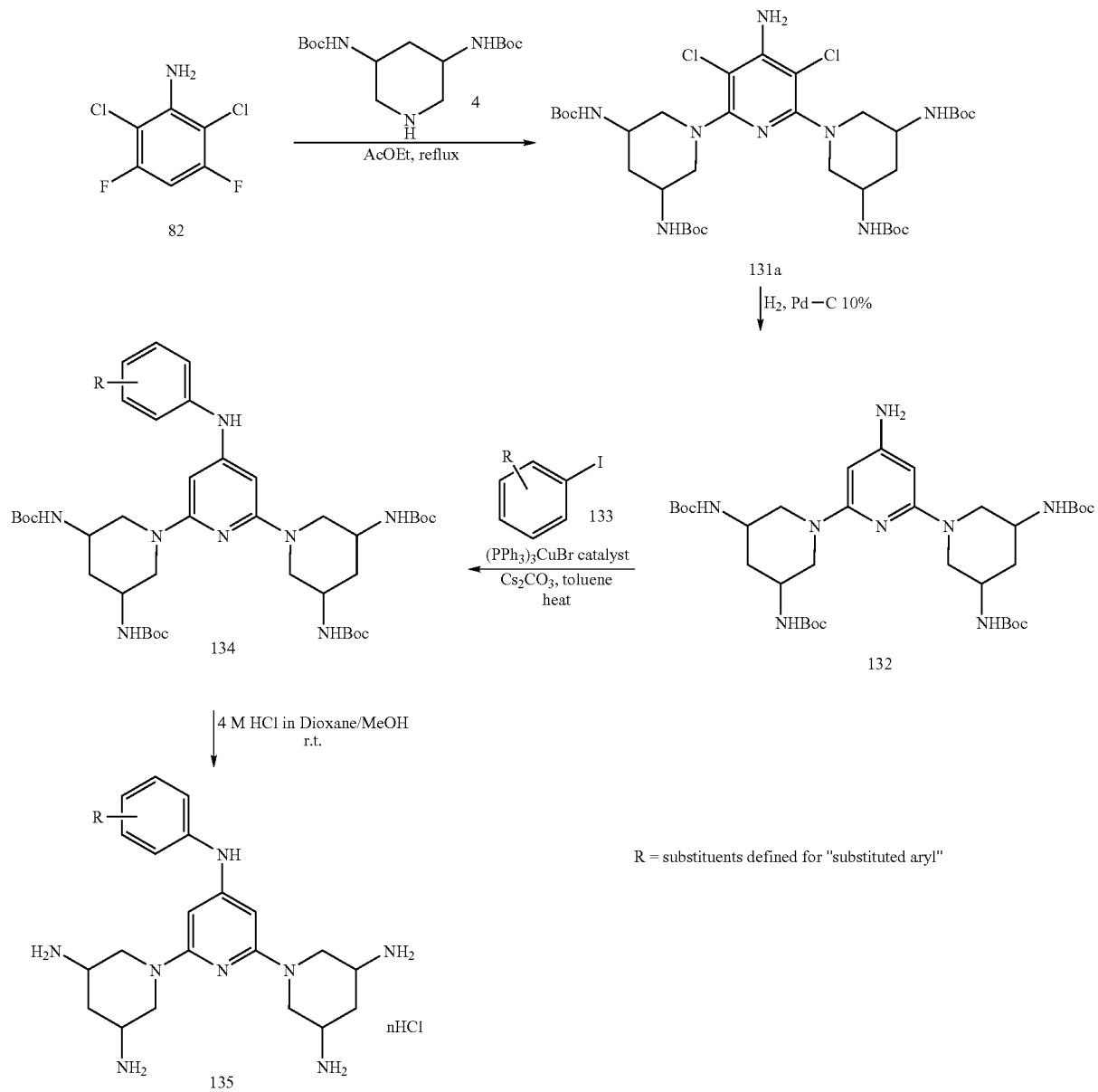

R = substituents defined for "substituted aryl"

4-Amino-3,5-dichloro-2,6-difluoropyridine (82) is reacted with (3R,5S)-3,5-bis(tert-butoxycarbonylamino)-piperidine (4) in a solvent selected from acetonitrile, THF, ethyl acetate, ethylene glycol dimethyl ether, dioxane, DMF, toluene or chlorobenzene, optionally in the presence of a base, selected from diisopropylethylamine, triethylamine, potassium or cesium carbonate, potassium or cesium fluoride or DBU at a temperature from 20° C. to 120° C., preferentially between 30 to 110° C. The reaction is checked for progress by TLC or HPLC and upon completion the mixture is diluted with chloroform or other suitable solvent extracted with water, dried with magnesium or sodium sulfate and concentrated in vacuo. The residue is column chromatographed on a silica gel column, using a gradient of chloroform-ethyl acetate or chloroform-methanol.

The purified bis-piperidino-dichloro derivative 131a is then hydrogenated over Pd—C or Pd—BaSO$_4$ at atmospheric, or elevated pressure of 1 to 500 psi, preferably 10 to 50 psi in a solvent selected from methanol, ethanol, tetrahydrofuran or ethyl acetate, optionally in the presence of a base, such as triethylamine, sodium, potassium or calcium carbonate. When the reaction is complete by LC/MS, the catalyst is removed by filtration and the product 132 is isolated by column chromatography on silica gel using a dichloromethane-ethyl acetate gradient, followed by concentration in vacuo. Related chemical transformations are described in Menichincheri et al., *Tetrahedron Letters*, 44 519–522 (2003).

Subsequent reaction of the 4-aminopyridine derivative 132 with an iodoarene derivative 133 in a solvent selected from toluene, xylenes, anisole or chlorobenzene in the presence of tris-triphenylphosphine copper bromide [Cu(PPh₃)₃Br] and cesium carbonate at an elevated temperature between 80 to 120° C., preferably 100 to 110° C., in an argon atmosphere furnishes after column chromatography on silica gel the arylamino derivative 134. Related chemical transformations are described in Gujadhur, R. et al., *Tetrahedron Letters*, 42, 4791–4793 (2001).

Treatment of 134 with excess of 4 M HCl in dioxane in methanol at room temperature, followed by evaporation under reduced pressure provides the target 135.

This methodology is useful for the production of various derivatives represented by Formula Ib. Other variations of this methodology would be apparent to those skilled in the art.

Another general method to synthesize Formula Ib compounds would follow Scheme 29, but using a different starting material with following changes shown in the scheme 30.

4.9.1 EXAMPLE 16

Synthesis of Compound 144 of Formula Ib

Scheme 30 describes the synthetic procedure for preparing compound 144 of Formula Ib.

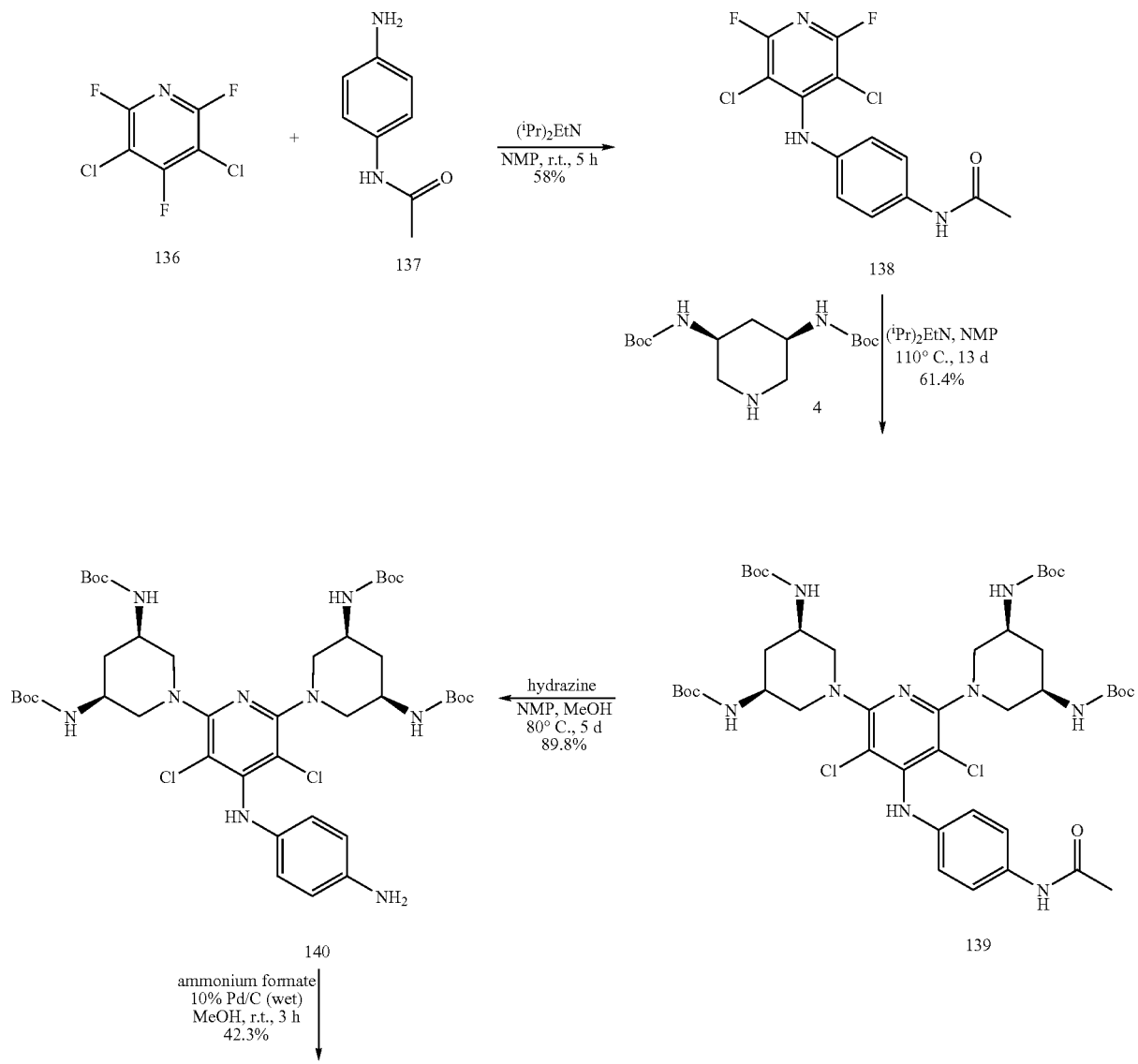

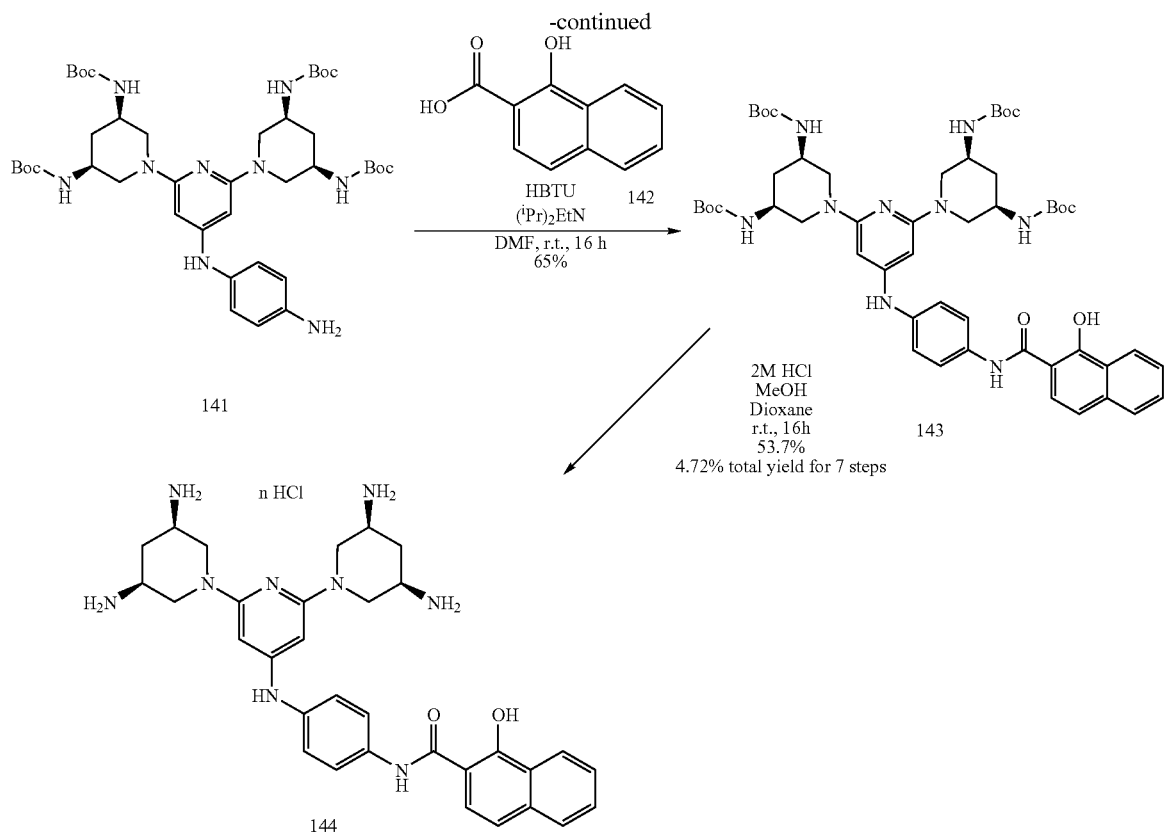

N-[4-(3,5-dichloro-2,6-difluoro-pyridin-4-ylamino)-phenyl]-acetamide (138)

3,5-Dichloro-2,4,6-trifluoro-pyridine (136) (1 g, 4.95 mmol) and N-(4-Amino-phenyl)-acetamide (137) (0.743 g, 4.95 mmol) were dissolved in NMP (12 mL), $^i$Pr$_2$EtN (9.9 mmol) was added and the mixture was shaken at room temperature for 5 hours. TLC and LC-MS indicated complete reaction at this point. The mixture was diluted with EtOAc (50 mL), washed with NaHCO$_3$ (aqueous sat., 50 mL) and passed through a plug of silica gel to remove any baseline impurities. Upon concentration, the desired product (138) precipitated as a beige/pink powder that was collected by filtration under reduced pressure followed by drying under high vacuum for 16 h (1.43 g, 2.88 mmol, 58% yield). LC-MS (ESI): (exact mass: 331.01) m/e=332.1 [M+1]$^+$ (100%), 664.9 [2M+1]$^+$ (30%), 996.2 [3M+1]$^+$ (10%). $^1$H NMR (400 MHz, DMSO-d$_6$): δ 2.03 (s, 3H), 6.99 (d, 2H, J=7.2 Hz), 7.49 (d, 2H, J=6.8 Hz), 9.00 (s, 1H), 9.89 (s, 1H). $^{19}$F NMR (400 MHz, DMSO-d$_6$): δ−76.55 (TFA reference), −75.89 (s, 2F).

N-[4-(3,5-dichloro-2,6-bis-((3R,5S)-3,5-bis-(tert-Butoxycarbonylamino)-piperidin-1-yl)-pyridin-4-ylamino)-phenyl]-acetamide (139)

N-[4-(3,5-dichloro-2,6-difluoro-pyridin-4-ylamino)-phenyl]-acetamide (138) (0.5 g, 1.5 mmol) and (3R,5S)-3,5-bis-(tert-butoxycarbonylamino)-piperidine (4) (1.01 g, 3.2 mmol) were combined in NMP (16 mL) and $^i$Pr$_2$EtN (4.8 mmol) was added. The mixture was heated at 110° C. for 120 h in a Teflon septum capped 40 mL I-Chem vial. LC-MS indicated nearly complete reaction at this point. The mixture was diluted with EtOAc (50 mL), washed with water (25 mL), NaHCO$_3$ (aqueous sat., 25 mL) and brine (25 mL) via extraction, dried over MgSO$_4$ and concentrated to give a white powder. Purification by flash chromatography on silica gel using a gradient of hexane and EtOAc (eluding with 15–100% EtOAc in hexane for 30 minutes) gave the desired product (139) as a white powder upon concentration (0.849 g, 0.92 mmol, 61.4% yield). LC-MS (ESI): (exact mass: 921.43) m/e=922.5 [M+1]$^+$ (100%).

N-(3,5-dichloro-2,6-bis-((3R,5S)-3,5-bis-(tert-Butoxycarbonylamino)-piperidin-1-yl)-pyridin-4-yl)-benzene-1,4-diamine (140)

N-[4-(3,5-dichloro-2,6-bis-((3R,5S)-3,5-bis-(tert-butoxycarbonylamino)-piperidin-1-yl)-pyridin-4-ylamino)-phenyl]-acetamide (139) (0.849 g, 0.92 mmol) was dissolved in MeOH (5 mL) and NMP (10 mL). Hydrazine (10 mL) was added and the mixture was heated at 80° C. with shaking in a 40 mL I-Chem vial for 5 days. LC-MS at this point indicated nearly complete deprotection. The mixture was diluted with EtOAc (50 mL), washed with water (4×25 mL) and brine (25 mL) via extraction, dried over MgSO$_4$ and concentrated to give a yellow oil. Purification by flash chromatography using a gradient of hexane and EtOAc (eluding with 15–100% EtOAc in hexane in 30 minutes) gave the desired product (140) as a beige powder upon concentration (0.728 g, 0.826 mmol, 89.8% yield). LC-MS (ESI): (exact mass: 879.42) m/e=880.5 [M+1]$^+$ (100%).

N-(2,6-bis-((3R,5S)-3,5-bis-(tert-butoxycarbonylamino)-piperidin-1-yl)-pyridin-4-yl)-benzene-1,4-diamine (141)

N-(3,5-dichloro-2,6-bis-((3R,5S)-3,5-bis-(tert-butoxycarbonylamino)-piperidin-1-yl)-pyridin-4-yl)-benzene-1,4-diamine (140) (0.205 g, 0.233 mmol) was dissolved in MeOH (15 mL). Pd/C (1 g, 10%, wet) was added followed by ammonium-formate (2 g). The mixture was shaken in a Teflon septum capped 40 mL I-Chem vial, with occasional venting, for 3 hours. LC-MS indicated complete de-chlorination at this point. The mixture was filtered through a plug of Celite and the filtrate was concentrated and purified by flash chromatography using a gradient of hexane and EtOAc (eluding with 15–100% EtOAc in hexane in 30 minutes followed by 100% EtOAc in 10 minutes) to give the desired product (141) as a yellow/green oil (0.08 g, 0.098 mmol, 42.3% yield). LC-MS (ESI): (exact mass: 811.50) m/e=812.7 [M+1]$^+$ (100%).

1-Hydroxy-naphthalene-2-carboxylic acid [4-(2,6-bis-((3R,5S)-3,5-bis-(tert-butoxycarbonylamino)-piperidin-1-yl)-pyridin-4-ylamino)-phenyl]-amide (143)

1-Hydroxy-naphthalene-2-carboxylic acid (142) (0.028 g, 0.148 mmol) was dissolved in DMF (1 mL), $^i$Pr$_2$EtN (0.222 mmol) was added followed by 2-(1H-benzotriazol-1-yl)-1,1,3,3-tetramethyl-uronium hexafluorophosphate (HBTU) (0.062 g, 0.163 mmol) and the mixture was shaken in an 8 mL Teflon septum capped vial for 20 minutes. N-(2,6-bis-((3R,5S)-3,5-bis-(tert-butoxycarbonylamino)-piperidin-1-yl)-pyridin-4-yl)-benzene-1,4-diamine (141) (0.08 g, 0.0986 mmol) was added and the mixture was shaken at room temperature for 16 h. LC-MS indicated complete coupling at this point. The mixture was diluted with EtOAc (25 mL), washed with water (15 mL), NaHCO$_3$ (aqueous sat., 15 mL) and brine (15 mL) via extraction, dried over MgSO$_4$ and concentrated to give an orange/green oil. Purification by flash chromatography using a gradient of hexane and EtOAc (eluding with 15–100% EtOAc in hexane in 30 minutes) gave the desired product (143) as a greenish-white powder upon concentration (0.063 g, 0.064 mmol, 65% yield). LC-MS (ESI): (exact mass: 981.53) m/e=982.6 [M+1]$^+$ (100%).

1-Hydroxy-naphthalene-2-carboxylic acid [4-(2,6-bis-((3R,5S)-3,5-bis-amino-piperidin-1-yl)-pyridin-4-ylamino)-phenyl]-amide (144)

1-Hydroxy-naphthalene-2-carboxylic acid [4-(2,6-(3R,5S)-((3R,5S)-3,5-bis-(tert-butoxycarbonylamino)-piperidin-1-yl)-pyridin-4-ylamino)-phenyl]-amide (143) (0.06 g=0.0611 mmol) was dissolved in MeOH (2 mL) and 4.0 M HCl/dioxane (2 mL) was added. The mixture was shaken at room temperature for 16 h in a sealed 40 mL I-Chem vial. LC-MS indicated complete deprotection at this point. The mixture was concentrated to give a greenish-brown solid. Purification by reverse-phase HPLC followed by concentrating and lyophilization from 0.25 M HCl/H$_2$O twice gave the desired product (144) as the HCl salt form as a green powder [0.028 g, 0.033 mmol (calculated based on the molecular weigh of the HCl salt determined by elemental analysis), 53.7% yield, 4.72% total yield for 6 steps]. LC-MS (ESI): (exact mass: 581.32) m/e=582.3 [M+1]$^+$ (100%). $^1$H NMR (400 MHz, DMSO-d$_6$): δ 1.71 (q, 2H, J=12 Hz), 2.44 (s, br, 2H), 2.68 (t, 4H, J=11.6 Hz), 3.17 (s, br, 4H), 3.85 (s, br, 2H), 4.60 (s, br, 4H), 5.80 (s, 2H), 7.20 (d, 2H, J=8.4 Hz), 7.44 (d, 1H, J=8.4 Hz), 7.56 (t, 1H, J=7.2 Hz), 7.70–7.63 (m, 3H), 7.86 (d, 1H, J=8 Hz), 8.16 (d, 1H, J=8.8 Hz), 8.28 (d, 1H, J=8.4 Hz), 8.52 (s, br, 12H), 10.49 (s, 1H). Elemental analysis calculated (%) for C$_{32}$H$_{39}$N$_9$O$_2$.5H$_2$O.5 HCl: C, 45.0; H, 6.37; N, 14.76. found: C, 44.66; H, 6.10; N, 14.39.

4.10 General Method of Synthesis of Formula Ic Compounds

Scheme 31 describes a general synthetic procedure for preparing compound of Formula Ic.

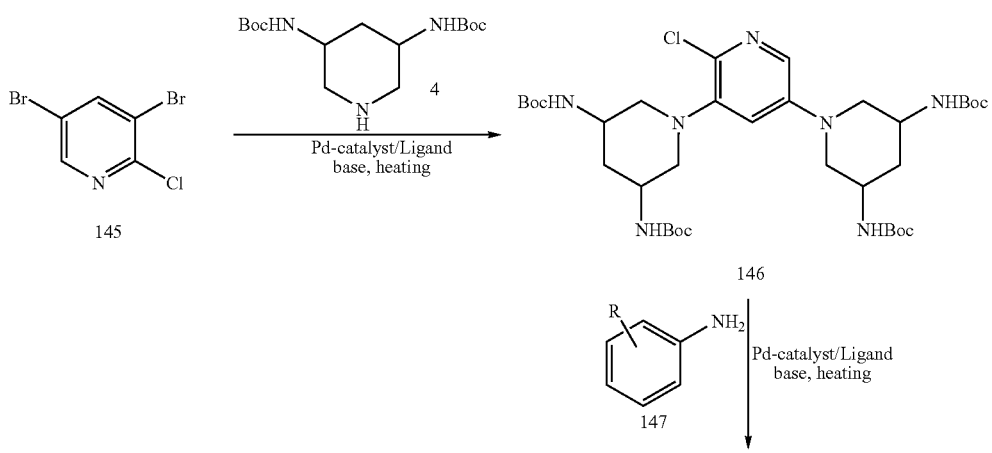

-continued

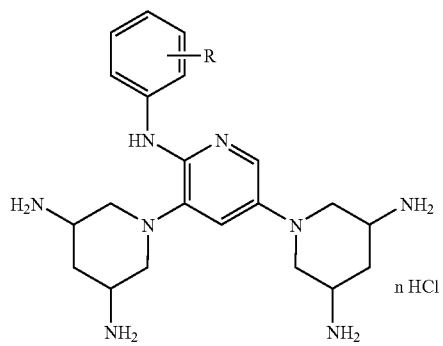

149

2 M HCl in Dioxane/MeOH r.t.

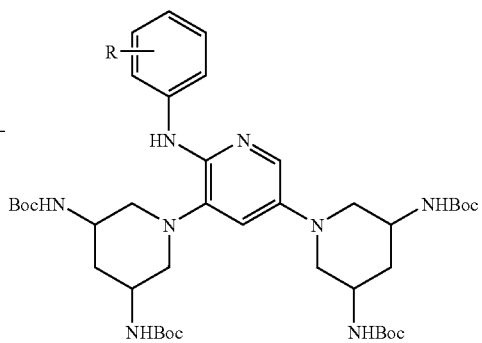

148 n HCl

R = substituents defined for "substituted aryl"

2-chloro-3,5-di-bromo-pyridine (145), in 30% excess relative to compound 4, reacts with (3R,5S)-3,5-bis(tert-butoxycarbonylamino)-piperidine (4) in the presence of Pd-catalyst selected from $Pd_2(dba)_3$, $Pd(OAc)_2$, $PdCl_2(PCy_3)_2$, $PdCl_2[P(^tBu)_2OH]$, ligand selected from Xantphos, $P(^tBu)_3$, BINAP, 2-(dicyclohexylphosphino)biphenyl, 2-(di-t-butylphosphino)biphenyl, 2-dicyclohexylphosphino-2'-(N,N-dimethylamino)biphenyl, (R)-(+)-2,2'-bis(dicyclohexylphosphino)-1,1'-binaphthyl, and base selected from $Cs_2CO_3$, $K_2CO_3$, $K_3PO_4$ in a solvent selected from PhMe, DME, O-xylenes, dioxane and HMPA at a temperature from 80° C. to 140° C., preferentially between 100° C. and 120° C. for 16–72 hours under $N_2$ atmosphere. The reaction is checked for progress by TLC or HPLC and upon completion, the mixture is diluted with chloroform or other suitable solvents and the inorganic solid was filtered off through Celite.

The resulting filtrate is washed with water via extraction, dried with magnesium or sodium sulfate and concentrated in vacuo. The residue is column chromato graphed on a silica gel column, using a gradient of chloroform-ethyl acetate or chloroform-methanol to generate the bis-aminated pure product 146. Related chemical transformations and the selectivity of the reaction are described in Jianguo Ji, Tao Li and William H. Bunnelle, *Organic Letters*, 5 (24), 4611–4614 (2003).

Compound 146 is treated with an aniline (147) to react the same way as in the previous step using excess aniline to give compound 148.

Treatment of 148 with excess of 2 M HCl in dioxane and methanol at room temperature overnight, followed by evaporation under reduced pressure provides the target 149.

4.10.1 Another General Method of Synthesis of Formula Ic Compounds.

Scheme 32 describes a general synthetic procedure for preparing compound 149 of Formula Ic.

Scheme 32

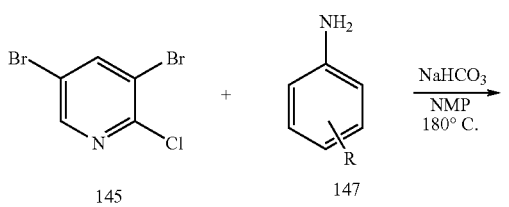

145     147

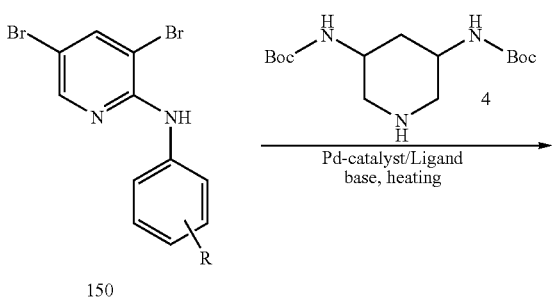

150

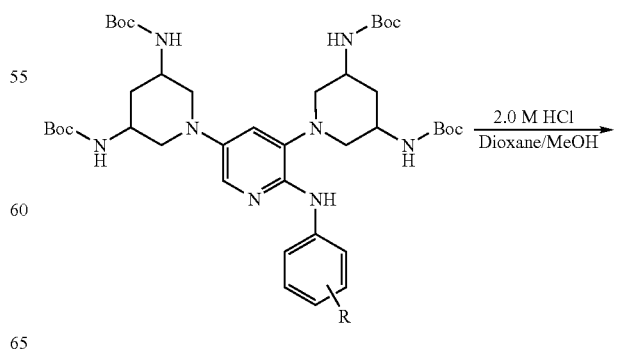

148

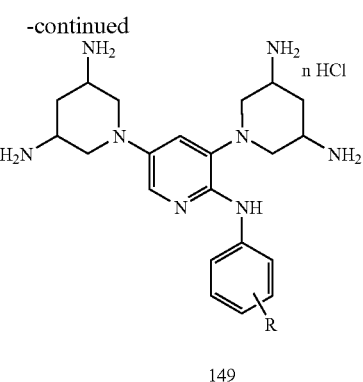

149

The 3,5-dibromo-2-chloro-pyridine (145) (1 equiv.), aniline (147) (3 equiv.), NaHCO$_3$ (2 equiv.) were mixed and suspended in NMP (0.5 M). The mixture was heated to 180° C. for 120 h. The reaction is monitored by TLC and LC-MS. Upon completion of the reaction, the mixture is diluted with EtOAc, washed with saturated aqueous NaHCO$_3$ and brine via extraction, dried over MgSO$_4$ and concentrated to give a crude product that is purified by flash chromatography on silica gel using a gradient of hexane and EtOAc to give the desired product 150.

Compound 150 reacts with (3R,5S)-3,5-bis(tert-butoxycarbonylamino)-piperidine (4) in the presence of Pd-catalyst selected from Pd$_2$(dba)$_3$, Pd(OAc)$_2$, PdCl$_2$(PCy$_3$)$_2$, PdCl$_2$[P($^t$Bu)$_2$OH], ligand selected from Xantphos, P($^t$Bu)$_3$, BINAP, 2-(dicyclohexylphosphino)biphenyl, 2-(di-t-butylphosphino)biphenyl, 2-dicyclohexylphosphino-2'-(N,N-dimethylamino)biphenyl, (R)-(+)-2,2'-bis(dicyclohexylphosphino)-1,1'-binaphthyl, and base selected from Cs$_2$CO$_3$, K$_2$CO$_3$, K$_3$PO$_4$ in a solvent selected from PhMe, DME, O-xylenes, dioxane and HMPA at a temperature from 80° C. to 140° C., preferentially between 100° C. and 120° C. for 16–72 hours under N$_2$ atmosphere. The reaction is checked for progress by TLC or HPLC and upon completion, the mixture is diluted with chloroform or other suitable solvents and the inorganic solid was filtered off through Celite. The resulting filtrate was washed with water via extraction, dried with magnesium or sodium sulfate and concentrated in vacuo. The residue is column chromatographed on a silica gel column, using a gradient of chloroform-ethyl acetate or chloroform-methanol to generate the bis-aminated pure product 148. Related chemical transformations and the selectivity of the reaction are described in Jianguo Ji, Tao Li and William H. Bunnelle, *Organic Letters*, 5 (24), 4611–4614 (2003).

The Boc-groups of compound 148 can be removed by treating with 2.0 M HCl in dioxane/MeOH at room temperature. The reaction is monitored by LC-MS. Upon completion of the reaction, the mixture is concentrated under reduced pressure to give a crude that is purified by reverse phase HPLC followed by lyophilization twice from aqueous 0.25 M HCl to give the desired product (149) as the HCl salt.

4.11 General Methods of Synthesis of Formula Ib and Id Compounds 4.11.1 Synthesis of Formula Ib and Id Compounds by Schemes 33 and 34

Schemes 33 & 34 describe the general synthetic procedures for preparing compounds 156 and 161 of Formulas Ib and Id.

Scheme 33

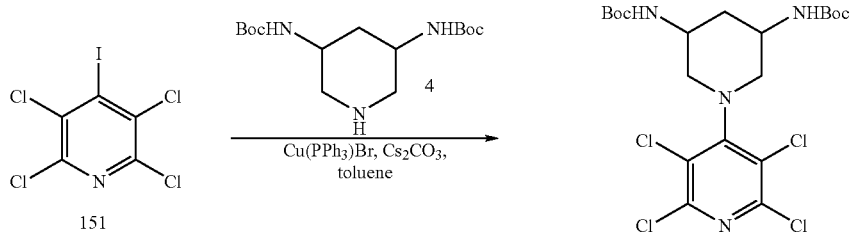

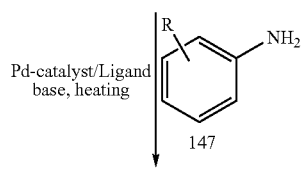

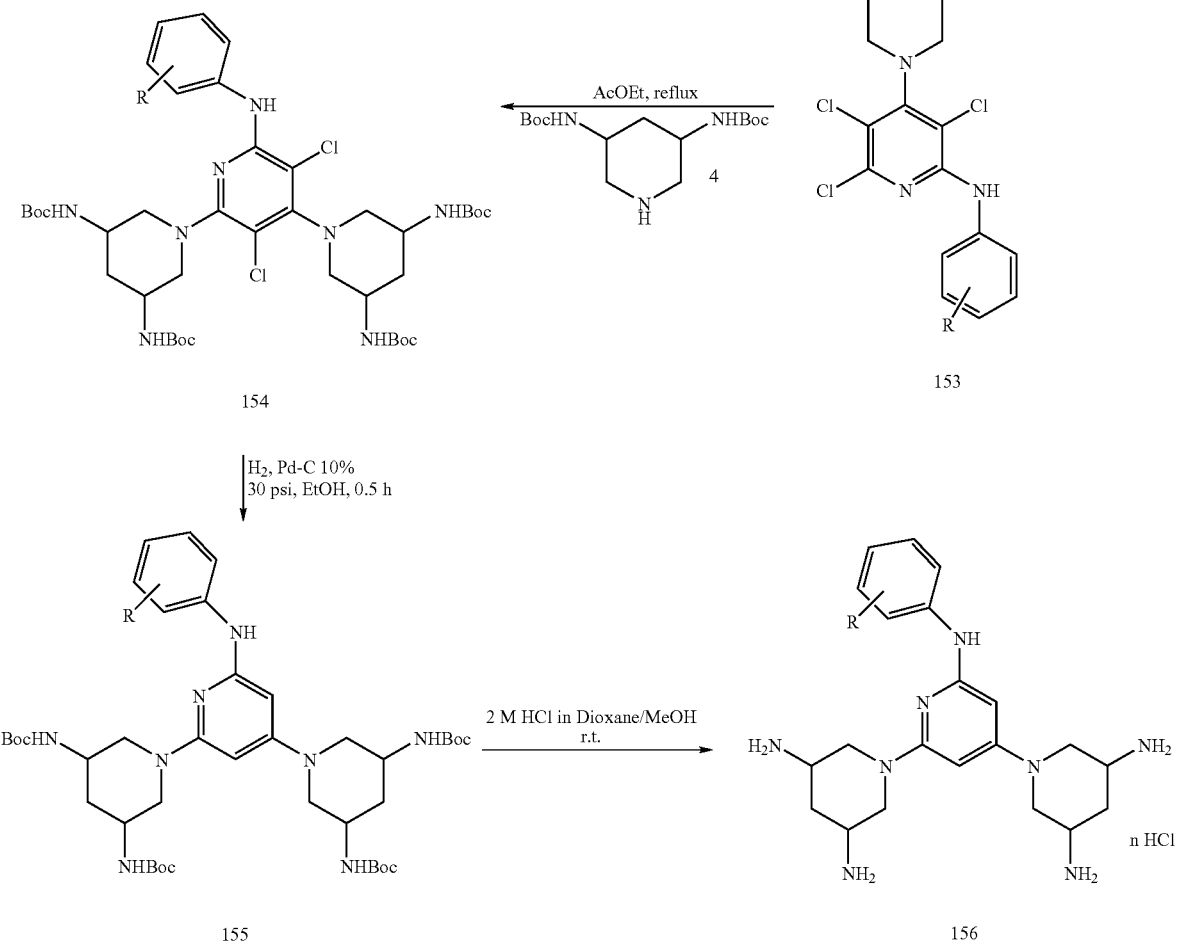

R = sustituents defined for "substituted aryl"

2,3,5,6-tetrachloro-4-iodo-pyridine (151) reacts with (3R,5S)-3,5-bis(tert-butoxycarbonylamino)-piperidine (4) in a solvent selected from toluene, xylenes, anisole or chlorobenzene in the presence of tris-triphenylphosphine copper bromide [Cu(PPh$_3$)$_3$Br] and cesium carbonate at an elevated temperature between 80 to 120° C., preferably 100 to 100° C., in an argon atmosphere to furnish after silica gel column chromatography, the arylamino derivative 152. Related chemical transformations are described in Gujadhur, R. et al., *Tetrahedron Letters*, 42, 4791–4793 (2001).

Compound 152 reacts with aniline 147 in the presence of Pd-catalyst selected from Pd$_2$(dba)$_3$, Pd(OAc)$_2$, PdCl$_2$(PCy$_3$)$_2$, PdCl$_2$[P($^t$Bu)$_2$OH], ligand selected from Xantphos, P($^t$Bu)$_3$, BINAP, 2-(dicyclohexylphosphino)biphenyl, 2-(di-t-butylphosphino)biphenyl, 2-dicyclohexylphosphino-2'-(N,N-dimethylamino)biphenyl, (R)-(+)-2,2'-bis(dicyclohexylphosphino)-1,1'-binaphthyl, and base selected from Cs$_2$CO$_3$, K$_2$CO$_3$, K$_3$PO$_4$ in a solvent selected from PhMe, DME, O-xylene, dioxane and HMPA at a temperature from 80° C. to 140° C. preferentially between 100–120° C. for 16–72 hours under N$_2$ atmosphere. The reaction is checked for progress by TLC or HPLC and upon completion, the mixture is diluted with chloroform or other suitable solvents and the inorganic solid is filtered off through Celite. The resulting filtrate is washed with water via extraction, dried with magnesium or sodium sulfate and concentrated in vacuo. The residue is chromatographed on a silica gel column, using a gradient of chloroform-ethyl acetate or chloroform-methanol to generate the bis-aminated pure product 153.

Compound 153 is reacted with (3R,5S)-3,5-bis(tert-butoxycarbonylamino)-piperidine (4) in a solvent selected from acetonitrile, THF, ethyl acetate, ethylene glycol dimethyl ether, dioxane, DMF, toluene or chlorobenzene, optionally in the presence of a base, selected from diisopropylethylamine, triethylamine, potassium or cesium carbonate, potassium or cesium fluoride or DBU at a temperature from 20° C. to 120° C., preferentially between 30 to 110° C. The reaction is checked for progress by TLC or HPLC and upon completion the mixture is diluted with chloroform or other suitable solvent extracted with water, dried with magnesium or sodium sulfate and concentrated in vacuo. The residue is column chromatographed on a silica gel column, using a gradient of chloroform-ethyl acetate or chloroform-methanol to give desired product 154.

Compound 154 is then hydrogenated over Pd—C or Pd—BaSO$_4$ at atmospheric, or elevated pressure of 1 to 500 psi, preferably 10 to 50 psi in a solvent selected from methanol, ethanol, tetrahydrofuran or ethyl acetate, optionally in the presence of a base, such as triethylamine, sodium, potassium or calcium carbonate. When the reaction is complete by LC/MS, the catalyst is removed by filtration and the product 155 is isolated by column chromatography on silica gel using a dichloromethane-ethyl acetate gradient, followed by concentration in vacuo. Related chemical transformations are described in Menichincheri et al., *Tetrahedron Letters*, 44 519–522 (2003).

Treatment of 155 with excess of 2 M HCl in dioxane and methanol at room temperature, followed by evaporation under reduced pressure provides the target 156.

This methodology is useful for the production of various derivatives represented by Formula Ib and Id. Other variations of this methodology would be apparent to those skilled in the art.

4.11.2 Synthesis of Formula Ib and Id Compounds by Scheme 34

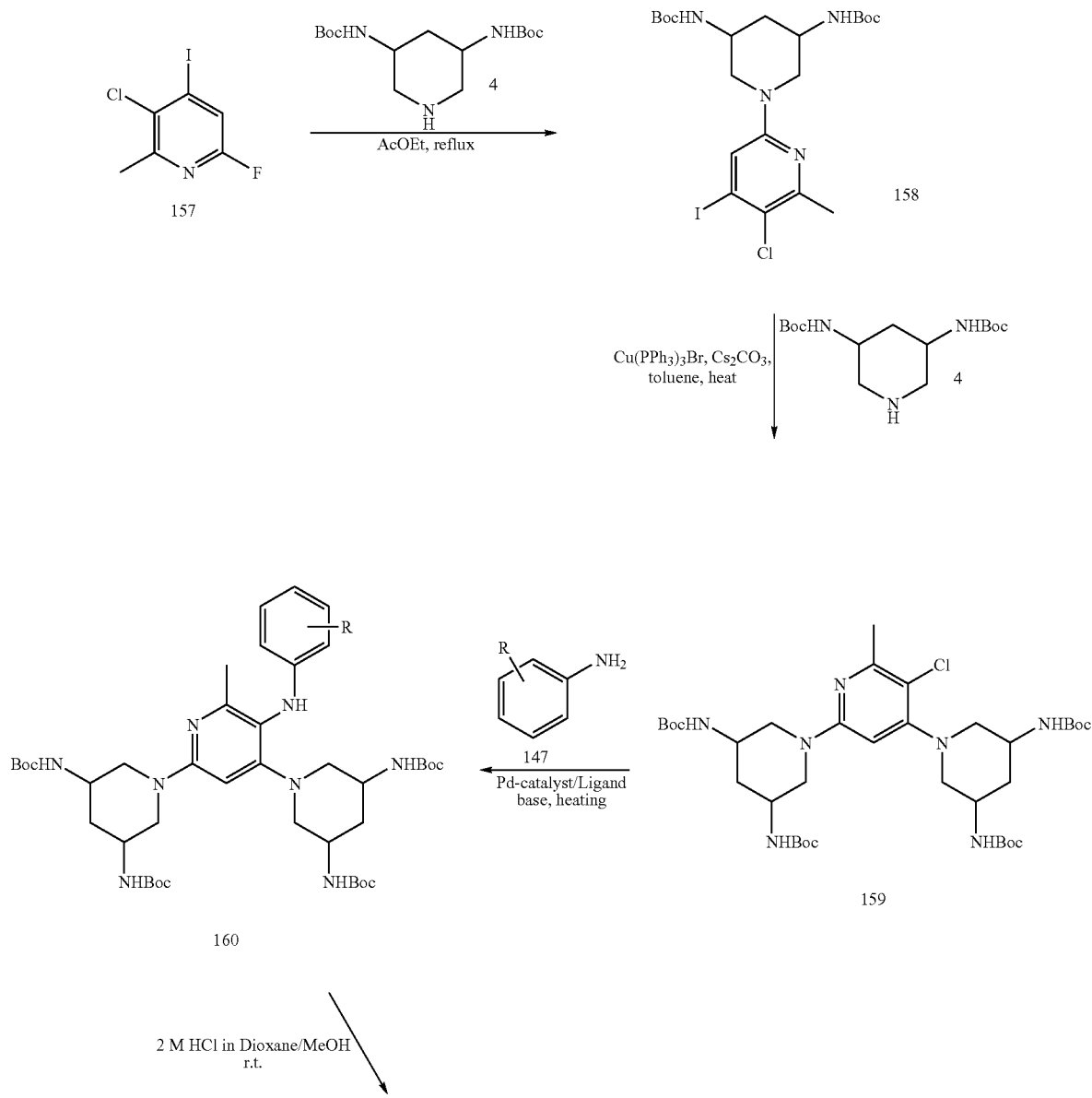

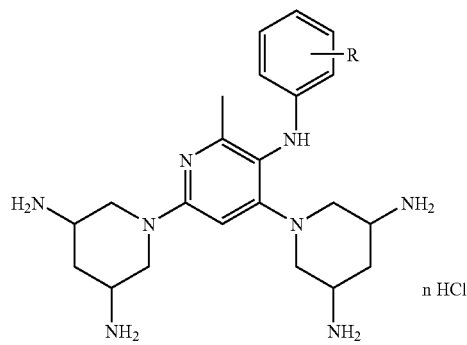

161

R = sustituents defined for "substituted aryl"

2-Fluoro-4-iodo-5-chloro-6-methylpyridine (157) is reacted with (3R,5S)-3,5-bis(tert-butoxycarbonylamino)-piperidine (4) in a solvent selected from acetonitrile, THF, ethyl acetate, ethylene glycol dimethyl ether, dioxane, DMW, toluene or chlorobenzene, optionally in the presence of a base, selected from diisopropylethylamine, triethylamine, potassium or cesium carbonate, potassium or cesium fluoride or DBU at a temperature from 20° C. to 120° C., preferentially between 30 to 80° C. The reaction is checked for progress by TLC or HPLC and upon completion the mixture is diluted with chloroform or other suitable solvent extracted with water, dried with magnesium or sodium sulfate and concentrated in vacuo. The residue is column chromatographed on a silica gel column, using a gradient of chloroform-ethyl acetate or chloroform-methanol to give 2-aminated desired product 158.

Compound 158 reacts with (3R,5S)-3,5-bis(tert-butoxycarbonylamino)-piperidine (4) in a solvent selected from toluene, xylenes, anisole or chlorobenzene in the presence of tris-triphenylphosphine copper bromide [Cu(PPh$_3$)$_3$Br] as catalyst and cesium carbonate at an elevated temperature between 80 to 140° C., preferably 100 to 110° C., in an argon atmosphere to furnish, after column chromatography on silica gel, the 4-aminated pyridine derivative 159. Related chemical transformations are described in Gujadhur, R. et al., *Tetrahedron Letters*, 42, 4791–4793 (2001).

Compound 159 reacts with aniline 147 in the presence of Pd-catalyst selected from Pd$_2$(dba)$_3$, Pd(OAc)$_2$, PdCl$_2$(PCy$_3$)$_2$, PdCl$_2$[P($^t$Bu)$_2$OH], ligand selected from Xantphos, P($^t$Bu)$_3$, BINAP, 2-(dicyclohexylphosphino)biphenyl, 2-(di-t-butylphosphino)biphenyl, 2-dicyclohexylphosphino-2'-(N,N-dimethylamino)biphenyl, (R)-(+)-2,2'-bis(dicyclohexylphosphino)-1,1'-binaphthyl, and base selected from Cs$_2$CO$_3$, K$_2$CO$_3$, K$_3$PO$_4$ in a solvent selected from PhMe, DME, O-xylene, dioxane and HMPA at a temperature from 80° C. to 140° C. preferentially between 100–120° C. for 16–72 hours under N$_2$ atmosphere. The reaction is checked for progress by TLC or HPLC and upon completion, the mixture is diluted with chloroform or other suitable solvents and the inorganic solid is filtered off through Celite. The resulting filtrate is washed with water via extraction, dried with magnesium or sodium sulfate and concentrated in vacuo. The residue is column chromatographed on a silica gel column, using a gradient of chloroform-ethyl acetate or chloroform-methanol to generate the Boc-protected pure product 160.

Treatment of 160 with excess of 2 M HCl in dioxane and methanol at room temperature, followed by evaporation under reduced pressure provides the target 161 as HCl salt.

This methodology is useful for the production of various derivatives represented by Formulas Ib and Id. Other variations of this methodology would be apparent to those skilled in the art.

4.11.3 Another General Method of Synthesis of Formula Ib & Id Compounds.

Scheme 35 describes the general synthetic procedures for preparing compounds of Formula Ib & Id.

Scheme 35
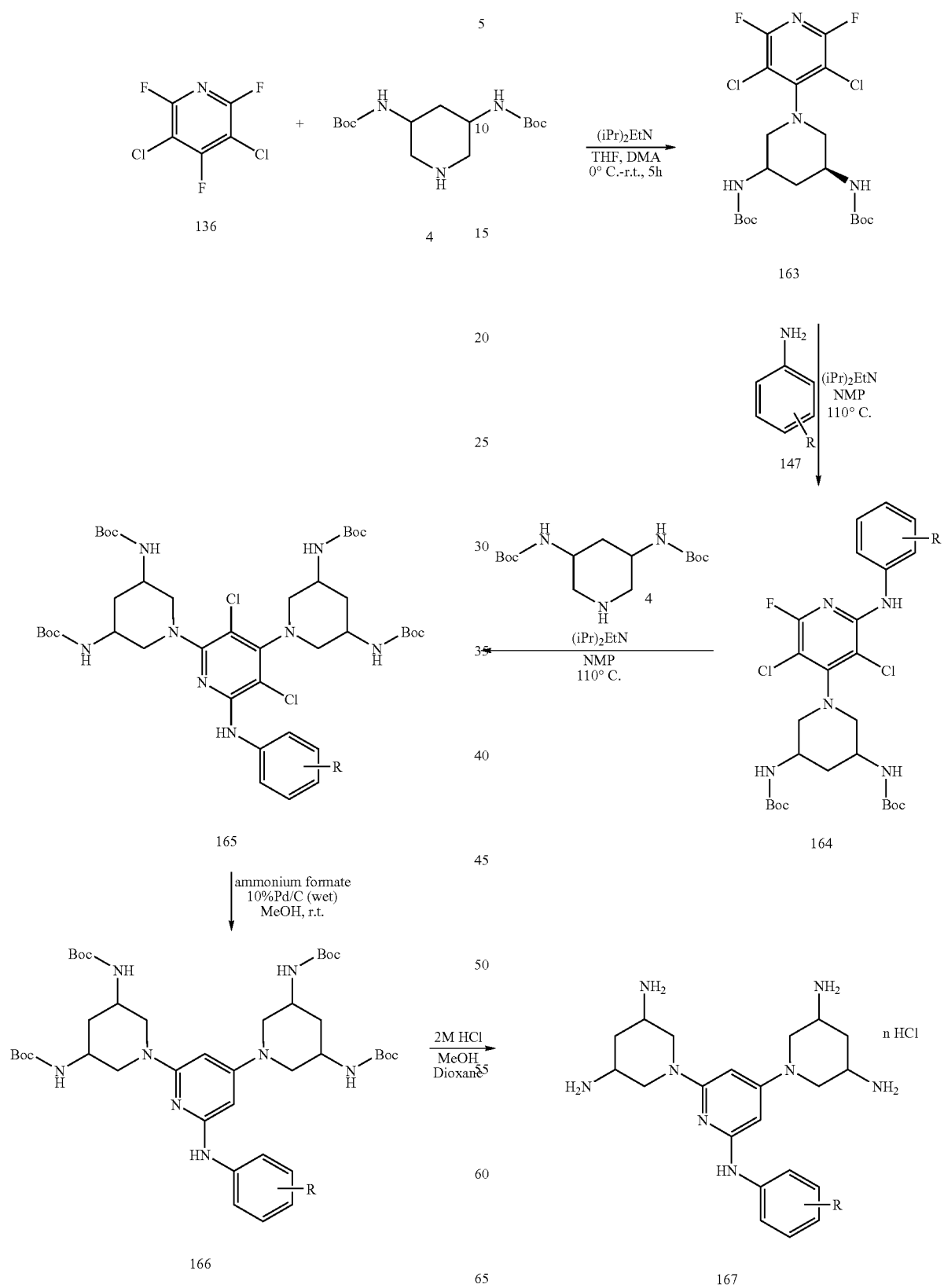

In this scheme R is as defined for substituted aryl.

Compound (4) (1 equiv.) was first dissolved in warm DMA, cooled to 0° C. and (iPr)₂EtN (1.1 equiv.) and then added to a solution of 3,5-dichloro-2,4,6-trifluoro-pyridine (136) (1 equiv.) in THF. The reaction mixture was shaken at 0° C. to room temp over 5 h. The precipitate was collected by filtration and dried under high vacuum to give the desired product (163). A related chemical transformation is described in Menichincheri, M.; Bassini, D. F.; Gude, M; Angiolini, M. *Tetrahedron Letters* 2003, 44, 519–522.

Compound 163 (1 equiv.) and aniline 147 (1.25 equiv.) were combined and suspended in NMP. (iPr)₂EtN (1.5 equiv.) was added and the mixture was heated at 110° C. for 10 days in a Teflon septum capped vial. Upon nearly complete consumption of the di-fluoro starting material (163) indicated by LC-MS, the mixture was diluted with EtOAc, washed with water, saturated aqueous NaHCO₃ and brine, dried over MgSO₄ and concentrated under reduced pressure. The crude product was purified by flash chromatography on silica gel to give the desired product (164).

Compound 164 (1 equiv.) and (3R,5S)-3,5-bis(tert-butoxycarbonylamino)-piperidine (6) (1.5 equiv.) were combined and suspended in NMP. iPr₂EtN (2 equiv.) was added and the mixture was heated at 110° C. with shaking for 5 days. Upon the completion of the reaction indicated by LC-MS, the solution was diluted with EtOAc, washed with H₂O, brine, dried over MgSO₄ and concentrated to give a crude that was purified by trituration with EtOAc gave the desired product (165).

Compound 165 was dissolved in MeOH. Pd/C (10%, wet) was added followed by ammonium-formate. The mixture was shaken at room temperature for 16 hours. Upon the completion of the de-chlorination indicated by LC-MS, the mixture was filtered through a plug of Celite. The filtrate was concentrated and the resulting crude was purified by flash chromatography to give the desired product (166).

Compound 166 (0.042 g=0.043 mmol) was dissolved in MeOH and an equal volume of 4.0 M of HCl in dioxane was added. The mixture was shaken at room temperature for 16 h, concentrated under reduced pressure to give a crude product that was purified by HPLC to give the desired product (167) as the HCl salt.

4.11.4 EXAMPLE 17

Synthesis of Formula Ib & Id Compound 171

Scheme 36 describes the synthetic procedure for preparing 171 of Formula Ib & Id.

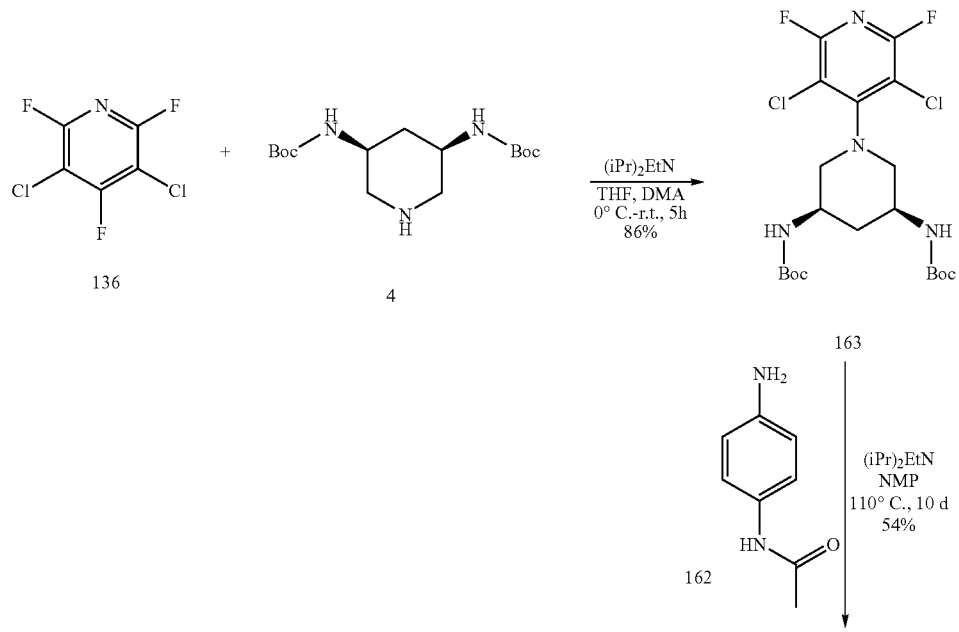

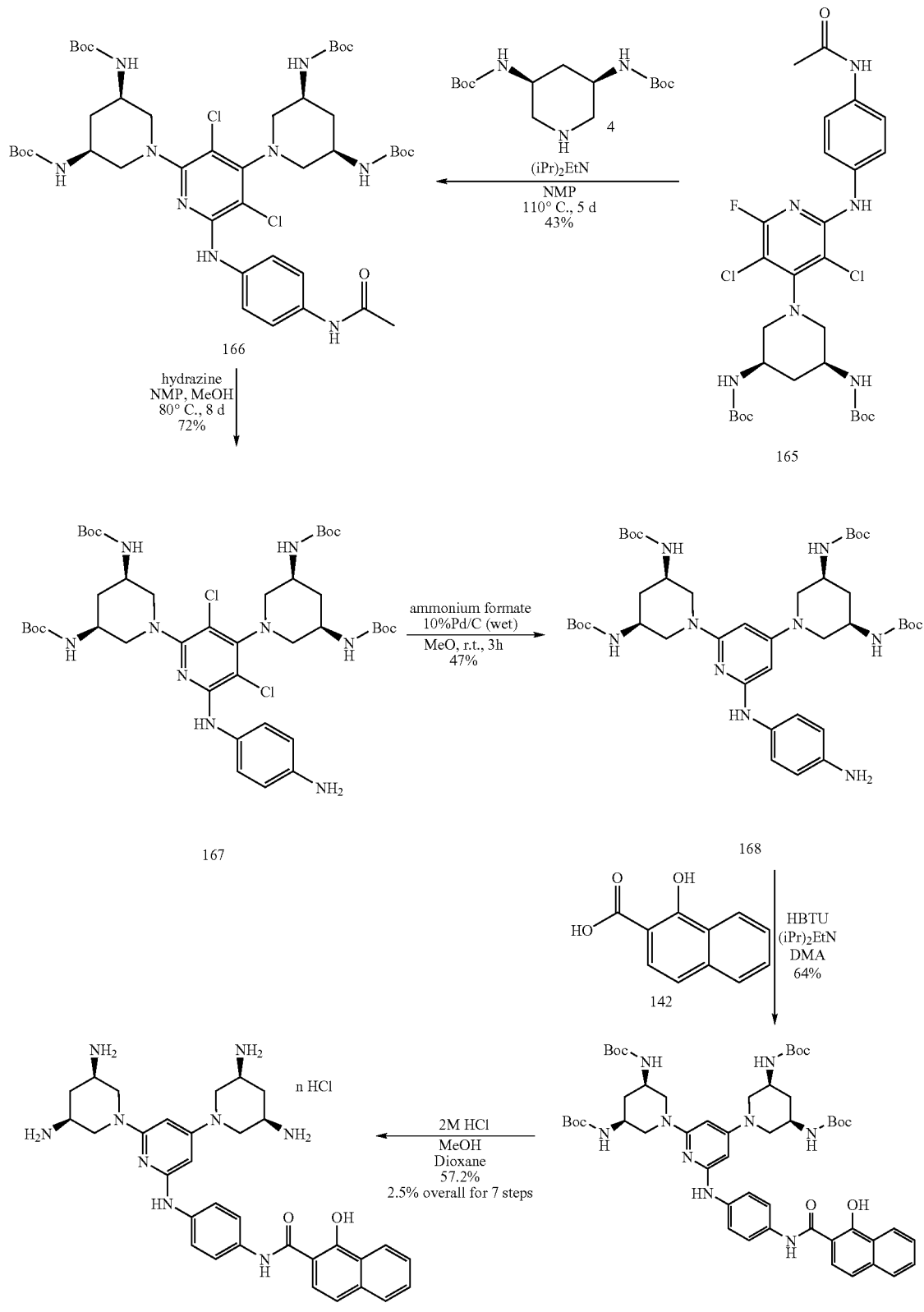
-continued

4-(3R,5S)-3,5-bis-(tert-Butoxycarbonylamino)-piperidin-]-yl)-3,5-dichloro-2,6-difluoro-pyridine (163)

(3R,5S)-3,5-bis-(tert-Butoxycarbonylamino)-piperidine (4) (0.25 g, 0.8 mmol) was dissolved in warm DMA (4 mL, via sonication and warming with the heat gun to ~60° C.). Upon cooling, the solution was chilled to 0° C. and ($^i$Pr)$_2$EtN (0.88 mmol) and 3,5-dichloro-2,4,6-trifluoro-pyridine (136) (0.161 g, 0.8 mmol) was added as a pre-dissolved mixture in THF (4 mL). The solution was shaken in a sealed 40 mL I-Chem vial while warming to room temp over 5 h. A white precipitate had formed. The precipitate was collected by filtration followed by rinsing with THF and water. The solid was dried under high vacuum for 16 h to give the desired product (163) as a white powder (0.343 g, 0.691 mmol, 86% yield). LC-MS (ESI): (exact mass: 496.15) m/e=497.1 [M+1]$^+$. $^1$H NMR (400 MHz, DMSO-d$_6$): δ 1.39 (s, br, 20H), 2.09–1.95 (m, 2H), 3.49 (s, br, 2H), 3.89 (s, br, 2H), 7.00 (s, 2H).

4-(3R,5S)-3,5-bis-(tert-Butoxycarbonylamino)-piperidin-1-yl)-3,5-dichloro-2-(4-acetylamino-phenyl-amino)-6-fluoro-pyridine (165)

4-((3R,5S)-3,5-bis-(tert-butoxycarbonylamino)-piperidin-1-yl)-3,5-dichloro-2,6-difluoro-pyridine (163) (0.343 g, 0.69 mmol) and N-(4-amino-phenyl)-acetamide (162) (0.129 g, 0.863 mmol) were combined and suspended in NMP (12 mL). $^i$Pr$_2$EtN (1.04 mmol) was added and the mixture was sonicated for 2 minutes. The mixture was heated to 110° C. in a Teflon septum capped vial. The solids dissolved within 2 h. Shaking of the solution was continued at 110° C. for 10 days. LC-MS indicated nearly complete consumption of the di-fluoro starting material. The mixture was diluted with EtOAc (50 mL), washed with water (25 mL), NaHCO$_3$ (aqueous sat., 25 mL), brine (25 mL), dried over MgSO$_4$ and concentrated to give a brown oil. Purification by flash chromatography on silica gel using a gradient of hexane and EtOAc (eluding with 15–100% EtOAc/hexane in 30 minutes) gave the desired product (165) as a beige powder upon concentration (0.290 g, 0.463 mmol, 54% yield). LC-MS (ESI): (exact mass: 626.22) m/e=627.3 [M+1]$^+$.

4,6-bis-((3R,5S)-3,5-bis-(tert-Butoxycarbonylamino)-piperidin-1-yl)-3,5-dichloro-2-(4-acetylamino-phenyl-amino)-pyridine (166)

4-((3R,5S)-3,5-bis-(tert-butoxycarbonylamino)-piperidin-1-yl)-3,5-dichloro-2-(4-acetylamino-phenyl-amino)-6-fluoro-pyridine (165) (0.29 g, 0.463 mmol) and cis-3,5-bis-(tert-butoxycarbonylamino)-piperidine (4) (0.219 g, 0.695 mmol) were combined and suspended in NMP (3.5 mL) in a 40 mL I-Chem vial. $^i$Pr$_2$EtN (0.926 mmol) was added and the mixture was sonicated for 2 minutes. The mixture was heated to 110° C. and within 30 minutes all of the solids had dissolved. The solution continued to shake in the Teflon septum capped vial for 5 days. LC-MS indicated nearly complete reaction at this point. The solution was diluted with EtOAc (100 mL), washed with H$_2$O (50 mL) and brine (50 mL), dried over MgSO$_4$ and concentrated to give a brown oil which eventually solidified. Trituration of the solid with EtOAc followed by collection via filtration under reduced pressure gave the desired product (166) as a beige powder (0.183 g, 0.198 mmol, 43% yield). LC-MS (ESI): (exact mass: 921.43) m/e=922.6 [M+1]$^+$.

4,6-bis-((3R,5S)-3,5-bis-(tert-Butoxycarbonylamino)-piperidin-1-yl)-3,5-dichloro-2-(4-aminophenyl-amino)-pyridine (167)

4,6-Bis-((3R,5S)-3,5-bis-(tert-butoxycarbonylamino)-piperidin-1-yl)-3,5-dichloro-2-(4-acetylamino-phenyl-amino)-pyridine (166) (0.183 g, 0.198 mmol) was dissolved in NMP (6 mL) and MeOH (8 mL). Hydrazine (8 mL) was added and the mixture was heated to 80° C. in a Teflon septum capped 40 mL I-Chem vial for 4 days. LCMS indicated incomplete deprotection at this point. An additional portion of hydrazine (8 mL) was added and the solution was heated for an additional 4 days. LC-MS indicated nearly complete deprotection at this point. The mixture was diluted with EtOAc (50 mL) and the organic layer was washed with water (25 mL), NaHCO$_3$ (aqueous sat., 25 mL) and brine (25 mL) via extraction, dried over MgSO$_4$ and concentrated to give a brown oil. Purification by flash chromatography on silica gel using a gradient of hexane and EtOAc (eluding with 15–100% EtOAc in hexane in 30 minutes) gave the desired product (166) as a beige powder upon concentration (0.127 g, 0.144 mmol, 72.7% yield). LC-MS (ESI): (exact mass: 879.42) m/e=880.5 [M+1]$^+$.

4,6-bis-((3R,5S)-3,5-bis-(tert-Butoxycarbonylamino)-piperidin-1-yl)-2-(4-aminophenyl-amino)-pyridine (168)

4,6-Bis-((3R,5S)-3,5-bis-(tert-butoxycarbonylamino)-piperidin-1-yl)-3,5-dichloro-2-(4-aminophenyl-amino)-pyridine (167) (0.127 g, 0.144 mmol) was dissolved in MeOH (15 mL). Pd/C (0.33 g, 10%, wet) was added followed by ammonium-formate (0.66 g). The mixture was shaken in a Teflon septum capped 40 mL I-Chem vial, with occasional venting, for 16 hours. LC-MS indicated complete de-chlorination at this point. The mixture was filtered through a plug of Celite and the filtrate was concentrated and purified by flash chromatography on silica gel (eluting with 15–100% EtOAc in hexane for 30 minutes followed by 100% EtOAc for 10 minutes) to give the desired product (168) as an off-white powder (0.055 g, 0.0677 mmol, 47% yield). LC-MS (ESI): (exact mass: 811.5) m/e=812.6 [M+1]$^+$.

1-Hydroxy-naphthalene-2-carboxylic acid [4-(4,6-bis-((3R,5S)-3,5-bis-(tert-Butoxycarbonylamino)-piperidin-1-yl)-pyridin-2-ylamino)-phenyl]-amide (170)

1-Hydroxy-naphthalene-2-carboxylic acid (142) (0.018 g, 0.096 mmol) was dissolved in DMA (2 mL), $^i$Pr$_2$EtN (0.096 mmol) was added followed by HBTU (0.036 g, 0.096 mmol) and the mixture was shaken in an 8 mL Teflon septum capped vial at room temperature for 20 minutes. 4,6-bis-((3R,5S)-3,5-bis-(tert-Butoxycarbonylamino)-piperidin-1-yl)-2-(4-aminophenyl-amino)-pyridine (168) (0.055 g, 0.0677 mmol) was added and the mixture was shaken at room temperature for 16 h. LC-MS indicated complete coupling at this point. The mixture was diluted with EtOAc (25 mL) and the organic layer washed with water (15 mL), NaHCO$_3$ (aqueous sat., 15 mL) and brine (15 mL) via extraction, dried over MgSO$_4$ and concentrated to give a brown oil. Purification by flash chromatography on silica gel using a gradient of hexane and EtOAc (eluding with 15–100% EtOAc in hexane for 30 min) gave the desired product (170) as an off-white powder upon concentration (0.042 g, 0.043 mmol, 64% yield). LC-MS (ESI): (exact mass: 981.53) m/e=982.6 [M+H$^+$].

1-Hydroxy-naphthalene-2-carboxylic acid [4-(4,6-bis-((3R,5S)-3,5-bis-amino-piperidin-1-yl)-pyridin-2-ylamino)-phenyl]-amide (171)

1-Hydroxy-naphthalene-2-carboxylic acid [4-(4,6-bis-((3R,5S)-3,5-bis-(tert-butoxycarbonylamino)-piperidin-1-yl)-pyridin-2-ylamino)-phenyl]-amide (170) (0.042 g, 0.043 mmol) was dissolved in MeOH (4 mL) and 4.0 M HCl in dioxane (4 mL) was added. The mixture was shaken at room temperature for 16 h in a Teflon septum capped 40 mL I-Chem vial. LC-MS indicated complete deprotection at this point. The mixture was concentrated to give a solid that was triturated with MeOH (1 mL) followed by collection by filtration under reduced pressure. The solid was lyophilized from 0.25 M of HCl in $H_2O$ twice to give the desired product (171) as the HCl salt form as a slightly yellow powder [0.021 g, 0.024 mmol (calculated based on the molecular weigh of the HCl salt determined by elemental analysis), 57.2% yield, 2.5% total yield for 7 steps]. LC-MS (ESI): (exact mass: 581.32) m/e=582.3 [M+1]$^+$. $^1$H NMR (400 MHz, DMSO-$d_6$): δ 1.66 (q, 2H, J=11.6 Hz), 2.38 (s, br, 2H), 2.61 (t, 4H, J=11.2 Hz), 3.11 (s, br, 4H), 3.62 (s, br, 2H), 4.54 (s, br, 4H), 5.73 (s, 2H), 7.13 (d, 2H, J=8.8 Hz), 7.37 (d, 1H, J=9.2 Hz), 7.49 (t, 1H, J=7.2 Hz), 7.63–7.56 (m, 3H), 7.83 (d, 1H, J=8 Hz), 8.10 (d, 1H, J=8.8 Hz), 8.21 (d, 1H, J=8 Hz), 8.48 (s, br, 12H), 10.44 (s, 1H). Elemental analysis calcd (%) for $C_{32}H_{39}N_9O_2$.5 $H_2O$.5 HCl: C, 45.00; H, 6.37; N, 14.76. found: C, 44.82; H, 6.12; N, 14.38.

4.12 General Method of Synthesis of Formula Ie & If Compounds

Scheme 37 describes a general synthetic procedure for preparing compound of Formula Ie and If.

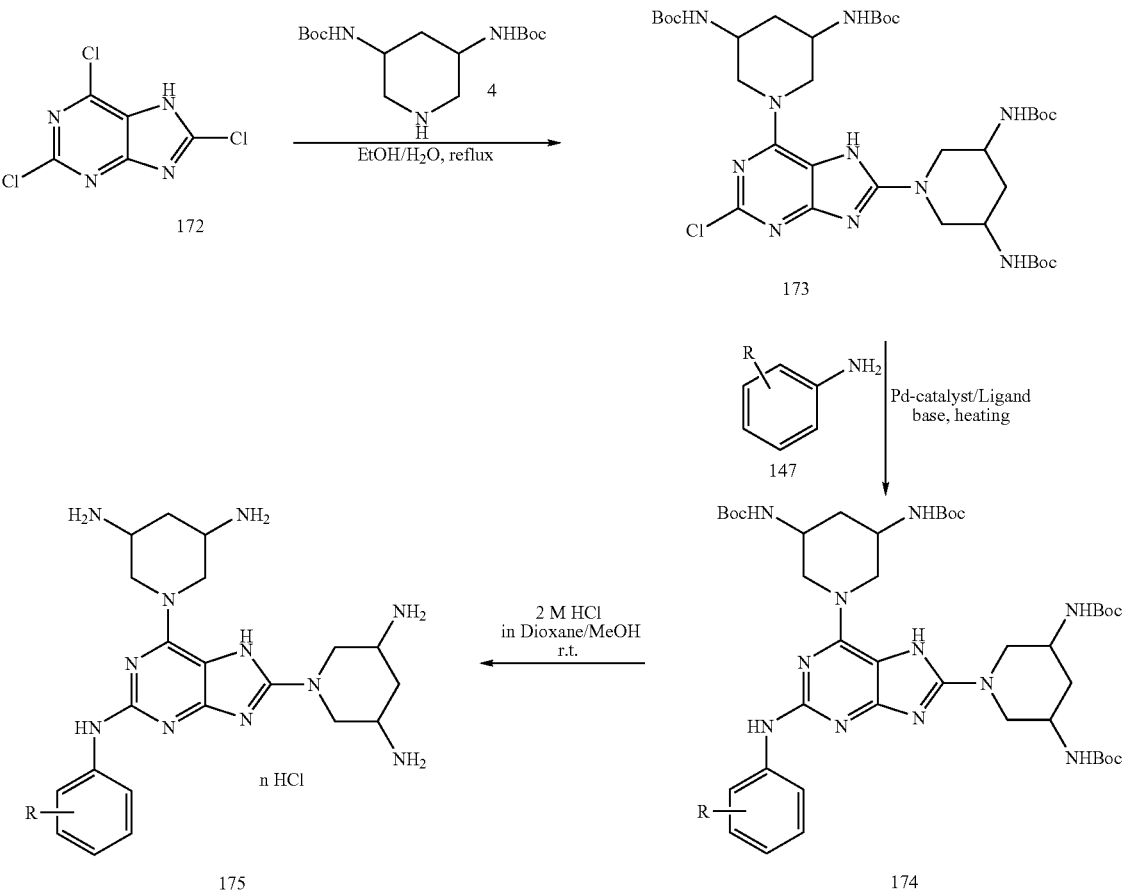

R = sustituents defined for "substituted aryl"

The trichloropurine (172) reacted with (3R,5S)-3,5-bis(tert-butoxycarbonylamino)-piperidine (4) under refluxing condition in the mixed solvents of EtOH and $H_2O$ to give the bis-aminated product 173. This product was purified by column chromatographed on a silica gel column, using a gradient of hexane-ethyl acetate to generate the desired pure product 173.

Compound 173 is reacted with aniline 147 in the presence of $Pd_2(dba)_3$ catalyst and Xantphos ligand, and $Cs_2CO_3$ as base in a toluene at 100° C. The reaction is checked for progress by LC-MS and upon completion, the mixture is diluted with EtOAc and methanol and the inorganic solid was filtered off through Celite. The resulting filtrate is concentrated in vacuo. The residue is purified by flash chromatography on a silica gel column, using a gradient of hexane-ethyl acetate to generate the desired pure product 147.

Treatment of 174 with excess of 2 M HCl in dioxane and methanol at room temperature overnight, followed by evaporation of the solvents under reduced pressure can provide the target 175 as a HCl salt.

A related chemical transformation is described in S. R. Breshears, S. S. Wang, S. G. Bechtolt and B. E. Christensen, *J. Am. Chem. Soc.*, Vol. 81, 1959, P3789–3792.

The methodology described in this section is useful for the production of various derivatives represented by Formula Ie & If.

4.12.1 EXAMPLE 18

Synthesis of Formula Ie & If Compound 178

Scheme 38 describes the synthesis of compound 178.

The trichloropurine (172) (483 mg, 2 mmol), was mixed with (3R,5S)-3,5-bis(tert-butoxycarbonylamino)-piperidine (4) (2.52 g, 8 mmol) in 15 mL of EtOH and 15 mL of $H_2O$. This mixture was heated to reflux (oil bath at 105° C.) for 22 hours. The mixture was then dried under vacuum. The crude material was purified by flash chromatography on a silica gel column using a gradient of hexane-ethyl acetate to generate the desired product 173 (620 mg, 0.794 mmol) as a white solid in 39.7% isolated yield. LC-MS: m/e 781.6 $[M+1]^+$ (exact ms: 780.4).

Compound 173 (479.4 mg, 613.6 µmol) was mixed with aniline 176 (256.2 mg, 920.6 µmol), $CsCO_3$ (700 mg, 2.15 mmol), $Pd_2(dba)_3$ (58.2 mg, 63.6 µmol), Xantphos (107.5 mg, 185.8 µmol) and 9 mL of toluene and then, purged with $N_2$ for a few minutes. The mixture was heated at 100° C. with stirring for 92 hours. The reaction mixture was cooled down, diluted with EtOAc (4 mL) and MeOH (4 mL) and the inorganic solid was filtered off through Celite. The resulting filtrate was concentrated in vacuo. The residue was purified

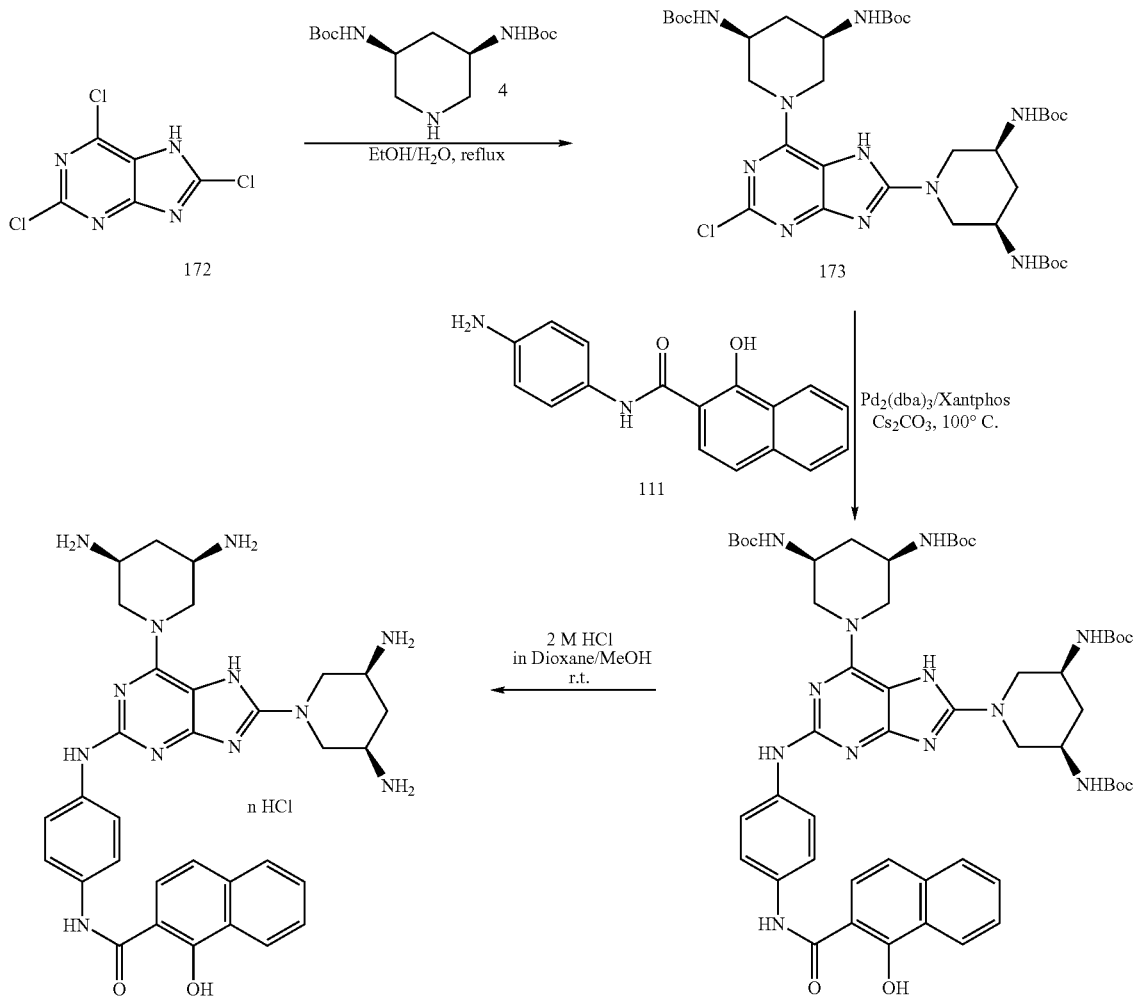

by flash chromatography on a silica gel column using a gradient of hexane-ethyl acetate to generate the desired product 177 (192 mg, 187.8 µmol) in 42.5% isolated yield (the isolated yield was calculated base on the consideration of the fact that 134 mg of the starting material of 173 was recovered during the purification). LC-MS: m/e 1023.9 [M+1]⁺ (exact ms: 1022.53).

Compound 177 (192 mg, 187.8 µmol) was dissolved in 4 mL of methanol. HCl (4.0 M, 4 mL) was added and the mixture was shaken at room temperature for 15 hours. The solvent was evaporated under vacuum and the residue was purified by MS-triggered HPLC using a gradient of $CH_3CN$ and $H_2O$ with 0.5% TFA to give the desired product (178) as a THF salt. This TFA salt was converted to HCl salt by first re-dissolving it in MeOH (8 mL) and then treating it with HCl (4.0 M in dioxane, 4 mL). The solvent was evaporated under reduced pressure on rotary evaporator and the residue was dried over oil pump for 2 days to give the 7.60–7.74 (m, 5H), 7.56 (t, J=8 Hz, 1H), 7.43 (d, J=8.8 Hz, 1H), 5.45 (br, 1H), 4.52–4.62 (m, 1H), 3.12–3.44 (m, 6H), 2.82–3.06 (m, 4H), 2.70 (t, J=11.8 Hz, 1H), 2.42–2.58 (m, 2H), 1.66–1.86 (m, 3H). Elemental analysis calcd (%) for $C_{32}H_{38}N12O_2 \cdot 5.5HCl \cdot 5H_2O$ (913.324): C, 42.08; H, 5.90; N, 18.40. found C: 42.02, H, 5.99; N, 18.08.

This methodology is useful for the production of various derivatives represented by Formula Ie & If.

Other variations of this methodology would be apparent to those skilled in the art.

4.13 General Method of Synthesis of Formula If & Ig Compounds

4.13.1 Synthesis of Formula If and Ig Compounds by Scheme 39

Scheme 39 describes a general synthetic procedure for preparing compound 181 of Formula If and Ig.

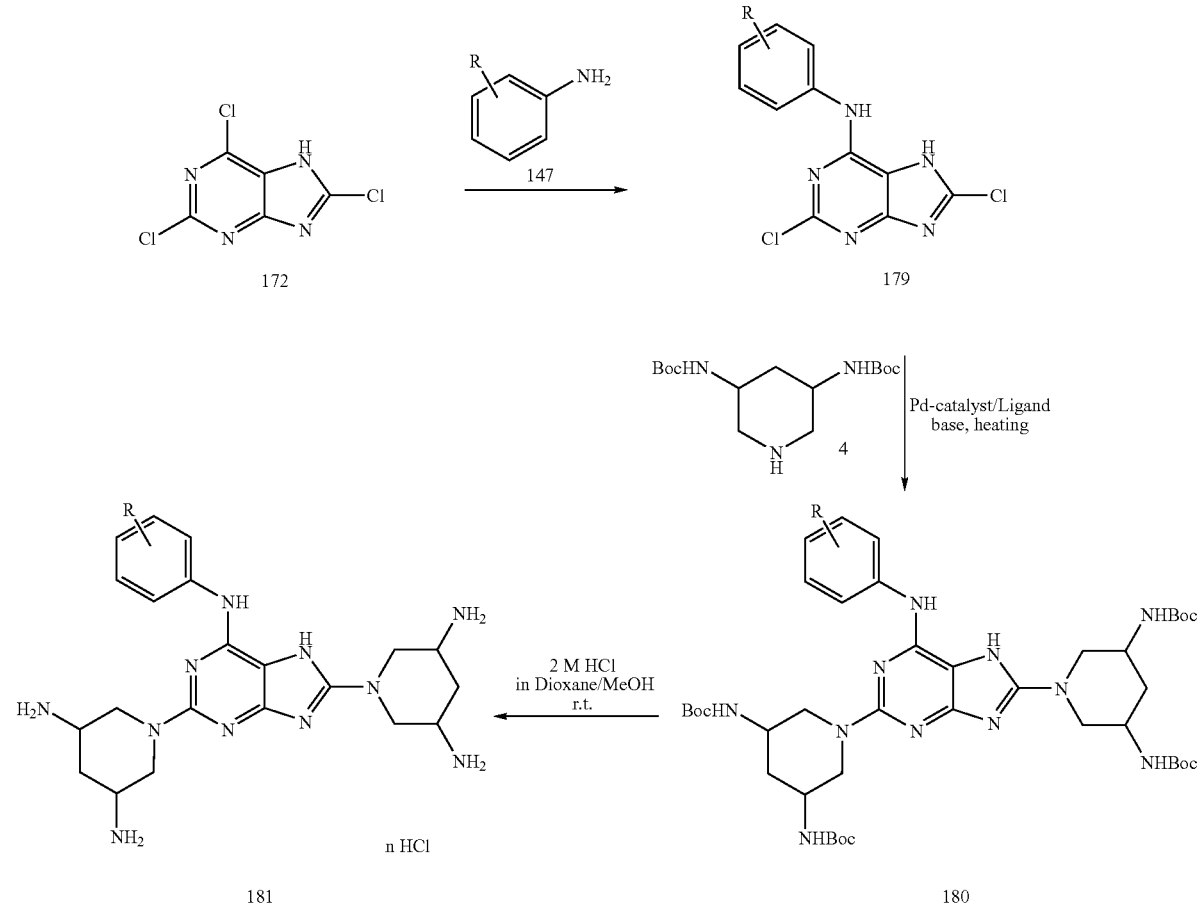

R = sustituents defined for "substituted aryl"

desired product 178 (56.6 mg, 90.95 µmol) in 48.4% isolated yield as the HCl salt with HPLC purity of 100% by ELSD. LC-MS: m/e 623.5 [M+1]⁺ (exact ms: 622.32). ¹H NMR (DMSO-dr): δ=10.47 (s, 1H), 8.44–8.78 (m, 13H), 8.27 (d, J=8 Hz, 1H), 8.16 (d, J=9.2 Hz, 1H), 7.89 (d, J=8.8 Hz, 1H), The trichloropurine (172) reacts with aniline 147 under refluxing condition in the mixed solvents of EtOH and $H_2O$ to give the 6-position aminated product 179.

Compound 179 reacts with (3R,5S)-3,5-bis(tert-butoxy-carbonylamino)-piperidine (4, >2 equiv.) in the presence of a Pd-catalyst selected from Pd$_2$(dba)$_3$, Pd(OAc)$_2$, PdCl$_2$(PCy$_3$)$_2$, PdCl$_2$[P($^t$Bu)$_2$OH], ligand selected from Xantphos, P($^t$Bu)$_3$, BINAP, 2-(dicyclohexylphosphino)biphenyl, 2-(di-t-butylphosphino)biphenyl, 2-dicyclohexylphosphino-2'-(N,N-dimethylamino)biphenyl, (R)-(+)-2,2'-bis(dicyclohexylphosphino)-1,1'-Binaphthyl, and base selected from Cs$_2$CO$_3$, K$_2$CO$_3$, K$_3$PO$_4$ in a solvent selected from PhMe, DME, xylenes, dioxane and HMPA at a temperature from 80° C. to 140° C. preferentially between 100–120° C. for 16–72 hours under N$_2$ atmosphere. The reaction is checked for progress by TLC or HPLC and upon completion, the mixture is diluted with chloroform or other suitable solvents and the inorganic solid was filtered off through Celite. The resulting filtrate is washed with water via extraction, dried with magnesium or sodium sulfate and concentrated in vacuo. The residue is column chromatographed on a silica gel column, using a gradient of chloroform-ethyl acetate or chloroform-methanol to generate the Boc-protected pure product 180.

Treatment of 180 with an excess of 2 M HCl in dioxane and methanol at room temperature overnight, followed by evaporation under reduced pressure provides the target 181 as an HCl salt.

This methodology is useful for the production of various derivatives represented by Formula If & Ig. Other variations of this methodology would be apparent to those skilled in the art.

4.13.2 Another General Method of Synthesis of Formula If Compounds

Scheme 40 describes a general synthetic procedure for preparing compound 186 of Formula If.

Scheme 40

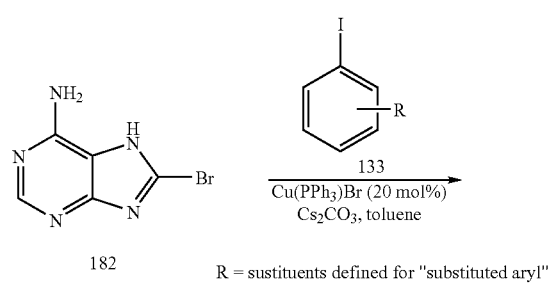

182

R = sustituents defined for "substituted aryl"

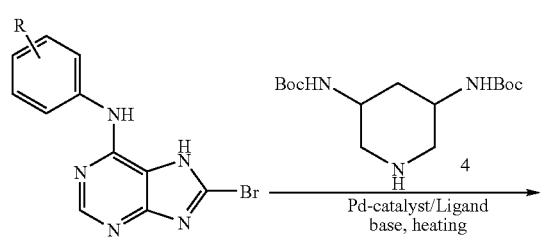

183

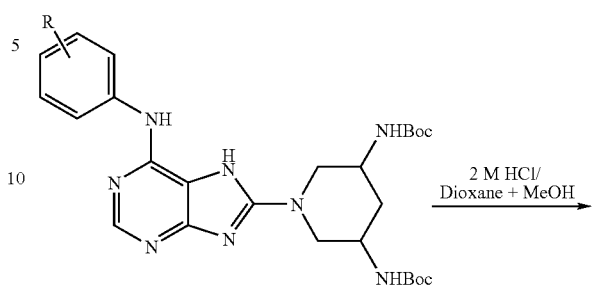

184

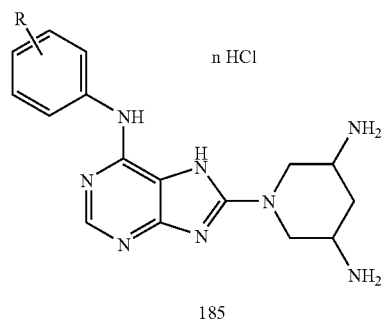

185

In this general method, starting material 182 reacts with iodoarene derivative 133 in a solvent selected from toluene, xylenes, anisole or chlorobenzene in the presence of tris-triphenylphosphine copper bromide [Cu(PPh$_3$)$_3$Br] as catalyst and cesium carbonate as base at an elevated temperature between 80 and 140° C., preferably from 110 to 120° C., in an argon atmosphere to furnish, after column chromatography on silica gel, the arylamino derivative 183. Related chemical transformations are described in Gujadhur, R. et al., *Tetrahedron Letters*, 42, 4791–4793 (2001).

Compound 183 reacts with (3R,5S)-3,5-bis(tert-butoxycarbonylamino)-piperidine (4) in the presence of Pd-catalyst selected from Pd$_2$(dba)$_3$, Pd(OAc)$_2$, PdCl$_2$(PCy$_3$)$_2$, PdCl$_2$[P($^t$Bu)$_2$OH], ligand selected from Xantphos, P($^t$Bu)$_3$, BINAP, 2-(dicyclohexylphosphino)biphenyl, 2-(di-t-butylphosphino)biphenyl, 2-dicyclohexylphosphino-2'-(N,N-dimethylamino)biphenyl, (R)-(+)-2,2'-bis(dicyclohexylphosphino)-1,1'-binaphthyl, and base selected from Cs$_2$CO$_3$, K$_2$CO$_3$, K$_3$PO$_4$ in a solvent selected from PhMe, DME, xylenes, dioxane and HMPA at a temperature from 80° C. to 140° C. preferentially between 100–120° C. for 16–72 hours under N$_2$ atmosphere. The reaction is checked for progress by TLC or HPLC and upon completion, the mixture is diluted with chloroform or other suitable solvents and the inorganic solid is filtered off through Celite.

The resulting filtrate is washed with water via extraction, dried with magnesium or sodium sulfate and concentrated in vacuo. The residue is column chromatographed on a silica gel column, using a gradient of chloroform-ethyl acetate or chloroform-methanol to generate the pure product 184.

Deprotection of the Boc groups of the compound 184 using 2 M HCl gives the desired product 185 as an HCl salt.

135

This methodology is useful for the production of various derivatives represented by Formula If. Other variations of this methodology would be apparent to those skilled in the art.

4.14 General Method of Synthesis of Formula Ih & Ii Compounds

Scheme 41 describes a general synthetic procedure for preparing compound 189 of Formula Ih & Ii.

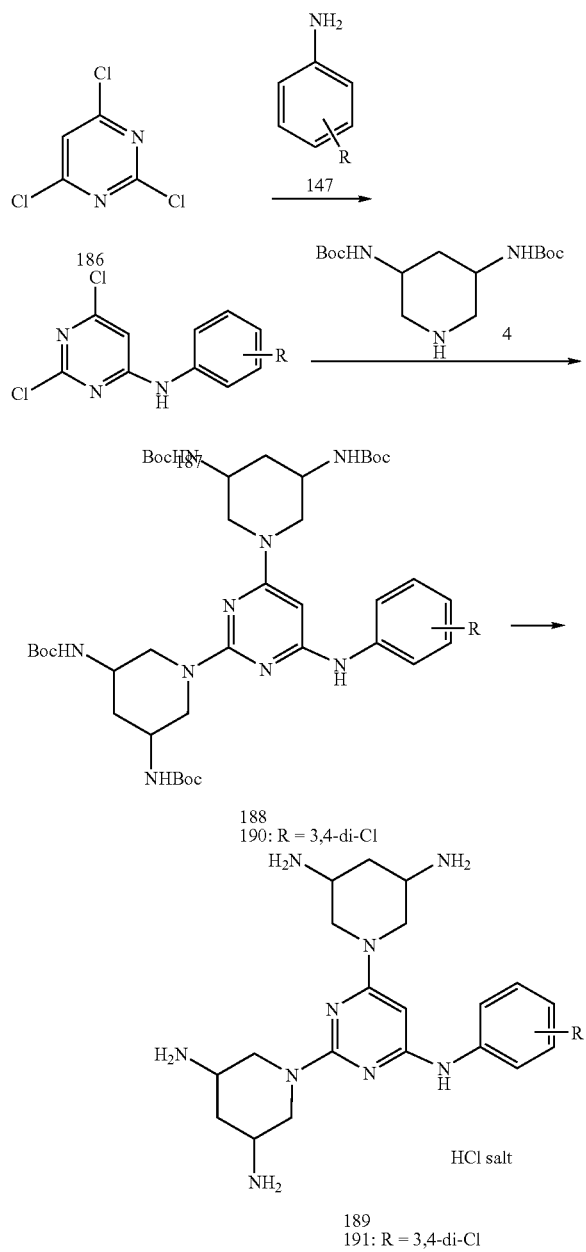

R = sustituents defined for "substituted aryl" group.

In this general method of producing compounds of Formula Ih and Ii, the 2,4,6-trichloropyrimidine (186) is reacted with an aromatic amine 147 at a temperature between negative 20° C. and +120° C., preferably between 0 to 80° C. in a solvent (or a mixture of solvents), selected from dioxane, ethylene glycol dimethyl ether, diglyme, diethyl ether, dichloromethane, chloroform, THF, DMF, dimethylacetamide, N-methylpyrrolidone, DMSO, sulfolane, toluene, chlorobenzene or o-dichlorobenzene in the presence of a base, such as diisopropylethylamine, triethylamine, N-methylmorpholine, DBU, DBN, DABCO, pyridine, picoline, lutidine, collidine, potassium carbonate, sodium carbonate, sodium hydride, sodium methoxide, potassium or sodium t-butoxide, or potassium fluoride in the presence, or absence of 18-crown-6. The progress of the reaction is monitored by standard means such as TLC or HPLC or LC/MS. Efficient stirring is maintained throughout the reaction.

When the reaction is complete, the reaction mixture is brought to room temperature, extracted with water, dried with sodium or magnesium sulfate and concentrated in vacuo. The above-obtained substituted pyrimidine derivative 187 is then reacted with 4 in a solvent (or a mixture of solvents), selected from dioxane, ethylene glycol dimethyl ether, diglyme, diethyl ether, dichloromethane, chloroform, THF, DMF, dimethylacetamide, N-methylpyrrolidone, DMSO, sulfolane, toluene, chlorobenzene or o-dichlorobenzene in the presence of a base, selected from diisopropylethylamine, triethylamine, N-methylmorpholine, DBU, DBN, DABCO, potassium carbonate, sodium carbonate, sodium hydride, sodium methoxide, potassium or sodium t-butoxide or potassium fluoride in the presence, or absence of 18-crown-6, in the presence or absence of a catalyst, selected from palladium acetate, palladium chloride, tetrakis triphenylphosphine palladium, tris(dibenzylideneacetone) dipalladium(0), nickel acetate, cuprous chloride or cuprous iodide in the presence or absence of a phosphine derivative, selected from triphenylphosphine, tri-o-tolylphosphine, BINAP, 1,1'-bis(diphenylphosphino)ferrocene, in a protective atmosphere of argon, at a temperature between 20 to 180° C., preferably 60 to 140° C. to give the protected 2,4,6-trisubstituted pyrimidine derivative 188. Efficient stirring is maintained throughout the reaction.

The reaction mixture is then concentrated in vacuo and the product is distributed between water and suitable solvent, such as chloroform, dichloromethane or ethyl acetate and purified by column chromatography on silica gel or reverse phase HPLC. In a specific example the aromatic amine 147 is 3,4-dichloroaniline, which gives the pyrimidine derivative 190. Deprotection (removal of the BOC protecting groups by HCl in dioxane provides the target compound 189. In case of the 3,4-dichlorophenylamino substitution, the target compound is 191.

4.14.1 EXAMPLE 19

Synthesis of 191 (R=3,4-di-Cl)

50 µmol of 2,4,6-trichloropyrimidine (186), 50 µmol 3,4-dichloroaniline, (50a) 110 mg of $Na_2CO_3$ and 1.4 mL of ethanol were mixed and shaken at room temperature for 4.5 hours. LC-MS of the reaction mixture confirmed the identity of the intermediate (192: R=3,4-di-Cl) with 93.2% HPLC purity by ELSD. The reaction mixture was then dried under vacuum. 2 mL of n-pentanol was added to dissolve the intermediate followed by 64 mg (200 µmol) of (3R,5S)-3, 5-bis(tert-butoxycarbonylamino)-piperidine (4) and 500 µL of 1M $^i$Pr$_2$NEt and the resulting mixture was heated at 140° C. for 4 days. The reaction mixture was dried under vacuum and purified by normal-phase HPLC using MS-triggered Waters purification system to give the corresponding BOC-intermediate (190). The Intermediate 88a was dissolved in 2 mL of MeOH. 2.0 mL of 4.0 M HCl in 1,4-dioxane was then added. The resulting reaction mixture was stirred at room temperature overnight and concentrated under vacuum. This crude material was then purified by reverse-phase HPLC to give the desired product, 3,4-dichloro-phenyl-(2,6-bis-((3R,5S)-3,5-diamino-piperidin-1-yl)-pyrimidin-4-yl)-amine, (191) (2.2 mg). LC-MS was used to confirm the identity of the desired product. LC-MS: MS m/e 466.5 [M+1]$^+$ (exact ms: 465.19).

This methodology is useful for the production of various derivatives represented by Formula Ih & Ii.

4.14.2 EXAMPLE 20

Synthesis of 193

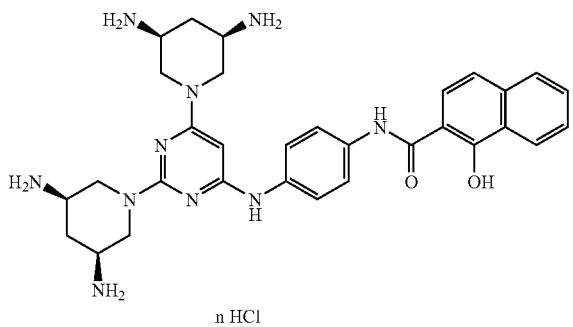

Scheme 42 describes the procedure for preparing compound 193 of Formula Ih & Ii.

Scheme 42

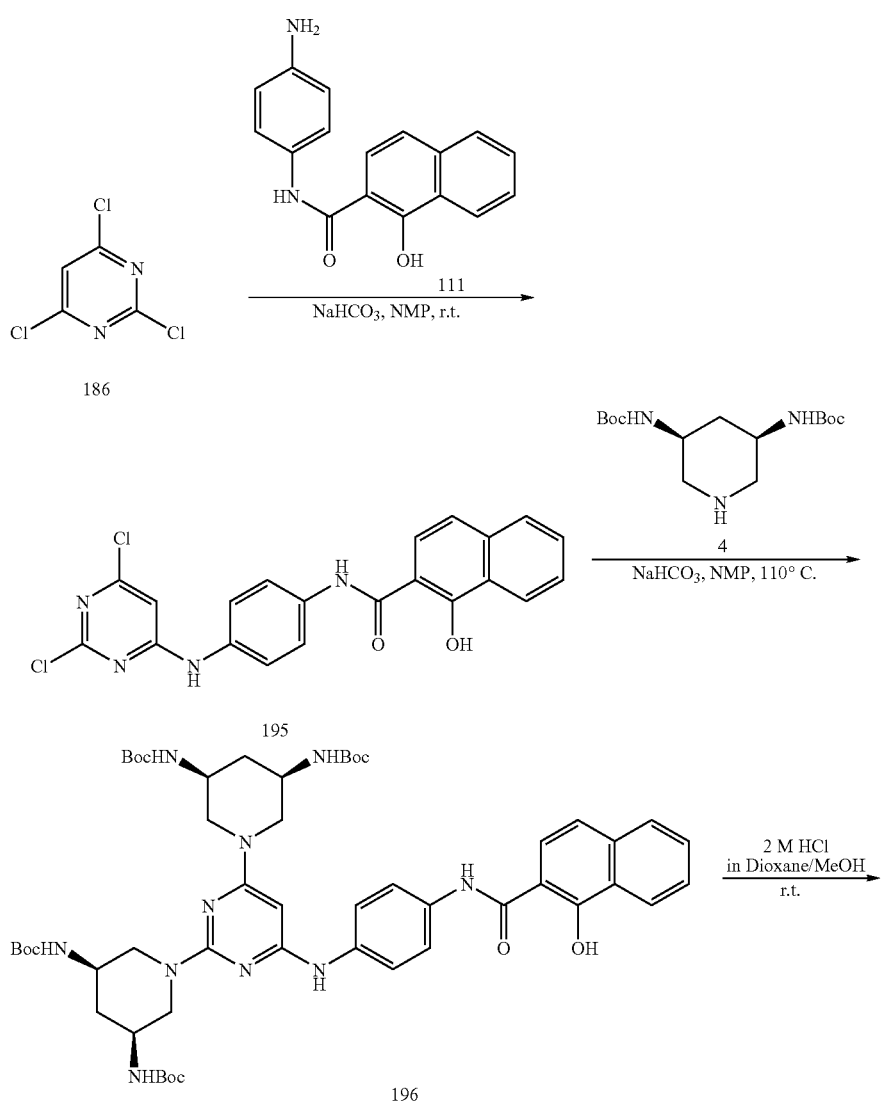

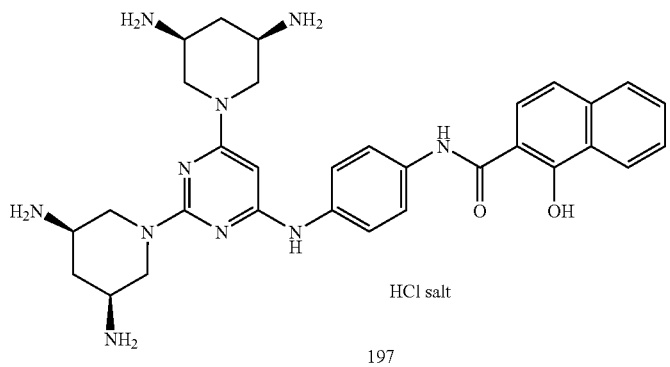

197 HCl salt 1 mmol of 2,4,6-trichloropyrimidine (186), 1 mmol of aniline (111), 504 mg (6 mmol) of NaHCO$_3$ and 8 mL of NMP were mixed and stirred at room temperature for 68 hours. LC-MS of the reaction mixture confirmed the identity of the intermediate (195) with 90% HPLC purity by ELSD. The reaction mixture was directly used in the next step.

(3R,5S)-3,5-bis(tert-butoxycarbonylamino)-piperidine (4) (757 mg, 2.4 mmol) was added into the above mixture and the resulting mixture was heated at 100° C. for 15 hours. 1.26 g (4 mmol) of additional compound 4 was added and the mixture was heated at 110° C. with stirring for 90 hours. LC-MS of the reaction mixture confirmed the disappearance of the starting material of 195 and the formation of the major desired product (196). After the reaction was cooled down, 70 mL of CHCl$_3$ and 20 mL of H$_2$O was added. After liquid-liquid extraction, the two layers were separated and the organic layer was washed twice more with H$_2$O (30 mL×2). The organic layer was dried under vacuum. The crude material was purified by flash chromatography using hexane and EtOAc to give the desired product 196 (260.3 mg, 265 μmol, 26.5% isolated yield for 2 steps). LC-MS: MS m/e 983.9 [M+1]$^+$ (exact ms: 982.53).

Compound 196 (260.3 mg, 265 μmol) was dissolved in 4 mL of MeOH. 4.0 mL of 4.0 M HCl in 1,4-dioxane was then added. The reaction mixture was stirred at room temperature overnight and concentrated under vacuum. This crude was then purified by reverse-phase HPLC (CH$_3$CN/H$_2$O) to give the desired product 193 (89.4 mg, 102.35 μmol, 38.6% isolated yield based the molecular weigh of the HCl salt determined by elemental analysis) as the HCl salt with HPLC purity of 100% by ELSD. LC-MS: m/e 583.3 [M+1]$^+$ (exact ms: 582.32). $^1$H NMR (400 MHz, D$_2$O): 8.17 (d, J=8.4 Hz, 1H), 7.80 (d, J=8 Hz, 1H), 7.60–7.68 (m, 2H), 7.55 (td, J$_1$=8 Hz, J$_2$=1.2 Hz, 1H), 7.37 (dd, J$_1$=8.6 Hz, J$_2$=7.2 Hz, 4H), 7.23 (d, J=8.8 Hz, 2H), 4.52–4.62 (m, 2H), 4.38–4.48 (m, 2H), 3.28–3.42 (m, 4H), 2.87 (dt, J$_1$=12.6 Hz, J$_2$=18.8 Hz, 4H), 2.56–2.66 (m, 2H), 1.76–1.90 (m, 2H). Elemental analysis calcd (%) for C$_{31}$H$_{38}$N$_{10}$O$_2$·6HCl·4H$_2$O (873.514): C, 42.62, H, 6.00, N, 16.04; found C, 42.35, H, 6.14, N, 16.28.

4.15 General Method of Synthesis of Formula Ij Compounds

Scheme 43 describes a general synthetic procedure for preparing compound 200 of Formula Ij.

Scheme 43

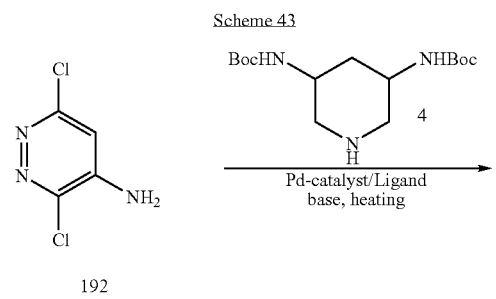

192

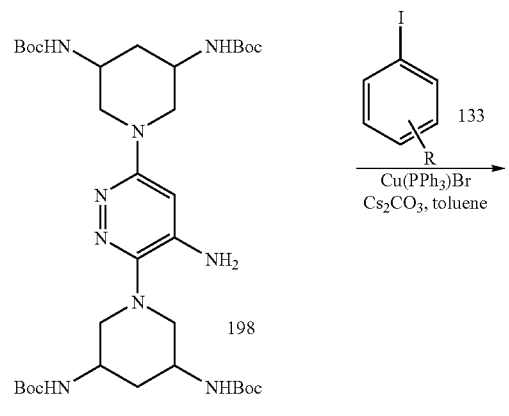

198

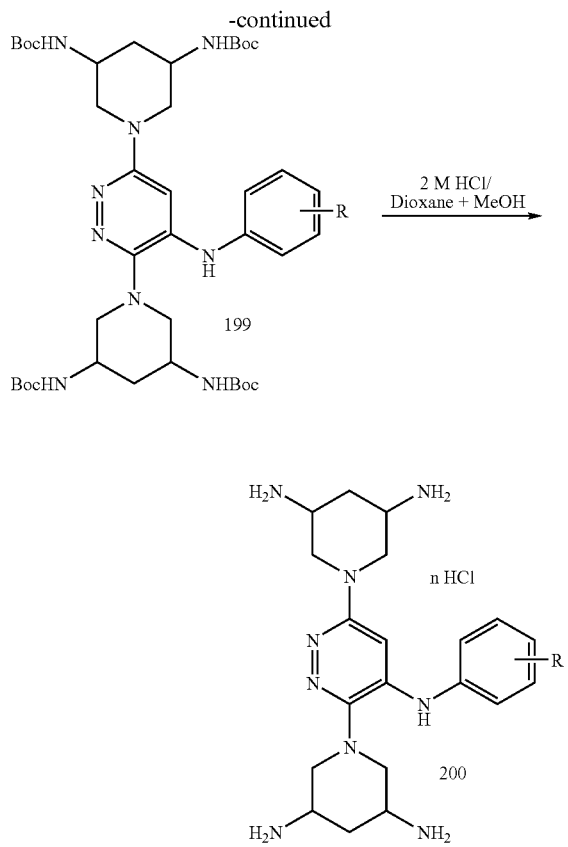

R = sustituents defined for "substituted aryl"

In this general method, starting material 192 reacts with 2–4 equivalents of (3R,5S)-3,5-bis(tert-butoxycarbonylamino)-piperidine (4) in the presence of Pd-catalyst selected from Pd$_2$(dba)$_3$, Pd(OAc)$_2$, PdCl$_2$(PCy$_3$)$_2$, PdCl$_2$[P($^t$Bu)$_2$OH], ligand selected from Xantphos, P($^t$Bu)$_3$, BINAP, 2-(dicyclohexylphosphino)biphenyl, 2-(di-t-butylphosphino)biphenyl, 2-dicyclohexylphosphino-2'-(N,N-dimethylamino)biphenyl, (R)-(+)-2,2'-bis(dicyclohexylphosphino)-1,1'-binaphthyl, and base selected from Cs$_2$CO$_3$, K$_2$CO$_3$, K$_3$PO$_4$ in a solvent selected from PhMe, DME, xylenes, dioxane and HMPA at a temperature from 80° C. to 140° C. preferentially between 100–120° C. for 16–72 hours under N$_2$ atmosphere. The reaction is checked for progress by TLC or HPLC and upon completion, the mixture is diluted with chloroform or other suitable solvents and the inorganic solid is filtered off through Celite. The resulting filtrate is washed with water via extraction, dried with magnesium or sodium sulfate and concentrated in vacuo. The residue is chromatographed on a silica gel column, using a gradient of chloroform-ethyl acetate or chloroform-methanol to generate the bis-aminated pure product 91.

Compound 198 reacts with iodoarene derivative 133 in a solvent selected from toluene, xylenes, anisole or chlorobenzene in the presence of tris-triphenylphosphine copper bromide [Cu(PPh$_3$)$_3$Br] as catalyst and cesium carbonate as base at an elevated temperature between 80 to 120° C., preferably 110 to 120° C., in an argon atmosphere to furnish after column chromatography on silica gel the arylamino derivative 199. Related chemical transformations are described in Gujadhur, R. et al., *Tetrahedron Letters*, 42, 4791–4793 (2001).

Compound 199 undergoes the deprotection of the Boc groups to give the crude product that is subsequently purified by HPLC to give the pure compound 200 as HCl salt.

This methodology is useful for the production of various derivatives represented by Formula Ij. Other variations of this methodology would be apparent to those skilled in the art.

4.15.1 Another General Method of Synthesis of Formula Ij Compound (Scheme 44).

Scheme 44 describes the general synthetic procedures for preparing compound of Formula Ij.

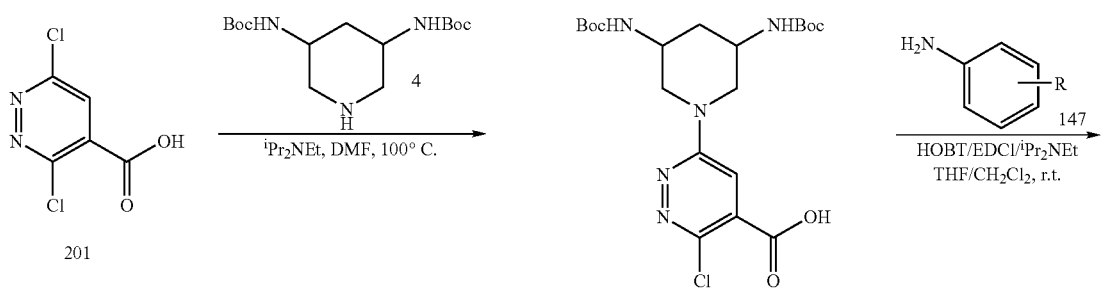

Scheme 44

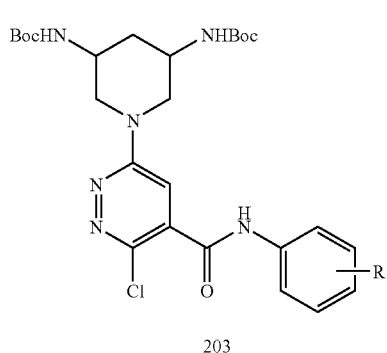

203

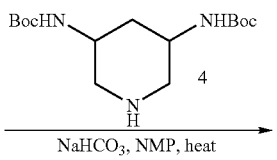

4

NaHCO₃, NMP, heat

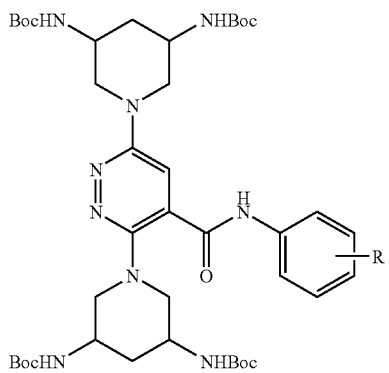

204

2 M HCl in Dioxane
MeOH, r.t. o.n.

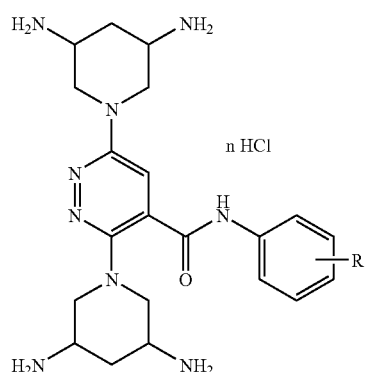

n HCl

205

One equivalent of 3,6-dichloro-pyridazine-4-carboxylic acid (201), 3 equivalents of 3,5-bis-(tert-butoxycarbonylamino)-piperidine (4) and 3 equivalents of $^i$Pr₂NEt in DMF are mixed. The mixture is heated at 100° C. with shaking. The reaction was monitored by TLC analysis and LC-MS. Upon the completion of the reaction, the solvent was removed under reduced pressure. When (3R,5S)-3,5-bis (tert-butoxycarbonylamino)-piperidine (4) was used, compound 202 with the following characteristics was obtained after purification by HPLC. LC-MS (ESI): m/e=472.3 [M+H]⁺.

A solution of four equivalents of $^i$Pr₂NEt in THF was added into a mixture of compound 2 and aniline (147) in THF and DMF. A solution of two equivalents of HOBT in THF (0.5 M) is added and the mixture is shaken at room temperature for 5 minutes. A solution of 2 equivalents of EDCI in CH₂Cl₂ (0.25 M) is added. The reaction mixture is shaken at room temperature for 24 h to 2 days. The solvent is removed under reduced pressure. The residue is dissolved in CHCl₃. The organic layer is washed with 10% aqueous NaHCO₃, followed by H₂O via extraction, dried over MgSO₄ and concentrated under reduced pressure. The crude material is purified by flash chromatography on silica gel using a gradient of hexane and ethyl acetate to give compound 203.

Excess of 3,5-bis-(tert-butoxycarbonylamino)-piperidine (4) is added into compound 203 in NMP, followed by NaHCO₃ (6 equiv.). The reaction mixture is heated at 110° C. for a few days with shaking. The reaction mixture is diluted with CHCl₃ and washed with H₂O via extraction. The organic layer is dried under reduced pressure and the crude is purified by flash chromatography to give the desired product (204).

Compound 204 is dissolved in MeOH. An equal volume of 4.0 M HCl in dioxane is then added and the reaction mixture is shaken at room temperature overnight. The solvent is evaporated and the residue is purified by HPLC using a gradient of CH₃CN and H₂O to give the desired product 205 as the HCl salt.

This methodology is useful for the production of various derivatives represented by Formula Ij. Other variations of this methodology would be apparent to those skilled in the art.
4.15.2 EXAMPLE 21
Scheme 45 Describes the Synthetic Procedures for Preparation of Compound
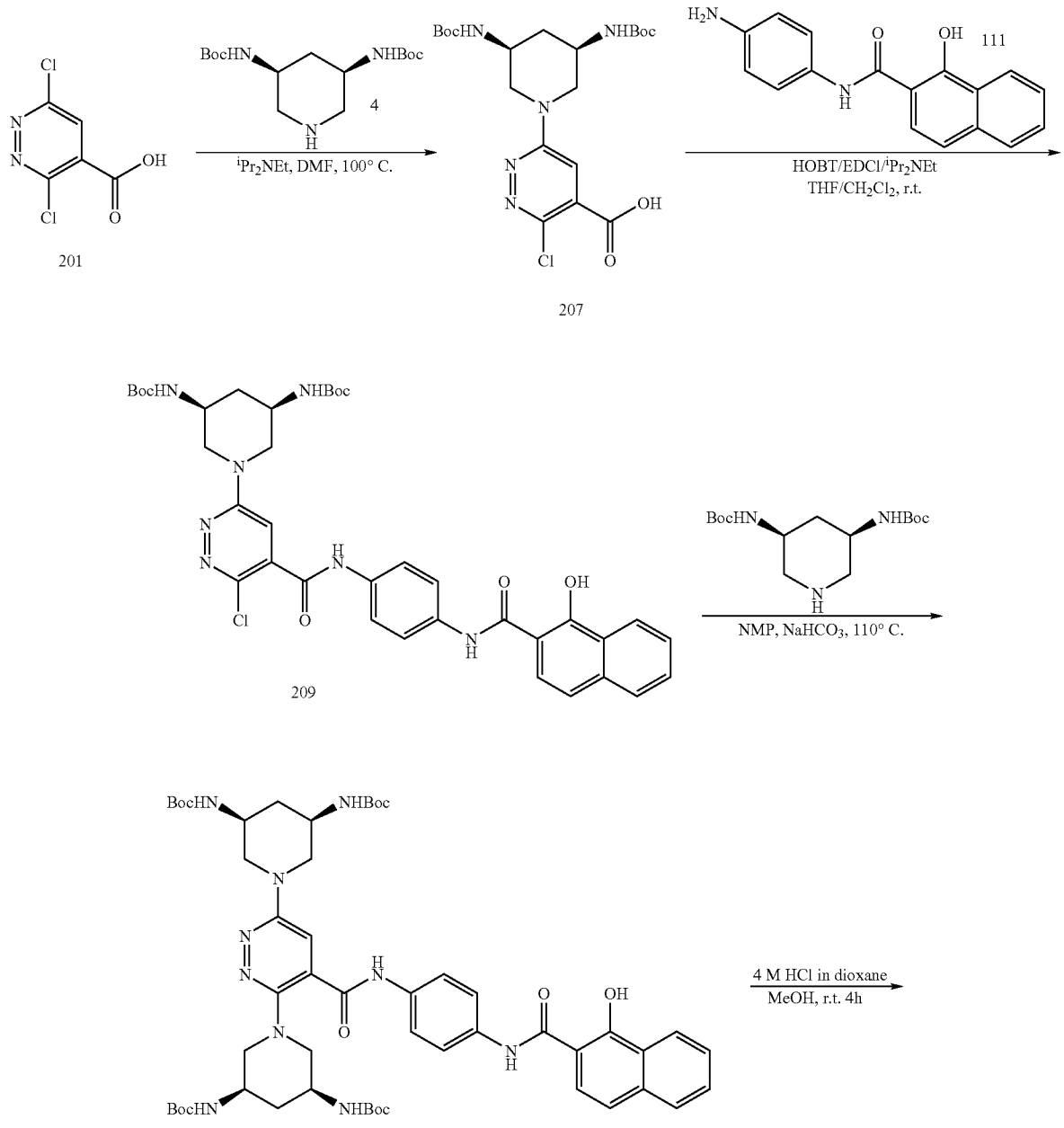

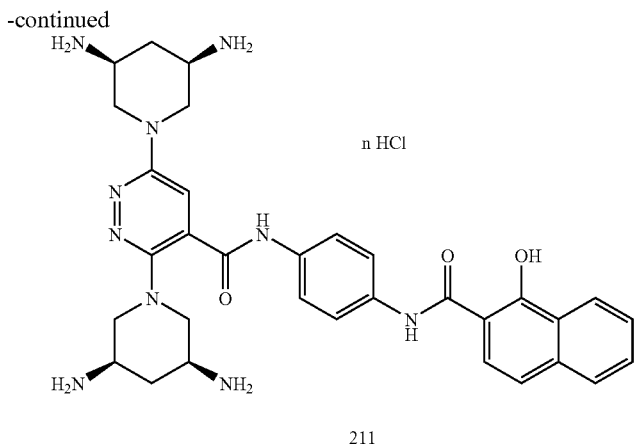

211

6-(3,5-Bis-tert-butoxycarbonylamino-piperidin-1-yl)-3-chloro-pyridazine-4-carboxylic acid (207)

A mixture of 3,6-Dichloro-pyridazine-4-carboxylic acid (201) (400 mg, 2 mmol) and (3R,5S)-3,5-bis-tert butoxy carbonyl amino piperdine (4) (1.3 g, 4 mmol) in 14 ml DMF containing $^i$Pr$_2$NEt (718 ∥l, 4 mmol) was heated at 100° C. for 25.6 h with shaking. The solvent was removed under reduced pressure. After HPLC purification, compound 207 (483 mg, 51.1%) was obtained as a solid. LC-MS (ESI): m/e=472.3 [M+1]$^+$

[5-tert-Butoxycarbonylamino-1-(6-chloro-5-{4-[(1-hydroxy-naphthalene-2-carbonyl)-amino]-phenylcarbamoyl}-pyridazin-3-yl)-piperidin-3-yl]-carbamic acid tert-butyl ester (209)

$^i$Pr$_2$NEt (360 μL, 2 mmol) in THF (1 ml) was added to a mixture of 207 (483 mg, 1.02 mmol) and 1-hydroxy-naphthalene-2-carboxylic acid 111 (4-amino-phenyl)-amide (283.88 mg, 1.02 μmol) in THF (5 mL). HOBT (306.3 mg, 2 mmol) in THF (2 mL) was added. The reaction mixture was vortexed for 1 minute. EDCI (383.4 mg, 2 mmol) in CH$_2$Cl$_2$ (4 mL) was added into the above reaction mixture. The reaction mixture was shaken at room temperature for 16 h. The solvent was removed under reduced pressure. The solid was dissolved in CHCl$_3$ (5 mL), washed with 10% NaHCO$_3$ (3 mL), H$_2$O (3 mL) and dried over MgSO$_4$. Solvent was removed under reduced pressure. After flash chromatography purification using ethyl acetate and hexane, 730 mg of compound 209 (98.4% yield) was obtained as a solid. LC-MS (ESI): m/z=732.5 [M+1]$^+$.

(3R,5S)-3,5-bis-tert butoxy carbonyl amino piperdine (4) (32 mg, 2 mmol) was added into compound 209 (730 mg, 1 mmol) in NMP (6 mL) followed by NaHCO$_3$ (504 mg, 6 mmol). The reaction mixture was heated at 110° C. for 107 h with shaking. The reaction mixture was diluted with CHCl$_3$ (8 mL) and washed with H$_2$O (4 mL×2). The water was back-extracted with CHC$_3$ (4 ml). The combined organic layers are dried under reduced pressure. After flash chromatography purification, compound 210 (25 mg, 2.5% yield) was obtained as a solid. LC-MS (ESI): m/e=1011.9 [M+1]$^+$;

3,6-Bis-(3,5-diamino-piperidin-1-yl)-pyridazine-4-carboxylic acid {4-[(1-hydroxy-naphthalene-2-carbonyl)-amino]-phenyl}-amide (211)

Compound 210 (25 mg, 25 μmol) was dissolved in MeOH (1 mL). HCl (4 M) in dioxane (1 mL) was then added at room temperature. After stirring at room temperature for 4 h, the reaction mixture was concentrated and the crude product was purified by HPLC to give the desired product (211) (2.6 mg, 13.6% yield) as a light yellow solid as HCl salt. LC-MS (ESI): m/e=611.3 [M+1]$^+$; $^1$H NMR (400 MHz, D$_2$O): δ 1.83–1.96 (m, 2H), 2.70 (s, br, 2H), 3.13 (t, 3H, J=11.6 Hz), 3.60–3.73 (m, 4H), 3.77–3.78 (m, 3H), 3.80–3.87 (m, 1H), 3.93 (d, 1H, J=8.4 Hz), 7.49 (d, 1H, J=8.8 Hz), 7.59 (s, 1H), 7.64 (m, 3H), 7.70 (m, 3H), 7.80 (d, 1H, J=8 Hz), 7.91 (d, 1H, J=7.2 Hz), 8.32 (d, 1H, J=7.6 Hz).

4.16 General Method of Synthesis of Formula Ij & Ik Compounds

Scheme 46 describes a general synthetic procedure for preparing compound of Formula Ij & Ik.

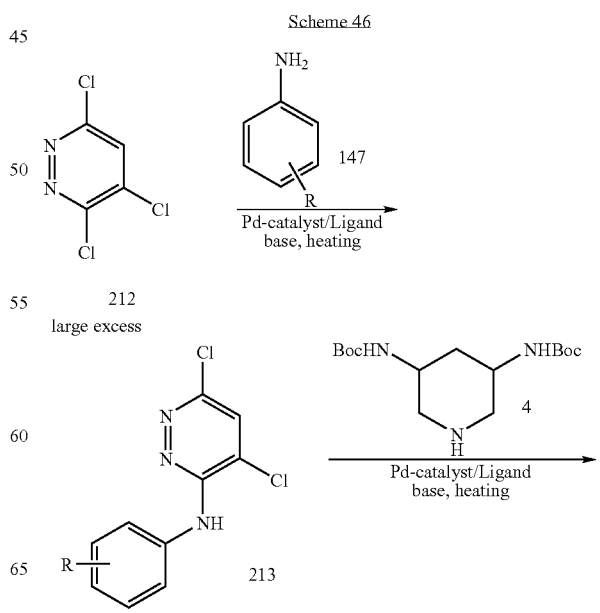

Scheme 46

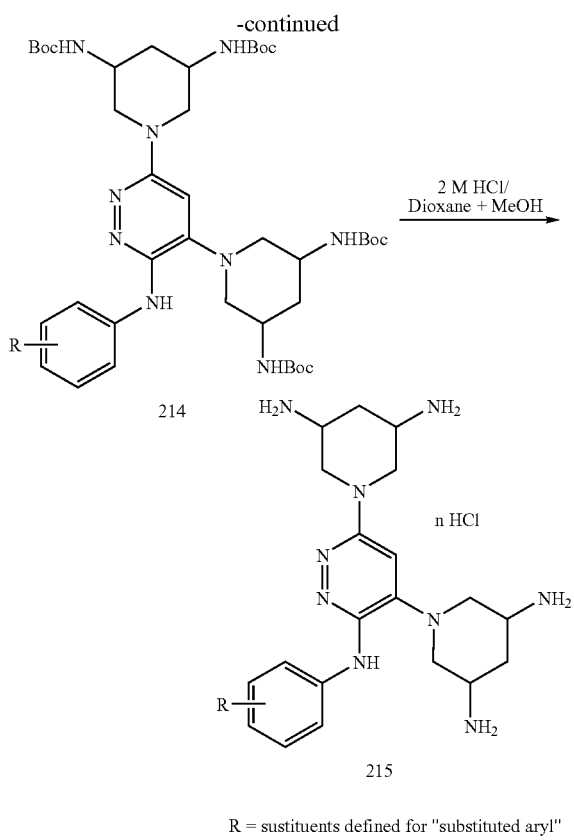

R = sustituents defined for "substituted aryl"

In this general method, 3–4 equivalents of starting material 212 react with one equivalent of aniline 147 in the presence of Pd-catalyst selected from Pd$_2$(dba)$_3$, Pd(OAc)$_2$, PdCl$_2$(PCy$_3$)$_2$, PdCl$_2$[P($^t$Bu)$_2$OH], ligand selected from Xantphos, P($^t$Bu)$_3$, BINAP, 2-(dicyclohexylphosphino)biphenyl, 2-(di-t-butylphosphino)biphenyl, 2-dicyclohexylphosphino-2'-(N,N-dimethylamino)biphenyl, (R)-(+)-2,2'-bis(dicyclohexylphosphino)-1,1'-binaphthyl, and base selected from Cs$_2$CO$_3$, K$_2$CO$_3$, K$_3$PO$_4$ in a solvent selected from PhMe, DME, xylenes, dioxane and HMPA at a temperature from 80° C. to 140° C. preferentially between 100–120° C. for 16–72 hours under N$_2$ atmosphere.

The reaction is checked for progress by TLC or HPLC and upon completion, the mixture is diluted with chloroform or other suitable solvents and the inorganic solid was filtered off through Celite. The resulting filtrate is washed with water via extraction, dried with magnesium or sodium sulfate and concentrated in vacuo. The residue is column chromatographed on a silica gel column, using a gradient of chloroform-ethyl acetate or chloroform-methanol to generate the bis-aminated pure product 213.

Bis-amination of the compound 213 by reacting with 2–3 equivalents of (3R,5S)-3,5-bis(tert-butoxycarbonylamino)-piperidine (4) in the presence of Pd-catalyst selected from Pd$_2$(dba)$_3$, Pd(OAc)$_2$, PdCl$_2$(PCy$_3$)$_2$, PdCl$_2$[P($^t$Bu)$_2$OH], ligand selected from Xantphos, P($^t$Bu)$_3$, BINAP, 2-(dicyclohexylphosphino)biphenyl, 2-(di-t-butylphosphino)biphenyl, 2-dicyclohexylphosphino-2'-(N,N-dimethylamino)biphenyl, (R)-(+)-2,2'-bis(dicyclohexylphosphino)-1,1'-binaphthyl, and base selected from Cs$_2$CO$_3$, K$_2$CO$_3$, K$_3$PO$_4$ in a solvent selected from PhMe, DME, xylenes, dioxane and HMPA at a temperature from 80° C. to 140° C. preferentially between 100–120° C. for 16–72 hours under N$_2$ atmosphere. The reaction is checked for progress by TLC or HPLC and upon completion, the mixture is diluted with chloroform or other suitable solvents and the inorganic solid was filtered off through Celite.

The resulting filtrate is washed with water via extraction, dried with magnesium or sodium sulfate and concentrated in vacuo. The residue is column chromatographed on a silica gel column, using a gradient of chloroform-ethyl acetate or chloroform-methanol to generate the Boc-protected pure product 214. Related chemical transformations are described in Donald E. Ames and Richard J. Ward, *Journal of the Chemical Society, Perkin Transactions 1: Organic and Bio-Organic Chemistry* (1972–1999), 6, 534–8 (1975).

Deprotection of the Boc groups of compound 214 gives the crude product that is subsequently purified by HPLC to give the pure compound 215 as HCl salt.

This methodology is useful for the production of various derivatives represented by Formula Ij & Ik. Other variations of this methodology would be apparent to those skilled in the art.

4.17 General Method of Synthesis of Formula Ii Compounds

Scheme 47 describes a general synthetic procedure for preparing compound 200 of Formula Il.

Scheme 47

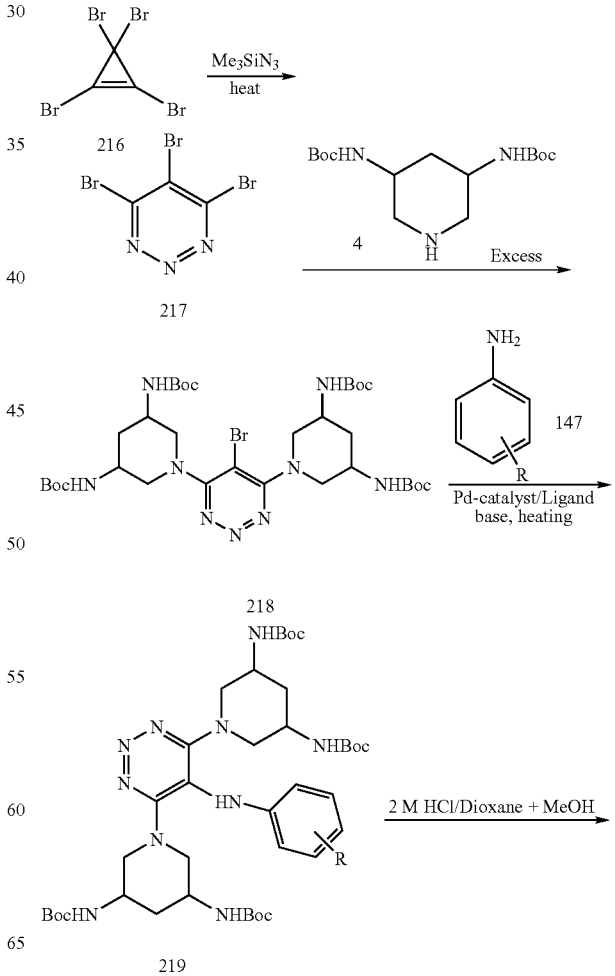

-continued

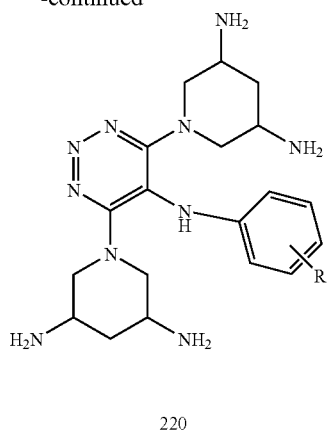

220

R = substituents defined for "substituted aryl"

In this general method based on the procedure described in the reference below, 3.55 g of tetrabromocyclopropene (216) (10 mmol) and 1.26 g trimethylsilylazide (11 mmol) are mixed and heated at 85° C. for 3 h. Upon cooling, a golden brown solid is precipitated out and that is filtered under vacuum. Recrystallization from CHCl$_3$/benzene gives 1.46 g product 217 in 46% yield. Compound 217 reacts with large excess of (3R,5S)-3,5-bis(tert-butoxycarbonylamino)-piperidine (4) in a solvent selected from diethyl ether, THF and DMF at a temperature from −30° C. to room temperature. Extraction with H$_2$O followed by drying the organic layer with Na$_2$SO$_4$ gives the crude product that was purified by re-crystallization to give the pure product 218. Related chemical transformations for the above 2 steps are described in R. Gompper and Schonafinger, *Chem. Ber*, 112, 1535–1544 (1979).

The mono-bromo compound 218 is then aminated by reacting with aniline derivative 147 in the presence of Pd-catalyst selected from Pd$_2$(dba)$_3$, Pd(OAc)$_2$, PdCl$_2$(PCy$_3$)$_2$, PdCl$_2$[P($^t$Bu)$_2$OH], ligand selected from Xantphos, P($^t$Bu)$_3$, BINAP, 2-(dicyclohexylphosphino)biphenyl, 2-(di-t-butylphosphino)biphenyl, 2-dicyclohexylphosphino-2'-(N,N-dimethylamino)biphenyl, (R)-(+)-2,2'-bis(dicyclohexylphosphino)-1,1'-binaphthyl, and base selected from Cs$_2$CO$_3$, K$_2$CO$_3$, K$_3$PO$_4$ in a solvent selected from PhMe, DME, xylenes, dioxane and HMPA at a temperature from 80° C. to 140° C. preferentially between 100–120° C. for 16–72 hours under N$_2$ atmosphere. The reaction is checked for progress by TLC or HPLC and upon completion, the mixture is diluted with chloroform or other suitable solvents and the inorganic solid is filtered off through Celite. The resulting filtrate is washed with water via extraction, dried with magnesium or sodium sulfate and concentrated in vacuo. The residue is column chromatographed on a silica gel column, using a gradient of chloroform-ethyl acetate or chloroform-methanol to generate the Boc-protected pure product 219.

Deprotection of the Boc groups of compound 219 gives the crude product that is subsequently purified by HPLC to give the pure compound 220 as HCl salt.

This methodology is useful for the production of various derivatives represented by Formula Il. Other variations of this methodology would be apparent to those skilled in the art.

4.18 EXAMPLE 22

Synthesis of Formula Im Compounds

Scheme 48 describes a synthetic procedure for preparing compound of 221 of Formula Im.

Scheme 48

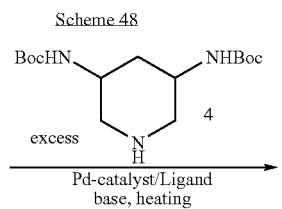

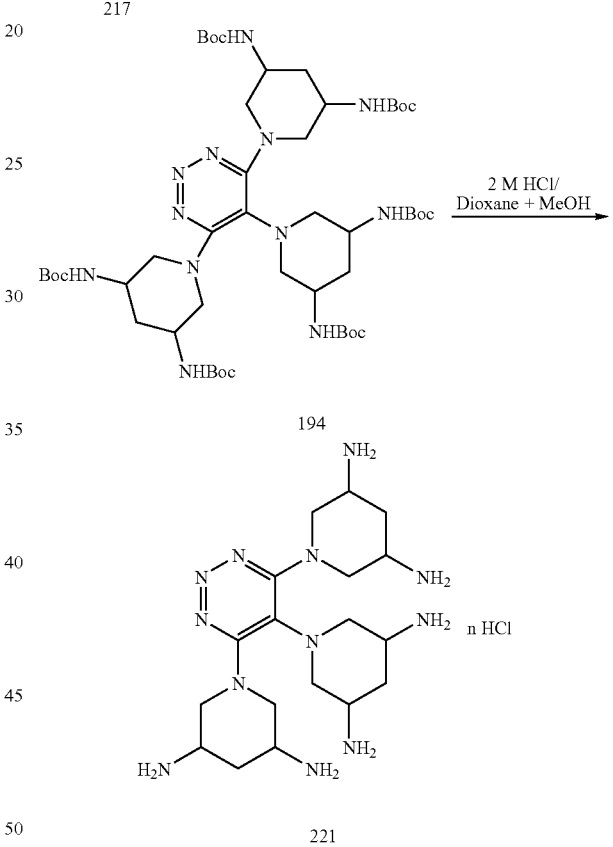

221

In the synthesis of compound 221 as shown above, triamination of the tribromo compound 217 is accomplished by reacting 3–4 equivalents of di-Boc-protected 3,5-diaminopiperidine (4) in the presence of Pd-catalyst selected from Pd$_2$(dba)$_3$, Pd(OAc)$_2$, PdCl$_2$(PCy$_3$)$_2$, PdCl$_2$[P($^t$Bu)$_2$OH], ligand selected from Xantphos, P($^t$Bu)$_3$, BINAP, 2-(dicyclohexylphosphino)biphenyl, 2-(Di-t-butylphosphino)biphenyl, 2-Dicyclohexylphosphino-2'-(N,N-dimethylamino)biphenyl, (R)-(+)-2,2'-Bis(dicyclohexylphosphino)-1,1'-Binaphthyl, and base selected from Cs$_2$CO$_3$, K$_2$CO$_3$, K$_3$PO$_4$ in a solvent selected from PhMe, DME, xylenes, dioxane and HMPA at a temperature from 80° C. to 140° C. preferentially between 100–120° C. for 16–72 hours under N$_2$ atmosphere. The reaction is checked for progress by TLC or HPLC and upon completion, the mixture is diluted with chloroform or other suitable solvents and the inorganic solid was filtered off through celite.

The resulting filtrate is washed with water via extraction, dried with magnesium or sodium sulfate and concentrated in vacuo. The residue is column chromatographed on a silica gel column, using a gradient of chloroform-ethyl acetate or chloroform-methanol to generate the Boc-protected pure product 194. Related chemical transformations are described in R. Gompper and Schonafinger, *Chem. Ber*, 112(5), 1535–1544 (1979).

Deprotection of the Boc groups of compound 194 gives the crude product that is subsequently purified by HPLC to give the pure compound 221 as HCl salt.

This methodology is useful for the production of various derivatives represented by Formula Im. Other variations of this methodology would be apparent to those skilled in the art.

4.19 General Method of Synthesis of Formula In Compounds

Scheme 49 describes a general synthetic procedure for preparing compound 225 of Formula In.

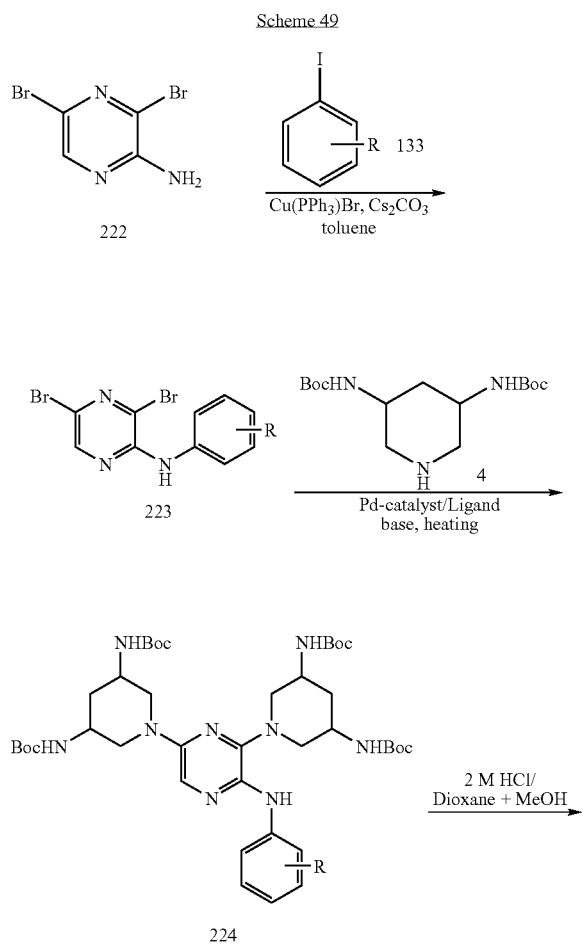

-continued

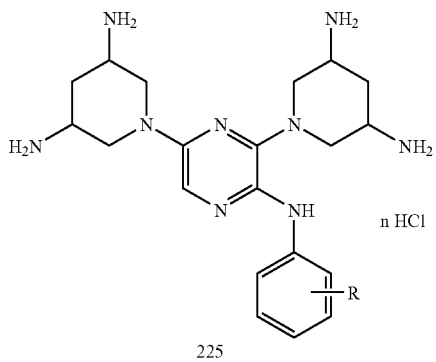

225

R = substituents defined for "substituted aryl"

In this general method, starting material 222 reacts with iodoarene derivative 133 in a solvent selected from toluene, xylenes, anisole or chlorobenzene in the presence of tris-triphenylphosphine copper bromide [Cu(PPh$_3$)$_3$Br] as catalyst and cesium carbonate as base at an elevated temperature between 80 to 140° C., preferably 110 to 120° C., in an argon atmosphere, and furnishes after column chromatography on silica gel the arylamino derivative 223. Related chemical transformations are described in Gujadhur, R. et al., *Tetrahedron Letters*, 42, 4791–4793 (2001).

Bis-amination of compound 223 is accomplished by reacting with 2–3 equivalents of (3R,5S)-3,5-bis-(tert-butoxycarbonylamino)-piperidine (4) in the presence of Pd-catalyst selected from Pd$_2$(dba)$_3$, Pd(OAc)$_2$, PdCl$_2$(PCy$_3$)$_2$, PdCl$_2$[P($^t$Bu)$_2$OH], ligand selected from Xantphos, P($^t$Bu)$_3$, BINAP, 2-(dicyclohexylphosphino)biphenyl, 2-(di-t-butylphosphino)biphenyl, 2-dicyclohexylphosphino-2'-(N,N-dimethylamino)biphenyl, (R)-(+)-2,2'-bis(dicyclohexylphosphino)-1,1'-Binaphthyl, and base selected from Cs$_2$CO$_3$, K$_2$CO$_3$, K$_3$PO$_4$ in a solvent selected from PhMe, DME, xylenes, dioxane and HMPA at a temperature from 80° C. to 140° C. preferentially between 100–120° C. for 16–72 hours under N$_2$ atmosphere. The reaction is checked for progress by TLC or HPLC and upon completion, the mixture is diluted with chloroform or other suitable solvents and the inorganic solid was filtered off through Celite. The resulting filtrate is washed with water via extraction, dried with magnesium or sodium sulfate and concentrated in vacuo. The residue is column chromatographed on a silica gel column, using a gradient of chloroform-ethyl acetate or chloroform-methanol to generate the Boc-protected pure product 224.

Compound 224 undergoes the de-protection of the Boc groups to give the crude product that is subsequently purified by HPLC to give the pure compound 225 as HCl salt.

This methodology is useful for the production of various derivatives represented by Formula In. Other variations of this methodology would be apparent to those skilled in the art.

4.20 General Method of Synthesis of Formula Io and Ip Compounds

Scheme 50 describes a general synthetic procedure for preparing compound of Formula Io and Ip.

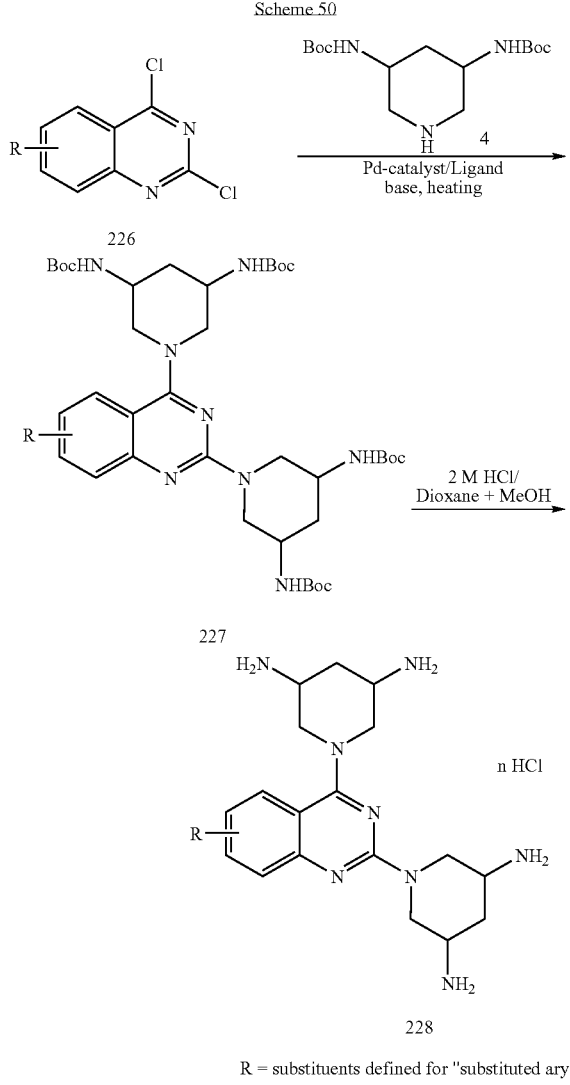

R = substituents defined for "substituted aryl"

In this general method, dichloro starting material 226 reacts with (3R,5S)-3,5-bis(tert-butoxycarbonylamino)-piperidine 4 in the presence of Pd-catalyst selected from $Pd_2(dba)_3$, $Pd(OAc)_2$, $PdCl_2(PCy_3)_2$, $PdCl_2[P(^tBu)_2OH]$, ligand selected from Xantphos, $P(^tBu)_3$, BINAP, 2-(dicyclohexylphosphino)biphenyl, 2-(di-t-butylphosphino)biphenyl, 2-dicyclohexylphosphino-2'-(N,N-dimethylamino)biphenyl, (R)-(+)-2,2'-bis(dicyclohexylphosphino)-1,1'-binaphthyl, and base selected from $Cs_2CO_3$, $K_2CO_3$, $NaHCO_3$, $K_3PO_4$ and $Et_3N$ in a solvent selected from PhMe, DME, O-xylene, dioxane, DMF and HMPA at a temperature from 50° C. to 140° C. preferentially between 80° C. and 110° C. for 16–72 hours under $N_2$ atmosphere. The reaction is checked for progress by TLC or HPLC and upon completion, the mixture is diluted with chloroform or other suitable solvents and the inorganic solid is filtered off through celite.

The resulting filtrate is washed with water via extraction, dried with magnesium or sodium sulfate and concentrated in vacuo. The residue is column chromatographed on a silica gel column, using a gradient of chloroform-ethyl acetate or chloroform-methanol to generate the Boc-protected pure product 227. Related chemical transformations are described in W. Karminski et al., *Jounal of Environmental Science and Health, Part B: Pesticides, Food Contaminants, and Agricultural Wastes*, B18(4–5), 599–610 (1983).

After purification by column chromatography using silica gel, compound 227 is deprotected to give the crude product 228 which is further purified by HPLC to give desired pure product 228 as HCl salt.

Starting material (226) is made according to the literature method described in Robert J. Ife, Thomas H. Brown, Peter Blurton, David J. Keeling, Colin A. Leach, Malcolm L. Meeson, Michael E. Parsons and Colin, *J. Theobald, J. Med. Chem*. 1995, 38, 2763–2773.

This methodology is useful for the production of various derivatives represented by Formula Io and Ip. Other variations of this methodology would be apparent to those skilled in the art.

4.20.1 Another General Method of Synthesis of Formula Io and/or Ip Compounds.

Scheme 51 describes the procedure to prepare compound 235 of Formula Io and/or Formula Ip.

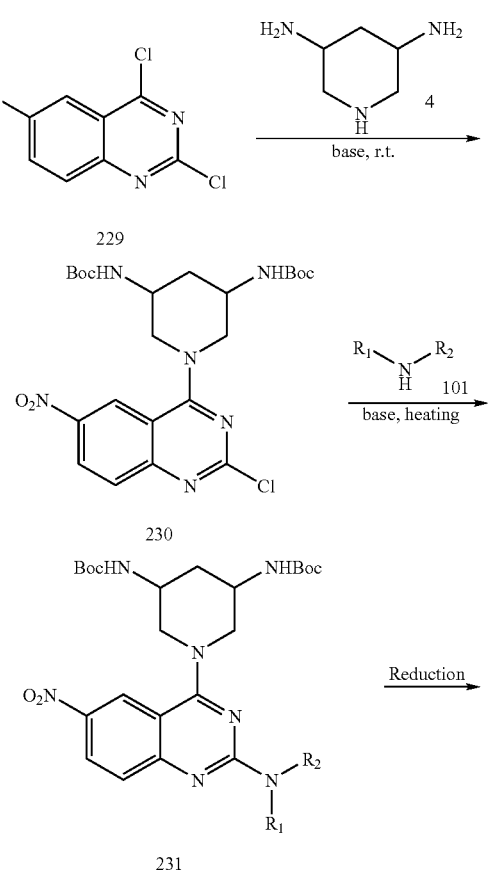

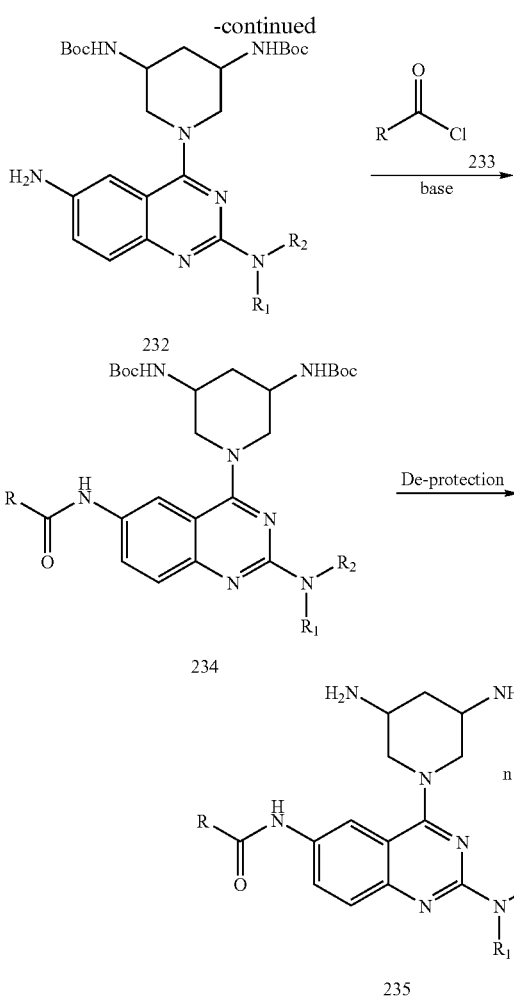

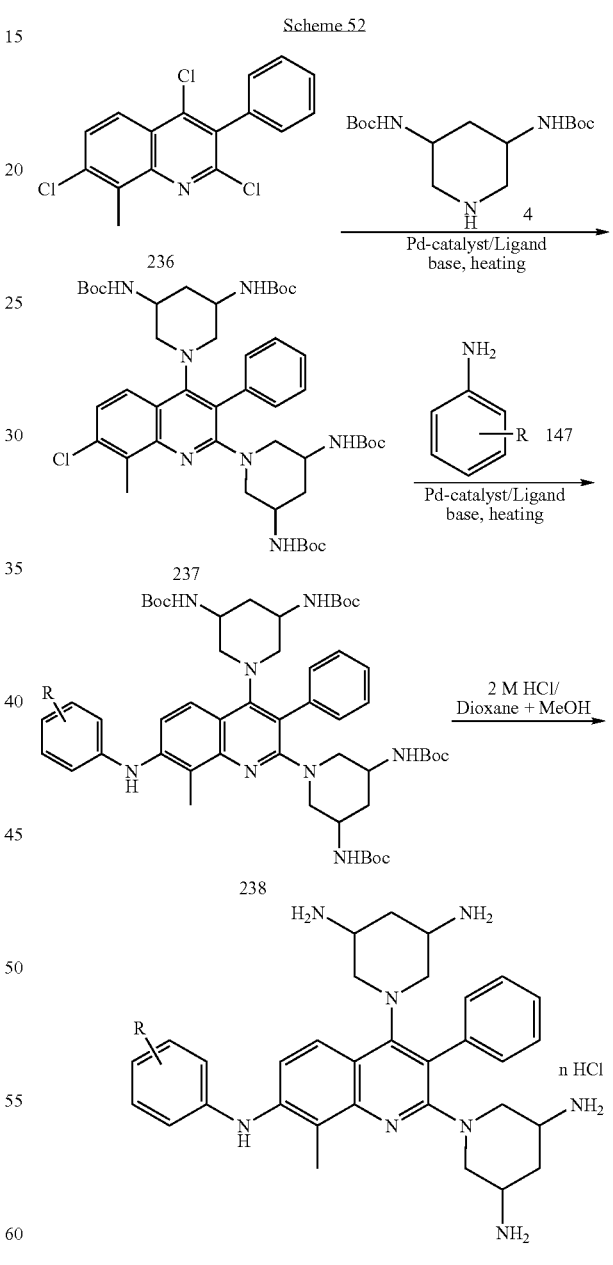

Meeson, Michael E. Parsons and Colin J. Theobald, *J. Med. Chem.* 1995, 38, 2763–2773; and (2) Sung J. Lee, Yoshitaka Konishi, Dingwei T. Yu, Tamara A. Miskowski, Christopher M. Riviello, Orest T. Macina, Manton R. Frierson, Kigen Kondo, Masafumi Sugitani, Jagadish C. Sircar and Kimberly M. Blazejewski, *J. Med. Chem.* 1995, 38, 3547–3557.

4.21 General Method of Synthesis of Formula Iq Compounds

Scheme 52 describes a general synthetic procedure for preparing compound of Formula Iq.

R = substituents defined for "substituted aryl"

R refers to $(C_1-C_6)$alkyl or alkylaryl.

In this general method, compound 229 is prepared in the same way as compound 226, as above, according to the literature method. Compound 229 is first treated with (3R, 5S)-bis-(tert-butoxycarbonylamino)-piperidine (4) at room temperature in a solvent selected from THF, EtOH, dioxane, DMF and NMP in the presence of a base selected from $^i$PrNEt, NaHCO$_3$, Et$_3$N, K$_2$CO$_3$ and Cs$_2$CO$_3$ to give compound 230 that is further treated with amine 101 in the presence of a base selected from $^i$Pr$_2$NEt, NaHCO$_3$, Et$_3$N, K$_2$CO$_3$ and Cs$_2$CO$_3$ with heating (100–120° C.) to give compound 231. In the case in which amine 101 is (3R,5S)-3,5-bis-(tert-butoxycarbonylamino)-piperidine (4), compound 229 is treated with amine (4) in refluxing THF to give compound 230.

The nitro-group in compound 230 is reduced to the corresponding amino-group using the reducing agent of Raney Nickel with hydrazine or, alternatively, hydrogenation in the presence of Pd/C catalyst to give compound 232.

Compound 232 is then coupled with acid chloride 233 in the presence of Et$_3$N or NaHCO$_3$ at room temperature to give compound 234. After removing the protecting groups of compound 234 using HCl, the desired product (235) is obtained as the HCl salt.

Chemical transformations related to above syntheses are described in (1) Robert J. Ife, Thomas H. Brown, Peter Blurton, David J. Keeling, Colin A. Leach, Malcolm L.

In this general method, starting material 236 reacts with 2–3 equivalents of (3R,5S)-3,5-bis(tert-butoxycarbonylamino)-piperidine (4) in the presence of Pd-catalyst selected from Pd$_2$(dba)$_3$, Pd(OAc)$_2$, PdCl$_2$(PCy$_3$)$_2$, PdCl$_2$[P($^t$Bu)$_2$OH], ligand selected from Xantphos, P($^t$Bu)$_3$, BINAP, 2-(dicyclohexylphosphino)biphenyl, 2-(di-t-butylphosphino)biphenyl, 2-dicyclohexylphosphino-2'-(N,N-dimethylamino)biphenyl, (R)-(+)-2,2'-bis(dicyclohexylphosphino)-1,1'-binaphthyl, and base selected from Cs$_2$CO$_3$, K$_2$CO$_3$, K$_3$PO$_4$ in a solvent selected from PhMe, DME, xylenes, dioxane and HMPA at a temperature from 80° C. to 140° C. preferentially between 100–120° C. for 16–72 hours under N$_2$ atmosphere. The reaction is checked for progress by TLC or HPLC and upon completion, the mixture is diluted with chloroform or other suitable solvents and the inorganic solid is filtered off through Celite.

The resulting filtrate is washed with water via extraction, dried with magnesium or sodium sulfate and concentrated in vacuo. The residue is column chromatographed on a silica gel column, using a gradient of chloroform-ethyl acetate or chloroform-methanol to generate the Boc-protected pure product 237.

Compound 237 reacts with aniline 147 in the presence of Pd-catalyst selected from Pd$_2$(dba)$_3$, Pd(OAc)$_2$, PdCl$_2$(PCy$_3$)$_2$, PdCl$_2$[P($^t$Bu)$_2$OH], ligand selected from Xantphos, P($^t$Bu)$_3$, BINAP, 2-(dicyclohexylphosphino)biphenyl, 2-(di-t-butylphosphino)biphenyl, 2-dicyclohexylphosphino-2'-(N,N-dimethylamino)biphenyl, (R)-(+)-2,2'-bis(dicyclohexylphosphino)-1,1'-binaphthyl, and base selected from Cs$_2$CO$_3$, K$_2$CO$_3$, K$_3$PO$_4$ in a solvent selected from PhMe, DME, xylenes, dioxane and HMPA at a temperature from 80° C. to 140° C. preferentially between 100–120° C. for 16–72 hours under N$_2$ atmosphere. The reaction is checked for progress by TLC or HPLC and upon completion, the mixture is diluted with chloroform or other suitable solvents and the inorganic solid is filtered off through celite.

The resulting filtrate is washed with water via extraction, dried with magnesium or sodium sulfate and concentrated in vacuo. The residue is column chromatographed on a silica gel column, using a gradient of chloroform-ethyl acetate or chloroform-methanol to generate the Boc-protected pure product 238.

Deprotection of the Boc groups of compound 238 gives the crude product that is subsequently purified by HPLC to give the pure compound 239 as HCl salt.

This methodology is useful for the preparation of various derivatives represented by Formula Iq (for example 240). Other variations of this methodology would be apparent to those skilled in the art.

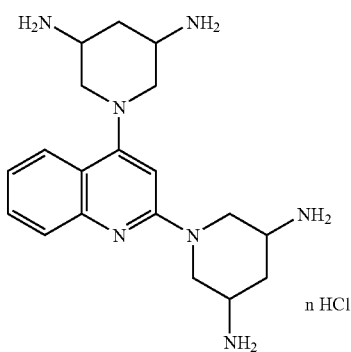

4.21.1 EXAMPLE 23

Synthesis of Bis-3,5-Diaminopiperidine Substituted Quinoline 119 of Formula Iq

Scheme 53 shows an exemplary synthetic procedure for preparing Formula Iq compounds (243) of the present invention.

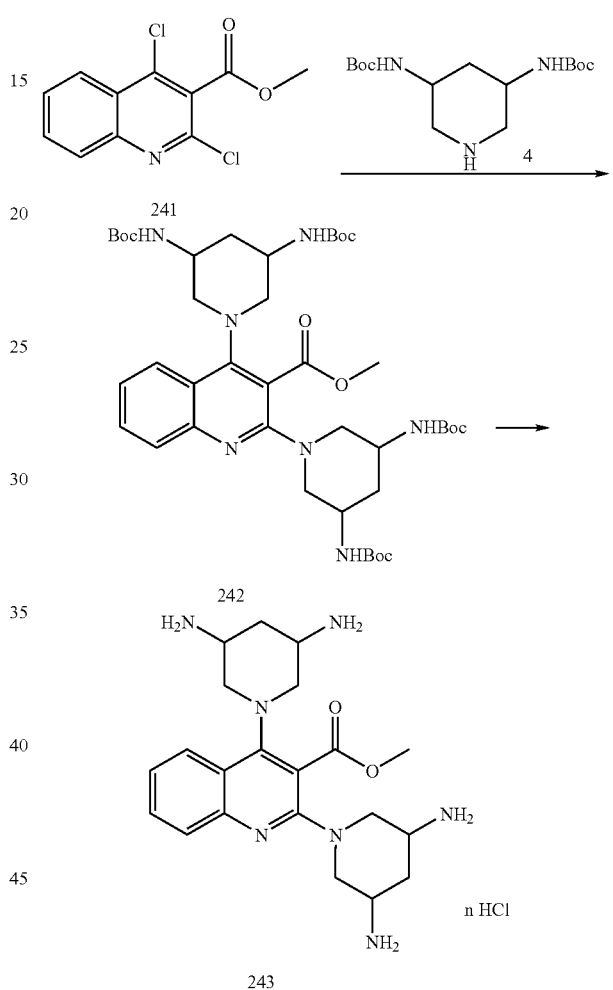

65 mg of 2,4-dichloro-3-carbomethoxyquinoline (241), 139 mg of (3R,5S)-3,5-bis(tert-butoxycarbonylamino)-piperidine 4, 500 µL of 1M iPr$_2$Net in DMF and DMF (2 mL) were mixed and heated at 100° C. overnight. LC-MS of the reaction mixture showed that only a small amount of desired product and majority was the mono-substituted product.

The reaction mixture was dried under vacuum and purified by HPLC to give 6.6 mg of the desired product (242) (yellow oil). The BOC-intermediate was dissolved in 1 mL of MeOH, then 1 mL of 4 M HCl in 1,4-dioxane was added. The resulting reaction mixture was stirred at room temperature overnight and concentrated under vacuum to give the desired product (243) (3.6 mg). LC-MS was used to confirm the identity of the desired product. LC-MS: a single peak (both ELSD and WV-254) with MS m/e 414.2 [M+1] was found (exact mass: 413.25).

4.22 General Method of Synthesis of Formula Ir Compounds
Scheme 54 describes another general synthetic procedure for preparing compound 249 of Formula Ir.
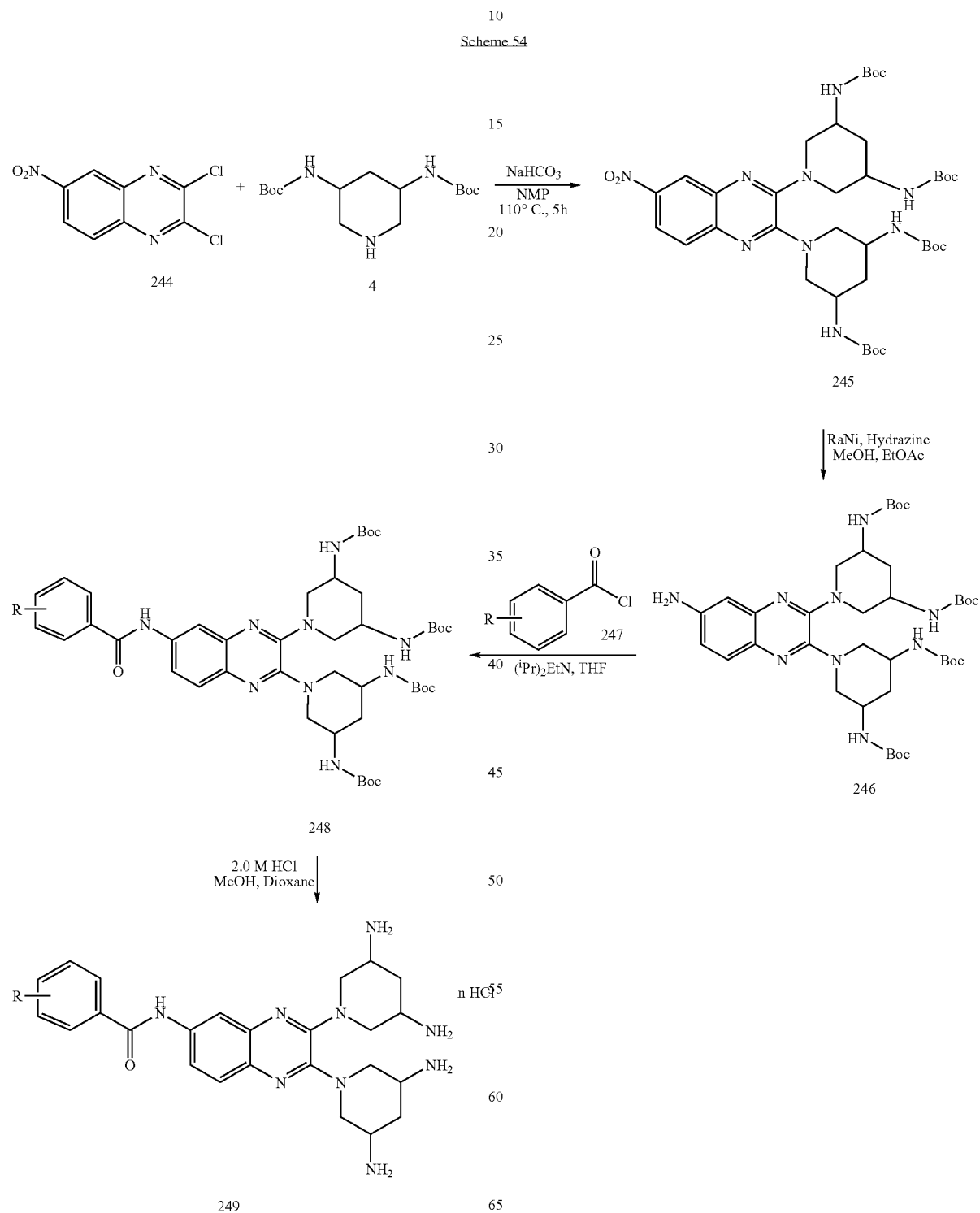
Scheme 54

R refers to substituents defined for substituted aryls.

2,3-Dichloro-6-nitro-quinoxaline (244) (1 equiv.), (3R,5S)-3,5-bis(tert-butoxycarbonylamino)-piperidine (4) (2.4 equiv.), NaHCO$_3$ (6 equiv.) and NMP were mixed. The mixture was heated at 110° C. in a Teflon septum capped 8 mL vial for 5 h. The reaction was monitored by TLC and LC-MS. The mixture was poured into ice-water and the resulting precipitate was collected by filtration under reduced pressure. The solid was purified by flash chromatography to give the desired product 245.

Compound 245 was dissolved in a mixture of EtOAc and MeOH. The solution was heated to 60° C. Raney Nickel (catalytic amount) was added followed by hydrazine (excess). The mixture continued to stir for 15 minutes at 60° C. in an opened vial. The reaction was monitored by TLC. After cooling, the mixture was passed through a plug of silica gel and the filtrate was concentrated. The crude was dissolved in EtOAc, washed with water and brine via extraction, dried over MgSO$_4$ and concentrated to give the desired product 246.

Same equivalent of compound 246, acid chloride (247) and $^i$Pr$_2$EtN were combined and dissolved in DMF (0.2 M). The mixture was shaken at room temperature for 16–24 h. Upon completion of the reaction indicated by TLC and LC-MS, the mixture was diluted with EtOAc, washed with saturated aqueous NaHCO$_3$ and brine via extraction, dried over MgSO$_4$ and concentrated to give the desired product 248.

Compound 248 is dissolved in MeOH and 4.0 M HCl in dioxane is added. The mixture is shaken at room temp for 16–24 hours. The solution is concentrated and the crude is purified by reverse phase HPLC to give the desired product (249) as the HCl salt.

4.22.1 EXAMPLE 24

Synthesis of Compound of Formula Ir (Scheme 55)

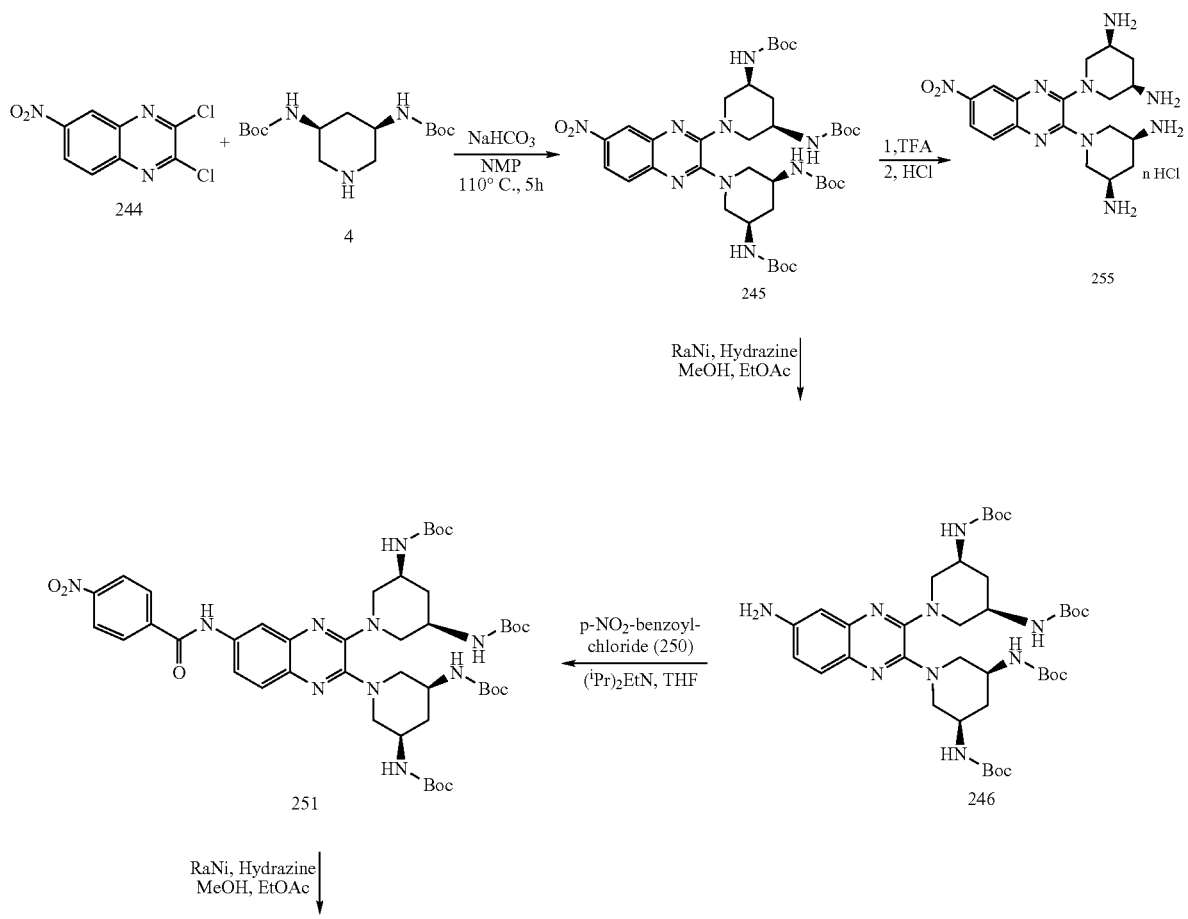

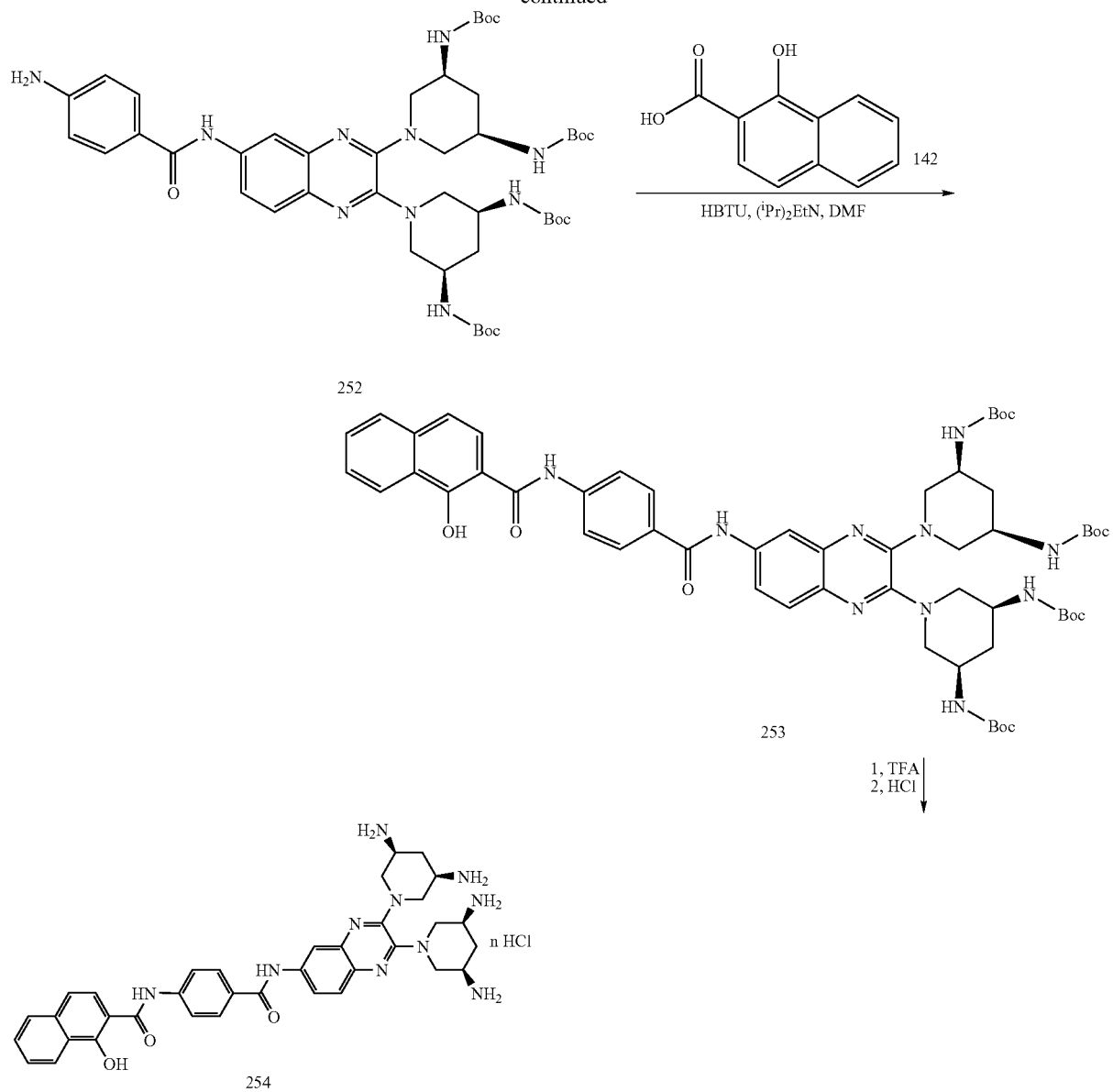

2,3-bis-((3R,5S)-3,5-bis-(tert-Butoxycarbonylamino)-piperidin-1-yl)-6-nitro-quinoxaline (245)

2,3-Dichloro-6-nitro-quinoxaline (244) (0.1 g, 0.409 mmol) and (3R,5S)-3,5-bis(tert-butoxycarbonylamino)-piperidine (4) (0.315 g, 1 mmol) were combined with NaHCO$_3$ (0.206 g, 2.45 mmol) and suspended in NMP (2.5 mL). The mixture was heated in a Teflon septum capped 8 mL vial for 5 h. TLC (R$_f$: 0.45–0.5 compared to R$_f$: 0.95 for compound 245 in 1:1 hexanes/EtOAc) and LC-MS indicated complete reaction at this point. The mixture was poured into ice-water (25 mL) and the resulting precipitate was collected by filtration under reduced pressure. The solid was purified by flash chromatography using a gradient of hexane and EtOAc (15–100% EtOAc in hexanes in 30 minutes) to give the desired product (245) as a yellow powder upon concentrating (0.212 g, 0.264 mmol, 64% yield). LC-MS (ESI): (exact mass: 801.44) m/e=802.5 [M+1]$^+$.

2,3-bis-((3R,5S)-3,5-bis-(tert-Butoxycarbonylamino)-piperidin-1-yl)-quinoxalin-6-ylamine (246)

2,3-Bis-((3R,5S)-3,5-bis-(tert-Butoxycarbonylamino)-piperidin-1-yl)-6-nitro-quinoxaline (3) (0.159 g, 0.198 mmol) was dissolved in a mixture of EtOAc (3 mL) and MeOH (3 mL). The solution was heated to 60° C. and Raney Nickel (0.25 mL, 50% slurry in water) and hydrazine (0.5 mL, anhydrous) were added. Bubbling was observed. The mixture continued to stir for 15 minutes at 60° C. TLC (R$_f$: 0.05 compared to R$_f$: 0.3 for compound 245 in 1:1 hexanes/EtOAc) indicated complete reduction at this point. The mixture was passed through a plug of silica gel and concentrated to give a white powder. The solid was dissolved in EtOAc (30 mL), washed with water (2×20 mL) and brine (2×20 mL) via extraction, dried over MgSO$_4$ and concentrated to give the desired product (246) as a white powder (0.135 g, 0.175 mmol, 88.3% yield). LC-MS (ESI): (exact mass: 771.46) m/e=772.6 [M+1]+.

N-(2,3-bis-((3R,5S)-3,5-bis-(tert-Butoxycarbonylamino)-piperidin-1-yl)-quinoxalin-6-yl)-4-nitrobenzamide (251)

2,3-bis-((3R,5S)-3,5-bis-(tert-Butoxycarbonylamino)-piperidin-1-yl)-quinoxalin-6-ylamine (246) (0.067 g, 0.087 mmol) and p-nitro-benzoylchloride (0.0167 g, 0.09 mmol) were combined and dissolved in DMF (0.45 mL). $^i$Pr$_2$EtN (0.016 mL, 0.09 mmol) was added and the mixture was shaken at room temperature for 16 h. TLC (R$_f$: 0.8 compared to R$_f$: 0.05 for compound 246 in 1:1 hexane/EtOAc) and LC-MS indicated complete coupling at this point. The mixture was diluted with EtOAc (30 mL), washed with saturated aqueous NaHCO$_3$ (2×10 mL) and brine (2×10 mL) via extraction, dried over MgSO$_4$ and concentrated to give the desired product (251) as an orange solid (0.063 g, 0.068 mmol, 78.6% yield). LC-MS (ESI): (exact mass: 920.48) m/e=921.8 [M+1]+.

4-Amino-N-(2,3-bis-((3R,5S)-3,5-bis-(tert-Butoxycarbonylamino)-piperidin-1-yl)-quinoxalin-6-yl)-benzamide (252)

N-(2,3-bis-((3R,5S)-3,5-bis-(tert-Butoxycarbonylamino)-piperidin-1-yl)-quinoxalin-6-yl)-4-nitro-benzamide (251) (0.063 g, 0.068 mmol) was dissolved in a mixture of EtOAc (3 mL) and MeOH (3 mL). The solution was heated to 60° C. and Raney Nickel (0.25 mL, 50% slurry in water) and hydrazine (0.5 mL, anhydrous) were added. Bubbling was observed. The mixture continued to stir for 15 minutes at 60° C. The mixture was passed through a plug of silica gel and concentrated to give an orange powder. The solid was dissolved in EtOAc (30 mL), washed with water (2×20 mL) and brine (2×20 mL) via extraction, dried over MgSO$_4$ and concentrated to give the desired product as an orange powder (0.061 g, 0.0684 mmol, 99% yield). LC-MS (ESI): (exact mass: 890.50) m/e=891.9 [M+1]+.

1-Hydroxy-naphthalene-2-carboxylic acid [4-(2,3-bis-((3R,5S)-3,5-bis-(tert-Butoxycarbonylamino)-piperidin-1-yl)-quinoxalin-6-ylcarbamoyl)-phenyl]-amide (253)

1-Hydroxy-naphthalene-2-carboxylic acid (142) (0.016 g, 0.085 mmol) was dissolved in DMF (0.8 mL) and HBTU (0.032 g, 0.085 mmol) followed by $^i$Pr$_2$EtN (0.022 mL, 0.128 mmol) were added. The mixture was shaken at room temperature for 25 minutes. 4-Amino-N-(2,3-bis-((3R,5S)-3,5-bis-(tert-Butoxycarbonylamino)-piperidin-1-yl)-quinoxalin-6-yl)-benzamide (252) (0.06 g, 0.068 mmol) was added and the mixture was shaken at room temperature for 16 h. The mixture was diluted with EtOAc, washed with sodium bicarbonate and brine via extraction, dried over MgSO$_4$ and concentrated under reduced pressure. Purification by flash chromatography on silica gel using a gradient of hexane and EtOAc gave the desired product (253) (0.009 g, 0.0085 mmol, 12.5% yield). LC-MS (ESI): (exact mass: 1060.54, mol. wt: 1061.23) m/e=1062.0 [M+1]+.

1-Hydroxy-naphthalene-2-carboxylic acid [4-(2,3-Bis-((3R,5S)-3,5-diamino-piperidin-1-yl)-quinoxalin-6-ylcarbamoyl)-phenyl]-amide (254)

1-Hydroxy-naphthalene-2-carboxylic acid [4-(2,3-bis-((3R,5S)-3,5-bis-(tert-Butoxycarbonylamino)-piperidin-1-yl)-quinoxalin-6-ylcarbamoyl)-phenyl]-amide (253) (9 mg, 8.5 μmmol) was dissolved in TFA (1 mL) and the mixture was shaken in a Teflon septum capped vial at room temperature for 3 hours. LC-MS indicated complete de-protection at this point. The solution was concentrated to give an orange oil. The oil was dissolved in MeOH (1 mL) and HCl (1 mL, 4.0 M in dioxane) was added and the mixture was vortexed for 20 seconds. A fine suspension was observed. The mixture was concentrated to an orange powder. Ethyl ether (5 mL) was added to the powder and vortexed for 2 minutes. The solid was collected by filtration and dried under high vacuum for 16 hours to give the desired product (254) as a yellow/green powder (5.4 mg, 6.69 μmmol, 78.7% yield, assuming a 4 HCl salt). LC-MS (ESI): (exact mass: 660.33) m/e=661.6 [M+1]+. $^1$H NMR (400 MHz, D$_2$O): δ 1.70–1.82 (m, 2H), 2.61–2.65 (m, 2H), 2.78–2.94 (m, 2H), 3.57–3.60 (m, 2H), 3.67–3.68 (m, 4H), 3.97 (d, 2H, J=9.6 Hz), 4.23 (d, 2H, J=9.6 Hz), 6.89 (d, 1H, J=8.8 Hz), 7.14 (d, 1H, J=8.4 Hz), 7.18–7.29 (m, 3H), 7.32–7.53 (m, 6H), 7.74 (d, 2H, J=7.6 Hz).

2,3-Bis-((3R,5S)-3,5-diamino-piperidin-1-yl)-quinoxalin-6-ylamine (255)

2,3-Bis-((3R,5S)-3,5-bis-(tert-Butoxycarbonylamino)-piperidin-1-yl)-6-nitro-quinoxaline (245) (0.05 g, 0.135 mmol) was dissolved in TFA (3 mL) and the mixture was shaken at room temperature in a Teflon septum capped vial for 3 hours. LC-MS indicated complete de-protection at this point. The solution was concentrated to give an orange oil. The oil was dissolved in MeOH (1 mL) and HCl (1 mL, 4.0 M in dioxane) was added and the mixture was vortexed for 20 seconds. A fine suspension was observed. The mixture was concentrated to an orange powder. Ethyl ether (5 mL) was added to the powder and vortexed for 2 minutes. The solid was collected by filtration and dried under high vacuum for 16 hours to give the desired product (255) as an orange powder (0.023 g, 0.042 mmol, 31% yield, assumed 4 HCl salt). LC-MS (ESI): (exact mass: 401.23) m/e=402.2 [M+1]+. $^1$H NMR (400 MHz, D$_2$O): δ 1.72 (q, 2H, J=12 Hz), 2.49 (d, 2H, J=10 Hz), 2.94 (q, 4H, J=12 Hz), 3.51–3.67 (m, 4H), 4.44 (dd, 2H, J$_1$=12 Hz, J$_2$=4.4 Hz), 4.57 (dd, 2H, J$_1$=12.8 Hz, J$_2$=3.6 Hz), 7.71 (d, 1H, J=9.2 Hz), 8.10 (dd, 1H, J$_1$=9.2 Hz, J$_2$=2.8 Hz), 8.44 (d, 1H, J=2.4 Hz).

4.23 General Method of Synthesis of Formula Is Compounds.

Scheme 56 describes the general synthetic procedures for preparing compound of Formula Is.

Scheme 56

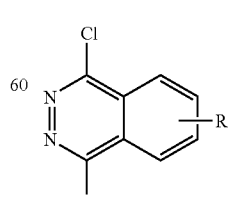
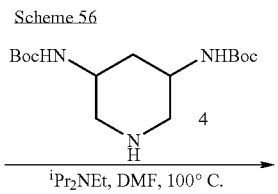

$^i$Pr$_2$NEt, DMF, 100° C.

256

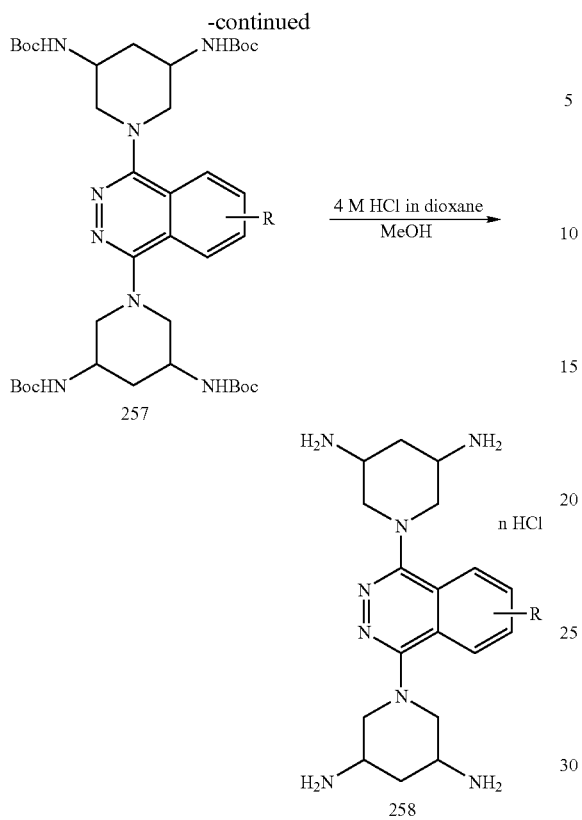

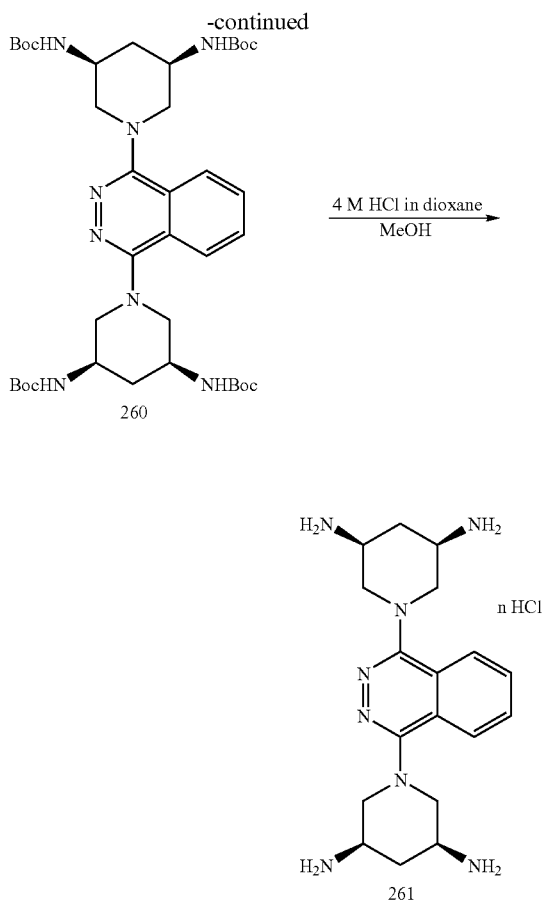

R refers to substituents as defined for substituted aryls.

One equivalent of 1,4-dichloro-phthalazine (246), (3R, 5S)-3,5-bis(tert-butoxycarbonylamino)-piperidine (4) and 4 equivalents of $^i$Pr$_2$NEt in DMF were mixed and the mixture was heated at 100° C. with shaking. Upon the completion of the reaction, the solvent was removed under reduced pressure and the crude was purified by flash chromatography to give the desired product 257.

A solution of compound 257 in MeOH was treated with an equal volume of 4.0 M of HCl in Dioxane. The reaction mixture was shaken at room temperature overnight. The solvent was removed under reduced pressure and the residue was purified by HPLC to give the desired product (258) as the HCl salt.

4.23.1 EXAMPLE 25

Synthesis of Formula Is Compound (Scheme 57)

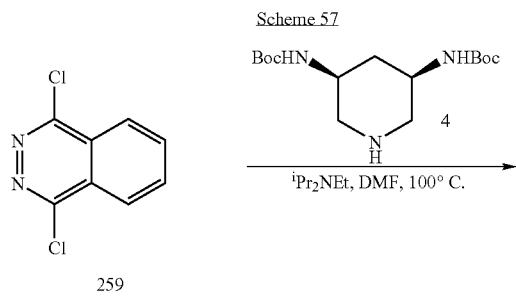

1,4-Dichloro-phthalazine (259) (199.04 mg, 1 mmol), (3R,5S)-3,5-bis(tert-butoxycarbonylamino)-piperidine (4) (1.26 g, 4 mmol) in 5 mL of DMF and $^i$Pr$_2$NEt (699 μL, 4 mmol) were mixed and the mixture was heated at 100° C. for 38 h with shaking. The solvent was removed under reduced pressure. After flash chromatography purification on silica gel using a gradient of hexane and ethyl acetate followed by reverse-phase HPLC purification, compound 260 (15.7 mg) was obtained as a solid. LC-MS (ESI): m/e=757.7 [M+H]$^+$ Compound 260 was dissolved in MeOH (2 mL). HCl (4.0 M) in dioxane (2 mL) was then added. After stirring at room temperature overnight, the reaction mixture was concentrated under reduced pressure. The crude was purified by reverse-phase HPLC using a gradient of CH$_3$CN and H$_2$O to give 32.3 mg of the desired product (261) as a light yellow solid as the HCl salt in 4.9% isolated yield for 2 steps. LC-MS (ESI): m/e=357.4 [M+H]$^+$. $^1$H NMR (400 MHz, D$_2$O): δ=1.91 (q, J=12 Hz, 2H), 2.76 (s, br, 2H), 3.24 (t, J=12 Hz, 4H), 3.92 (m, 4H), 4.20 (m, 4H), 8.11 (m, 2H), 8.19 (m, 2H).

4.24 General Method of Synthesis of Formula It Compounds

Scheme 58 describes a general synthetic procedure for preparing compound of Formula It.

Scheme 58

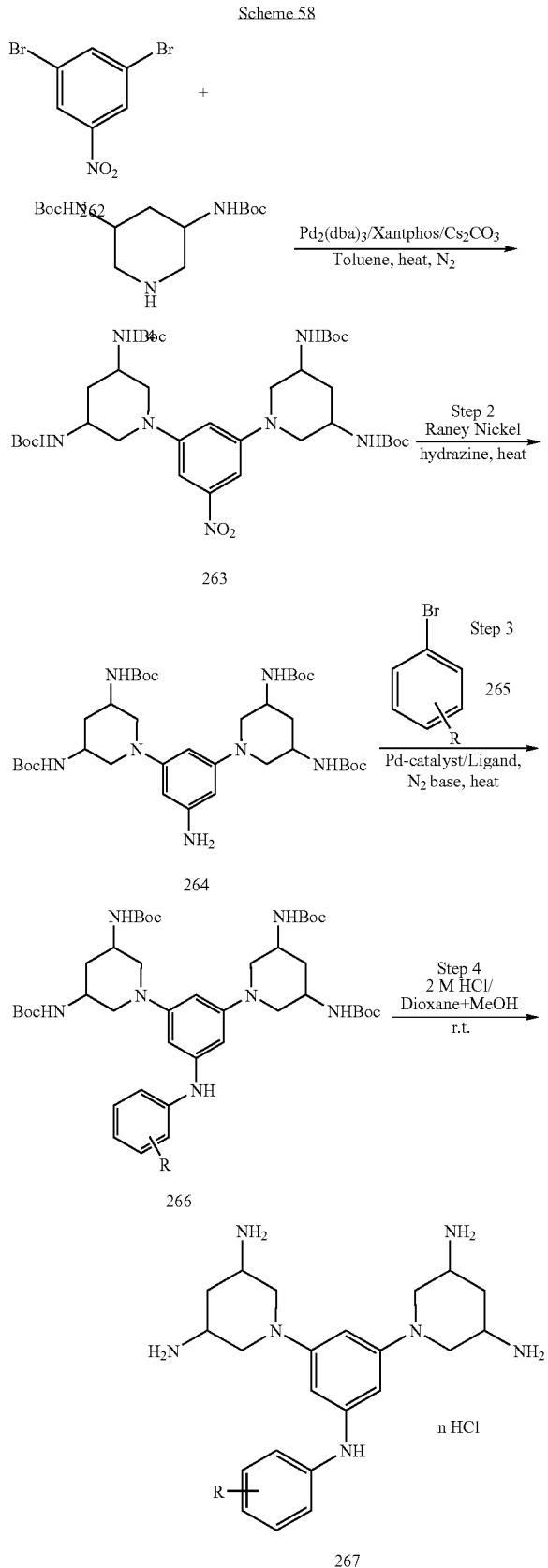

R = substituents defined for "substituted aryl"

In this general method of producing compounds of Formula It, the amination of the both halides of 3,5-dibromonitrobenzene (262) is accomplished by treating with (3R,5S)-3,5-bis(tert-butoxycarbonylamino)-piperidine (4) using Pd$_2$(dba)$_3$ catalyst, Xantphos as ligand and Cs$_2$CO$_3$ as base to give compound 263. The nitro group is then reduced by Raney Nickel and hydrazine combination.

The resulting aniline (264) reacts with aromatic bromide (265) in the presence of Pd-catalyst selected from Pd$_2$(dba)$_3$, Pd(OAc)$_2$, PdCl$_2$(PCy$_3$)$_2$, PdCl$_2$[P($^t$Bu)$_2$OH], ligand selected from Xantphos, P($^t$Bu)$_3$, BINAP, 2-(dicyclohexylphosphino)biphenyl, 2-(di-t-butylphosphino)biphenyl, 2-dicyclohexylphosphino-2'-(N,N-dimethylamino)biphenyl, (R)-(+)-2,2'-bis(dicyclohexylphosphino)-1,1'-binaphthyl, and base selected from Cs$_2$CO$_3$, K$_2$CO$_3$, K$_3$PO$_4$ in a solvent selected from PhMe, DME, xylenes, dioxane, HMPA in the temperature range of 80–140° C. preferably at 100–110° C. to generate crude product 266 that is purified by column chromatography to give the desired pure product 266.

Finally, all the Boc-protecting groups of compound 266 are removed by 2 M HCl in the mixed solvents of dioxane and methanol to give the desired product 267 as HCl salt.

This methodology is useful for the production of various derivatives represented by Formula It. Other variations of this methodology would be apparent to those skilled in the art.

4.24.1 EXAMPLE 26

Synthesis of Formula It Compounds 268 and 269

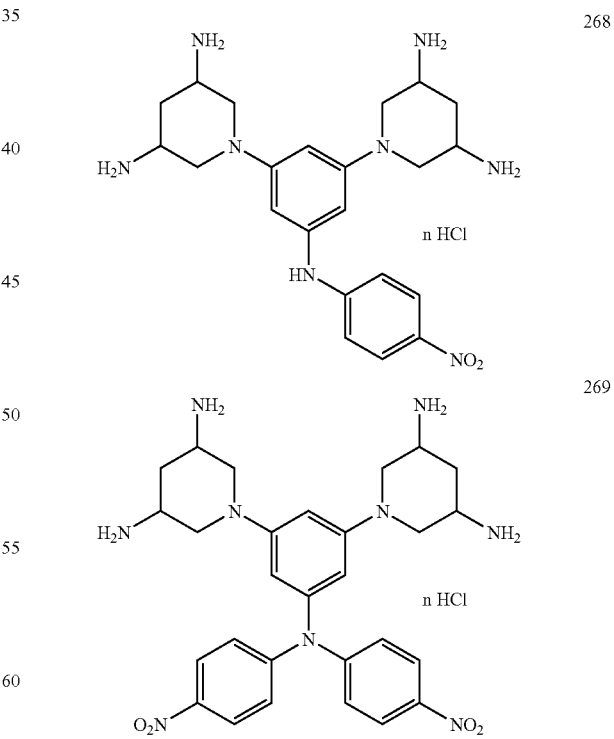

Step 1: Buchwald Reaction to Give Compound 263

1,3-di-bromo-5-NO$_2$-benzene (262) (140.5 mg, 0.5 mmol), (3R,5S)-3,5-bis(tert-butoxycarbonylamino)-piperidine (4) (410 mg, 1.3 mmol), $Cs_2CO_3$ (488.7 mg, 1.5 mmol), Xantphos (87 mg, 0.15 mmol), $Pd_2(dba)_3$ (46 mg, 0.05 mmol) and 5 mL of anhydrous toluene were added into a 40-mL vial. $N_2$ was purged and bubbled through the mixture for 2 minutes. The vial was capped with a piercing septa cap right away. A $N_2$ balloon was then added on the cap through a needle. The reaction mixture was heated at 100° C. with good stirring for 27 h. The reaction mixture was checked by LC-MS. The mixture had 50% desired product, 45% of compound 4 and 5% (by ELSD) of other undefined impurity. The reaction mixture was diluted by a mixture of $CHCl_3$, MeOH and EtOAc (total 10 mL) first and the solid was then filtered off through Celite under vacuum. The majority of the excess (3R,5S)-3,5-bis(tert-butoxycarbonylamino)-piperidine (4) was removed by scavenger resin by adding isocyanate resin (800 mg) and heating at 80° C. in THF (15 mL) overnight. After the resin was removed, the solution was concentrated down on rotary evaporator and was further purified by flash chromatography using neutral $Al_2O_3$ ($CHCl_3$/MeOH/$NH_4OH$=20:1:0.1). The final product (263) was confirmed by LC-MS with MS of 750.5 $[M+1]^+$ with HPLC purity of 90% by ELSD.

Step 2: Nitro Reduction to Give Compound 264

Compound 263 (57.9 mg) and 4 mL of absolute EtOH were added into an 8-mL vial and the mixture was preheated at 55° C. to get more homogeneous solution. 24 μL of anhydrous $NH_2$—$NH_2$ was added followed immediately by 216 uL of Raney Nickel (50% slurry in $H_2O$). The reaction mixture immediately started bubbling. The bubbling stopped after 10 minutes. The reaction mixture was monitored by LC-MS and the reaction was not completed yet. 24 μL of anhydrous $NH_2NH_2$ and 216 μL of Raney Nickel were added again and this addition was repeated 3 more times. At that point, the reaction was completed based on LC-MS spectrum. The solid was filtered off through Celite and washed with EtOH and MeOH. The filtrate was concentrated down under vacuum and dried on oil pump vacuum for 3 h. 50.5 mg of gray solid of the desired product 264 was obtained (90.9% yield). LC-MS: (m/e: 720.4 $[M+1]^+$) with HPLC purity of 95% (with 5% remaining (3R,5S)-3,5-bis(tert-butoxycarbonylamino)-piperidine 4 as the impurity based on ELSD).

Step 3: The Second Buchwald Reaction with Aniline 264

50.5 mg of compound 264 (70.14 μmol), 1-bromo-4-nitro-benzene (208) (14.2 mg, 70.14 μmol), $Cs_2CO_3$ (34.3 mg, 105.3 μmol), Xantphos (12.2 mg, 21.1 μmol), $Pd_2(dba)_3$ (6.4 mg, 7 μmol) and toluene (1 mL) were added into a 40-mL vial. $N_2$ was purged through the mixture (bubbled through) for 2 minutes, the vial was capped and heated at 100° C. for 15 hours with good stirring. The reaction was monitored by LC-MS. After the reaction was completed, $CHCl_3$ (2 mL) and MeOH (2 mL) were added to dilute the mixture. The solid was filtered off through Celite under vacuum and washed with $CHCl_3$ (2 mL) and MeOH (2 mL). The filtrate was concentrated and the crude product was first purified by liquid-liquid extraction between $CHCl_3$ (6 mL) and $H_2O$ (3 mL×2). The organic layer was dried and a dark brown solid (product 266a and 266b) as a mixture of mono-(55% by ELSD) and bis-adducts (45% by ELSD) was obtained. LC-MS: m/e 841.5 $[M+1]^+$mono-adduct and 962.7 $[M+1]^+$ for bis-adduct.

Step 4: De-protection of Boc to Give Compound 268 and 269.

The above crude product (a mixture of 266a and 266b) was dissolved in MeOH (2 mL) first with assistance of sonication. 2 mL of 4 M HCl in dioxane was then added at r.t. and the resulting mixture was shaken at room temperature overnight. The reaction was completed based on the LC-MS result. The mixture was concentrated to give 70.3 mg dark yellow solid as the crude product (a mixture of 268 and 269). The crude product was further purified by reverse phase HPLC purification to give 8.02 mg of compound 268 and 9.05 mg of compound 268 in total yield of 32.2% for 2 steps (step 3 & 4) as HCl salt with HPLC purity >95% for both products.

4.24.2 Another General Method of Synthesis of Compounds of Formula It

Scheme 59 describes another general synthetic procedure for preparing compound 284 of Formula It.

Scheme 59

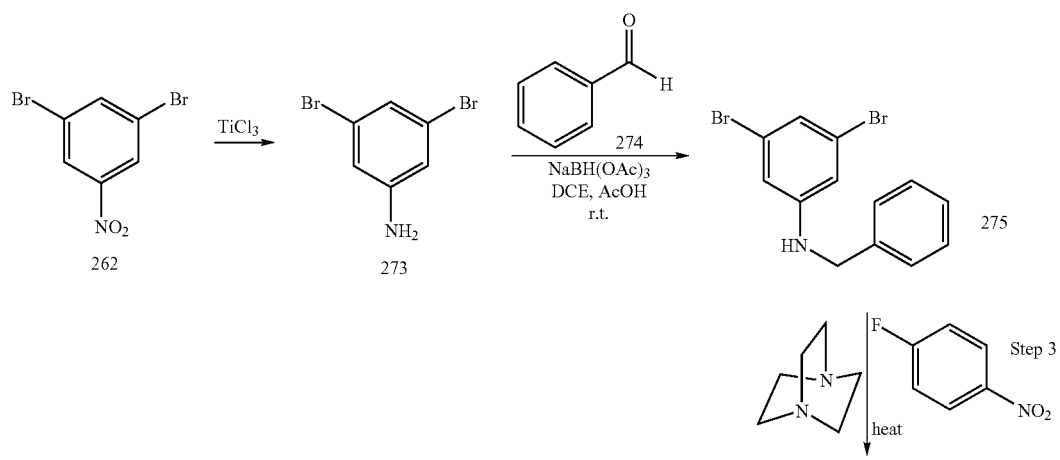

-continued
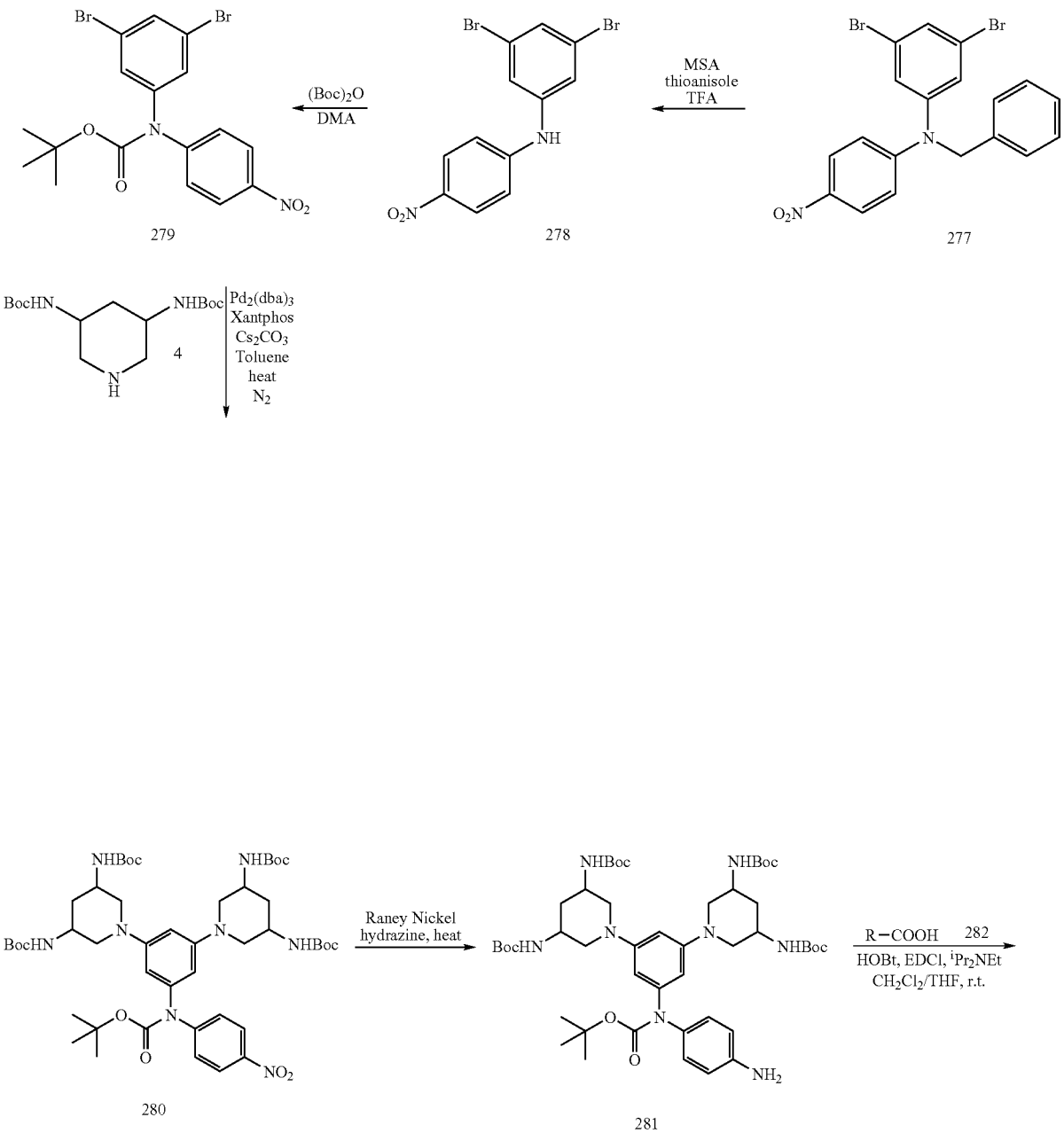

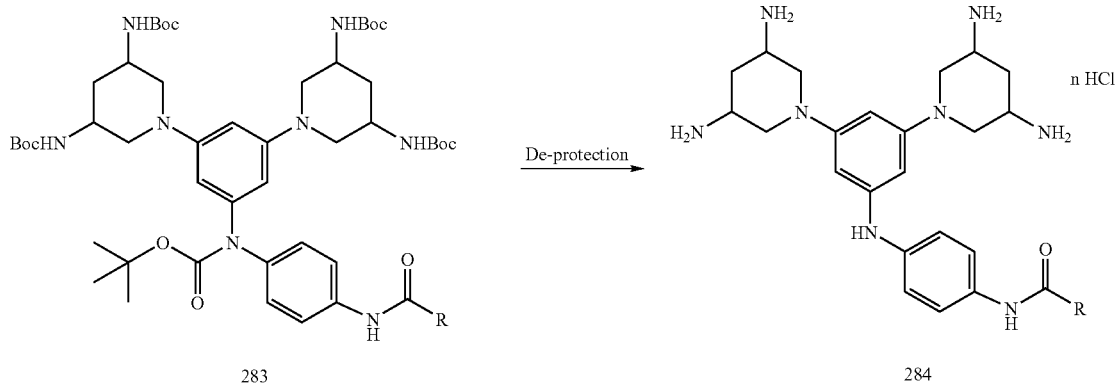

283 → 284

R=optionally substituted $(C_1-C_6)$alkyl, aryl, heteroaryl, —$(CH_2)_n$-aryl, —$(CH_2)_n$-heteroaryl, —$(CH=CH)_n$-aryl, —$(CH=CH)_n$-heteroaryl, —$(C≡C)_n$-aryl, and —$C≡C)_n$-heteroaryl.

In this general method of producing compounds of Formula It, the 3,5-di-bromo-nitro-benzene (262) is reduced to 3,5-di-bromo-aniline (273), followed by reductive amination to form the benzylated secondary aniline (275). Compound 275 is then reacted with 4-F-nitrobenzene (276) to give 3,5-dibromo-teriary aniline (271) that is then de-benzylated to give the secondary aniline 278. Aniline 278 is protected by Boc to give compound 279. Dibromo-compound 279 is aminated by reacting with (3R,5S)-3,5-bis(tert-butoxycarbonylamino)-piperidine (4) using palladium catalyst to give compound 280. The reduction of the nitro group of compound 280 followed by an amide coupling with carboxylic acid 281 affords compound 283. De-protection of Boc and other protecting groups if R contains other protecting groups give compound 284 as HCl salt.

This methodology is useful for the production of various derivatives represented by Formula It. Other variations of this methodology would be apparent to those skilled in the art.

4.24.3 EXAMPLE 27

Synthesis of Formula It Compounds 285 and 286

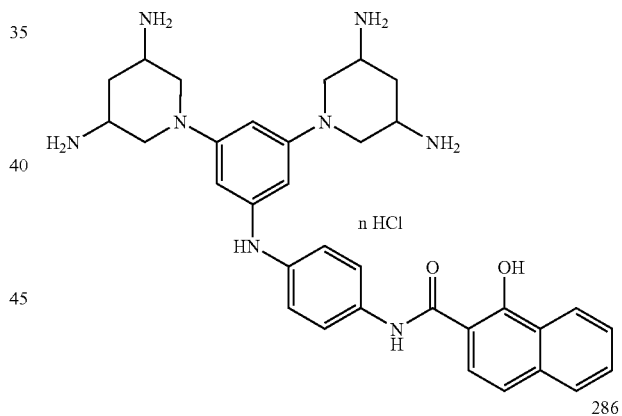

Scheme 60 describes the synthetic procedure for preparing compounds 285 and 286 of Formula It.

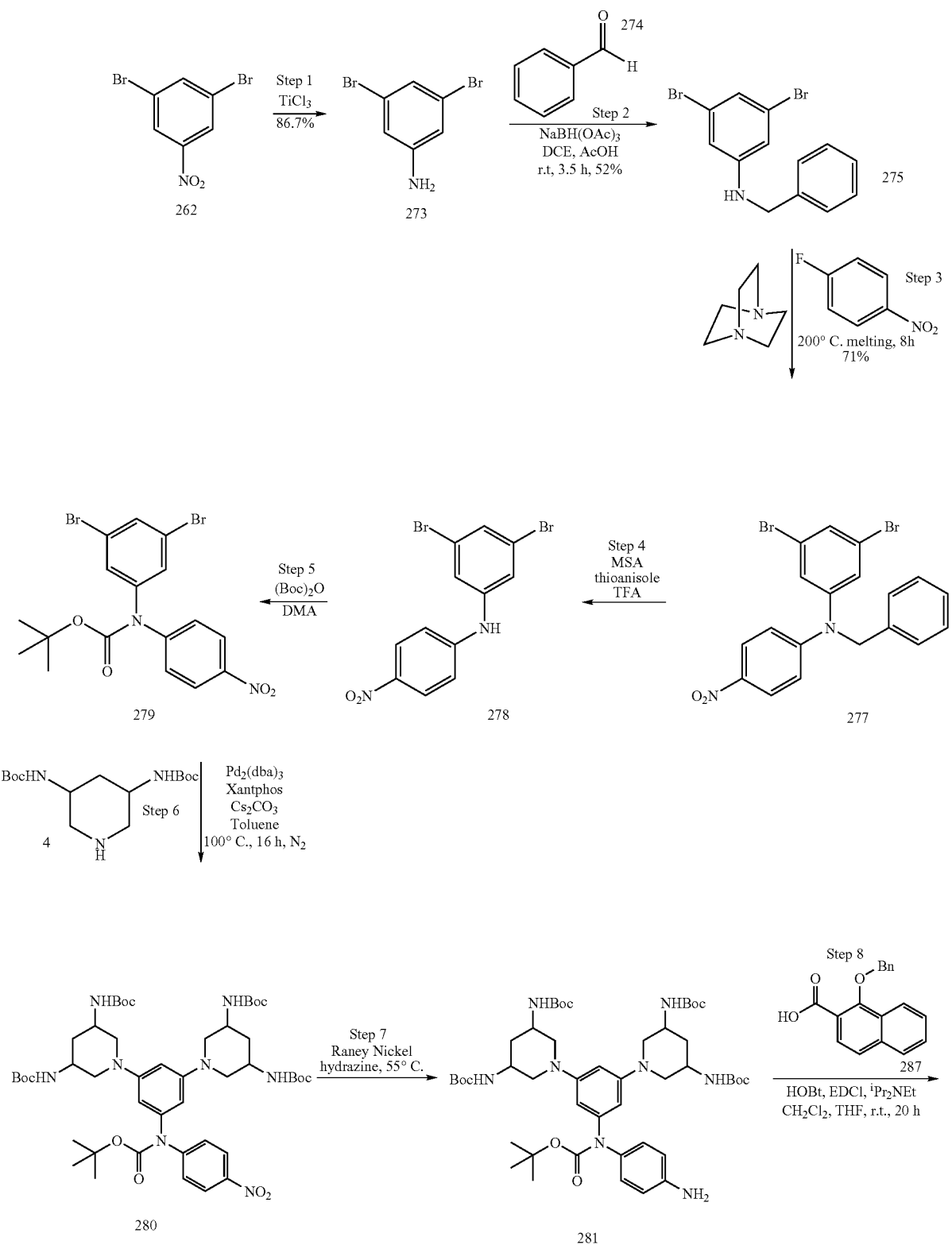
Scheme 60

-continued

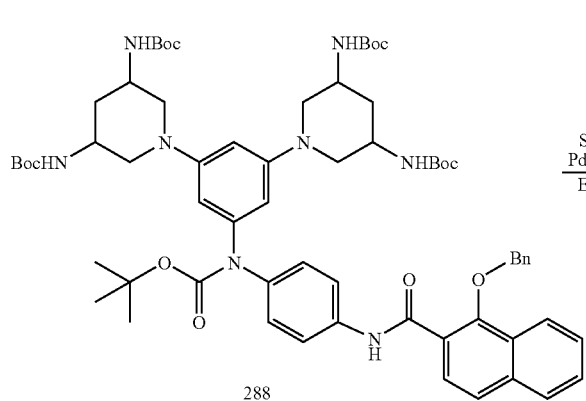

288

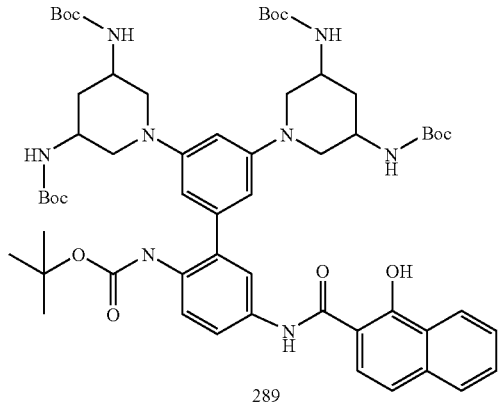

289

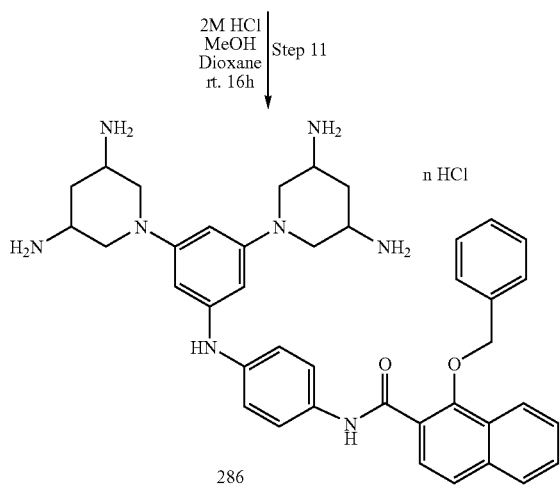

286

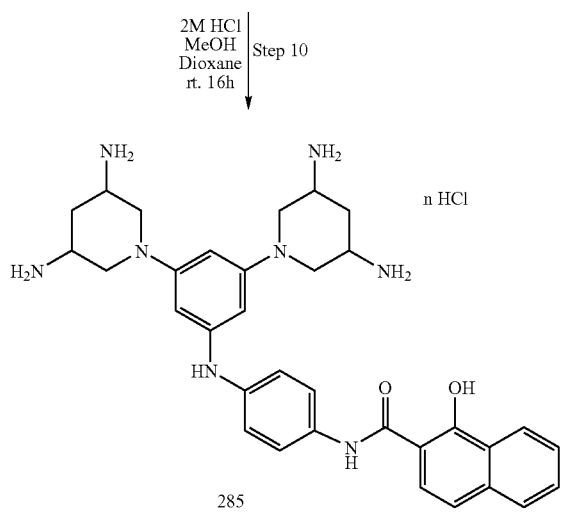

285

Step 1: NO₂ Reduction of 3,5-dibromonitrobenzene (262) to Give Compound 273

3,5-dibromo-nitro-benzene (262) (500 mg, 1.78 mmol) was dissolved in 4 mL of glacial acetic acid first. TiCl₃ with 30 wt % in 2 N HCl was added gradually until the purple color disappeared even after long stirring at room temperature. The reaction was monitored by TLC. After the reaction was completed, the reaction mixture was concentrated down under vacuum to remove the acetic acid. H₂O and 1 M NaOH was then added to neutralize the product followed by adding EtOAc solvent. The resulting wax like solid was filtered off under vacuum. Liquid-liquid extraction was then performed twice using EtOAc and H₂O as solvents and the organic layer was dried over anhydrous Na₂SO₄ for 0.5 h. The drying reagent was then filtered off under vacuum and the filtrate was first dried under vacuum on rotary evaporator and then dried over oil pump overnight. 387.3 mg of the desired product (273) was obtained as a neutral base in 86.7% yield with HPLC purity of >95% (ELSD). LC-MS: m/e 250 [M+1]⁺, 252.

In a scale up reaction using the same procedure as described above, 5 g (17.9 mmol) of 3,5-dibromonitrobenzene (262), 30 mL of TiCl₃ (30% wt. in 2.0 N aqueous HCl) and AcOH (125 mL) were used. After 4 h reaction and subsequent work-up, 3.85 g (85.7% yield) of 3,5-dibromoaniline (273) was obtained.

Step 2: Reductive Amination Gave Compound 275

3,5-dibromoaniline (273) (295 mg, 1.18 mmol), benzaldehyde (274) (120 uL, 1.18 mmol), NaBH(OAc)₃ (400 mg, 1.89 mmol), AcOH (142 mg, 2.36 mmol) and 6 mL of dichloroethane (DCE) were mixed and shaken at room temperature for 3.5 hours. TLC by analysis showed some remaining starting material but mostly product 275 while LC-MS spectrum showed mostly product with very little starting material left. The reaction was then stopped and the reaction mixture was concentrated down on a rotary evaporator. Liquid-liquid extraction was then performed three times between EtOAc (6 mL) and 1M NaOH (3 mL), H₂O (3 mL) and H₂O (3 mL). The organic layer was dried under vacuum and the crude product was purified by preparative TLC plate using developing solvent of hexane and ethyl acetate (hexane/ethyl acetate=4:1). 208 mg of the pure desired product (271) was obtained in 51.7% isolated yield with KPLC purity of 100%. LC-MS: m/e 340 [M+1]⁺, 342.

The same procedure as described above was used in a scale up reaction where 3,5-dibromoaniline (273) (3.85 g, 15.35 mmol), benzaldehyde (274) (1.61 g, 15.35 mmol), Na(OAc)₃BH (6.47 g, 30.7 mmol), AcOH (1.11 g, 18.42 mmol) and DCE (38 mL) were used. After 3 h reaction and purification (flash chromatography), benzyl-(3,5-dibromophenyl)-amine (275) (3.64 g, 10.67 mmol) was obtained in 69.6% isolated yield.

Step 3: Secondary Aniline 275 Reaction with 4-F-nitrobenzene (276) to Give Compound 277

3,5-dibromo-secondary aniline (275) (208 mg, 0.61 mmol), 1 mL of 4-F-nitro-benzene (276) (large excess), 1,4-diazabicyclo [2,2,2] octane (68.4 mg, 0.61 mmol) and $K_2CO_3$ 300 mg) were mixed together and heated to melt at 200° C. under $N_2$ for 8 hours. The reaction was stopped and cooled down. Liquid-liquid extraction was performed ($CHCl_3/H_2O \times 2$) and the organic layer was dried down. The crude product was purified by preparative TLC plate (hexane/EtOAc =6/1). 196 mg desired product (277) was obtained in 70% isolated yield with HPLC purity of >95% (by ELSD). LC-MS: m/e 460.9 [M+1]$^+$, 462.9; $^1$H NMR (DMSO-$d_6$): δ 8.30 ppm (d, 2H, J=9.2 Hz), 8.05 (d, 2H, J=9.2 Hz), 7.65 (t, 1H, J=1.6 Hz), 7.57 (d, 2H, J=1.2 Hz), 7.20–7.32 (m, 3H), 6.97 (d, 2H, J=9.2 Hz), 5.12 (s, 2H).

This reaction was scaled up to gram-scale using the same method. In this case, 3.64 g (10.7 mmol) of benzyl-(3,5-dibromophenyl)-amine (275), 1-fluoro-4-nitro-benzene (276) (4.5 g, 32 mmol) and 1,4-diazabicyclo [2,2,2] octane (2.4 g, 21.3 mmol) were mixed and heated to 170° C. for 16 h then 205° C. for 8 h without solvent. After flash column chromatography purification, 1.35 g (27.4% isolated yield) of benzyl-(3,5-dibromo-phenyl)-(4-nitro-phenyl)-amine (42) was obtained.

Step 4: De-benzylation of 277 to Give Compound 278

Compound 277 (850 mg, 1.84 mmol) was dissolved in a mixture of methanesulfonic acid (MSA), trifluoroacetic acid and thioanisole (1:8:2, total 10 mL). The mixture was shaken in a sealed 40 mL I-Chem vial for 30 minutes. TLC indicated complete de-benzylation at this point. The mixture was diluted with EtOAc (50 mL), washed with $H_2O$ (3×20 mL), $NaHCO_3$ (3×20 mL, sat. aqueous), dried over $MgSO_4$ and concentrated to give an orange powder. The powder was prepared as a slurry in a mixture of EtOAc and hexanes (3:1, total 6 mL), filtered and dried under high vacuum to give the desired product (278) as a yellow powder (478 mg, 1.28 mmol) in 70% isolated yield with HPLC purity >99% by ELSD. $^1$H NMR (400 MHz, DMSO-$d_6$): δ 7.15 (d, 2H, J=9.6 Hz), 7.36 (d, 2H, J=1.6 Hz), 7.42 (t, 1H, J=1.6 Hz), 8.13 (d, 2H, J=9.2 Hz), 9.45 (s, 1H).

Step 5: Boc Protection of Compound 278 to Give Compound 279

Compound 278 (478 mg, 1.28 mmol) and (Boc)$_2$O (2.79 g, 12.8 mmol) were combined and heated to 75° C. Addition of 300 uL of DMA dissolved all solids. The mixture was kept at 75° C. with shaking for 3 h. A distinct color change from an orange solution to a pale yellow solution was observed. TLC indicated complete protection at this point ($R_f$: 0.7 compared to $R_f$: 0.4 for compound 278 in 4:1 hexanes/EtOAc). In order to consume the excess (Boc)$_2$O, N,N-Dimethyl-ethylenediamine (1.13 g, 12.8 mmol) was added followed by $CH_2Cl_2$ (8 mL) and MeOH (2 mL). The mixture was shaken for 24 h in a sealed 40 mL I-Chem vial at room temperature. The mixture was diluted with $CH_2Cl_2$ (20 mL) and hexanes (10 mL) and passed through a plug of silica gel, rinsing with a mixture of $CH_2Cl_2$/hexane (1:1) to give the desired product (279) as a yellow oil upon concentration (562 mg, 1.19 mmol) in 93% isolated yield with HPLC purity >99% by ELSD.

Step 6: Buchwald Reaction to Give Compound 280

Compound 279 (562 mg, 1.19 mmol), (3R,5S)-3,5-bis(tert-butoxycarbonylamino)-piperidine (4) (968 mg, 3.07 mmol), $Cs_2CO_3$ (1.157 g, 3.55 mmol), Xantphos (216 mg, 0.373 mmol), $Pd_2(dba)_3$ (109 mg, 0.119 mmol) were combined in a 40 mL I-Chem vial. $N_2$ was purged and bubbled through 20 mL of anhydrous toluene for 10 minutes. The $N_2$ purged toluene (11.84 mL) was added to the vial containing the above mixture. The vial was charged with $N_2$ and sealed. The mixture was then heated at 100° C. with stirring for 20 h. LC-MS and TLC results indicated complete consumption of compound 279, with no indication of the mono-substituted intermediate. The mixture was diluted with EtOAc (50 mL) and filtered through Celite to remove the solids. The filtrate was concentrated to give a greenish brown oil. Purification by flash column chromatography (eluted with 25–30% EtOAc in $CH_2Cl_2$) gave the desired product 280 as a yellow powder upon drying (248 mg, 0.264 mmol) in 22.2% isolated yield with HPLC purity of >99% by ELSD. LC-MS: m/e: 941.7 [M+1]$^+$.

Step 7: Nitro Reduction of 280 to Give Compound 281

Compound 280 (150 mg, 0.159 mmol), 12 mL of absolute EtOH and 4 mL of EtOAc were added into an open 40 mL I-Chem vial. While stirring and with a stream of $N_2$ blowing into the vial, the mixture was heated to 55° C. 51 μL of anhydrous hydrazine was added followed immediately by 450 uL of Raney Nickel (50% slurry in $H_2O$). The reaction mixture immediately started bubbling. The temperature was maintained at 55° C. with stirring. The bubbling ceased within 5 min. An additional 51 μL of anhydrous hydrazine was added and the reaction mixture immediately started bubbling. The temperature was maintained at 55° C. with stirring. TLC and LC-MS results indicated complete reduction after a total reaction time of 10 minutes. The solution was passed through a plug of Celite and rinsed with MeOH and EtOAc. The solution was concentrated to give 281 as an off-white powder (146 mg, 160 μmol) with quantitative yield. LC-MS: m/e: 911.6 [M +1]$^+$ with HPLC purity >99% by ELSD.

Step 8: Amide Coupling of 281 and 287a to Give Compound 288

Compound 281 (146 mg, 0.160 mmol) and compound 287 (0.278 g, 0.176 mmol) were combined and dissolved in anhydrous THF (1 mL). HOBT (0.64 uL of 0.5 M solution in THF, 0.32 mmol) and $^i$Pr$_2$NEt (111 uL, 0.64 mmol) were added. The mixture was shaken at room temperature for 10 minutes. EDCI (2.56 mL of 0.25M solution in $CH_2Cl_2$, 0.64 mmol) was added and the mixture was shaken at room temperature for 20 h. TLC and LC-MS results indicated complete coupling at this point. The mixture was diluted with EtOAc (30 mL), washed with $NaHCO_3$ (2×10 mL, sat. aqueous), dried over $MgSO_4$ and concentrated to a beige foam-like oil. Purification by flash column chromatography (30% EtOAc in $CH_2Cl_2$) gave the desired product 288 as a beige powder (91 mg, 77.7 μmol) in 49% isolated yield with HPLC purity of >99% by ELSD. LC-MS: m/e 1171.8 [M+1]$^+$.

Step 9: De-benzylation of Compound 288 to Give Compound 289 Via Pd/C and $H_2$ Compound 288 (50 mg, 0.0427 mmol) was dissolved in EtOAc (2 mL) in a 40 mL I-Chem vial. 10% Pd/C (18 mg) was added. The solution was degassed and the vial was charged with $H_2$ via balloon. The mixture was stirred at room temperature under the $H_2$ atmosphere for 4 h. TLC and LC-MS results indicated >95% de-benzylation at this point. The mixture was filtered through Celite and rinsed with MeOH and EtOAc to give compound 289 as a clear oil upon concentration (43 mg, 0.0398 mmol) in 93% yield with HPLC purity of >95% by ELSD. LC-MS: m/e 1081.8 [M+1]$^+$.

Step 10: De-Boc of Compound 289 to Give Compound 285

Compound 289 (43 mg, 0.0398 mmol) was dissolved in MeOH (2 mL) in a 40 mL I-Chem vial. 4.0 M HCl in dioxane (2 mL) was added and the mixture was shaken overnight at room temperature. A yellow precipitate was observed. LC-MS result indicated complete de-protection after 20 h. The mixture was concentrated to give a yellow powder (33 mg). MeOH (2 mL) was added and the mixture was sonicated for 2 minutes. The vial was centrifuged, the supernatant decanted, and the solid was dried under high vacuum for 4 h to give 285 as a yellow powder as the HCl salt with HPLC purity >98% by ELSD (20 mg, 69.1% isolated yield assuming 4 HCl based on NMR). LC-MS: m/e 581.3 [M+1]$^+$ (60%), 291.4 [M/2+1]$^+$ (100%). $^1$H NMR (400 MHz, DMSO-d$_6$): δ 1.66 (q, 2H, J=12 Hz), 2.38 (s, br, 2H), 2.72 (t, 4H, J=11.6 Hz), 3.18 (s, br, 4H), 3.992 (d, 4H, J=9.2 Hz), 6.00 (s, 1H), 6.08 (s, 2H), 7.03 (d, 2H, J=8.8 Hz), 7.36 (d, 1H, J=8.4 Hz), 7.50 (m, 3H), 7.58 (t, 1H, J=6.4 Hz), 7.82 (d, 1H, J=7.6 Hz), 8.08 (d, 1H, J=8.8 Hz), 8.20 (d, 1H, J=8.4 Hz), 8.39 (s, br, 12H), 10.34 (s, 1H).

Step 11: De-Boc of Compound 288 to Give Compound 286

Compound 288 (41 mg, 0.035 mmol) was dissolved in MeOH (2 mL) in a 40 mL I-Chem vial. 4.0 M HCl in dioxane (2 mL) was added and the mixture was shaken for 20 h at room temperature. LC-MS result indicated complete de-protection at this point. The mixture was concentrated to give a yellow powder. MeOH (1 mL) was added and the mixture was sonicated for 1 minute. The vial was centrifuged and the supernatant was decanted. The solid was dried under high vacuum for 2 h to give 286 as an orange-yellow powder as the HCl salt form (23 mg, assuming 4 HCl, 80.6% isolated yield). LC-MS: m/e 671.5 [M+1]$^+$ with HPLC purity of >99% by ELSD.

4.25 Synthesis of cis-3,5-Diaminopiperidine and Determination of the Stereo-Configuration of 3,5-bis-(tert-Butoxycarbonylamino)-Piperidine (4)

Scheme 71 describes the transformation of (3R,5S)-bis(tert-butoxycarbonylamino)-piperidine (4) to 3,5-Cis-diaminopiperidine (4a).

Scheme 71

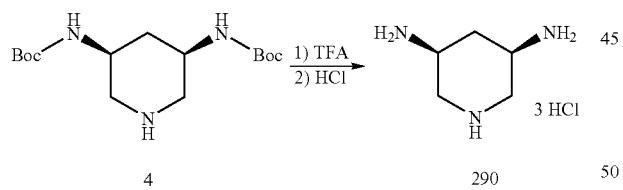

(3R,5S)-bis(tert-butoxycarbonylamino)-piperidine (4) (0.5 g, 1.59 mmol) as made in scheme 1 was dissolved in TFA (4 mL) and the mixture was shaken in a Teflon-septum capped 40 mL I-Chem vial for 16 hours. HCl (4.0 M in dioxane, 15 mL) was added to precipitate the product as the HCl salt form. The solid was collected by filtration, dried under high vacuum for 16 hours, dissolved in aqueous HCl (1.0 M, 10 mL) and concentrated to give the desired product (290) as a white powder upon drying under high vacuum for 16 hours (0.12 g, 1.04 mmol, 65.6% isolated yield). Elemental analysis calcd (%) for C$_5$H$_{13}$N$_3$·0.25H$_2$O·3HCl: C, 26.22, H, 7.26, N, 18.34; found C, 26.35, H, 7.22, N, 18.13. $^{13}$C NMR (400 MHz, DMSO-d$_6$): δ=31.01, 43.60, 44.10. $^1$H NMR (400 MHz, D$_2$O-d$_6$, pD=3–5): δ=1.92 (q, 1H, J=11.6 Hz), 2.66–2.69 (1H), 3.13 (t, 2H, J=13.2 Hz), 3.74–3.82 (m, 4H).

The H-NMR data matched the reported literature data for the cis-3,5-diaminopiperidine-3-HCl, the absolute structure of which was determined by X-ray crystal structure. Therefore 3,5-bis-(tert-butoxycarbonylamino)-piperidine (4) synthesized by this method was the cis-isomer. A related synthesis, NMR data and x-ray data for the cis-3,5-diaminopiperidine are described in Jörg W. Pauly, Jürgen Sander, Dirk Kuppert, Manuela Winter, Guido J. Reiss, Fabio Zürcher, Rudolf Hoffmann, Thomas F. Fässler, and Kaspar Hegetschweiler, *Chem. Eur. J.* 6, No. 15, 2830–2846 (2000).

4.26 Synthesis of Amine Intermediates

4.26.1 Synthesis of 291

Scheme 62 describes the synthesis of compound 291.

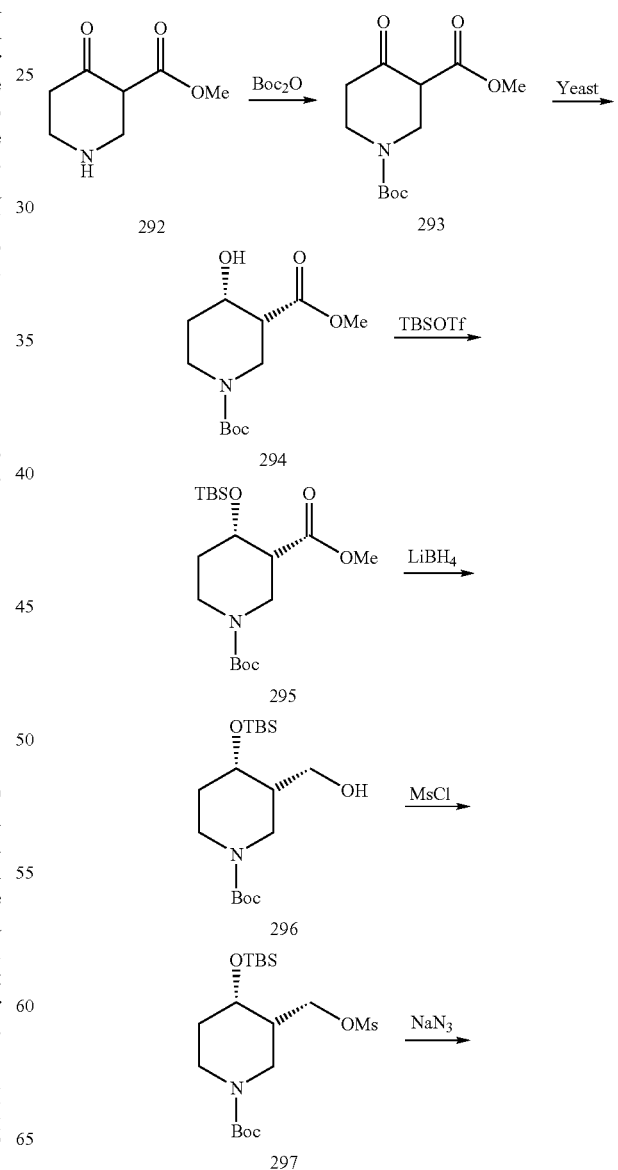

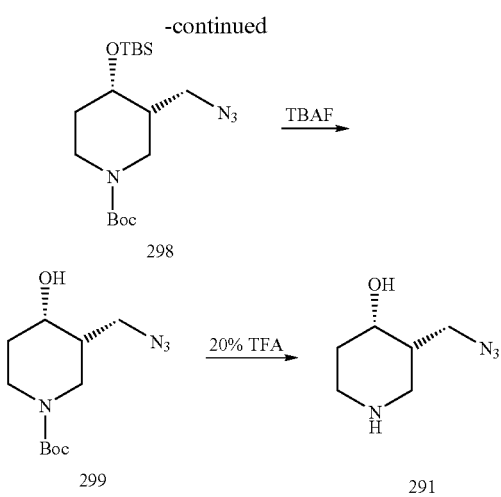

To a solution of 292 (1.00 g, 5.16 mmol) in 30 mL dichloromethane (DCM) was added (1.24 g, 5.68 mmol) of di-tert-butyl dicarbonate and the mixture was stirred at room temperature for 20 h. The solution was washed with water and dried (MgSO$_4$), concentrated and purified by column chromatography. The product was eluted with 30% ethyl acetate in hexanes to give the product 293 in quantitative yield.

Compound 293 was prepared according to a procedure given in the literature (Knight, D. W.; Lewis, N.; Share, A.; W. Haigh, D. *J. Chem Soc. Perks Trans.* 1. 1998, 3673–3683). To a suspension of the β-keto ester, 293 (1.33 g, 5.17 mmol) in 50 mL autoclaved water, was added 5 g of sucrose and 3 g of Bakers yeast. The suspension was stirred for 4 days at room temperature under aerobic conditions. The suspension was filtered through celite and the filtrate extracted with DCM, 5×10 mL. The combined organic phase was washed with brine, dried (MgSO$_4$) and concentrated under reduced pressure. The residue was purified by flash chromatography (70% ethyl acetate in hexane) to give a yellow oil, 294 (1.03 g, 77% yield).

Protection of the 2O alcohol was effected by treating a solution of 294 (520 mg, 2.00 mmol) in 8 mL DCM at −78° C. with lutidine (584 uL, 5.01 mmol) followed by tert-butyldimethylsilyl trifluoromethanesulfonate (TBSOTf) (599 μL, 2.61 mmol) drop wise. The reaction was allowed to warm to room temperature in 2 h. and the mixture carefully quenched with saturated NaHCO$_3$ aqueous, 10 mL. The aqueous phase was extracted by DCM (2×8 mL). The combined organic phase was dried (MgSO$_4$), concentrated and purified by flash chromatography (30% ethyl acetate in hexane) to give 295 (680 mg, 90% yield).

A stirred solution of 295 (890 mg, 2.38 mmol) in 40 mL dry THF was treated with LiBH$_4$ (2.38 mL; 2M solution, 4.76 mmol) and refluxed for 24 h. The reaction mixture was cooled to room temperature and carefully quenched with saturated NaHSO$_4$ (aqueous, 30 mL). The aqueous phase was extracted with DCM, 4×15 mL. The combined organic phase was washed with brine, dried (MgSO$_4$), and the solution concentrated under reduced pressure. The residue was purified by flash chromatography (30% ethyl acetate in hexane) to give 296 (600 mg, 73% yield).

A solution of 296 (600 mg, 1.74 mmol) in 10 mL of dry pyridine at 0° C. was treated with MsCl (269 μL, 3.47 mmol) and stirred for 0.5 h. The ice bath was removed and the solution was allowed to warm to room temperature over 3.5 h. The solvent was removed under reduced pressure and the residue was taken up in DCM, washed with water, dried over (MgSO$_4$), and concentrated. The product (297) was used for the next step without further purification.

A mixture of crude 297 and sodium azide (226 mg, 3.47 mmol) in DMF was heated at 80° C. for 16 h. The solvent was removed under reduced pressure and the residue dissolved in ethyl acetate, washed with saturated aqueous NaHCO$_3$, and concentrated. The residue was purified by flash chromatography (30% ethyl acetate in hexane) to give 298 (440 mg, 68% yield).

To a stirred solution of 298 (440 mg, 1.19 mmol) in 10 mL THF was added TBAF (1.5 mL; 1M solution, 1.54 mmol) and stirred at room temperature for 3 h. The solvent was concentrated down and DCM added. The solution was washed with water 3×5 mL, brine, dried (MgSO$_4$), and the solvent removed under reduced pressure. The residue (299) was used without further purification.

A solution of 299 in 20% TFA in DCM was stirred at room temperature for 16 h. The solution was concentrated under reduced pressure and the residue dissolved in DCM. This was then washed with dilute NaHCO$_3$ aqueous solution, and dried over MgSO$_4$. The solution was concentrated and the residue was purified by column chromatography with 10% methanol in DCM to give 291 (150 mg) in 81% yield over two steps with HPLC purity of 96% by ELSD. LC-MS: m/e 157.1 [M+1]$^+$.

4.26.2 Synthesis of 306

Scheme 63 Describes the Synthesis of Compound 306.

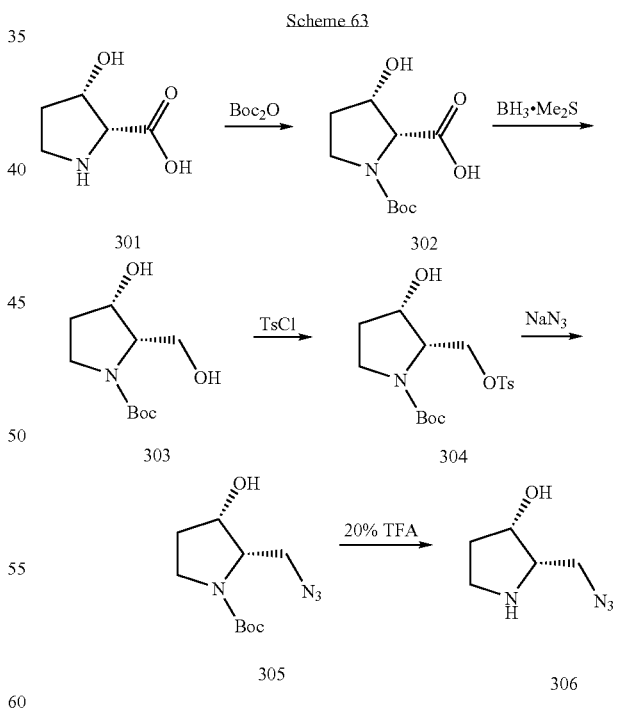

To the commercially available 301 (1.00 g, 7.63 mmol) in a mixture of THF/dioxane (40 mL, 1:1) was added NaHCO$_3$ (1.92 g, 22.88 mmol) and di-tert-butyl dicarbonate (1.99 g, 9.15 mmol), and the mixture was stirred for 14 h. The solvent was removed under reduced pressure and the residue dissolved in DCM, washed with water dried (MgSO$_4$) and concentrated. The residue was purified by flash chromatography (20% methanol in DCM) to give 302 (940 mg, 53% yield).

To a flame dried flask was transferred 302 (840 mg, 3.63 mmol) under nitrogen and dissolved in dry THF. To the stirring mixture was added BH$_3$.MeS (3.63 mL; 1M solution, 7.26 mmol) and stirred at room temperature for 18 h. The excess BH$_3$.Me$_2$S was carefully quenched with water and concentrated under reduced pressure. To the residue was added dilute NaHCO$_3$ aqueous solution and extracted with DCM 5×10 mL. The combined organic phase was dried (MgSO$_4$) and concentrated. The residue (303) was used in the subsequent step without further purification.

Intermediate 304 was synthesized following the same procedure for compound 297: 303 (832 mg, 3.83 mmol), TsCl (912 mg, 4.79 mmol) in 30 mL pyridine, to give 304 (890 mg, 63% yield) after purification by column chromatography.

Intermediate 305 was synthesized following the same procedure for compound 298: 304 (890 mg, 2.40 mmol), sodium azide (311 mg, 4.80 mmol), to give 305 (420 mg, 72% yield) after purification by flash chromatography.

Intermediate 306 was synthesized following the same procedure for compound 291 to give 306 (246 mg, 100% yield) with 95% HPLC purity by ELSD. LC-MS: m/e 143.2 [M+1]$^+$ $^1$H NMR (CD$_3$OD): δ 1.65 ppm (1H, d, J=14 Hz), 2.29 (1H, m), 3.19 (2H, d, J=3.6 Hz), 3.60–3.80 (4H, m) and 4.45 (1H, m).

4.26.3 Synthesis of 310

Scheme 64 describes the synthesis of compound 310.

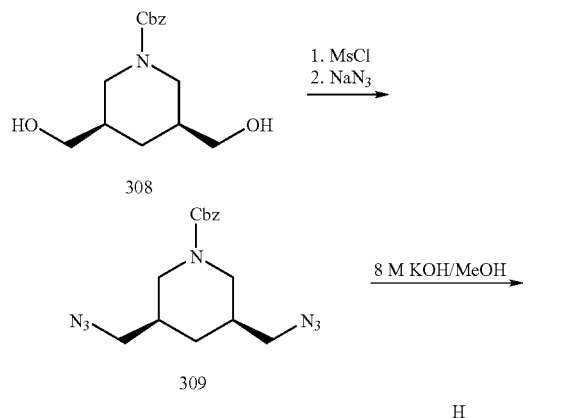

Synthesis of bis(azidomethyl)piperidine, 310, proceeded from the intermediate 308, which was synthesized according to literature procedure (1, Danieli, B. Lesma, G.; Passarella, D.; Silvani, A. *J. Org. Chem*. 1998, 63, 3492–3496. 2, Danieli, B. Lesma, G.; Passarella, D.; Silvani, A; Viviani, N. *Tetrahedron* 1999, 55, 11871–11878). Further manipulation was effected in a similar manner to treatment of 294 in scheme 62 to afford the azido compound 309, in overall yield of 95%. To complete the synthesis, the Carbobenzyloxy(Cbz)-protected bis(azidomethyl)piperidine (309) (460 mg, 1.40 mmol) was refluxed at 100° C. in 8M KOH/MeOH for 5 h. The mixture was concentrated to approximately 2 mL and extracted with DCM. The combined organic phase was dried (MgSO$_4$) and concentrated. The residue was purified by column chromatography with 20% NH$_4$OH in methanol to give 310 (234 mg, 86% yield) with 99% HPLC purity based on ELSD. LC-MS m/e 196.2 [M+1]$^+$; $^1$H NMR (CDCl$_3$): δ 0.80 (2H, q, J=12 Hz), 1.80 (4H, m), 2.20 (2H, t, J=12 Hz) and 3.19 (6H, m).

4.26.4 Synthesis of 311

Scheme 65 describes the synthesis of compound 311.

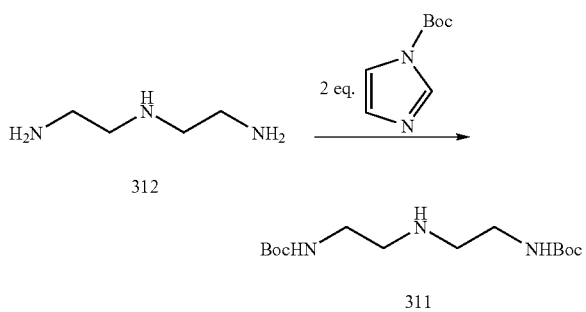

To a stirring mixture of the commercially available N-tert-butoxycarbonyl-imidazole (3.34 g, 19.85 mmol) in dry toluene at 60° C. and under nitrogen, was added 312 (1.00 g, 9.69 mmol) drop wise. Heating was continued for 3 h at 60° C. The solvent was removed and the residue dissolved in DCM, washed with water (2×20 mL), saturated aqueous NaHCO$_3$ and dried over (MgSO$_4$). The solution was concentrated under reduced pressure to give the product 311 (2.55 g, 87% yield) with 100% HPLC pure based on ELSD and was used without further purification. LC-MS: m/e 304.3 [M+1]$^+$; $^1$H NMR (CDCl$_3$): δ 1.45 (9H, s), 2.72 (4H, t, J=6.0 Hz), 3.21 (4H, q, J=5.2 Hz) and 4.90 (1H, bs). This above synthesis was performed according to literature procedure described in Steve P. Rannard and Nicola J. Davis, *Organic Letters*, 2 (14), 2117–2120 (2000).

4.26.5 Synthesis of 313

Scheme 66 describes the synthesis of compound 313.

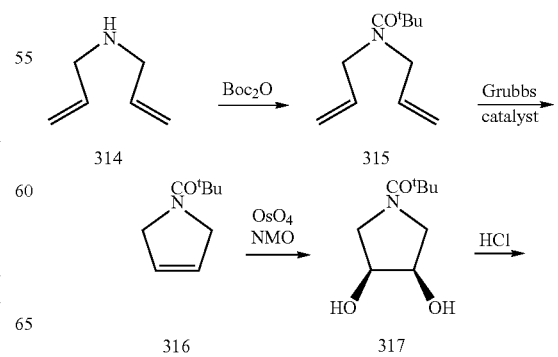

-continued

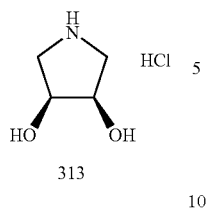

313

A solution of N,N-diallylamine (314) (40.6 mmol) in pyridine (20 mL) was prepared and cooled to 0° C. Di-tert-butyl dicarbonate (48.7 mmol, 1.2 equiv.) was added in a single portion with stirring and the solution was allowed to warm to room temperature. After 2 h, TLC indicated complete conversion. The reaction was diluted with toluene (80 mL) and concentrated. The resulting syrup was dissolved in EtOAc (200 mL) and washed with saturated NaHCO₃ (200 mL), brine (100 mL), dried over MgSO₄ and concentrated to give compound 315 as a colorless oil (31.7 mmol, 78% yield).

The above oil was dissolved in freshly distilled $CH_2Cl_2$ (300 mL) and degassed. Under nitrogen (1 atm) the Grubb's Catalyst {RuCl₂(CHC₆H₅)[P(C₆H₁₁)₂], 0.5 mol %} was added. After 2.5 h reaction at room temperature, TLC indicated complete conversion of the starting material to a more polar product and the reaction was quenched by bubbling air through the solution. The solution was concentrated and subjected to flash chromatography purification (5–20% EtOAc in hexane) to yield the compound 316 (27.0 mmol, 85% yield). $^1$H NMR (400 MHz, CDCl₃) δ=1.48 ppm (s, 9H), 4.09 (m, 4H), 5.76 (m, 2H).

2,5-Dihydro-pyrrole-1-carboxylic acid tert-butyl ester (316) (27.0 mmol) and N-methylmorpholine N-oxide monohydrate (43.0 mmol) were dissolved in acetone/H₂O (1:1, v/v; 80 mL). OsO₄ (0.4 mmol, 1.5 mol %) was added and the resulting pale yellow solution was stirred at room temperature for 16 h. Na₂S₂O₅ (3.9 mmol) was then added and the solution was stirred for 1 h. The solution was acidified to pH=4 with 6 M HCl and extracted with CH₂Cl₂ (4×70 mL). The organic phase was washed with saturated NaHCO₃ (50 mL), brine (50 mL), dried over MgSO₄ and concentrated.

The resulting foam (317) was dissolved in MeOH (80 mL) and 4 M HCl in dioxane (18 mL) was added with stirring.

After 2 h stirring at room temperature the reaction solution was concentrated to yield an oil. This oil was dissolved in hot ethanol (80 mL) and was allowed to stand at room temperature for two days yielding the desired compound (313) as colorless needles (17.2 mmol, 64% yield). $^1$H NMR (400 MHz, D₂O) δ=3.16 (br d, 2H, J=12 Hz), 3.38 (br d, 2H, J=12 Hz), 4.30 (br s, 2H); $^{13}$C NMR (100 MHz, D₂O) δ=48.7, 70.0 ppm.

4.26.6 Synthesis of 318

Scheme 67 Describes the Synthesis of Compound 318.

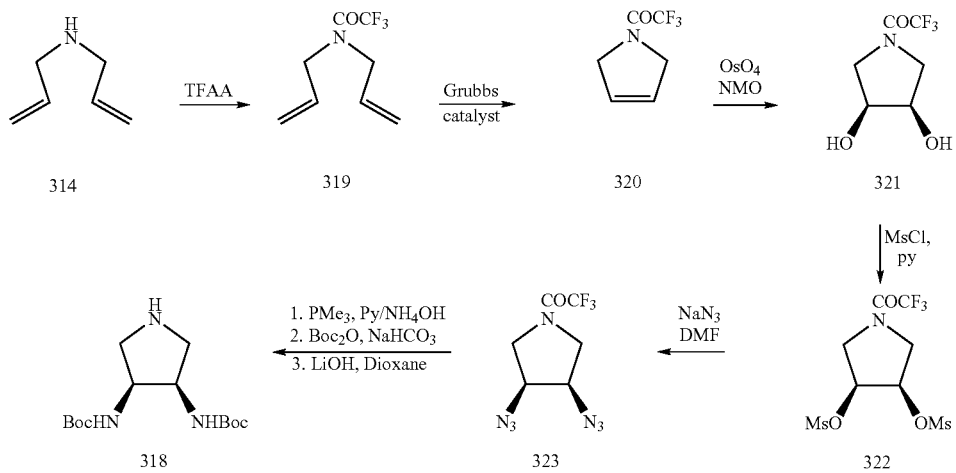

Scheme 67

A solution of N,N-diallylamine (214) (40.6 mmol) in pyridine (40 mL) was prepared and cooled to 0° C. Trifluoroacetic anhydride (TFAA) (52.8 mmol, 1.3 equiv.) was added dropwise with stirring. After 2 h, TLC indicated complete conversion. The reaction was diluted with 1M HCl (300 mL) and EtOAc (200 mL). The organic phase was washed with 1M HCl (200 mL), saturated NaHCO₃ (200 mL), brine (100 mL), dried over MgSO₄ and concentrated to give N,N-Diallyl-2,2,2-trifluoro-acetamide (319) as a colorless oil (26.9 mmol, 68% yield) that was used in next step without further purification.

To a stirred solution of 319 (26.9 mmol) in freshly distilled CH₂Cl₂ (250 mL), under nitrogen (1 atm) was added Grubb's Catalyst {RuCl₂(CHC₆H₅)[P(C₆H₁₁)₂], 0.5 mol %}. After 1.5 h stirring at room temperature, TLC indicated complete conversion of the starting material to a more polar product. The reaction was quenched by bubbling air through the solution. The solution was concentrated and subjected to chromatography purification (5–20% EtOAc in hexanes) to yield 1-(2,5-dihydro-pyrrol-1-yl)-2,2,2-trifluoro-ethanone (320) (22.0 mmol, 82% yield).

Compound 320 (22.0 mmol) and N-methylmorpholine N-oxide monohydrate (35.0 mmol) were dissolved in a mixture of acetone and H₂O (1:1, v/v; 60 mL). OsO₄ (0.4 mmol, 2 mol %) was added and the resulting pale yellow solution was stirred at room temperature for 16 h. Na₂S₂O₅ (3.9 mmol) was then added and the solution was stirred for an additional 1 h. The solution was acidified to pH=2 with 6 M HCl and extracted with CH₂Cl₂ (4×70 mL). The organic phase was washed with saturated NaHCO₃ (50 mL), brine (50 mL), dried over MgSO₄, concentrated and purified by column chromatography (0–5% MeOH in CH₂Cl₂) to give 1-(cis-3,4-Dihydroxy-pyrrolidin-1-yl)-2,2,2-trifluoro-ethanone (321) (17 mmol, 78% yield) as a colorless oil. ¹H NMR (400 MHz, CD₃OD) δ=3.95 ppm (dd, 1H, J=4, 13 Hz), 3.59 (dd, 1 H, J=6, 12 Hz), 3.65 (dd, 1H, J=6, 13 Hz), 3.84 (dd, 1H, J=5, 12 Hz), 4.19–4.27 (m, 2H).

Compound 321 (10 mmol) was dissolved in dry pyridine (60 mL) under nitrogen (1 atm) and the resulting solution was cooled to −10° C. (ice/NaCl). Methanesulfonyl chloride (22.0 mmol) was added dropwise with stirring. The ice bath was removed and the mixture was stirred for 2 h at room temperature. The resulting suspension was diluted with Et₂O (200 mL), filtered through a pad of MgSO₄ on a fritted funnel, concentrated and purified by column chromatography (10–40% EtOAc in hexanes) to yield 1-(cis-3,4-di-O-(methanesulfonyl)-pyrrolidin-1-yl)-2,2,2-trifluoro-ethanone (322) as a foam (9.1 mmol, 91% yield). ¹H NMR (400 MHz, acetone-d₆) δ=3.30 ppm (s, 3H), 3.31 (s, 3H), 3.82 (dd, 1H, J=4, 13 Hz), 3.95 (dd, 1H, J=6, 12 Hz), 4.06 (dd, 1H, J=6, 14 Hz), 4.29 (dd, 1H, J=6, 12 Hz), 5.50–5.59 (m, 2H).

A stirred mixture of 322 (9.0 mmol) and NaN₃ (45.0 mmol) in dry DMF (50 mL) was heated to 80° C. for 16 h. TLC analysis indicated complete conversion of the starting material to a less polar compound that has higher $R_f$ on TLC (2:1, hexanes/EtOAc). The reaction was cooled to room temperature, diluted with EtOAc (200 mL), washed with water (100 mL), saturated NaHCO₃ (100 mL), brine (100 mL), dried over MgSO₄, concentrated. The residue was purified by column chromatograph (5–15% EtOAc in hexanes) to give 1-(cis-3,4-diazido-pyrrolidin-1-yl)-2,2,2-trifluoro-ethanone (323) as a colorless oil (8.4 mmol, 93% yield). Due to the potentially hazardous nature of this compound, it was used immediately without characterization.

To a stirred solution of 323 (8.4 mmol) in a mixture of pyridine and NH₄OH (7:1, v/v; 60 mL) was added PMe₃ (2 M in THF, 12.6 mL). A slight elevation in temperature occurred with a concurrent evolution of gas. After 3 h stirring at room temperature, TLC analysis indicated conversion to a compound that had much lower $R_f$ (5% NH₄OH in MeOH) on TLC plate that stained with ninhydrin. The solution was diluted with EtOH (60 mL) and water (5 mL) and concentrated. The resulting syrup was dissolved in a mixture of toluene and EtOH (1:1, v/v; 80 mL) and concentrated again. The resulting oil was placed on a high vacuum line for 16 h. The oil was then dissolved in dry pyridine (70 mL), cooled to 0° C. and di-tert-butyl dicarbonate (25 mmol, 3 equiv) was added in portions with stirring. The solution was allowed to warm to room temperature, stirred for 5 h, concentrated, diluted with EtOAc (200 mL), washed with 0.1 M HCl (100 mL), saturated NaHCO₃ (100 mL), brine (100 mL), dried (MgSO₄) and concentrated.

The resulting oil was dissolved in 1,4-dioxane (30 mL) and LiOH.H₂O (20 mmol) was added with stirring. A precipitate gradually formed in the solution and after 2 h stirring at room temperature, TLC analysis indicated conversion to a more polar product (15:2:0.1, CH₂Cl₂/MeOH/NH₄OH). The suspension was filtered through a glass wool plug, diluted with CH₂Cl₂ (200 mL), washed with saturated NaHCO₃ (100 mL), brine (100 mL), dried (MgSO₄), concentrated and purified by column chromatography (5% MeOH in CH₂Cl₂ with 0–1% NH₄OH) to yield cis-3,4-(di-N-tert-butoxycarbonyl)-diaminopyrrolidine (318) as a colorless foam (4.9 mmol, 58% yield). ¹H NMR (400 MHz, CD₃OD) δ=1.41–1.56 ppm (br s, 18H), 2.64 (dd, 2H, J=6, 11 Hz), 3.17 (dd, 2H, J=7, 12 Hz), 3.98–4.26 (br s, 2H).

4.26.7 Synthesis of 328, 331, and 336

Scheme 68 describes the synthesis of compound 145, 148 and 152.

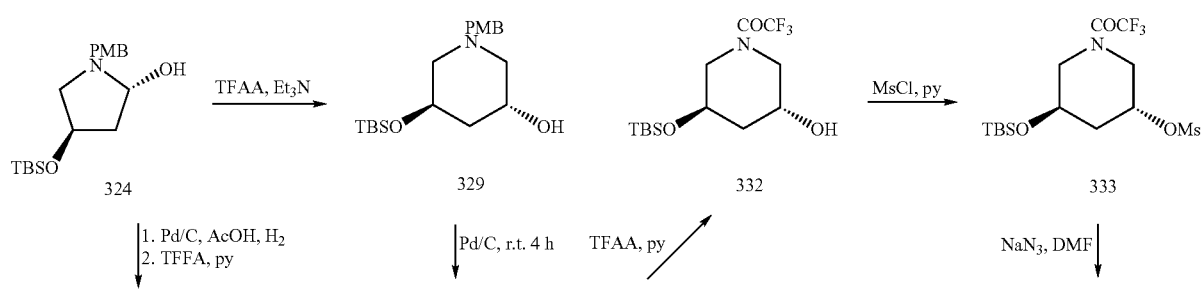

Scheme 68

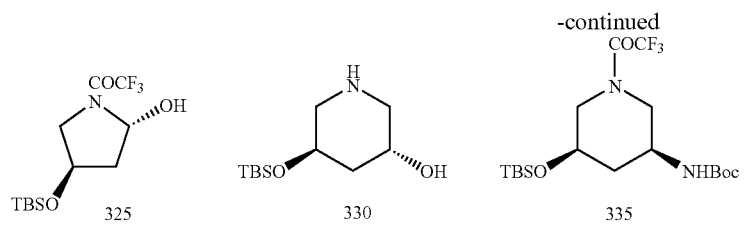
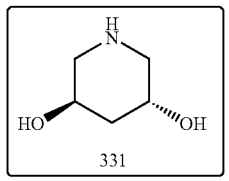
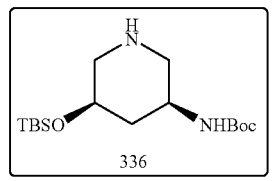
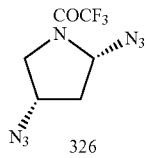
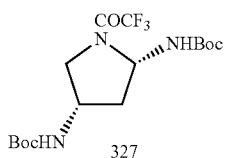
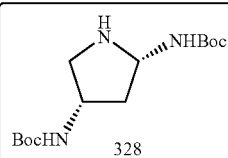

[4-(R)-(tert-Butyl-dimethyl-silanyloxy)-1-(4-methoxy-benzyl)-pyrrolidin-2-(S)-yl]-methanol (324) was prepared according to the literature procedure as described by P. W. Davis, S. A. Osgood, N. Hebert, K. G. Sprankle and E. E. Swayze; *Biotechnol Bioeng* 1998, 61(3), 143–154.

A stirred suspension of 324 (28.4 mmol) and 10% Pd/C (1 mol %) in MeOH (200 mL) was fitted with a hydrogen balloon and allowed to stir at room temperature for 4 h at which point the balloon was removed and a vacuum was applied to remove any traces of hydrogen. The suspension was filtered through a pad of celite and concentrated to yield a syrup which was dissolved in dry $CH_2Cl_2$ (100 mL) and $Et_3N$ (140.0 mmol, 5 equiv). The solution was stirred, cooled to 0° C. and trifluoroacetic anhydride (57.0 mmol, 2 equiv) was added dropwise. The solution was allowed to warm to room temperature and stirred under nitrogen for 3 h at which point it was diluted with $EtOH/H_2O$ (5:1, 30 mL) and stirred for another hour.

The resulting solution was concentrated to dryness, dissolved in EtOAc (200 mL) and washed with saturated $NaHCO_3$ (100 mL), brine (100 mL), dried ($MgSO_4$), adsorbed on to silica gel (~30 g) and concentrated. The silica gel was rinsed with hexane, filtered on a fritted funnel and rinsed with EtOAc (200 mL). Concentration of the EtOAc afforded 1-[4-(R)-(tert-butyl-dimethyl-silanyloxy)-2-(S)-hydroxymethyl-pyrrolidin-1-yl]-2,2,2-trifluoro-ethanone (325) (24.1 mmol, 85% yield) as a colorless oil. $^1$H NMR (400 MHz, $CDCl_3$) δ=0.08 ppm (s, 3H), 0.09 (s, 3H), 0.78 (s, 9H), 1.82–1.90 (m, 1H), 2.02–2.11 (m, 1H), 3.22–3.69 (m, ½H), 3.62–3.73 (m, 3H), 3.87–3.94 (m, 1H), 4.37–4.47 (m, ½H).

To a stirred solution of 325 (24.0 mmol) in MeOH (200 mL) was added 5 M HCl in 2-propanol (20 mL, 100 mmol). The solution was allowed to stand at room temperature for 3 h at which point it was concentrated to yield a colorless foam. The resulting material was dissolved in MeOH (200 mL) and concentrated again to insure removal of any remaining HCl. The resulting syrup was dissolved in $CH_2Cl_2$ (50 mL) and $Et_3N$ (145 mmol, 6 equiv), cooled to 0° C. with stirring and under a nitrogen atmosphere, methanesulfonyl chloride (84 mmol, 3.5 equiv) was added dropwise. The reaction was allowed to stir at room temperature for another 2 h at which point TLC analysis (10% MeOH in $CH_2Cl_2$) indicated conversion to a single spot. The reaction was quenched by the addition of water (30 mL) with vigorous stirring and partitioned between EtOAc (200 mL) and water (100 mL). The organic phase was washed again with $H_2O$ (100 mL), saturated $NaHCO_3$ (100 mL), brine (100 mL), dried ($MgSO_4$) and concentrated to give a white solid. DMF (50 mL) and $NaN_3$ (190 mmol, 8 equiv) were added and the resulting suspension was stirred at 70° C. for 16 h at which time a new spot ($R_f$=0.8, 2:1 hexanes:EtOAc) was observed on TLC.

The reaction was diluted with $H_2O$ (100 mL), brine (100 mL) and EtOAc (200 mL). The organic phase was washed again with $H_2O$ (100 mL), saturated $NaHCO_3$ (100 mL), brine (100 mL), dried ($MgSO_4$), concentrated and purified by column chromatography (5–15% EtOAc in hexanes) to give [1-(4-(S)-Azido-2-(S)-azidomethyl-pyrrolidin-1-yl)-2,2,2-trifluoro-ethanone] (326) as a colorless oil (17.8 mmol, 74% yield). $^1$H NMR (400 MHz, $CDCl_3$) δ=2.15 ppm (dt, 1H, J=5, 5, 14 Hz), 2.32–2.39 (m, 1H), 3.58 (dd, 1H, J=6, 12 Hz), 3.66–3.75 (m, 2H), 3.98 (dd, 1H, J=6, 12 Hz), 4.21–4.27 (m, 1H), 4.29–4.36 (m, 1H).

To a stirred solution of 326 (17.8 mmol) in a mixture of pyridine and $NH_4OH$ (7:1, 80 mL) was added trimethylphosphine (54 mL, 1 M in toluene, 3 equiv). The solution was allowed to stir at room temperature for 3 h at which point it was diluted with EtOH (100 mL) and concentrated to give a slightly yellow oil. The oil was again dissolved in EtOH and concentrated to insure complete removal of any residual $NH_4OH$. The resulting syrup was dissolved in 1,4-dioxane (80 mL) and saturated NaHCO₃ (80 mL) was added with cooling (0° C.) and vigorous stirring. Di-tert-butyl dicarbonate was added dropwise as a solution (72 mmol, 4 equiv, in 40 mL THF) with continued stirring and the reaction was allowed to warm to room temperature over the course of 2 h. The suspension was diluted with EtOAc (200 mL) and filtered through a glass frit. The resulting biphasic mixture was diluted with H₂O (100 mL) and the organic phase was washed with saturated NaHCO₃ (100 mL), brine (100 mL), dried (MgSO₄) and purified via column chromatography (0–5% MeOH in CH₂Cl₂) to give [5-(S)-(tert-Butoxycarbonylamino-methyl)-1-(2,2,2-trifluoro-acetyl)-pyrrolidin-3-(S)-yl]-carbamic acid tert-butyl ester (327) (16.0 mmol, 90% yield) as a colorless foam. ¹H NMR (400 MHz, CDCl₃) δ=1.43 ppm (s, 9H), 1.54 (s, 9H), 1.85–1.88 (m, 1H), 2.44–2.51 (m, 1H), 3.11 (dd, 1H, J=6, 12 Hz), 3.60–3.66 (m, 1H), 3.73–3.77 (m, 1H), 3.85–3.90 (m, 1H), 4.04–4.16 (m, 2H), 4.68 (br s, 1H).

To a stirred solution of 327 (16.0 mmol) in 1,4-dioxane (120 mL) was added LiOH.H₂O (32.0 mmol, 2 equiv). The suspension was allowed to stir at room temperature for 16 h at which point TLC indicated complete consumption of starting material (KMnO₄ stain for S.M.). The reaction was diluted with THF (120 mL), filtered through a glass frit and concentrated. The resulting syrup was diluted with THF/CHCl₃ (1:1, 200 mL) and washed with saturated NaHCO₃ (100 mL), brine (100 mL), dried (MgSO₄), and purified via column chromatography (0–10% MeOH in CH₂Cl₂ with 0–1% NH₄OH) to give [5-(S)-(tert-Butoxycarbonylamino-methyl)-pyrrolidin-3-(S)-yl]-carbamic acid tert-butyl ester (328) as a colorless foam. ¹H NMR (400 MHz, CD₃OD) δ=1.45 ppm (s, 9H), 1.47 (s, 9H), 1.69 (br s, 1H), 2.32–2.39 (m, 1H), 2.82 (dd, 1H, J=6, 13 Hz), 2.89 (dd, 1H, J=4, 13 Hz), 3.00 (dd, 1H, J=7, 11 Hz), 3.81 (dd, 1H, J=7, 11 Hz), 3.92–3.98 (m, 1H); ¹³C NMR (100 MHz, DMSO-d₆) δ=26.0, 29.0, 29.1, 58.9, 67.8, 78.5, 79.1, 154.3, 155.7 pm.

5-(R)-(tert-butyl-dimethyl-silanyloxy)-1-(4-methoxy-benzyl)-piperidin-3-(S)-ol (329) was prepared according to the literature procedure as described by P. W. Davis, S. A. Osgood, N. Hebert, K. G. Sprankle and E. E. Swayze; *Biotechnol Bioeng* 1998, 61(3), 143–154.

A suspension of 329 (25.5 mmol) and 10% Pd/C (1 mol %) in MeOH (250 mL) was fitted with a balloon of hydrogen and allowed to stir at room temperature for 4 h. At that time, a vacuum was applied to remove any remaining hydrogen, the vessel was purged with nitrogen, diluted with MeOH (100 mL) and filtered through a pad of Celite on a fritted funnel. The resulting solution was concentrated to give 5-(R)-(tert-Butyl-dimethyl-silanyloxy)-piperidin-3-(R)-ol (330) as a colorless oil (25.0 mmol, 98% yield). ¹H NMR (400 MHz, CD₃OD) δ=0.13 ppm (s, 3H), 0.14 (s, 3H), 0.929 (s, 9H), 1.84 (br t, 2H, J=5 Hz), 2.71–2.78 (m, 2H), 2.97–3.05 (m, 2H), 4.04–4.09 (m, 1H), 4.19–4.24 (m, 1H).

To a stirred solution of 330 (5.0 mmol) in EtOH (30 mL) was added 10 M HCl (15 mL). The solution was heated to reflux for 16 h and allowed to cool to room temperature and concentrated to yield a syrup. This syrup was dissolved in a minimal amount of hot EtOH (~20 mL) and allowed to stand at room temperature overnight to yield the compound 331 as colorless crystals (4.2 mmol, 84% yield).

To a stirred solution of 330 (25.0 mmol) in dry pyridine (40 mL) at 0° C. was added trifluoroacetic anhydride (50 mmol, 2 equiv.). The reaction was allowed to warm to room temperature and stirring was continued under a nitrogen atmosphere for 3 h. H₂O was added (5 mL) and stirring was continued for 1 h. At this time the reaction was diluted with EtOH (100 mL) and the resulting solution was concentrated. The solid was dissolved in EtOAc (150 mL) and washed with 0.1 M HCl (2×100 mL), saturated NaHCO₃ (100 mL), brine (100 mL), dried (MgSO₄) and concentrated to yield 1-[3-(tert-Butyl-dimethyl-silanyloxy)-5-hydroxy-piperidin-1-yl]-2,2,2-trifluoro-ethanone (332) (23.8 mmol, 95% yield). ¹H NMR (400 MHz, CDCl₃) δ=0.08 (s, 2H), 0.11 (s, 4H), 0.79 (s, 3H), 0.81 (s, 6H), 1.70–1.76 (m, 1H), 1.82–1.89 (m, 1H), 3.16–3.26 (m, 1H), 3.42–3.68 (m, 3H), 3.98–4.13 (m, 2H). LC-MS; m/e 327.42 [M+1]⁺=328.2

To a cooled (0° C.), stirred solution of 332 (18.2 mmol) and Et₃N (50.0 mmol) in dry CH₂Cl₂ (60 mL) was added methanesulfonyl chloride (37 mmol, 2 equiv). The solution was allowed to warm to room temperature and stirred for 2 h. The suspension was diluted with Et₂O (140 mL), filtered through a frit to remove solids and the supernatant was washed with cold 0.1 M HCl (100 mL), saturated NaHCO₃ (100 mL), brine (100 mL), dried (MgSO₄) and concentrated to afford 1-[3-(R)-(tert-Butyl-dimethyl-silanyloxy)-5-(R)-O-Methanesulfonyl-piperidin-1-yl]-2,2,2-trifluoro-ethanone (333) (17.9 mmol, 98% yield) as a white solid. ¹H NMR (400 MHz, CDCl₃) δ=0.1 ppm (s, 2H), 0.11 (s, 4H), 0.89 (s, 3H), 0.90 (s, 6H), 1.93–2.05 (m, 1H), 2.14–2.30 (m, 1H), 3.03 (s, 1H), 3.06 (s, 2H), 3.21 (dd, ⅔ H, J=8, 14 Hz), 3.41–3.51 (m, 1H), 3.69 (dd, ⅓ H, J=6, 14 Hz), 3.76–3.81 (m, 1H), 4.02–4.18 (m, 1H), 4.99–5.08 (m, 1H).

To a solution of 333 (17.9 mmol) in DMF (50 mL) was added NaN₃ (60 mmol, 3.3 equiv). The reaction was stirred and heated to 80° C. for 16 h at which point it was allowed to cool and quenched by the addition of H₂O (20 mL). The solution was diluted with EtOAc (200 mL) and the organic phase was washed with saturated NaHCO₃ (2×100 mL), brine (3×100 mL), dried (MgSO₄), concentrated and passed through a silica gel plug on a fritted funnel. Concentration of the resulting solution gave 1-[3-(S)-Azido-5-(R)-(tert-butyl-dimethyl-silanyloxy)-piperidin-1-yl]-2,2,2-trifluoro-ethanone (334) as a dense oil (15.1 mmol, 84% yield). ¹H NMR (400 MHz, CDCl₃) δ=0.10 ppm (d, 4H, J=2 Hz), 0.12 (d, 2H, J=3 Hz), 0.90 (s, 6H), 0.91 (s, 3H), 1.52–1.61 (m, 1H), 2.35–2.39 (m, 1H), 2.55–2.61 (m, 1H), 2.85–2.94 (m, 1H), 3.41–3.46 (m, 1H), 3.66–3.72 (m, 1H), 3.90–4.02 (m, 1H), 4.43–4.48 (m, ⅓H), 4.57–4.62 (m, ⅔H)

To a stirred solution of 334 (15.0 mmol) in a mixture of pyridine and NH₄OH (7:1, v/v, 80 mL) was added trimethylphosphine (1 M in toluene, 22.5 mL, 1.5 equiv.). The addition was followed by a slight increase in temperature, coupled with effervescence. After stirring at room temperature for 4 h, the solution was diluted with EtOH (100 mL) and concentrated to yield a slightly yellow oil. The oil was again dissolved in EtOH (100 mL) and concentrated. The resulting syrup was dissolved in 1,4-dioxane (60 mL) and saturated NaHCO₃ was added with stirring and cooling (0° C.). Di-tert-butyl dicarbonate (30 mmol) was added dropwise (as a solution in 40 mL of MeOH) with vigorous stirring. After the addition was complete, the reaction was allowed to stir for 3 h at room temperature at which time it was diluted with EtOAc (100 mL), filtered through a fritted funnel and concentrated to yield a stiff syrup. The syrup was dissolved in EtOAc (200 mL) and the organic phase was washed with H₂O (100 mL), saturated NaHCO₃ (100 mL), brine (100 mL), dried (MgSO₄) and concentrated. The resulting residue was dissolved in CH₂Cl₂ (50 mL) and silica gel was added (~15 g). The suspension was diluted with hexanes (200 mL) and poured on to a fritted funnel, rinsed with hexane and the desired product was eluted with EtOAc (200 mL) and concentrated to give the desired product (335) as an oil.

The above oil (335) was dissolved in 1,4-dioxane (100 mL), LiOH.H₂O (60.0 mmol) was added and the suspension was allowed to stir at room temperature for 16 h. TLC indicated complete conversion to a more polar compound ($R_f$=0.6, 15:2:0.1 CHCl₃/MeOH/NH₄OH, stained with ninhydrin). The solution was diluted with THF (100 mL), filtered through a glass frit, concentrated to dryness and purified by column chromatography (CHCl₃/MeOH/NH₄OH) to afford [5-(R)-(tert-Butyl-dimethyl-silanyloxy)-piperidin-3-(S)-yl]-carbamic acid tert-butyl ester (336) (10.9 mmol, 73% yield) as a colorless oil that solidified on standing. ¹H NMR (400 MHz, CDCl₃) δ=0.01 ppm (s, 3H), 0.02 (s, 3H), 0.85 (s, 9H), 1.35 (s, 9H), 1.52–1.68 (m, 3H), 1.75–1.86 (m, 1H), 2.62–2.78 (m, 4H), 3.51–3.59 (m, 1H), 3.67–3.74 (m, 1H), 5.82–5.96 (m, 1H); ¹³C NMR (100 MHz, CDCl₃) δ=−4.6, −4.4, 18.3, 26.2, 28.8, 36.6, 45.5, 50.7, 52.9, 67.1, 79.0, 155.2 ppm; LC-MS: m/e 331.0 [M+1]⁺.

4.26.8 Synthesis of Intermediate 340.

Scheme 69 describes the synthetic procedure for preparation of intermediate 340.

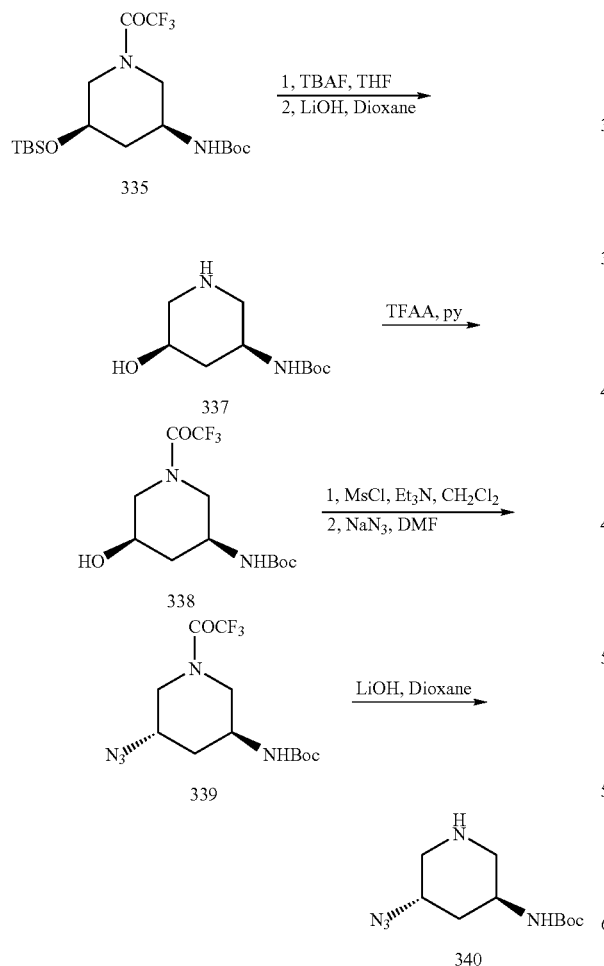

Compound 335 (crude material, 12.2 mmol) was dissolved in THF and 2 equivalents of TBAF was added at 0° C. The reaction mixture was stirred at 0° C.—room temperature for 2 hours. TLC (Rf=0.4 EtOAc/Hexane=2:1) confirmed the completion of reaction. The mixture was concentrated and purified by flash chromatography. It was dissolved in 1,4-dioxane (20 mL), LiOH.H₂O (800 mg) in 4 mL of H₂O was added and the suspension was allowed to stir at room temperature for 30 minutes. TLC indicated the complete conversion to a more polar compound ($R_f$=0.6, 2% of NH₄OH in MeOH). The mixture was concentrated under reduced pressure, dissolved the residue in MeOH that resulted in the formation of crystals, filtered, concentrated under reduced pressure and purified by column chromatography to afford 1.2 g of compound 337.

Compound 337 (1.42 g, 6.55 mmol), pyridine (15 mL) and TFAA (1 mL, 1.1 equiv.) were mixed and cooled to 0° C. and stirred for 30 minutes. Second equivalent of TFAA was added and the mixture was stirred at room temperature for 1 hour. EtOH (20 mL) was added and the mixture was then concentrated under reduced pressure and purified by flash chromatography to give the desired product 338.

Compound 338 (800 mg, 2.63 mmol), Et₃N (750 µL, 2 equiv.) and 10 mL of CH₂Cl₂ were mixed and the resulting solution was cooled down to 0° C. MsCl (244 µL, 1.2 equiv.) was added and the reaction mixture was stirred at 0° C. to room temperature. The reaction progress was monitored by TLC (5% MeOH in CH₂Cl₂, stained with KMnO₄). Upon the completion of the reaction, the suspension was concentrated to yield a solid. This solid was dissolved in DMF. NaN₃ (3.3 equiv.) was added and the mixture was heated at 60° C. Upon the completion of the reaction as determined by TLC, the reaction mixture was allowed to cool and quenched by the addition of H₂O. The solution was diluted with EtOAc and the organic phase was washed with saturated NaHCO₃, brine, dried (MgSO₄), concentrated and passed through a silica gel plug on a fritted funnel. Concentration of the resulting solution gave the desired product (339).

Compound 339 was dissolved in 1,4-dioxane. LiOH.H₂O (4 equiv.) in H₂O was added and the suspension was allowed to stir at room temperature for 16 hours. TLC indicated the complete reaction. The solution was diluted with THF, filtered through a glass frit, concentrated to dryness and purified by column chromatography to afford the desired product 340 (266.7 mg). ¹H NMR (CD₃OD, 400 MHz): δ=3.81 (s, br, 1H), 3.64–3.74 (m, 1H), 2.95 (dd, 1H, J₁=12.8 Hz, J₂=3.6 Hz), 2.77 (d, 2H, J=3.6 Hz), 2.44 (dd, 1H, J₁=12.8 Hz, J₂=8.4 Hz), 1.92–2.01 (m, 1H), 1.70–1.80 (m, 1H), 1.44 (s, 9H).

4.26.9 Synthesis of 341

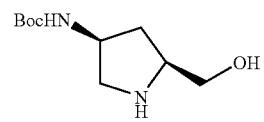

Compound 341 was prepared using a similar reaction sequence as that used for the synthesis of 336. This process used 325 as a starting material and invoked an eight-step reaction sequence to appropriately displace the secondary hydroxyl group with a nitrogen moiety, and remove any unnecessary protecting groups.

4.26.10 Scheme 70 Describes the Synthesis of Intermediate 349.

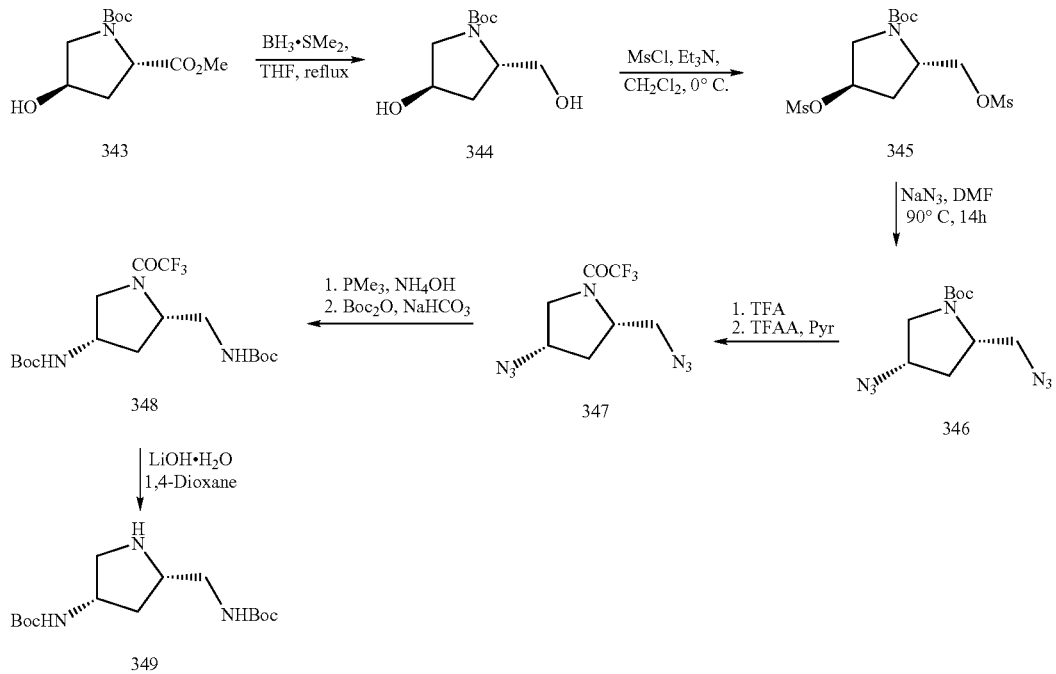

Scheme 70

4-Hydroxy-2-hydroxymethyl-pyrrolidine-1-carboxylic acid tert-butyl ester (344)

To a stirred solution of N-Boc-hydroxyproline-methyl ester (343) (15 g, 65 mmol) in THF (70 mL) was added BH$_3$·SMe$_2$ (55 mL, 2.0 M in Et$_2$O, 110 mmol). The solution was heated to reflux with stirring for four hours and reaction progress was monitored by TLC (5% MeOH/CHCl$_3$, product had lower $R_f$ than starting material, stained with K$_2$MnO$_4$). The heat was removed and the reaction was quenched by the slow addition of MeOH (40 mL). The resulting solution was heated to reflux again for 45 minutes, allowed to cool and concentrated to yield an oil that was purified by flash chromatography (1–15% MeOH in CHCl$_3$) to give 12.68 g (~90% yield) of the desired product (344).

4-Methanesulfonyloxy-2-methanesulfonyloxymethyl-pyrrolidine-1-carboxylic acid tert-butyl ester (345)

To a stirred solution of the diol (344) (12.7 g, 58.5 mmol) and triethylamine (5 equiv., 41 mL) in CH$_2$Cl$_2$ (200 mL) at 0° C. was added methanesulfonyl chloride (NsCl) (2.4 equiv., 10.9 mL). The resulting suspension was removed from the ice bath and allowed to warm to room temperature with stirring at which point TLC analysis indicated complete consumption of the starting material and conversion to a single spot of higher $R_f$ (5% MeOH/CHCl$_3$, stained with K$_2$MnO$_4$). The reaction was quenched by the addition of water (20 mL) with vigorous stirring. NaHCO$_3$ (sat., aqueous, 200 mL) was added and the organic layer was separated, washed with brine, dried (MgSO$_4$) and purified by flash chromatography (1–10% MeOH/CHCl$_3$) to yield the desired compound (345) as a colorless oil.

4-Azido-2-azidomethyl-pyrrolidine-1-carboxylic acid tert-butyl ester (346)

To a stirred solution of the di-methanesulfonate (345) in DMF (100 mL) was added NaN$_3$ (13.0 g, 4 equiv.). The suspension was heated to 80° C. and allowed to stir under a nitrogen atmosphere for 16 h at which point TLC (5% MeOH/CHCl$_3$, stained with Ce/PMA) indicated the complete consumption of the starting material. The reaction was allowed to cool to room temperature, diluted with toluene (200 mL) to precipitate the inorganic matter and filtered through a pad of celite on a glass frit. The resulting solution was concentrated to yield a brown liquid that was purified by flash chromatography (5–30% EtOAc in hexanes) to provide the desired compound (346) as a golden liquid.

1-(4-Azido-2-azidomethyl-pyrrolidin-1-yl)-2,2,2-trifluoro-ethanone (347)

To a solution of the above diazide (5) in CH$_2$Cl$_2$ (60 mL) at 0° C. was added trifluoroacetic acid (40 mL) which was accompanied by a vigorous evolution of gas and immediate color change. After warming to room temperature, TLC analysis (20% EtOAc in hexanes, stained with Ce/PMA) indicated the complete conversion of the starting material ($R_f$=0.6) to a spot at the baseline. The reaction was concentrated to dryness to yield a dark brown liquid that was diluted with EtOH (50 mL) and concentrated again. The resulting oil was dissolved in CH$_2$Cl$_2$ (50 mL) and pyridine (25 mL, 5 equiv.) and cooled to 0° C. To this stirred solution was added trifluoroacetic anhydride (16 mL, 2 equiv.). TLC analysis indicated immediate conversion to a less polar spot ($R_f$=0.5, 20% EtOAc/hexanes, stained with Ce/PMA) and the solution was concentrated to dryness. The resulting oil was partitioned between toluene (200 mL) and NaHCO$_3$ (sat., aqueous 200 mL). The aqueous phase was discarded and the toluene layer was again washed with NaHCO$_3$ (200 mL), brine (200 mL), dried (MgSO$_4$), concentrated and subjected to chromatography purification (5–25% EtOAc in hexanes) to yield the desired compound (347) as a golden liquid (8.64 g, 32.8 mmol, 56% total yield for four steps).

[5-(tert-Butoxycarbonylamino-methyl)-1-(2,2-trifluoro-acetyl)-pyrrolidin-3-yl]-carbamic acid tert-butyl ester (348)

To the above compound 348 (8.64 g, 32.8 mmol) in a stirred solution of pyridine (50 mL) and NH$_4$OH (10 mL) was added PMe$_3$ (1 M in THF, 75 mL, 2.2 equiv). The reaction was stirred for 2 h at room temperature at which point TLC analysis (20% NH$_4$OH in MeOH, stained with ninhydrin) indicated conversion to a single spot. The reaction was concentrated to dryness to yield an oil that began to solidify. The resulting solid was suspended in THF (120 mL) and NaHCO$_3$ (sat., 100 mL). To the stirred suspension (cooled to 0° C.) was added a solution of Boc$_2$O in THF (28.2 g, 4 equiv, in 50 mL). The suspension was stirred for 2 h at room temperature at which point TLC analysis indicated the complete conversion of the diamine to a less polar spot ($R_f$=0.85 1:1 hexanes/EtOAc, stained with ninhydrin). The suspension was diluted with EtOAc (200 mL) and the organic phase was decanted, washed with brine, dried (MgSO$_4$) and concentrated to yield an oil that was subjected to flash chromatography purificaton (5–30% EtOAc in hexanes). Chromatography did not yield an entirely pure material with indication that there was some di-protection of one of the amines. This material (348) was directly used in the next step.

[5-(tert-Butoxycarbonylamino-methyl)-pyrrolidin-3-yl]-carbamic acid tert-butyl ester (349)

To a stirred solution of the oil (348) in 1,4-dioxane (95 mL) was added LiOH.H$_2$O (11.0 g, 8 equiv). Water (5 mL) was added and the reaction mixture was sonicated briefly to disperse the solids, then stirred overnight at room temperature. TLC analysis indicated the complete consumption of the starting material (top for starting material, $R_f$=0.35 for product 15:2:0.1 CHCl$_3$/MeOH/NH$_4$OH). The reaction was diluted with CHCl$_3$ (150 mL) and dried over MgSO$_4$. The suspension was filtered and the resulting yellow solution was concentrated to yield an oil that was purified by flash chromatography on a short column of silica (0–10% MeOH in CHCl$_3$, with a small amount of NH$_4$OH added at the end to insure complete elution of the product). The desired compound was collected as a sticky syrup (7.0 g, 68% total yield for 3 steps). $^1$H NMR (CD$_3$OD): δ=1.45 (s, 9H), 1.49 (s, 9H), 1.60–1.74 (m, 1H), 2.41 (1H, dt, J$_1$=7.2 Hz, J$_2$=12.8 Hz), 2.96–3.12 (m, 3H), 3.83 (dd, 1H, J$_1$=7.2 Hz, J$_2$=11.2 Hz), 3.90–4.20 (m, 2H).

4.26.11 Synthesis of Intermediate 352 Scheme 71

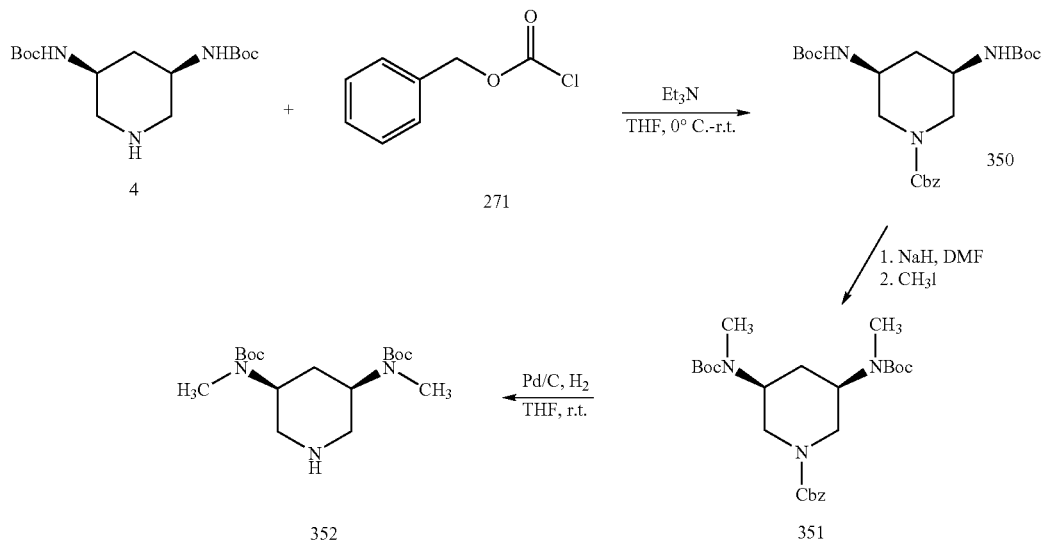

Scheme 71

Compound 4 (1.0 g, 3.17 mmol) was dissolved in 12 mL of THF and 2 mL of DMF. Triethylamine (844 μL, 6 mmol) was added and the mixture was cooled to 0° C. using an ice-H$_2$O bath. The acid chloride (271) (545 μL, 3.82 mmol) was added at 0° C. and the reaction mixture was stirred at 0° C. to room temperature overnight. The reaction mixture was concentrated under reduced pressure and the residue was purified by liquid-liquid extraction using CHCl$_3$ (10 mL) and H$_2$O (4 mL×2). The organic layer was concentrated and dried over high vacuum to give 1.54 g of crude product 350 with HPLC purity of 95% by ELSD. LC-MS: m/e 450.4 [M+1]$^+$ (exact ms: 449.25). This crude material was directly used in the next step.

Compound 350 (0.71 g, 1.59 mmol) was dissolved in 10 mL of DMF and cooled down to 0° C. using an ice-H$_2$O bath. NaH (60% dispersion in mineral oil, 153 mg, 3.82 mmol) was added at 0° C. and stirred at 0° C. for 1 hour. MeI (0.59 mL, 9.54 mmol) was added and the mixture was stirred at room temperature for 17 hours. The solvent was evaporated under reduced pressure and the residue was purified by liquid-liquid extraction between EtOAc (6 mL) and H₂O (4 mL×2). The organic layer was concentrated under reduced pressure to give the desire product 3. LC-MS: m/e 478.3 [M+1]⁺ (exact ms: 477.28).

yield) with the HPLC purity of 100% by ELSD. LC-MS: m/e 344.3 [M+1]⁺ (exact ms: 343.25).

4.26.12 Scheme 72 Describes the Synthesis of Intermediate 357.

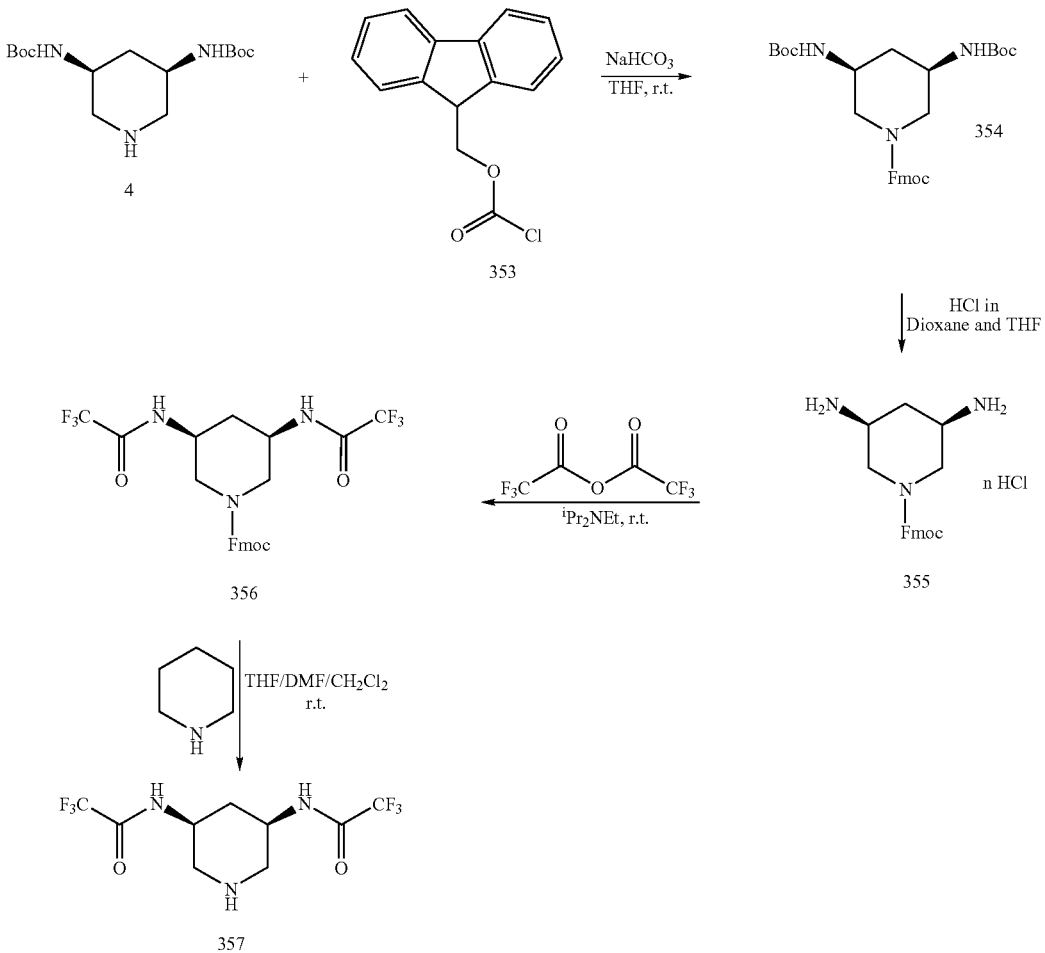

Compound 351 (200 μmol) was dissolved in 1 mL of THF. The solution was degassed by alternately connecting with vacuum and N₂. Pd/C (10 wt %, 22 mg, 20 μmol) was added under N₂. A H₂ balloon was then attached and the reaction mixture was stirred at room temperature overnight. LC-MS result indicated that no product formed. Pd/C (40 mg, wet) and additional 2 mL of THF was added. The reaction mixture was degassed the same way as before and a H₂ balloon was attached. The mixture was stirred at room temperature overnight and the LC-MS result indicated 50% conversion by ELSD. Additional Pd/C (10 wt %, wet, 100 mg) was added and the mixture was degassed and a H₂ balloon was attached. The reaction mixture was continued to stir at room temperature overnight. The LC-MS result confirmed 80% conversion by ELSD. The inorganic solid was then filtered off through Celite, washed with methanol (3 mL). The filtrate was concentrated and purified by reverse-phase HPLC using a gradient of CH₃CN and H₂O to give the desired product (352) (50.45 mg, 147 μmol, 73.5% isolated Compound 4 (0.5 g, 1.59 mmol), compound 353 (452.5 mg, 1.75 mmol), NaHCO₃ (267.2 mg, 3.18 mmol) and 8 mL of THF were mixed. The mixture was shaken at room temperature for 2 days. LC-MS confirmed the completion of the reaction. The reaction mixture was dried under reduced pressure to give the desired product (354). LC-MS: m/e 538.3 [M+1]⁺ (exact ms: 537.28).

The above compound 354 was dissolved in 6 mL of THF. HCl (4.0 M in dioxane, 8 mL, 32 mmol) was added and the mixture was shaken at room temperature for 68 hours. The mixture was dried under reduced pressure to give the desired product (355) as the HCl salt with HPLC purity of 90% by ELSD. LC-MS: m/e 338.2 [M+1]⁺ (exact ms: 337.18). This crude product was directly used in the next step.

The above compound 355 was dissolved in 12 mL of THF and 2 mL of DMF. ⁱPr₂NEt₃ (1.0 M, 4.74 mL, 4.74 mmol) in THF was added followed by tri-fluoroacetic anhydride (483 μL, 3.48 mmol). The mixture was stirred at room temperature overnight and concentrated under reduced pressure. The residue was purified by liquid-liquid extraction work-up by using EtOAc (6 mL) and H$_2$O (4 mL×2). The organic layer was dried under reduced pressure to give the desired product 356. LC-MS: m/e 530.2 [M+1]$^+$ (exact ms: 529.14).

Piperidine (2 mL) was added into a slurry of the above compound 356 in 8 mL of THF, 1 mL of DMF and 1 mL of CH$_2$Cl$_2$. The mixture was shaken at room temperature over a weekend and was then concentrated under reduced pressure. The crude product was purified by HPLC using a gradient of CH$_3$CN and H$_2$O to give 76.7 mg (0.25 mmol, 15.8% isolated yield for 4 steps) of the desired product 357. LC-MS: m/e 308.2 [M+1]$^+$ (exact ms: 37.08).

4.26.13 Scheme 73 Describes the Synthesis of Intermediate 360.

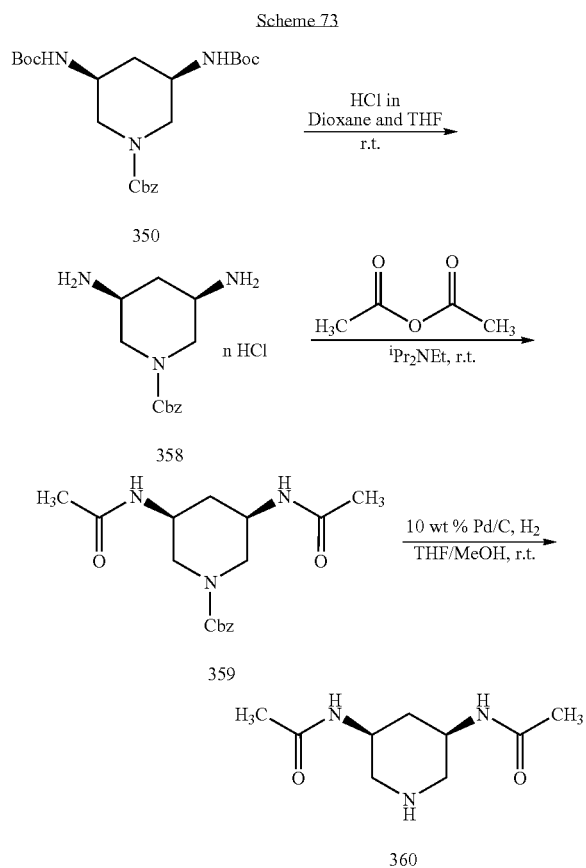

Compound 350 (1.58 μmol) was dissolved in 6 mL of THF. HCl (4.0 M in dioxane, 8 mL, 32 mmol) was added and the mixture was shaken at room temperature for 68 hours. The mixture was dried under reduced pressure to give the desired product (358) as the HCl salt with HPLC purity of 100% by ELSD. LC-MS: m/e 250.2 [M+1]$^+$ (exact ms: 249.15).

The above compound 358 was dissolved in 12 mL of THF and 2 mL of DMF. $^i$Pr$_2$NEt$_3$ (1.0 M, 4.74 mL, 4.74 mmol) in THF was added followed by acetic anhydride (326 μL, 3.48 mmol). The mixture was stirred at room temperature overnight and concentrated under reduced pressure. The residue was purified by liquid-liquid extraction work-up by using EtOAc (6 mL) and H$_2$O (4 mL×2). The organic layer was dried under reduced pressure to give the desired product 359. LC-MS: m/e 334.2 [M+1]$^+$ (exact ms: 333.17).

The above compound 359 was dissolved in 1 mL of THF and 1 mL of methanol. The solution was degassed by alternately connecting with vacuum and N$_2$. Pd/C (10 wt %, wet, 800 mg) was added under N$_2$. A H$_2$ balloon was then attached and the reaction mixture was stirred at room temperature under H$_2$ atmosphere for 2 days. The inorganic solid was then filtered off through Celite. The filtrate was concentrated to give the desired product (360) (59.6 mg, 178.9 μmol, 11.3% isolated yield for 3 steps) as a brown solid with the HPLC purity of 90% by ELSD. LC-MS: m/e 200.3 [M+1]$^+$ (exact ms: 199.13). This material was directly used without further purification.

4.27 Synthesis of Intermediates: Aniline Derivatives 4.27.1 General Procedure to Synthesize β-keto-amide Substituted Anilines (368)

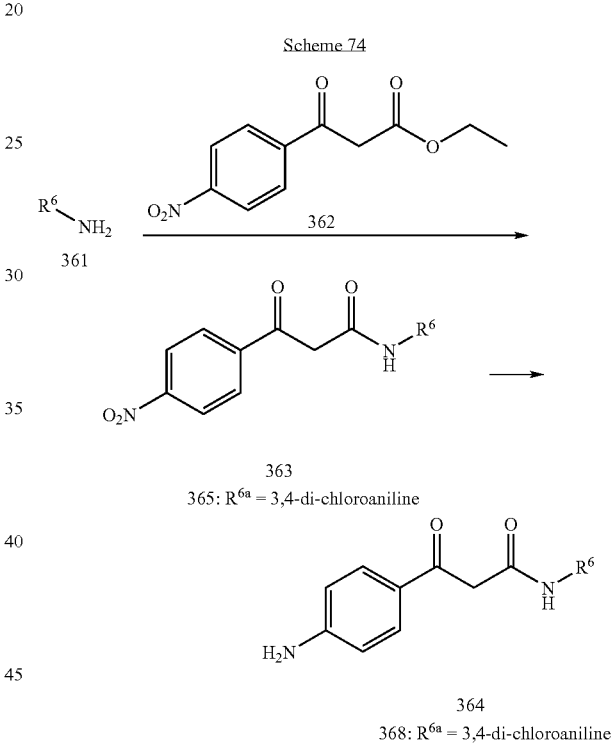

R is optionally substituted alkyl, aryl, heteroaryl, cycloalkyl, or heterocycloalkyl.

β-ketone ester (500 mg, 2.11 mmol, 362) and an equivalent mole amount of aniline (361) (2.11 mmol) were mixed and heated at 180° C. for 20 minutes with stirring (without solvent). After cooling down the reaction mixture, 3 mL of EtOH was added, sonicated and centrifuged. The top clear solution was removed and the resulting solid was dried under vacuum to give desired product (363). LC-MS and NMR was used to confirm the identity of the desired products.

β-ketoamide substituted nitro-aniline (150 μmol, 364) was dissolved upon heating (or slurry) in 1.2 mL of EtOH (or a mixture of EtOH and DMF if low solubility) and heated at 50° C. 50 μL of neat NH$_2$NH$_2$ (98% anhydrous) was added followed by immediately 300 μL of Raney-Nickel (50% slurry in H$_2$O) at 50° C. The reaction stopped bubbling 20 minutes later after the addition. The TLC result showed the completion of the reaction. The reaction mixture was then cooled down, filtered through a plug of Celite, washed with small amount of MeOH and concentrated under vacuum to give the desired product (364). LC-MS and ¹H NMR were used to confirm the identity of the desired products. This methodology can be used for the preparation of the meta-analogs of compound 364.

4.27.2 EXAMPLE 28

Synthesis of 4-(β-ketoamide) Substituted Anilines (368)

500 mg of β-ketone ester (362) (2.11 mmol) and same equivalent of 3,4-dichloroaniline (367) (2.11 mmol) were mixed and heated at 180° C. for 20 minutes with stirring (without solvent). After cooling down the reaction mixture, 3 mL of EtOH was added, sonicated and centrifuged. The top clear solution was removed and the resulting solid was dried under vacuum to give the desired product (365). LC-MS and NMR were used to confirm the identity of the desired product. LC-MS: MS m/e 353 [M+1] was found (exact MS: 352.0); ¹H NMR (DMSO-d₆): A mixture of the isomers (1:1) as listed below 366 and 367) was identified. 1H NMR (DMSO-d₆): δ 10.62 (s, 1H), 10.51 (s, 1H), 8.34 (t, 3H), 8.20 (d, 2H), 7.93–8.0 (m, 3H), 7.58 (dd, 2H), 7.49 (dd, 1H), 7.42 (dd, 1H), 6.08 (s, 1H), 4.26 (s, 2H).

150 μmol of above β-ketoamide (365) was dissolved upon heating in 1.2 mL of EtOH and then heated at 50° C. 50 uL of neat NH₂NH₂ (98% anhydrous) was added and immediately followed by 300 μL of Raney-Nickel (50% slurry in H₂O) at 50° C. The reaction stopped bubbling 20 minutes later after the addition. The TLC result showed the completion of the reaction. The reaction mixture was then cooled down, filtered through a plug of Celite, washed with small amount of MeOH and dried under vacuum to give the desired product (368).

4.27.3 General Procedure to Synthesize 3-hydroxy-4-amide Substituted Anilines (370 and 372)

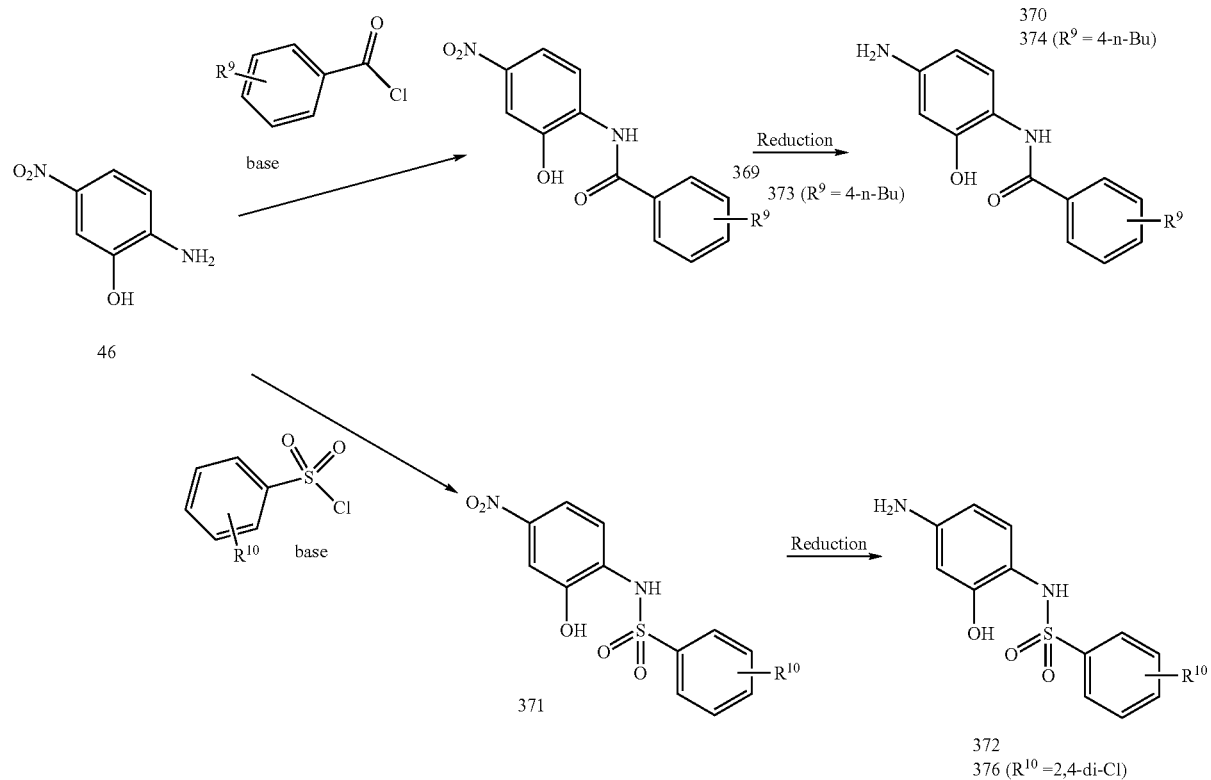

Scheme 75

$R^9$ and $R^{10}$ refer to substituents as defined for substituted aryls.

Into 150 μmol of acid chloride (neat) was added 600 μL of $CH_2Cl_2$ followed by 600 μL of a solution of 0.25 M 2-hydroxy-4-nitro-aniline (46) in anhydrous THF containing 150 μmol of $Et_3N$. The reaction mixture was shaken at room temperature overnight (>16 h) or heated at 50° C. for 2 hours. The resulting solution was concentrated under vacuum and pre-purified by liquid-liquid extraction ($CHCl_3$/ $H_2O$) and the organic layer was dried under vacuum to give the desired product (369). The nitro group was further reduced as described below.

The nitro-compound (150 μmol, 369) was dissolved upon heating (or slurry, at 80° C.) in 1.2 mL of EtOH (or a mixture of EtOH and DMF if low solubility) and decreased the temperature to 50° C. 50 μL of neat $NH_2NH_2$ (98% anhydrous) was added followed immediately by 300 μL of Raney-Nickel (50% slurry in $H_2O$) at 50° C. The reaction stopped bubbling 20 minutes later after the addition. The TLC result showed the completion of the reaction. The reaction mixture was then cooled down, filtered through a plug of Celite, washed with small amount of MeOH and dried under vacuum to give the desired product (370). LC-MS was used to confirm the identity of the desired products.

4.27.4 EXAMPLE 29

Synthesis of 3-hydroxy-4-amide Substituted Aniline (374) where $R^9$=4-n-Butyl

Into 150 μmol of 4-n-butylbenzoyl chloride (neat) was added 600 μL of $CH_2Cl_2$ followed immediately by 600 μL of a solution of 0.25 M 2-hydroxy-4-nitro-aniline (46) in anhydrous THF containing 150 μmol of $Et_3N$. The reaction mixture was shaken at room temperature overnight (for at least 16 h). The resulting solution was concentrated under vacuum and pre-purified by liquid-liquid extraction ($CHCl_3$/ $H_2O$) and the organic layer was dried under vacuum to give the desired product (373). The nitro group was further reduced as described below.

The above nitro-compound (150 μmol, 373) was dissolved upon heating (80° C.) in 1.2 mL of EtOH and then decreased to 50° C. 50 μL of neat $NH_2NH_2$ (98% anhydrous) was added immediately followed by 300 μL of Raney Nickel (50% slurry in $H_2O$) at 50° C. The reaction stopped bubbling 20 minutes later after the addition. The TLC result showed the completion of the reaction. The reaction mixture was then cooled down, filtered through a plug of Celite, washed with small amount of MeOH and dried under vacuum to give the desired product (374). LC-MS was used to confirm the identity of the desired products. MS m/e 285.2 [M+1] (exact ms: 284.15). This crude product was directly used in the next step without further purification.

4.27.5 General Procedure to Synthesize 3-hydroxy-4-sulfonamide Substituted Anilines (372)

Into 150 μmol of sulfonyl chloride (neat) was added 600 μL of $CH_2Cl_2$ followed immediately by 600 μL of a solution of 0.25 M 2-hydroxy-4-nitro-aniline (46) in anhydrous THF containing 150 μmol of $Et_3N$. The reaction mixture was shaken at room temperature overnight (>16 h) or heated at 50° C. for 2 hours. The resulting solution was concentrated under vacuum and pre-purified by liquid-liquid extraction ($CHCl_3$/$H_2O$) and the organic layer was dried under vacuum to give the desired product (371). The nitro group was further reduced as described below.

The nitro-compound (150 μmol, 371) was dissolved upon heating (or slurry, at 80° C.) in 1.2 mL of EtOH (or a mixture of EtOH and DMF if low solubility) and heated at 50° C. 50 μL of neat $NH_2NH_2$ (98% anhydrous) was added followed immediately by 300 μL of Raney Nickel (50% slurry in $H_2O$) at 50° C. The reaction stopped bubbling 20 minutes later after the addition. The TLC result showed the completion of the reaction. The reaction mixture was then cooled down, filtered through a plug of Celite, washed with small amount of MeOH and dried under vacuum to give the desired product (372). LC-MS was used to confirm the identity of the desired products.

4.27.6 EXAMPLE 30

Synthesis of N-(4-amino-o-hydroxyphenyl)-2,4-dichloro-benzenesulfonamide (376)

Into 150 μmol of 2,4-di-chlorobenzenesulfonyl chloride (neat) was added 600 μL of $CH_2Cl_2$ followed immediately by 600 μL of a solution of 0.25 M 2-hydroxy-4-nitro-aniline (46) in anhydrous THF containing 150 μmol of $Et_3N$. The reaction mixture was shaken at room temperature overnight (> or =16 h). The resulting solution was concentrated under vacuum and pre-purified by liquid-liquid extraction ($CHCl_3$/ $H_2O$) and the organic layer was dried under vacuum to give the desired product (375). The nitro group was further reduced as described below.

150 μmol of the above nitro-compound 375 was dissolved upon heating (80° C.) in 1.2 mL of EtOH and then decreased to 50° C. 50 μL of neat $NH_2NH_2$ (98% anhydrous) was added followed immediately by 300 μL of Raney Nickel (50% slurry in $H_2O$) at 50° C. The reaction stopped bubbling 20 minutes after the addition. The TLC result showed the completion of the reaction. The reaction mixture was then cooled down, filtered through a plug of Celite, washed with small amount of MeOH and dried under vacuum to give the desired product (376). LC-MS was used to confirm the identity of the desired products. MS m/e 333.1 [M+1] (exact ms: 331.98). This crude product was directly used in the next step without further purification.-

4.27.7 General Procedure to Synthesize o-hydroxybenzamide Substituted Anilines (380)

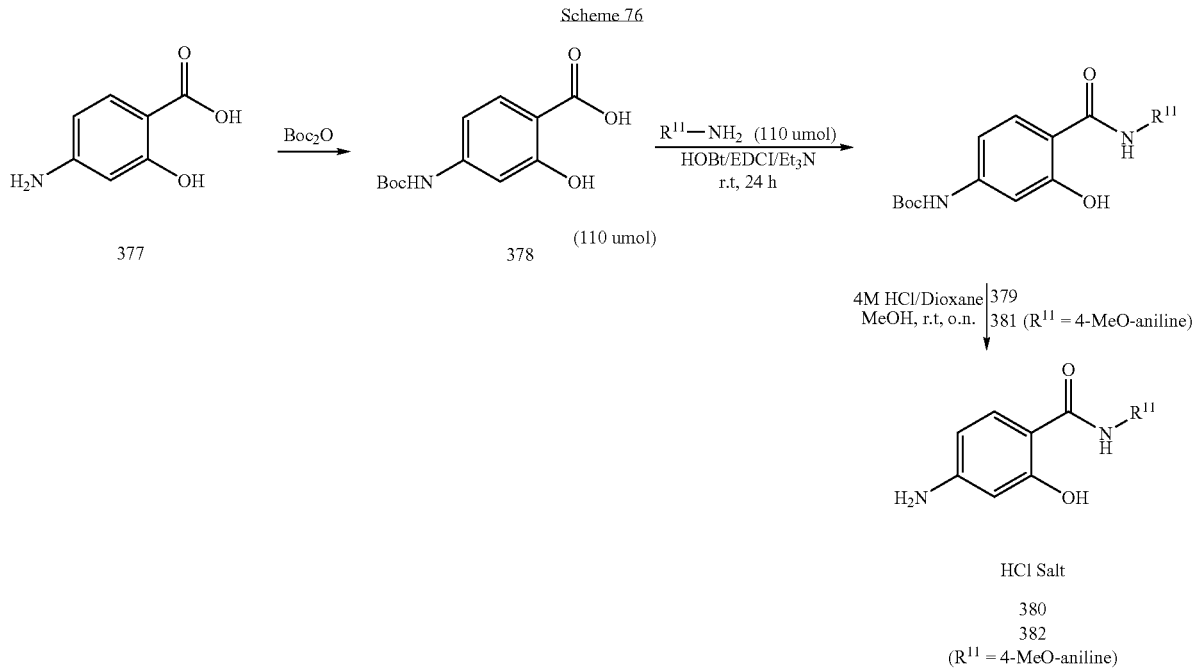

Scheme 76

R is optionally substituted alkyl, aryl, heteroaryl, cycloalkyl, or heterocycloalkyl.

10 g (85.3 mmol) of 2-hydroxy-4-aminobenzoic acid (377) was dissolved in 140 mL of ethanol. Triethylamine (18.4 mL neat, 130.6 mmol) was added at room temperature followed by a solution of 28.5 g (130.6 mmol) of $Boc_2O$ in 200 mL of THF and the reaction mixture was stirred at room temperature overnight. TLC result showed the completion of the reaction.

The reaction mixture was dried down under vacuum to get the crude product. 75 mL of 1M of NaOH solution was added into the crude product and this aqueous solution was extracted with organic solvent three times (40 mL hexane, 50 mL of hexane, 40 mL hexane plus 20 mL diethyl ether) to remove impurity. The separated aqueous layer was then cooled to 0° C. and a solution of 1M HCl (60 mL) was added and the pH of resulting solution was 4. The white precipitate was collected by filtration under vacuum, washed with water and dried in a vacuum oven at 50° C. The off-white solid (13.97 g, 84.5% isolated yield) was obtained. LC-MS and $^1$H-NMR confirmed the identity of the desired product (378) with HPLC purity of 94%. LC-MS: HPLC purity was 97.7%; MS m/e 254.1 [M+1] found (exact ms: 253.1).

110 µmol of the above Boc-protected 4-amino-2-hydroxy benzoic acid (378) was dissolved in 220 µL of DMF. A solution of 220 µL of 0.5 M of amine solutions in THF containing 4 equivalent of $Et_3N$ was added followed by 440 µL of 0.5 M of HOBt in THF. The resulting reaction mixture was vortexed to mix very well. 880 uL of 0.25 M EDCI solution in methylene chloride was then added, vortexed and shaken at room temperature for 24 hours. The reaction mixture was then dried down under vacuum and purified by liquid-liquid extraction between $CHCl_3$ (2 mL) and $H_2O$ (1 mL×2). LC-MS of the organic layer confirmed the identity of the desired product (379) and the organic layer was concentrated under vacuum until very dry. 2 mL of methanol was added into above compound (379) to dissolve followed by 2 mL of 4 M HCl in 1,4-dioxane at room temperature. The resulted solution was shaking at room temperature overnight, concentrated under vacuum with heating (50–60° C.) to give the desired product (380) as solid. LC-MS confirmed the identity of the product as HCl salt.

4.27.8 EXAMPLE 31

Synthesis of 4-amino-2-hydroxy-N-(4-methoxyphenyl)-benzamide (382)

110 µmol of the BOC-protected 4-amino-2-hydroxy benzoic acid (378) was dissolved in 220 µL of DMF. A solution of 220 µL of 0.5 M of 4-methoxyaniline in THF containing 4 equivalent of $Et_3N$ was added followed by 440 µL of 0.5 M of HOBt in THF. The resulting reaction mixture was vortexed to mix very well. 880 µL of 0.25 M EDCI solution in methylene chloride was then added, vortexed and shaken at room temperature for 24 hours. The reaction mixture was then dried down under vacuum and purified by liquid-liquid extraction between $CHCl_3$ (2 mL) and $H_2O$ (1 mL×2). LC-MS of the organic layer confirmed the identity of the desired product (381) and the organic layer was concentrated under vacuum until very dry. MS m/e 359.2 [M+1] (exact MS: 358.15).

2 mL of methanol was added into above compound (381) to dissolve followed by 2 mL of 4 M HCl in 1,4-dioxane at room temperature. The resulted solution was shaking at room temperature overnight, concentrated under vacuum with heating (50–60° C.) to give the desired product (382) as solid. LC-MS confirmed the identity of the product. MS m/e 259.1 [M+1] (exact MS 258.1).

4.27.9 Synthesis of 386

Scheme 77 describes the synthesis of compound 386.

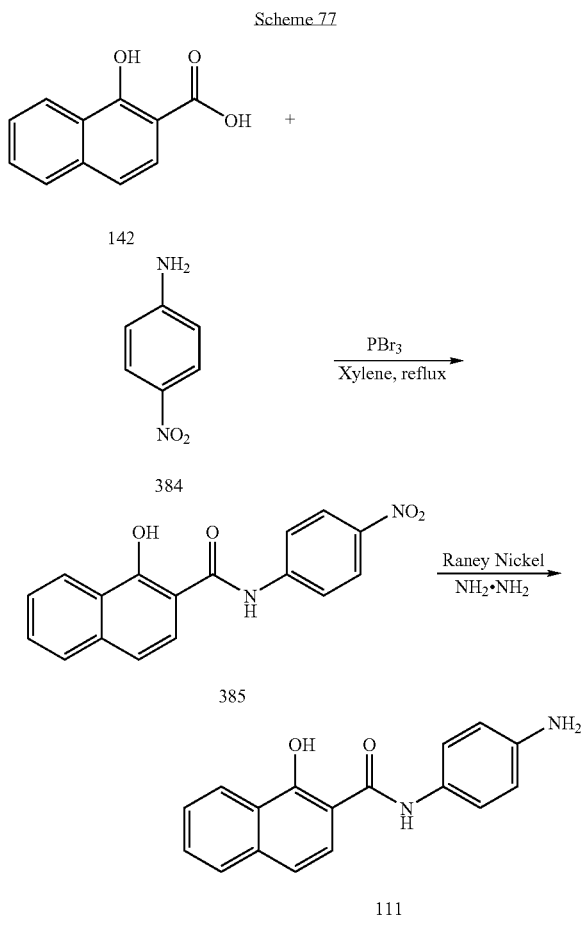

A flask containing a stirred suspension of 2-hydroxy-napthoic acid (142) (21.3 mmol) and 4-nitroaniline (384) (21.3 mmol) in xylenes (160 mL) was fitted with a condenser and heated to reflux (130° C.). Phosphorous tribromide ($PBr_3$, 8.5 mmol, 0.4 equiv) was carefully added to the resulting solution. An immediate precipitate was observed, the top of the condenser was left open to allow any HBr to vent and the suspension was allowed to reflux for another 3 h, at which point it was allowed to cool. At room temperature, THF (200 mL) and saturated $NaHCO_3$ (200 mL) were added. The organic phase was collected on a separatory funnel and washed with 2 M $NaHSO_4$ (2×150 mL), saturated $NaHCO_3$ (150 mL), brine (150 mL), dried ($MgSO_4$) and concentrated. The resulting dark syrup was dissolved in hot EtOH/MeOH (1:1, v/v, 100 mL) and allowed to stand at room temperature overnight and filtered to yield N-(4-nitrophenyl)-2-hydroxy-napthoanilide (385) (19.5 mmol, 91% yield) as dark yellow crystals. $^1$H NMR (400 MHz, DMSO-$d_6$) δ=7.49 ppm (d, 1H, J=9 Hz), 7.58 (appeared td, 1H, J=1, 8 Hz), 7.68 (appeared td. 1H, J=1, 7 Hz), 7.91 (d, 1H, J=8 Hz), 8.06 (dt, 2H, J=2, 9 Hz), 8.10 (d, 1H, J=9 Hz), 8.26–8.32 (m, 3H), 10.82 (s, 1H).

To a stirred solution of 385 (8.11 mmol) in a mixture of THF and MeOH (1:1, v/v, 100 mL) was added Raney nickel (~2 mL, 50% suspension in water). Hydrazine ($N_2H_4$, 32.0 mmol, 4 equiv) was added in portions over a period of 30 minutes. Once effervescence had ceased, TLC analysis (15: 2:0.1, $CH_2Cl_2$/MeOH/$NH_4OH$) indicated complete conversion of the starting material to a compound that had lower $R_f$ than the starting material (stained spontaneously with PMA/ Ce stain without requiring heating). The suspension was diluted with THF (100 mL) and filtered through a pad of Celite on a fritted funnel. The supernatant was concentrated to yield 1-hydroxy-[2]naphthoic acid-(4-amino-anilide) (111) (7.8 mmol, 96% yield) as a dark purple solid. $^1$H NMR (400 MHz, DMSO-$d_6$) δ=5.06 ppm (br s, 2H), 6.57 (br d, 2H, J=9 Hz), 7.29 (br d, 2H, J=9 Hz), 7.39 (d, 1H, J=9 Hz), 7.53 (app. td, 1H, J=1, 8 Hz), 7.62 (app. td, 1H, J=1, 7 Hz), 7.86 (d, 1H, J=8 Hz), 8.05 (d, 1H, J=9 Hz), 8.26 (d, 1H, J=8 Hz), 10.13 (br s, 1H). LC-MS: m/e 279.2 [M+1]$^+$.

The aniline 111 (102 mg) was further purified by reverse-phase MS-triggered HPLC using gradient of $CH_3CN$ and $H_2O$ with 0.05% TFA to generate the TFA salt of 111 that was further converted to the HCl salt by treating with HCl (2.0 M) to give 70.4 mg of 111 as the HCl salt. LC-MS: m/e 279.2 [M+1]$^+$. $^1$H NMR (400 MHz, DMSO-$d_6$): δ=10.60 (s, 1H, CONH), 8.29 (d, J=7.6 Hz, 1H), 8.14 (d, J=9.2 Hz, 1H), 7.90 (d, J=8 Hz, 1H), 7.78–7.83 (m, 2H), 7.63–7.68 (m, 1H), 7.54–7.60 (m, 1H), 7.45 (d, J=8.4 Hz, 1H), 7.32–7.37 (m, 2H). Elemental analysis calcd (%) for $C_{17}H_{14}N_2O_2$·HCl (314.767): C, 64.87, H, 4.80, N, 8.90; found C, 64.75, H, 5.12, N, 9.13.

4.27.10 Synthesis of Aniline 391 (Scheme 78)

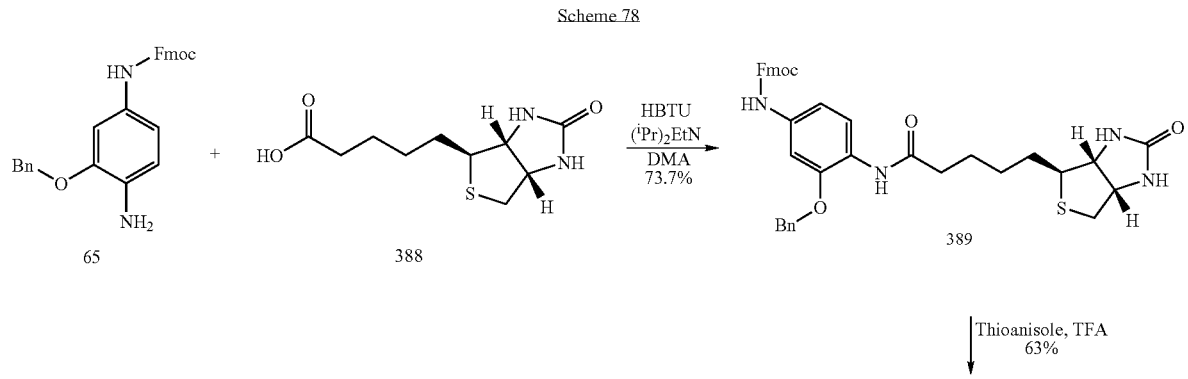

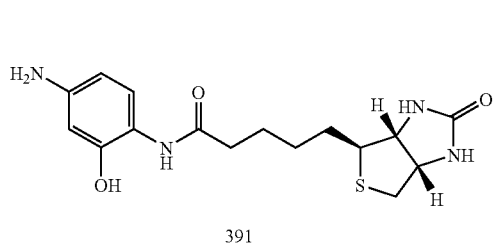

391

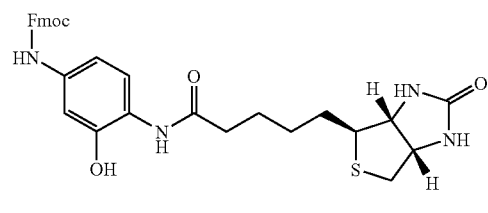

390

Piperidine
THF, DMF
rt., 3h
81.6%

{3-Benzyloxy-4-[5-(2-oxo-hexahydro-thieno[3,4-d]imidazol-4-yl)-pentanoylamino]-phenyl}-carbamic acid 9H-fluoren-9-ylmethyl ester (389)

5-(2-Oxo-hexahydro-thieno[3,4-d]imidazol-4-yl)-pentanoic acid (388) (0.293 g, 1.2 mmol) and 2-(1H-benzotriazol-1-yl)-1,1,3,3-tetramethyl-uronium hexafluorophosphate (HBTU) (0.455 g, 1.2 mmol) were combined and dissolved in DMA (24 mL). $^{i}Pr_2EtN$ (0.313 mL, 1.8 mmol) was added and the mixture was shaken for 30 minutes at room temperature. The (4-amino-3-benzyloxy-phenyl)-carbamic acid 9H-fluoren-9-ylmethyl ester (65) (0.25 g, 0.573 mmol) was added and the mixture was shaken in a 40 mL I-Chem vial for 16 h. LC-MS indicated complete coupling at this point. The mixture was poured into ice-water and a very pale/purple powder precipitated. Collection by filtration under reduced pressure followed by drying under high vacuum for 16 h gave the desired product (389) as a white/purple solid (0.28 g, 0.422 mmol, 73.7% yield). LC-MS (ESI): (exact mass: 662.26) m/e 663.2 [M+1]$^{+}$ (100%).

{3-Hydroxy-4-[5-(2-oxo-hexahydro-thieno[3,4-d]imidazol-4-yl)-pentanoylamino]-phenyl}-carbamic acid 9H-fluoren-9-ylmethyl ester (390)

{3-Benzyloxy-4-[5-(2-oxo-hexahydro-thieno[3,4-d]imidazol-4-yl)-pentanoylamino]-phenyl}-carbamic acid 9H-fluoren-9-ylmethyl ester (389) (0.28 g, 0.422 mmol) was dissolved in TFA (2 mL) and thioanisole (0.4 mL) was added. The mixture was shaken at room temperature in a Teflon septum capped 40 mL I-Chem vial for 3 h. LC-MS indicated complete de-benzylation at this point. The mixture was diluted with water (15 mL) and a pink/orange precipitate formed. Collection by filtration under reduced pressure followed by rinsing with water followed by drying under high vacuum for 16 h gave the desired product (390) as a pink/orange powder (0.152 g, 0.266 mmol, 63% yield). LC-MS (ESI): (exact mass: 572.21) m/e=573.1 [M+1]$^{+}$.

5-(2-Oxo-hexahydro-thieno[3,4-d]imidazol-4-yl)-pentanoic acid (4-amino-2-hydroxy-phenyl)-amide (391)

{3-Hydroxy-4-[5-(2-oxo-hexahydro-thieno[3,4-d]imidazol-4-yl)-pentanoylamino]-phenyl}-carbamic acid 9H-fluoren-9-ylmethyl ester (390) (0.152 g, 0.266 mmol) was dissolved in a mixture of THF (10 mL) and DMF (4 mL). Piperidine (0.53 mL, 5.3 mmol) was added. The mixture was shaken at room temperature for 3 h. LC-MS indicated complete de-protection at this point. The mixture was diluted with EtOAc (100 mL), water (2×50 mL) and brine (2×50 mL) via extraction, dried over MgSO$_4$ and concentrated under reduced pressure to give an oil. Purification by flash chromatography on silica gel using a gradient of hexane and EtOAc (eluting with 15–100% EtOAc/hexane in 30 minutes) gave the desired product (391) as a beige oil (0.076 g, 0.217 mmol, 81.6% yield). LC-MS (ESI): (exact mass: 350.14) m/e=351.3 [M+1]$^{+}$ (100%), 701.3 [2M+1]$^{+}$ (15%).

4.27.11 Synthesis of 396 (Scheme 79)

Scheme 79

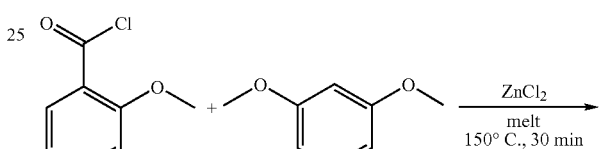

392              393

ZnCl$_2$
melt
150° C., 30 min
84%

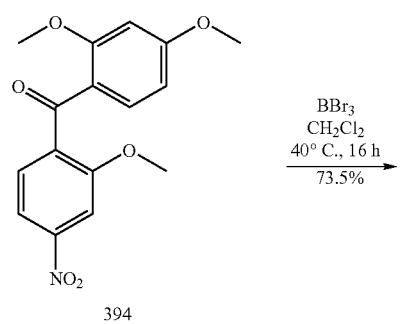

394

BBr$_3$
CH$_2$Cl$_2$
40° C., 16 h
73.5%

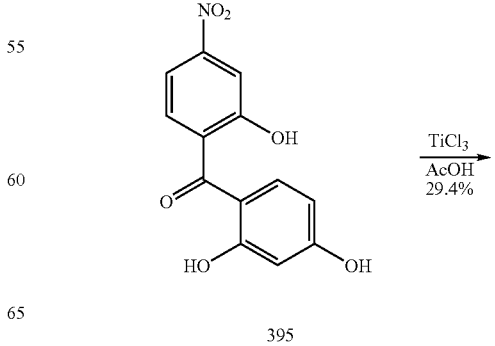

395

TiCl$_3$
AcOH
29.4%

-continued

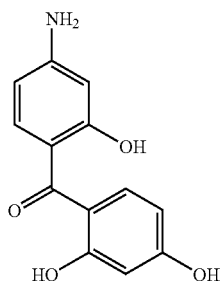

396

(2,4-Dimethoxy-phenyl)-(2-methoxy-4-nitro-phenyl)-methanone (394)

2-Methoxy-4-nitro-benzoyl chloride (392) (0.5 g, 2.32 mmol), 1,3-dimethoxy-benzene (393) (0.962 g, 6.96 mmol) and zinc (II) chloride (0.063 g, 0.46 mmol) were combined. The mixture was heated to 150° C. for 30 minutes. TLC indicated product formation. The mixture was diluted with EtOAc (200 mL), washed with aqueous HCl (100 mL, 1.0 M), NaHCO$_3$ (aqueous saturated, 100 mL) and brine (100 mL) via extraction, dried over MgSO$_4$ and concentrated under reduced pressure. Purification by flash chromatography on silica gel using a gradient of hexane and EtOAc (eluting with 15–100% EtOAc/hexane in 30 minutes) gave the desired product along with the corresponding o-acylated product (10:1 ratio by NMR). Recrystallization from acetone followed by filtration under reduced pressure gave the desired product (394) as yellow cubic crystals (0.618 g, 2.0 mmol, >99% pure, 84% yield). $^1$H NMR (400 MHz, Acetone-d$_6$): δ 3.53 (s, 3H), 3.78 (s, 3H), 3.85 (s, 3H), 6.58 (d, 1H, J=2.4 Hz), 6.64 (dd, 1H, J=8.4 Hz, 2 Hz), 7.44 (d, 1H, J=8 Hz), 7.63 (d, 1H, J=9.2 Hz), 7.81 (d, 1H, J=2 Hz), 7.84 (dd, 1H, J$_1$=8.4 Hz, J$_2$=2.4 Hz).

(2,4-Dihydroxy-phenyl)-(2-hydroxy-4-nitro-phenyl)-methanone (395)

(2,4-Dimethoxy-phenyl)-(2-methoxy-4-nitro-phenyl)-methanone (394) (0.4 g, 1.26 mmol) was dissolved in CH$_2$Cl$_2$ and BBr$_3$ was added. The mixture was heated to 40° C. while shaking in a sealed 40 mL I-Chem vial for 16 h. TLC (R$_f$: 0.5 compared to R$_f$: 0.65 for compound 394 in 1:1 hexane/EtOAc, single spot) indicated the complete de-methylation at this point. Purification by flash chromatography on silica gel using a gradient of hexane and EtOAc (eluding with 15–100% EtOAc/hexane in 30 minutes) gave the desired product (395) as a yellow solid upon concentration (0.255 g, 0.927 mmol, 73.5%). The product was used in the next step without further characterization.

(4-Amino-2-hydroxy-phenyl)-(2,4-dihydroxy-phenyl)-methanone (396)

(2,4-Dihydroxy-phenyl)-(2-hydroxy-4-nitro-phenyl)-methanone (395) (0.255 g, 0.927 mmol) was dissolved in warm AcOH (10 mL) and TiCl$_3$ (2.0 M solution in aqueous 1M HCl, 5 mL) was added portion wise over a period of 2 hours until the color of the solution remained purple. TLC (R$_f$: 0.5 compared to R$_f$: 0.35 for compound 395 in 1:1 hexane/EtOAc, single spot) indicated complete reaction at this point. The mixture was concentrated to remove nearly all the AcOH. The mixture was diluted with EtOAc (100 mL), washed with NaHCO$_3$ (aqueous sat., 500 mL) and brine (500 mL) via extraction, dried over MgSO$_4$ and concentrated under reduced pressure. Purification by flash chromatography on silica gel using a gradient of hexane and EtOAc (eluding with 15–100% EtOAc/hexane in 30 minutes) gave the desired product (396) as a yellow/orange oil (0.067 g, 0.273 mmol, 29.4% yield). LC-MS (ESI): (exact mass: 245.07) m/e=246.2 [M+1]$^+$.

4.27.12 Synthesis of Aniline 398 (Scheme 80).

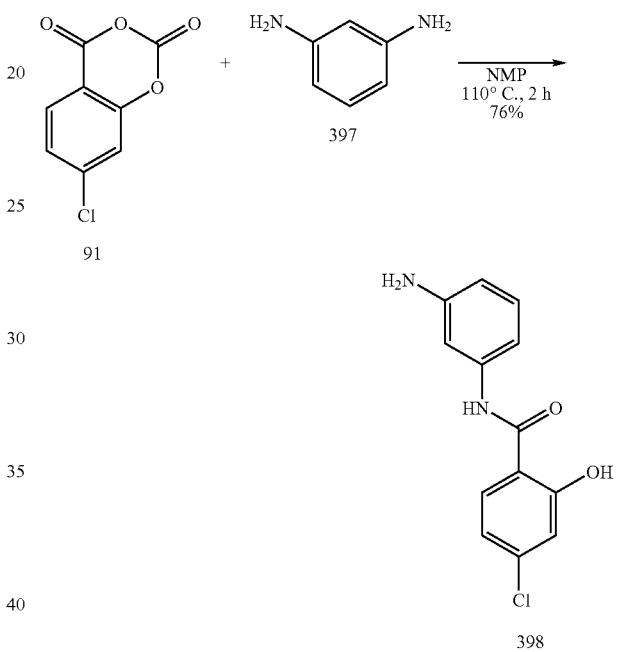

N-(3-Amino-phenyl)-4-chloro-2-hydroxy-benzamide (398)

7-Chloro-benzo[1,3]dioxine-2,4-dione (91) (0.090 g, 0.455 mmol) and benzene-1,3-diamine (397) (0.17 g, 1.57 mmol) were combined and dissolved in NMP (6 mL). The mixture was heated to 110° C. for 2 h. TLC was inconclusive, it was later determined that the desired product had same R$_f$ as the aniline (397). LC-MS indicated complete reaction. The mixture was diluted with MeOH (2 mL) and LiOH (aqueous, 2.0 M, 4 mL). The mixture was stirred for 10 minutes. The solution was diluted with EtOAc (25 mL), washed with water (2×15 mL), saturated aqueous NaHCO$_3$ (2×15 mL) and brine (2×15 mL) via extraction, dried over MgSO$_4$ and concentrated to give a brown oil. Purification by flash chromatography on silica gel using a gradient of hexane and EtOAc (15–100% EtOAc in hexane) gave the desired product (398) as an off-white solid upon concentration (0.091 g, 0.347 mmol, 76% yield). LC-MS (ESI): (exact mass: 262.05) m/e=263.0 [M+1]$^+$ (100%), 525.3 [2M+1]$^+$ (10%).

4.28 Synthesis of Intermediate: Triazine Substituted Aniline Intermediates

4.28.1 Synthesis of Intermediate 402 (Scheme 81).

Scheme 81

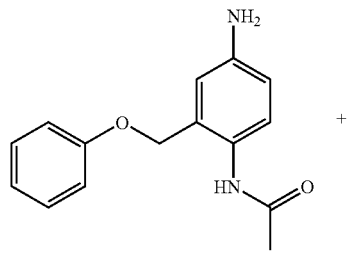

399

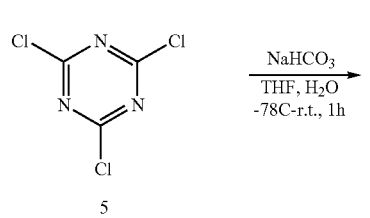

5

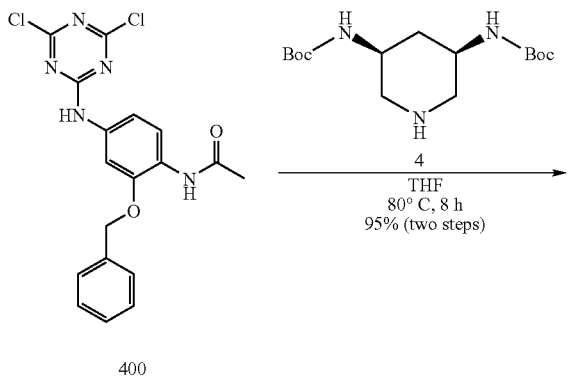

400

401

402

N-[2-Benzyloxy-4-(4,6-dichloro-[1,3,5]triazin-2-ylamino)-phenyl]-acetamide (400)

N-(4-Amino-2-benzyloxy-phenyl)-acetamide (399) (0.65 g, 2.54 mmol) and NaHCO$_3$ (1.28 g, 15.24 mmol) were suspended in THF (100 mL) and chilled on a dry-ice/acetone bath. The cyanuric chloride (5) (0.465 g, 2.54 mmol) was dissolved in THF (4 mL) and added to the chilled solution. The ice-bath was removed and the mixture was stirred while warming to room temperature over a period of 45 minutes. TLC (R$_f$: 0.6 compared to R$_f$: 0.1 for compound 399 and R$_f$: 0.95 for compound 400 in 1:1 hexane/EtOAc, single spot) indicated complete reaction at this point. This reaction mixture was used directly in the next step without further purification or characterization.

N-[2-Benzyloxy-4-(4,6-bis-((3R,5S)-3,5-bis-(tert-Butoxycarbonylamino)-piperidin-1-yl)-[1,3,5]triazin-2-ylamino)-phenyl]-acetamide (401)

(3R,5S)-3,5-bis-(tert-Butoxycarbonylamino)-piperidine (4) (1.68 g, 5.33 mmol) was suspended in DMF (20 mL), sonicated for 2 minutes and added to the crude reaction mixture containing N-[2-benzyloxy-4-(4,6-dichloro-[1,3,5]triazin-2-ylamino)-phenyl]-acetamide (400). The mixture was heated to 80° C. for 8 h. LC-MS indicated complete reaction at this point. The mixture was concentrated to a volume of 50 mL and poured into ice-water. A white solid precipitated immediately and was collected by filtration under reduced pressure followed by drying under high vacuum for 16 h to give the desired product (401) as a white powder (2.32 g, 2.4 mmol, 95% total yield for two steps). LC-MS (ESI): (exact mass: 961.54) m/e=962.7 [M+1]$^+$ (100%).

2-Benzyloxy-N4-(4,6-bis-((3R,5S)-3,5-bis-(tert-Butoxycarbonylamino)-piperidin-1-yl)-[1,3,5]triazin-2-yl)-benzene-1,4-diamine (402)

N-[2-Benzyloxy-4-(4,6-bis-((3R,5S)-3,5-bis-(tert-butoxycarbonylamino)-piperidin-1-yl)-[1,3,5]triazin-2-ylamino)-phenyl]-acetamide (401) (2.32 g, 2.4 mmol) was dissolved in an mixture of MeOH and dioxane (150 mL, 4:1). Hydrazine monohydrate (100 mL) was added and the mixture was heated to reflux for 10 days. LC-MS indicated complete de-protection at this point. Upon cooling, a white precipitate formed. The mixture was poured into ice water, forcing additional precipitate to form. The solid was collected by filtration under reduced pressure, rinsed with water (100 mL), and dried under high vacuum for 16 h to give the desired product (402) as a white powder (1.48 g, 1.62 mmol, 68% yield). LC-MS (ESI): (exact mass: 919.53) m/e=920.6 [M+1]$^+$ (100%).

4.28.2 Synthesis of Intermediate 406 (Scheme 82).

Scheme 82 describes the procedure for synthesis of intermediate 406.

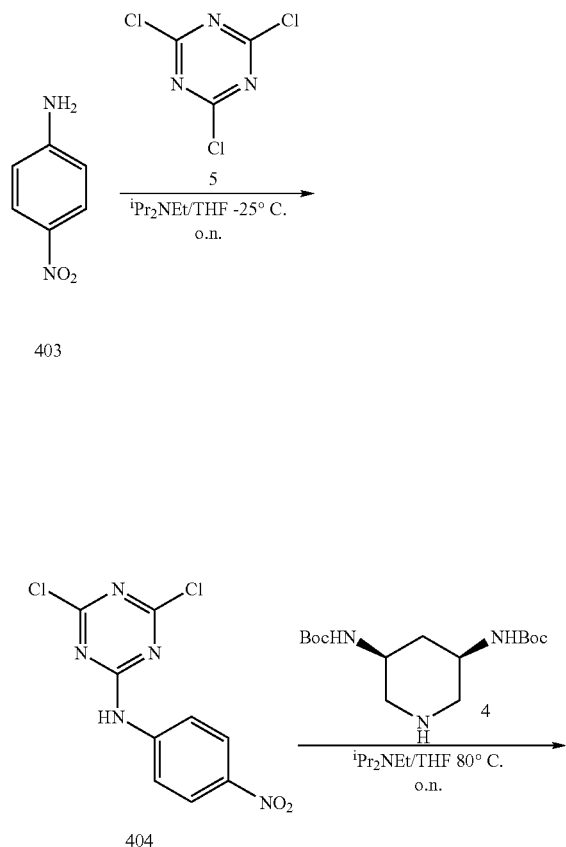

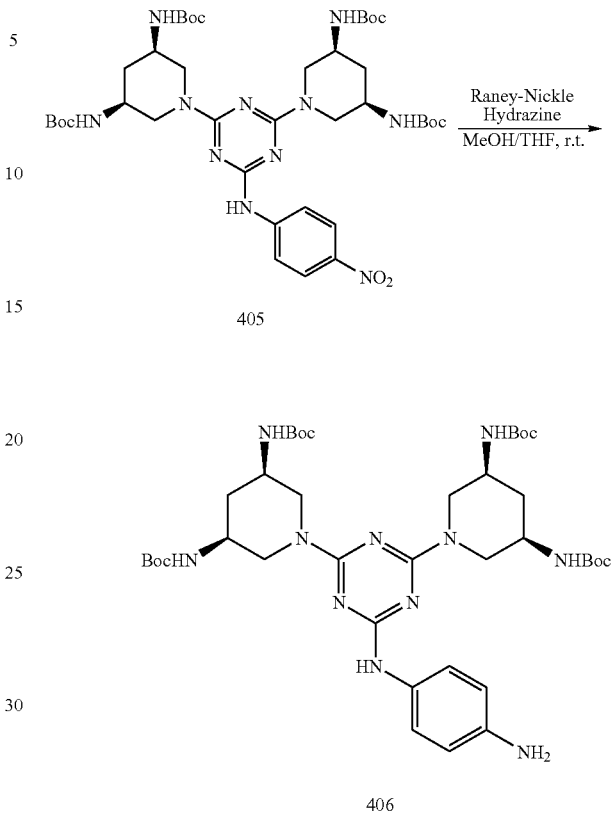

Cyanuric chloride (5) (500 mg, 2.711 mmol) in THF (5 ml) was allowed to sit in the refrigerator for half an hour at −25° C. 4-Nitro-phenylamine (403) (374 mg, 2.711 mmol) in THF (10 ml) with $^i$Pr$_2$NEt (472 µL, 2.711 mmol) was then added into the above solution. The reaction mixture was allowed to sit in the refrigerator overnight at −25° C. The reaction mixture was shaken at room temperature for 2 h to give compound 404. The reaction was monitored by TLC. The reaction mixture was directly used in next step.

(3R,5S)-3,5-bis-(tert-butoxycarbonylamino)-piperidine (4) (1.717 g, 5.423 mmol) and $^i$Pr$_2$NEt (1.8 ml, 5.423 mmol) were added into the previous reaction mixture. The mixture was heated at 80° C. overnight. The solvent was removed under reduced pressure. Liquid-liquid extraction was performed with CHCl$_3$ and H$_2$O. The organic layer was dried over MgSO$_4$. After filtration, the solvent was removed under reduced pressure. The resulting solid was purified by flash chromatography to give the intermediate 405 (1.66 g, 72.7% yield) as a solid. LC-MS (ESI): m/e=844.6 [M+H]$^+$.

Compound 405 (1.660 g, 1.97 mmol) was dissolved in MeOH (50 ml) and THF (50 ml). Raney Nickel (50% slurry in water) (6 ml) was added to the reaction mixture followed by anhydrous hydrazine (3 ml). The reaction mixture was stirred at room temperature for 45 minutes until stop bubbling. The solid was filtered off through celite under nitrogen and washed with MeOH. The solvent was removed under reduced pressure. Liquid-liquid extraction was performed using CHCl$_3$ (100 mL) and H$_2$O (50 mL×3). The organic layer was dried over MgSO$_4$, filtered and concentrated to give the compound 406 (1.48 g) as a solid in 92% yield. LC-MS (ESI): m/e=814.6 [M+H]$^+$

4.28.3 Synthesis of Intermediate 410

Scheme 83 describes the procedure for synthesis of intermediate 410.

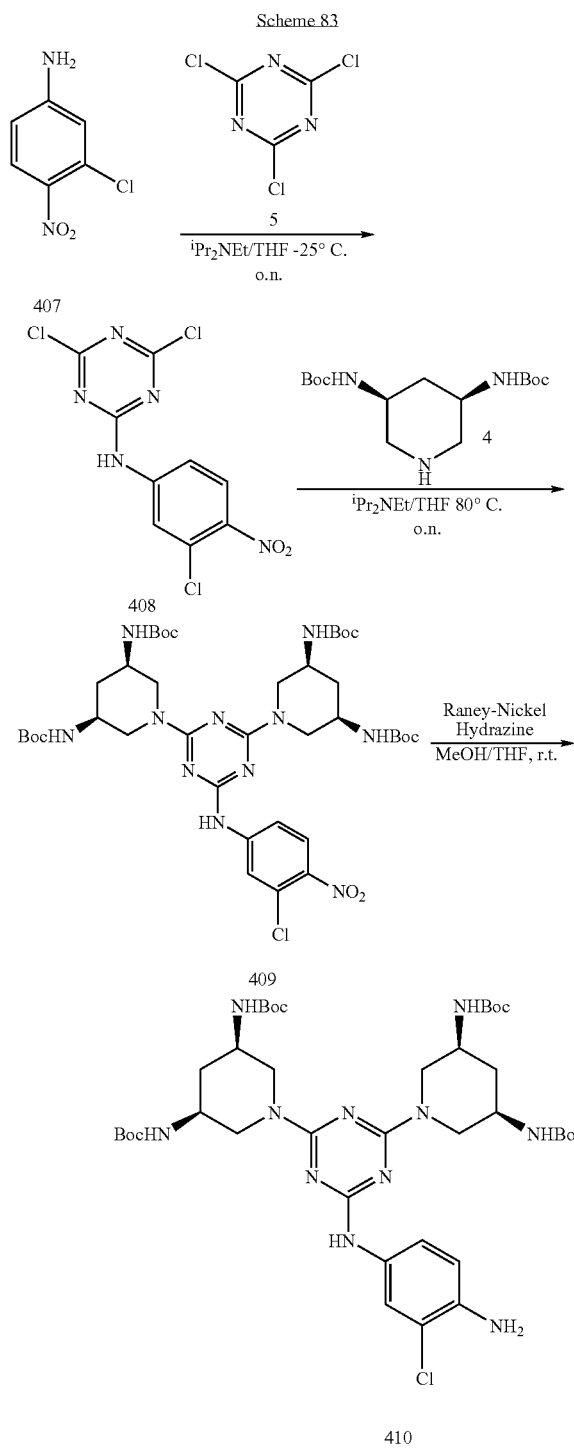

Cyanuric chloride (5) (500 mg, 2.711 mmol) in THF (5 ml) was allowed to sit in the refrigerator for half an hour at −25° C. 3-Chloro-4-nitro-phenylamine (407) (467 mg, 2.711 mmol) in THF (10 ml) with $^i$Pr$_2$NEt (472 μL, 2.711 mmol) was then added into the above solution. The reaction mixture was allowed to sit in the refrigerator overnight at −25° C. The reaction mixture was shaken at room temperature for 2 h to give compound 408. The reaction was monitored by TLC. The reaction mixture was directly used in next step.

(3R,5S)-3,5-bis-(tert-butoxycarbonylamino)-piperidine (1.717 g, 5.423 mmol) and $^i$Pr$_2$NEt (1.8 ml, 5.423 mmol) were added into the previous reaction mixture. The mixture was heated at 80° C. overnight. The solvent was removed under reduced pressure. Liquid-liquid extraction was performed using CHCl$_3$ and H$_2$O. The organic layer was dried over MgSO$_4$. After filtration, the solvent was removed under reduced pressure. The resulting solid was purified by flash chromatography to give the intermediate 409 (1.16 g, 48.7%) as a solid. LC-MS (ESI): m/e=878.8 [M+1]$^+$ Compound 409 (1.16 g, 1.32 mmol) was dissolved in MeOH (50 ml) and THF (50 ml). Raney Nickel (50% slurry in water) (6 ml) was added to the reaction mixture followed by anhydrous hydrazine (3 ml). The reaction mixture was stirred at room temperature for 30 minutes until bubbling stopped. The solid was filtered off through celite under nitrogen and washed with MeOH. The solvent was removed under reduced pressure. Liquid-liquid extraction was performed using CHCl$_3$ (100 mL) and H$_2$O (50 mL×3). The organic layer was dried over MgSO$_4$, filtered and concentrated to give the compound 410 (850.5 mg) as a solid in yield 75.8%. LC-MS (ESI): m/e=848.8 [M+1]$^+$

4.28.4 Synthesis of Intermediate 414 (Scheme 84)

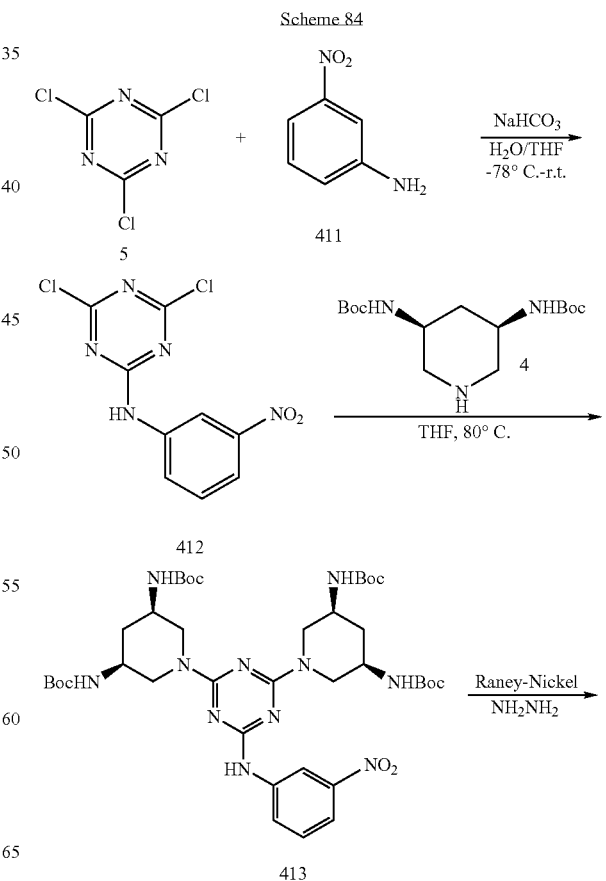

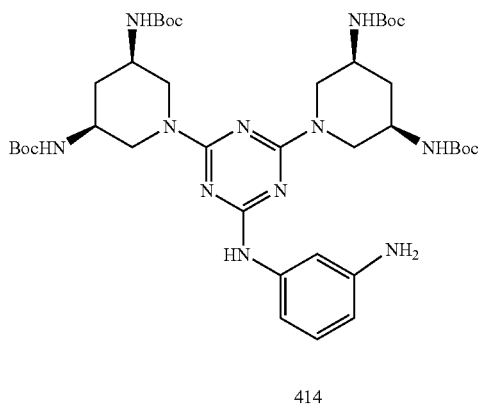

414

3-Nitroaniline (411) (138 mg, 1 mmol) was dissolved in 12 mL of THF. NaHCO₃ (504.1 mg, 6 mmol) was added followed by 10 drops of water. The mixture was cooled to −78° C. A solution of cyanuric chloride (5) (184.4 mg, 1 mmol) in 8 mL of THF was added with stirring. The mixture was shaken at −78° C. to room temperature for 15 hours.

A slurry of amine 4 (726 mg, 2.3 mmol) in 4.6 mL of THF was added and the mixture was heated at 80° C. overnight with stirring. LC-MS result confirmed the completion of the reaction. The solvent was evaporated under reduced pressure and the residue was purified by liquid-liquid extraction using CHCl₃ (10 mL) and H₂O (5 mL×2) to give a pale yellow solid. The organic layer was concentrated to give the desired product 413. LC-MS: m/e 844.6 [M+1]⁺ (expect ms: 843.46).

Compound 413 was dissolved in 12 mL of THF and 8 mL of MeOH with the help of heating at 55° C. NH₂NH₂ (98%, 700 μL) was added immediately followed by Raney Nickel (50% slurry, 1.4 mL). The mixture was stirred at 55° C. for 0.5 hours. LC-MS result showed the incompletion of the reaction. Additional NH₂NH₂ (700 uL) and Raney Nickel (50% slurry, 1.4 mL) was added. After stirring for 0.5 hours, additional NH₂NH₂ (98%, 700 μL) was added immediately followed by Raney Nickel (50% slurry, 1.4 mL). After 20 minutes stirring at 55° C., the LC-MS result confirmed the completion of the reaction. The inorganic solid was filtered off and the filtrate was concentrated under reduced pressure. The crude product was purified by flash chromatography on silica gel using a gradient of hexane and EtOAc to give the desired product 414 (174.8 mg, 21.5% isolated yield for 3 steps) as a pale yellow solid. This intermediate was directly used without further characterization.

4.29 Synthesis of Intermediates: Other Intermediates

4.29.1 Synthesis of Intermediate 90 of Benzo-dioxine-diones (Scheme 85)

Scheme 85

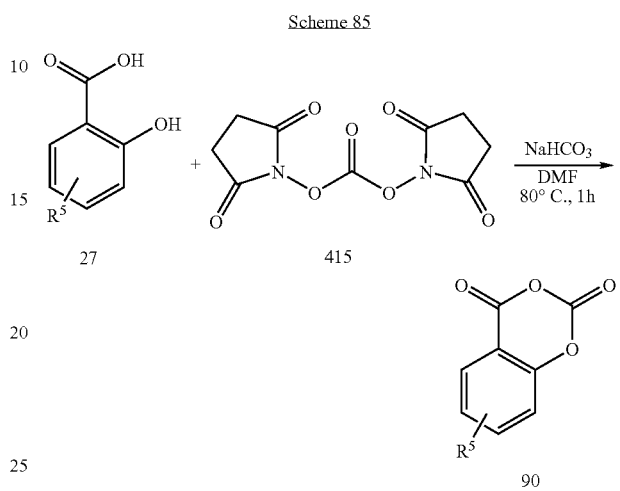

90

R⁵ refers to a substituent as defined for substituted aryls.

The salicylic acid derivative (27) (1 equiv.), N,N'-disuccinimidyl carbonate (415) (1 equiv.) and NaHCO₃ (1 equiv.) were combined. DMF (0.2M) was added and the mixture was heated at 80° C. with shaking in a 40 mL I-Chem vial for 1 h. Occasional venting may be needed. The reaction was monitored by TLC (the benzo-dioxine-dione is generally less polar than the corresponding salicylic-acid). Upon the complete cyclization, the mixture was diluted with EtOAc, washed with water, saturated aqueous NaHCO₃ and brine via extraction, dried over MgSO₄ and concentrated to give the desired product (90) in good yield. The product was used in the next step without further purification.

4.29.2 Synthesis of Intermediate 65 (Scheme 86).

Scheme 86

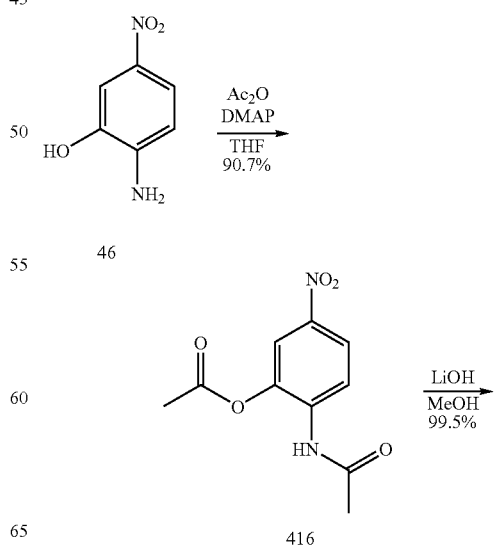

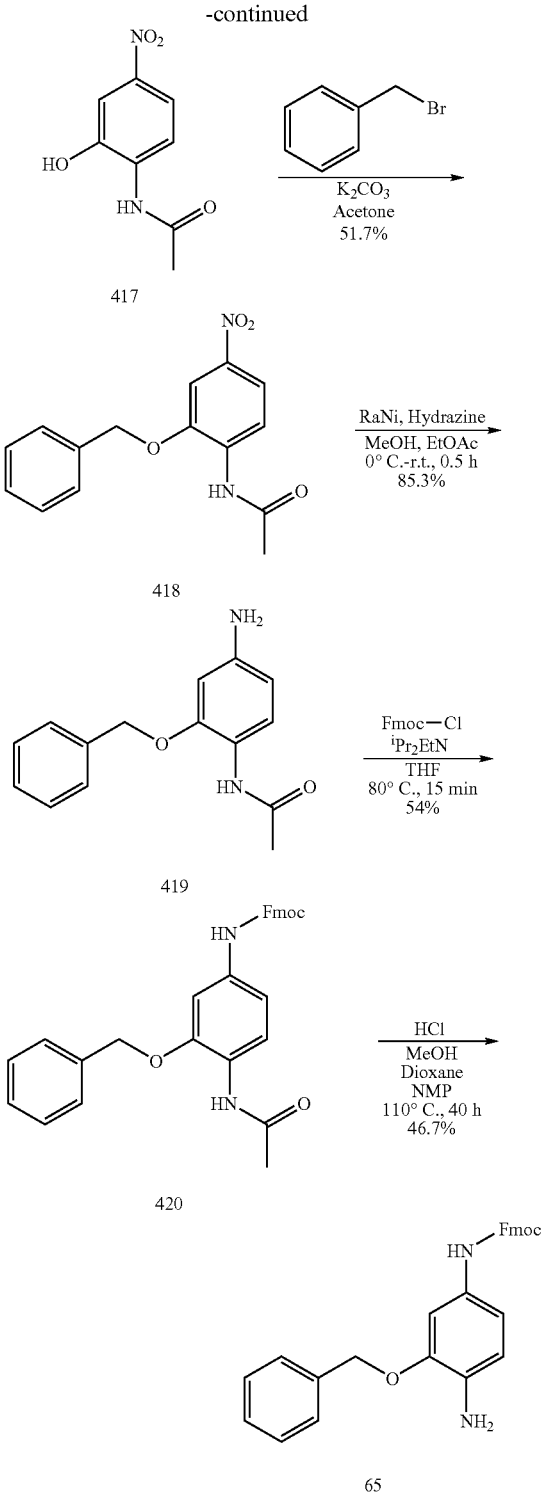

Acetic acid 2-acetylamino-5-nitro-phenyl ester (416)

2-Amino-5-nitro-phenol (46) (20 g, 97.3 mmol) was suspended in THF (125 mL) and Acetic-anhydride (75 mL) was added. Di-methyl-amino-pyridine (DMAP) (300 mg, 2.45 mmol) was added and the mixture was stirred for 16 h at room temperature. A solid precipitated and was collected by filtration followed by rinsing with 3:1 hexane/EtOAc (3×100 mL). The solid was dried under high vacuum for 8 h to give the desired product (416) as a yellow powder (21 g, 88.2 mmol, 90.7% yield). LC-MS (ESI): (exact mass: 238.06) m/e=239.2 [M+1]$^+$ (15%), 477.1 [2M+1]$^+$ (100%).

N-(2-Hydroxy-4-nitro-phenyl)-acetamide (417)

Acetic acid 2-acetylamino-5-nitro-phenyl ester (416) (21 g, 88.2 mmol) was suspended in MeOH (185 mL) and 2M aqueous LiOH (185 mL) was added. An instantaneous reaction occurred, the solution turned red, everything dissolved and a slight exothermic reaction was felt by the warmth of the flask. TLC ($R_f$: 0.55 compared to $R_f$: 0.45 for compound 416 in EtOAc) after 10 minutes indicated complete hydrolysis. Addition of 1.0 M aqueous HCl (500 mL) caused the color to fade and a precipitate to form. Collection of the precipitate via vacuum filtration followed by rinsing with water (2×100 mL) and drying under high vacuum for 16 h gave the desired product (417) as a yellow powder. (17.2 g, 87.8 mmol, 99.5% yield). LC-MS was inconclusive. The product was used in the next step without further characterization N-(2-Benzyloxy-4-nitro-phenyl)-acetamide (418)

N-(2-Hydroxy-4-nitro-phenyl)-acetamide (417) (17 g, 86.7 mmol) was dissolved in a mixture of acetone (200 mL) and THF (200 mL). Potassium-carbonate (24 g, 173.4 mmol, 2 equiv.) was added as a dry powder and the solution turned deep red. Benzyl-bromide (16.3 g, 95.37 mmol, 1.1 equiv.) was added and the mixture stirred at room temperature for 20 h. TLC ($R_f$: 0.5 compared to $R_f$: 0.2–0.3 for compound 417 in 1:1 hexane/EtOAc) indicated complete alkylation at this point. The mixture was poured into ice water (~1000 mL) and a precipitate formed while stirring for 20 min. The precipitate was collected by filtration under reduced pressure, washed with water (3×100 mL) and dried under high vacuum for 16 h to give the desired product (418) as a faintly yellow powder (13 g, 45.4 mmol, 51.7% yield). LC-MS was inconclusive. The product was used in the next step without further characterization N-(4-Amino-2-benzyloxy-phenyl)-acetamide (419)

N-(2-Benzyloxy-4-nitro-phenyl)-acetamide (418) (5 g, 17.5 mmol) was dissolved in a mixture of EtOAc (25 mL) and EtOH (25 mL). The solution was chilled on an ice bath. Raney Nickel (5 mL, 50% slurry in water) followed immediately by anhydrous hydrazine (10 mL) were added. Violent bubbling was observed. The ice bath was removed after 10 minutes and the slurry continued to stir until all bubbling had ceased (~30 minutes). LC-MS and TLC ($R_f$: 0.15 compared to $R_f$: 0.5 for compound 418 in 1:1 hexane/EtOAc) indicated complete reduction at this point. The reaction mixture was passed through a plug of silica gel, concentrated, dissolved in EtOAc (250 mL), washed with water (2×75 mL), brine (2×75 mL), dried over MgSO$_4$ and concentrated to give the desired product (419) as a beige solid (3.82 g, 14.9 mmol, 85.3% yield). LC-MS (ESI): (exact mass: 256.12) m/e=257.1 [M+1]$^+$ (100%), 513.2 [2M+1]$^+$ (15%).

(4-Acetylamino-3-benzyloxy-phenyl)-carbamic acid 9H-fluoren-9-ylmethyl ester (420)

N-(4-Amino-2-benzyloxy-phenyl)-acetamide (419) (3 g, 11.72 mmol) and Fmoc-Cl (3.1 g, 12 mmol) were combined and dissolved in THF (60 mL). $^i$Pr$_2$EtN (18 mmol, 1.2 equiv.) was added and the mixture was heated to 80° C. for 15 minutes while stirring. TLC indicated complete reaction at this point. The mixture was poured into ice-water (500 mL) and a white solid precipitated. The solid was collected by filtration under reduced pressure followed by drying under high vacuum to give the desired product (420) as a white powder (3 g, 6.28 mmol, 54% yield). LC-MS (ESI): (exact mass: 478.19) m/e=479.2 [M+1]$^+$ (70%), 957.6 [2M+1]$^+$ (100%).

(4-Amino-3-benzyloxy-phenyl)-carbamic acid 9H-fluoren-9-ylmethyl ester (65)

(4-Acetylamino-3-benzyloxy-phenyl)-carbamic acid 9H-fluoren-9-ylmethyl ester (420) (3 g, 6.28 mmol) was dissolved in a mixture of MeOH (15 mL) and NMP (10 mL). 4.0 M HCl in dioxane (20 mL) was added and the mixture was refluxed for 40 h. LC-MS indicated complete deprotection at this point. The mixture was diluted with EtOAc (200 mL), washed with saturated aqueous NaHCO$_3$ (3×300 mL), water (100 mL) and brine (100 mL) via extraction, dried over MgSO$_4$ and upon concentration under reduced pressure, a precipitate formed. Collection by filtration under reduced pressure followed by drying under high vacuum for 16 h gave the desired product (65) as a beige/pink powder (1.28 g, 2.93 mmol, 46.7% yield). LC-MS (ESI): (exact mass: 436.18) m/e=437.2 [M+1]$^+$ (100%), 873.5 [2M+1]$^+$ (100%).

4.29.3 Synthesis of Intermediates 423 & 425 (Scheme 87)

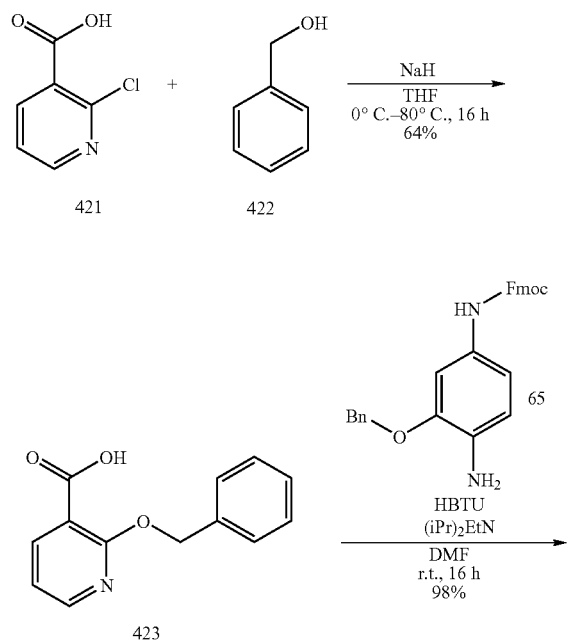

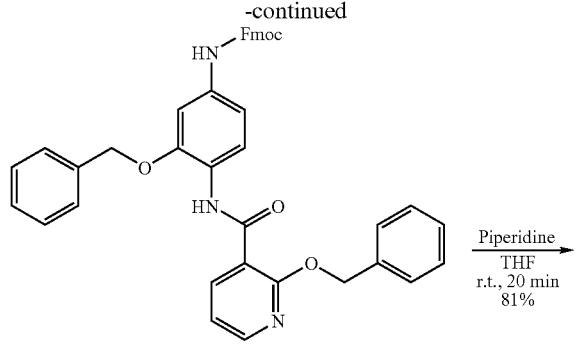

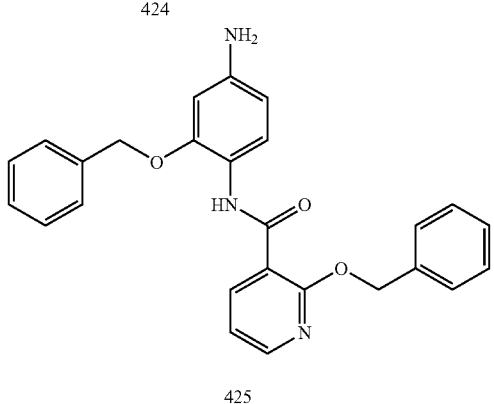

2-Benzyloxy-nicotinic acid (423)

2-Chloro-nicotinic acid (421) (3 g, 19.04 mmol) was dissolved in anhydrous THF (50 mL) and chilled to 0° C. on an ice bath. NaH (50 mmol, 60% suspension in mineral oil) was added portion wise to the solution over a period of 5 minutes. The resulting mixture was stirred at 0° C. for 30 minutes. Benzyl-alcohol (422) (2.27 g, 21 mmol) was added drop wise over a period of 10 minutes. The ice bath was removed and the mixture was warmed to room temperature over a period of 2 h. The mixture was refluxed for 16 h. LC-MS and TLC (R$_f$: 0.4–0.5 compared to R$_f$: 0.1 for compound 421 in 1:1 hexane/EtOAc, single spot) indicated complete reaction at this point. The mixture was diluted with water (300 mL) and the pH was adjusted to ~6 by the addition of HCl (aqueous, 1M) and the product was extracted with EtOAc (3×200 mL). The combined organic layers were washed with brine (100 mL) via extraction, dried over MgSO$_4$ and concentrated under reduced pressure to give a yellow oil. Recrystallization from EtOAc/hexane gave the desired product (423) as a white powder (2.8 g, 12.2 mmol, 64% yield). LC-MS (ESI): (exact mass: 229.07) m/e=230.2 [M+1]$^+$ (100%), 459.3 [2M+1]$^+$ (90%).

{3-Benzyloxy-4-[(2-benzyloxy-pyridine-3-carbonyl)-amino]-phenyl}-carbamic acid 9H-fluoren-9-ylmethyl ester (424)

2-Benzyloxy-nicotinic acid (423) (0.157 g, 0.687 mmol) was dissolved in DMF (4 mL), 2-(1H-benzotriazol-1-yl)-1,1,3,3-tetramethyl-uronium hexafluorophosphate (HBTU) (0.273 g, 0.721 mmol) was added followed by $^i$Pr$_2$EtN (0.143 mL, 0.824 mmol) and the mixture was shaken in a Teflon septum capped 40 mL vial at room temperature for 25 minutes. (4-Amino-3-benzyloxy-phenyl)-carbamic acid 9H-fluoren-9-ylmethyl ester (65) (0.3 g, 0.687 mmol) was added and the mixture was shaken at room temperature for 16 h. LC-MS indicated complete coupling at this point. The mixture was diluted with EtOAc (25 mL), washed with water (15 mL), NaHCO$_3$ (aqueous saturated, 15 mL) and brine (15 mL) via extraction, dried over MgSO$_4$ and concentrated to give a brown oil. Purification by flash chromatography (eluding with 15–100% EtOAc/hexane in 30 minutes) gave the desired product (424) as a yellow powder upon concentration (0.436 g, 0.673 mmol, 98% yield). LC-MS (ESI): (exact mass: 647.24) m/e=648.3 [M+1]$^+$ (100%).

N-(4-Amino-2-benzyloxy-phenyl)-2-benzyloxy-nicotinamide (425)

{3-Benzyloxy-4-[(2-benzyloxy-pyridine-3-carbonyl)-amino]-phenyl}-carbamic acid 9H-fluoren-9-ylmethyl ester (424) (0.430 g, 0.664 mmol) was dissolved in a mixture of THF (6 mL) and DMF (3 mL). Piperidine (12.88 mmol) was added. The mixture was shaken at room temperature for 1 h. LC-MS indicated complete de-protection at this point. The mixture was concentrated under reduced pressure to give a dark brown/purple oil. Purification by flash chromatography on silica gel using a gradient of hexane and EtOAc (15–100% EtOAc/hexane 25 minutes) gave the desired product (425) as an orange oil upon concentration (0.229 g, 0.538 mmol, 81% yield). LC-MS (ESI): (exact mass: 425.17) m/e=426.2 [M+1]$^+$ (100%).

4.29.4 Synthesis of Intermediate 428 (Scheme 88)

Scheme 88 describes the synthetic procedure for preparing intermediate 428.

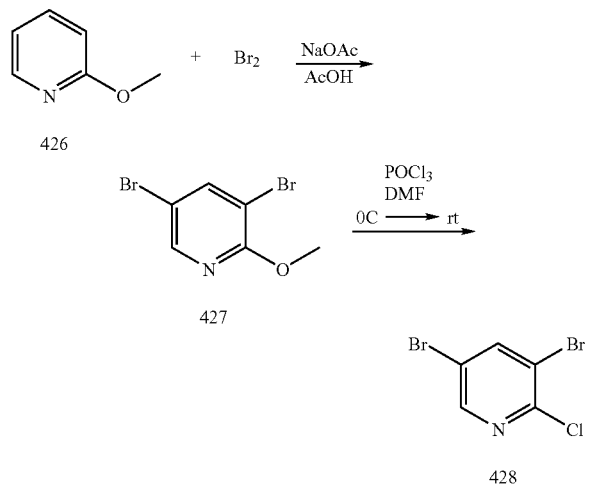

Scheme 88

3,5-Dibromo-2-methoxy-pyridine (427)

2-Methoxy-pyridine (426) (4.45 g, 40.8 mmol) was dissolved in AcOH (20 mL). While stirring, NaOAc (6.56 g) was added portion wise to form a homogeneous slurry. Bromine (7.17 mL) was added drop wise over a period of 5 minutes. The mixture continued to stir at room temperature for 16 h. TLC (R$_f$: 0.8 compared to R$_f$: 0.65 for compound 426 in 3:1 hexanes/EtOAc) and LC-MS indicated complete reaction at this point. The mixture was concentrated under reduced pressure to give an orange solid. The solid was dissolved in a mixture of water (50 mL) and EtOAc (100 mL). The organic phase was washed with saturated aqueous NaHCO$_3$ (2×20 mL) and brine (2×20 mL) via extraction, dried over MgSO$_4$ and concentrated to give a yellow oil. Purification by flash column on silica gel eluded with hexanes to give the desired product (427) as a white powder upon concentration (3.1 g, 11.61 mmol, 28.5% yield). $^1$H NMR (400 MHz, CDCl$_3$): δ 3.99 (s, 3H), 7.92 (d, 1H, J=1.6 Hz), 8.13 (d, 1H, J=2 Hz).

3,5-Dibromo-2-chloro-pyridine (428)

3,5-Dibromo-2-methoxy-pyridine (427) (1.5 g, 5.62 mmol) was dissolved in anhydrous DMF (14 mL) and chilled to 0° C. While stirring, POCl$_3$ (2.1 mL, 22.48 mmol) was added drop wise over a period of 5 minutes. The mixture was stirred at 0° C. for 1 h. The mixture was then heated to 100° C. under N$_2$, for 16 h. TLC indicated complete reaction at this point. Ice-chips (10 g) were added to the cooled solution and the mixture was stirred for 20 minutes. The mixture was diluted with EtOAc (200 mL), washed with saturated aqueous NaHCO$_3$ (2×50 mL) and brine (2×50 mL) via extraction, dried over MgSO$_4$ and concentrated to give a brown oil. Purification by column chromatography gave the desired product (428) as an off white solid upon concentration (1.01 g, 3.722 mmol, 66.2% yield). $^1$H NMR (400 MHz, CDCl$_3$): δ 8.07 (d, 1H, J=2 Hz), 8.38 (d, 1H, J=1.6 Hz).

Compound 428 was synthesized according to the literature method described in (1) Thomas M. Bargar, Jacqueline K. Dulworth, Michael T. Kenny, Renee Massad, John K. Daniel, Thomas Wilson and Roger N. Sargent, *J. Med. Chem.* 1986, 29, 1590–1595, and (2) Min-Jen Shiao, Li-Ming Shyu and Kai-Yih Tarng, *Synthetic Communications*, 1990, 20(19), 2971–2977.

4.30 General Methods for Purification of Formula I Compounds

The Formula I compounds and the Boc-protected precursors of Formula I compounds were purified by one or more of the four following methods:

Method A: Precipitation (trituration/recrystallization): In some cases, the reaction product precipitated in the reaction solution, then the solid was filtered and washed with a small amount of a solvent in which the compound was sparingly soluble and dried.

Method B: HPLC purification: The majority of the final products compounds were purified by reverse-phase HPLC based on the MS-triggered method using Waters purification system using solvent mixture of HPLC grade of CH$_3$CN and H$_2$O containing 0.05% TFA.

Method C: Preparative TLC purification: In some cases, compounds were purified by preparative TLC plate using Merck 1000 mm TLC plates using developing solvent of ethyl acetate and chloroform in the ratio of 4:1–1:1.

Method D: Flash column chromatography: Some of the compounds of type B were purified by flash chromatography.

4.31 Biological Testing

The antibacterial activity of the Formula I compounds was evaluated against standard bacterial strains by determining the minimal inhibitory concentration (MIC) to block growth. Each drug was assayed by the microdilution method in Mueller-Hinton medium, as recommended by the National Committee for Clinical Laboratory Standards. *Approved Standard M7-A5: Methods for Dilution Antimicrobial Susceptibility Tests for Bacteria That Grow Aerobically* 5th Ed. (National Committee for Clinical Laboratory Standards, Wayne, Pa., 2000).

The tested bacterial strains included *Escherichia coli* (American Type Collection ATCC25922), *Staphylococcus aureus* (ATCC25923), and *Pseudomonas aeruginosa* (ATCC27853).

Two-fold serial dilutions of each compound ranging from 64 to 0.5 μg/ml were tested in duplicate. The MIC was determined as the lowest concentration of each compound that prevented bacterial growth after 18 hours of incubation at 35° C. The results are summarized in Table 1, wherein ++ means MIC<16 μg/ml in *E. coli* or *S. aureus*, + means MIC<64 μg/ml in *E. coli* or *S. aureus*, and – means MIC>64 μg/ml in *E. coli* or *S. aureus*. The mass of each compound in the Table was confirmed by LC-MS.

| Structure | Name | Potency |
|---|---|---|
| 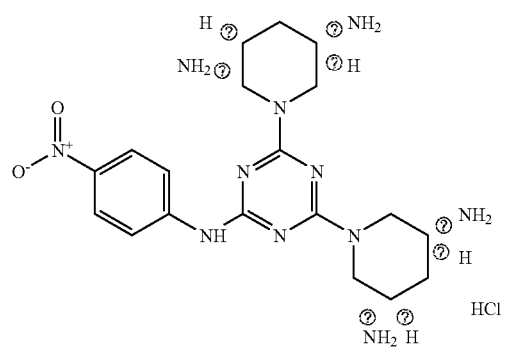 ⑦ indicates text missing or illegible when filed | N-(4-nitro-phenyl)-4,6-Bis-((3R,5S)-3,5-diamino-piperidin-1-yl)-[1,3,5]triazine-2-amine | + |
| 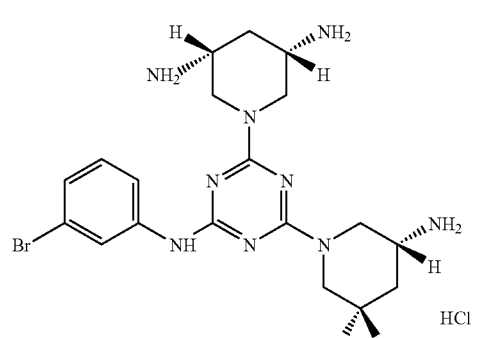 | N-(3-bromo-phenyl)-4,6-Bis-((3R,5S)-3,5-diamino-piperidin-1-yl)-[1,3,5]triazine-2-amine | + |
| 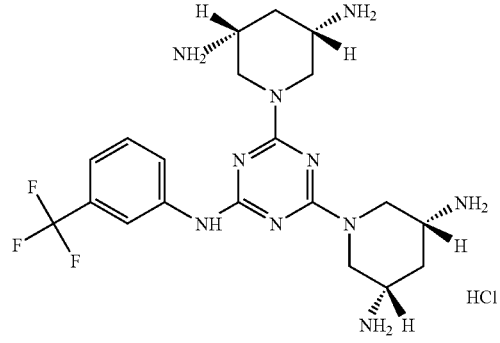 | N-(3-trifluoromethyl-phenyl)-4,6-Bis-((3R,5S)-3,5-diamino-piperidin-1-yl)-[1,3,5]triazine-2-amine | + |

| Structure | Name | Potency |
|---|---|---|
| 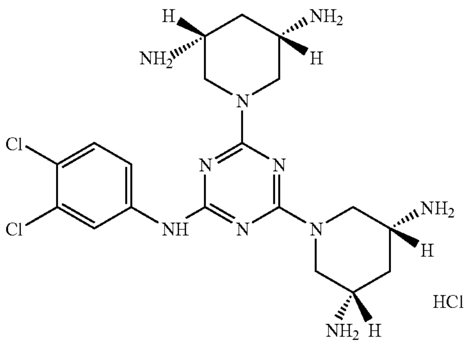 | N-(3,4-dichloro-phenyl)-4,6-Bis-((3R,5S)-3,5-diamino-piperidin-1-yl)-[1,3,5]triazine-2-amine | + |
| 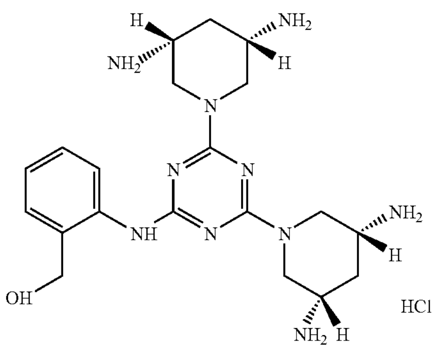 | N-(2-hydroxymethyl-phenyl)-4,6-Bis-((3R,5S)-3,5-diamino-piperidin-1-yl)-[1,3,5]triazine-2-amine | |
| 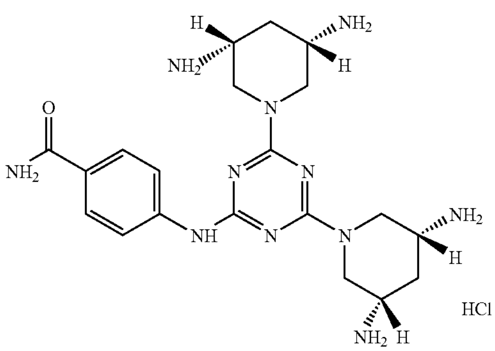 | N-(4-carbamoyl-phenyl)-4,6-Bis-((3R,5S)-3,5-diamino-piperidin-1-yl)-[1,3,5]triazine-2-amine | − |
| 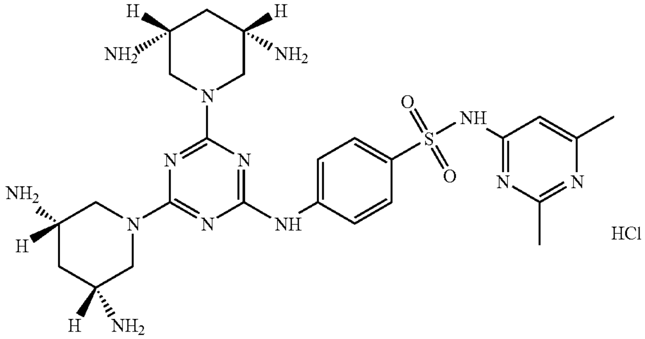 | N-[4-(2,6-dimethyl-pyrimidin-4-ylsulfamoyl)-phenyl]-4,6-Bis-((3R,5S)-3,5-diamino-piperidin-1-yl)-[1,3,5]triazine-2-amine | − |

-continued

| Structure | Name | Potency |
|---|---|---|
| 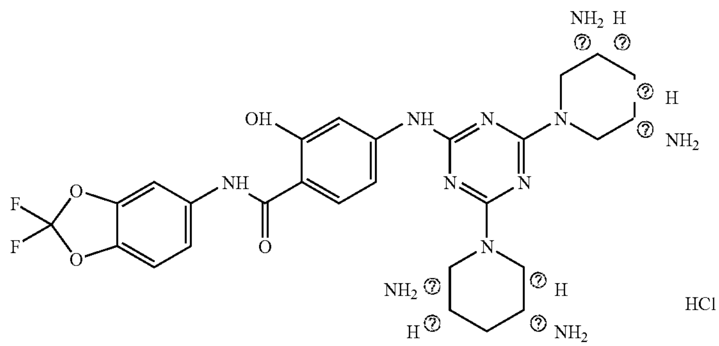 | N-[4-(2,2-difluoro-benzo[1,3]dioxol-5-ylcarbamoyl)-3-hydroxy-phenyl]-4,6-Bis-((3R,5S)-3,5-diamino-piperidin-1-yl)-[1,3,5]triazine-2-amine | ++ |
| 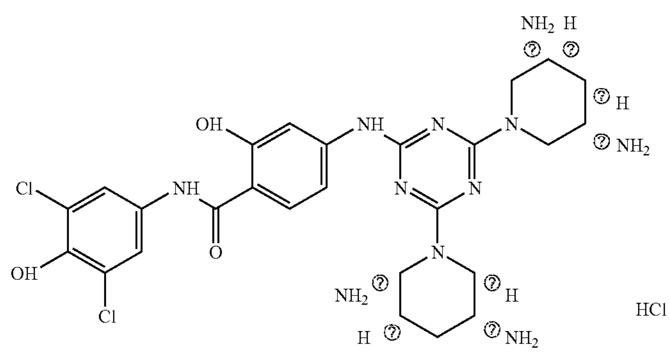 | N-[4-(3,5-dichloro-4-hydroxy-phenylcarbamoyl)-3-hydroxy-phenyl]-4,6-Bis-((3R,5S)-3,5-diamino-piperidin-1-yl)-[1,3,5]triazine-2-amine | + |
| 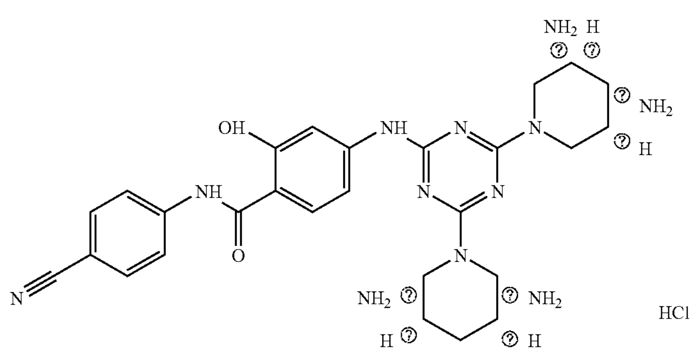 | N-[4-(4-cyano-phenylcarbamoyl)-3-hydroxy-phenyl]-4,6-Bis-((3R,5S)-3,5-diamino-piperidin-1-yl)-[1,3,5]triazine-2-amine | + |

-continued

| Structure | Name | Potency |
|---|---|---|
| 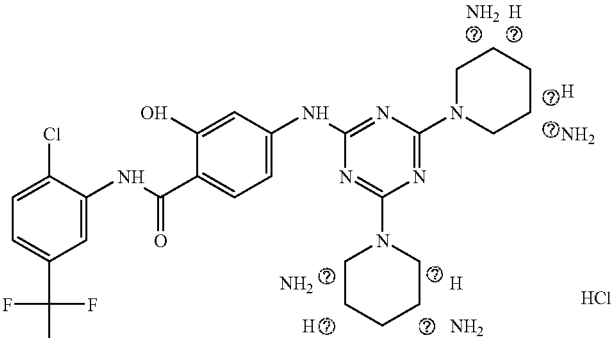 | N-[4-(2-chloro-5-trifluoromethyl-phenylcarbamoyl)-3-hydroxy-phenyl]-4,6-Biss-((3R,5S)-3,5-diamino-piperidin-1-yl)-[1,3,5]triazine-2-amine | + |
| ⑦ indicates text missing or illegible when filed | | |
| 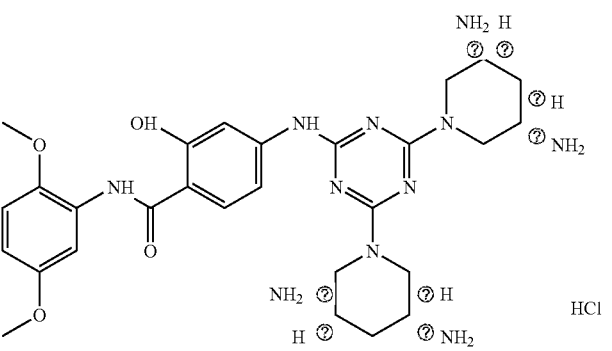 | N-[4-(4-chloro-2,5-dimethoxy-phenylcarbamoyl)-3-hydroxy-phenyl]-4,6-Bis-((3R,5S)-3,5-diamino-piperidin-1-yl)-[1,3,5]triazine-2-amine | ++ |
| ⑦ indicates text missing or illegible when filed | | |
| 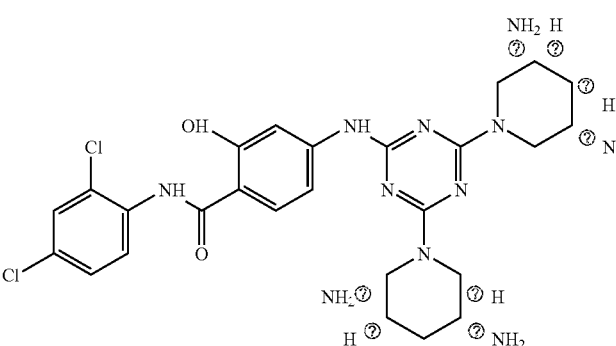 | N-[4-(2,4-dichloro-phenylcarbamoyl)-3-hydroxy-phhenyl]-4,6-Bis-((3R,5S)-3,5-diamino-piperidin-1-yl)-[1,3,5]triazine-2-amine | ++ |
| ⑦ indicates text missing or illegible when filed | | |

-continued

| Structure | Name | Potency |
|---|---|---|
| 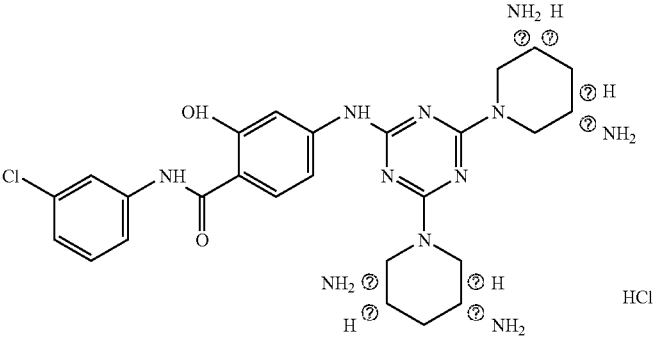 | N-[4-(3-chloro-phenylcarbamoyl)-3-hydroxy-phenyl]-4,6-Bis-((3R,5S)-3,5-diamino-piperidin-1-yl)-[1,3,5]triazine-2-amine | ++ |

⑦ indicates text missing or illegible when filed

| | | |
|---|---|---|
| 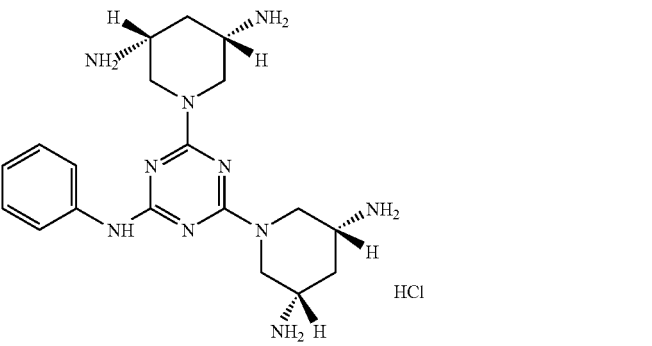 | N-phenyl-44,6-Bis-((3R,5S)-3,5-diamino-piperidin-1-yl)-[1,3,5]triazine-2-amine | – |
| 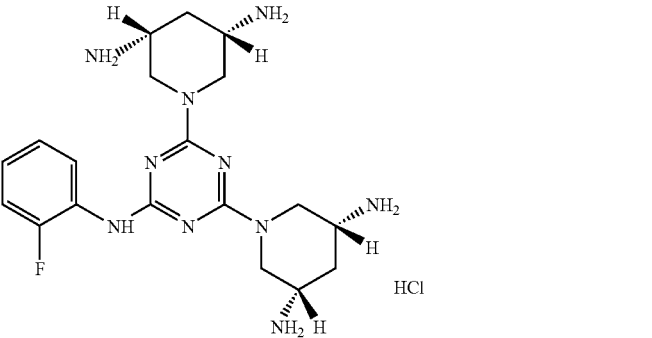 | N-(2-fluoro-phenyl)-4,6-Bis-((3R,5S)-3,5-diamino-piperidin-1-yl)-[1,3,5]triazine-2-amine | – |
| 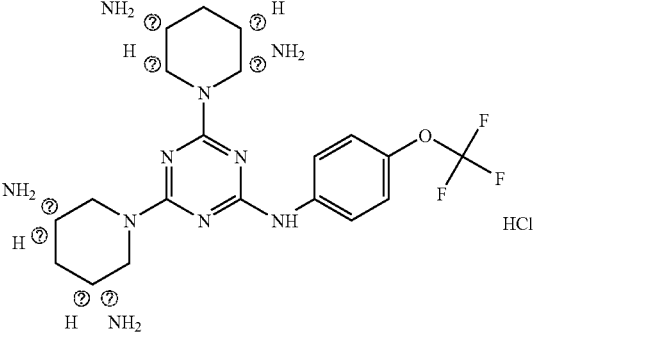 | N-(4-trifluoromethoxy-phenyl)-4,6-Bis-((3R,5S)-3,5-diamino-piperidin-1-yl)-[1,3,5]triazine-2-amine | |

⑦ indicates text missing or illegible when filed

-continued
| Structure | Name | Potency |
|---|---|---|
| 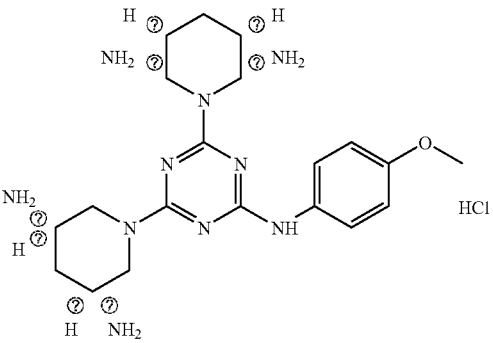 | N-(4-methoxy-phenyl)-4,6-Bis-((3R,5S)-3,5-diamino-piperidin-1-yl)-[1,3,5]triazine-2-amine | – |
| 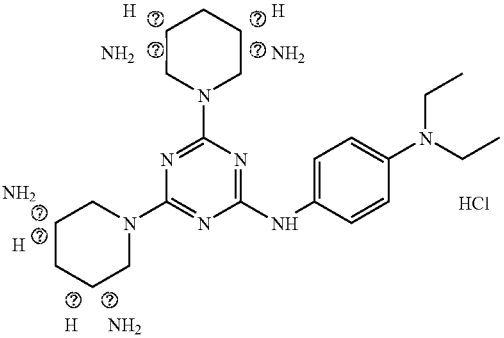 | N-(4-diethylamino-phenyl)-4,6-Bis-((3R,5S)-3,5-diamino-piperidin-1-yl)-[1,3,5]triazine-2-amine | – |
| 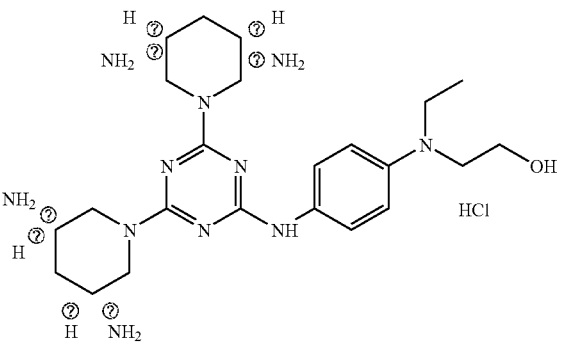 | N-{4-[ethyl-(2-hydroxy-ethyl)-amino]phenyl}-4,6-Bis-((3R,5S)-3,5-diamino-piperidin-1-yl)-[1,3,5]triazine-2-amine | – |
| 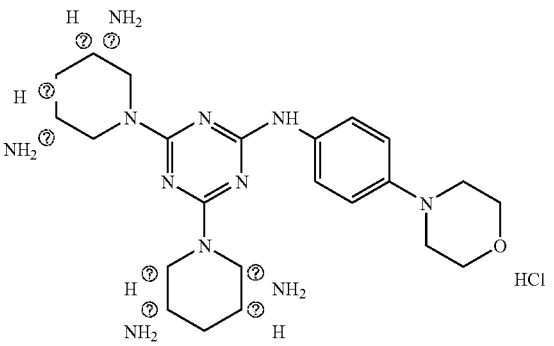 | N-(4-morpholin-4-yl-phenyl)-4,6-Bis-((3R,5S)-3,5-diamino-piperidin-1-yl)-[1,3,5]triazine-2-amine | – |

| Structure | Name | Potency |
|---|---|---|
| 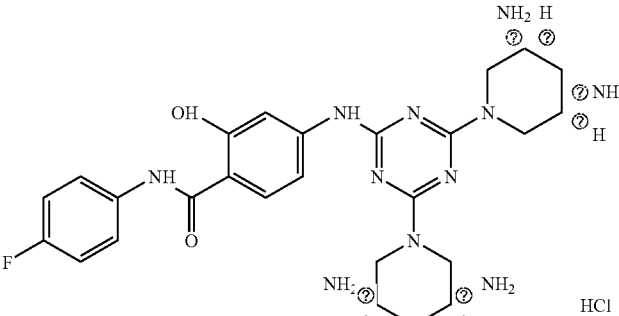 | N-[4-(4-fluoro-phenylcarbamoyl)-3-hydroxy-phenyl]-4,6-Bis-((3R,5S)-3,5-diamino-piperidin-1-yl)-[1,3,5]triazine-2-amine | ++ |
| ⑦ indicates text missing or illegible when filed | | |
| 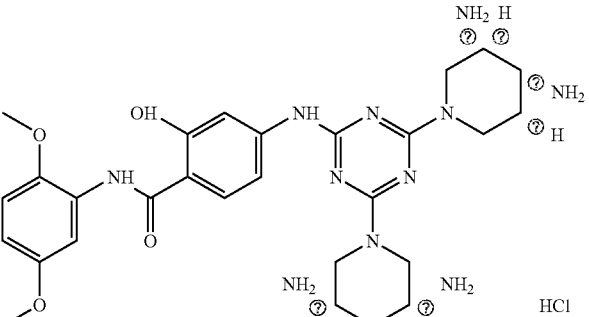 | N-[4-(2,5-dimethoxy-phenylcarbamoyl)-3-hydroxy-phenyl]-4,6-Bis-((3R,5S)-3,5-diamino-piperidin-1-yl)-[1,3,5]triazine-2-amine | ++ |
| ⑦ indicates text missing or illegible when filed | | |
| 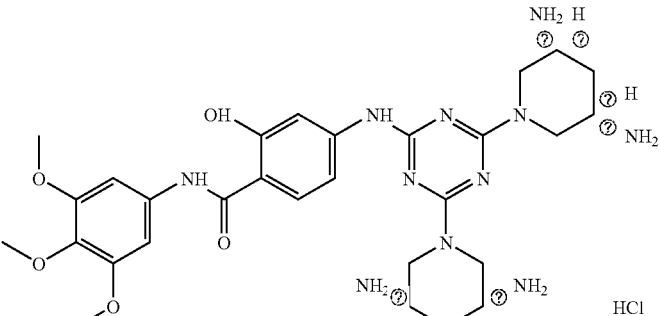 | N-[3-hydroxy-4-(3,4,5-trimethoxy-phenylcarbamoyl)-phenyl]-4,,6-Bis-((3R,5S)-33,5-diamino-piperidin-1-yl)-[1,3,5]triazine-2-amine | + |
| ⑦ indicates text missing or illegible when filed | | |

-continued

| Structure | Name | Potency |
|---|---|---|
| 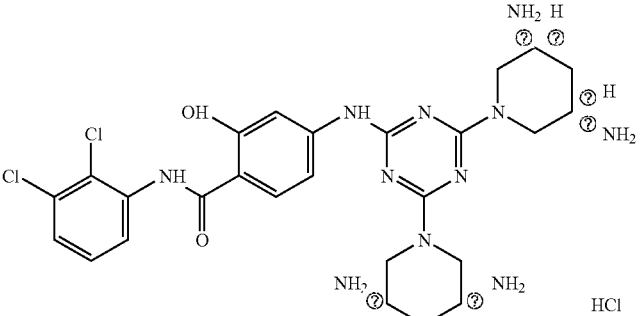 ⊕ indicates text missing or illegible when filed | N-[4-(2,3-dichloro-phenylcarbamoyl)-3-hydroxy-phenyl]-4,6-Bis-((3R,5S)-3,5-diamino-piperidin-1-yl)-[1,3,5]triazine-2-amine | |
| 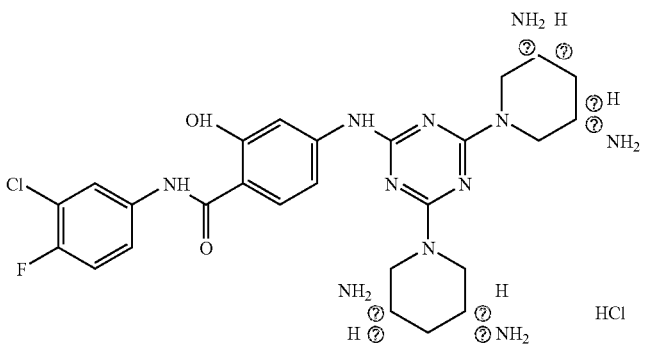 ⊕ indicates text missing or illegible when filed | N-[4-(3-chloro-4-fluoro-phenylcarbamoyl)-3-hydroxy-phenyl]-4,6-Bis-((3R,5S)-3,5-diamino-piperidin-1-yl)-[1,3,5]triazine-2-amine | ++ |
| 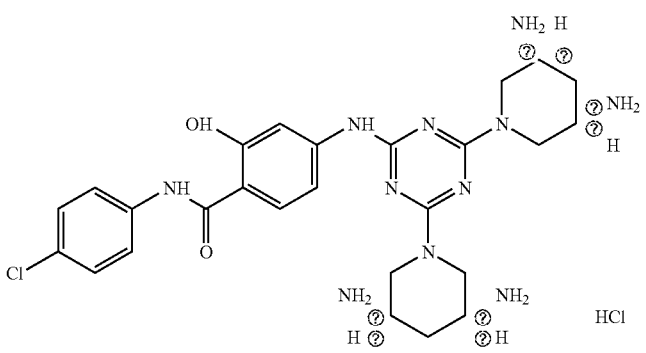 ⊕ indicates text missing or illegible when filed | N-[4-(4-chloro-phenylcarbamoyl)-3-hydroxy-phenyl]-4,6-Bis-((3R,5S)-3,5-diamino-piperidin-1-yl)-[1,3,5]triazine-2-amine | + |

| Structure | Name | Potency |
|---|---|---|
| 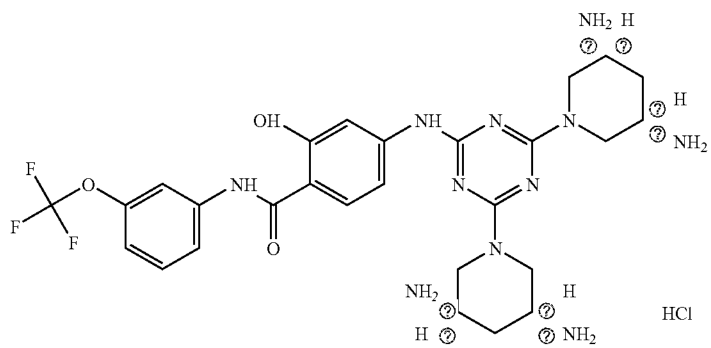 | N-[3-hydroxy-4-(3-trifluoromethoxy-phenylcarbamoyl)-phenyl]-4,6-Bis-((3R,5S)-3,5-diamino-piperidin-1-yl)-[1,3,5]triazine-2-amine | ++ |
| 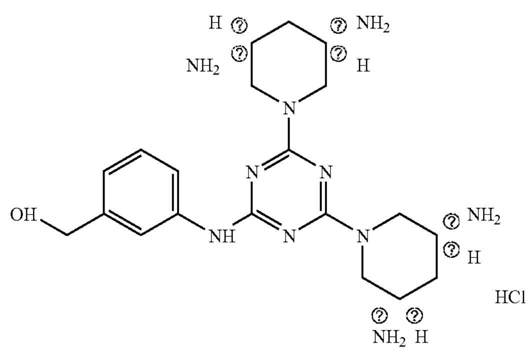 | N-(3-hydroxymethyl-phenyl)-4,6-Bis-((3R,5S)-3,5-diamino-piperidin-1-yl)-[1,3,5]triazine-2-amine | − |
| 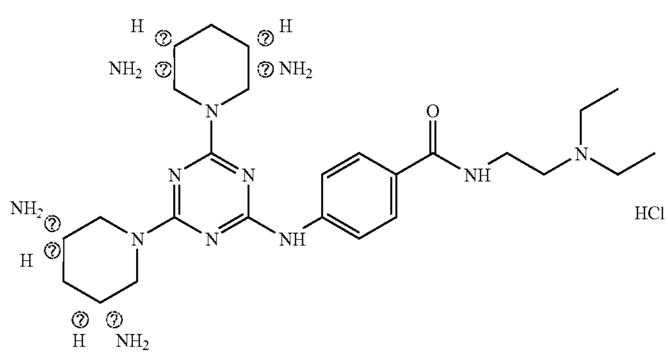 | N-[4-(2-diethylamino-ethylcarbamoyl)-phenyl]-4,6-Bis-((3R,5S)-3,5-diamino-piperidin-1-yl)-[1,3,5]triazine-2-amine | + |
| 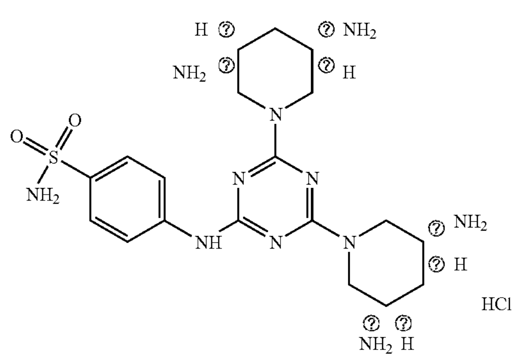 | N-(4-sulfamoyl-phenyl)-4,6-Bis-((3R,5S)-3,5-diamino-piperidin-1-yl)-[1,3,5]triazine-2-amine | − |

⑦ indicates text missing or illegible when filed

-continued

| Structure | Name | Potency |
|---|---|---|
| 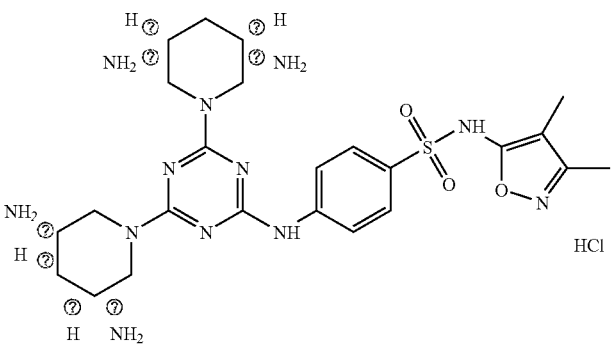 | N-[4-(pyridin-2-ylsulfamoyl)-phenyl]-4,6-Bis-((3R,5S)-3,5-diamino-piperidin-1-yl)-[1,3,5]triazine-2-amine | − |
| ⓘ indicates text missing or illegible when filed | | |
| 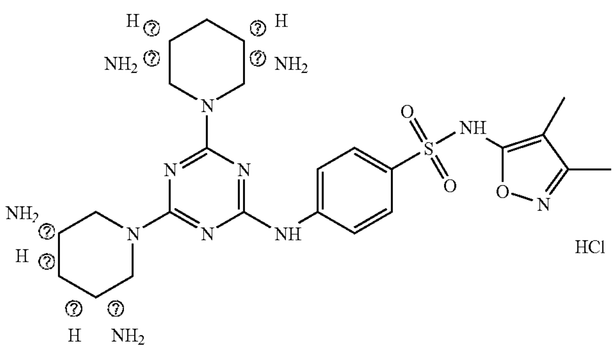 | N-[4-(3,4-dimethyl-isoxazol-5-ylsulfamoyl)-phenyl]-4,6-Bis-((3R,5S)-3,5-diamino-piperidin-1-yl)-[1,3,5]triazine-2-amine | − |
| ⓘ indicates text missing or illegible when filed | | |
| 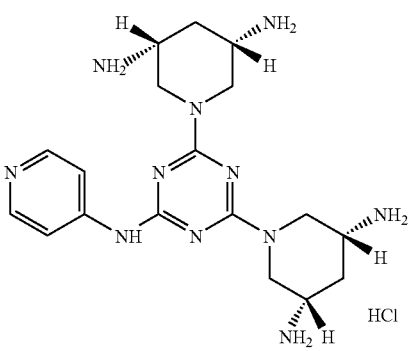 | N-pyridin-4-yl-4,6-Bis-((3R,5S)-3,5-diamino-piperidin-1-yl)-[1,3,5]triazine-2-amine | |
| 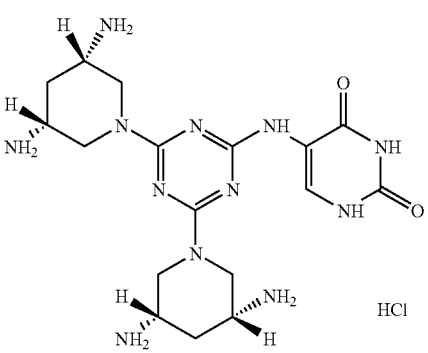 | N-(2,4-dioxo-1,2,3,4-tetrahydro-pyrimidin-5-yl)-4,6-Bis-((3R,5S)-3,5-diamino-piperidin-1-yl)-[1,3,5]triazine-2-amine | + |

| Structure | Name | Potency |
|---|---|---|
| | N-[4-(3,4-difluoro-phenylcarbamoyl)-3-hydroxy-phenyl]-4,6-Bis-((3R,5S)-3,5-diamino-piperidin-1-yl)-[1,3,5]triazine-2-amine · HCl | ++ |
| | N-[4-(4-chloro-2-fluoro-phenylcarbamoyl)-3-hydroxy-phenyl]-4,6-Bis-((3R,5S)-3,5-diamino-piperidin-1-yl)-[1,3,5]triazine-2-amine · HCl | ++ |
| | N-[4-(benzo[1,3]dioxol-5-ylcarbamoyl)-3-hydroxy-phenyl]-4,6-Bis-((3R,5S)-3,5-diamino-piperidin-1-yl)-[1,3,5]triazine-2-amine · HCl | ++ |
| | N-[3-hydroxy-4-(3-trifluoromethylsulfanyl-phenylcarbamoyl)-phenyl]-4,6-Bis-((3R,5S)-3,5-diamino-piperidin-1-yl)-[1,3,5]triazine-2-amine · HCl | ++ |

-continued

| Structure | Name | Potency |
|---|---|---|
| (structure) | N-(3-hydroxy-4-[4-(1H-indazol-6-ylsulfamoyl)-phenylcarbamoyl]-phenyl)-4,6-Bis-((3R,5S)-3,5-diamino-piperidin-1-yl)-[1,3,5]triazine-2-amine · HCl | + |
| (structure) | N-[3-hydroxy-4-(3-trifluoromethyl-phenylcarbamoyl)-phenyl]-4,6-Bis-((3R,5S)-3,5-diamino-piperidin-1-yl)-[1,3,5]triazine-2-amine · HCl | ++ |
| (structure) | N-[4-(2-fluoro-phenylcarbamoyl)-3-hydroxy-phenyl]-4,6-Bis-((3R,5S)-3,5-diamino-piperidin-1-yl)-[1,3,5]triazine-2-amine · HCl | + |
| (structure) | N-(5-amino-pyridin-3-yl)-4,6-Bis-((3R,5S)-3,5-diamino-piperidin-1-yl)-[1,3,5]triazine-2-amine | − |

⟨?⟩ indicates text missing or illegible when filed

-continued

| Structure | Name | Potency |
|---|---|---|
| 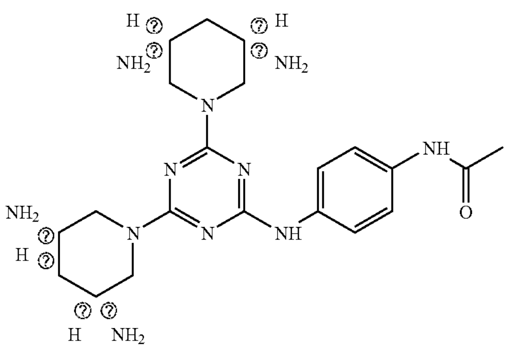 | N-(4-acetylamino-phenyl)-4,6-Bis-((3R,5S)-3,5-diamino-piperidin-1-yl)-[1,3,5]triazine-2-amine | – |
| 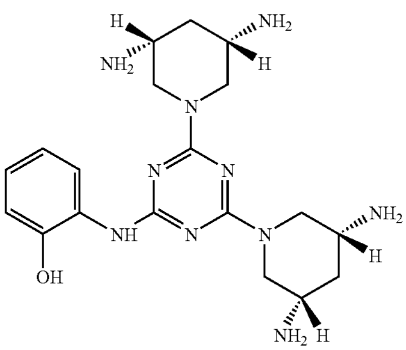 | N-(2-hydroxy-phenyl)-4,6-Bis-((3R,5S)-3,5-diamino-piperidin-1-yl)-[1,3,5]triazine-2-amine | – |
| 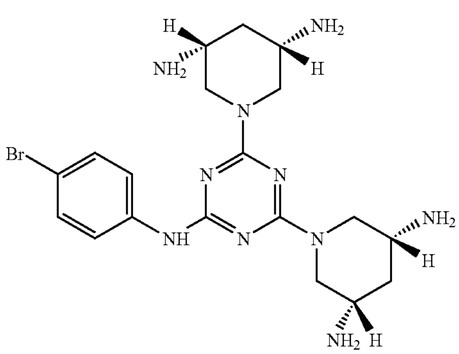 | N-(4-bromo-phenyl)-4,6-Bis-((3R,5S)-3,5-diamino-piperidin-1-yl)-[1,3,5]triazine-2-amine | – |
| 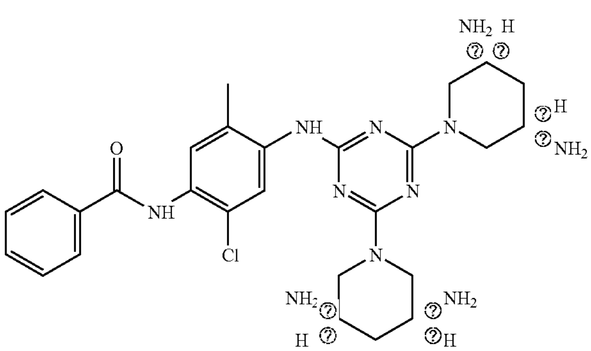 | N-(4-benzoylamino-5-chloro-23-methyl-phenyl)-4,6-Bis((3R,5S)-3,5-diamino-piperidin-1-yl)-[1,3,5]triazine-2-amine | – |

⊚ indicates text missing or illegible when filed

-continued

| Structure | Name | Potency |
|---|---|---|
| 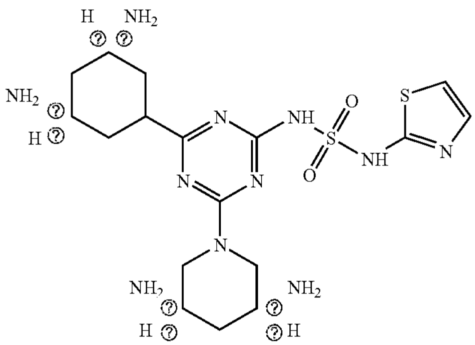 | N-[4-(thiazol-2-ylsulfamoyl)-phenyl]-4,6-Bis-((3R,5S)-3,5-diamino-piperidin-1-yl)-[1,3,5]triazine-2-amine | − |
| 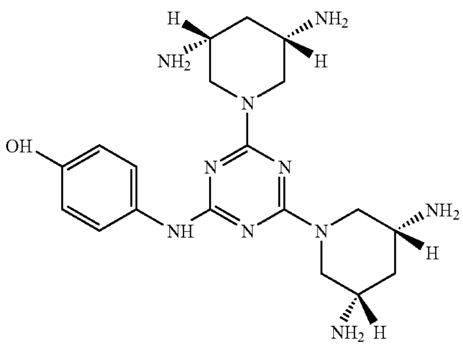 | N-(4-hydroxy-phenyl)-4,6-Bis-((3R,5S)-3,5-diamino-piperidin-1-yl)-[1,3,5]triazine-2-amine | − |
| 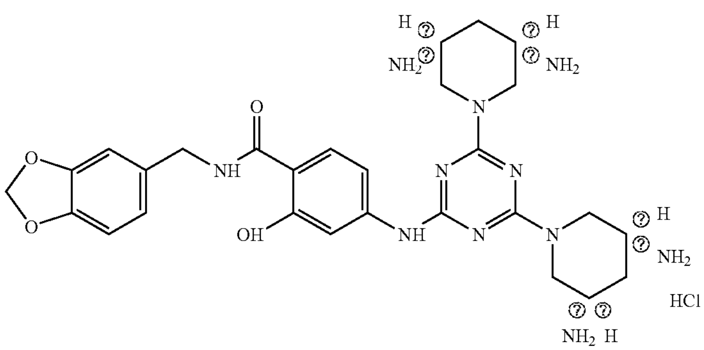 | N-{4-[(benzo[1,3]dioxol-5-ylmethyl)-carbamoyl]-3-hydroxy-phenyl}-4,6-Bis-((3R,5S)-3,5-diamino-piperidin-1-yl)-[1,3,5]triazine-2-amine | + |
| 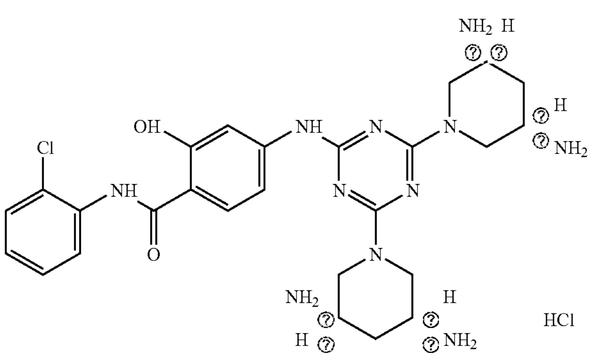 | N-[4-(2-choro-phenylcarbamoyl)-3-hydroxy-phenyl]-4,6-Bis-((3R,5S)-3,5-diamino-piperidin-1-yl)-[1,3,5]triazine-2-amine | + |

⑦ indicates text missing or illegible when filed

-continued

| Structure | Name | Potency |
|---|---|---|
| 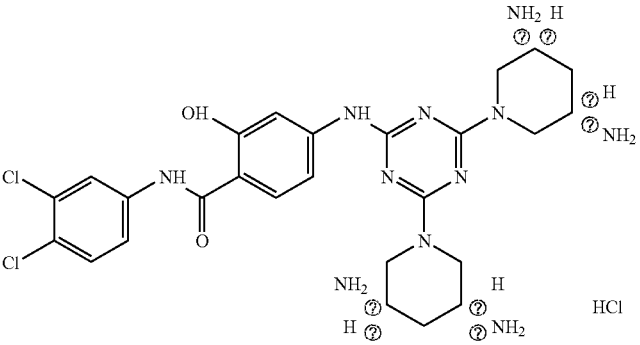 | N-[4-(3,4-dichloro-phenylcarbamoyl)-3-hydroxy-phenyl]-4,6-Bis-((3R,5S)-3,5-diamino-piperidin-1-yl)-[1,3,5]triazine-2-amine | ++ |
| ⑦ indicates text missing or illegible when filed | | |
| 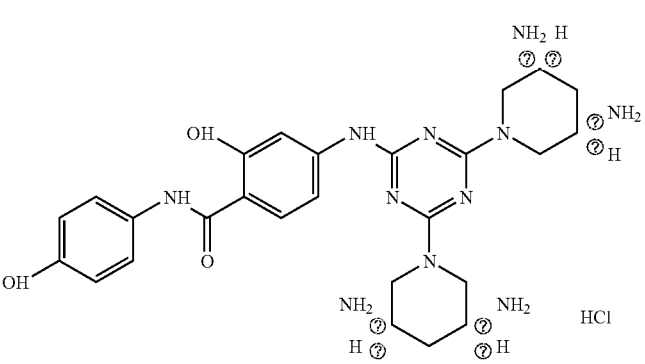 | N-[3-hydroxy-4-(4-hydroxy-phenylcarbamoyl)-phenyl]-4,6-Bis((3R,5S)-3,5-0 diamino-piperidin-1-yl)-[1,3,5]triazine-2-amine | ++ |
| ⑦ indicates text missing or illegible when filed | | |
| 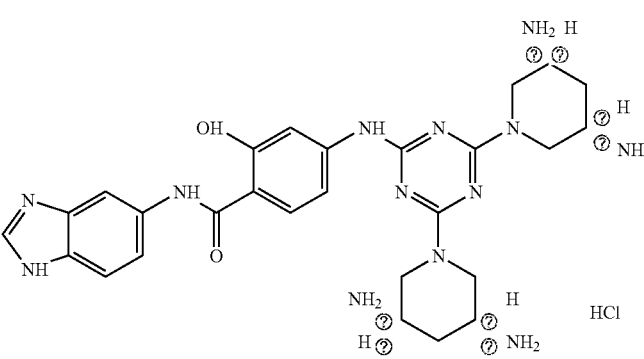 | N-[4-(1H-benzoimidazol-5-ylcarbamoyl)-3-hydroxy-phenyl]-4,6-Bis-((3R,5S)-3,5-diamino-piperidin-1-yl)-[1,3,5]triazine-2-amine | ++ |
| ⑦ indicates text missing or illegible when filed | | |
| 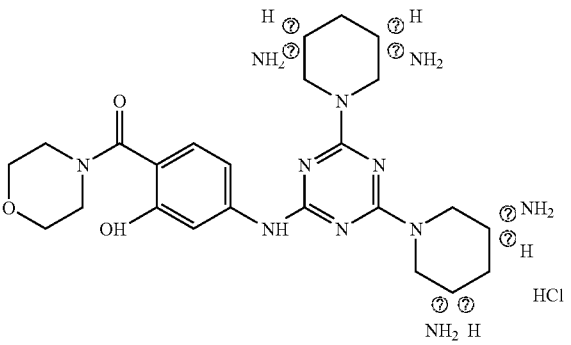 | N-[3-hydroxy-4-(morpholine-4-carbonyl)-phenyl]-4,6-Bis-((3R,5S)-3,5-diamino-piperidin-1-yl)-[1,3,5]triazine-2-amine | – |
| ⑦ indicates text missing or illegible when filed | | |

-continued

| Structure | Name | Potency |
|---|---|---|
| 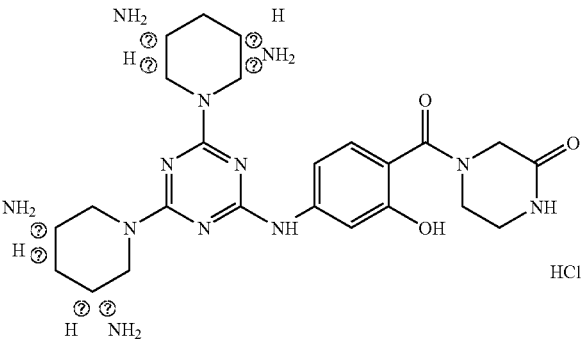 | N-[3-hydroxy-4-(3-oxo-piperazine-1-carbonyl)-phenyl]-4,6-Bis-((3R,5S)-3,5-diamino-piperidin-1-yl)-[1,3,5]triazine-2-amine | – |
| 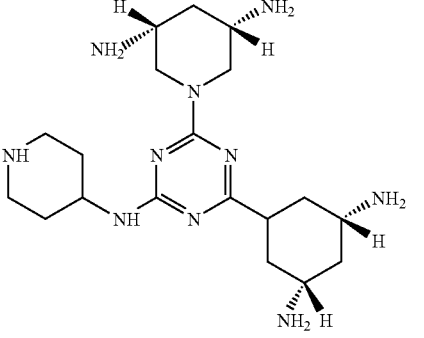 | N-piperidin-4-yl-4,6-Biss-((3R,5S)-3,5-diamino-piperidin-1-yl)-[1,3,5]triazine-2-amine | – |
| 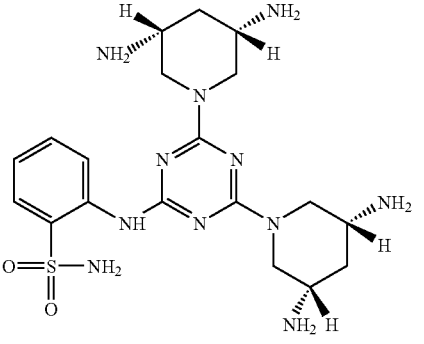 | N-(2-sulfamoyl-phenyl)-4,6-Bis-((3R,5S)-3,5-diamino-piperidin-1-yl)-[1,3,5]triazine-2-amine | – |
| 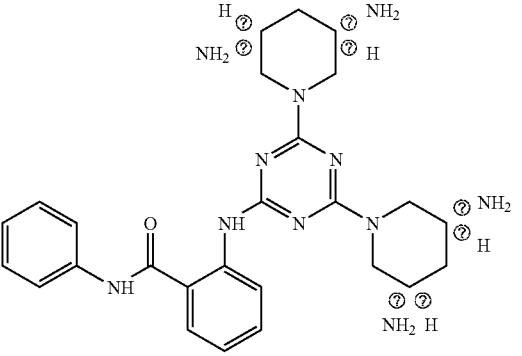 | N-(2-phenylcarbamoyl-phenyl)-44,6-Bis-((3R,5S)-3,5-diamino-piperidin-1-yl)-[1,3,5]triazine-2-amine | – |

⊘ indicates text missing or illegible when filed

-continued

| Structure | Name | Potency |
|---|---|---|
| 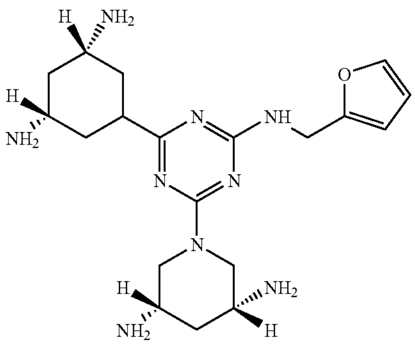 | N-furan-2-ylmethyl-44,6-Bis-((3R,5S)-3,5-diamino-piperidin-1-yl)-[1,3,5]triazine-2-amine | – |
| 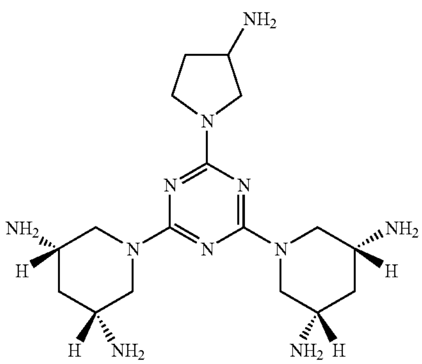 | 2,4-Bis-((3R,5S)-3,5-diamino-piperidin-1-yl)-6-(3-methyl-4-p-tolyl-piperazin-1-yl)-[1,3,5]triazine | – |
| 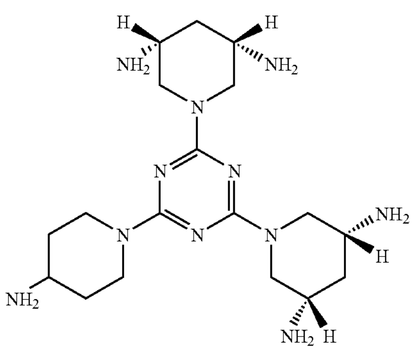 | 1-(4,6-Bis-((3R,5S)-3,5-diamino-piperidin-1-yl)-[1,3,5]triazin-2-yl)-piperidine-3-carboxylic acid diethylamide | – |
| 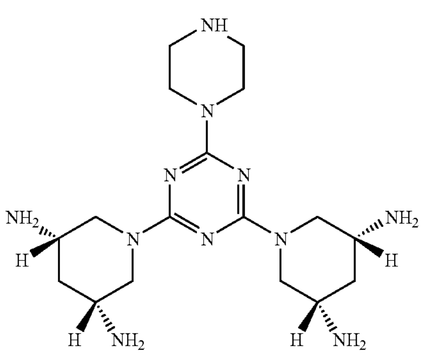 | 2,4-Bis-((3R,5S)-3,5-diamino-piperidin-1-yl)-6-(2-propyl-piperidin-1-yl)-[1,3,5]triazine | – |

-continued

| Structure | Name | Potency |
|---|---|---|
| 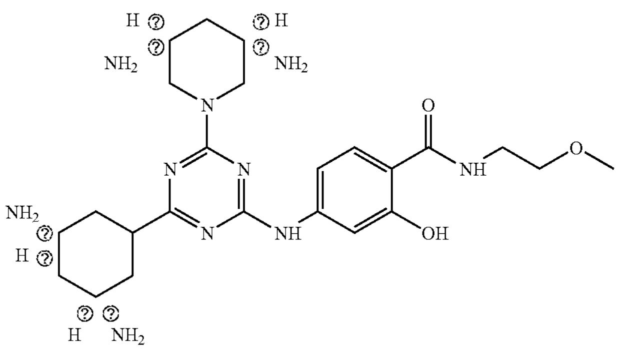 | N-[3-hydroxy-4-(2-methoxy-ethylcarbamoyl)-phenyl]-4,6-Bis-((3R,5S)-3,5-diamino-piperidin-1-yl)-[1,3,5]triazine-2-amine | − |
| 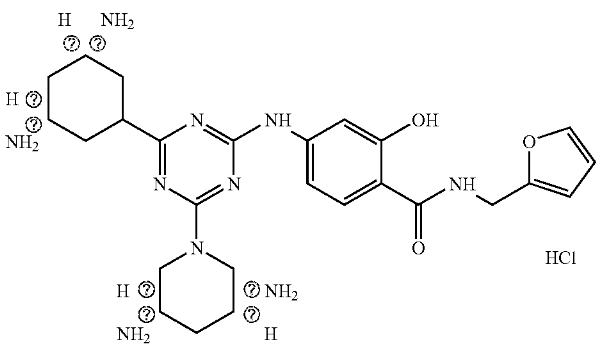 | N-{4-[(furan-2-ylmethyl)-carbamoyl]-3-hydroxy-phenyl}-4,6-Bis-((3R,5S)-3,5-diamino-piperidin-1-yl)-[1,3,5]triazine-2-amine | + |
| 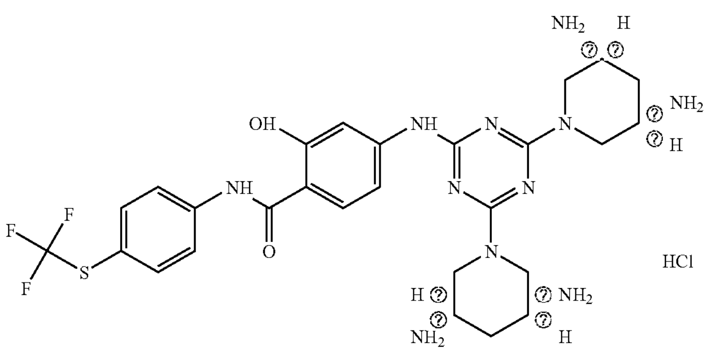 | N-[3-hydroxy-4-(4-trifluoromethylsulfanyl-phenylcarbamoyl)-phenyl]-4,6-Bis-((3R,5S)-3,5-diamino-piperidin-1-yl)-[1,3,5]triazine-2-amine | + |
| 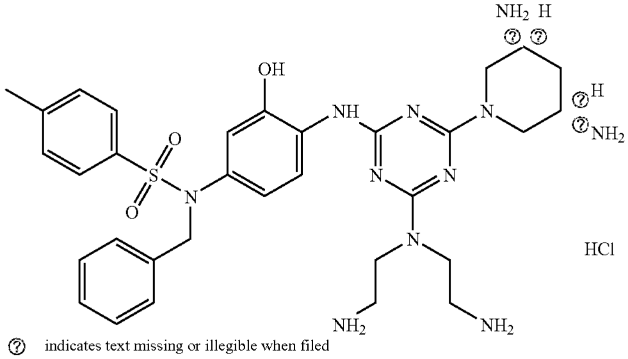 | N-Benzyl-N-{4-[4-[bis-(2-amino-ethyl)-amino]-6-((3R,5S)-3,5-diamino-piperidin-1-yl)-[1,3,5]triazin-2-ylamino]-3-hydroxy-phenyl}-4-methyl-benzenesulfonamide | + |

-continued

| Structure | Name | Potency |
|---|---|---|
| 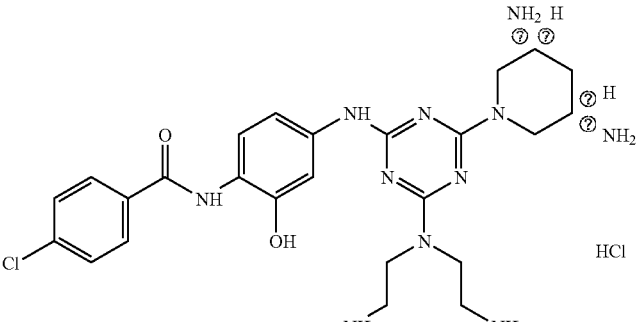 | N-{4-[4-[Bis-(2-amino-ethyl)-amino]-6-((3R,5S)-3,5-diamino-piperidin-1-yl)-[1,3,5]triazin-2-ylamino]-2-hydroxy-phenyl}-4-chloro-benzamide | + |
| 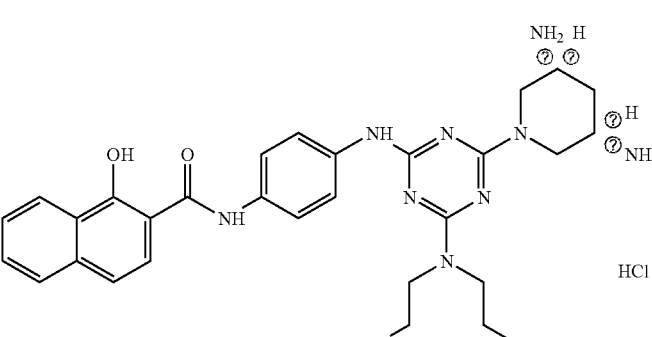 | 1-Hydroxy-naphthalene-2-carboxylic acid {4-[4-[bis-(2-amino-ethyl)-amino]-6-((3R,5S)-3,5-diamino-piperidin-1-yl)-[1,3,5]triazin-2-ylamino]-phenyl}-amide | ++ |
| 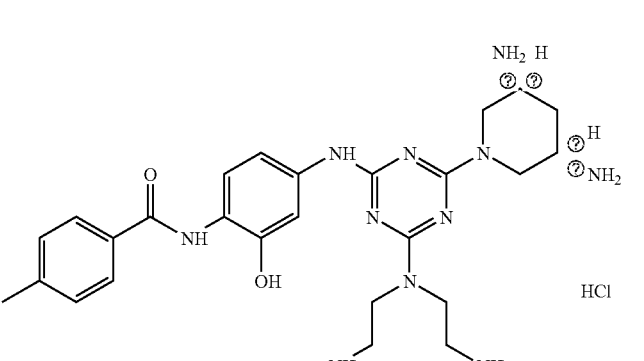 | N-{4-[4-[Bis-(2-amino-ethyl)-amino]-6-((3R,5S)-3,5-diamino-piperidin-1-yl-[1,3,5]triazin-2-ylamino]-2-hydroxy-phenyl}-4-methyl-benzamide | + |
| 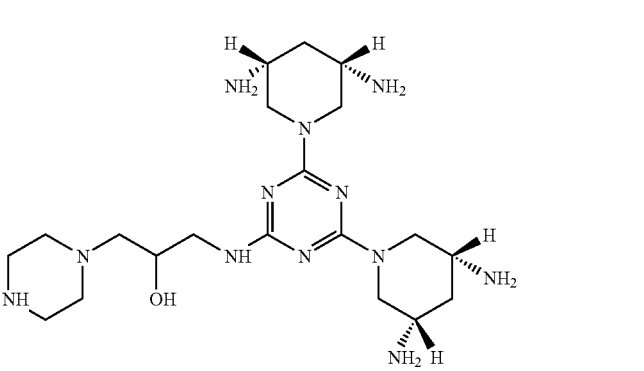 | N-(2-hydroxy-3-piperazin-1-yl-propyl)-4,6-Bis-((3R,5S)-3,5-diamino-piperidin-1-yl)-[1,3,5]triazine-2-amine | |

-continued

| Structure | Name | Potency |
|---|---|---|
| 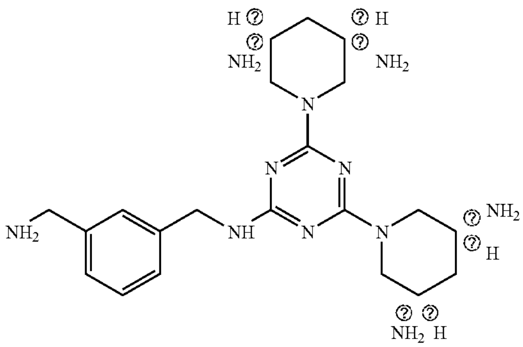 | N-(3-aminomethyl-benzyl)-4,6-Bis-((3R,5S)-3,5-diamino-piperidin-1-yl)-[1,3,5]triazine-2-amine | |
| 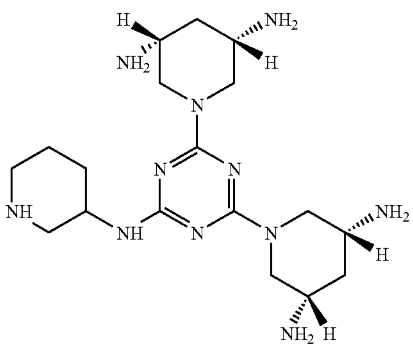 | N-piperidin-3-yl-4,6-Bis-((3R,5S)-3,5-diamino-piperidin-1-yl)-[1,3,5]triazine-2-amine | – |
| 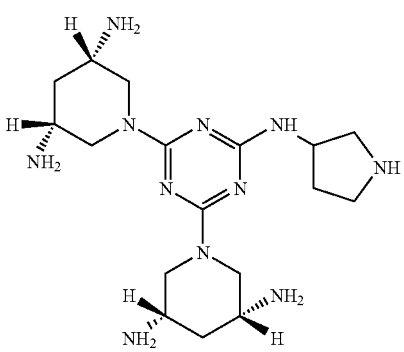 | N-pyrrolidin-3-yl-4,6-Bis-((#r,5S)-3,5-diamino-piperidin-1-yl)-[1,3,5]triazine-2-amine | – |
| 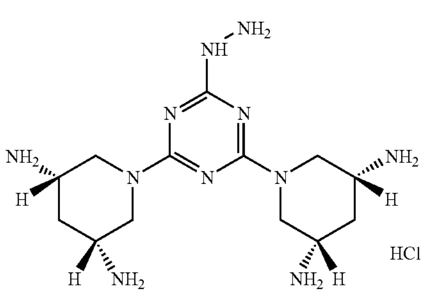 | N-(4,6-Bis((3R,5S)-3,5-diamino-piperidin-1-yl)-[1,3,5]triazin-2-yl)-hydrazine | |

⑦ indicates text missing or illegible when filed

-continued

| Structure | Name | Potency |
|---|---|---|
| 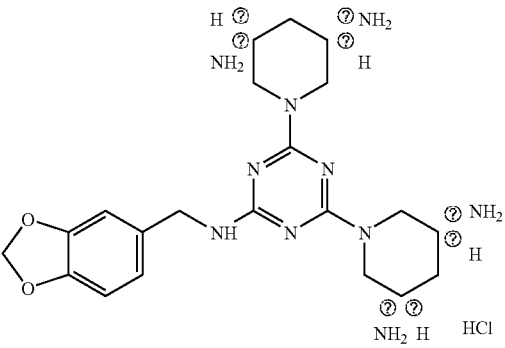 | N-benzo[1,3]dioxol-5-ylmethyl-4,6-Bis-((3R,5S)-3,5-diamino-piperidin-1-yl)-[1,3,5]triazine-2-amine | – |
| 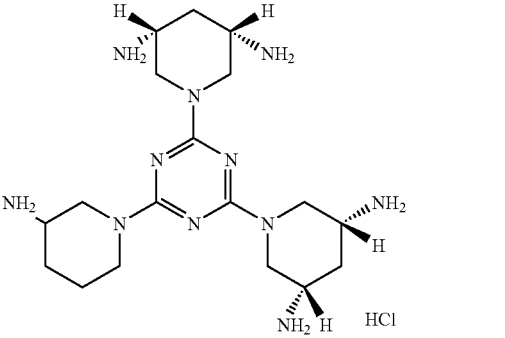 | 1-(4,6-Bis((3R,5S)-3,5-diamino-piperidin-1-yl)-[1,3,5]triazin-2-yl)-piperidin-3-ol | – |
| 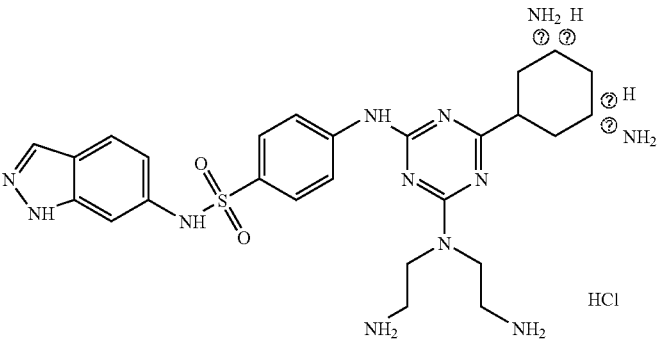 | 4-[4-[Bis-(2-amino-ethyl)-amino]-6-((3R,5S)-3,5-diamino-piperidin-1-yl)-[1,3,5]triazin-2-ylamino]-N-(1H-indazol-6-yl)-benzenesulfonamide | – |
| 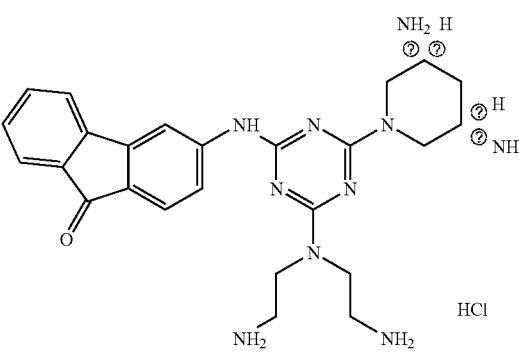 | 3-[4-[Bis(2-amino-ethyl)-amino]-6-((3R,5S)-3,5-diamino-piperidin-1-yl)-[1,3,5]triazin-2-ylamino]-fluoren-9-one | – |

⑦ indicates text missing or illegible when filed

-continued

| Structure | Name | Potency |
|---|---|---|
| 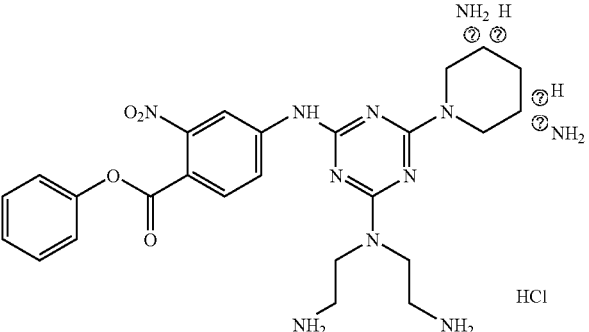 | 4-[4-[Bis-(2-amino-ethyl)-amino]-6-((3R,5S)-3,5-diamino-piperidin-1-yl)-[1,3,5]triazin-2-ylamino]-2-hydroxy-benzoic acid phenyl ester | + |
| 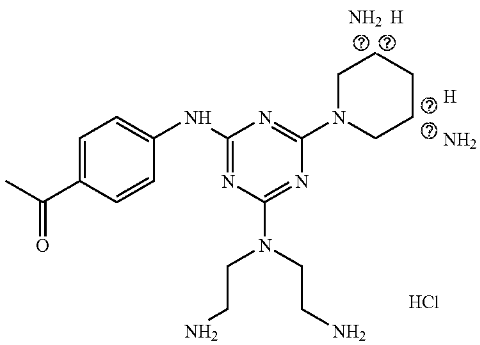 | 1-{4-[4-[Bis-(2-amino-ethyl)-amino]-6-((3R,5S)-3,5-diamino-piperidin-1-yl)-[1,3,5]triazin-2-ylamino]-phenyl}-ethanone | + |
| 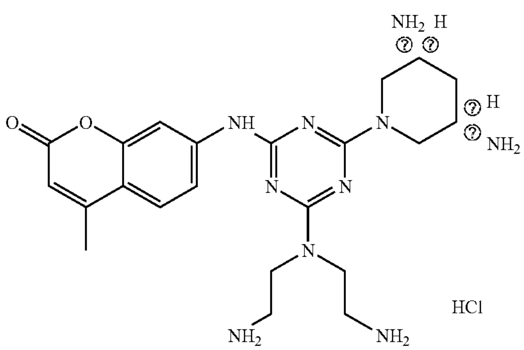 | 7-[4-[Bis-(2-amino-ethyl)-amino]-6-((3R,5S)-3,5-diamino-piperidin-1-yl)-[1,3,5]triazin-2-ylamino]-4-methyl-chromen-2-one | − |
| 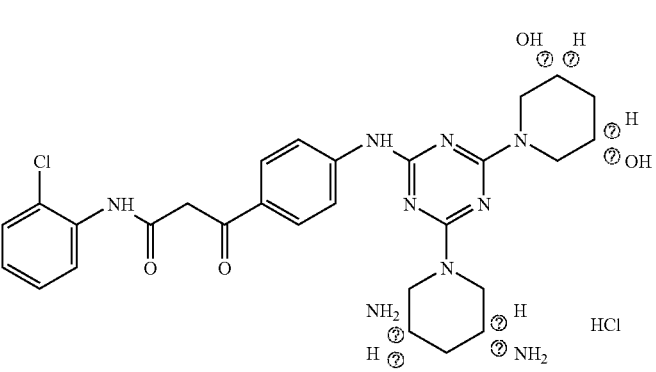 | N-(2-Chloro-phenyl)-3-{4-[4-((3R,5S)-3,5-diamino-piperidin-1-yl)-6-((3R,5S)-3,5-dihydroxy-piperidin-1-yl)-[1,3,5]triazin-2-ylamino]-phenyl}-3-oxo-propionamide | + |

-continued

| Structure | Name | Potency |
|---|---|---|
| | N-Benzyl-N-{4-[4-((3R,5S)-3,5-diamino-piperidin-1-yl)-6-((3R,5R)-3,5-dihydroxy-piperidin-1-yl)-[1,3,5]triazin-2-ylamino]-2-hydroxy-phenyl}-4-methyl-benzenesulfonamide · HCl | + |
| | 2,4-Bis-((3R,5S)-3,5-diamino-piperidin-1-yl)-6-(4-pyridin-2-yl-piperazin-1-yl)-[1,3,5]triazine | − |
| | 2-Chloro-4,6-Bis-((3R,5S)-3,5-diamino-piperidin-1-yl)-[1,3,5]triazine · HCl | |
| | N-(2-allyloxy-4,5-dihydroxy-6-hydroxymethyl-tetrahydro-pyran-3-yl)-4,6-Bis-((3R,5S)-3,5-diamino-piperidin-1-yl)-[1,3,5]triazine-2-amine · HCl | − |

⊘ indicates text missing or illegible when filed

| Structure | Name | Potency |
|---|---|---|
| 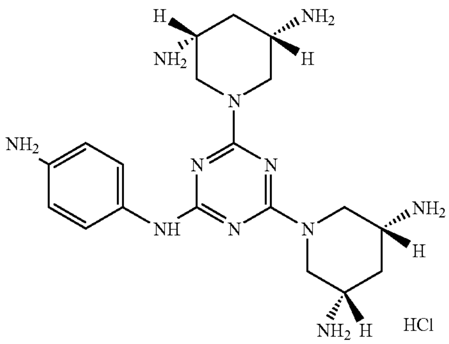 | N-(4-amino-phenyl)-4,6-Biss-((3R,5S)-3,5-diamino-piperidin-1-yl)-[1,3,5]triazine-2-amine | − |
| 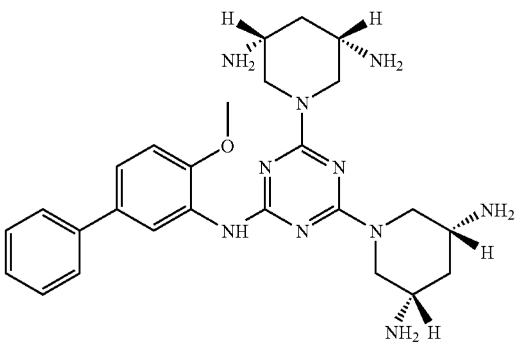 | N-(4-methoxy-biphenyl-3-yl)-4,6-Bis-((3R,5S)-3,5-0 diamino-piperidin-1-yl)-[1,3,5]triazine-2-amine | + |
| 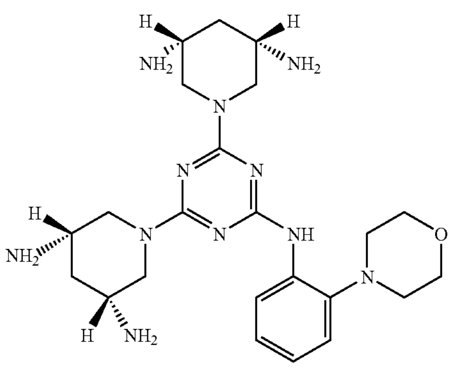 | N-(2-morpholin-44-yl-phenyl)-4,6-Bis-((3R,5S)-3,5-diamino-piperidin-1-yl)-[1,3,5]triazine-2-amine | − |
| 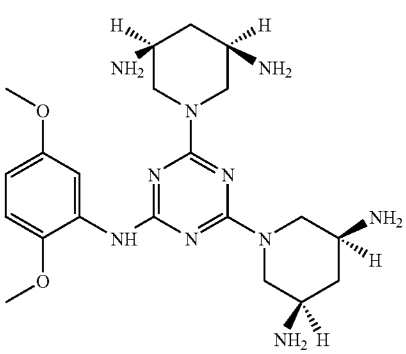 | N-(2,5-dimethoxy-phenyl)-4,6-Bis-((3R,5S)-3,5-diamino-piperidin-1-yl)-[1,3,5]triazine-2-amine | − |

-continued

| Structure | Name | Potency |
|---|---|---|
| 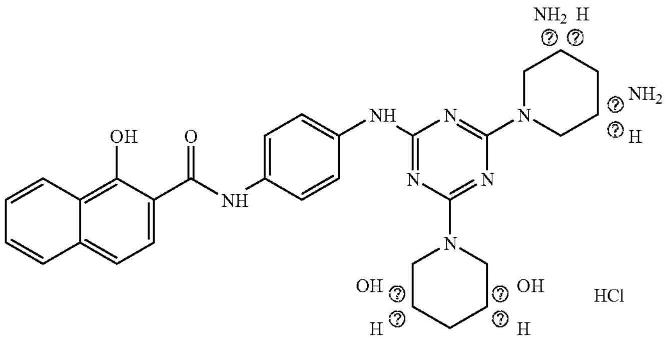 | 1-Hydroxy-naphthalene-2-carboxylic acid {4-[4-((3S,5R)-3,5-diamino-piperidin-12-yl)-6-((3R,5R)-3,5-dihydroxy-piperidin-1-yl)-[1,3,5]triazin-2-ylamino]-phenyl}-amide | + |
| 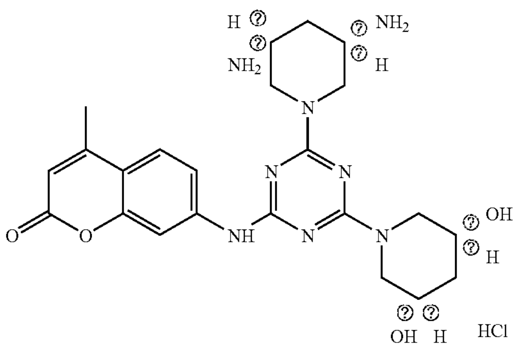 | 7-[4-((3R,5S)-3,5-Diamino-piperidin-1-yl)-6-((3R,5R)-3,5-dihydroxy-piperidin-1-yl)-[1,3,5]triazin-2-ylamino]-4-methyl-chromen-2-one | − |
| 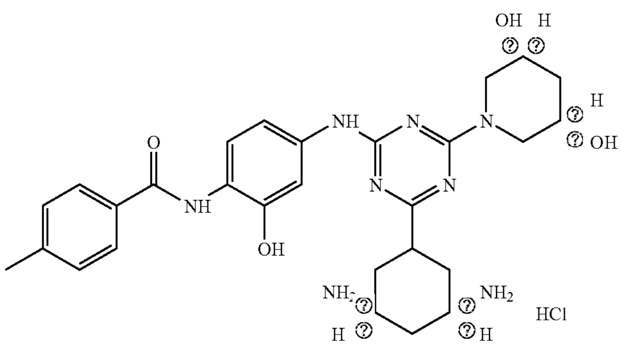 | N-{4-[4-((3R,5S)-3,5-Diamino-piperidin-1-yl)-6-((3R,5R)-3,5-dihydroxy-piperidin-1-yl)-[1,3,5]triazin-2-ylamino]-2-hydroxy-phenyl}-4-methyl-benzamide | − |
| 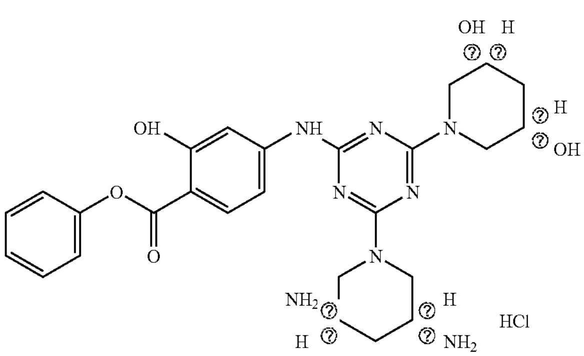 | 4-[4-((3S,5R)-3,5-diamino-piperidin-1-yl)-6-((3R,5R)-3,5-dihydroxy-piperidin-1-yl)-[1,3,5]triazin-2-ylamino]-2-hydroxy-benzoic acid phenyl ester | − |

| Structure | Name | Potency |
|---|---|---|
| 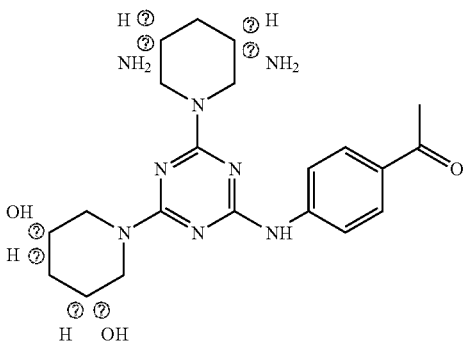 | 4-[4-((3S,5R)-3,5-Diamino-piperidin-1-yl)-6-((3R,5R)-3,5-dihydroxy-piperidin-1-yl)-[1,3,5]triazin-2-ylamino]-N-(1H-indazol-6-yl)-benzenesulfonamide | − |
| ⑦ indicates text missing or illegible when filed | | |
| 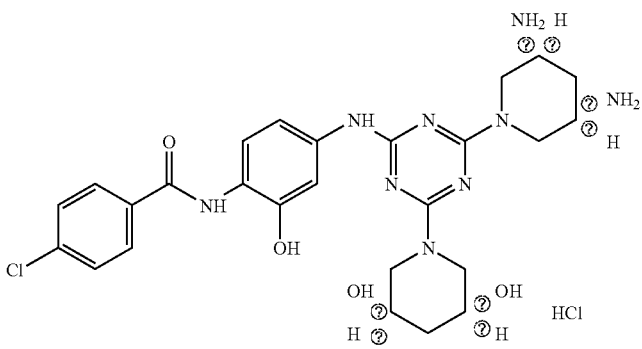 | 1-{4-[4-((3R,5S)-3,5-Diamino-piperidin-1-yl)-6-((3R,5R)-3,5-dihydroxy-piperidin-1-yl)-[1,3,5]triazin-2-ylamino]-phenyl}-ethanone | − |
| ⑦ indicates text missing or illegible when filed | | |
| 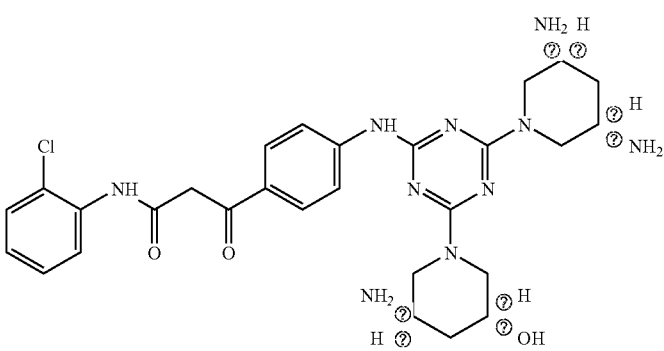 | 4-Chloro-N-{4-[4-((3S,5R)-3,5-diamino-piperidin-1-yl)-6-((3R,5R)-3,5-dihydroxy-piperidin-1-yl)-[1,3,5]triazin-2-ylamino]-2-hydroxy-phenyl}-benzamide | + |
| ⑦ indicates text missing or illegible when filed | | |
| 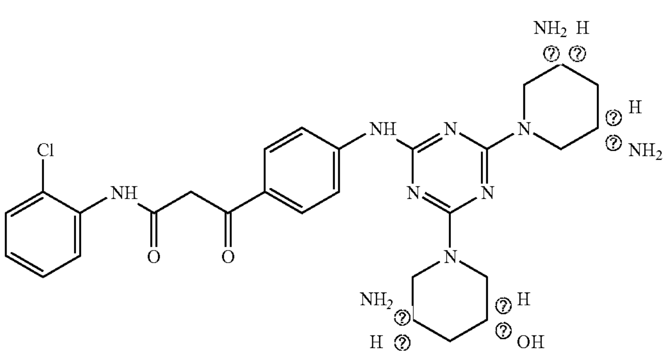 | N-{4-[2-(2-chloro-phenylcarbamoyl)-acetyl]-phenyl}-4,6-Bis((3R,5S)-3,5-diamino-piperidin-1-yl)-[1,3,5]triazine-2-amine | ++ |
| ⑦ indicates text missing or illegible when filed | | |

-continued

| Structure | Name | Potency |
|---|---|---|
| 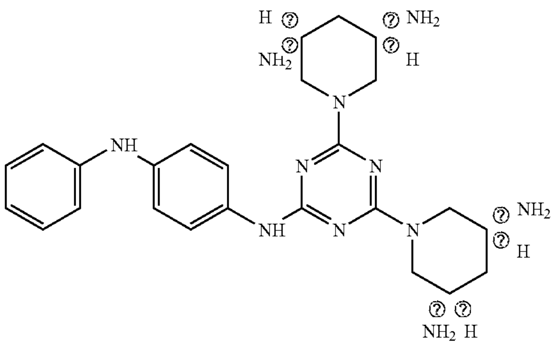 | N-(4-phenylamino-phenyl)-4,6-Bis((3R,5S)-3,5-diamino-piperidin-1-yl)-[1,3,5]triazine-2-amine | + |
| 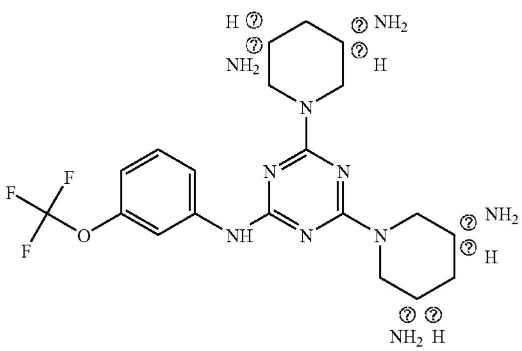 | N-(3-trifluoromethoxy-phenyl)-4,6-Bis-((3R,5S)-3,5-diamino-piperidin-1-yl)-[1,3,5]triazine-2-amine | − |
| 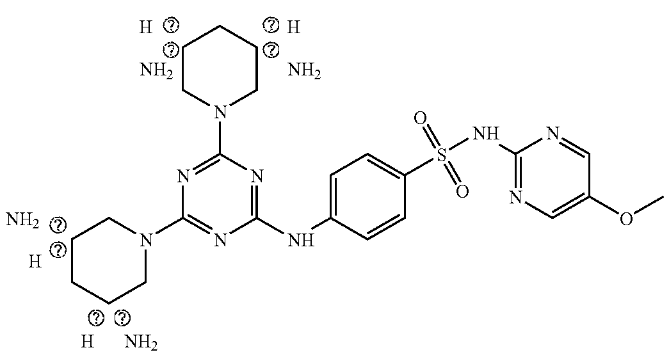 | N-{4-(5-methoxy-pyrimidin-2-ylsulfamoyl)-phenyl]-4,6-Bis-((3R,5S)-3,5-diamino-piperidin-1-yl)-[1,3,5]triazine-2-amine | − |
| 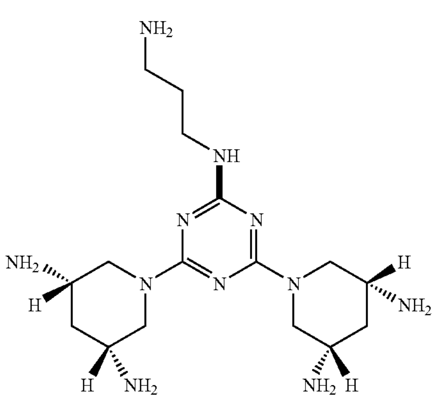 | N-(3-amino-propyl)-4,6-Bis-((3R,5S)-3,5-diamino-piperidin-1-yl)-[1,3,5]triazine-2-amine | |

-continued

| Structure | Name | Potency |
|---|---|---|
| 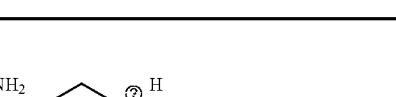 ⓘ indicates text missing or illegible when filed | N-(4-trifluoromethylsulfanyl-phenyl)-4,6-Bis-((3R,5S)-3,5-diamino-piperidin-1-yl)-[1,3,5]triazine-2-amine | + |
| 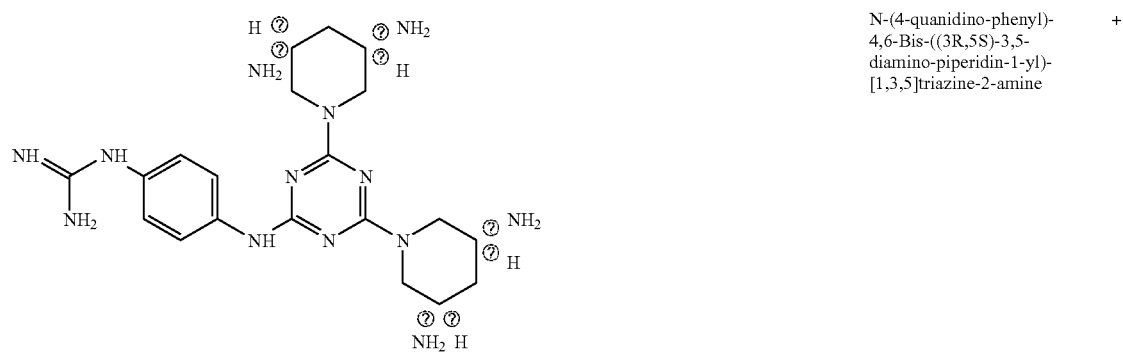 ⓘ indicates text missing or illegible when filed | N-(4-quanidino-phenyl)-4,6-Bis-((3R,5S)-3,5-diamino-piperidin-1-yl)-[1,3,5]triazine-2-amine | + |
| 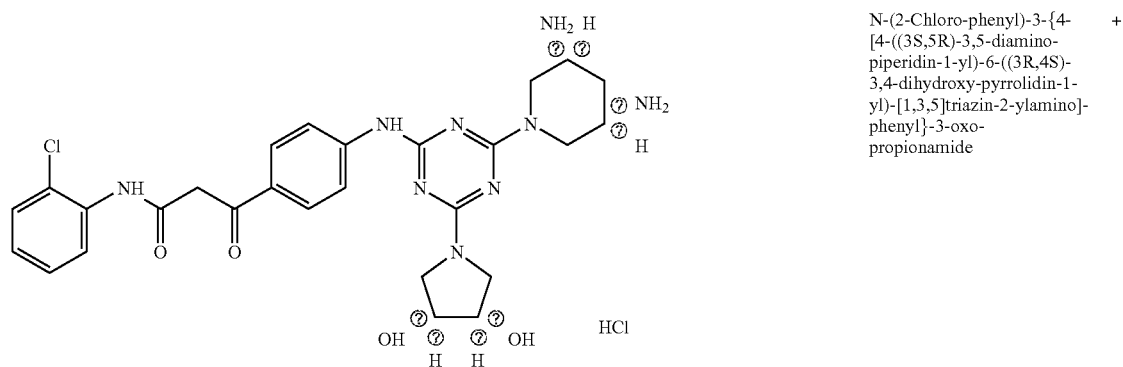 ⓘ indicates text missing or illegible when filed | N-(2-Chloro-phenyl)-3-{4-[4-((3S,5R)-3,5-diamino-piperidin-1-yl)-6-((3R,4S)-3,4-dihydroxy-pyrrolidin-1-yl)-[1,3,5]triazin-2-ylamino]-phenyl}-3-oxo-propionamide | + |

-continued

| Structure | Name | Potency |
|---|---|---|
| 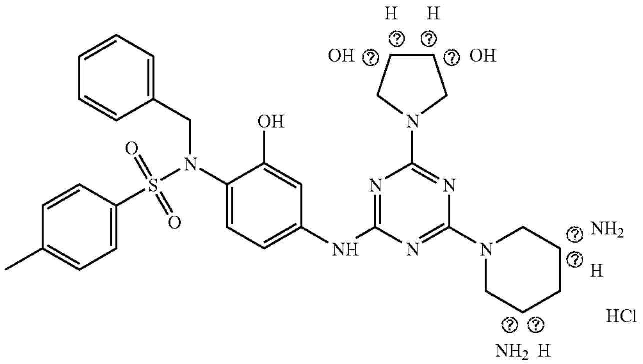 | N-Benzyl-N-{4-[4-((3R,5S)-3,5-diamino-piperidin-1-yl)-6-((3R,4S)-3,4-dihydroxy-pyrrolidin-1-yl)-[1,3,5]triazin-2-ylamino]-2-hydroxy-phenyl}-4-methyl-benzenesulfonamide | + |
| 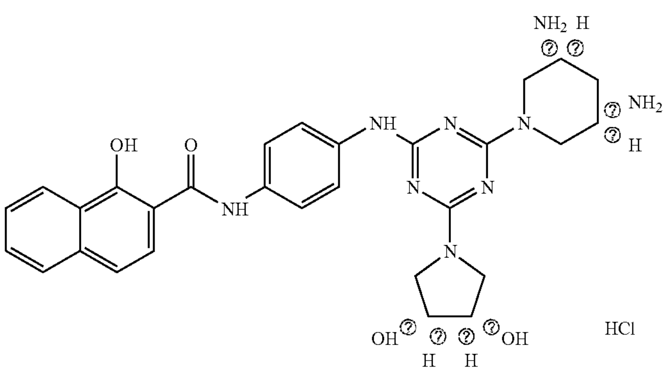 | 1-Hydroxy-naphthalene-2-carboxylic acid {4-[4-((3S,5R)-3,5-diamino-piperidin-1-yl)-6-((3R,4S)-3,4-dihydroxy-pyrrolidin-1-yl)-[1,3,5]triazin-2-ylamino]-phenyl}-amide | + |
| 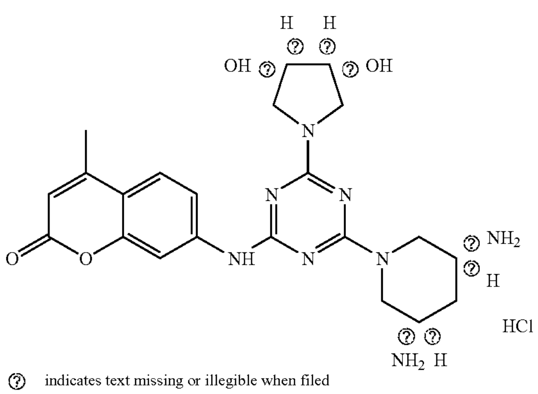 | 7-[4-((3R,5S)-33,5-Diamino-piperidin-1-yl)-6-((3R,4S)-3,4-dihydroxy-pyrrolidin-1-yl)-[1,3,5]triazin-2-ylamino]-4-methyl-chromen-2-one | − |

⑦ indicates text missing or illegible when filed

| Structure | Name | Potency |
|---|---|---|
| 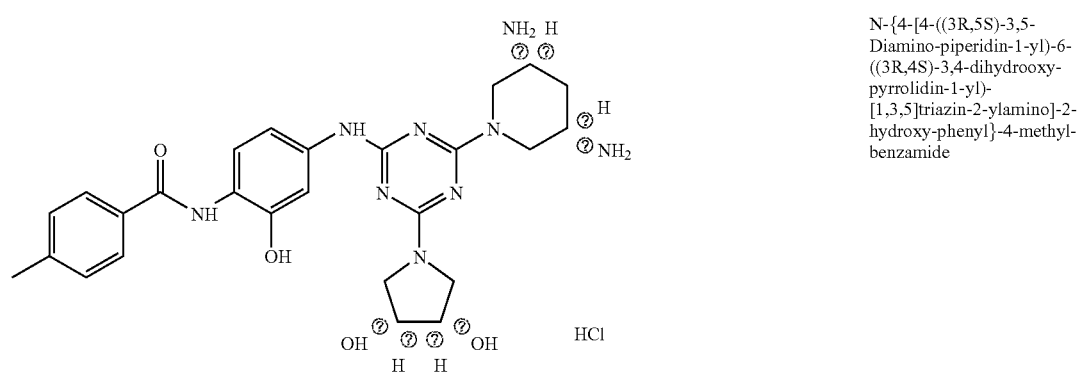 | N-{4-[4-((3R,5S)-3,5-Diamino-piperidin-1-yl)-6-((3R,4S)-3,4-dihydrooxy-pyrrolidin-1-yl)-[1,3,5]triazin-2-ylamino]-2-hydroxy-phenyl}-4-methyl-benzamide | − |
| ⑦ indicates text missing or illegible when filed | | |
| 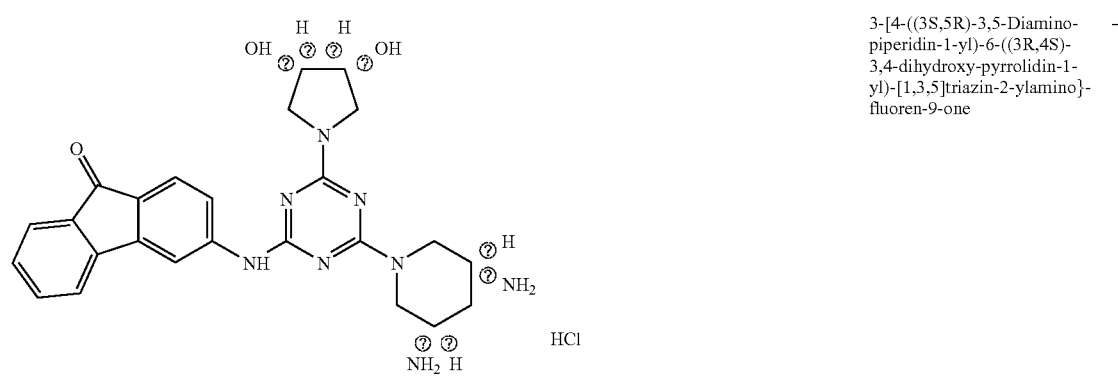 | 3-[4-((3S,5R)-3,5-Diamino-piperidin-1-yl)-6-((3R,4S)-3,4-dihydroxy-pyrrolidin-1-yl)-[1,3,5]triazin-2-ylamino}-fluoren-9-one | − |
| ⑦ indicates text missing or illegible when filed | | |
|  | 4-[4-((3S,5R)-3,5-Diamino-piperidin-1-yl)-6-((3R,4S)-3,4-dihydroxy-pyrrolidin-1-yl)-[1,3,5]triazin-2-ylamino]-2-hydroxy-benzoic acid phenyl ester | + |
| ⑦ indicates text missing or illegible when filed | | |

| Structure | Name | Potency |
|---|---|---|
| 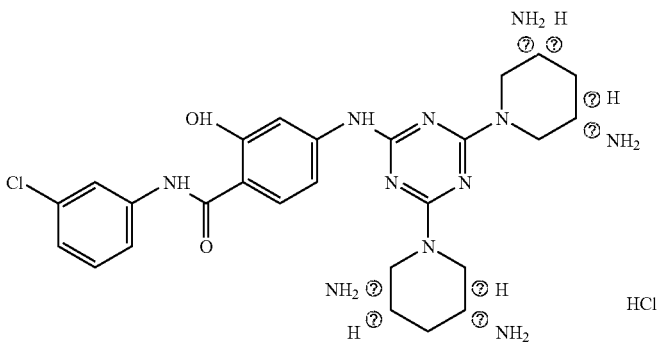 | N-(4,6-Bis-((3R,5S)-3,5-diamino-piperidin-1-yl)-[1,3,5]triazin-2-yl)-N'-Phenyl-hydrazine | − |
| 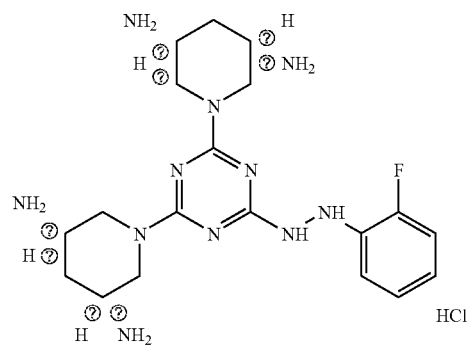 | N-(4,6-Bis((3R,5S)-3,5-diamino-piperidin-1-yl)-[1,3,5]triazin-2-yl)-N'-(2-Chloro-phenyl)-hydrazine | − |
| 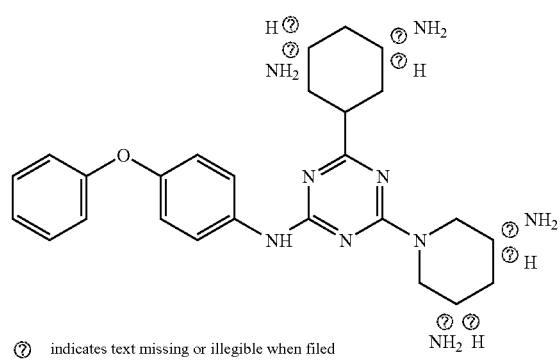 | N-(4,6-Bis-((3R,5S)-3,5-diamino-piperidin-1-yl)-[1,3,5]triazin-2-yl)-N'-(2-Fluoro-phenyl)-hydrazine | − |
| 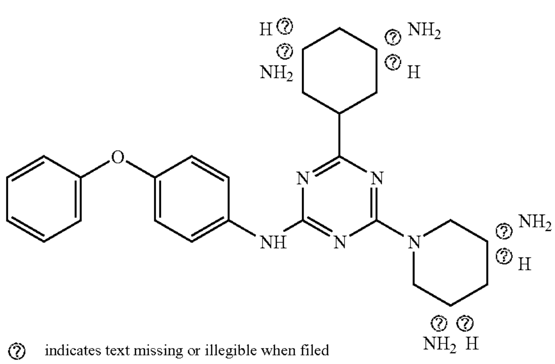 | N-(4-phenoxy-phenyl)-4,6-Bis-((3R,5S)-3,5-diamino-piperidin-1-yl)-[1,3,5]triazine-2-amine | + |
⟨?⟩ indicates text missing or illegible when filed -continued

| Structure | Name | Potency |
|---|---|---|
| 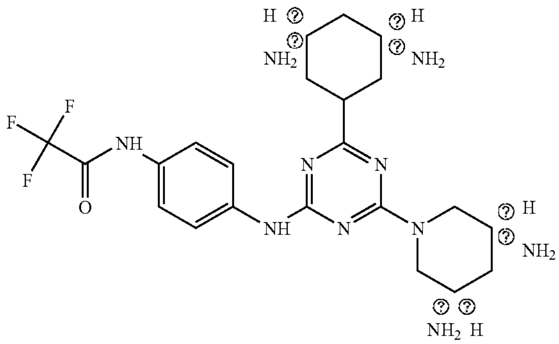 | N-[4-(2,2,2-trifluoro-acetylamino)-phenyl]-4,6-Bis-((3R,5S)-3,5-diamino-piperidin-1-yl)-[1,3,5]triazine-2-amine | − |
| 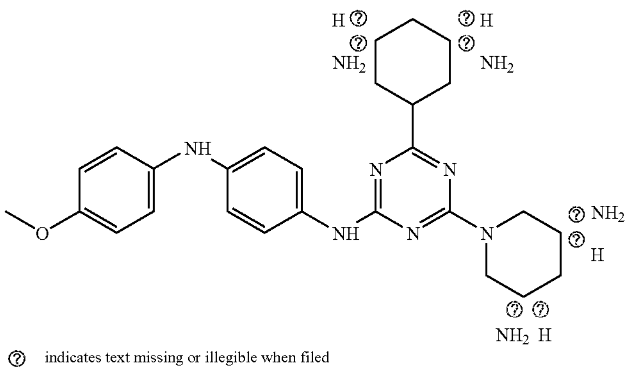 | N-[4-(4-methoxy-phenylamino)-phenyl]-4,6-Bis-((3R,5S)-3,5-diamino-piperidin-1-yl)-[1,3,5]triazine-2-amine | + |
| 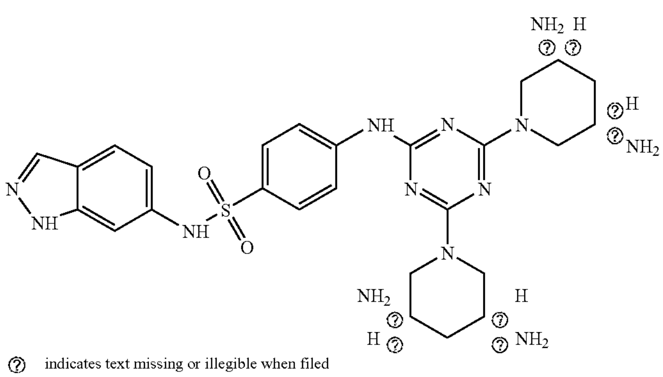 | N-[4-(1H-indazol-6-ylsulfamoyl)-phenyl]-4,6-Bis-((3R,5S)-3,5-diamino-piperidin-1-yl)-[1,3,5]triazine-2-amine | − |
| 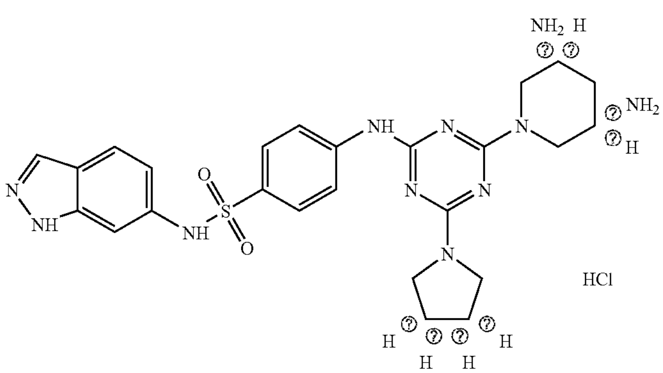 | 4-[4-((3S,5R)-3,5-Diamino-piperidin-1-yl)-6-((3R,4S)-3,4-dihydroxy-pyrrolidin-1-yl)-[1,3,5]triazin-2-ylamino]-N-(1H-indazol-6-yl)-benzenesulfonamide | − |

⊙ indicates text missing or illegible when filed

-continued

| Structure | Name | Potency |
|---|---|---|
| 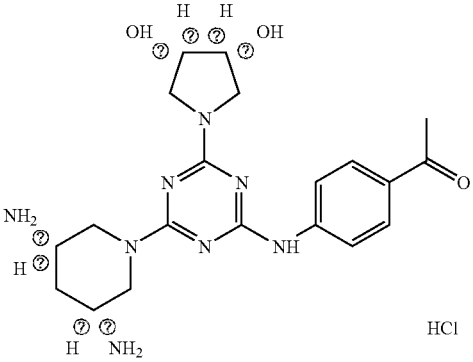 | 1-{4-[4-((3R,5S)-3,5-Diamino-piperidin-1-yl)-6-((3R,4S)-3,4-dihydroxy-pyrrolidin-1-yl)-[1,3,5]triazin-2-ylamino]-phenyl}-ethanone | − |
| 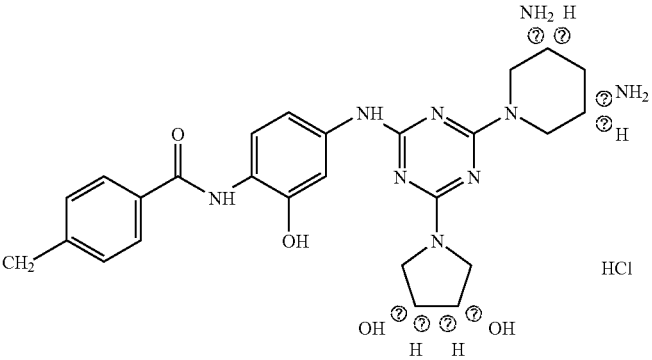 | 4-Chloro-N-{4-[4-((3S,5R)-3,5-diamino-piperidin-1-yl)-6-((3R,4S)-3,4-dihydroxy-pyrrolidin-1-yl)-[1,3,5]triazin-2-ylamino]-2-hydroxy-phenyl}-benzamide | + |
| 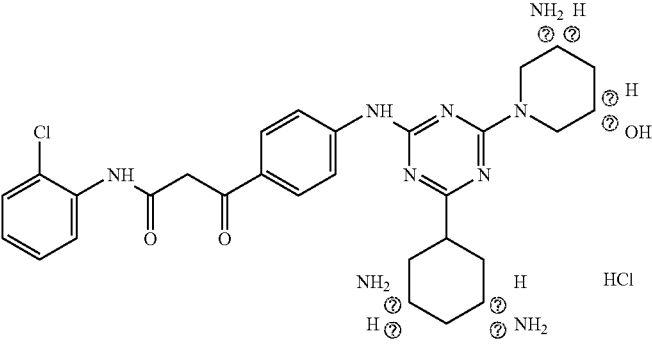 | 3-{4-[4-((3S,5R)-3-Amino-5-hydroxy-piperidin-1-yl)-6-((3S,5R)-3,5-diamino-piperidin-1-yl)-[1,3,5]triazin-2-ylamino]-phenyl}-N-(2-chloro-phenyl)-3-oxo-propionamide | ++ |
| 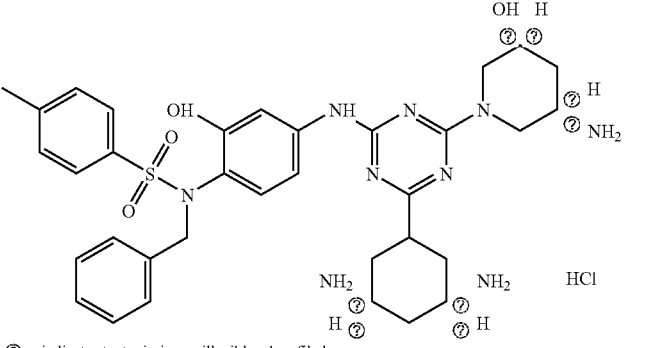 | N-{4-[4-((3S,5R)-3-Amino-5-hydroxy-piperidin-1-yl)-6-((3R,5S)-3,5-diamino-piperidin-1-l)-[1,3,5]triazin-2-ylamino]-2-hydroxy-phenyl}-N-benzyl-4-methyl-benzenesulfonamide | + |

| Structure | Name | Potency |
|---|---|---|
| 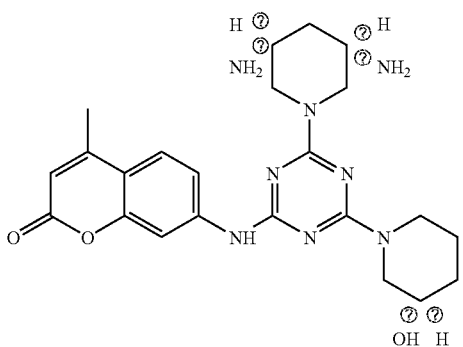 | 1-Hydroxy-naphthalene-2-carboxylic acid {4-[4-((3S,5R)-3-amino-5-hydroxy-piperidin-1-yl)-6-((3S,5R)-3,5-diamino-piperidin-1-yl)-[1,3,5]triazin-2-ylamino]-phenyl}-amide | ++ |
| 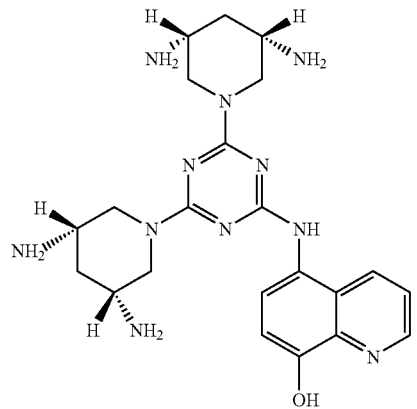 | 7-[4-((3S,5R)-3-Amino-5-hydroxy-piperidin-1-yl)-6-((3R,5S)-3,5-diamino-piperidin-1-yl)-[1,3,5]triazin-2-ylamino]-4-methyl-chromen-2-one | – |
| 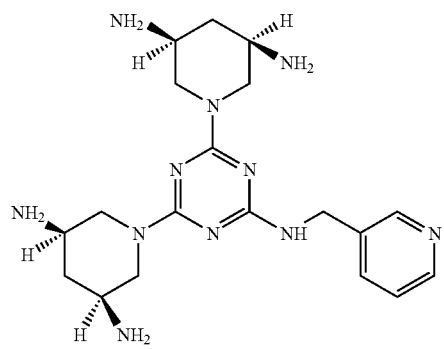 | N-(8-hydroxy-quinolin-5-yl)-4,6-Bis-((3R,5S)-3,5-diamino-piperidin-1-yl)-[1,3,5]triazine-2-amine | + |
| 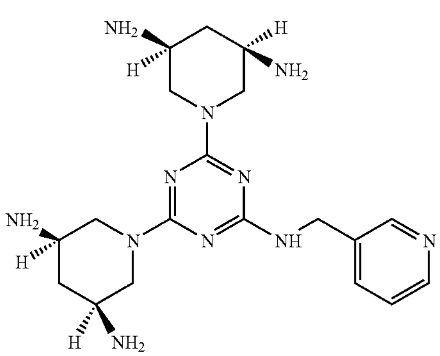 | N-pyridin-3-ylmethyl-4,6-Bis-((3R,5S)-3,5-diamino-piperidin-1-yl)-[1,3,5]triazine-2-amine | |

⊚ indicates text missing or illegible when filed

-continued

| Structure | Name | Potency |
|---|---|---|
| 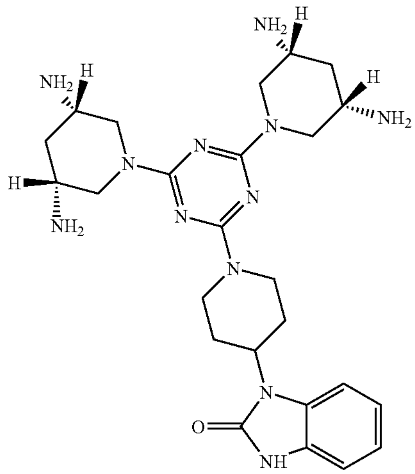 | 8-(4,6-Bis-((3R,5S)-3,5-0 diamino-piperidin-1-yl)-[1,3,5]triazin-2-yl)-1-phenyl-1,3,8-triaza-spiro[4.5]decan-4-one | – |
| 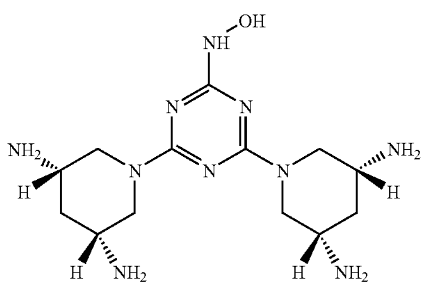 | N-[4-((3R,5S)-3,5-Diamino-piperidin-1-yl)-6-((3S,5R)-3,5-diamino-piperidin-1-yl)-[1,3,5]triazin-2-yl]-hydroxylamine | |
| 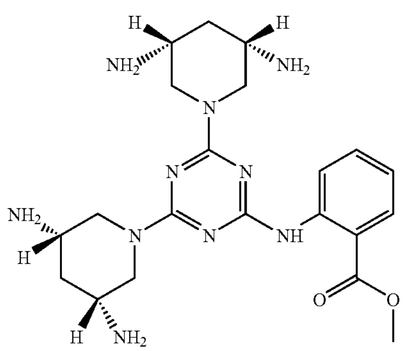 | 2-[4,6-Bis-((3R,5S)-3,5-diamino-piperidin-1-yl)-[1,3,5]triazin-2-ylamino]-benzoic acid methyl ester | – |
| 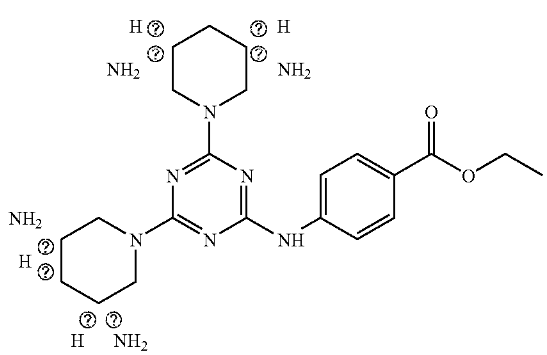 | 4-[4,6-Bis-((3R,5S)-3,5-diamino-piperidin-1-yl)-[1,3,5]triazin-2-ylamino]-benzoic acid ethyl ester | – |

⑦ indicates text missing or illegible when filed

-continued

| Structure | Name | Potency |
|---|---|---|
| 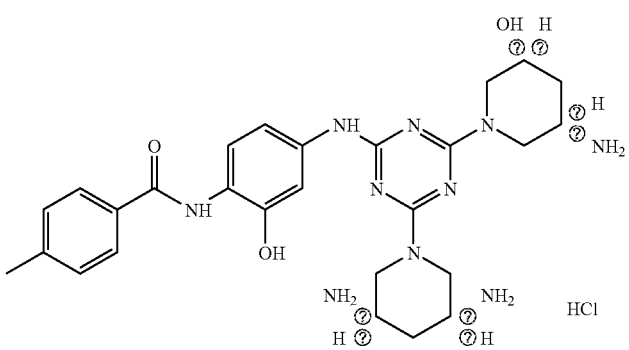 ⓘ indicates text missing or illegible when filed | N-(5-acetylamino-2-methoxy-phenyl)-4,6-Bis-((3R,5S)-3,5-diamino-piperidin-1-yl)-[1,3,5]triazine-2-amine | – |
| ⓘ indicates text missing or illegible when filed | N-{4-[4-((3S,5R)-3-Amino-5-hydroxy-piperidin-1-yl)-6-((3R,5S)-3,5-diamino-piperidin-1-yl)-[1,3,5]triazin-2-ylamino]-2-hydroxy-phenyl}-4-methyl-benzamide | + |
| 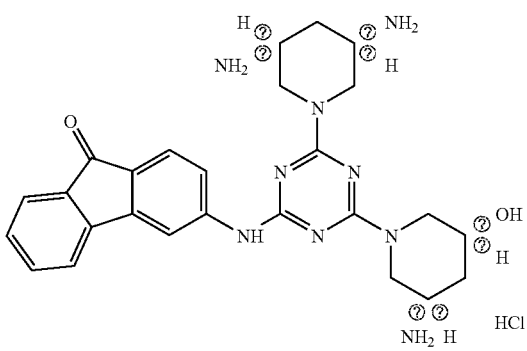 ⓘ indicates text missing or illegible when filed | 3-[4-((3S,5R)-3-Amino-5-hydroxy-piperidin-1-yl)-6-((3S,5R)-3,5-diamino-piperidin-1-yl)-[1,3,5]triazin-2-ylamino]-fluoren-9-one | ++ |
| 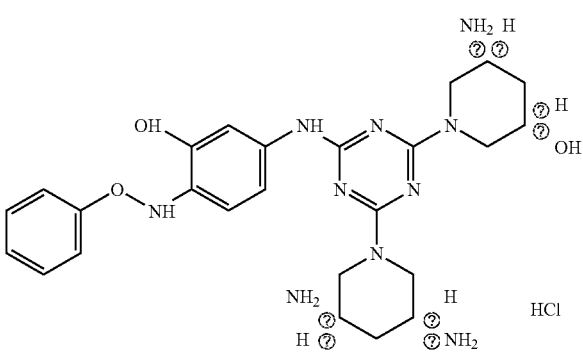 ⓘ indicates text missing or illegible when filed | 4-[4-((3S,5R)-3-Amino-5-hydroxy-piperidin-1-yl)-6-((3S,5R)-3,5-diamino-piperidin-1-yl)-[1,3,5]triazin-2-ylamino]-2-hydroxy-benzoic acid phenyl ester | ++ |

-continued

| Structure | Name | Potency |
|---|---|---|
| 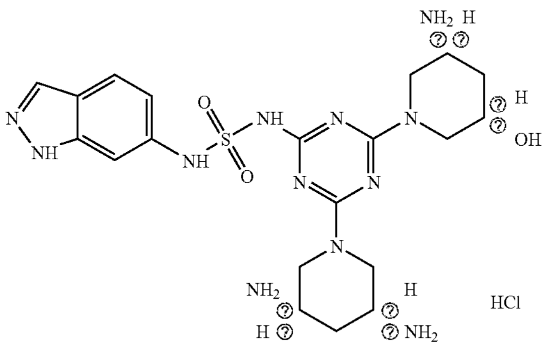 | 4-[4-((3S,5R)-3-Amino-5-hydroxy-piperidin-1-yl)-6-((3S,5R)-3,5-diamino-piperidin-1-yl)-[1,3,5]triazin-2-ylamino]-N-(1H-indazol-6-yl)-benzenesulfonamide | − |
| 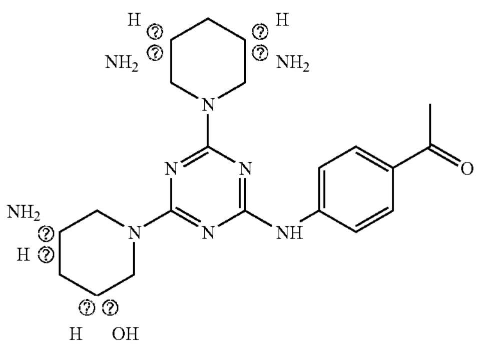 | 1-{4-[4-((3S,5R)-3-Amino-5-hydroxy-piperidin-1-yl)-6-((3R,5S)-3,5-diamino-piperidin-1-yl)-[1,3,5]triazin-2-ylamino]-phenyl}-ethanone | − |
| 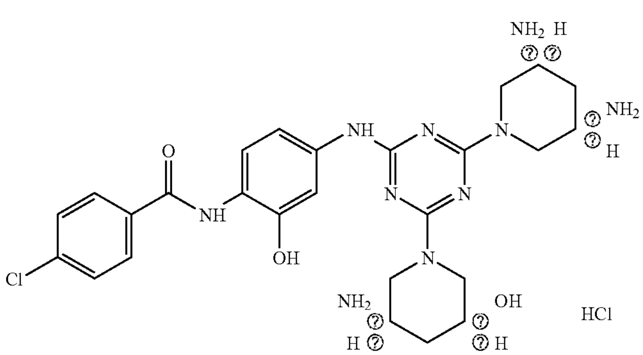 | N-{4-[4-((3S,5R)-3-Amino-5-hydroxy-piperidin-1-yl)-6-((3S,5R)-3,5-diamino-piperidin-1-yl)-[1,3,5]triazin-2-ylamino]-2-hydroxy-phenyl}-4-chloro-benzamide | ++ |

-continued

| Structure | Name | Potency |
|---|---|---|
| 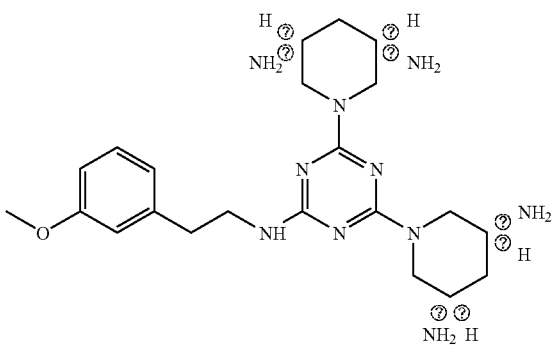 | N-(2-Chloro-phenyl)-3-{4-[4-((3R,5S)-3,5-diamino-piperidin-1-yl)-6-((3R,4S)-3,4-diamino-pyrrolidin-1-yl)-[1,3,5]triazin-2-ylamino]-phenyl}-3-oxo-propionamide | + |
| ⓘ indicates text missing or illegible when filed | | |
| 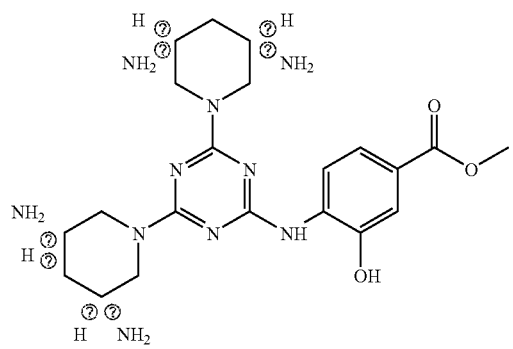 | N-[2-(3-methoxy-phenyl)-ethyl]-4,6-Bis-((3R,5S)-3,5-diamino-piperidin-1-yl)-[1,3,5]triazine-2-amine | |
| ⓘ indicates text missing or illegible when filed | | |
| 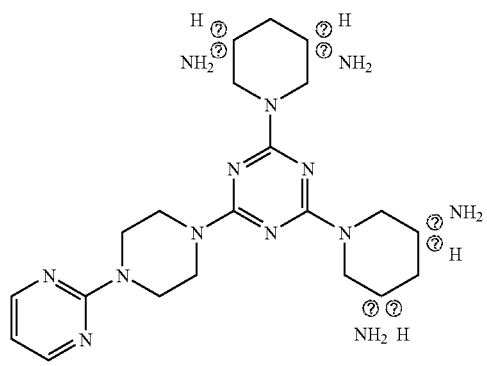 | 44-[4,6-Bis-((3R,5S)-3,5-diamino-piperidin-1-yl)-[1,3,5]triazin-2-ylamino]-3-hydroxy-benzoic acid methyl ester | – |
| ⓘ indicates text missing or illegible when filed | | |
| 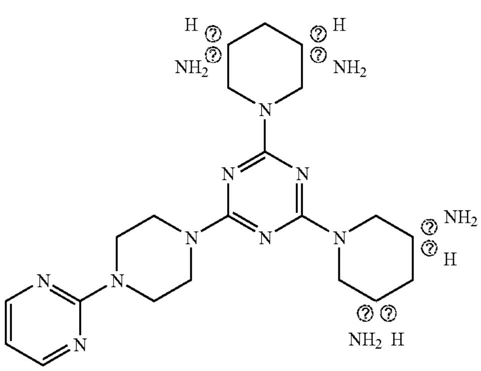 | [1-(4,6-Bis-((3R,5S)-3,5-diamino-piperidin-1-yl)-[1,3,5]triazin-2-yl)-piperidin-2-yl]-methanol | – |
| ⓘ indicates text missing or illegible when filed | | |

-continued
| Structure | Name | Potency |
|---|---|---|
| 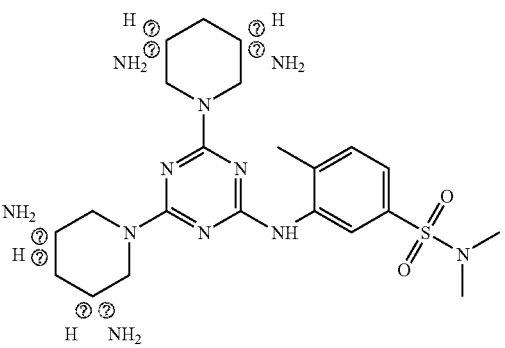 | N-(5-dimethylsulfamoyl-2-methyl-phenyl)-4,6-Bis-((3R,5S)-3,5-diamino-piperidin-1-yl)-[1,3,5]triazine-2-amine | – |
| 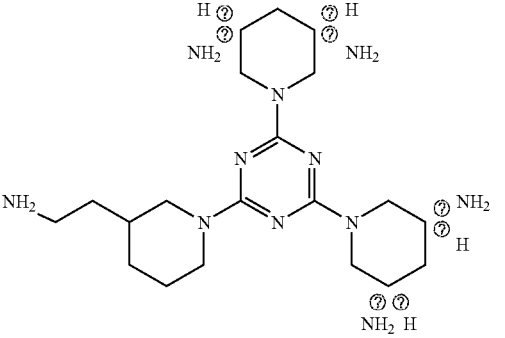 | 4-(4,6-Bis-((3R,5S)-3,5-diamino-piperidin-1-yl)-[1,3,5]triazin-2-yl)-piperazin-2-one | – |
| 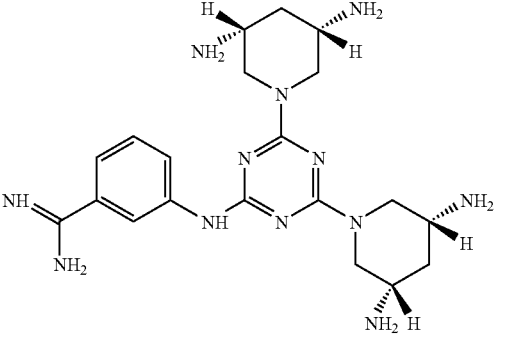 | N-(3-carbamimidolyl-phenyl)-4,6-Bis-((3R,5S)-3,5-diamino-piperidin-1-yl)-[1,3,5]triazine-2-amine | |
| 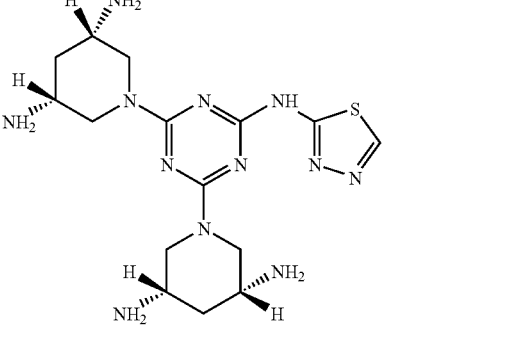 | N-[1,3,4]thiadiazol-2-yl-4,6-Bis-((3R,5S)-3,5-diamino-piperidin-1-yl)-[1,3,5]triazine-2-amine | |
⑦ indicates text missing or illegible when filed -continued

| Structure | Name | Potency |
|---|---|---|
| 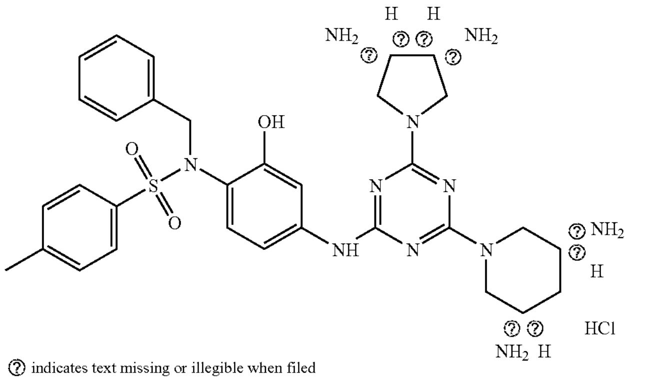 | N-Benzyl-N-{4-[4-((3R,5S)-3,5-diamino-piperidin-1-yl)-6-((3R,4S)-3,4-diamino-pyrrolidin-1-yl)-[1,3,5]triazin-2-ylamino]-2-hydroxy-phenyl}-4-methyl-benzenesulfonamide | ++ |
| 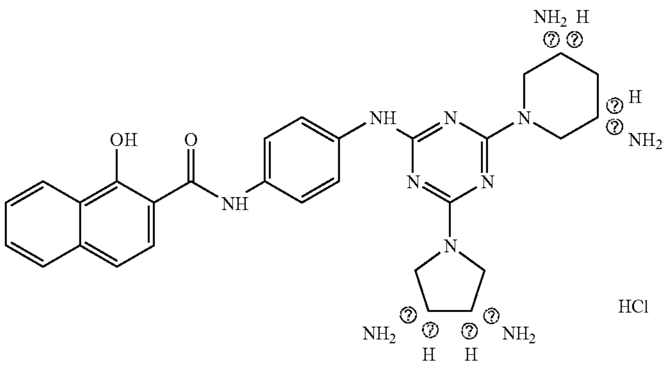 | 1-Hydroxy-naphthalene-2-carboxylic acid {4-[4-((3R,5S)-3,5-diamino-piperidin-1-yl)-6-((3R,4S)-3,4-diamino-pyrrolidin-1-yl)-[1,3,5]triazin-2-ylamino]-phenyl}-amide | ++ |
| 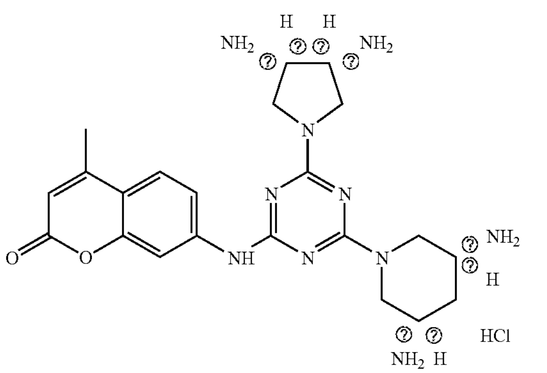 | 7-[4-((3R,5S)-3,5-diamino-piperidin-1-yl)-6-((3R,4S)-3,4-diamino-pyrrolidin-1-yl)-[1,3,5]triazin-2-ylamino]-4-methyl-chromen-2-one | − |
| 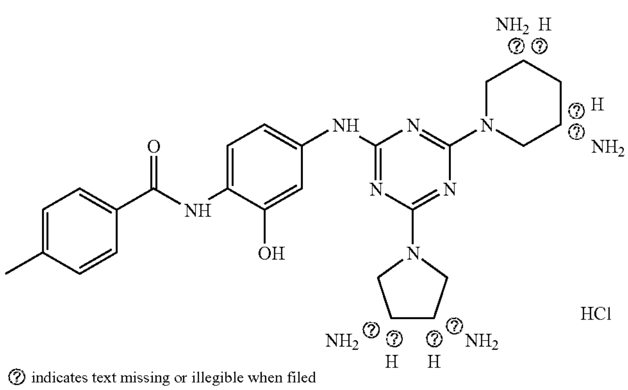 | NM-{4-[4-((3R,5S)-3,5-Diamino-piperidin-1-yl)-6-((3R,4S)-3,4-diamino-pyrrolidin-1-yl)-[1,3,5]triazin-2-ylamino]-2-hydroxy-phenyl}-4-methyl-benzamide | + |

-continued

| Structure | Name | Potency |
|---|---|---|
| 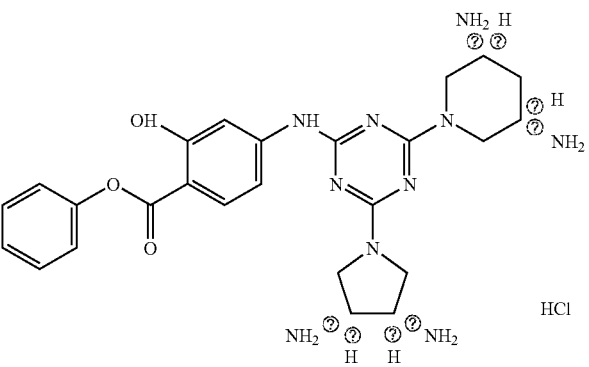 | 3-[4-((3R,5S)-3,5-Diamino-piperidin-1-yl)-6-((3R,4S)-3,4-diamino-pyrrolidin-1-yl)-[1,3,5]triazin-2-ylamino]-fluoren-9-one | + |
| ⑦ indicates text missing or illegible when filed | | |
| 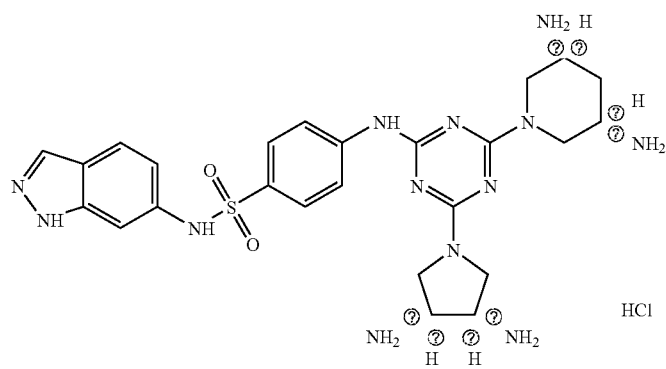 | 4-[4-((3R,5S)-3,5-Diamino-piperidin-1-yl)-6-((3R,4S)-3,4-diamino-pyrrolidin-1-yl)-[1,3,5]triazin-2-ylamino]-2-hydroxy-benzoic acid phenyl ester | + |
| ⑦ indicates text missing or illegible when filed | | |
| 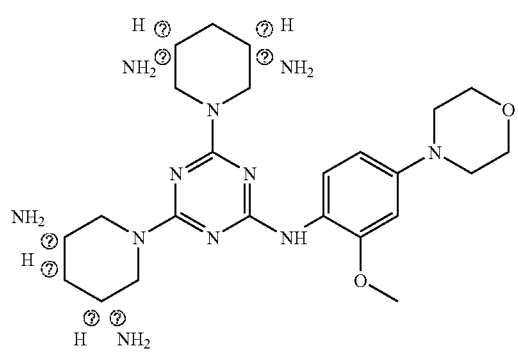 | 4-[4-((3R,5S)-3,5-Diamino-piperidin-1-yl)-6-((3R,4S)-3,4-diamino-pyrrolidin-1-yl)-[1,3,5]triazin-2-ylamino]-N-(1H-indazol-6-yl)-benzenesulfonamide | − |
| ⑦ indicates text missing or illegible when filed | | |
| 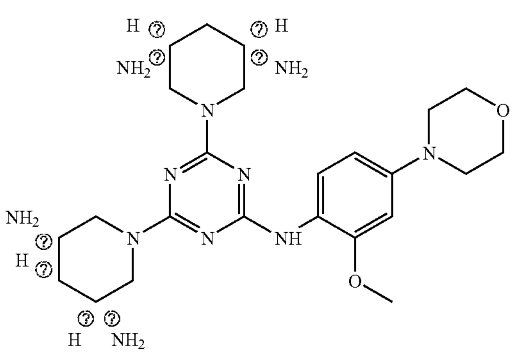 | N-(2-methoxy-4-morpholin-4-yl-phenyl)-4,6-Bis-((3R,5S)-3,5-diamino-piperidin-1-yl)-[1,3,5]triazine-2-amine | |
| ⑦ indicates text missing or illegible when filed | | |

-continued
| Structure | Name | Potency |
|---|---|---|
| 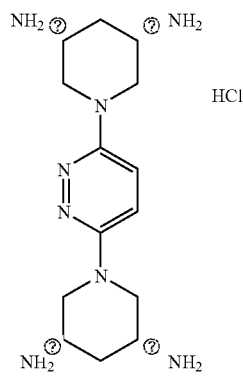 | 1,4-Bis-((3R,5S)-3,5-diamino-piperidin-1-yl)-phthalazine | |
| 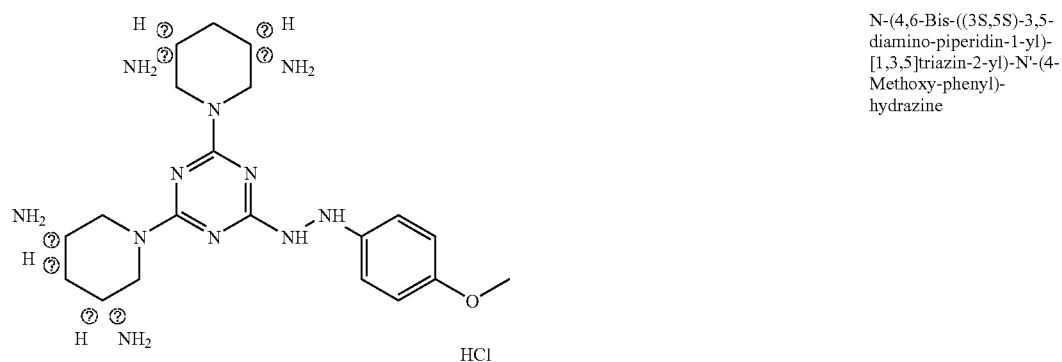 | N-(4,6-Bis-((3S,5S)-3,5-diamino-piperidin-1-yl)-[1,3,5]triazin-2-yl)-N'-(4-Methoxy-phenyl)-hydrazine | |
| 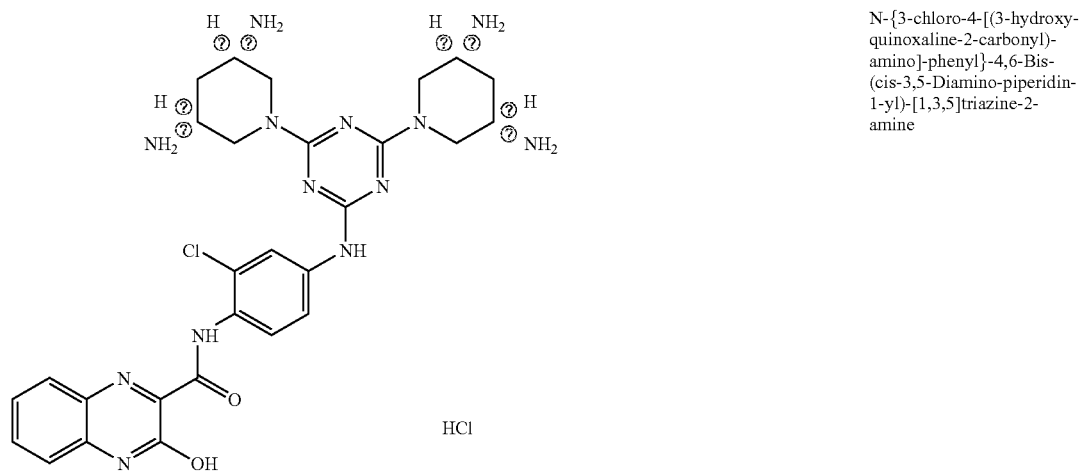 | N-{3-chloro-4-[(3-hydroxy-quinoxaline-2-carbonyl)-amino]-phenyl}-4,6-Bis-(cis-3,5-Diamino-piperidin-1-yl)-[1,3,5]triazine-2-amine | |
? indicates text missing or illegible when filed -continued
| Structure | Name | Potency |
|---|---|---|
| 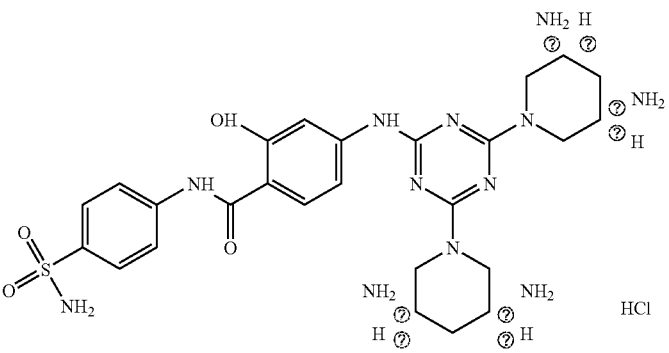 | N-[3-hydroxy-4-{4-sulfamoyl-phenylcarbamoyl)-phenyl]-4,6-Bis-((3R,5S)-3,5-diamino-piperidin-1-yl)-[1,3,5]triazine-22-amine | – |
| 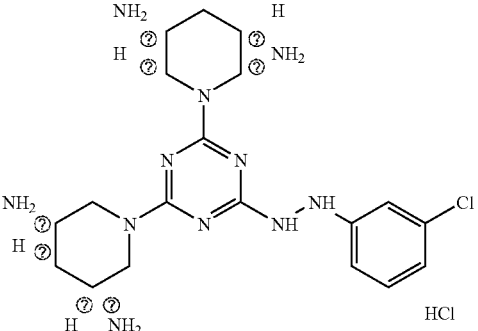 | N-(4,6-Bis-((3R,5S)-3,5-diamino-piperidin-1-yl)-[1,3,5]triazin-2-yl)-N'-(3-Chloro-phenyl)-hydrazine | + |
| 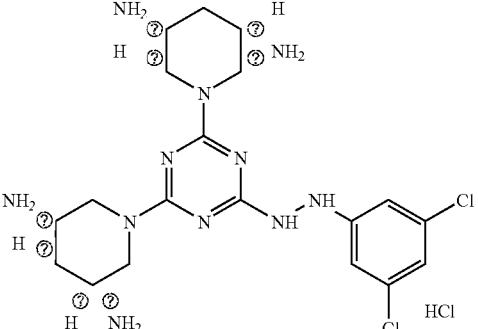 | N-(4,6-Bis-((3R,5S)-3,5-diamino-piperidin-1-yl)-[1,3,5]triazin-2-yl)-N'-(3,5-Dichloro-phenyl)-hydrazine | + |
⊚ indicates text missing or illegible when filed -continued

| Structure | Name | Potency |
|---|---|---|
| 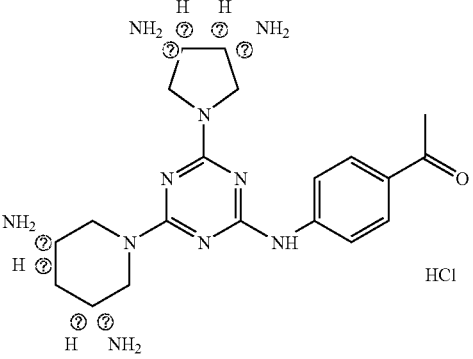 | 1-{4-[4-((3R,5S)-3,5-Diamino-piperidin-1-yl)-6-((3R,4S)-3,4-diamino-pyrrolidin-1-yl)-[1,3,5]triazin-2-ylamino]-phenyl}-ethanone | − |
| ⑦ indicates text missing or illegible when filed | | |
| 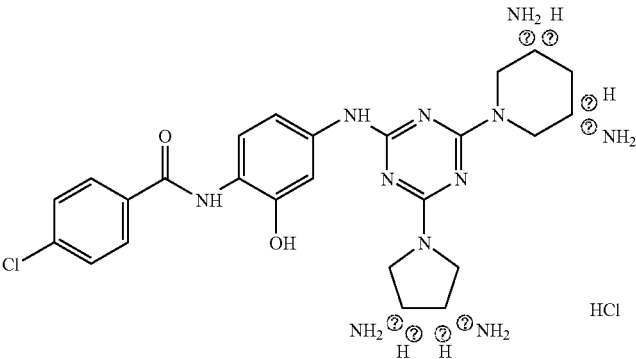 | 4-Chloro-N-{4-[4-((3R,5S)-3,5-diamino-piperidin-1-yl)-6-((3R,4S)-3,4-diamino-pyrrolidsin-1-yl)-[1,3,5]triazin-2-ylamino]-2-hydroxy-phenyl}-benzamide | + |
| ⑦ indicates text missing or illegible when filed | | |
| 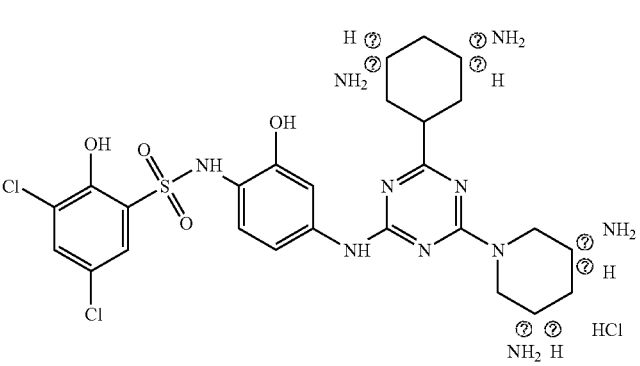 | N-[4-(3,5-dichloro-2-hydroxy-benzenesulfonylamino)-3-hydroxy-phenyl]-4,6-Bis-((3R,5S)-3,5-diamino-piperidin-1-yl)-[1,3,5]triazine-2-amine | ++ |
| ⑦ indicates text missing or illegible when filed | | |
| 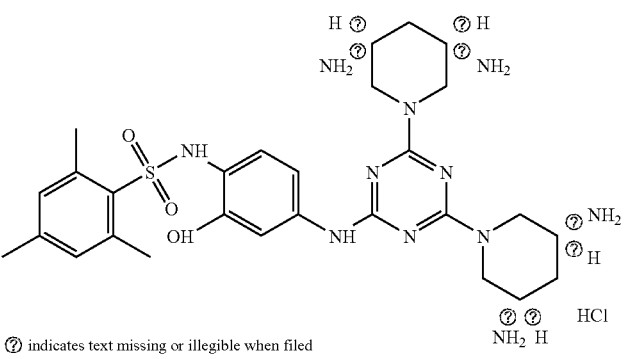 | N-[3-hydroxy-(2,4,6-trimethyl-benzenesulfonylamino)-phenyl]-4,6-Bis-((3R,5S)-3,5-diamino-pperidin-1-yl)-[1,3,5]triazine-2-amine | + |
| ⑦ indicates text missing or illegible when filed | | |

-continued

| Structure | Name | Potency |
|---|---|---|
| 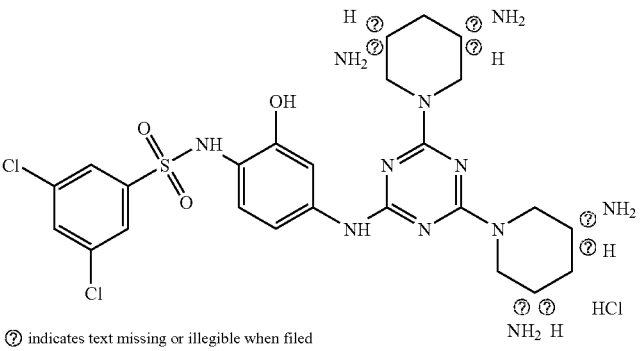 | N-[4-(3,5-dichloro-benzenesulfonylamino)-3-hydroxy-phenyl]-4,6-Bis-((3R,5S)-3,5-diamino-piperidin-1-yl)-[1,3,5]triazine-2-amine | + |
| 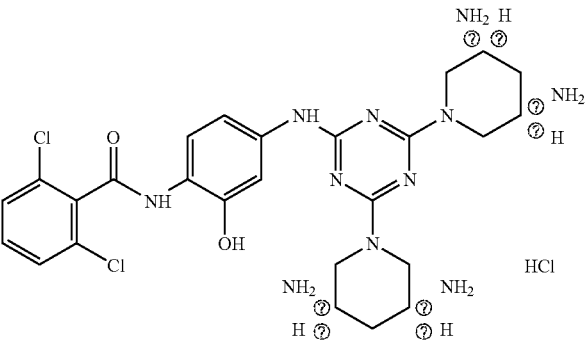 | N-[4-(2,6-dichloro-benzoylamino)-3-hydroxy-phenyl]-4,6-Bis-((3R,5S)-3,5-diamino-piperidin-1-yl)-[1,3,5]triazine-2-amine | + |
| 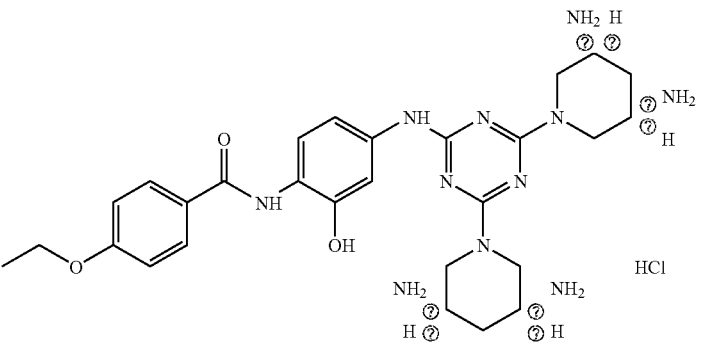 | N-[4-(4-ethoxy-benzoylamino)-3-hydroxy-phenyl]-4,6-Bis-((3R,5S)-3,5-diamino-piperidin-1-yl)-1,3,5]triazine-2-amine | ++ |
| 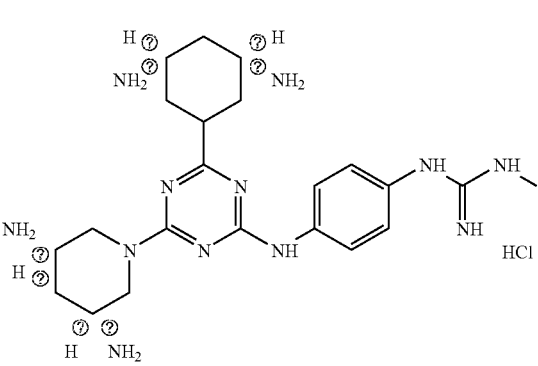 | N-[4-(N-methyl-quanidino)-phenyl]-4,6-Bis-((3R,5S)-3,5-diamino-piperidin-1-yl)-[1,3,5]triazine-2-amine | − |

? indicates text missing or illegible when filed

-continued
| Structure | Name | Potency |
|---|---|---|
| 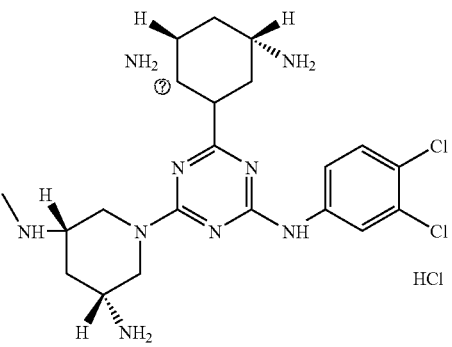 | N-(3,4-dichloro-phenyl)-4,6-Bis-((3R,5S)-3,5-diamino-piperidin-1-yl)-[1,3,5]triazine-2-amine | + |
| 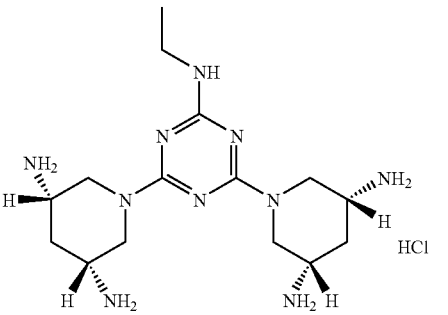 | N-ethyl-4,6-Bis-((3R,5S)-3,5-diamino-piperidin-1-yl)-[1,3,5]triazine-2-amine | |
| 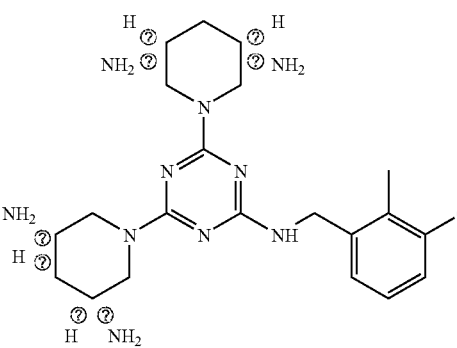 | N-(3-chloro-2-methyl-benzyl)-4,6-Bis-((3R,5S)-3,5-diamino-piperidin-1-yl)-[1,3,5]triazine-2-amine | − |
| 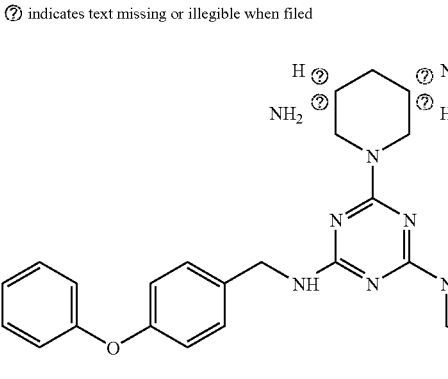 | N-(4-phenoxy-benzyl)-4,6-Bis-((3R,5S)-3,5-diamino-piperidin-1-yl)-[1,3,5]triazine-2-amine | − |
⟨?⟩ indicates text missing or illegible when filed -continued
| Structure | Name | Potency |
|---|---|---|
| 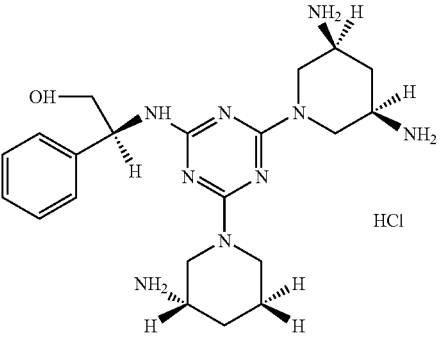 | (S)-2-[4-((3R,5S)-3,5-Diamino-piperidin-1-yl)-6-((3S,5R)-3,5-diamino-piperidin-1-yl)-[1,3,5]triazin-2-ylamino]-2-phenyl-ethanol | |
| 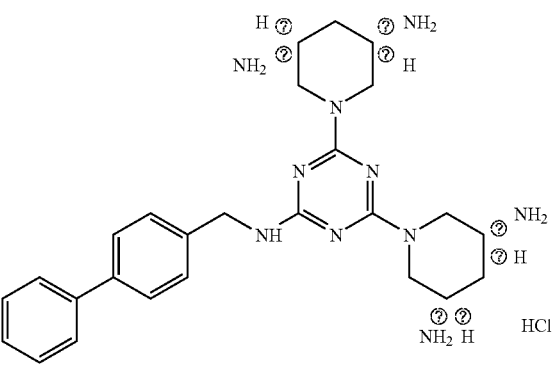 | N-biphenyl-4-ylmethyl-4,6-Bis-((3R,5S)-3,5-diamino-piperidin-1-yl)-[1,3,5]triazine-2-amine | + |
| 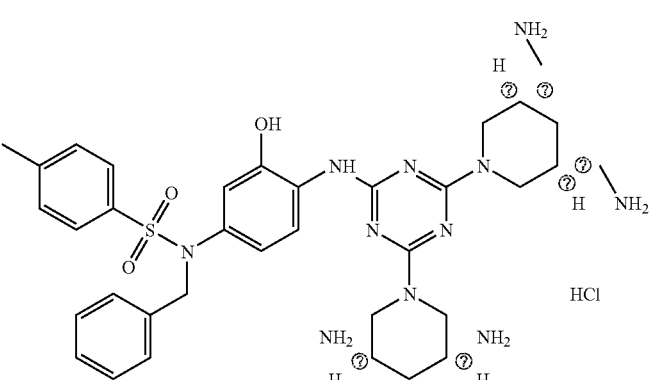 | N-Benzyl-N-{4-[4-((3S,5R)-3,5-bis-(aminomethyl)-piperidin-1-yl)-6-((3R,5S)-3,5-diamino-piperidin-1-yl)-[1,3,5]triazin-2-ylamino]-3-hydroxy-phenyl}-4-methyl-benzenesulfonamide | + |
? indicates text missing or illegible when filed -continued

| Structure | Name | Potency |
|---|---|---|
| 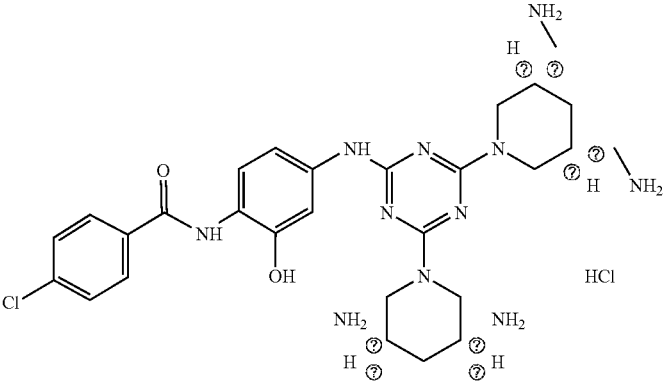 | N-{4-[4-((3R,5S)-3,5-Bis-(aminomethyl)-piperidin-1-yl)-6-((3R,5S)-3,5-diamino-piperidin-1-yl)-[1,3,5]triazin-2-ylamino]-2-hydroxy-phenyl}-4-chloro-benzamide | ++ |
| 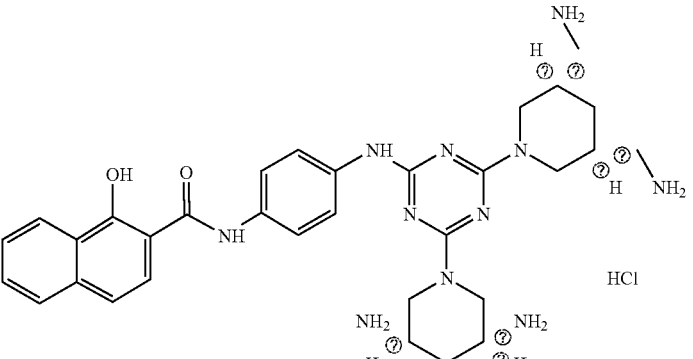 | 1-Hydroxy-naphthalene-2-carboxylic acid {4-[4-((3R,5S)-3,5-bis-(aminomethyl)-piperidin-1-yl)-6-((3R,5S)-3,5-diamino-piperidin-1-yl)-[1,3,5]triazine-2-ylamino]-phenyl}-amide | ++ |
| 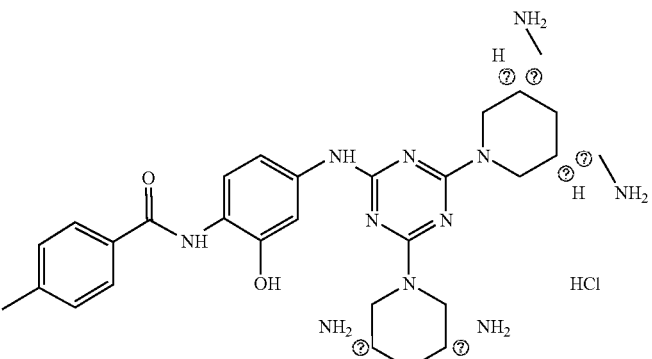 | N-{4-[4-((3S,5R)-3,5-Bis-(aminomethyl)-piperidin-1-yl)-6-((3R,5S)-3,5-diamino-piperidin-1-yl)-[1,3,5]triazin-ylamino]-2-hydroxy-phenyl}-4-methyl-benzamide | + |

-continued

| Structure | Name | Potency |
|---|---|---|
| 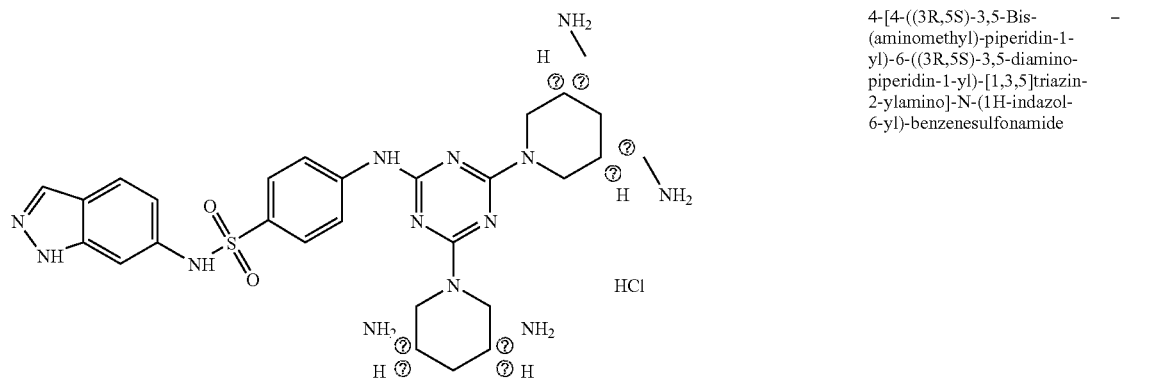 | 4-[4-((3R,5S)-3,5-Bis-(aminomethyl)-piperidin-1-yl)-6-((3R,5S)-3,5-diamino-piperidin-1-yl)-[1,3,5]triazin-2-ylamino]-N-(1H-indazol-6-yl)-benzenesulfonamide | − |
| ⑦ indicates text missing or illegible when filed | | |
| 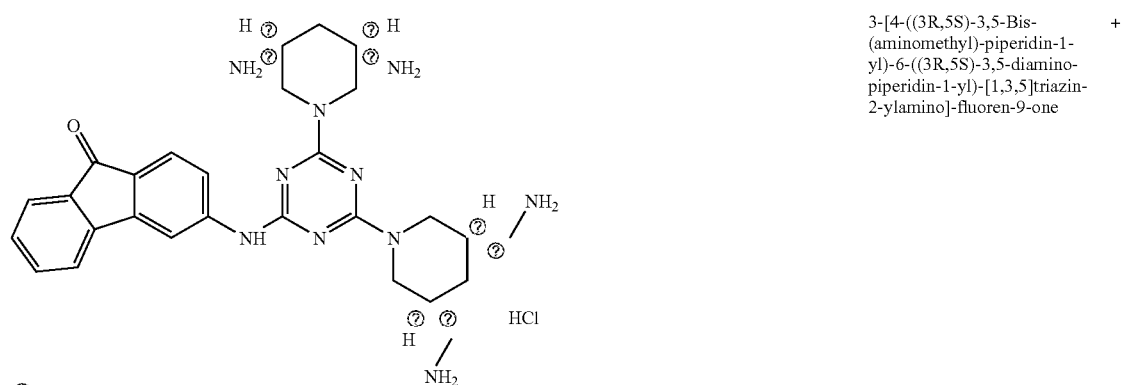 | 3-[4-((3R,5S)-3,5-Bis-(aminomethyl)-piperidin-1-yl)-6-((3R,5S)-3,5-diamino-piperidin-1-yl)-[1,3,5]triazin-2-ylamino]-fluoren-9-one | + |
| ⑦ indicates text missing or illegible when filed | | |
| 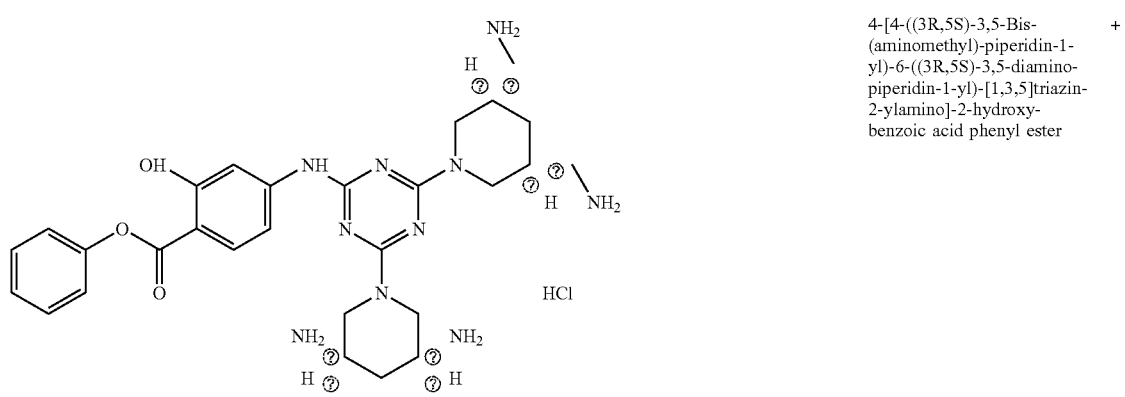 | 4-[4-((3R,5S)-3,5-Bis-(aminomethyl)-piperidin-1-yl)-6-((3R,5S)-3,5-diamino-piperidin-1-yl)-[1,3,5]triazin-2-ylamino]-2-hydroxy-benzoic acid phenyl ester | + |
| ⑦ indicates text missing or illegible when filed | | |

-continued
| Structure | Name | Potency |
|---|---|---|
| 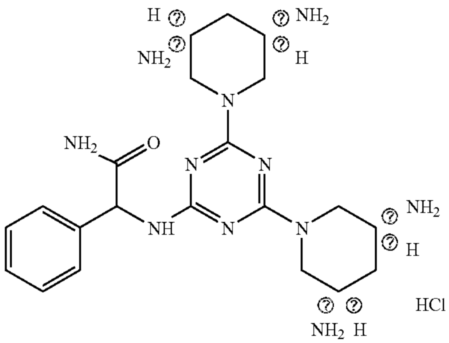 | N-(carbamoyl-phenyl-methyl)-4,6-Bis-((3R,5S)-3,5-diamino-piperidin-1-yl)-[1,3,5]triazine-2-amine | |
| 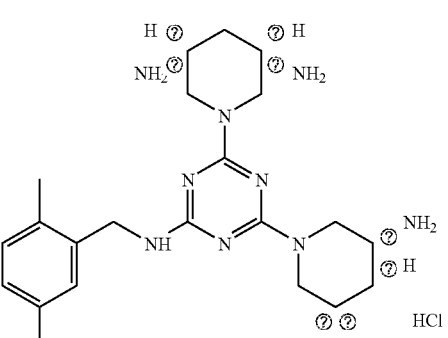 | N-(2,5-dimethyl-benzyl)-4,6-Bis((3R,5S)-3,5-diamino-piperidin-1-yl)-[1,3,5]triazine-2-amine | |
| 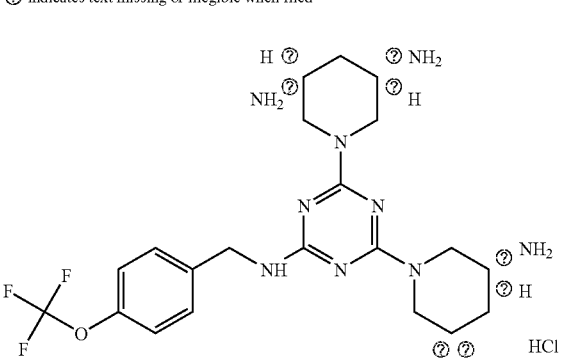 | N-(4-trifluoromethoxy-benzyl)-4,6-Bis-((3R,5S)-3,5-diamino-piperidin-1-yl)-[1,3,5]triazine-2-amine | |
| 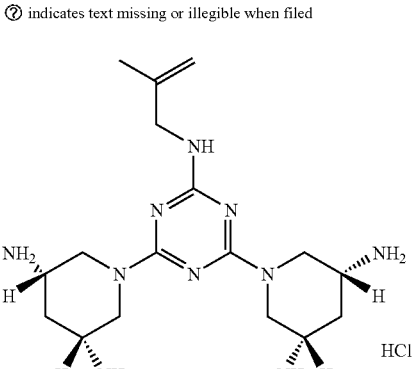 | N-(2-methyl-allyl)-4,6-Bis-((3R,5S)-3,5-diamino-piperidin-1-yl)-[1,3,5]triazine-2-amine | |
⑦ indicates text missing or illegible when filed -continued
| Structure | Name | Potency |
|---|---|---|
| 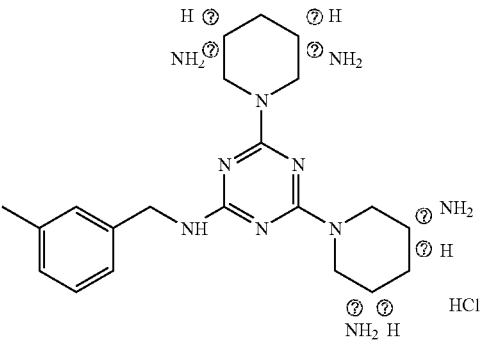 | N-(3-methyl-benzyl)-4,6-Bis-((3R,5S)-3,5-diamino-piperidin-1-yl)-[1,3,5]triazine-2-amine | |
| 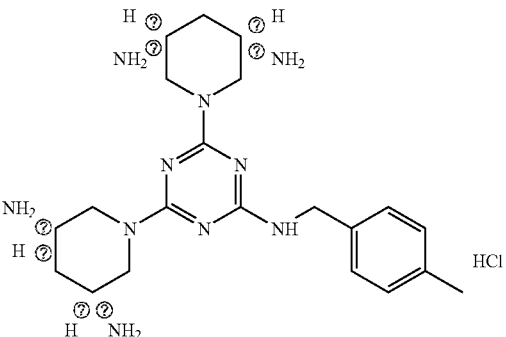 | N-(4-methyl-benzyl)-4,6-Bis-((3R,5S)-3,5-diamino-piperidin-1-yl)-[1,3,5]triazine-2-amine | |
| 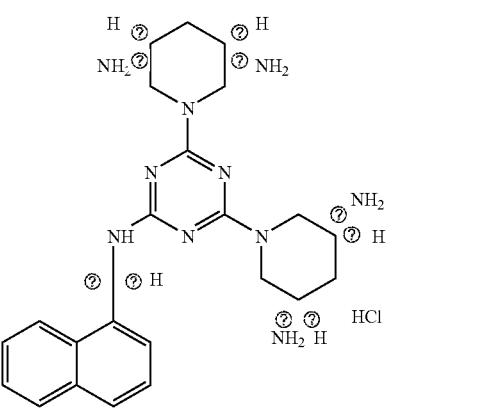 | N-((S)-1-naphthalen-1-yl-ethyl)-4,6-Bis-((3R,5S)-3,5-diamino-piperidin-1-yl)-[1,3,5]triazine-2-amine | – |

-continued
| Structure | Name | Potency |
|---|---|---|
| 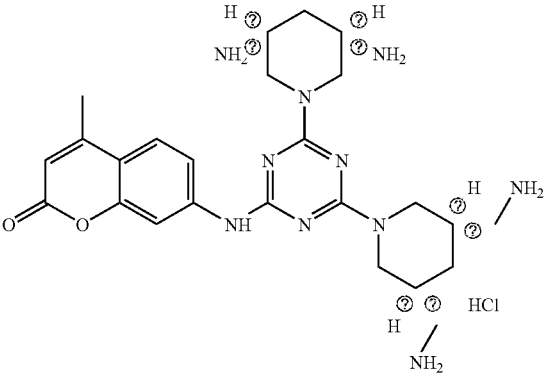 | 7-[4-((3S,5R)-3,5-Bis-(aminomethyl)-piperidin-1-yl)-6-((3R,5S)-3,5-diamino-piperidin-1-yl)-[1,3,5]triazin-2-ylamino]-4-methyl-chromen-2-one | − |
| 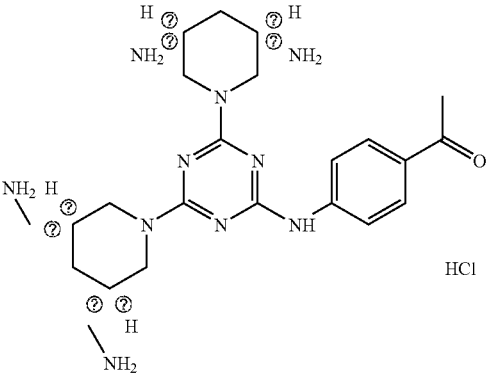 | 1-{4-[4-((3S,5R)-3,5-Bis-(aminomethyl)-piperidin-1-tl)-6-((3R,5S)-3,5-diamino-piperidin-1-l)-[1,3,5]triazin-2-ylamino]-phenyl}-ethanone | − |
| 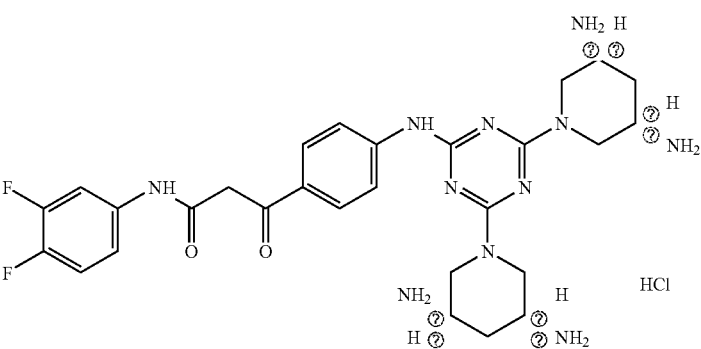 | N-{4-[2-(3,4-difluoro-phenylcarbamoyl)-acetyl]-phenyl}-4,6-Bis-((3R,5S)-3,5-diamino-piperidin-1-yl)-[1,3,5]triazine-2-amine | ++ |

-continued

| Structure | Name | Potency |
|---|---|---|
| 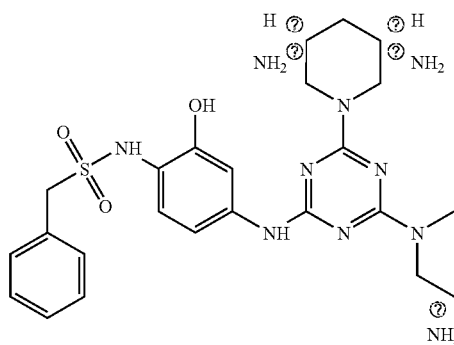 | N-{4-[2-(2,2-difluoro-benzo[1,3]dioxol-5-ylcarbamoyl)-acetyl]-phenyl}-4,6-Bis-((3R,5S)-3,5-diamino-piperidin-1-yl)-[1,3,5]triazine-2-amine | ++ |
|  ⓘ indicates text missing or illegible when filed | | |
| 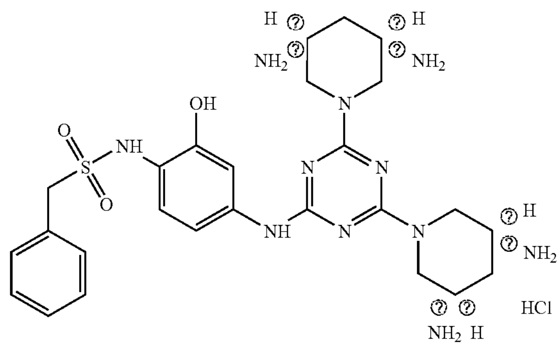 | N-(3-hydroxy-4-phenylmethanesulfonyl-amino-phenyl)-4,6-Bis-((3R,5S)-3,5-diamino-piperidin-1-yl)-[1,3,5]triazine-2-amine | − |
| ⓘ indicates text missing or illegible when filed | | |
| 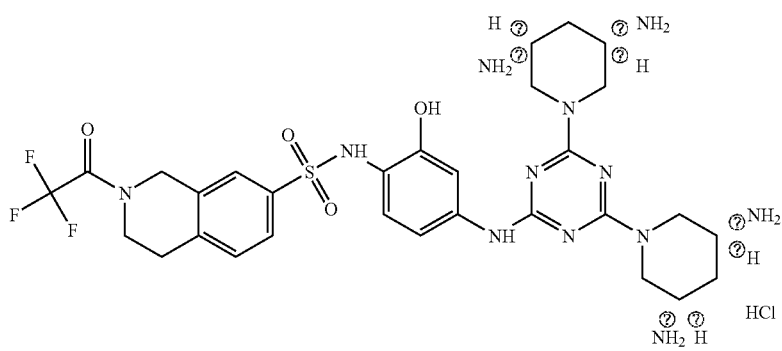 | N-{3-hydroxy-4-[2-(2,2,2-trifluoro-acetyl)-1,2,3,4-tetrahydro-isoquinoline-7-sulfonylamino]-phenyl}-4,6-Bis-((3R,5S)-3,5-diamino-piperidin-1-yl)-[1,3,5]triazine-2-amine | − |
| ⓘ indicates text missing or illegible when filed | | |
| 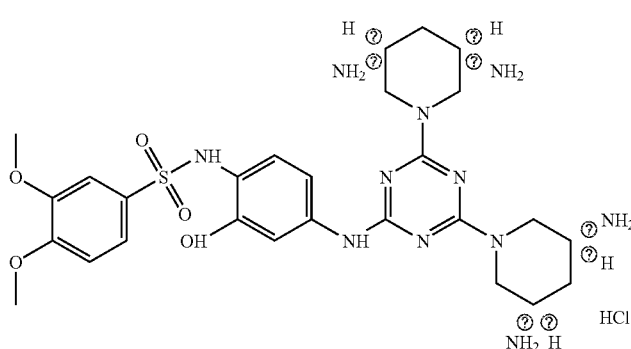 | N-[4-(3,4-dimethoxy-benzenesulfonylamino)-3-hydroxy-phenyl]-4,6-Bis-((3R,5S)-3,5-diamino-piperidin-1-yl)-[1,3,5]triazine-2-amine | − |
| ⓘ indicates text missing or illegible when filed | | |

-continued
| Structure | Name | Potency |
|---|---|---|
| 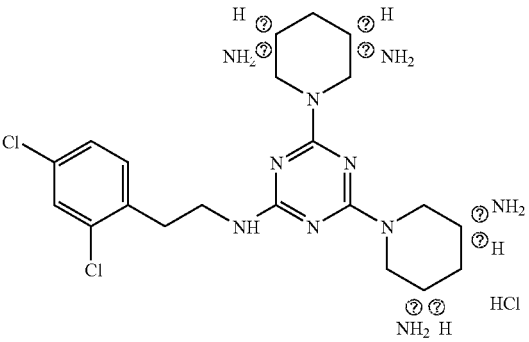 | N-[2-(2,4-dichloro-phenyl)-ethyl]-4,6-Bis-((3R,5S)-3,5-diamino-piperidin-1-yl)-[1,3,5]triazine-2-amine | – |
| 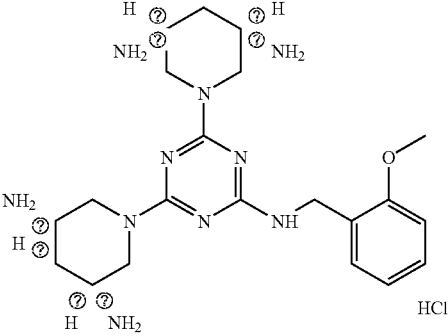 | N-(2-methoxy-benzyl)-4,6-Bis-((3R,5S)-3,5-diamino-piperidin-1-yl)-[1,3,5]triazine-2-amine | |
| 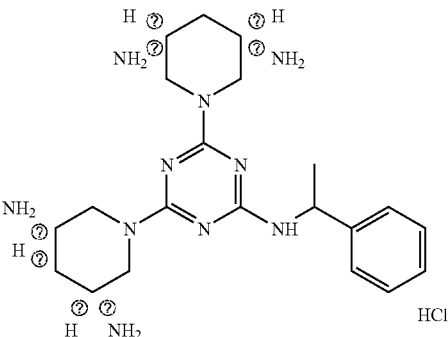 | N-(1-phenyl-ethyl)-4,6-Bis-((3R,5S)-3,5-diamino-piperidin-1-yl)-[1,3,5]triazine-2-amine | |
⊘ indicates text missing or illegible when filed -continued
| Structure | Name | Potency |
|---|---|---|
| 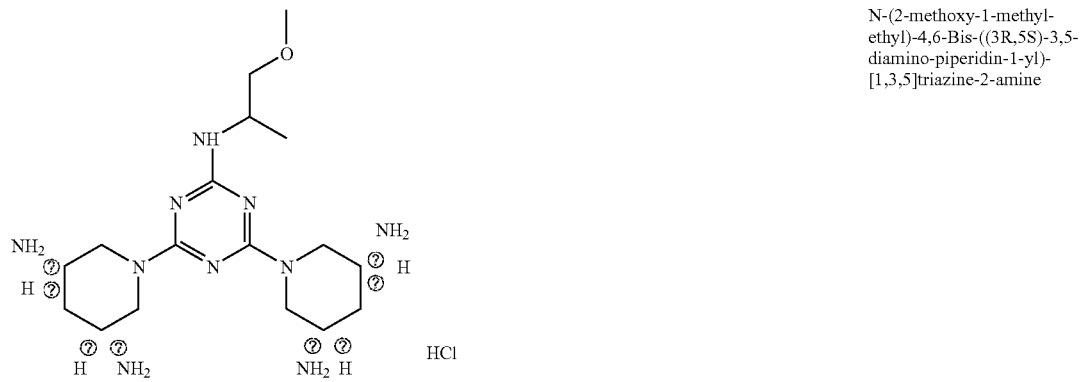 | N-(2-methoxy-1-methyl-ethyl)-4,6-Bis-((3R,5S)-3,5-diamino-piperidin-1-yl)-[1,3,5]triazine-2-amine | |
| 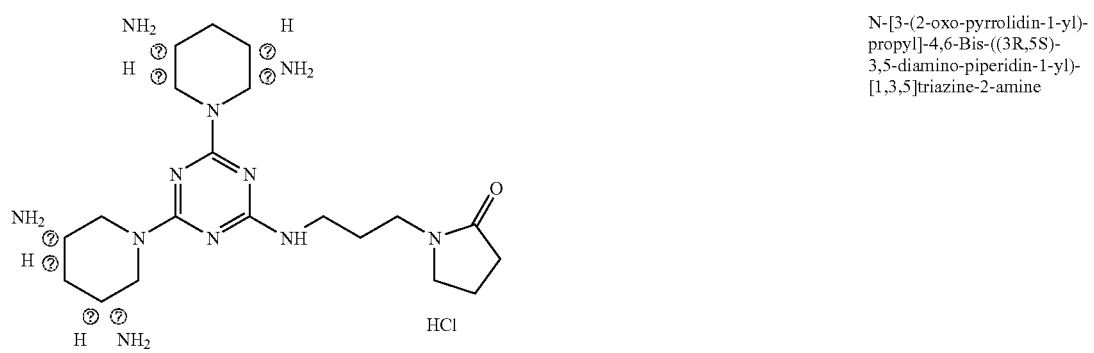 | N-[3-(2-oxo-pyrrolidin-1-yl)-propyl]-4,6-Bis-((3R,5S)-3,5-diamino-piperidin-1-yl)-[1,3,5]triazine-2-amine | |
| 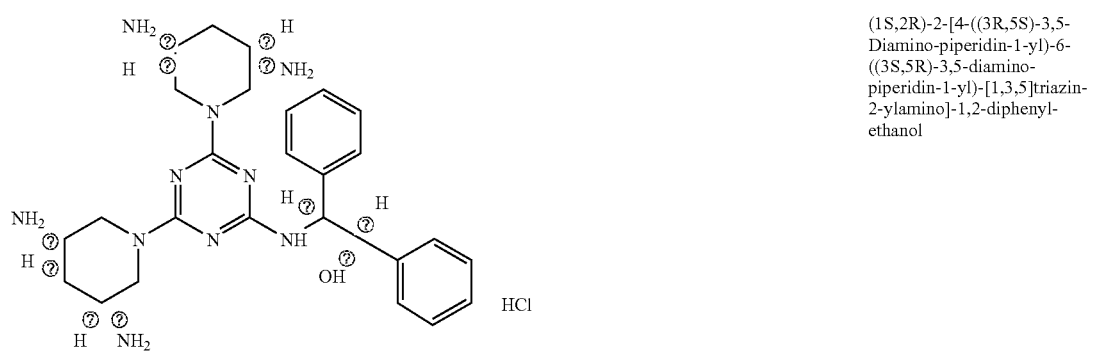 | (1S,2R)-2-[4-((3R,5S)-3,5-Diamino-piperidin-1-yl)-6-((3S,5R)-3,5-diamino-piperidin-1-yl)-[1,3,5]triazin-2-ylamino]-1,2-diphenyl-ethanol | |
⊙ indicates text missing or illegible when filed -continued

| Structure | Name | Potency |
|---|---|---|
| 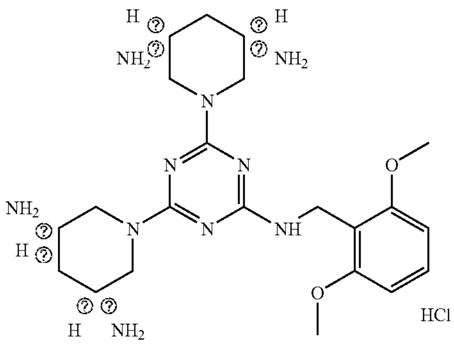 | N-(2,6-dimethoxy-benzyl)-4,6-Bis-((3R,5S)-3,5-diamino-piperidin-1-yl)-[1,3,5]triazine-2-amine | − |
| 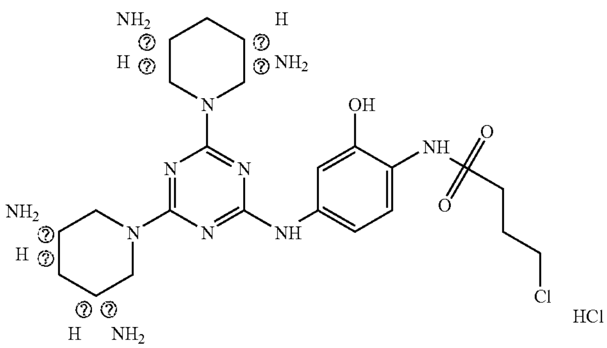 | N-[4-(3-chloro-propane-1-sulfonylamino)-3-hydroxy-phenyl]-4,6-Bis-((3R,5S)-3,5-diamino-piperidin-1-yl)-[1,3,5]triazine-2-amine | − |
| 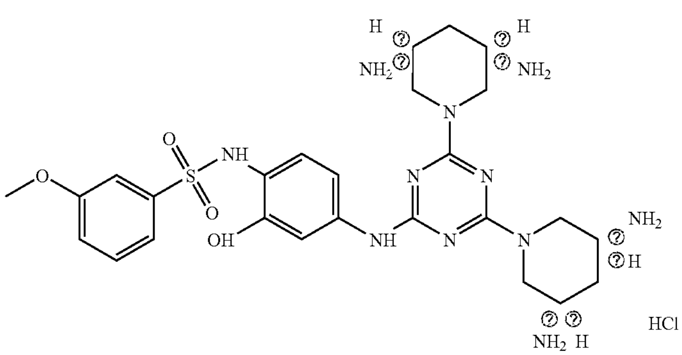 | N-[3-hydroxy-4-(3-methoxy-benzenesulfonylamino)-phenyl]-4,6-Bis-((3R,5S)-3,5-diamino-piperidin-1-yl)-[1,3,5]triazine-2-amine | + |
| 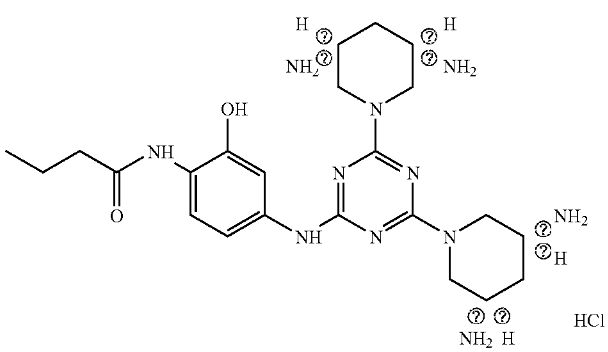 | N-(4-butyrylamino-3-hydroxy-phenyl)-4,6-Bis-((3R,5S)-3,5-diamino-piperidin-1-yl)-[1,3,5]triazine-2-amine | − |

| Structure | Name | Potency |
|---|---|---|
| 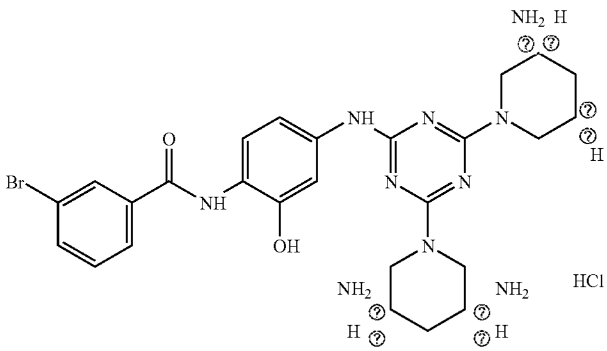 | N-[4-(3-bromo-benzoylamino)-3-hydroxy-phenyl]-4,6-Bis-((3R,5S)-3,5-diamino-piperidin-1-yl)-[1,3,5]triazine-2-amine | ++ |
| 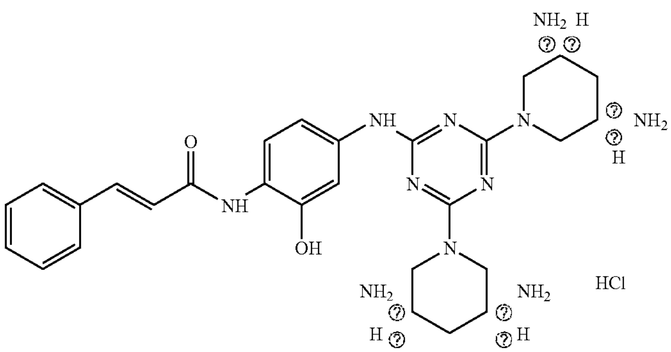 | N-[3-hydroxy-4-(3-phenyl-acryloylamino)-phenyl]-4,6-Bis-((3R,5S)-3,5-diamino-piperidin-1-yl)-[1,3,5]triazine-2-amine | ++ |
| 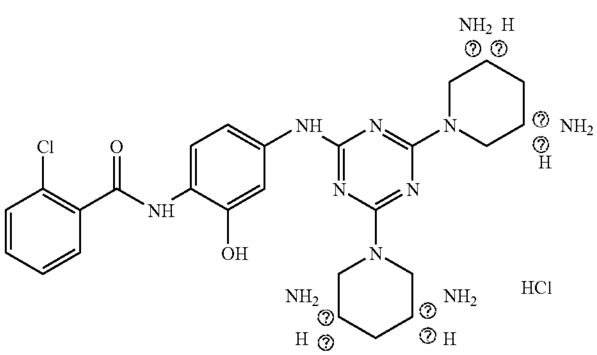 | N-[4-(2-chloro-benzoylamino)-3-hydroxy-phenyl]-4,6-Bis-((3R,5S)-3,5-diamino-piperidin-1-yl)-[1,3,5]triazine-2-amine | + |
| 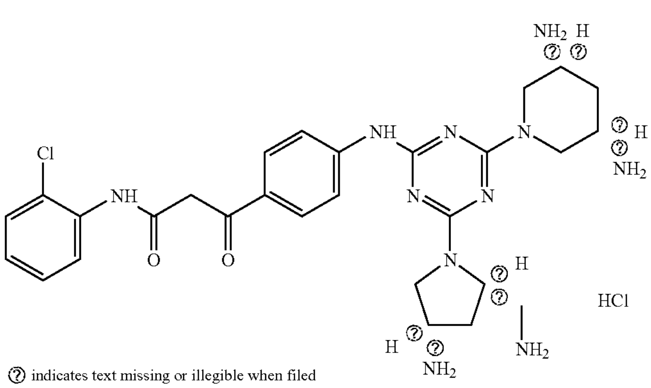 | 3-{4-[4-((2S,4S)-4-Amino-2-aminomethyl-pyrrolidin-1-yl)-6-((3R,5S)-3,5-diamino-piperidin-1-yl)-[1,3,5]triazine-2-ylamino]-phenyl}-N-(2-chloro-phenyl)-3-oxo-propionamide | + |

-continued

| Structure | Name | Potency |
|---|---|---|
| 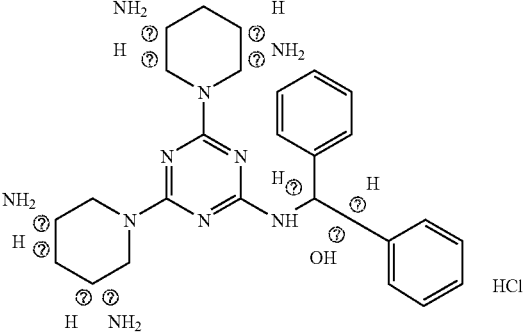 | (1R,2S)-2-[4-((3R,5S)-3,5-Diamino-piperidin-1-yl)-6-((3S,5R)-3,5-diamino-piperidin-1-yl)-[1,3,5]triazin-2-ylamino]-1,2-diphenyl-ethanol | |

⑦ indicates text missing or illegible when filed

| | | |
|---|---|---|
| 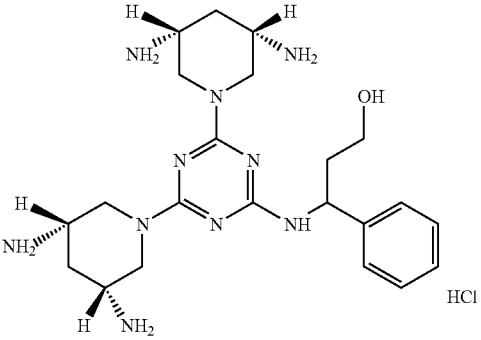 | N-(3-hydroxy-1-phenyl-propyl)-4,6-Bis-((3R,5S)-3,5-diamino-piperidin-1-yl)-[1,3,5]triazine-2-amine | |
| 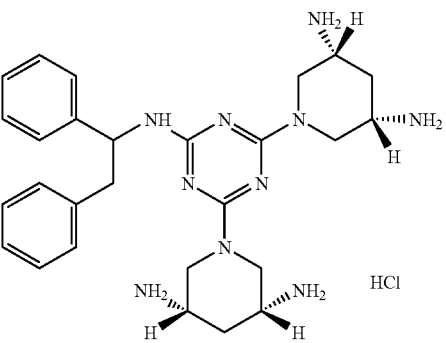 | N-(1,2-diphenyl-ethyl)-4,6-Bis-((3R,5S)-3,5-diamino-piperidin-1-yl)-[1,3,5]triazine-2-amine | |
| 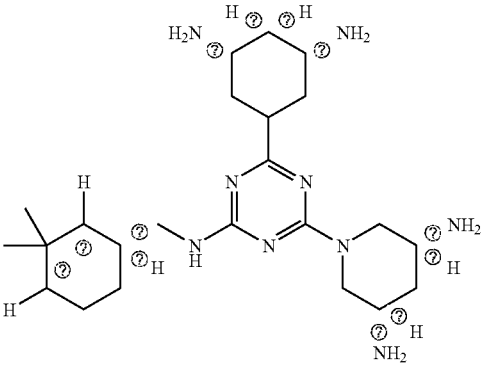 | N-((1S,2R,5R)-6,6-dimethyl-bicyclo[3.1.1]hept-2-ylmethyl)-4,6-Bis-((3R,5S)-3,5-diamino-piperidin-1-yl)-[1,3,5]triazine-2-amine | |

⑦ indicates text missing or illegible when filed

| Structure | Name | Potency |
|---|---|---|
| 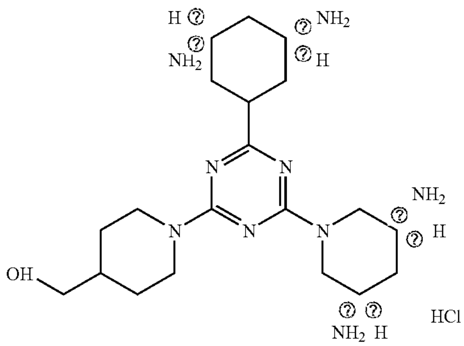 | (4aR,8aS)-2-(4,6-Bis-((3R,5S)-3,5-diamino-piperidin-1-yl)-[1,3,5]triazin-2-yl)-decahydro-isoquinoline | |
| 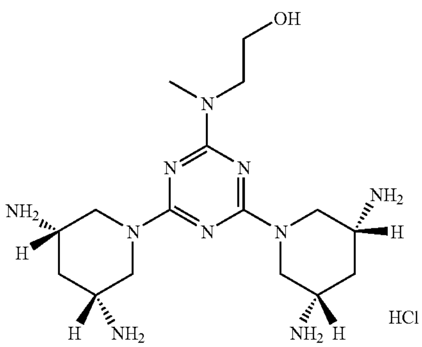 | 2-{[4,6-Bis-((3R,5S)-3,5-diamino-piperidin-1-yl)-[1,3,5]triazine-2-yl]-methyl-amino}-ethanol | |
| 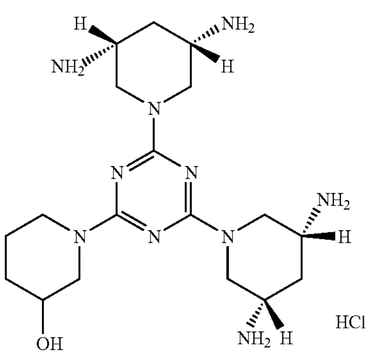 | 2-[1-(4,6-Bis-((3R,5S)-3,5-diamino-piperidin-1-yl)-[1,3,5]triazin-2-yl)-piperidin-2-yl]-ethanol | |
| 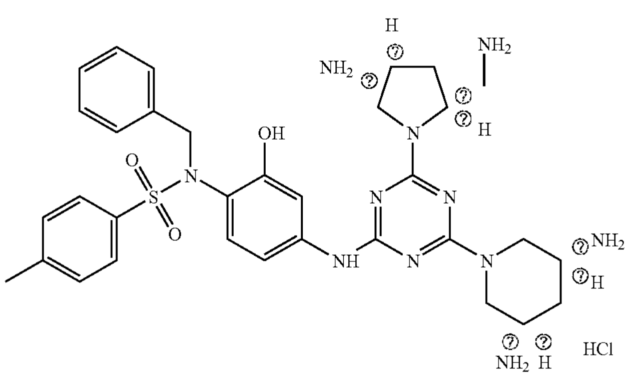 | N-{4-[4-((2S,4S)-4-Amino-2-aminomethyl-pyrrolidin-1-yl)-6-((3R,5S)-3,5-diamino-piperidin-1-yl)-[1,3,5]triazin-2-ylamino]-2-hydroxy-phenyl}-N-benzyl-4-methyl-benzenesulfonamide | + |

⑦ indicates text missing or illegible when filed

-continued

| Structure | Name | Potency |
|---|---|---|
| 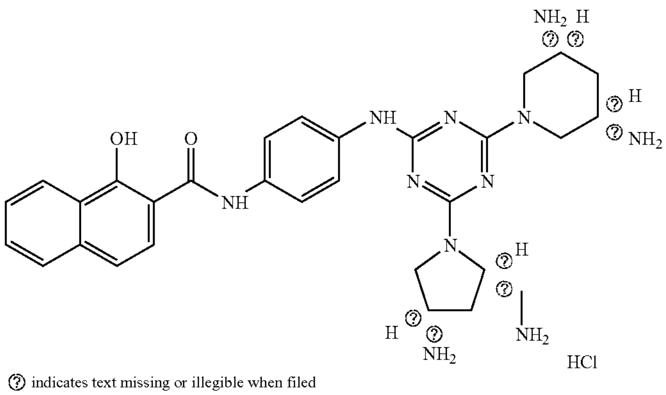 | 1-Hydroxy-naphthalene-2-carboxylic acid {4-[4-((2S,4S)-4-amino-2-aminomethyl-pyrrolidin-1-yl)-6-((3R,5S)-3,5-diamino-piperidin-1-yl)-[1,3,5]triazine-2-ylamino]-phenyl}-amide | ++ |
| 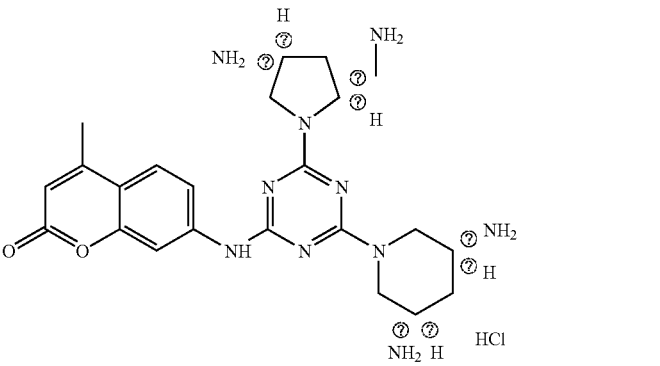 | 7-[4-((2S,4S)-4-Amino-2-aminomethyl-pyrrolidin-11-yl)-6-((3R,5S)-3,5-diamino-piperidin-1-yl)-[1,3,5]triazin-2-ylamino]-4-methyl-chromen-2-one | – |
| 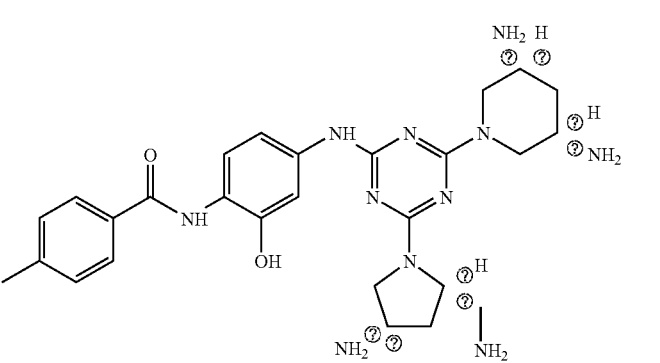 | N-{4-[4-((2S,4S)-4-Amino-2-aminomethyl-pyrrolidin-1-yl)-6-((3R,5S)-3,5-diamino-piperidin-1-yl)-[1,3,5]triazin-2-ylamino]-2-hydroxy-phenyl}-4-methyl-benzamide | + |

⑦ indicates text missing or illegible when filed

-continued

| Structure | Name | Potency |
|---|---|---|
| | 3-{4-[4-((2S,4S)-4-Amino-2-aminomethyl-pyrrolidin-1-yl)-6-((3R,5S)-3,5-diamino-piperidin-1-yl)-[1,3,5]triazin-2-ylamino]-phenyl}-3-oxo-N-(4-trifluoromethylsulfanyl-phenyl)-propionamide | ++ |
| | 2-[4-((2S,4S)-4-Amino-2-aminomethyl-pyrrolidin-1-yl)-6-((3R,5S)-3,5-diamino-piperidin-1-yl)-[1,3,5]triazin-2-ylamino]-fluoren-9-one | − |
| | 4-[4-((2S,4S)-4-Amino-2-aminomethyl-pyrrolidin-1-yl)-6-((3R,5S)-3,5-diamino-piperidin-1-yl)-[1,3,5]triazin-2-ylamino]-2-hydroxy-benzoic acid phenyl ester | ++ |

-continued
| Structure | Name | Potency |
|---|---|---|
| 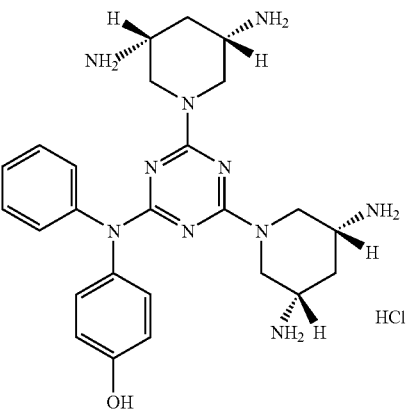 | 4-{[4,6-Bis-((3R,5S)-3,5-diamino-piperidin-1-yl)-[1,3,5]triazin-2-yl]-phenyl-amino}-phenyl | – |
| 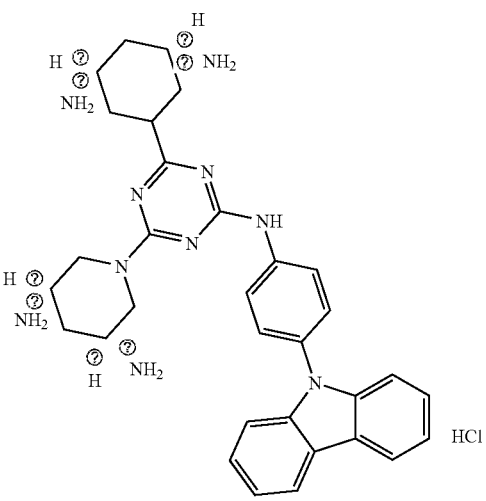 | N-(4-carbazol-9-yl-phenyl)-4,6-Bis-((3R,5S)-3,5-diamino-piperidin-1-yl)-[1,3,5]triazine-2-amine | ++ |
| 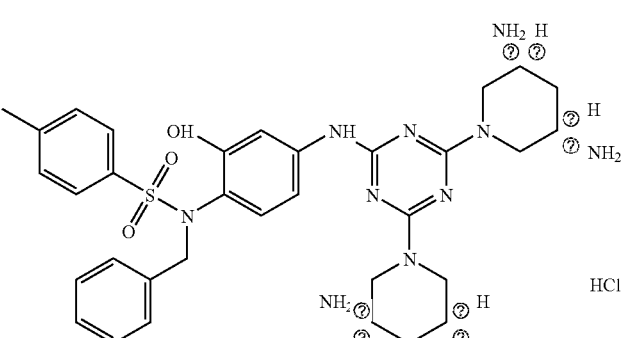 | N-{4-[benzyl-(toluene-4-sulfonyl)-amino]-3-hydroxy-phenyl}-4,6-Bis-((3R,5S)-3,5-diamino-piperidin-1-yl)-[1,3,5]triazine-2-amine | ++ |
⊘ indicates text missing or illegible when filed

| Structure | Name | Potency |
|---|---|---|
| 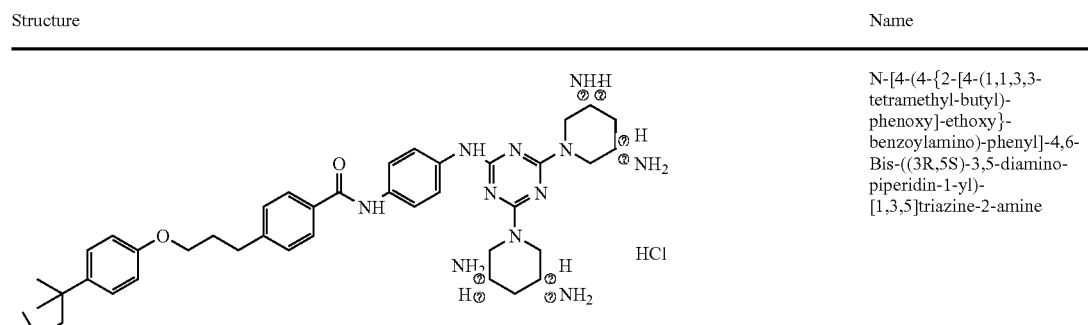 | N-[4-(4-{2-[4-(1,1,3,3-tetramethyl-butyl)-phenoxy]-ethoxy}-benzoylamino)-phenyl]-4,6-Bis-((3R,5S)-3,5-diamino-piperidin-1-yl)-[1,3,5]triazine-2-amine | – |
| 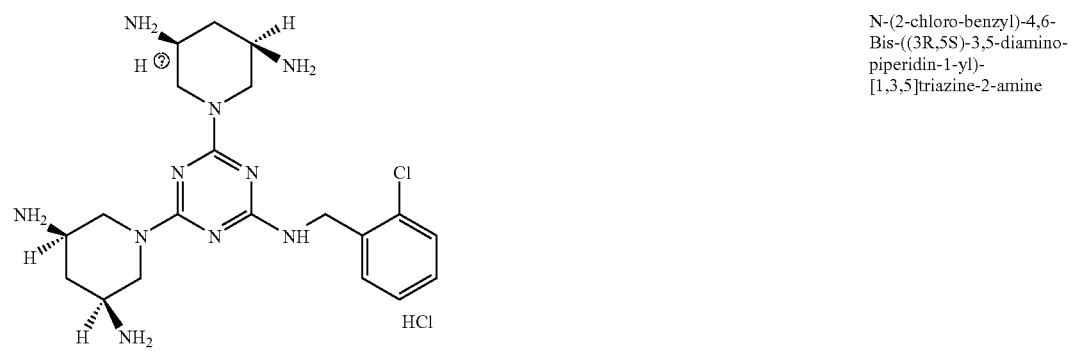 | N-(2-chloro-benzyl)-4,6-Bis-((3R,5S)-3,5-diamino-piperidin-1-yl)-[1,3,5]triazine-2-amine | |
| 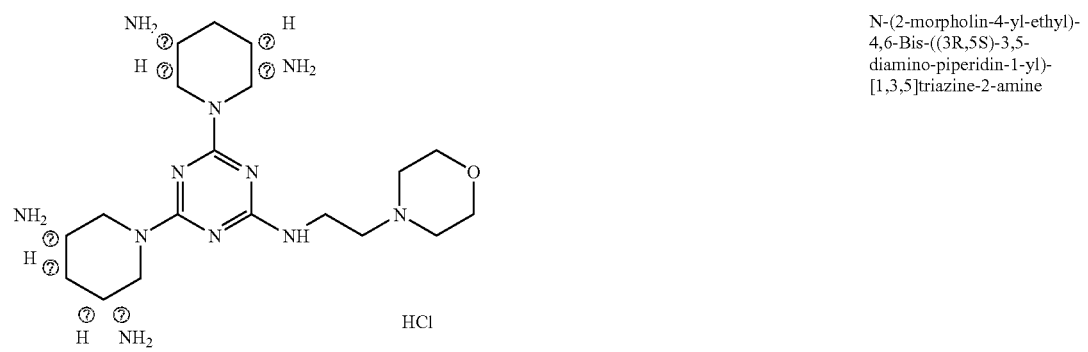 | N-(2-morpholin-4-yl-ethyl)-4,6-Bis-((3R,5S)-3,5-diamino-piperidin-1-yl)-[1,3,5]triazine-2-amine | |
| 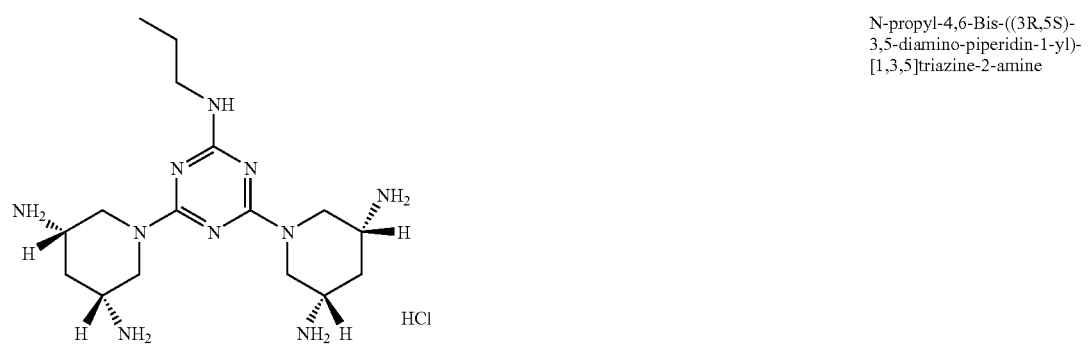 | N-propyl-4,6-Bis-((3R,5S)-3,5-diamino-piperidin-1-yl)-[1,3,5]triazine-2-amine | |

-continued
| Structure | Name | Potency |
|---|---|---|
| 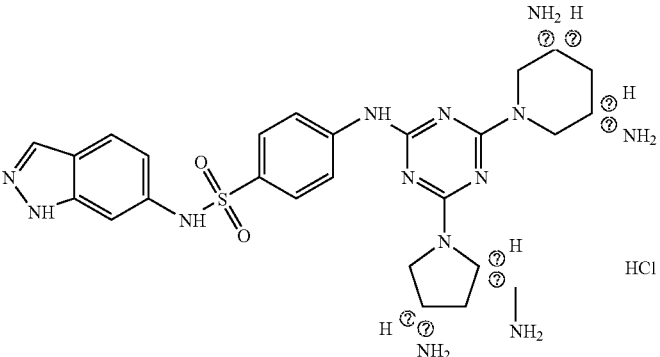 | 4-[4-((2S,4S)-4-Amino-2-aminomethyl-pyrrolidin-1-yl)-6-((3R,5S)-3,5-diamino-piperidin-1-yl)-[1,3,5]triazin-2-ylamino]-N-(1H-indazol-6-yl)-benzenesulfonamide | − |
| 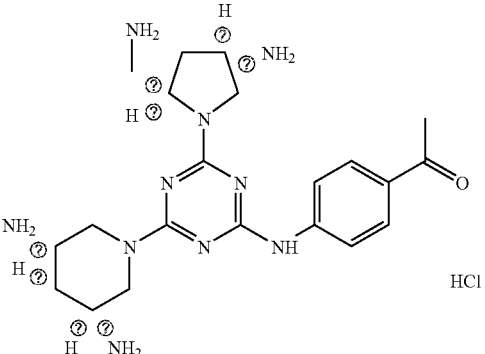 | 1-{4-[4-((2S,4S)-4-Amino-2-aminomethyl-pyrrolidin-1-yl)-6-((3R,5S)-3,5-diamino-piperidin-1-yl)-[1,3,5]triazin-2-ylamino]-phenyl}-ethanone | − |
| 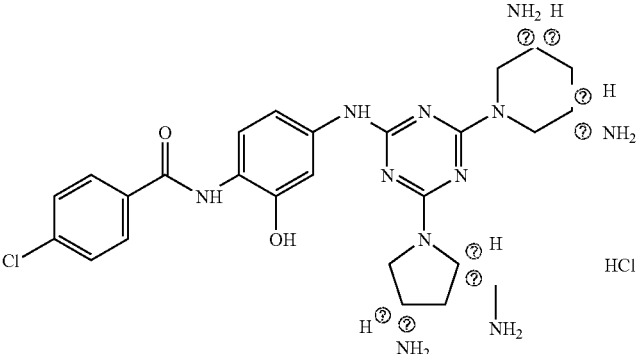 | N-{4-[4-((2S,4S)-4-Amino-2-aminomethyl-pyrrolidin-1-yl)-6-((3R,5S)-3,5-diamino-piperidin-1-yl)-[1,3,5]triazin-2-ylamino]-2-hydroxy-phenyl}-4-chloro-benzamide | ++ |

-continued

| Structure | Name | Potency |
|---|---|---|
| | 3-{4-[4-((2S,4S)-4-Amino-2-aminomethyl-pyrrolidin-1-yl)-6-((3R,5S)-3,5-diamino-piperidin-1-yl)-[1,3,5]triazin-2-ylamino]-phenyl}-N-(3,4-difluoro-phenyl)-3-oxo-propionamide | + |
| 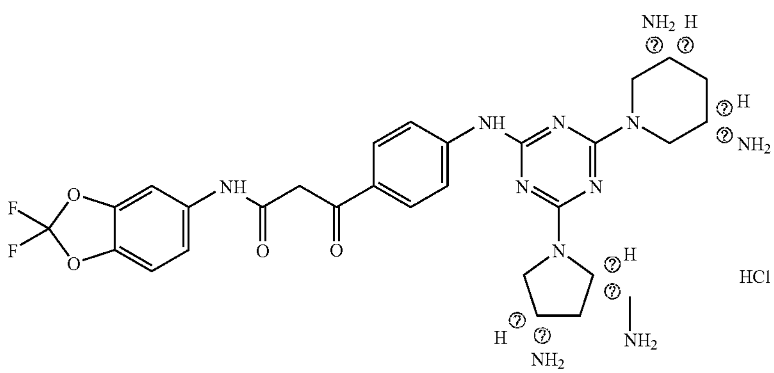 | 3-{4-[4-((2S,4S)-4-Amino-2-aminomethyl-pyrrolidin-1-yl)-6-((3R,5S)-3,5-diamino-piperidin-1-yl)-[1,3,5]triazin-2-ylamino]-phenyl}-N-(2,2-difluoro-benzo[1,3]dioxol-5-yl)-3-oxo-propionamide | |
| 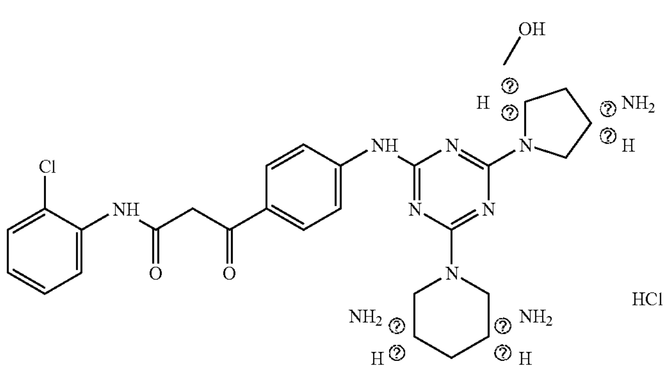 | 3-{4-[4-((2S,4S)-4-Amino-2-hydroxymethyl-pyrrolidin-1-yl)-6-((3R,5S)-3,5-diamino-piperidin-1-yl)-[1,3,5]triazin-2-ylamino]-phenyl}-N-(2-chloro-phenyl)-3-oxo-propionamide | + |

-continued

| Structure | Name | Potency |
|---|---|---|
| 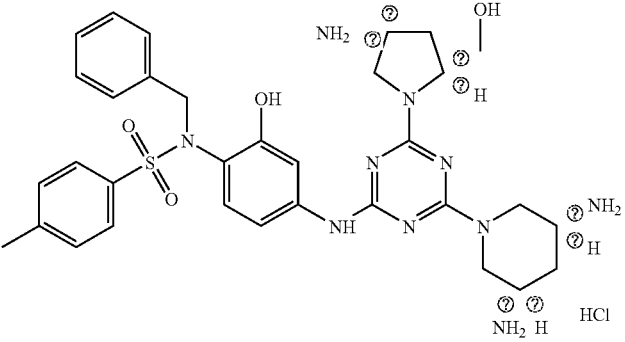 | N-{4-[4-((2S,4S)-4-Amino-2-hydroxymethyl-pyrrolidin-1-yl)-6-((3R,5S)-3,5-diamino-piperidin-1-yl)-[1,3,5]triazin-2-ylamino]-2-hydroxy-phenyl}-N-benzyl-4-methyl-benzenesulfonamide | + |

⑦ indicates text missing or illegible when filed

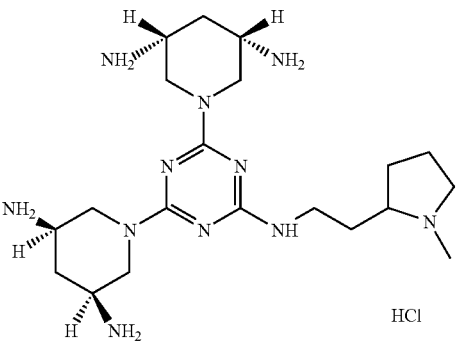

N-[2-(1-medthyl-pyrrolidin-2-yl)-ethyl]-4,6-Bis-((3R,5S)-3,5-diamino-piperidin-1-yl)-[1,3,5]triazine-2-amine   −

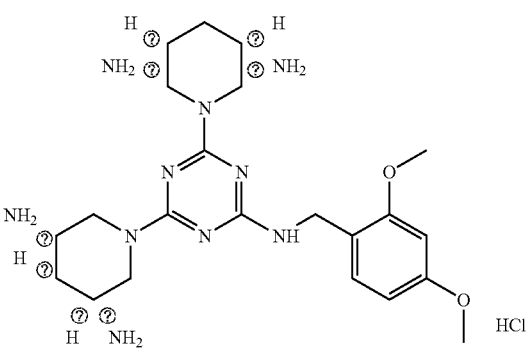

N-(2,4-dimethoxy-benzyl)-4,6-Bis((3R,5S)-3,5-diamino-piperidin-1-yl)-[1,3,5]triazine-2-amine ⑦ indicates text missing or illegible when filed

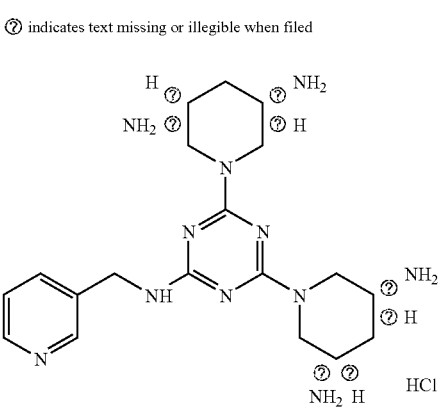

N-pyridin-3-ylmethyl-4,6-Bis-((3R,5S)-3,5-diamino-piperidin-1-yl)-[1,3,5]triazine-2-amine ⑦ indicates text missing or illegible when filed -continued
| Structure | Name | Potency |
|---|---|---|
| 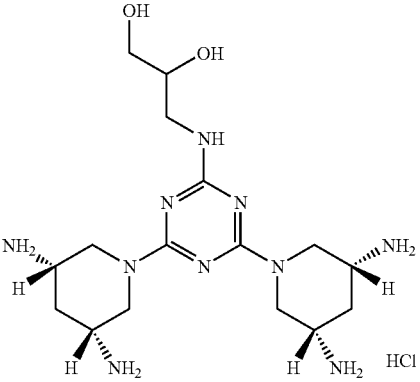 | N-(2,3-dihydroxy-propyl)-4,6-Bis-((3R,5S)-3,5-diamino-piperidin-1-yl)-[1,3,5]triazine-2-amine | |
| 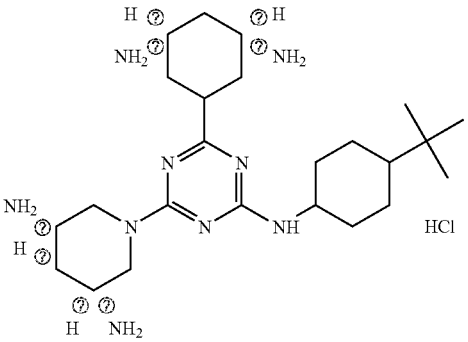 | N-(4-tert-butyl-cyclohexyl)-4,6-Bis-((3R,5S)-3,5-diamino-piperidin-1-yl)-[1,3,5]triazine-2-amine | |
| 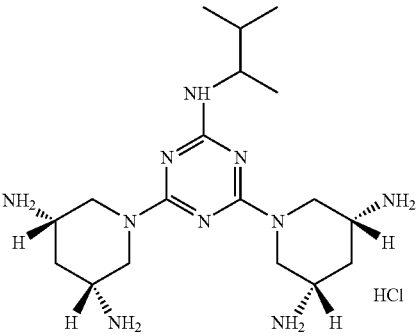 | N-(1,2-dimethyl-propyl)-4,6-Bis-((3R,5S)-3,5-diamino-piperidin-1-yl)-[1,3,5]triazine-2-amine | |
| 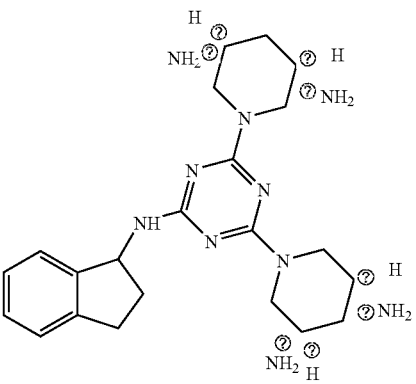 | N-indan-1-yl-4,6-Bis-((3R,5S)-3,5-diamino-piperidin-1-yl)-[1,3,5]triazine-2-amine | |
⑦ indicates text missing or illegible when filed -continued

| Structure | Name | Potency |
|---|---|---|
| 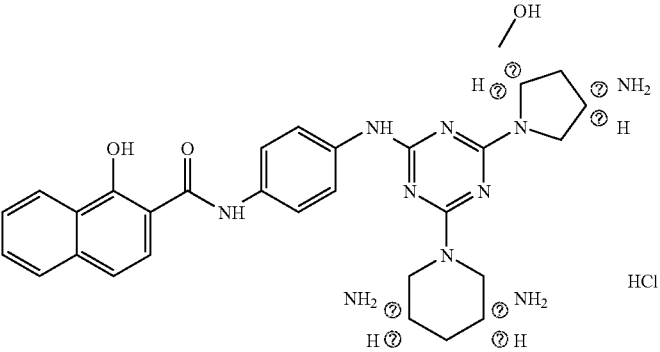 | carboxylic acid {4-[4-((2S,4S)-4-amino-2-hydroxymethyl-pyrrolidin-1-yl)-6-((3R,5S)-3,5-diamino-piperidin-1-yl)-[1,3,5]triazine-2-ylamino]-phenyl}-amide | ++ |
| ⑦ indicates text missing or illegible when filed | | |
| 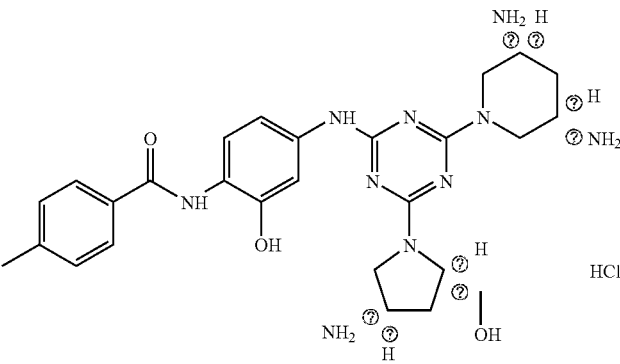 | N-{4-[4-((2S,4S)-4-Amino-2-hydroxymethyl-pyrrolidin-1-yl)-6-((3R,5S)-3,5-diamino-0piperidin-1-yl)-[1,3,5]triazin-2-ylamino]-2-hydroxy-phenyl}-4-methyl-benzamide | |
| ⑦ indicates text missing or illegible when filed | | |
| 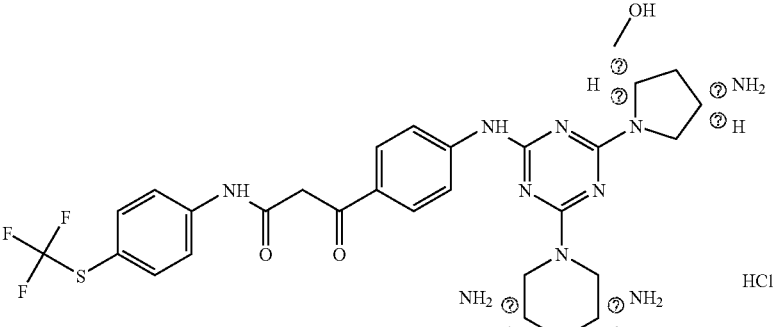 | 3-{4-[4-((2S,4S)-4-Amino-2-hydroxymethyl-pyrrolidin-1-yl)-6-((3R,5S)-3,5-diamino-piperidin-1-yl)-[1,3,5]triazin-2-ylamino]-phenyl}-3-oxo-N-(4-trifluoromethylsulfanyl-phenyl)-propionamide | ++ |
| ⑦ indicates text missing or illegible when filed | | |

| Structure | Name | Potency |
|---|---|---|
| 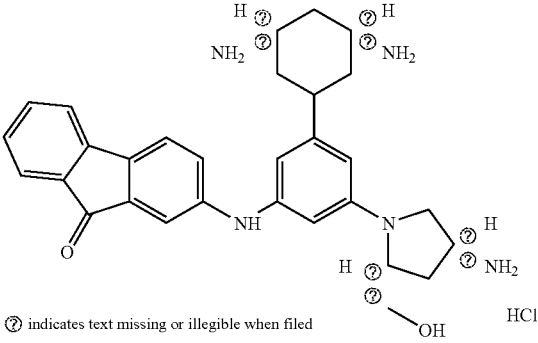 | 2-[4-((2S,4S)-4-Amino-2-hydroxymethyl-pyrrolidin-1-yl)-6-((3R,5S)-3,5-diamino-piperidin-1-yl)-[1,3,5]triazin-2-ylamino]-fluoren-9-one | – |
| 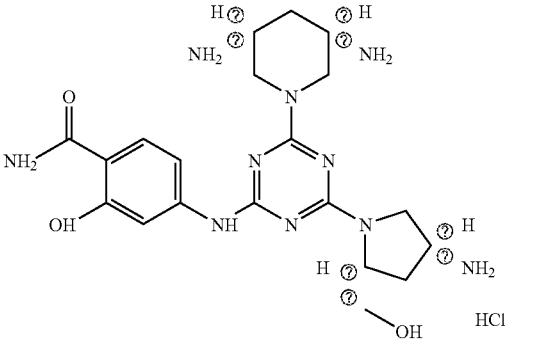 | 4-[4-((2S,4S)-4-Amino-2-hydroxymethyl-pyrrolidin-1-yl)-6-((3R,5S)-3,5-diamino-piperidin-1-yl)-[1,3,5]triazin-2-ylamino]-2-hydroxy-benzamide | – |
| 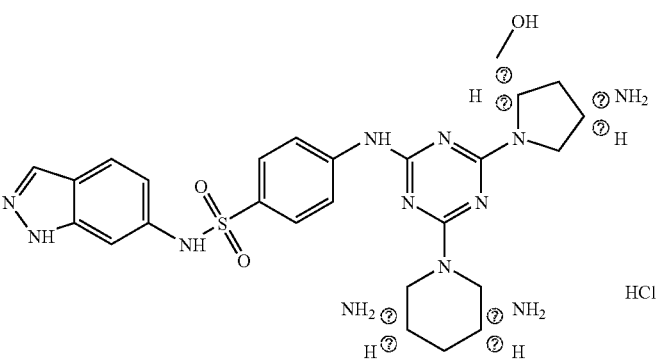 | 4-[4-((2S,4S)-4-Amino-2-hydroxymethyl-pyrrolidin-1-yl)-6-((3R,5S)-3,5-diamino-piperidin-1-yl)-[1,3,5]triazin-2-ylamino]-N-(1H-indazol-6-yl)-benzenesulfonamide | – |
| 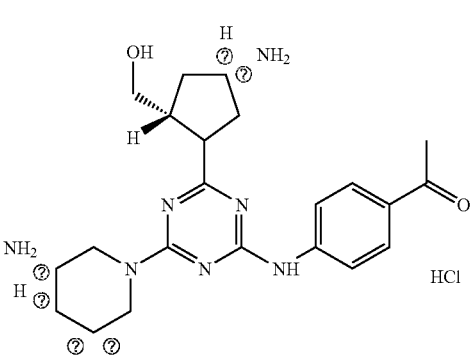 | 1-{4-[4-((2S,4S)-4-Amino-2-hydroxymethyl-pyrrolidin-1-yl)-6-((3R,5S)-3,5-diamino-piperidin-1-yl)-[1,3,5]triazin-2-ylamino]-phenyl}-ethanone | – |

-continued

| Structure | Name | Potency |
|---|---|---|
| 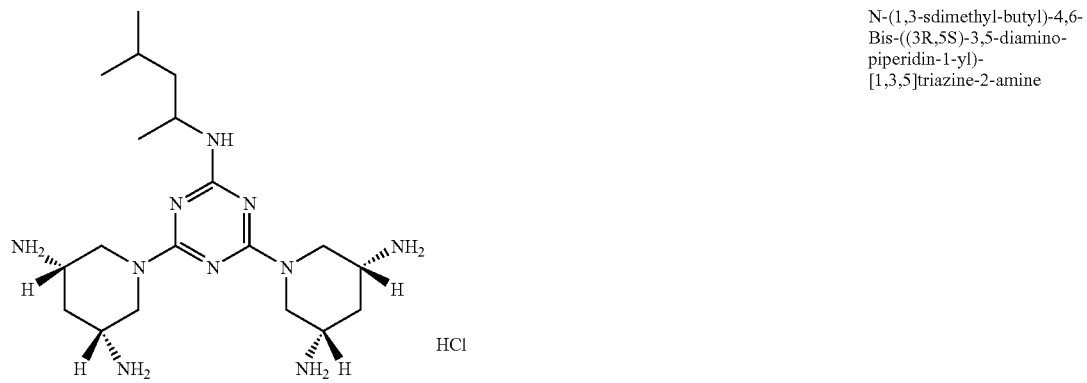 | N-(1,3-sdimethyl-butyl)-4,6-Bis-((3R,5S)-3,5-diamino-piperidin-1-yl)-[1,3,5]triazine-2-amine | |
| 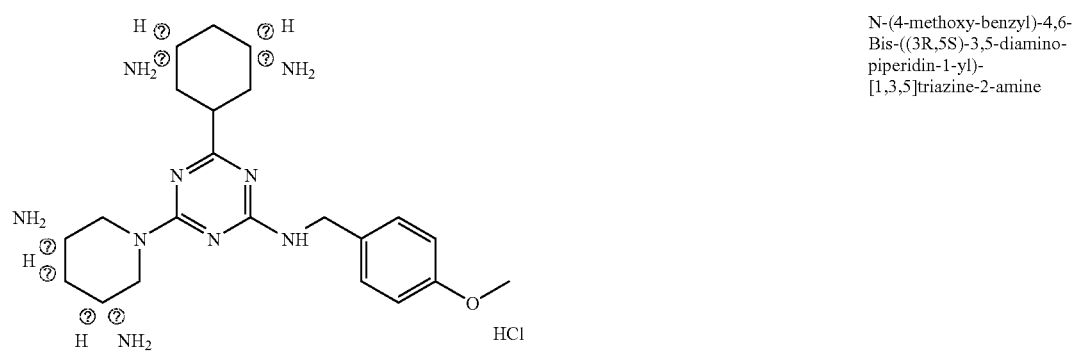 | N-(4-methoxy-benzyl)-4,6-Bis-((3R,5S)-3,5-diamino-piperidin-1-yl)-[1,3,5]triazine-2-amine | |
| 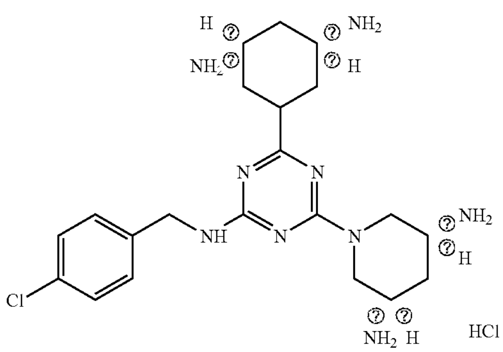 | N-(4-chloro-benzyl)-4,6-Bis-((3R,5S)-3,5-diamino-piperidin-1-yl)-[1,3,5]triazine-2-amine | |
| 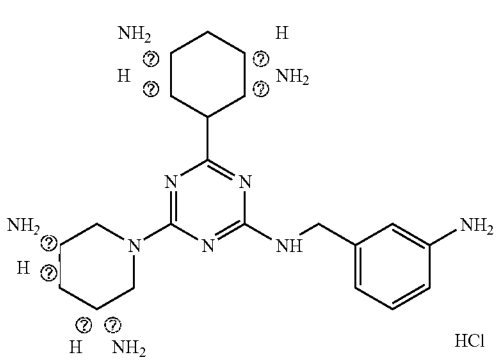 | N-(3-amino-benzyl)-4,6-Bis-((3R,5S)-3,5-diamino-piperidin-1-yl)-[1,3,5]triazine-2-amine | |

⑦ indicates text missing or illegible when filed

⑦ indicates text missing or illegible when filed

⑦ indicates text missing or illegible when filed

-continued

| Structure | Name | Potency |
|---|---|---|
| 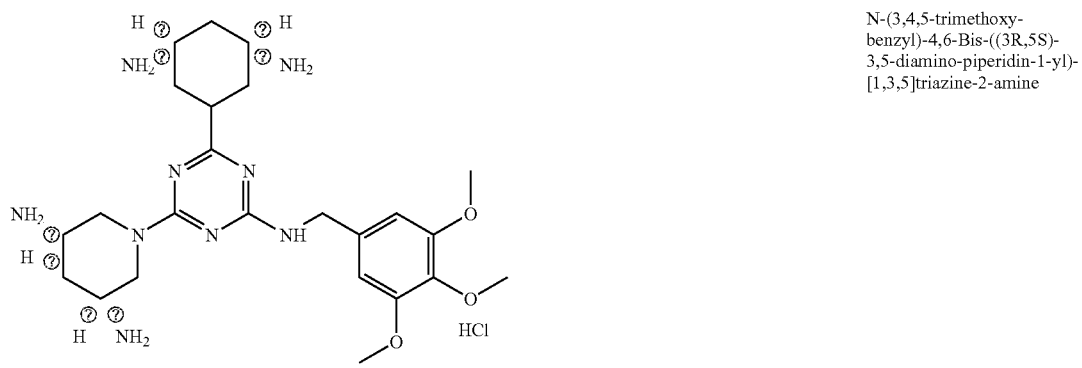 ⑦ indicates text missing or illegible when filed | N-(3,4,5-trimethoxy-benzyl)-4,6-Bis-((3R,5S)-3,5-diamino-piperidin-1-yl)-[1,3,5]triazine-2-amine | |
| 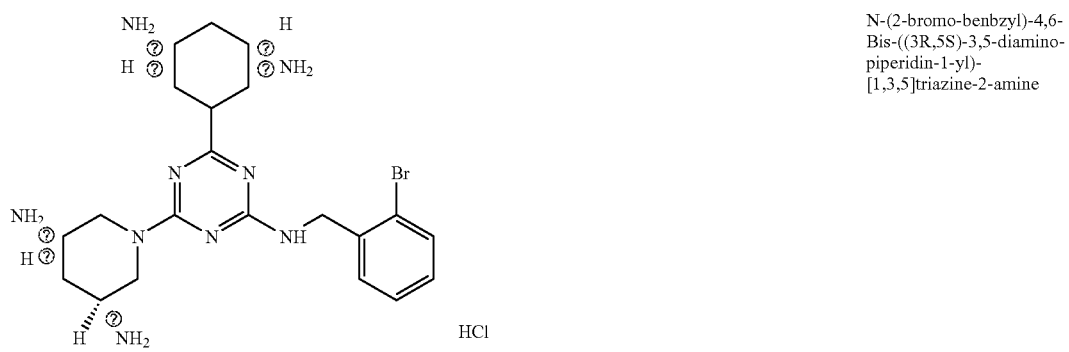 ⑦ indicates text missing or illegible when filed | N-(2-bromo-benbzyl)-4,6-Bis-((3R,5S)-3,5-diamino-piperidin-1-yl)-[1,3,5]triazine-2-amine | |
| 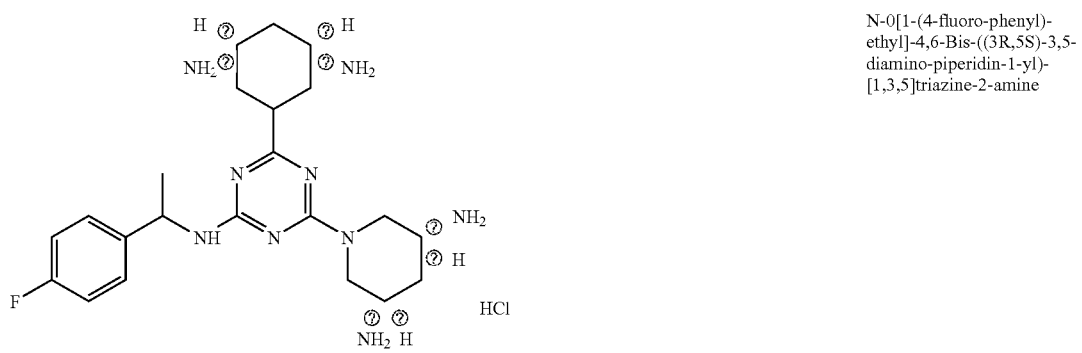 ⑦ indicates text missing or illegible when filed | N-0[1-(4-fluoro-phenyl)-ethyl]-4,6-Bis-((3R,5S)-3,5-diamino-piperidin-1-yl)-[1,3,5]triazine-2-amine | |

-continued

| Structure | Name | Potency |
|---|---|---|
| | N-{4-[4-((2S,4S)-4-Amino-2-hydroxymethyl-pyrrolidin-1-yl)-6-((3R,5S)-3,5-diamino-piperidin-1-yl)-[1,3,5]triazin-2-ylamino]-2-hydroxy-phenyl}-4-chlorobenzamide | + |
| 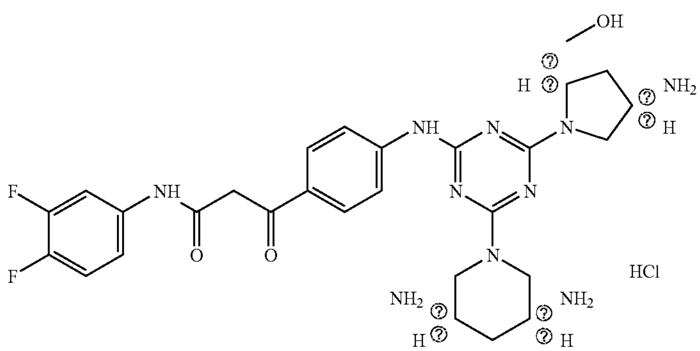 | 3-{4-[4-((2S,4S)-4-Amino-2-hydroxymethyl-pyrrolidin-1-yl)-6-((3R,5S)-3,5-diamino-piperidin-1-yl)-[1,3,5]triazin-2-ylamino]-phenyl}-N-(3,4-difluoro-phenyl)-3-oxo-propionamide | + |
| 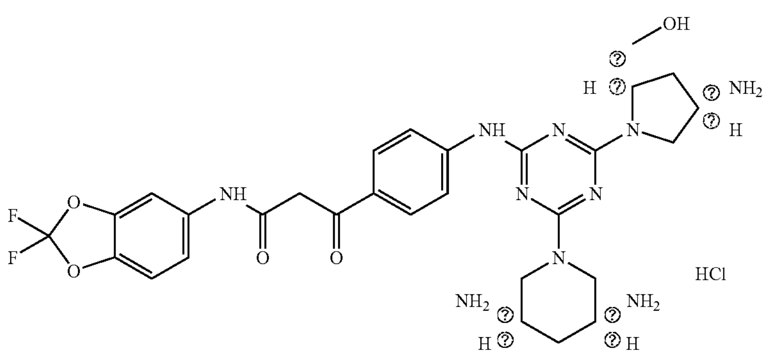 | 3-{4-[4-((2S,4S)-4-Amino-2-hydroxymethyl-pyrrolidin-1-yl)-6-((3R,5S)-3,5-diamino-piperidin-1-yl)-[1,3,5]triazin-2-ylamino]-phenyl}-N-(2,2-difluoro-benzo[1,3]dioxol-5-yl)-3-oxo-propionamide | ++ |
| 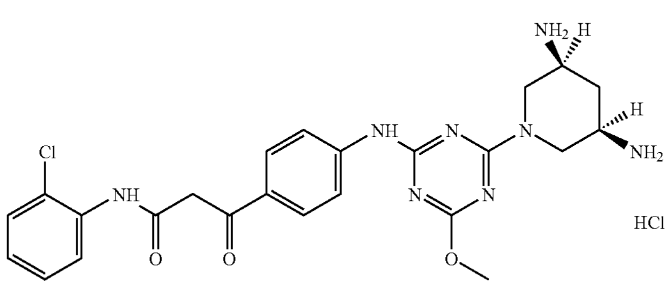 | N-(2-Chloro-phenyl)-3-{4-[4-((3R,5S)-3,5-diamino-piperidin-1-yl)-6-methoxy-[1,3,5]triazin-2-ylamino]-phenyl}-3-oxo-propionamide | ++ |

-continued

| Structure | Name | Potency |
|---|---|---|
|  | N-Benzyl-N-{4-[4-((3R,5S)-3,5-diamino-piperidin-1-yl)-6-methoxy-[1,3,5]triazin-2-ylamino]-2-hydroxy-phenyl}-4-methyl-benzenesulfonamide | ++ |
| 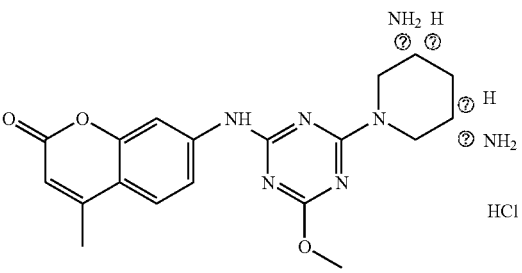 | 1-Hydroxy-naphthalene-2-carboxylic acid {4-[4-((3R,5S)-3,5-diamino-piperidin-1-yl)-6-methoxy-[1,3,5]triazin-2-ylamino]-phenyl}-amide | ++ |
| 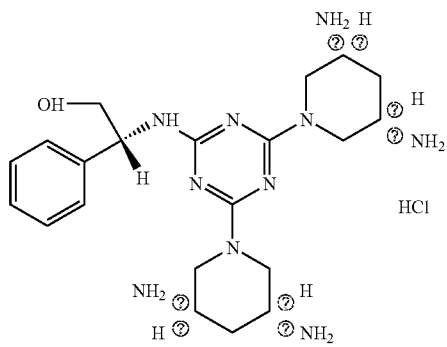 | 7-[4-((3R,5S)-3,5-DSiamino-piperidin-1-yl)-6-methoxy-[1,3,5]triazin-2-ylamino]-4-methyl-chromen-2-one | − |
| 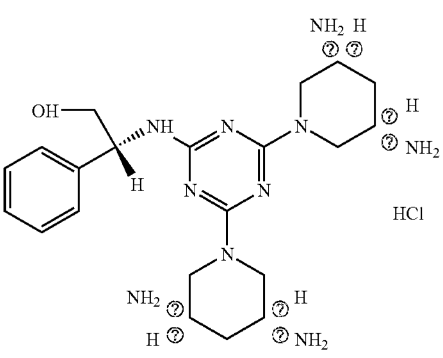 | (R)-2-[4-((3R,5S)-3,5-Diamino-piperidin-1-yl)-6-((3S,5R)-3,5-diamino-piperidin-1-yl)-[1,3,5]triazin-2-ylamino]-2-phenyl-ethanol | |

-continued
| Structure | Name | Potency |
|---|---|---|
| 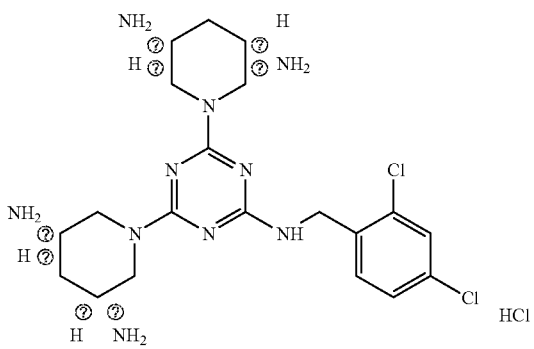 | N-indan-2-yl-4,6-Bis-((3R,5S)-3,5-diamino-piperidin-1-yl)-[1,3,5]triazine-2-amine | |
| 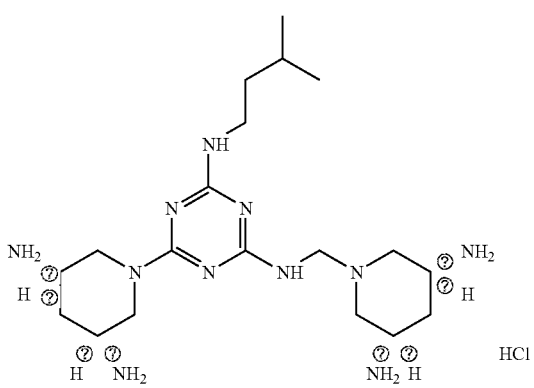 | N-(2,4-dichloro-benzyl)-4,6-Bis-((3R,5S)-3,5-diamino-piperidin-1-yl)-[1,3,5]triazin-2-amine | — |
| 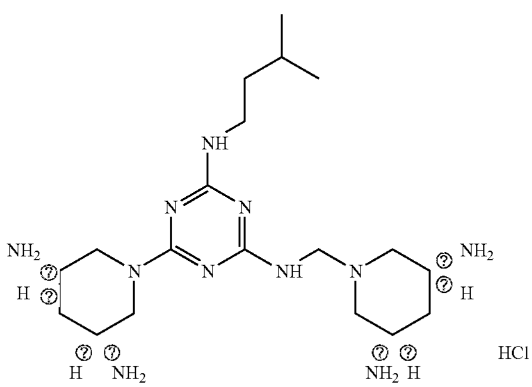 | N-(3-methyl-butyl)-4,6-Bis-((3R,5S)-3,5-diamino-piperidin-1-yl)-[1,3,5]triazine-2-amine | |
| 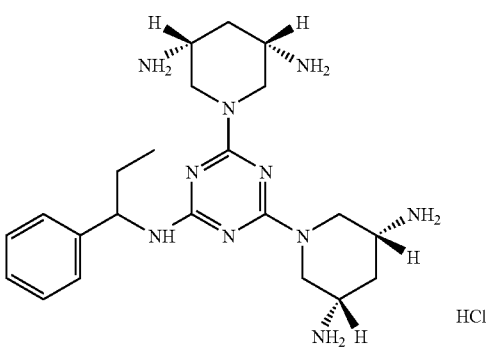 | N-(1-phenyl-propyl)-4,6-Bis-((3R,5S)-3,5-diamino-piperidin-1-yl)-[1,3,5]triazine-2-amine | |
⑦ indicates text missing or illegible when filed -continued

| Structure | Name | Potency |
|---|---|---|
| 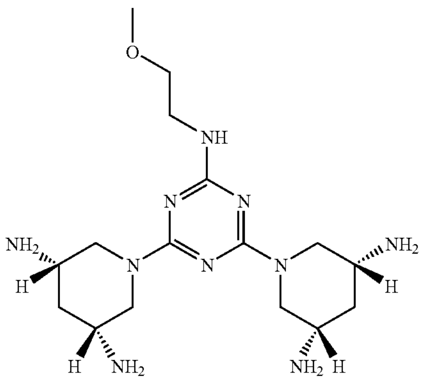 | N-(2-methoxy-ethyl)-4,6-Bis-((3R,5S)-3,5-diamino-piperidin-1-yl)-[1,3,5]triazine-2-amine | |
| 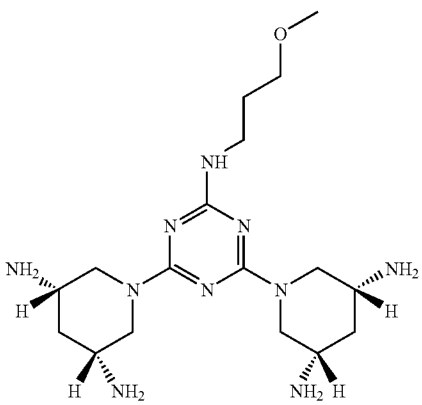 | N-(3-methoxy-propyl)-4,6-Bis-((3R,5S)-3,5-diamino-piperidin-1-yl)-[1,3,5]triazine-2-amine | |
| 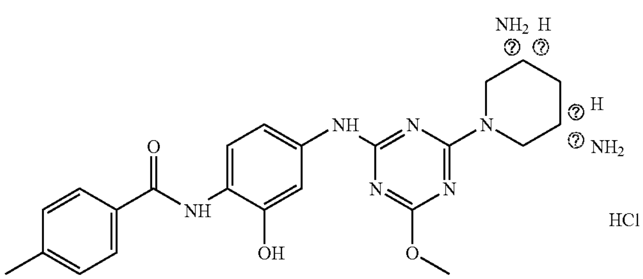 | N-{4-[4-((3R,5S)-3,5-Diamino-piperidin-1-yl)-6-methoxy-[1,3,5]triazin-2-ylamino]-2-hydroxy-phenyl}-4-methyl-benzamide | + |

⑦ indicates text missing or illegible when filed

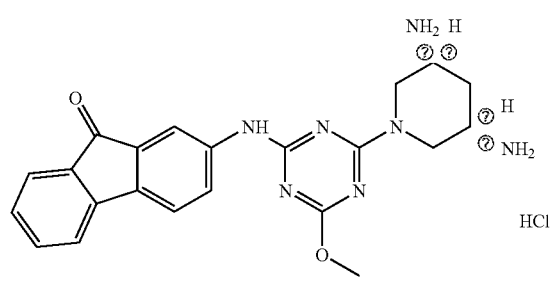

| | 3-{4-[4-((3R,5S)-3,5-Diamino-piperidin-1-yl)-6-methoxy-[1,3,5]triazin-2-ylamino]-phenyl}-3-oxo-N-(4-trifluoromethylsulfanyl-phenyl)-propionamide | ++ |

⑦ indicates text missing or illegible when filed

-continued
| Structure | Name | Potency |
|---|---|---|
| 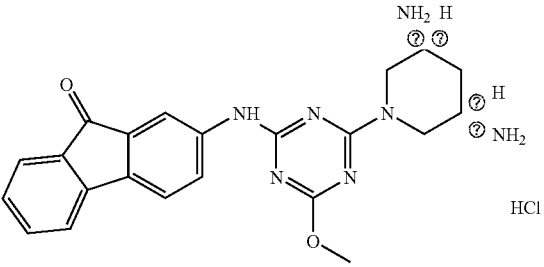 | 2-[4-((3R,5S)-3,5-Diamino-piperidin-1-yl)-6-methoxy-[1,3,5]triazin-2-ylamino]-fluoren-9-one | − |
| 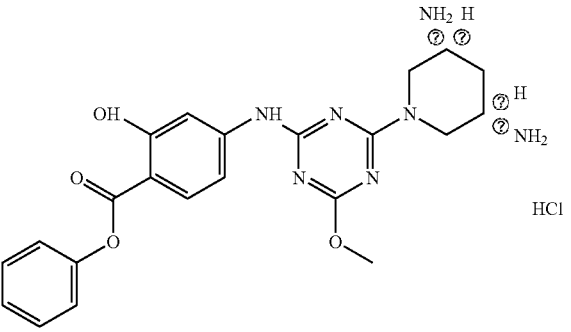 | 4-[4-((3R,5S)-3,5-Diamino-piperidin-1-yl)-6-methoxy-[1,3,5]triazin-2-ylamino]-2-hydroxy-benzoic acid phenylester | ++ |
| 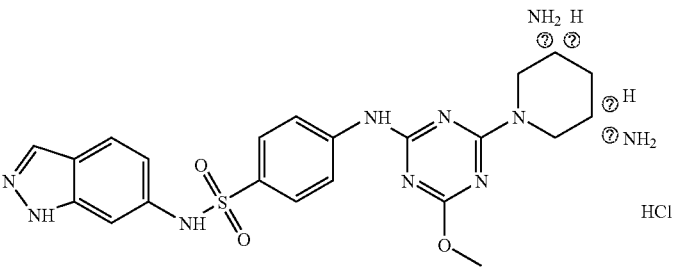 | 4-[4-((3R,5S)-3,5-Diamino-piperidin-1-yl)-6-methoxy-[1,3,5]triazin-2-ylamino]-N-(1H-indazol-6-yl)-benzenesulfonamide | − |
| 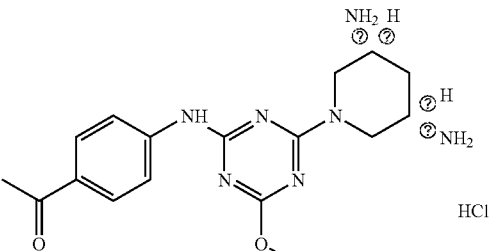 | 1-{4-[4-((3R,5S)-3,5-Diamino-piperidin-1-yl)-6-methoxy-[1,3,5]triazin-2-ylamino]-phenyl}-ethanone | − |

-continued

| Structure | Name | Potency |
|---|---|---|
| 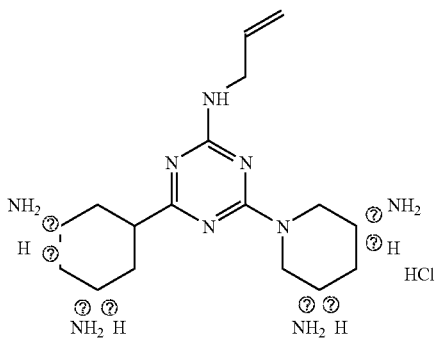 | 4-Chloro-N-{4-[4-((3R,5S)-3,5-diamino-piperidin-1-yl)-6-methoxy-[1,3,5]triazin-2-ylamino]-2-hydroxy-phenyl}-benzamide | ++ |
| ⑦ indicates text missing or illegible when filed | | |
| 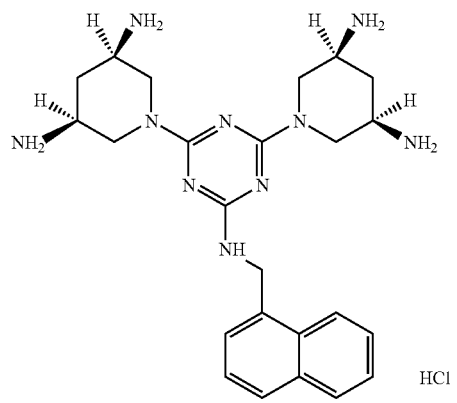 | N-allyl-4,6-Bis-((3R,5S)-3,5-diamino-piperidin-1-yl)-[1,3,5]triazine-2-amine | |
| ⑦ indicates text missing or illegible when filed | | |
| 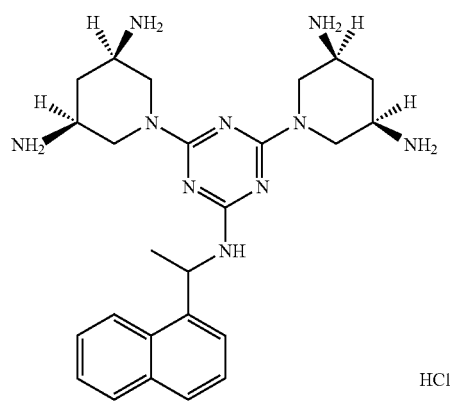 | N-naphthalene-1-ylmethyl-4,6-Bis-((3R,5S)-3,5-diamino-piperidin-1-yl)-[1,3,5]triazine-2-amine | |
| 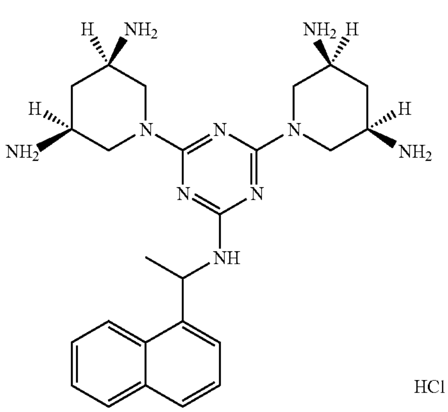 | N-(1-naphthalen-1-yl-ethyl)-4,6-Bis-((3R,5S)-3,5-diamino-piperidin-01-yl)-[1,3,5]triazine-2-amine | |

-continued

| Structure | Name | Potency |
|---|---|---|
| 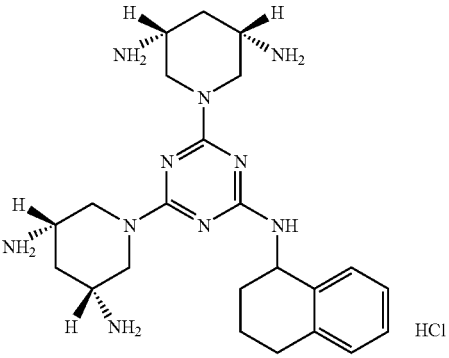 | N-(1,2,3,4-tetrahydro-naphthalen-1-yl)-4,6-Bis-((3R,5S)-3,5-diamino-piperidin-1-yl)-[1,3,5]triazine-2-amine | |
| 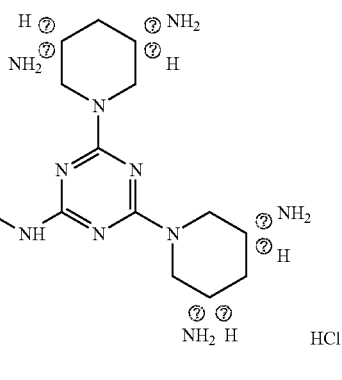 | N-(3,5-bis-trifluoromethyl-benzyl)-4,6-Bis-((3R,5S)-3,5-diamino-piperidin-1-yl)-[1,3,5]triazine-2-amine | |

⑦ indicates text missing or illegible when filed

| | | |
|---|---|---|
| 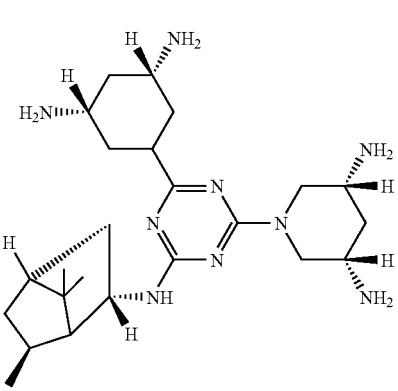 | N-((1R,2S,4R)-1,7,7-trimethyl-bicyclo[2.2.1]hept-2-yl)-4,6-Biss-((3R,5S)-3,5-diamino-piperidin-1-yl)-[1,3,5]triazine-2-amine | |
| 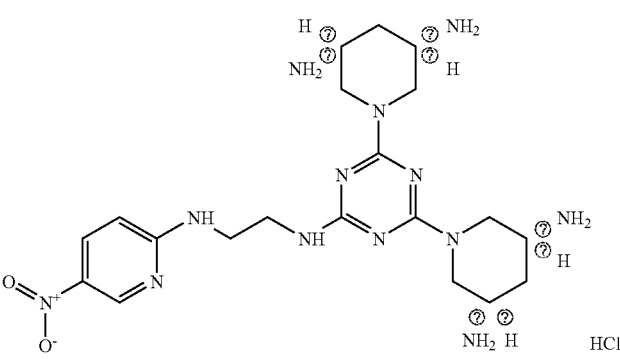 | N-[2-(5-nitro-pyridin-2-ylamino)-ethyl]-4,6-Bis-((3R,5S)-3,5-diamino-piperidin-1-yl)-[1,3,5]triazine-2-amine | – |

⑦ indicates text missing or illegible when filed

-continued

| Structure | Name | Potency |
|---|---|---|
| 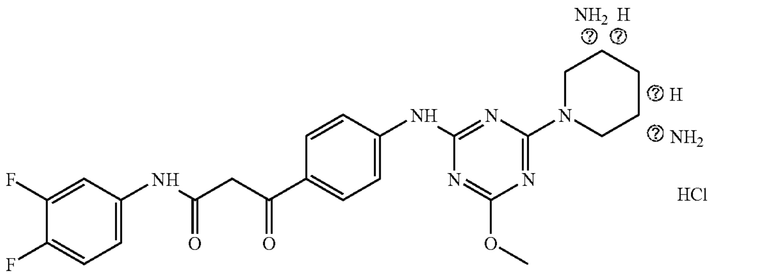 | 3-{4-[4-((3R,5S)-3,5-Diamino-piperidin-1-yl)-6-methoxy-[1,3,5]triazin-2-ylamino]-phenyl}-N-(3,4-difluoro-phenyl)-3-oxo-propionamide | ++ |
| 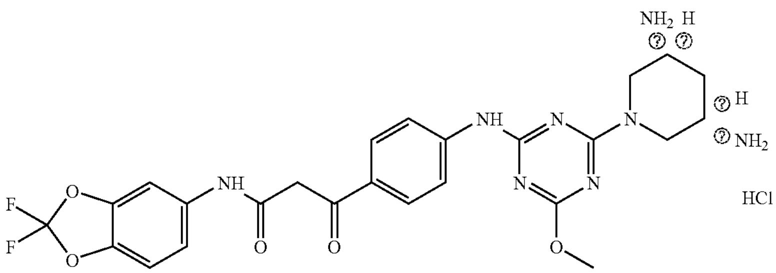 | 3-{4-[4-((3R,5S)-3,5-Diamino-piperidin-1-yl)-6-methoxy-[1,3,5]triazin-2-ylamino]-phenyl}-N-(2,2-difluoro-benzo[1,3]dioxol-5-yl)-3-oxo-propionamide | ++ |
| 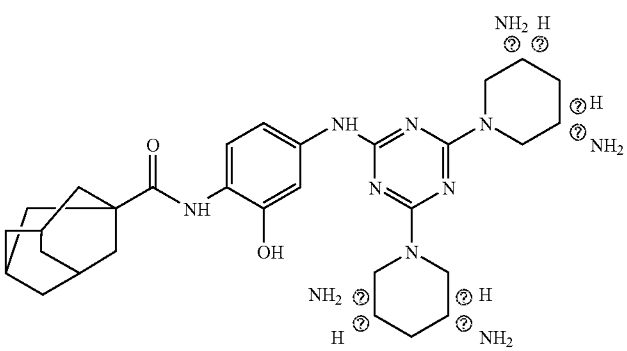 | N-{4-[(adamantane-1-carbonyl)-amino]-3-hydroxy-phenyl}-4,6-Bis-((3R,5S)-3,5-diamino-piperidin-1-yl)-[1,3,5]triazine-2-amine | ++ |
| 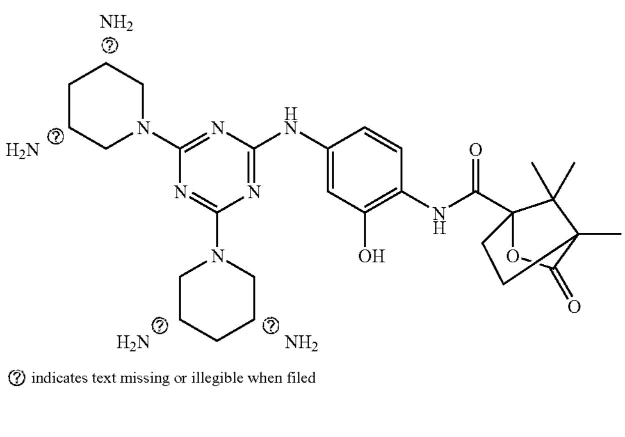 | (S)-4,7,7-Trimethyl-3-oxo-2-oxa-bicyclo[2.2.1]heptane-1-carboxylic acid {4-[4,6-bis-((3R,5S)-3,5-diamino-piperidin-1-yl)-[1,3,5]triazin-2-ylamino]-2-hydroxy-phenyl}-amide | + |

⊙ indicates text missing or illegible when filed

-continued

| Structure | Name | Potency |
|---|---|---|
| 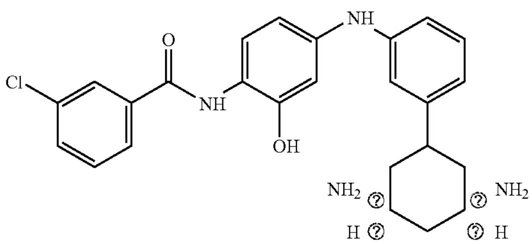 | N-[4-(3-chloro-benzoylamino)-3-hydroxy-phenyl]-4,6-Bis-((3R,5S)-3,5-diamino-piperidin-1-yl)-[1,3,5]triazine-2-amine | ++ |
| 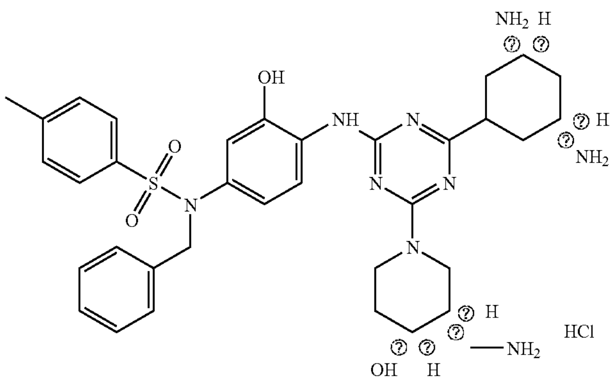 | N-{4-[4-((3R,4S)-3-Aminomethyl-4-hydroxy-piperidin-1-yl)-6-((3R,5S)-3,5-diamino-piperidin-1-yl)-[1,3,5]triazin-2-ylamino]-3-hydroxy-phenyl}-N-benzyl-4-methyl-benzenesulfonamide | + |
| 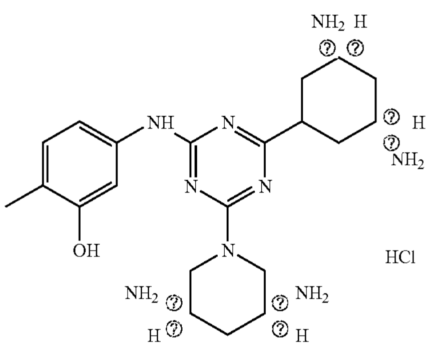 | N-{4-[4-((3R,4S)-3-Aminomethyl-4-hydroxy-piperidin-1-yl)-6-((3R,5S)-3,5-diamino-piperidin-1-yl)-[1,3,5]triazin-2-ylamino]-2-hydroxy-phenyl}-4-chloro-benzamide | + |
| 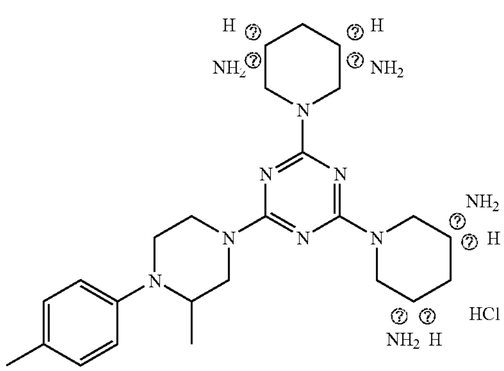 | 2,4-Bis-((3R,5S)-3,5-diamino-piperidin-1-yl)-6-(3-methyl-piperidin-1-yl)-[1,3,5]triazine | |

-continued

| Structure | Name | Potency |
|---|---|---|
| 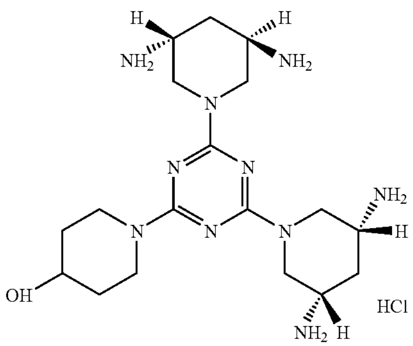 | 1-(4,6-Bis-((3R,5S)-3,5-diamino-piperidin-1-yl)-[1,3,5]triazin-2-yl)-decahydro-quinoline | |
| 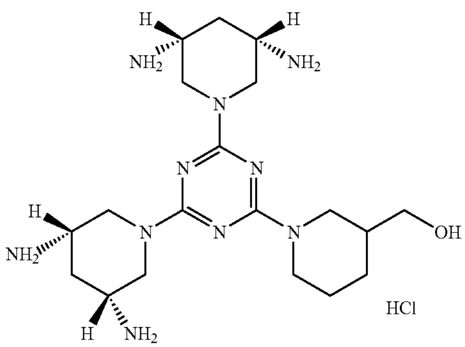 | 2,4-Bis-((3R,5S)-3,5-diamino-piperidin-1-yl)-6-morpholin-4-yl-[1,3,5]triazine | |
| 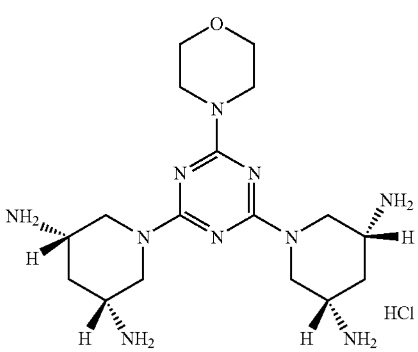 | 2-[4-(2,4-Bis-((3R,5S)-3,5-diamino-piperidin-1-yl)-phenyl)-piperazin-1-yl]-4,6-Bis-((3R,5S)-3,5-diamino-piperidin-1-yl)-[1,3,5]triazine | |
| 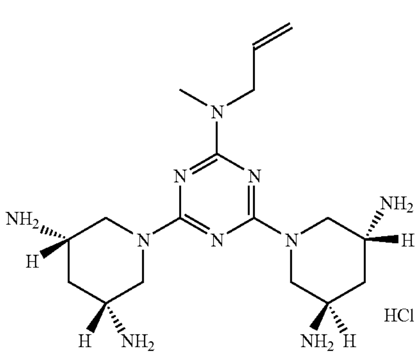 | N-allyl-N-methyl-4,6-Bis-((3R,5S)-3,5-diamino-piperidin-1-yl)-[1,3,5]triazine-2-amine | |

-continued

| Structure | Name | Potency |
|---|---|---|
| 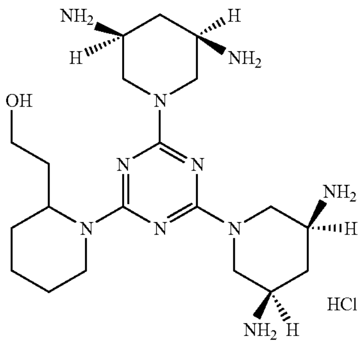 | 5-Bromo-1-(4,6-Bis-((3R,5S)-3,5-diamino-piperidin-1-yl)-[1,3,5]triazin-2-yl)-2,3-dihydro-1H-indole | |
| 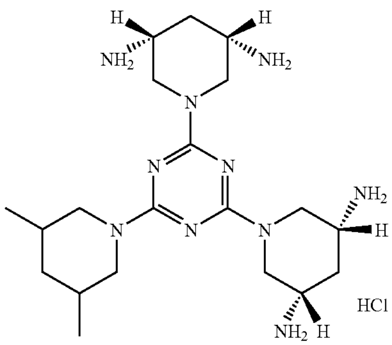 | 2-[1-(4,6-Bis-((3R,5S)-3,5-diamino-piperidin-1-yl)-[1,3,5]triazin-2-yl)-piperidin-3-yl]-ethylamine | |
| 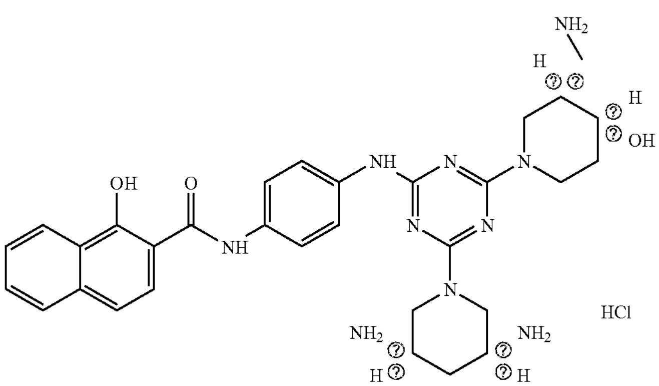 | 1-Hydroxy-naphthalene-2-carboxylic acid {4-[4-((3R,4S)-3-aminomethyl-4-hydroxy-piperidin-1-yl)-6-((3R,5S)-3,5-diamino-piperidin-1-yl)-[1,3,5]triazin-2-ylamino]-phenyl}-amide | ++ |
| 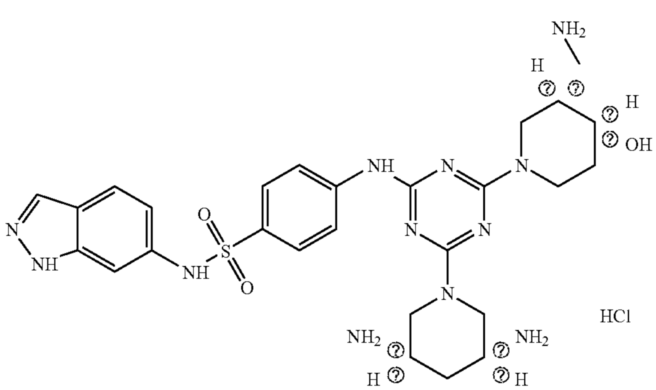 | 4-[4-((3R,4S)-3-Aminomethyl-4-hydroxy-piperidin-1-yl)-6-((3RE,5S)-3,5-diamino-piperidin-1-yl)-[1,3,5]triazin-2-ylamino]-N-(1H-indazol-6-yl)-benzenesulfonamide | − |

⑦ indicates text missing or illegible when filed

-continued

| Structure | Name | Potency |
|---|---|---|
| 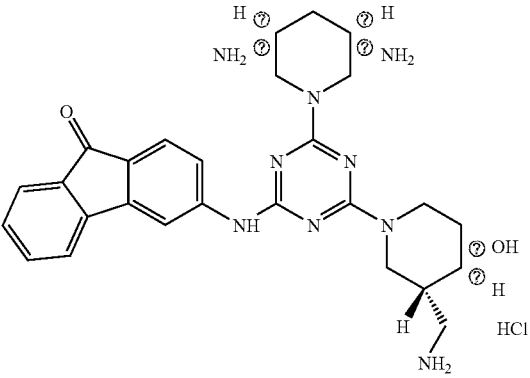 | 3-[4-((3R,4S)-3-Aminomethyl-4-hydroxy-piperidin-1-yl)-6-((3R,5S)-3,5-diamino-piperidin-1-yl)-[1,3,5]triazin-2-ylamino]-fluoren-9-one | – |
| ⑦ indicates text missing or illegible when filed | | |
| 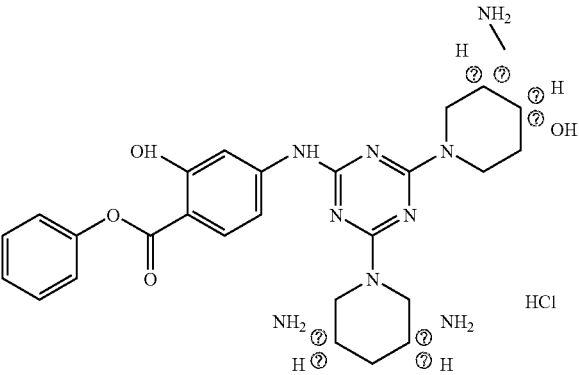 | 4-[4-((3R,4S)-3-Aminomethyl-4-hydroxy-piperidin-1-yl)-6-((3R,5S)-3,5-diamino-piperidin-1-yl)-[1,3,5]triazin-2-ylamino]-2-hydroxy-benzoic acid phenylester | – |
| ⑦ indicates text missing or illegible when filed | | |
| 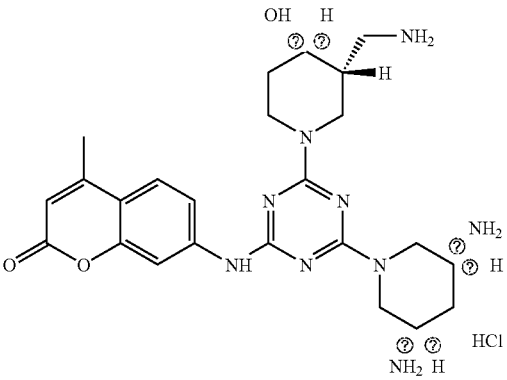 | 7-[4-((3R,4S)-3-Aminomethyl-4-hydroxy-piperidin-1-yl)-6-((3R,5S)-3,5-diamino-piperidin-1-yl)-[1,3,5]triazin-2-ylamino]-4-methyl-chromen-2-one | – |
| ⑦ indicates text missing or illegible when filed | | |

-continued

| Structure | Name | Potency |
|---|---|---|
| 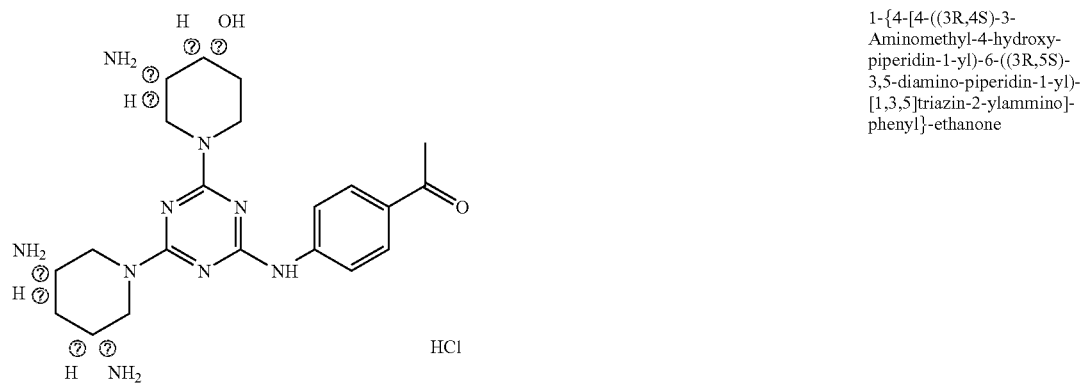 | 1-{4-[4-((3R,4S)-3-Aminomethyl-4-hydroxy-piperidin-1-yl)-6-((3R,5S)-3,5-diamino-piperidin-1-yl)-[1,3,5]triazin-2-ylamino]-phenyl}-ethanone | – |
| 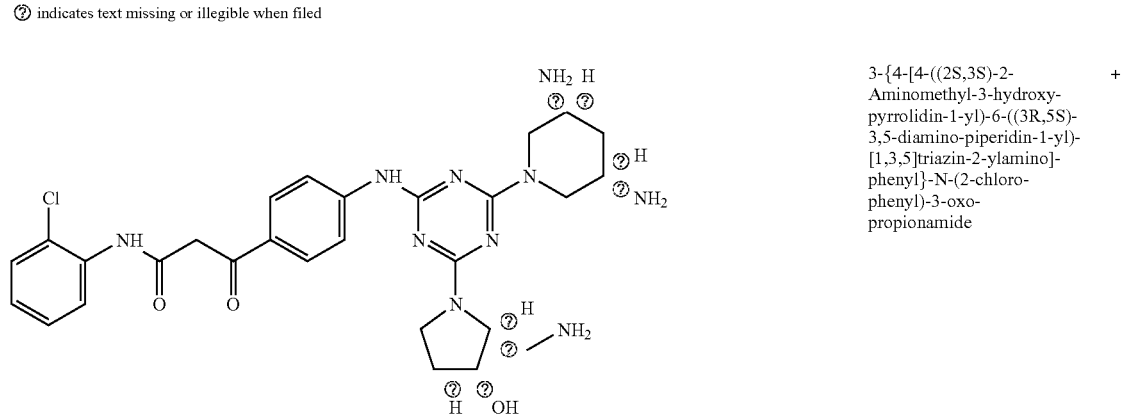 | 3-{4-[4-((2S,3S)-2-Aminomethyl-3-hydroxy-pyrrolidin-1-yl)-6-((3R,5S)-3,5-diamino-piperidin-1-yl)-[1,3,5]triazin-2-ylamino]-phenyl}-N-(2-chloro-phenyl)-3-oxo-propionamide | + |
| 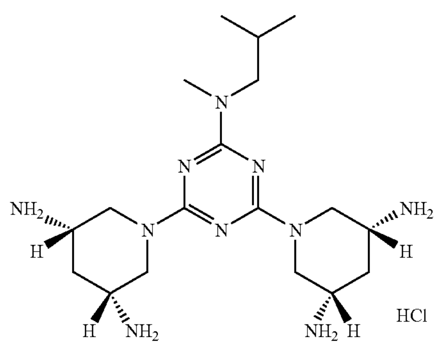 | N-isobutyl-N-methyl-4,6-Bis-((3R,5S)-3,5-diamino-piperidin-1-yl)-[1,3,5]triazine-2-amine | |
| 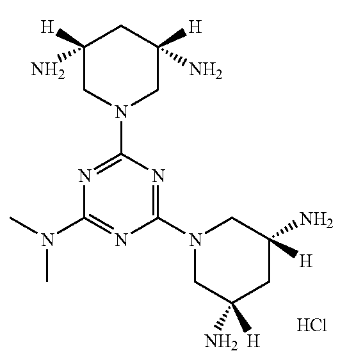 | N-cyclohexyl-N-methyl-4,6-Bis-((3R,5S)-3,5-diamino-piperidin-1-yl)-[1,3,5]triazine-2-amine | |

-continued
| Structure | Name | Potency |
|---|---|---|
| 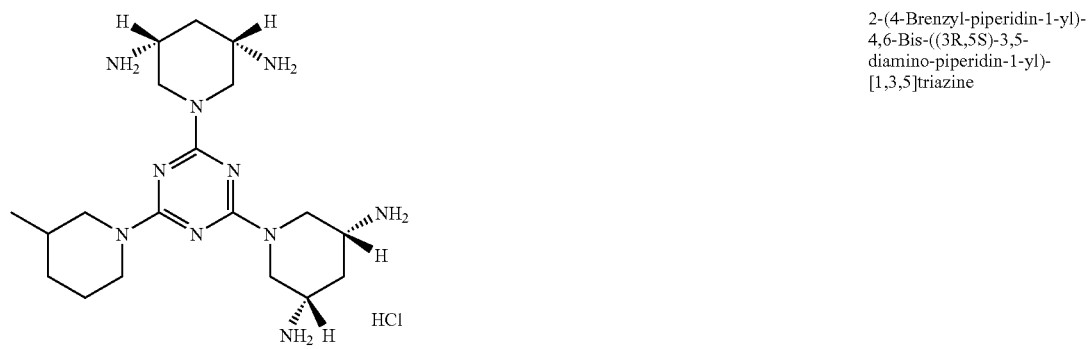 | 2-(4-Brenzyl-piperidin-1-yl)-4,6-Bis-((3R,5S)-3,5-diamino-piperidin-1-yl)-[1,3,5]triazine | |
| 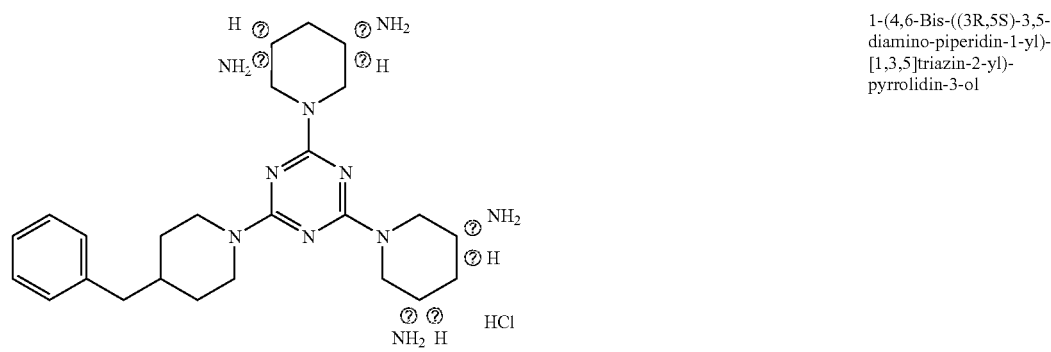 | 1-(4,6-Bis-((3R,5S)-3,5-diamino-piperidin-1-yl)-[1,3,5]triazin-2-yl)-pyrrolidin-3-ol | |
| 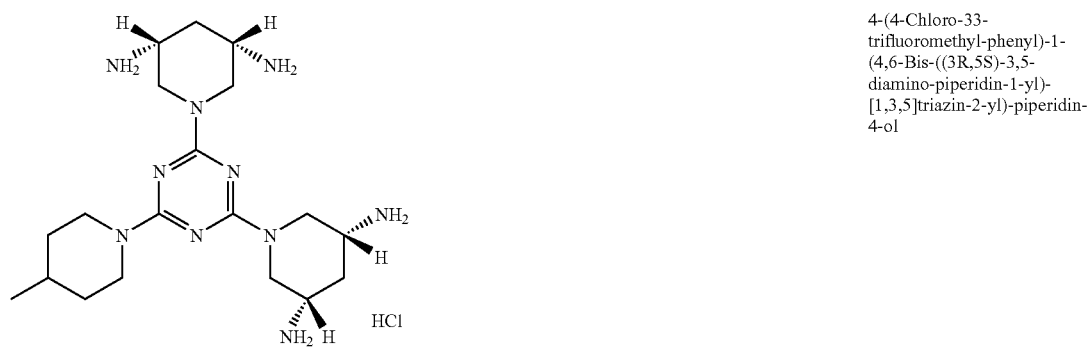 | 4-(4-Chloro-33-trifluoromethyl-phenyl)-1-(4,6-Bis-((3R,5S)-3,5-diamino-piperidin-1-yl)-[1,3,5]triazin-2-yl)-piperidin-4-ol | |
| 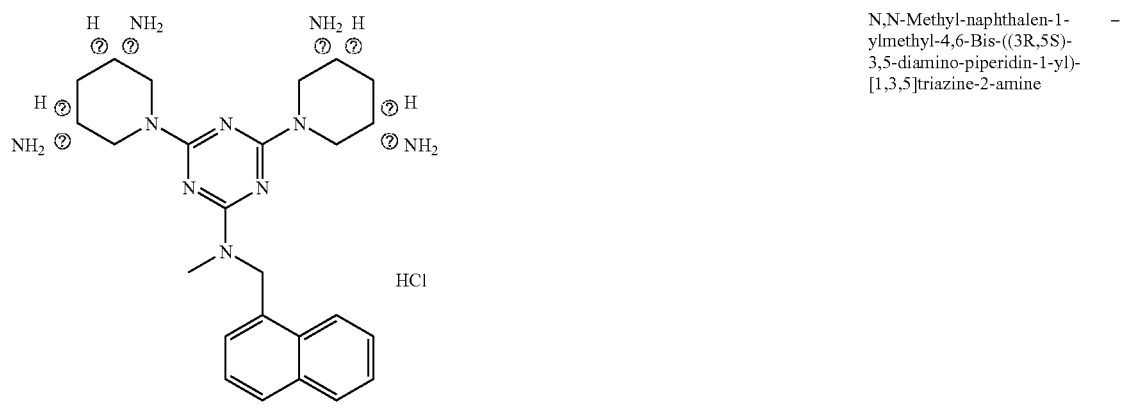 | N,N-Methyl-naphthalen-1-ylmethyl-4,6-Bis-((3R,5S)-3,5-diamino-piperidin-1-yl)-[1,3,5]triazine-2-amine | – |
? indicates text missing or illegible when filed -continued

| Structure | Name | Potency |
|---|---|---|
| | 1-[1-(4,6-Bis-((3R,5S)-3,5-diamino-piperidin-1-yl)-[1,3,5]triazin-2-yl)-piperidin-4-yl]-1,3-dihydro-benzoimidazol-2-one | |
| | N-⸫4-[4-((2S,3S)-2-Aminomethyl-3-hydroxy-pyrrolidin-1-yl)-6-((3R,5S)-3,5-diaminop-piperidin-1-yl)-[1,3,5]triazin-2-ylamino]-3-hydroxy-phenyl}-N-benzyl-4-methyl-benzenesulfonamide | + |
| 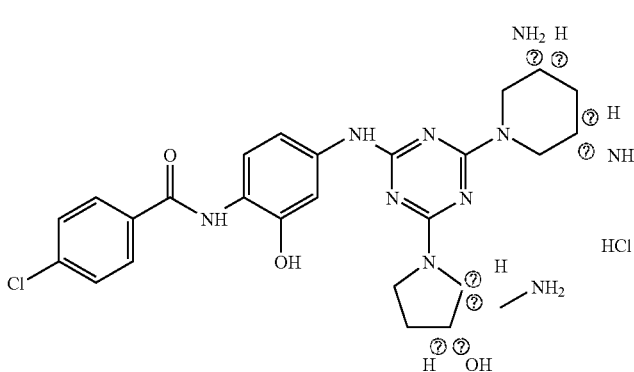 | N-{4-[4-((2S,3S)-2-Aminomethyl-3-hydroxy-pyrrolidin-1-yl)-6-((3R,5S)-3,5-diamino-piperidin-1-yl)-[1,3,5]triazin-2-ylamino]-2-hydroxy-phenyl}-4-chloro-benzamide | + |

⊘ indicates text missing or illegible when filed

-continued

| Structure | Name | Potency |
|---|---|---|
| (structure) | 1-Hydroxy-naphthalene-2-carboxylic acid {4-[4-((2S,3S)-2-aminomethyl-3-hydroxy-pyrrolidin-1-yl)-6-((3R,5S)-3,5-diamino-piperidin-1-yl)-[1,3,5]triazin-2-ylamino]-phenyl}-amide | ++ |
| (structure) | N-{4-[4-((2S,3S)-2-Aminomethyl-3-hydroxy-pyrrolidin-1-yl)-6-((3R,5S)-3,5-diamino-piperidin-1-yl)-[1,3,5]triazin-2-ylamino]-2-hydroxy-phenyl}-4-methyl-benzamide | ++ |
| (structure) | 4-[4-((2S,3S)-2-Aminomethyl-3-hydroxy-pyrrolidin-1-yl)-6-((3R,5S)-3,5-diamino-piperidin-1-yl)-[1,3,5]triazin-2-ylamino]-N-(1H-indazol-6-yl)-benzenesulfonamide | − |

⁇ indicates text missing or illegible when filed

-continued
| Structure | Name | Potency |
|---|---|---|
| 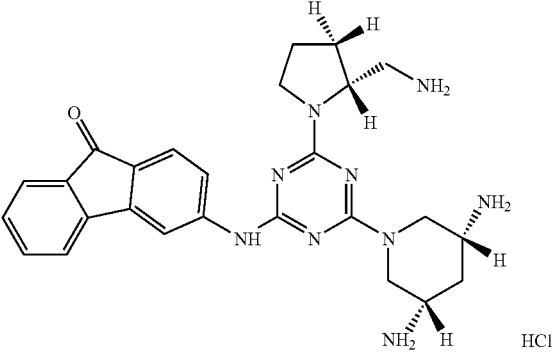 | 3-[4-((2S,3S)-2-Aminomethyl-3-hydroxy-pyrrolidin-1-yl)-6-((3R,5S)-3,5-diamino-piperidin-1-yl)-[1,3,5]triazin-2-ylamino]-fluoren-9-one | + |
| 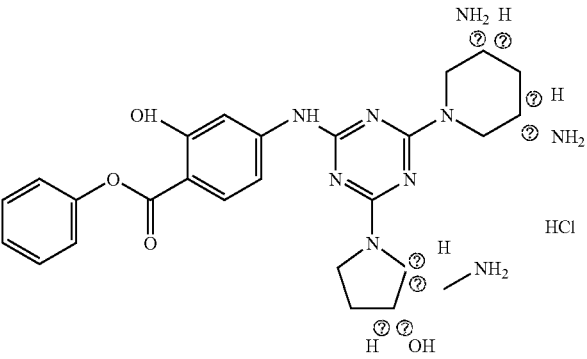 | 4-[4-((2S,3S)-2-Aminomethyl-3-hydroxy-pyrrolidin-1-yl)-6-((3R,5S)-3,5-diamino-piperidin-1-yl)-[1,3,5]triazin-2-ylamino]-2-hydroxy-benzoic acid phenylester | − |
| 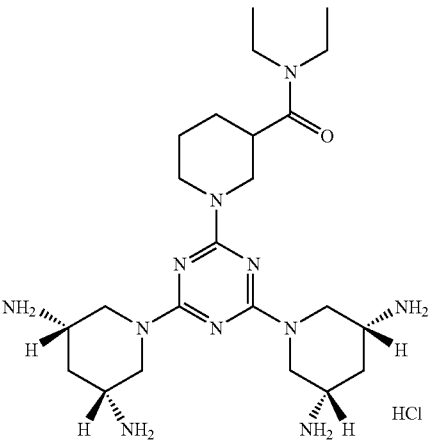 | [1-(4,6-Bis-((3R,5S)-3,5-diamino-piperidin-1-yl)-[1,3,5]triazin-2-yl)-piperidin-3-yl]-methanol | |
⑦ indicates text missing or illegible when filed -continued
| Structure | Name | Potency |
|---|---|---|
| 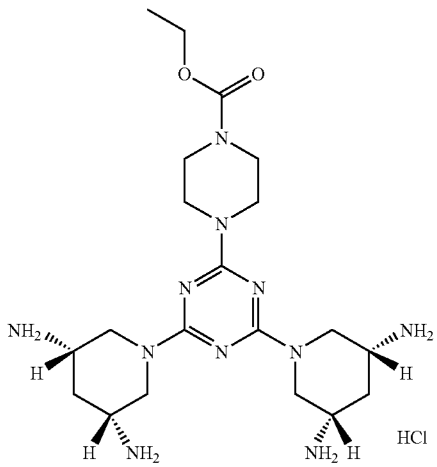 | 4-[4,6-Bis-((3R,5S)-3,5-diamino-piperidin-1-yl)-[1,3,5]triazin-2-yl]-piperiazine-1-carbboxylic acid ethyl ester | |
| 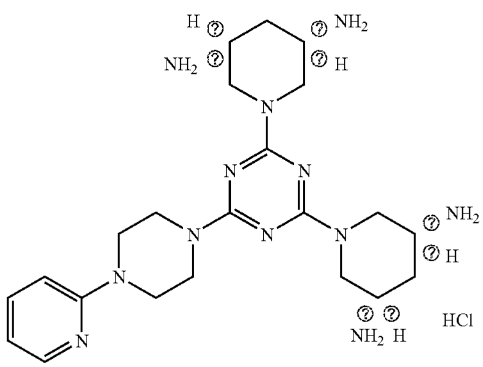 | 2-[4-(4-Fluoro-phenyl)-piperiazin-1-yl]-4,6-Bis-((3R,5S)-3,5-diamino-piperidin-1-yl)-[1,3,5]triazine | – |
| 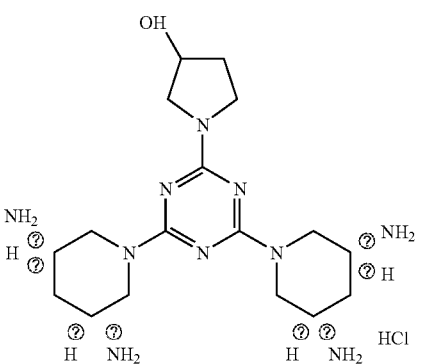 | 2-(3,5-Dimethyl-piperidin-1-yl)-4,6-Bis-((3R,5S)-3,5-diamino-piperidin-1-yl)-[1,3,5]triazine | |
⊚ indicates text missing or illegible when filed -continued

| Structure | Name | Potency |
|---|---|---|
| 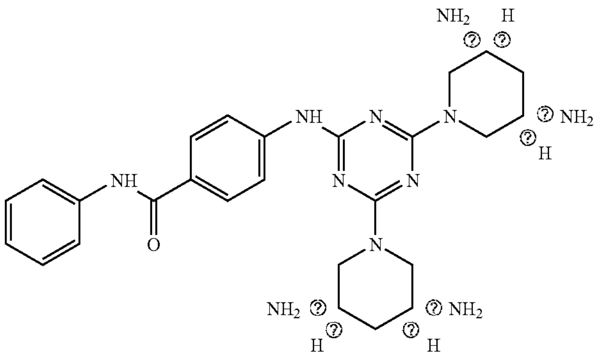 | N-(4-phenylcarbamoyl-phenyl)-4,6-Bis-((3R,5S)-3,5-diamino-piperidin-1-yl)-[1,3,5]triazine-2-amine | – |
| 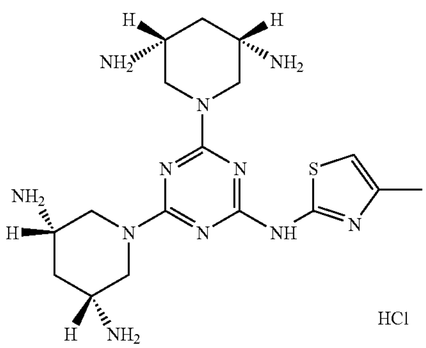 | N-(4-methyl-thiazol-2-yl)-4,6-Bis-((3R,5S)-3,5-diamino-piperidin-1-yl)-[1,3,5]triazine-2-amine | – |
| 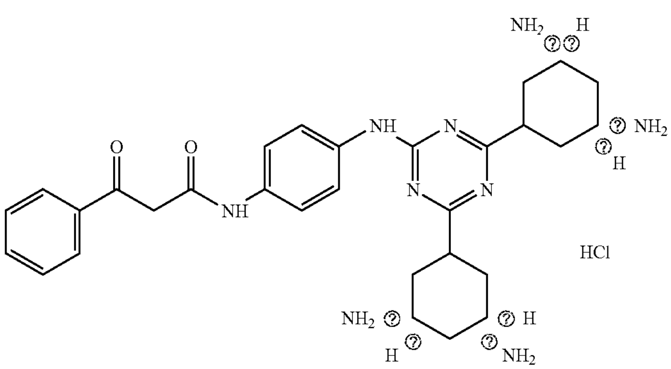 | N-[4-(3-oxo-3-phenyl-propionylamino)-phenyl]-4,6-Bis-((3R,5S)-3,5-diamino-piperidin-1-yl)-[1,3,5]triazine-2-amine | |

⑦ indicates text missing or illegible when filed

-continued

| Structure | Name | Potency |
|---|---|---|
| 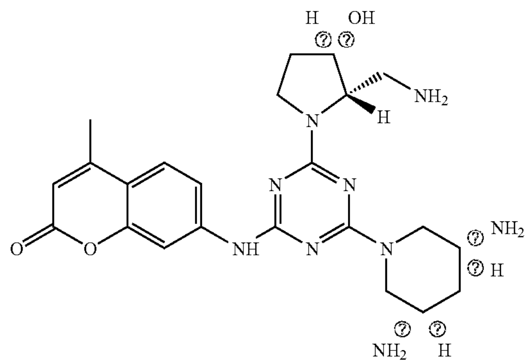 | 7-[4-((2S,3S)-2-Aminomethyl-3-hydroxy-pyrrolidin-1-yl)-6-((3R,5S)-3,5-diamino-piperidin-1-yl)-[1,3,5]triazin-2-ylamino]-4-methyl-chromen-2-one | − |
| 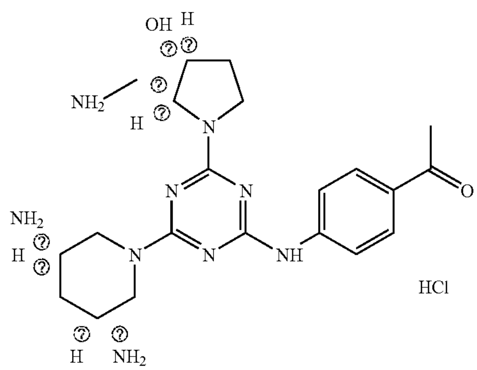 | 1-{4-[4-((2S,3S)-2-Aminomethyl-3-hydroxy-pyrrolidin-1-yl)-6-((3R,5S)-3,5-diamino-piperidin-1-yl)-[1,3,5]triazin-2-ylamino]-phenyl}-ethanone | − |
| | N-{3-hydroxy-4-[2-(1H-indol-3-yl)-2-oxo-acetylamino]-phenyl}-4,6-Bis-((3R,5S)-3,5-diamino-piperidin-1-yl)-[1,3,5]triazine-2-amine | ++ | indicates text missing or illegible when filed

-continued

| Structure | Name | Potency |
|---|---|---|
| 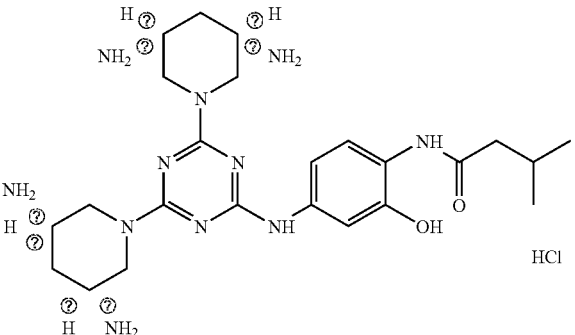 | N-[3-hydroxy-4-(3-methyl-butyrylamino)-phenylk]-4,6-Bis-((3R,5S)-3,5-diamino-piperidin-1-yl)-[1,3,5]triazine-2-amine | + |
| 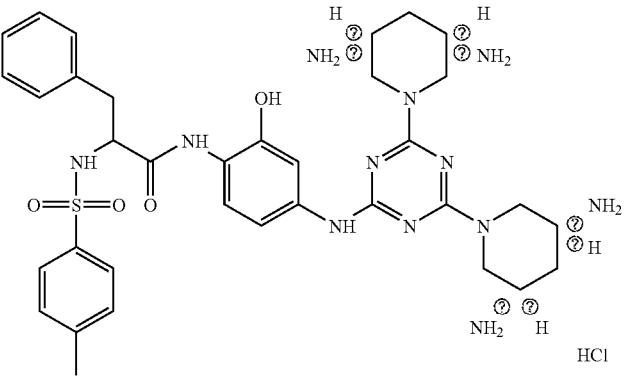 | N-{3-hydroxy-4-[3-phenyl-2-(toluene-4-sulfonylamino)-propionylamino]-phjenyl}-4,6-Bis-((3R,5S)-3,5-diamino-piperidin-1-yl)-[1,3,5]triazine-2-amine | ++ |
| 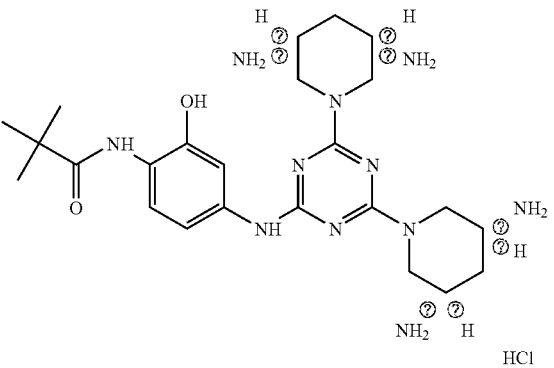 | N-[4-(2,2-dimethyl-propionylammino)-3-hydroxy-phenyl]-4,6-Bis-((3R,5S)-3,5-diamino-piperidin-1-yl)-[1,3,5]triazine-2-amine | + |

⑦ indicates text missing or illegible when filed

-continued

| Structure | Name | Potency |
|---|---|---|
| 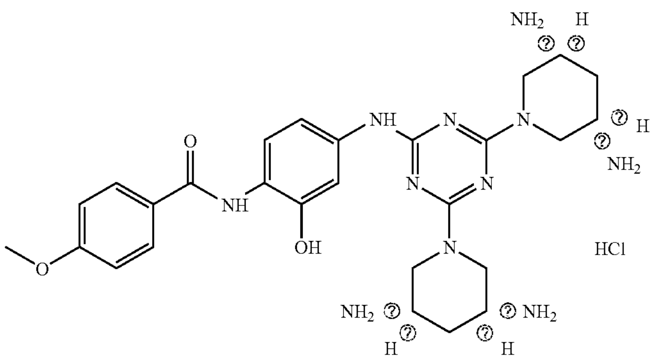 | N-[3-hydroxy-4-(4-methoxy-benzoylamino)-phenyl]-4,6-Bis-((3R,5S)-3,5-diamino-piperidin-1-yl)-[1,3,5]triazine-2-amine | ++ |
| ⑦ indicates text missing or illegible when filed | | |
| 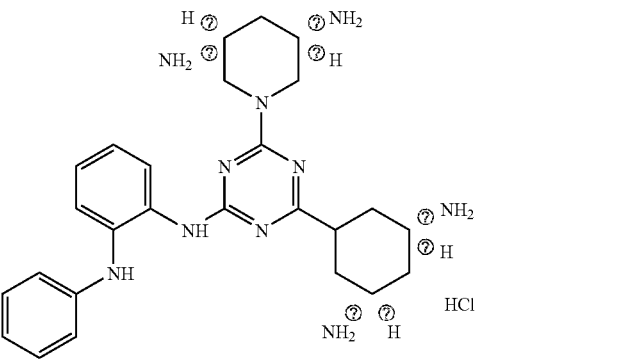 | N-(2-pohenylamino-phenyl)-4,6-Bis-((3R,5S)-3,5-diamino-piperidin-1-yl)-[1,3,5]triazine-2-amine | – |
| ⑦ indicates text missing or illegible when filed | | |
| 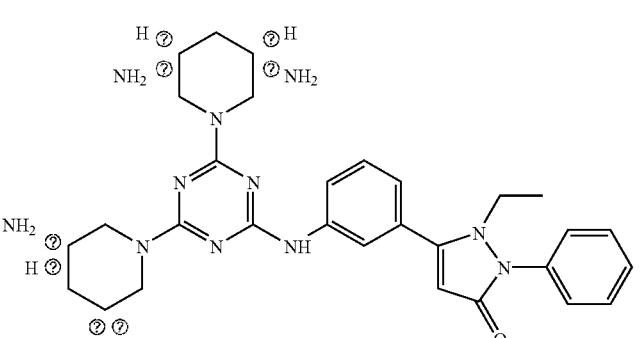 | N-[3-(2-ethyl-5-oxo-1-phenyl-2,5-dihydro-1H-pyrazol-3-yl)-phenyl]-4,6-Bis-((3R,5S)-3,5-diamino-piperidin-1-yl)-[1,3,5]triazine-2-amine | – |
| ⑦ indicates text missing or illegible when filed | | |

-continued

| Structure | Name | Potency |
|---|---|---|
| 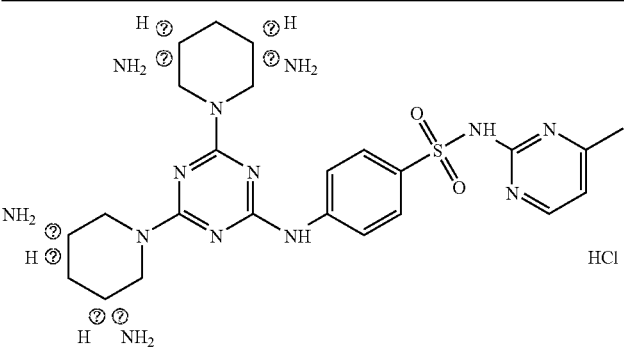 | N-[4-(4-methyl-pyrimidin-2-ylsulfamoyl)-phenyl]-4,6-Bis-((3R,5S)-3,5-diamino-piperidin-1-yl)-[1,3,5]triazine-2-amine | – |
| 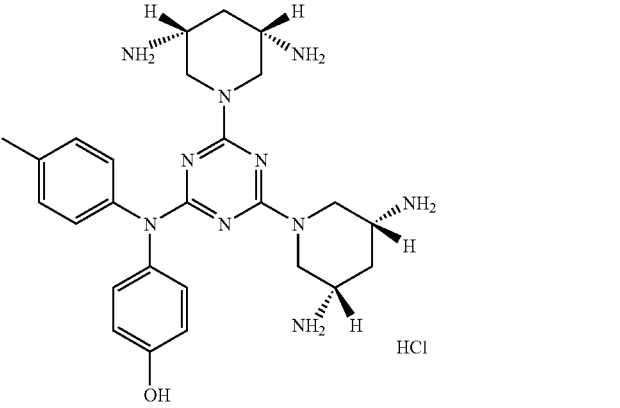 | 4-{[4,6-Bis-((3R,5S)-3,5-diamino-piperidin-1-yl)-[1,3,5]triazin-2-yl]-p-tolyl-amino}-phenol | |
| 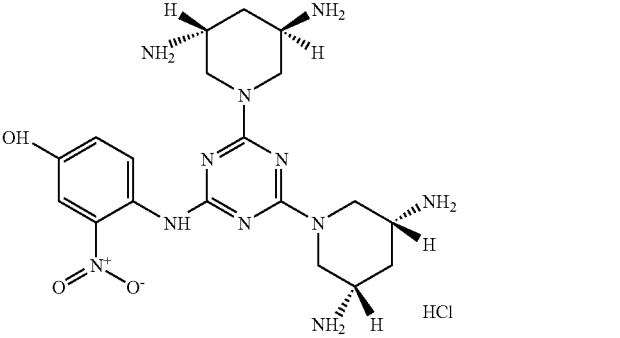 | N-(4-hydroxy-2-nitro-phenyl)-4,6-Bis-((3R,5S)-3,5-diamino-piperidin-1-yl)-[1,3,5]triazine-2-amine | – |
| 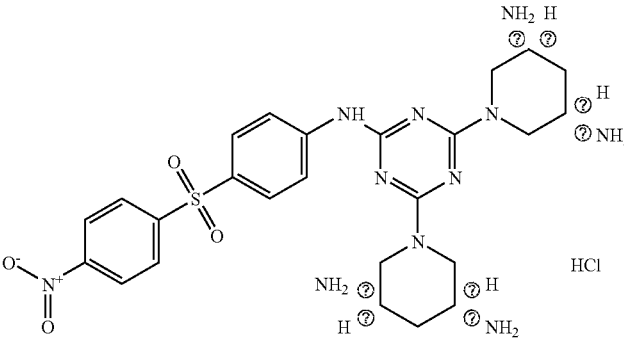 | N-[4-(4-nitro-benzenesulfonyl)-phenyl]-4,6-Bis((3R,5S)-3,5-diamino-piperidin-1-yl)-[1,3,5]triazine-2-amine | + |

⑦ indicates text missing or illegible when filed

| Structure | Name | Potency |
|---|---|---|
| 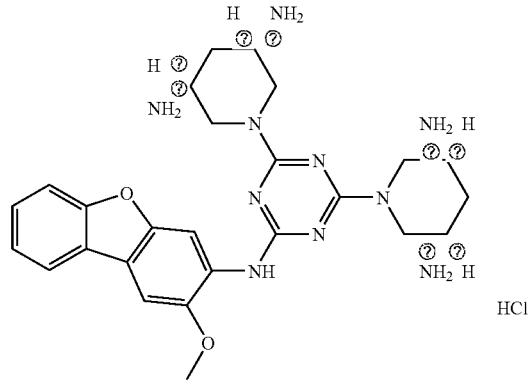 HCl | N-(2-methoxy-dibenzofuran-3-yl)-4,6-Bis-((3R,5S)-3,5-diamino-piperidin-1-yl)-[1,3,5]triazine-2-amine | + |
| 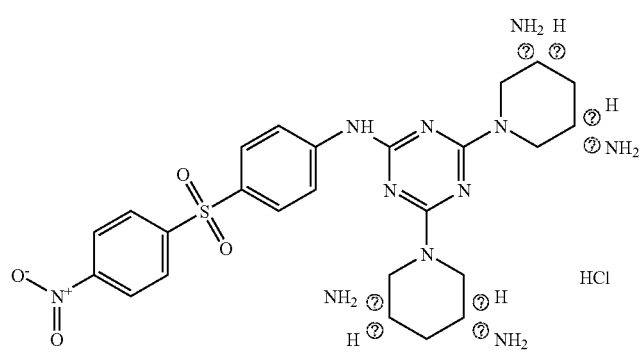 HCl | N-[4-((2,4-dimethoxy-benzoylamino)-3-hydroxy-phenyl]-4,6-Bis-((3R,5S)-3,5-diamino-piperidin-1-yl)-[1,3,5]triazine-2-amine | ++ |
| 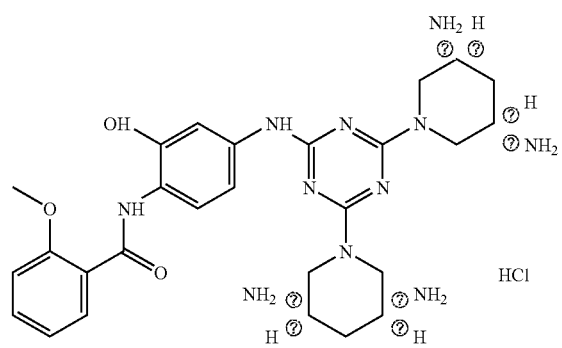 HCl | N-[3-hydroxy-4-(2-methoxy-benzoylamino)-phenyl]-4,6-Bis-((3R,5S)-3,5-diamino-piperidin-1-yl)-[1,3,5]triazine-2-amine | ++ |
⑦ indicates text missing or illegible when filed -continued

| Structure | Name | Potency |
|---|---|---|
| 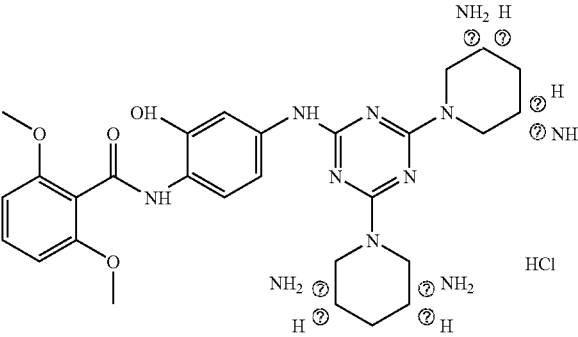 | N-[4-(2,6-dimethoxy-benzoylamino)-3-hydroxy-phenyl]-4,6-Bis-((3R,5S)-3,5-diamino-piperidin-1-yl)-[1,3,5]triazine-2-amine | + |
| ⑦ indicates text missing or illegible when filed | | |
| 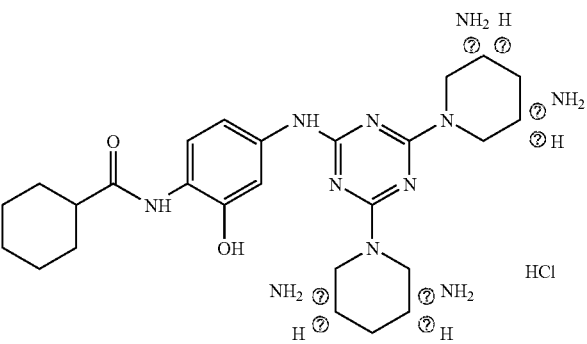 | N-[4-(cyclohexanecarbonyl-amino)-3-hydroxy-phenyl]-4,6-Bis-((3R,5S)-3,5-0 diamino-piperidin-1-yl)-[1,3,5]triazine-2-amine | + |
| ⑦ indicates text missing or illegible when filed | | |
| 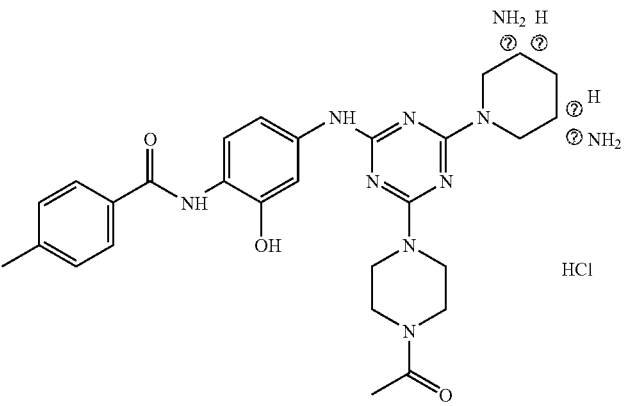 | N-{4-[4-(4-Acetyl-piperazin-1-yl)-6-((3R,5S)-3,5-diamino-piperidin-1-yl)-[1,3,5]triazin-2-ylamino]-2-hydroxy-phenyl}-4-methyl-benzamide | |
| ⑦ indicates text missing or illegible when filed | | |

-continued

| Structure | Name | Potency |
|---|---|---|
| 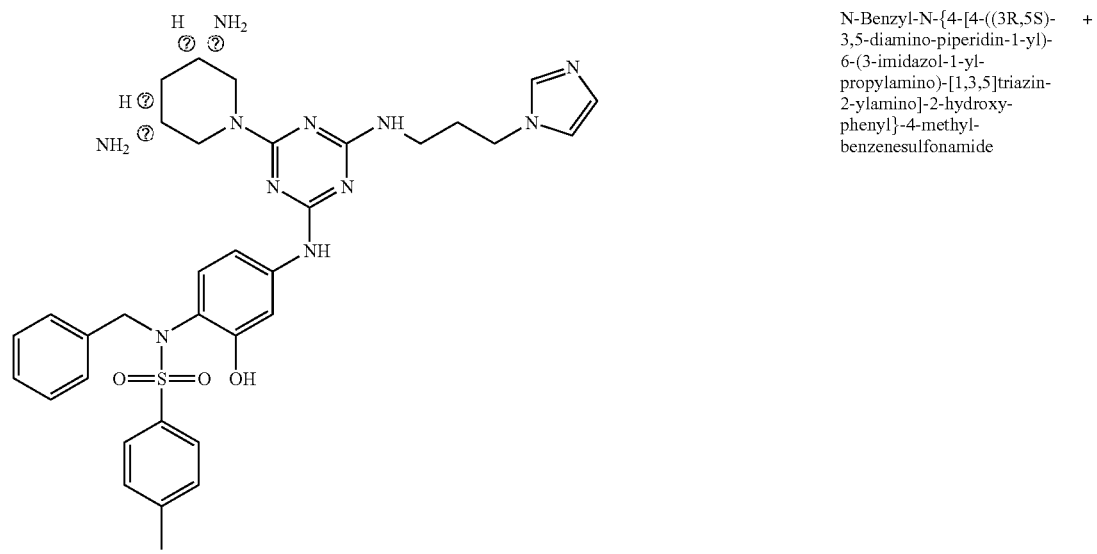 | 4-[4-(4-Acetyl-piperazin-1-yl)-6-((3R,5S)-3,5-diamino-piperidin-1-yl)-[1,3,5]triazin-2-ylamino]-N-(1H-indazol-6-yl)-benzenesulfonamide | − |
| ⑦ indicates text missing or illegible when filed | | |
| 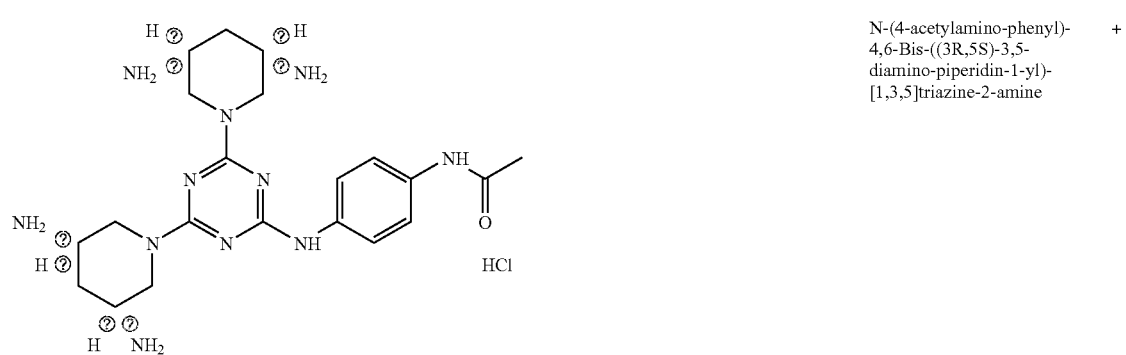 | N-Benzyl-N-{4-[4-((3R,5S)-3,5-diamino-piperidin-1-yl)-6-(3-imidazol-1-yl-propylamino)-[1,3,5]triazin-2-ylamino]-2-hydroxy-phenyl}-4-methyl-benzenesulfonamide | + |
| ⑦ indicates text missing or illegible when filed | | |
| 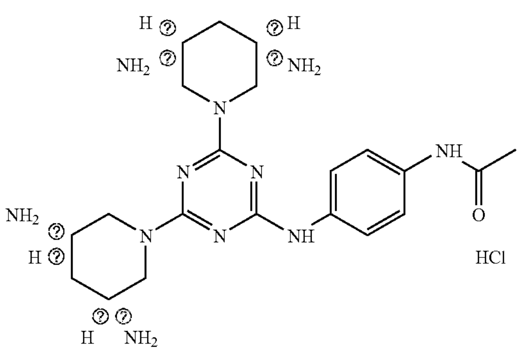 | N-(4-acetylamino-phenyl)-4,6-Bis-((3R,5S)-3,5-diamino-piperidin-1-yl)-[1,3,5]triazine-2-amine | + |
| ⑦ indicates text missing or illegible when filed | | |

-continued
| Structure | Name | Potency |
|---|---|---|
| 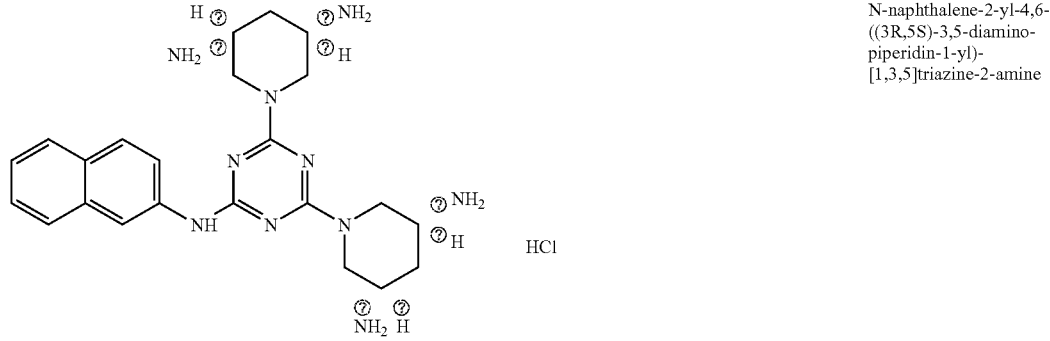 | N-naphthalene-2-yl-4,6-Bis-((3R,5S)-3,5-diamino-piperidin-1-yl)-[1,3,5]triazine-2-amine | + |
| 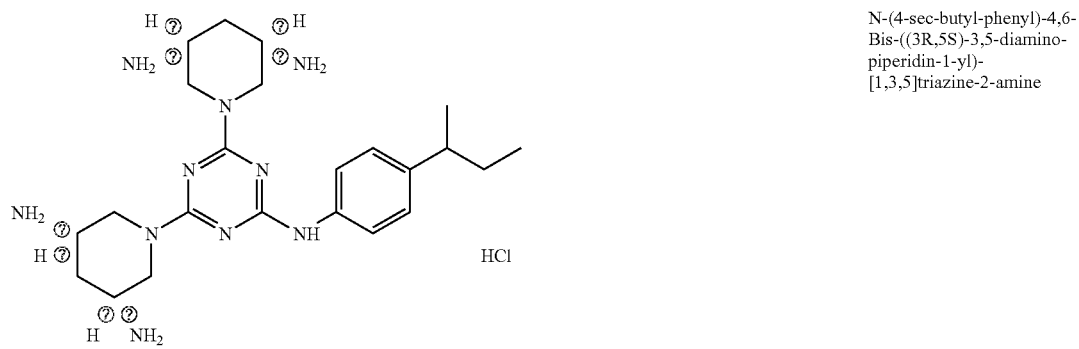 | N-(4-sec-butyl-phenyl)-4,6-Bis-((3R,5S)-3,5-diamino-piperidin-1-yl)-[1,3,5]triazine-2-amine | |
| 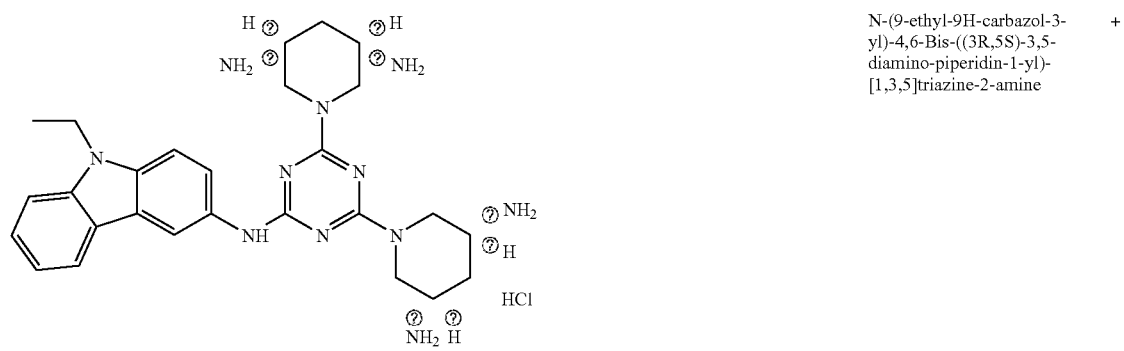 | N-(9-ethyl-9H-carbazol-3-yl)-4,6-Bis-((3R,5S)-3,5-diamino-piperidin-1-yl)-[1,3,5]triazine-2-amine | + |
| 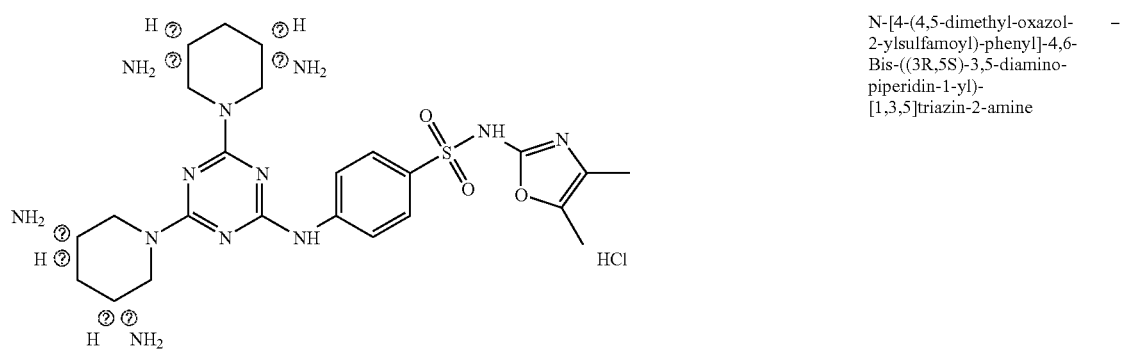 | N-[4-(4,5-dimethyl-oxazol-2-ylsulfamoyl)-phenyl]-4,6-Bis-((3R,5S)-3,5-diamino-piperidin-1-yl)-[1,3,5]triazin-2-amine | − |
⑦ indicates text missing or illegible when filed

| Structure | Name | Potency |
|---|---|---|
| 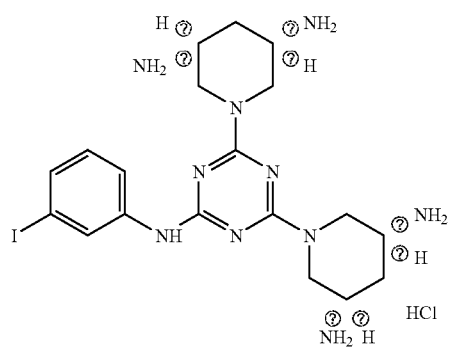 | N-(3-Iodo-phenyl)-4,6-Bis-((3R,5S)-3,5-diamino-piperidin-1-yl)-[1,3,5]triazine-2-amine | + |
| 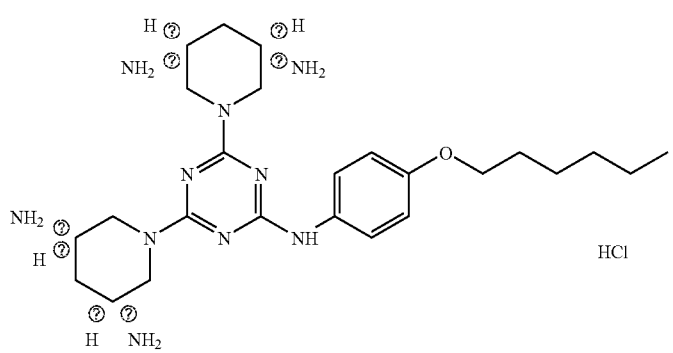 | N-(4-hexyloxy-phenyl)-4,6-Bis-((3R,5S)-3,5-diamino-piperidin-1-yl)-[1,3,5]triazine-2-amine | ++ |
| 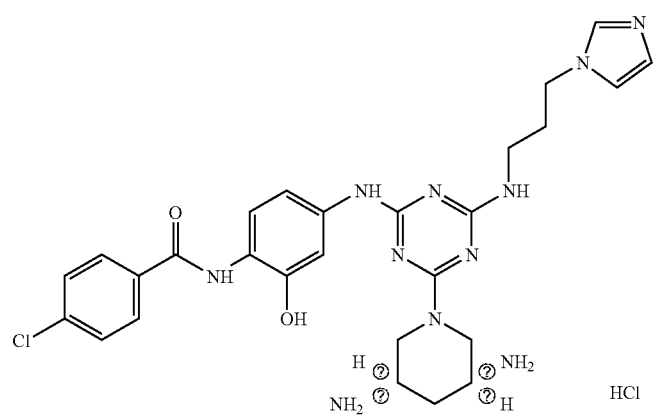 | 3,5-diamino-piperidin-1-yl)-6-(3-imidazol-1-yl-propylamino)-[1,3,5]triazin-2-ylamino]-2-hydroxy-phenyl)-benzamide | + |

-continued

| Structure | Name | Potency |
|---|---|---|
| 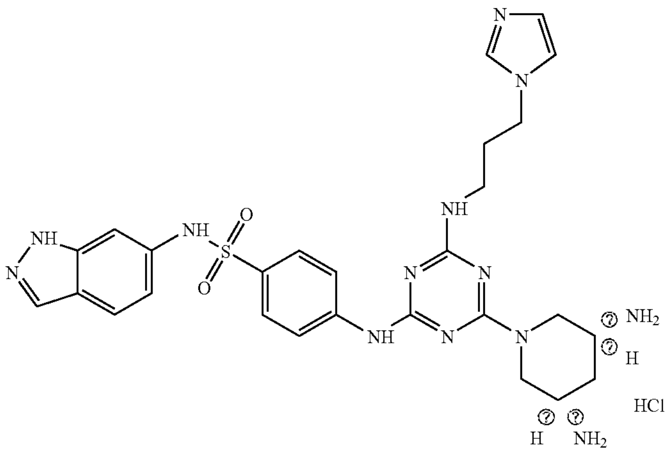 | 4-[4-((3S,5R)-3,5-Diamino-piperidin-1-yl)-6-(3-imidazol-1-yl-propylamino)-[1,3,5]triazin-2-ylamino]-N-(1H-indazol-6-yl)-benzenesulfonamide | − |
| 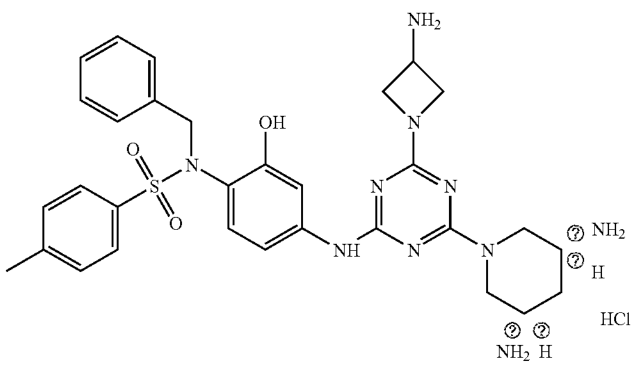 | N-{4-[4-(3-Amino-azetidin-1-yl)-6-((3R,5S)-3,5-diamino-piperidin-1-yl)-[1,3,5]triazin-2-ylamino]-2-hydroxy-phenyl}-N-benzyl-4-methyl-benzenesulfonamidce | |
| 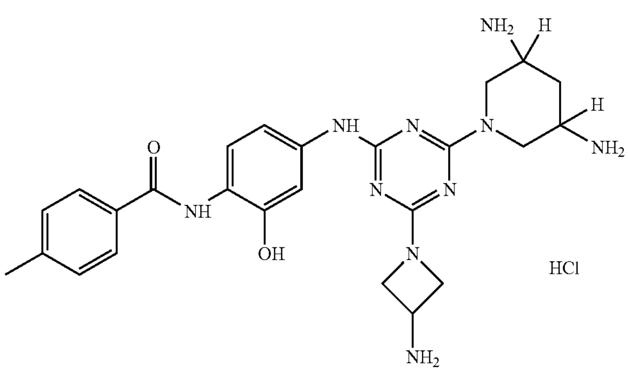 | N-{4-[4-(3-Amino-azetidin-1-yl)-6-((3R,5S)-3,5-diamino-piperidin-1-yl)-[1,3,5]triazin-2-ylamino]-2-hydroxy-phenyl}-4-methyl-benzamide | + |

⑦ indicates text missing or illegible when filed

-continued

| Structure | Name | Potency |
|---|---|---|
| 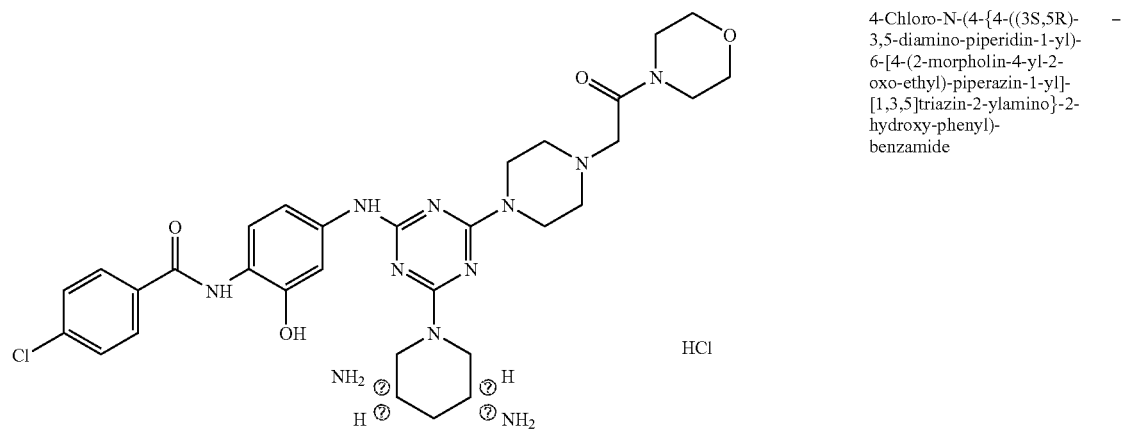 | 4-Chloro-N-(4-{4-((3S,5R)-3,5-diamino-piperidin-1-yl)-6-[4-(2-morpholin-4-yl-2-oxo-ethyl)-piperazin-1-yl]-[1,3,5]triazin-2-ylamino}-2-hydroxy-phenyl)-benzamide | – |
| ⑦ indicates text missing or illegible when filed | | |
| 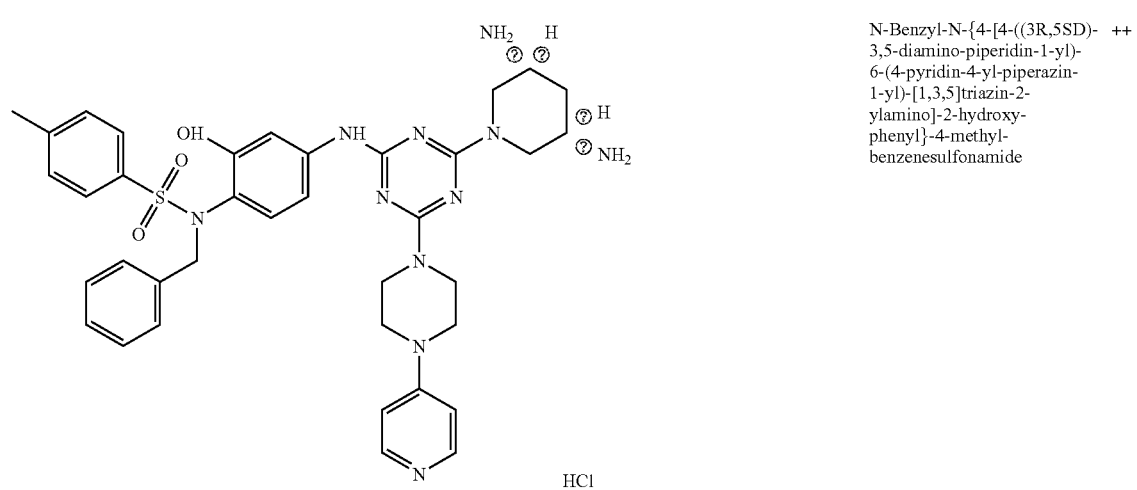 | N-Benzyl-N-{4-[4-((3R,5SD)-3,5-diamino-piperidin-1-yl)-6-(4-pyridin-4-yl-piperazin-1-yl)-[1,3,5]triazin-2-ylamino]-2-hydroxy-phenyl}-4-methyl-benzenesulfonamide | ++ |
| ⑦ indicates text missing or illegible when filed | | |
| 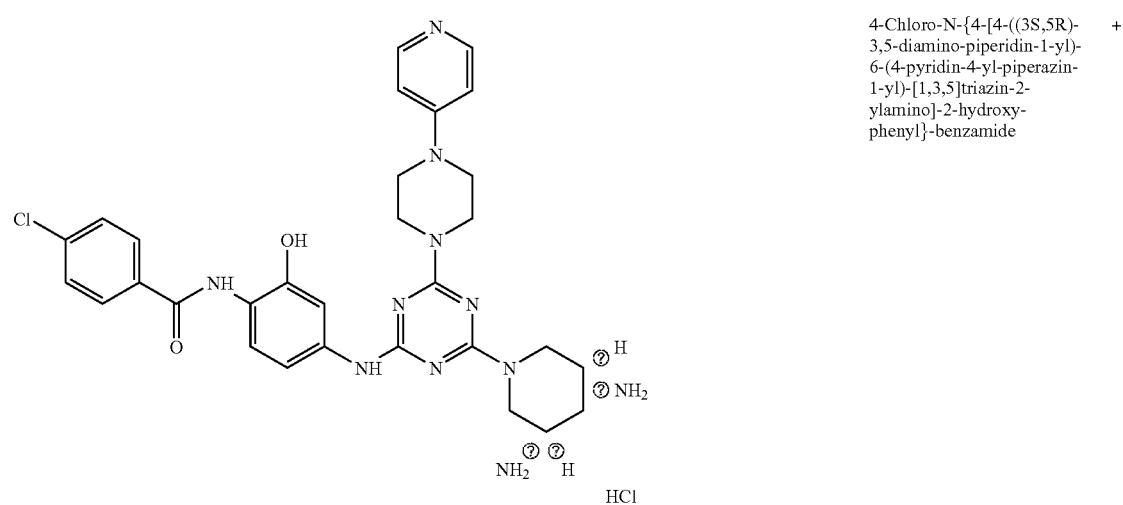 | 4-Chloro-N-{4-[4-((3S,5R)-3,5-diamino-piperidin-1-yl)-6-(4-pyridin-4-yl-piperazin-1-yl)-[1,3,5]triazin-2-ylamino]-2-hydroxy-phenyl}-benzamide | + |
| ⑦ indicates text missing or illegible when filed | | |

-continued
| Structure | Name | Potency |
|---|---|---|
| 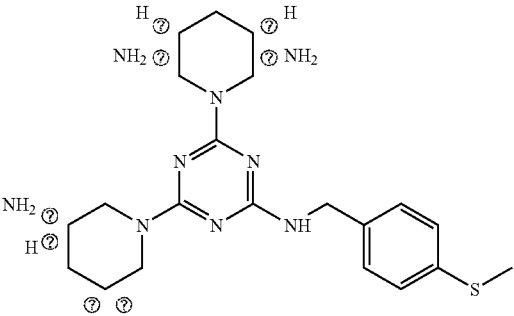 | N-(4-methylsulfanyl-benzyl)-4,6-Bis-((3R,5S)-3,5-diamino-piperidin-1-yl)-[1,3,5]triazine-2-amine | + |
| 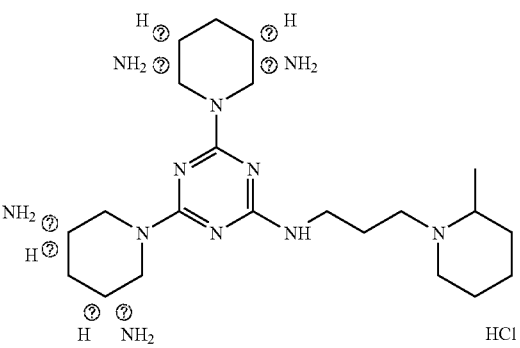 | N-[3-(2-methyl-piperidin-1-yl)-propyl]-4,6-Bis-((3R,5S)-3,5-diamino-piperidin-1-yl)-[1,3,5]triazine-2-amine | |
| 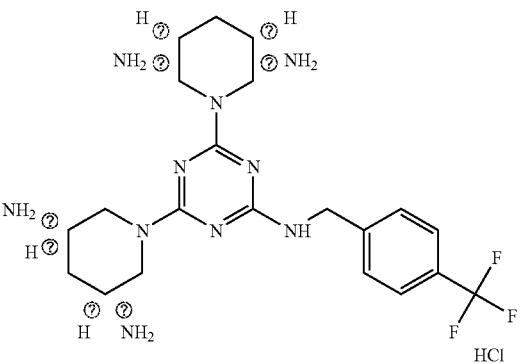 | N-(4-trifluoromethyl-benzyl)-4,6-Bis-((3R,5S)-3,5-diamino-piperidin-1-yl)-[1,3,5]triazine-2-amine | |
⑦ indicates text missing or illegible when filed -continued

| Structure | Name | Potency |
|---|---|---|
| 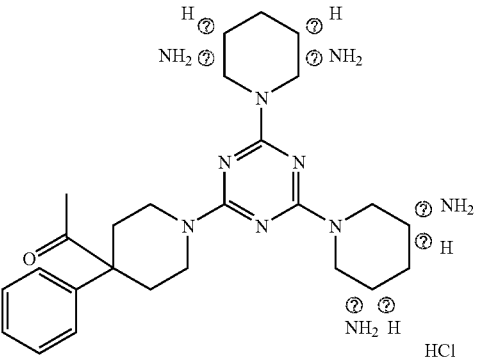 | 2,4-Bis-((3R,5S)-3,5-diamino-piperidin-1-yl)-6-(2-methyl-piperidin-1-yl)-[1,3,5]triazine | – |
| ⑦ indicates text missing or illegible when filed | | |
| 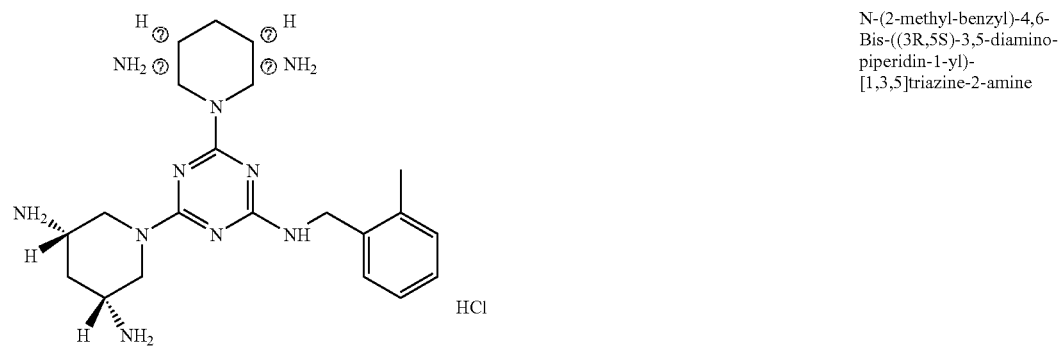 | N-(2-methyl-benzyl)-4,6-Bis-((3R,5S)-3,5-diamino-piperidin-1-yl)-[1,3,5]triazine-2-amine | |
| ⑦ indicates text missing or illegible when filed | | |
| 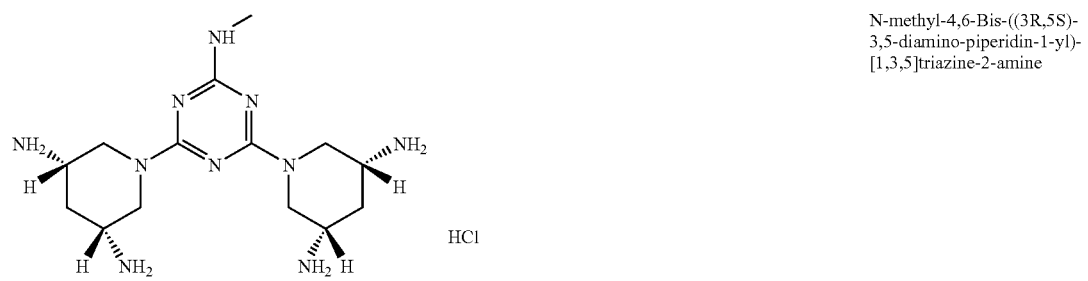 | N-methyl-4,6-Bis-((3R,5S)-3,5-diamino-piperidin-1-yl)-[1,3,5]triazine-2-amine | |
| 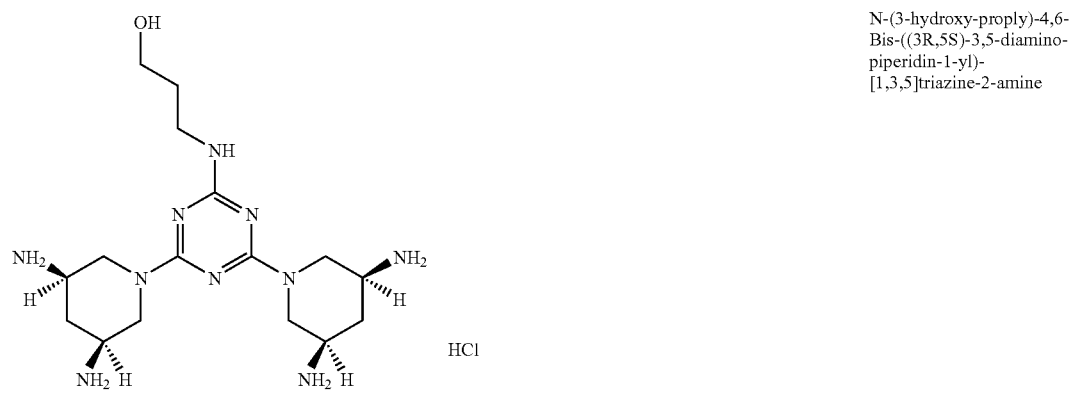 | N-(3-hydroxy-proply)-4,6-Bis-((3R,5S)-3,5-diamino-piperidin-1-yl)-[1,3,5]triazine-2-amine | |

-continued

| Structure | Name | Potency |
|---|---|---|
| 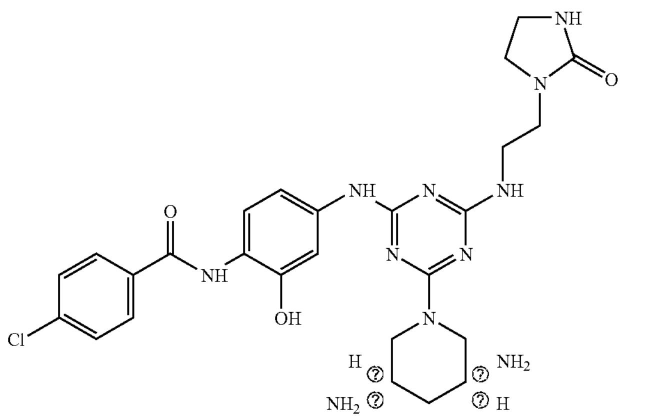 | 4-Chloro-N-{4-[4-((3S,5R)-3,5-diamino-piperidin-1-yl)-6-[2-(2-oxo-imidazolidin-1-yl)-ethylamino]-[1,3,5]triazin-2-ylamino}-2-hydroxy-phenyl)-benzamide | + |
| 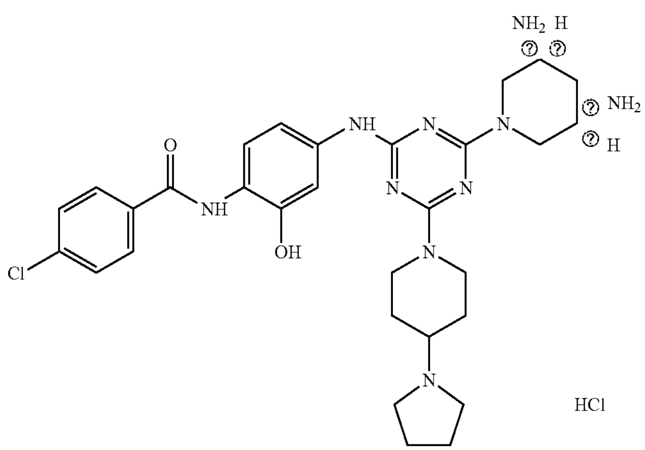 | 4-Chloro-N-{4-[4-((3S,5R)-3,5-diamino-piperidin-1-yl)-6-(4-pyrrolidin-1-yl-piperidin-1-yl)-[1,3,5]triazin-2-ylamino]-2-hydroxy-phenyl}-benzamide | + |
| 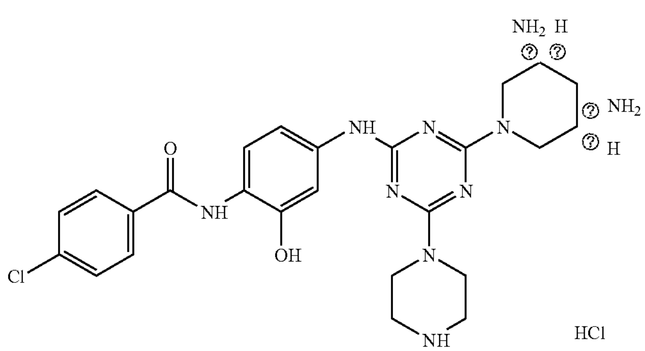 | 4-Chloro-N-{4-[4-((3S,5R)-3,5-diamino-piperidin-1-yl)-6-piperazin-1-yl-[1,3,5]triazin-2-ylamino]-2-hydroxy-phenyl}-benzamide | ++ |

| Structure | Name | Potency |
|---|---|---|
| (structure) | N-{4-[4-((3R,5S)-3,5-Diamino-piperidin-1-yl)-6-(piperidin-4-ylamino)-[1,3,5]triazin-2-ylamino]-2-hydroxy-phenyl}-4-methyl-benzamide | ++ |
| (structure) | 4-Chloro-N-{4-[4-((3S,5R)-Diamino-piperidin-1-yl)-6-(piperidin-4-ylamino)-[1,3,5]triazin-2-ylamino]-2-hydroxy-phenyl}-benzamide | ++ |
| (structure) | N-Benzyl-N-{4-[4-((3R,5S)-3,5-diamino-piperidin-1-yl)-6-(piperidin-3-ylamino)-[1,3,5]triazin-2-ylamino]-2-hydroxy-phenyl}-4-methyl-benzenesulfonamide | + |

-continued

| Structure | Name | Potency |
|---|---|---|
| 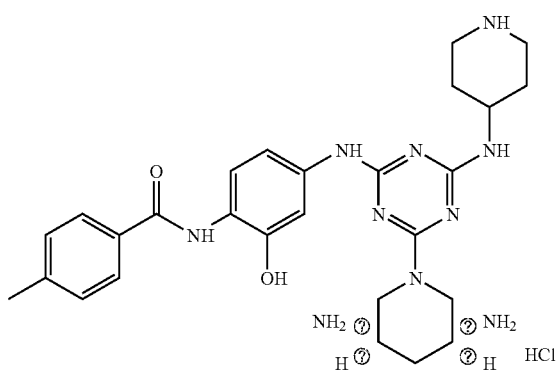 | N-{4-[4-((3R,5S)-3,5-Diamino-piperidin-1-yl)-6-(piperidin-3-ylamino)[1,3,5]triazin-2-ylamino]-2-hydroxy-phenyl}-4-methyl-benzamide | + |
| ⑦ indicates text missing or illegible when filed | | |
| 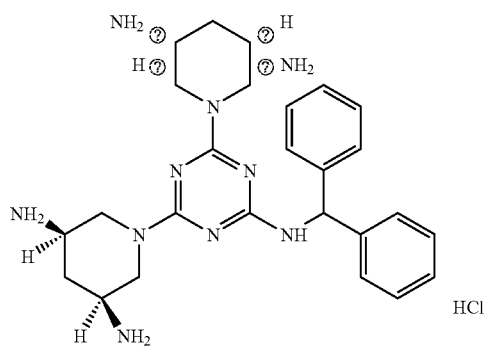 | N-benzhydryl-4,6-Bis-((3R,5S)-3,5-diamino-piperidin-1-yl)-[1,3,5]triazine-2-amine | |
| ⑦ indicates text missing or illegible when filed | | |
| 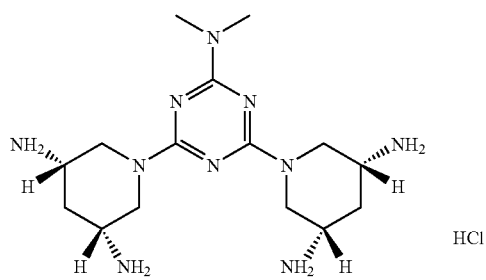 | N,N-di-Methyl-4,6-Bis-((3R,5S)-3,5-diamino-piperidin-1-yl)-[1,3,5]triazine-2-amine | |
| ⑦ indicates text missing or illegible when filed | | |
| 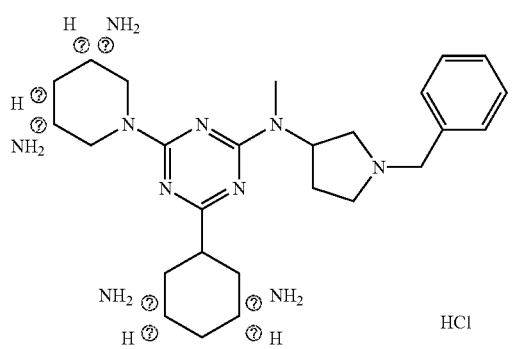 | N-(1-Benzyl-pyrrolidin-3-yl)-N-methyl-4,6-Bis-((3R,5S)-3,5-diamino-piperidin-1-yl)-[1,3,5]triazine-2-amine | + |
| ⑦ indicates text missing or illegible when filed | | |

-continued
| Structure | Name | Potency |
|---|---|---|
| 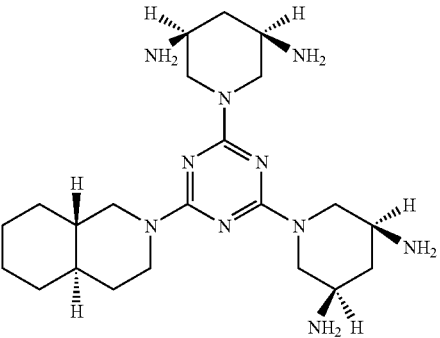 HCl | 1-(4,6-Bis-((3R,5S)-3,5-diamino-piperidin-1-yl)-[1,3,5]triazin-2-yl)-piperidine-3-carboxylic acid amide | |
| 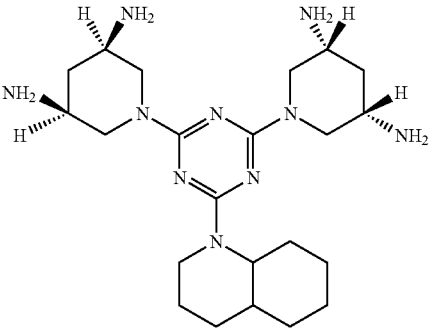 HCl | 1-(4,6-Bis-((3R,5S)-3,5-diamino-piperidin-1-yl)-[1,3,5]triazin-2-yl)-2,3-dihydro-1H-indole | |
| 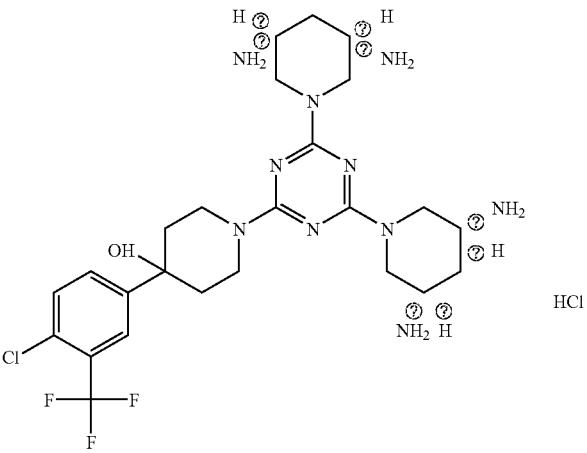 HCl | 2,4-Bis-((3R,5S)-3,5-diamino-piperidin-1-yl)-6-[4-(4-nitro-phenyl)-piperiazin-1-yl]-[1,3,5]triazine | |
ⓘ indicates text missing or illegible when filed -continued

| Structure | Name | Potency |
|---|---|---|
| 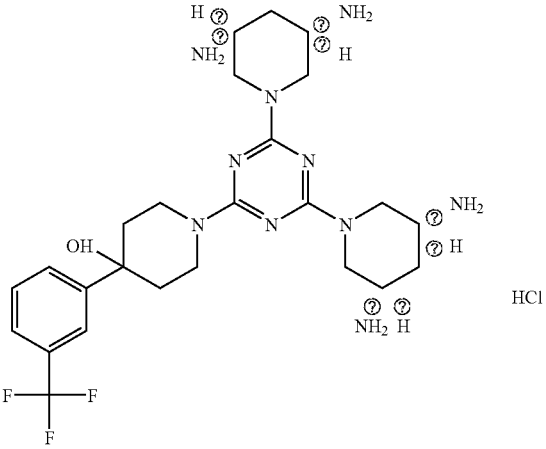 | [1-(4,6-Bis-((3R,5S)-3,5-diamino-piperidin-1-yl)-[1,3,5]triazin-2-yl)-pyrrolidin-2-yl]-methanol | |
| ⑦ indicates text missing or illegible when filed | | |
| 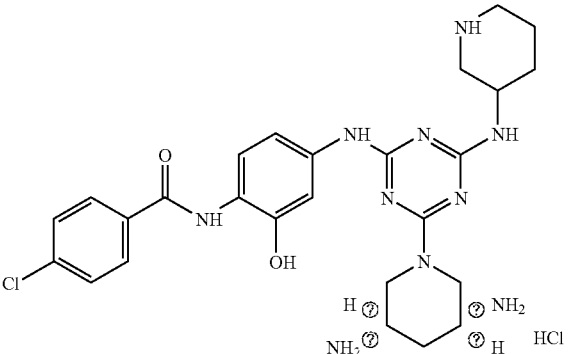 | 4-Chloro-N-{4-[4-((3S,5R)-3,5-diamino-piperidin-1-yl)-6-(piperidin-3-ylamino)-[1,3,5]triazin-2-ylamino]-2-hydroxy-phenyl}-benzamide | ++ |
| ⑦ indicates text missing or illegible when filed | | |
| 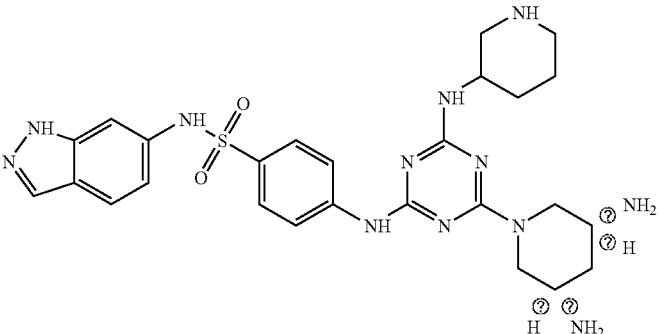 | 4-[4-((3S,5R)-3,5-Diamino-piperidin-1-yl)-6-(piperidin-3-ylamino)-[1,3,5]triazin-2-ylamino]-N-(1H-indazol-6-yl)-benzenesulfonamide | − |
| ⑦ indicates text missing or illegible when filed | | |

-continued

| Structure | Name | Potency |
|---|---|---|
| 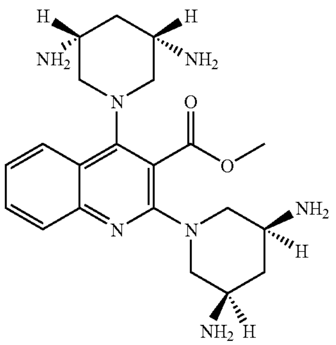 | 2,4-Bis-((3R,5S)-3,5-diamino-piperidin-1-yl)-quinoline-3-carboxylic acid methylester | – |
| 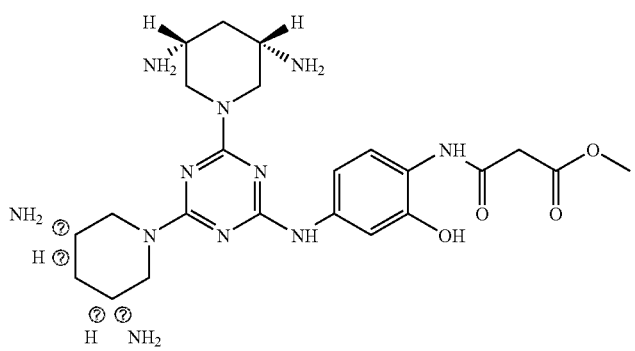 | N-{4-[4,6-Bis-((3R,5S)-3,5-diamino-piperidin-1-yl)-[1,3,5]triazin-2-ylamino]-2-hydrocy-phenyl}-2-((1R,2S,5R)-2-isopropyl-5-methyl-cyclohexyloxy)-acetamide | |
| ⓘ indicates text missing or illegible when filed | | |
| 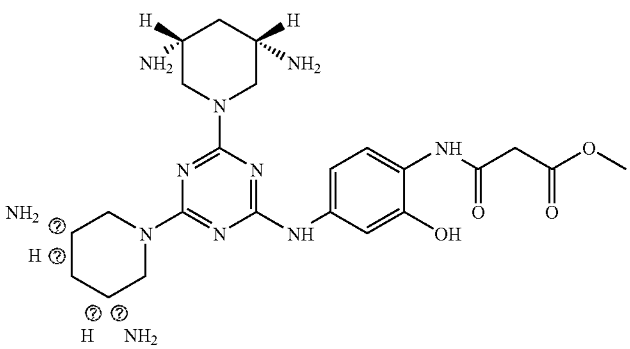 | N-{4-[4,6-Bis-((3R,5S)-3,5-diamino-piperidin-1-yl)-[1,3,5]triazin-2-ylamino]-2-hydroxy-phenyl}-malonamic acid methyl ester | – |
| ⓘ indicates text missing or illegible when filed | | |
| 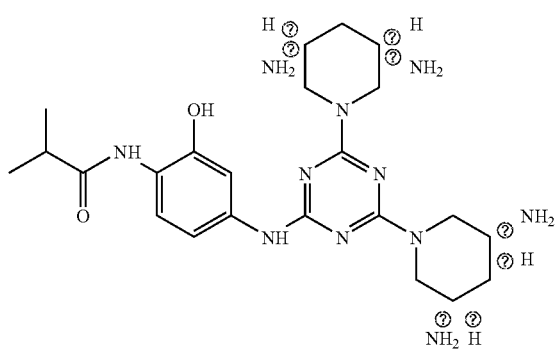 | N-(3-hydroxy-4-isobutyrylamino-phenyl)-4,6-Bis-((3R,5S)-3,5-diamino-piperidin-1-yl)-[1,3,5]triazine-2-amine | – |
| ⓘ indicates text missing or illegible when filed | | |

| Structure | Name | Potency |
|---|---|---|
| 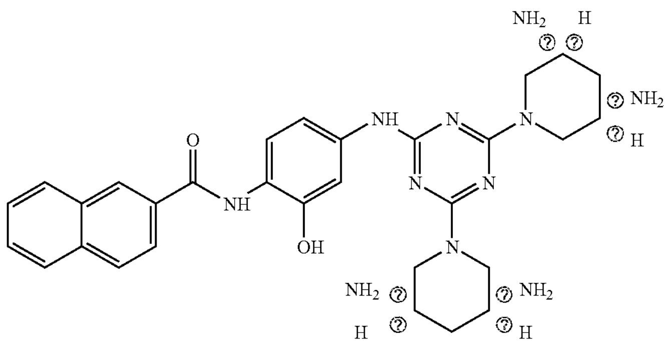 | N-{3-hydroxy-4-[(naphthalene-2-carbonyl)-amino]-phenyl}-4,6-Bis-((3R,5S)-3,5-diamino-piperidin-1-yl)-[1,3,5]triazine-2-amine | + |
| 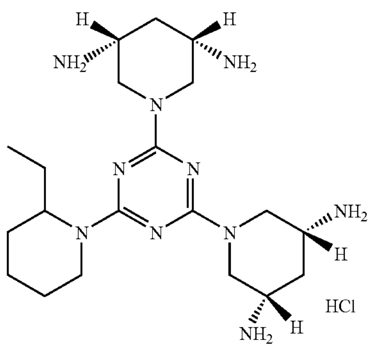 | 2,4-Bis-((3R,5S)-3,5-diamino-piperidin-1-yl)-6-piperiazin-1-yl-[1,3,5]triazine | |
| | N-(5-chloro-2-methyl-benzyl)-4,6-Bis-((3R,5S)-3,5-diamino-piperidin-1-yl)-[1,3,5]triazine-2-amine | |
| 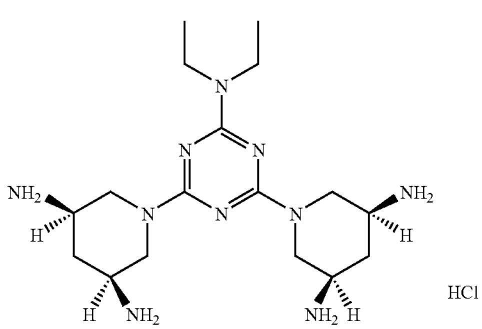 | N,N-di-ethyl-4,6-Bis-((3R,5S)-3,5-diamino-piperidin-1-yl)-[1,3,5]triazine-2-amine | |

⑦ indicates text missing or illegible when filed

-continued
| Structure | Name | Potency |
|---|---|---|
| 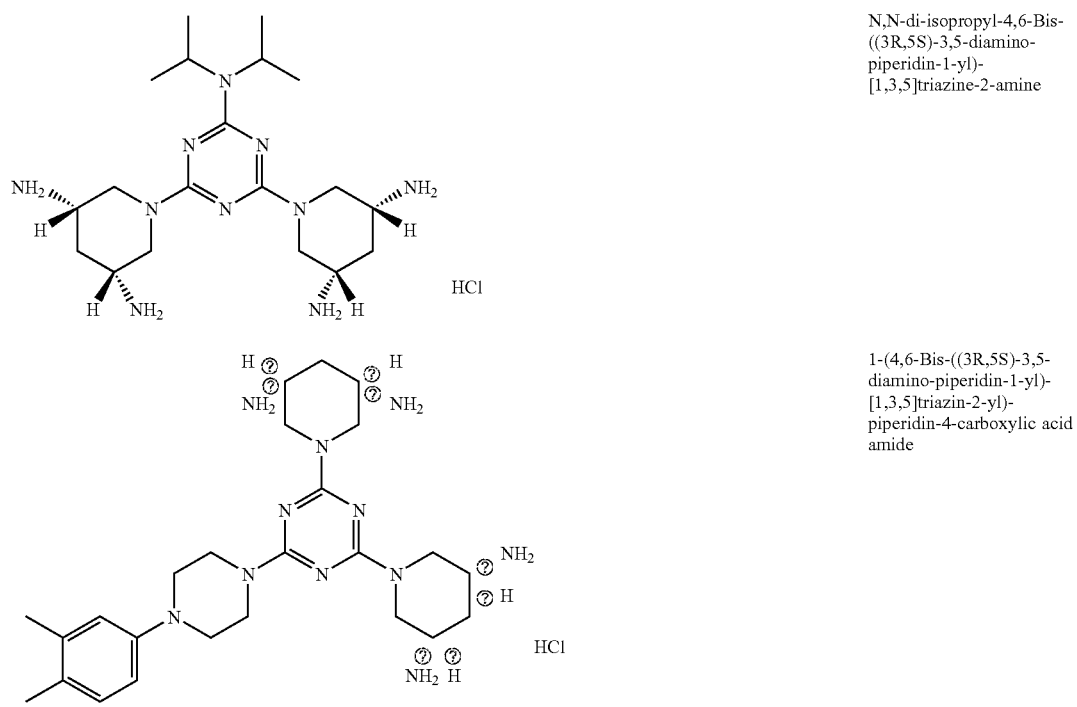 | N,N-di-isopropyl-4,6-Bis-((3R,5S)-3,5-diamino-piperidin-1-yl)-[1,3,5]triazine-2-amine | |
| 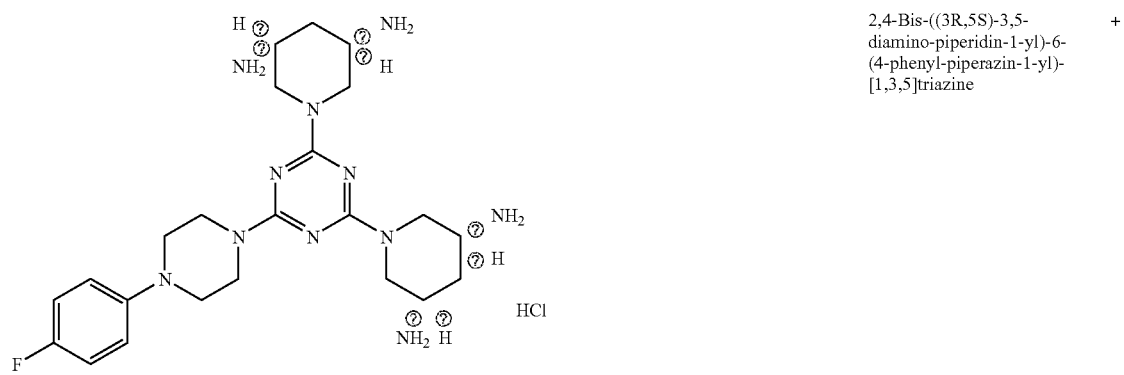 | 1-(4,6-Bis-((3R,5S)-3,5-diamino-piperidin-1-yl)-[1,3,5]triazin-2-yl)-piperidin-4-carboxylic acid amide | |
| 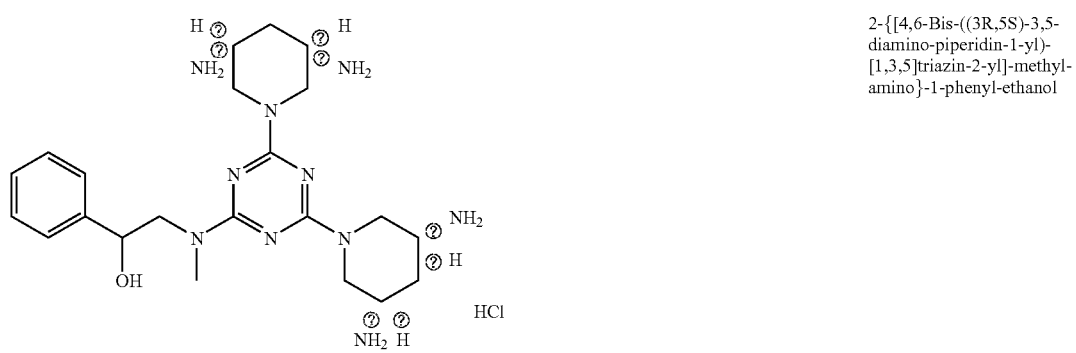 | 2,4-Bis-((3R,5S)-3,5-diamino-piperidin-1-yl)-6-(4-phenyl-piperazin-1-yl)-[1,3,5]triazine | + |
| 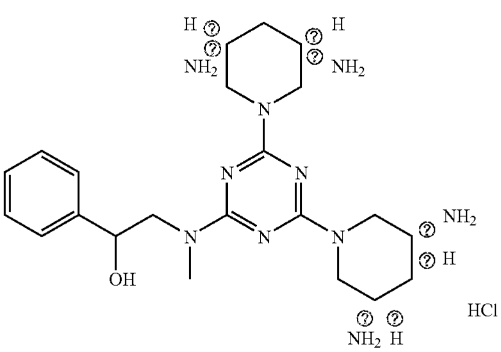 | 2-{[4,6-Bis-((3R,5S)-3,5-diamino-piperidin-1-yl)-[1,3,5]triazin-2-yl]-methyl-amino}-1-phenyl-ethanol | |
ⓘ indicates text missing or illegible when filed

| Structure | Name | Potency |
|---|---|---|
| (structure) | N-(3-hydroxy-4-phenylacetylamino-phenyl)-4,6-Bis-((3R,5S)-3,5-diamino-piperidin-1-yl)-[1,3,5]triazine-2-amine | + |
| (structure) | N-(3-hydroxy-4-propionylamino-phenyl)-4,6-Bis-((3R,5S)-3,5-diamino-piperidin-1-yl)-[1,3,5]triazine-2-amine | + |
| (structure) | N-{3-hydroxy-4-[(quinoxaline-2-carbonyl)-amino]-phenyl}-4,6-Bis-((3R,5S)-3,5-diamino-piperidin-1-yl)-[1,3,5]triazine-2-amine | + |
| (structure) | N-[4-(2,2-dimethyl-propionylamino)-3-hydroxy-phenyl]-4,6-Biss-((3R,5S)-3,5-diamino-piperidin-1-yl)-[1,3,5]triazine-2-amine | + |

-continued

| Structure | Name | Potency |
|---|---|---|
| 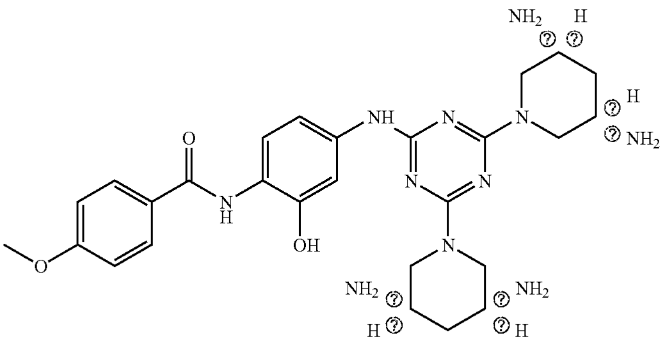 | N-[3-hydroxy-4-(4-methoxy-benzoylamino)-phenyl]-4,6-Bis-((3R,5S)-3,5-diamino-piperidin-1-yl)-[1,3,5]triazine-2-amine |  |
| 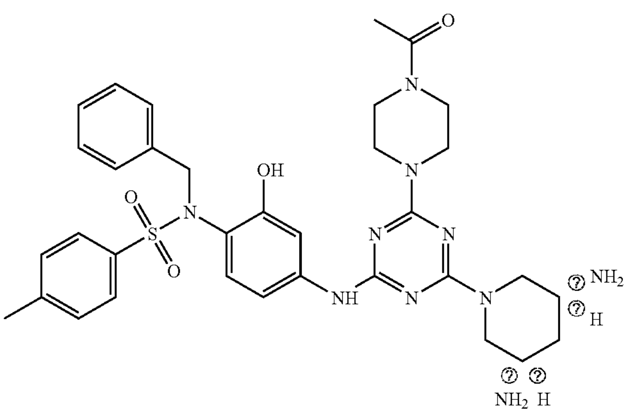 | N-{4-[4-(4-Acetyl-piperazin-1-yl)-6-((3R,5S)-3,5-diamino-piperidin-1-yl)-[1,3,5]triazin-2-ylamino]-2-hydroxy-phenyl}-N-benzyl-4-methyl-benzenesulfonamide |  |
| 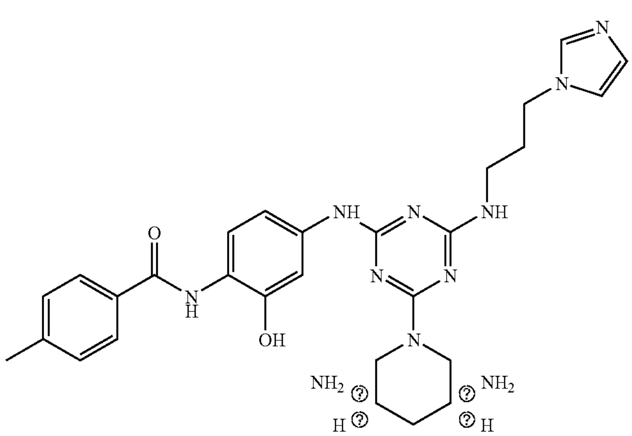 | N-{4-[4-((3R,5S)-3,5-Diamino-piperidin-1-yl)-6-(3-imidazol-1-yl-propylamino)-[1,3,5]triazin-2-ylamino]-2-hydroxy-phenyl}-4-methyl-benzamide |  |

⊚ indicates text missing or illegible when filed

-continued

| Structure | Name | Potency |
|---|---|---|
| 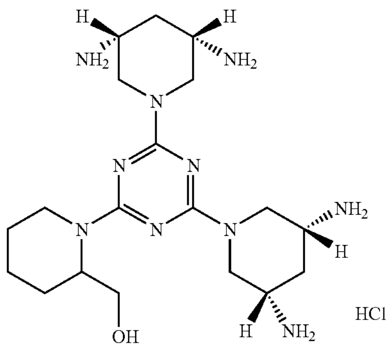 | 1-(4,6-Bis-((3R,5S)-3,5-diamino-piperidin-1-yl)-[1,3,5]triazin-2-yl)-piperidin-3-ylamine | |
| 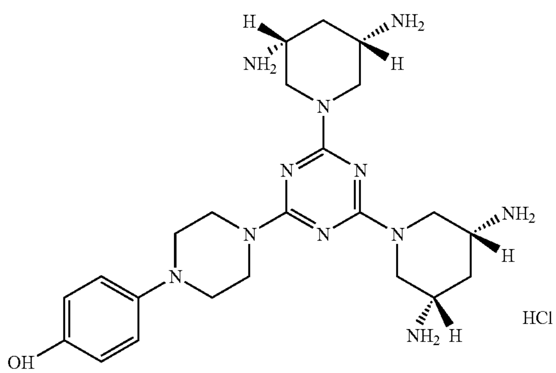 | 2-(3,6-Dihydro-2H-pyridin-1-yl)-4,6-Bis-((3R,5S)-3,5-diamino-piperidin-1-yl)-[1,3,5]triazine | – |
| 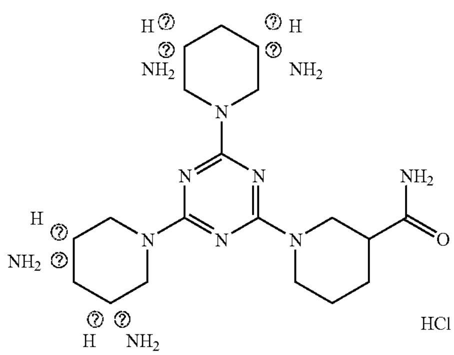 | 1-(4,6-Bis-((3R,5S)-3,5-diamino-piperidin-1-yl)-[1,3,5]triazin-2-yl)-piperidin-4-ol | |
| 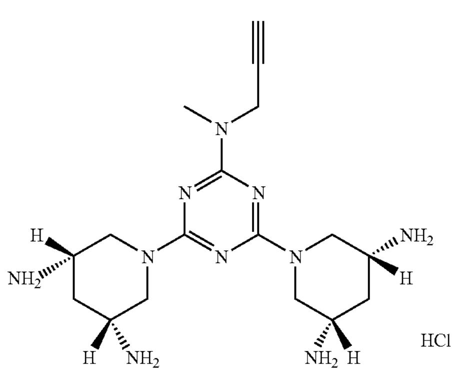 | N-Methyl-N-prop-2-ynyl-4,6-Bis-((3R,5S)-3,5-diamino-piperidin-1-yl)-[1,3,5]triazine-2-amine | |

⟨?⟩ indicates text missing or illegible when filed

-continued

| Structure | Name | Potency |
|---|---|---|
| 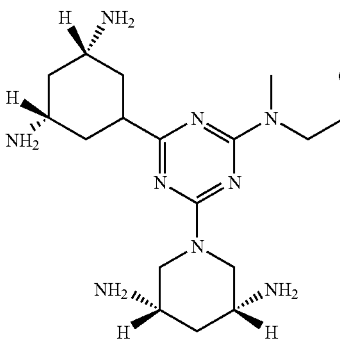 | N-[1,3]Dioxolan-2-ylmethyl-N-methyl-4,6-Bis-((3R,5S)-3,5-diamino-piperidin-1-yl)-[1,3,5]triazine-2-amine | |
| 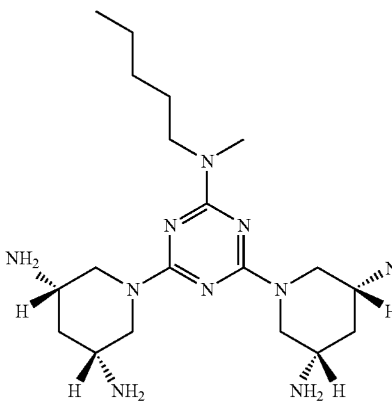 | N-Methyl-N-pentyl-4,6-Bis-((3R,5S)-3,5-diamino-piperidin-1-yl)-[1,3,5]triazine-2-amine | |
| 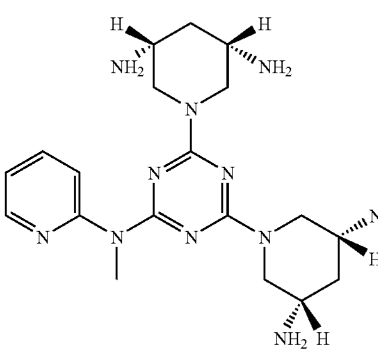 | N-Methyl-N-pyridin-2-yl-4,6-Bis-((3R,5S)-3,5-diamino-piperidin-1-yl)-[1,3,5]triazine-2-amine | |
| 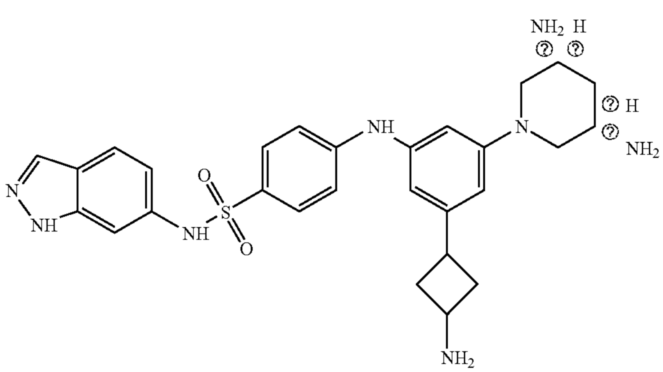 | 4-[4-(3-Amino-azetidin-1-yl)-6-((3R,5S)-3,5-diamino-piperidin-1-yl)-[1,3,5]triazin-2-ylamino]-N-(1H-indazol-6-yl)-benzenesulfonamide | – |

⑦ indicates text missing or illegible when filed

-continued

| Structure | Name | Potency |
|---|---|---|
| 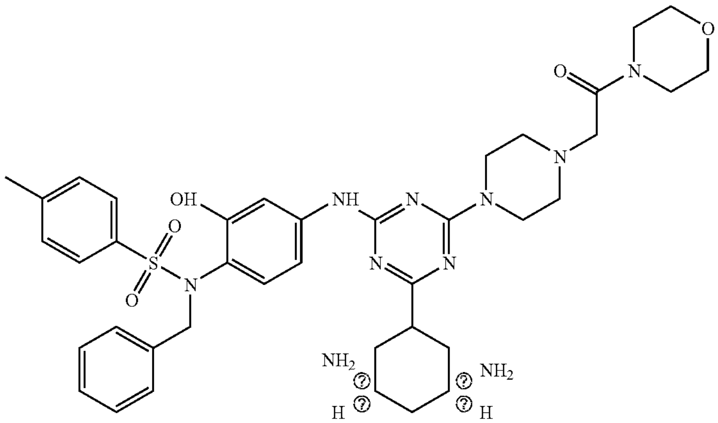 | N-Benzyl-N-(4-{4-((3R,5S)-3,5-diamino-piperidin-1-yl)-6-[4-(2-morpholin-4-yl-2-oxo-ethyl)-piperazin-1-yl]-[1,3,5]triazin-2-ylamino}-2-hydroxy-phenyl)-4-methyl-benzenesulfonamide | |
| 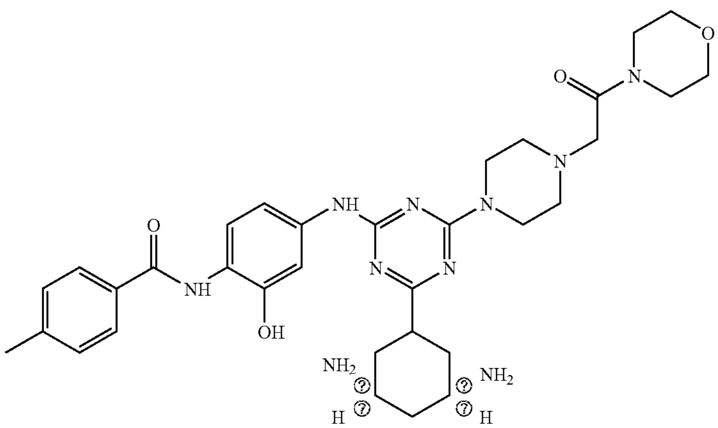 | N-(4-{4-((3R,5S)-3,5-Diamino-piperidin-1-yl)-6-[4-(2-morpholin-4-yl-2-oxo-ethyl)-piperazin-1-yl]-[1,3,5]triazin-2-ylamino}-2-hydroxy-phenyl)-4-methyl-benzamide | |
| 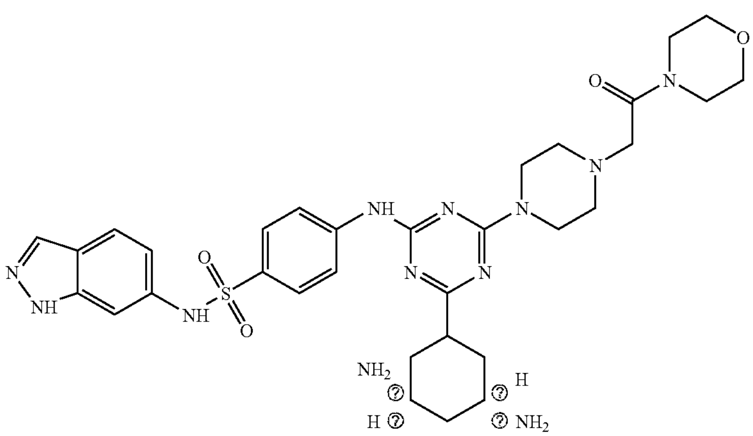 | 4-[4-((3S,5R)-3,5-Diamino-piperidin-1-yl)-6-[4-(2-morpholin-4-yl-2-oxo-ethyl)-piperazin-1-yl]-[1,3,5]triazin-2-ylamino}-N-(1H-indazol-6-yl)-benzenesulfonamide | |

⑦ indicates text missing or illegible when filed

-continued

| Structure | Name | Potency |
|---|---|---|
| (structure) | N-{4-[4-((3R,5S)-3,5-Diamino-piperidin-1-yl)-6-(4-pyridin-4-yl-piperazin-1-yl)-[1,3,5]triazin-2-ylamino]-2-hydroxy-phenyl}-4-methyl-benzamide | + |
| (structure) | 4-[4-((3S,5R)-3,5-DSiamino-piperidin-1-yl)-6-(4-pyridin-4-yl-piperazin-1-yl)-[1,3,5]triazin-2-ylamino]-N-(1H-indazol-6-yl)-benzenesulfonamide | + |
| (structure) | N-(4-{4-((3R,5S)-3,5-Diamino-piperidin-1-yl)-6-[2-(2-oxo-imidazolidin-1-yl)-ethylamino]-[1,3,5]triazin-2-ylamino}-2-hydroxy-phenyl)-4-methyl-benzamide | |

⑦ indicates text missing or illegible when filed

-continued

| Structure | Name | Potency |
|---|---|---|
| 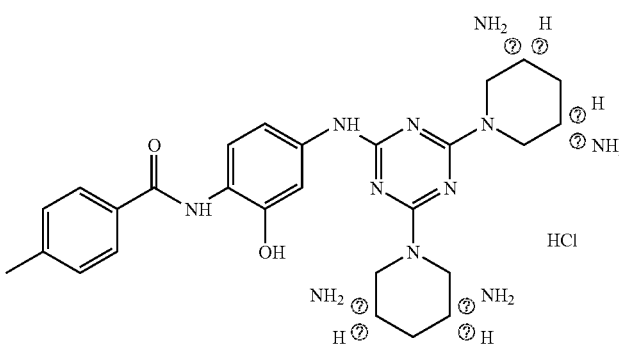 | 2-[4-(3,4-Dimethyl-phenyl)-piperazin-1-yl]-4,6-Bis-((3R,5S)-3,5-diamino-piperidin-1-yl)-[1,3,5]triazine | |
| 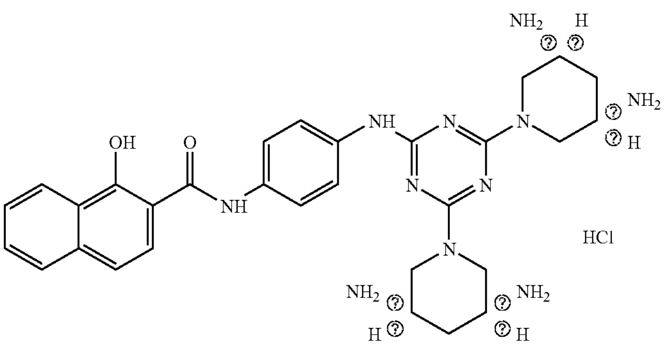 | N-{4-[(1-hydroxy-naphthalene-2-carbonyl)-amino]-phenyl}-4,6-Bis-((3R,5S)-3,5-diamino-piperidin-1-yl)-[1,3,5]triazine-2-amine | ++ |
| ⑦ indicates text missing or illegible when filed | | |
| 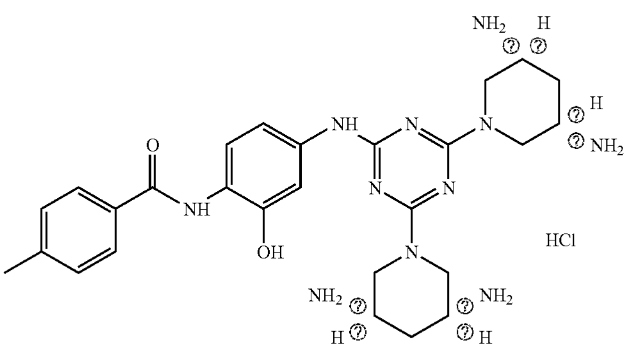 | N-[3-hydroxy-4-(4-methyl-benzoylamino)-phenyl]-4,6-Bis-((3R,5S)-3,5-diamino-piperidin-1-yl)-[1,3,5]triazine-2-amine | ++ |
| ⑦ indicates text missing or illegible when filed | | |
| 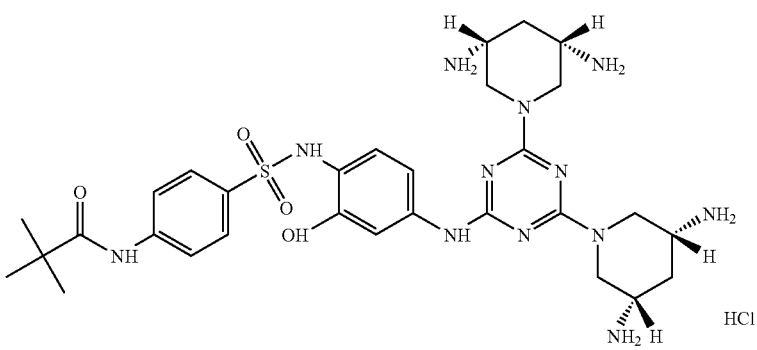 | N-{4-[4-(2,2-dimethyl-propionylamino)-benzenesulfonylamino]-3-hydroxy-phenyl}-4,6-Bis-((3R,5S)-3,5-diamino-piperidin-1-yl)-[1,3,5]triazine-2-amine | – |

| Structure | Name | Potency |
|---|---|---|
| 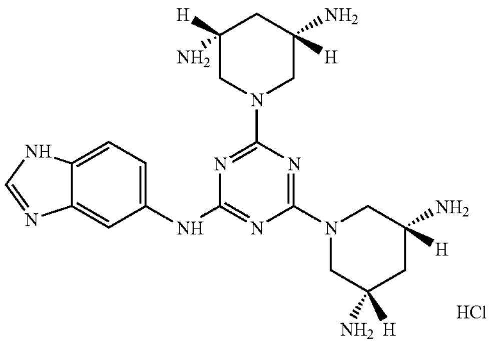 | N-(1H-benzoimidazol-5-yl)-4,6-Bis-((3R,5S)-3,5-diamino-piperidin-1-yl)-[1,3,5]triazine-2-amine | + |
| 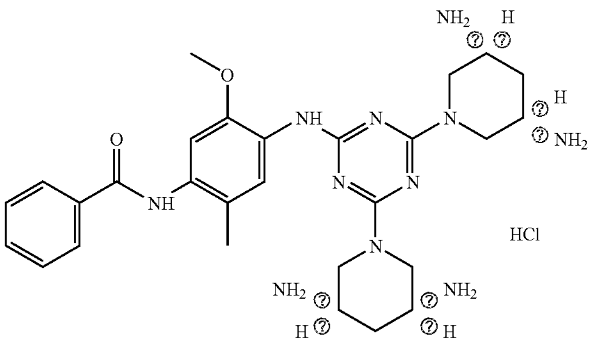 | N-(4-benzoylamino-2-methoxy-5-methyl-phenyl)-4,6-Bis-((3R,5S)-3,5-diamino-piperidin-1-yl)-[1,3,5]triazine-2-amine | |
| 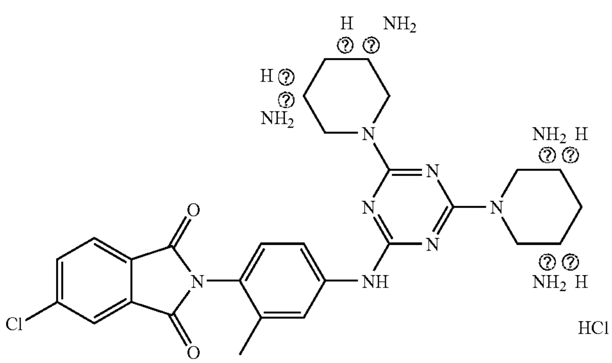 | N-[4-(5-chloro-1,3-dioxo-1,3-dihydro-isoindol-22-yl)-3-methyl-phenyl]-4,6-Bis-((3R,5S)-3,5-diamino-piperidin-1-yl)-[1,3,5]triazine-2-amine | + |
| 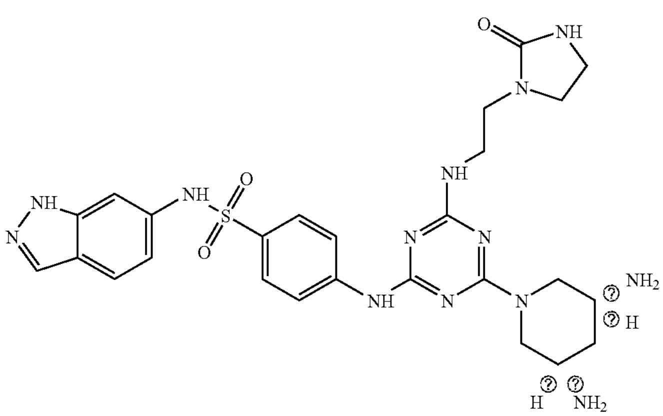 | 4-{4-((3S,5R)-3,5-Diamino-piperidin-1-yl)-6-[2-(2-oxo-imidazolidin-1-yl)-ethylamino]-[1,3,5]triazin-2-ylamino}-N-(1H-indazol-6-yl)-benzenesulfonamide | |

⑦ indicates text missing or illegible when filed

-continued

| Structure | Name | Potency |
|---|---|---|
| 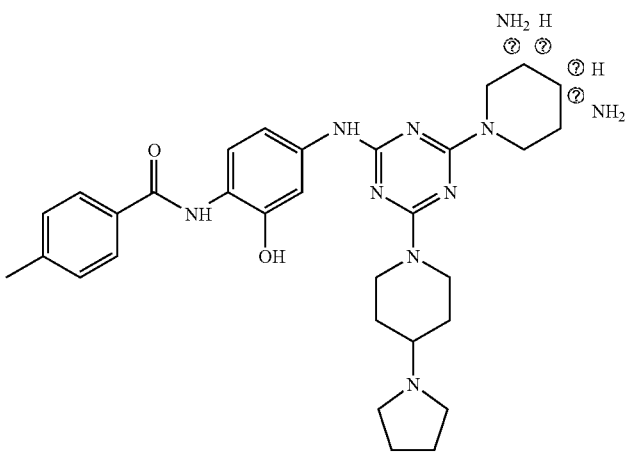 | N-Benzyl-N-{4-[4-((3R,5S)-33,5-diamino-piperidin-1-yl)-6-(4-pyrrolidin-1-yl-piperidin-1-yl)-[1,3,5]triazin-2-ylamino]-2-hydroxy-phhenyl}-4-methyl-benzenesulfonamide | |
| 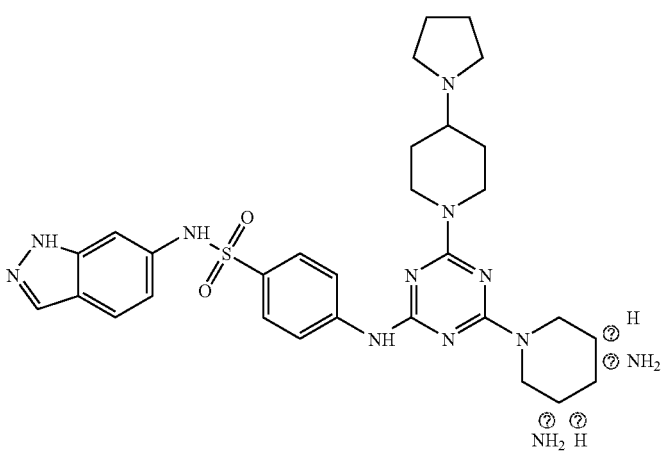 | N-{4-[4-((3R,5S)-3,5-Diamino-piperidin-1-yl)-6-(4-pyrrolidin-1-yl-piperidin-1-yl)-[1,3,5]triazin-2-ylamino]-2-hydroxy-phhenyl}-4-methyl-benzamide | + |
| 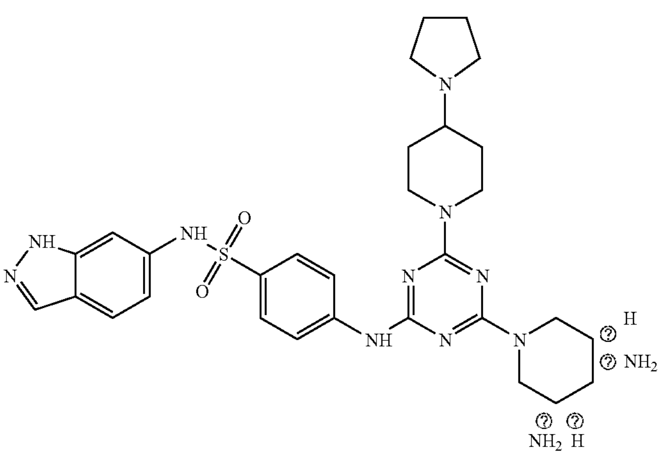 | 4-[4-((3S,5R)-3,5-Diamino-piperidin-1-yl)-6-(4-pyrrolidin-1-yl-piperidin-1-yl)-[1,3,5]triazin-2-ylamino]-N-(1H-indazol-6-yl)-benzenesulfonamide | − |

⊘ indicates text missing or illegible when filed

-continued

| Structure | Name | Potency |
|---|---|---|
| 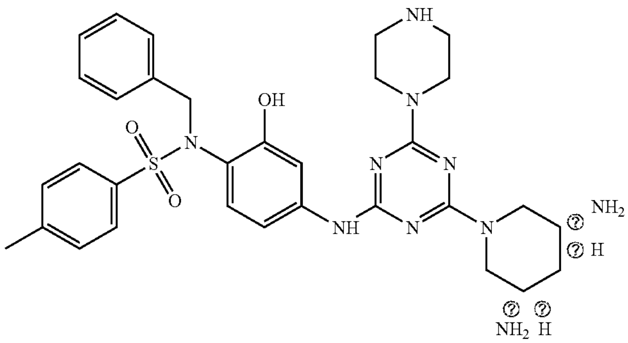 | N-Benzyl-N-{4-[4-((3R,5S)-3,5-diamino-piperidin-1-yl)-6-piperazin-1-yl-[1,3,5]triazin-2-ylamino]-2-hydroxy-phenyl}-4-methyl-benzenesulfonamide | + |
| 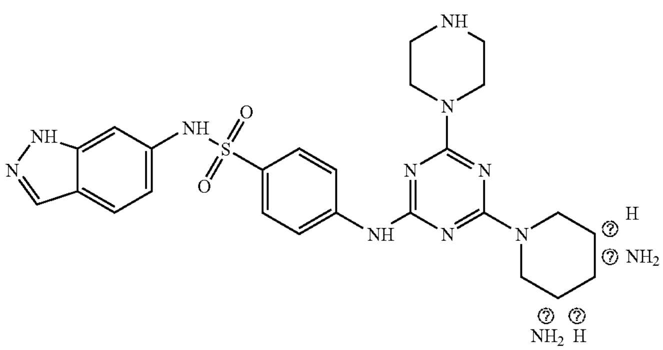 | 4-[4-((3S,5R)-3,5-Diamino-piperidin-1-yl)-6-piperazin-1-yl[1,3,5,-triazin-2-ylamino]-N-(1H-indazol-6-yl)-benzenesulfonamide | − |
| 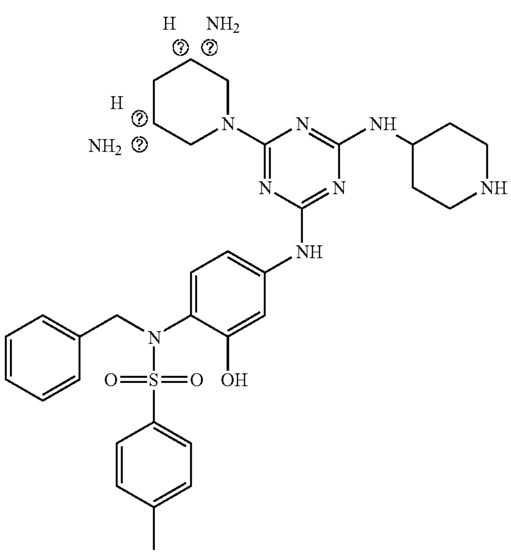 | N-Benzyl-N-{4-[4-((3R,5S)-3,5-diamino-piperidin-1-yl)-6-(piperidin-4-ylamino)-[1,3,5]triazin-2-ylamino]-2-hydroxy-phenyl}-4-methyl-benzenesulfonamide | + |

⑦ indicates text missing or illegible when filed

-continued

| Structure | Name | Potency |
|---|---|---|
| 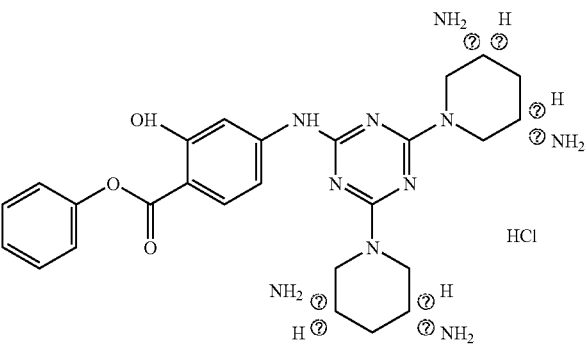 ⓘ indicates text missing or illegible when filed | 4-[4,6-Bis-((3R,5S)-3,5-diamino-piperidin-1-yl)-[1,3,5]triazin-2-ylamino]-2-hydroxy-benzoic acid phenyl ester | ++ |
| 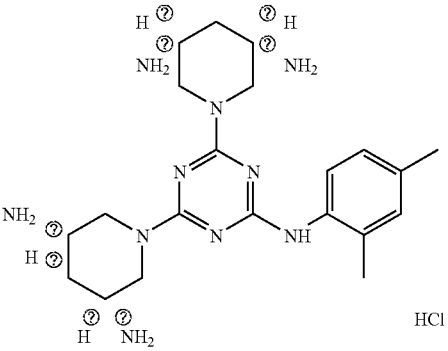 ⓘ indicates text missing or illegible when filed | N-(2,4-dimethyl-phenyl)-4,6-Bis-((3R,5S)-3,5-diamino-piperidin-1-yl)-[1,3,5]triazine-2-amine | |
| 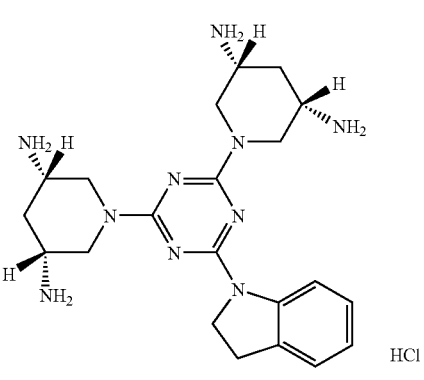 | 1-(4,6-Bis-((3R,5S)-3,5-diamino-piperidin-1-yl)-[1,3,5]triazin-2-yl)-piperidin-4-ylamine | − |
| 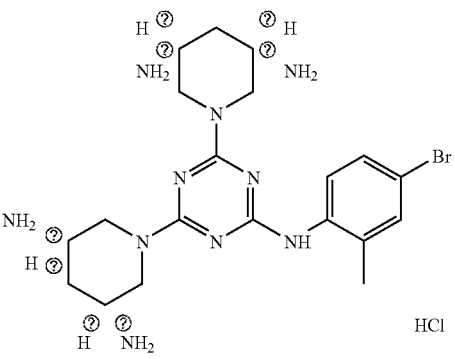 ⓘ indicates text missing or illegible when filed | N-(4-bromo-2-methyl-phenyl)-4,6-Bis-((3R,5S)-3,5-diamino-piperidin-1-yl)-[1,3,5]triazine-2-amine | − |

-continued

| Structure | Name | Potency |
|---|---|---|
| 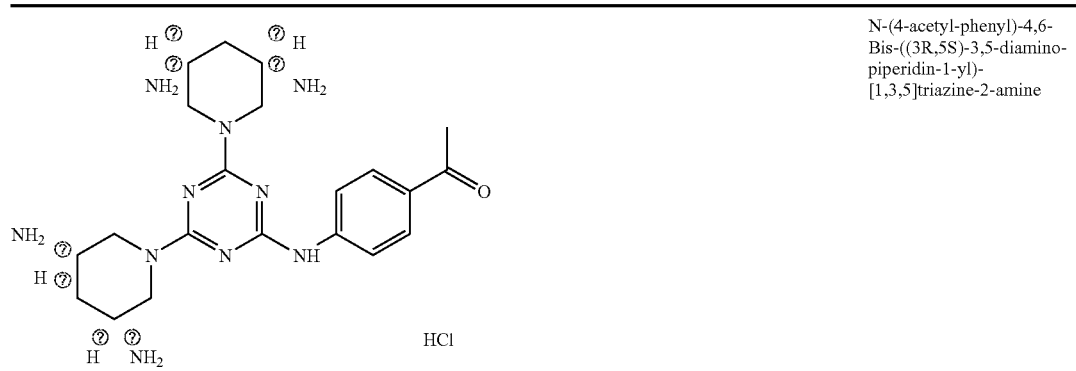 | N-(4-acetyl-phenyl)-4,6-Bis-((3R,5S)-3,5-diamino-piperidin-1-yl)-[1,3,5]triazine-2-amine | + |
| 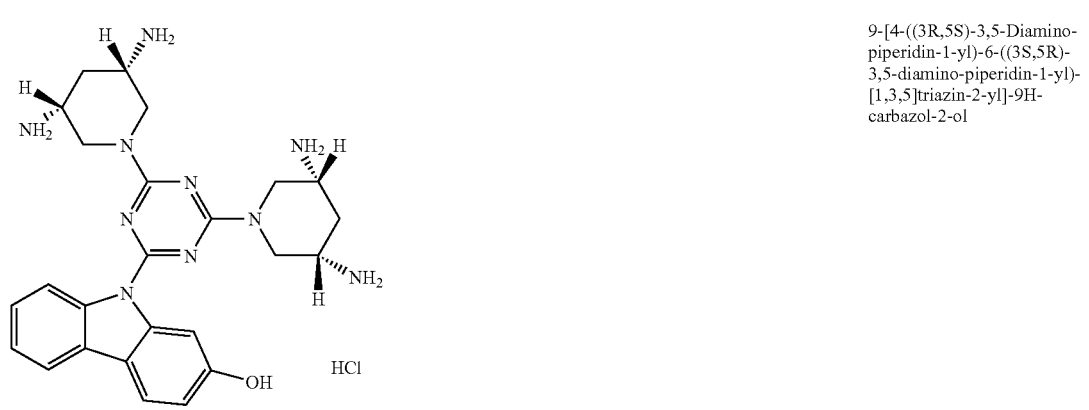 | 9-[4-((3R,5S)-3,5-Diamino-piperidin-1-yl)-6-((3S,5R)-3,5-diamino-piperidin-1-yl)-[1,3,5]triazin-2-yl]-9H-carbazol-2-ol | |
| 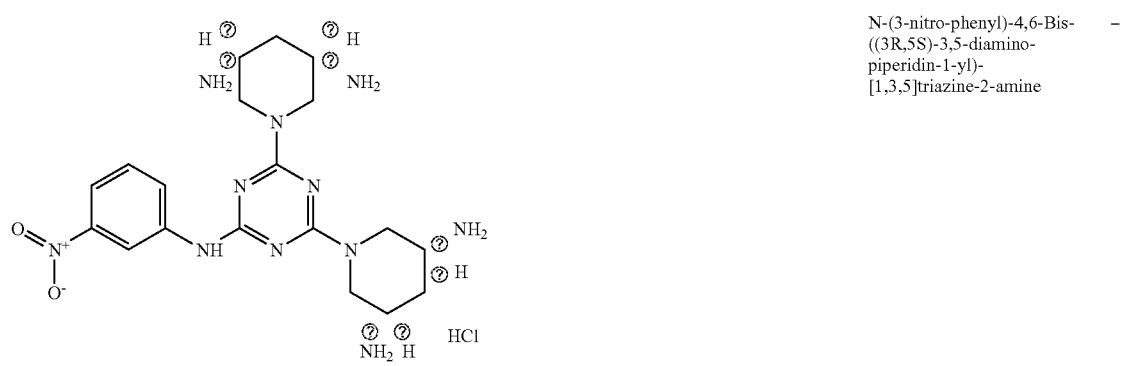 | N-(3-nitro-phenyl)-4,6-Bis-((3R,5S)-3,5-diamino-piperidin-1-yl)-[1,3,5]triazine-2-amine | − |
| 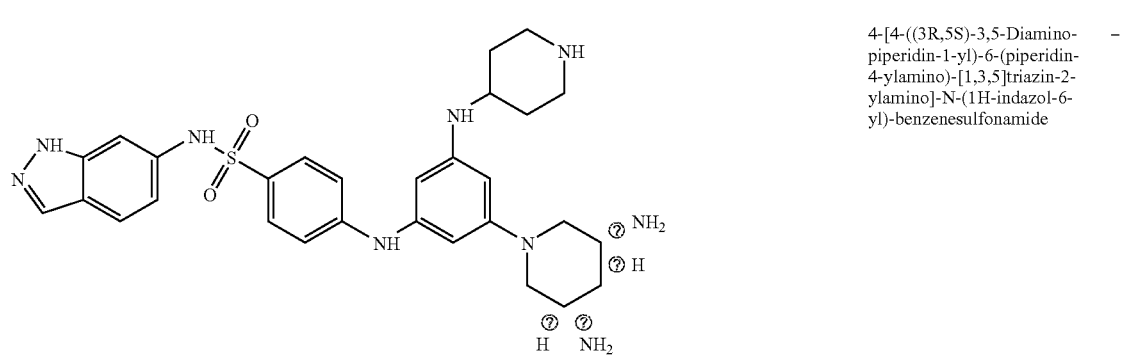 | 4-[4-((3R,5S)-3,5-Diamino-piperidin-1-yl)-6-(piperidin-4-ylamino)-[1,3,5]triazin-2-ylamino]-N-(1H-indazol-6-yl)-benzenesulfonamide | − |

⑦ indicates text missing or illegible when filed

-continued

| Structure | Name | Potency |
|---|---|---|
| 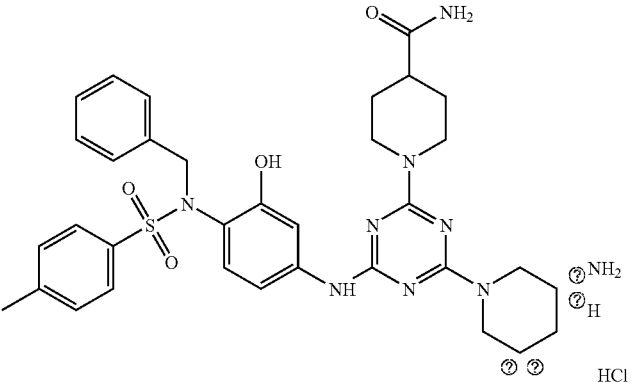 ⓘ indicates text missing or illegible when filed | 1-[4-{4-[Benzyl-(toluene-4-sulfonyl)-amino⋎-3hydroxy-phenylamino}-6-((3R,5S)-3,5-diamino-piperidin-1-yl)-[1,3,5]triazin-2-yl]-piperidine-4-carboxylic acid amide | |
| 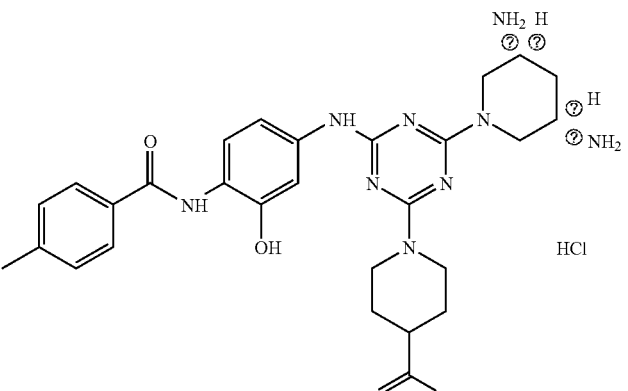 ⓘ indicates text missing or illegible when filed | 1-{4-((3R,5S)-3,5-Diamino-piperidin-1-yl)-6-[3-hydroxy-4-(4-methyl-benzoylamino)-phenylamino]-[1,3,5]triazin-2-yl}-piperidine-4-carboxylic acid amide | |
| 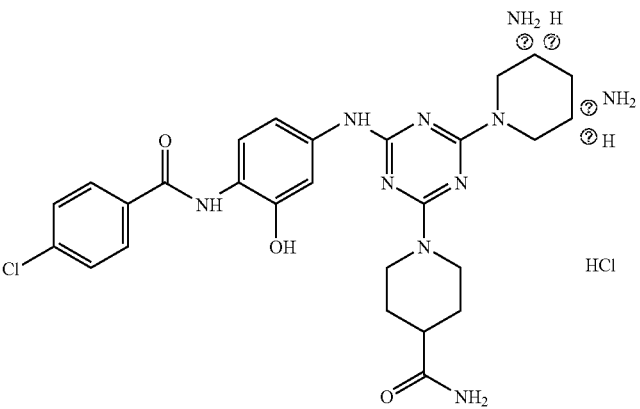 ⓘ indicates text missing or illegible when filed | 1-[4-[4-(4-Chloro-benzoylamino)-3-hydroxy-phenylamino]-6-((3S,5R)-3,5-diamino-piperidin-1-yl)-[1,3,5]trazin-2-yl]-piperidine-4-carboxylic acid amide | |

-continued

| Structure | Name | Potency |
|---|---|---|
| 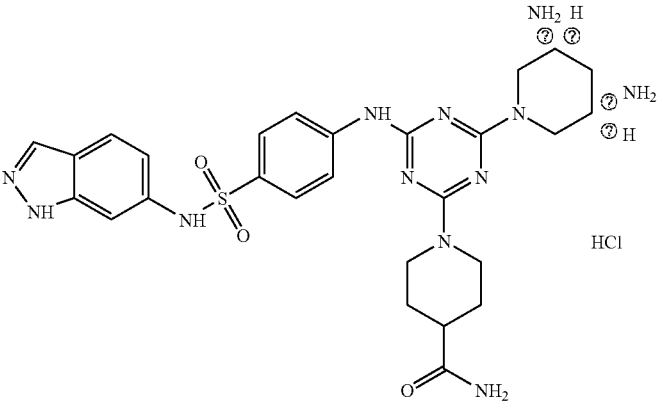 | 1-[4-((3S,5R)-3,5-Diamino-piperidin-1-yl)-6-[4-(1H-indazol-6-ylsulfamoyl)-phenylamino]-[1,3,5]triazin-2-yl}-piperidine-4-carboxylic acid amide | |
| 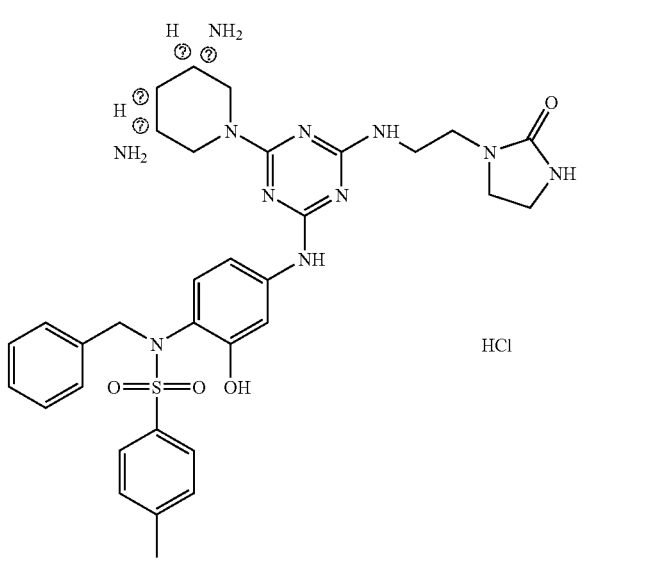 | N-Benzyl-N-(4-{4-((3R,5S)-3,5-diamino-piperidin-1-yl)-6-[2-(2-oxo-imidazolidin-1-yl)-ethylamino]-[1,3,5]triazin-2-ylamino}-2-hydroxy-phenyl)-4-methyl-benzenesulfonamide | |
| 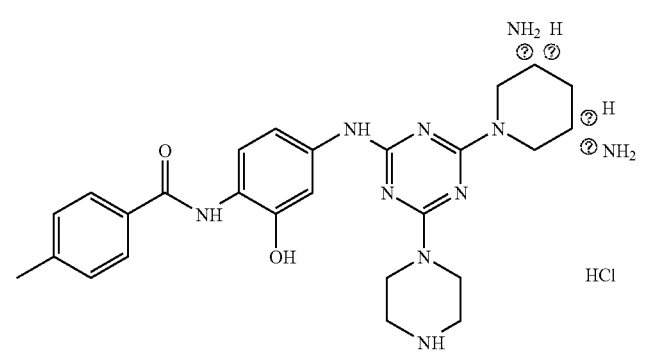 | N-{4-[4-((3R,5S)-3,5-Diamino-piperidin-1-yl)-6-piperazin-1-yl-[1,3,5]triazin-2-ylamino]-2-hydroxy-phenyl}-4-methyl-benzamide | |

⑦ indicates text missing or illegible when filed

-continued

| Structure | Name | Potency |
|---|---|---|
| 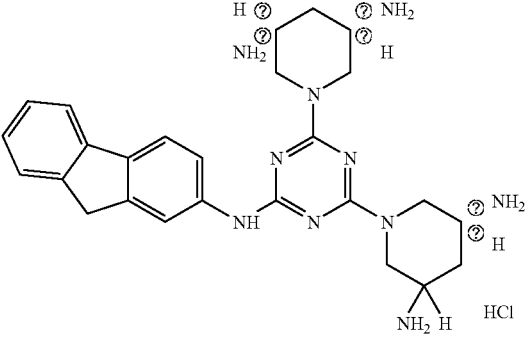 | N-(9H-fluoren-2-yl)-4,6-Bis-((3R,5S)-3,5-diamino-piperidin-1-yl)-[1,3,5]triazine-2-amine | ++ |
| ⑦ indicates text missing or illegible when filed | | |
| 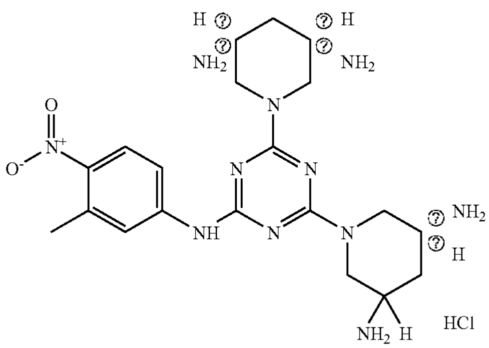 | N-(3-methyl-4-nitro-phenyl)-4,6-Bis-((3R,5S)-3,5-diamino-piperidin-1-yl)-[1,3,5]triazine-2-amine | + |
| ⑦ indicates text missing or illegible when filed | | |
| 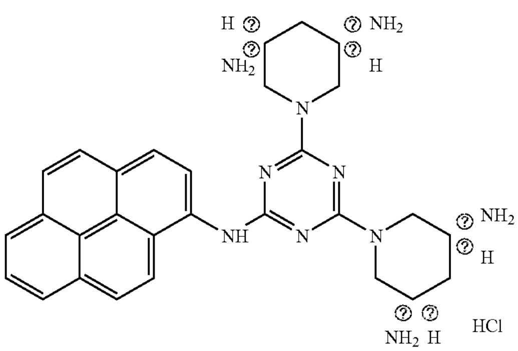 | N-pyren-1-yl-4,6-Bis-((3R,5S)-3,5-diamino-piperidin-1-yl)-[1,3,5]triazine-2-amine | ++ |
| ⑦ indicates text missing or illegible when filed | | |
| 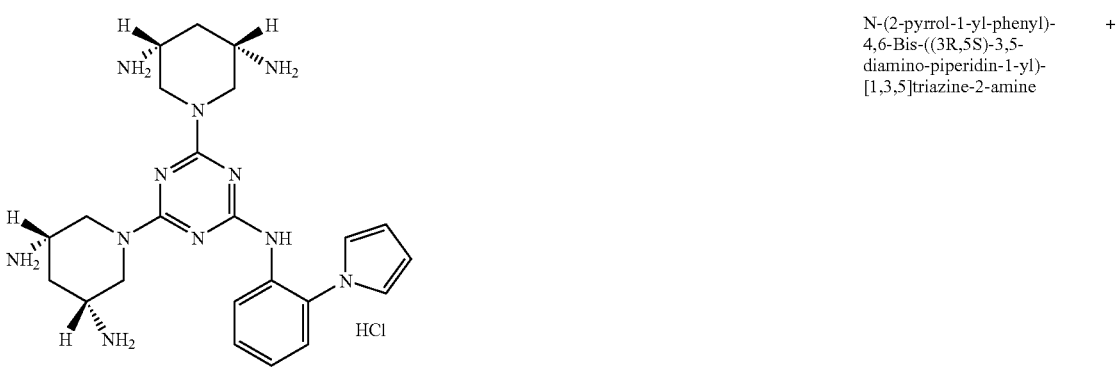 | N-(2-pyrrol-1-yl-phenyl)-4,6-Bis-((3R,5S)-3,5-diamino-piperidin-1-yl)-[1,3,5]triazine-2-amine | + |

-continued
| Structure | Name | Potency |
|---|---|---|
| 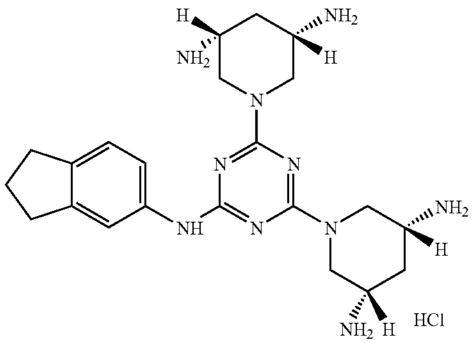 | N-indan-5-yl-4,6-Bis-((3R,5S)-3,5-diamino-piperidin-1-yl)-[1,3,5]triazine-2-amine | − |
| 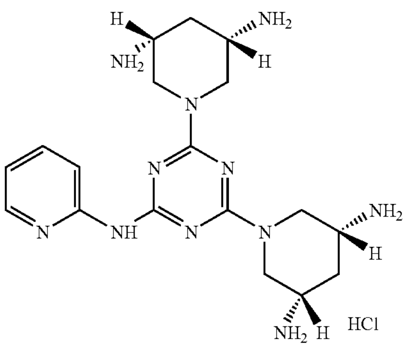 | N-pyridin-22-yl-4,6-Bis-((3R,5S)-3,5-diamino-piperidin-1-yl)-[1,3,5]triazine-2-amine | |
| 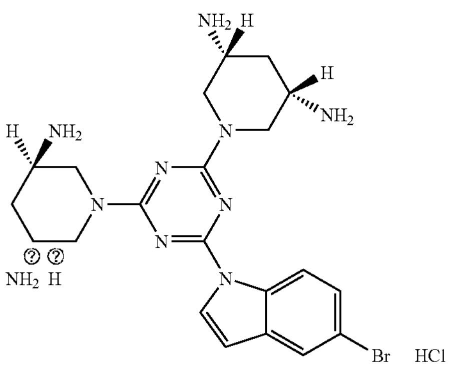 | 5-Bromo-1-(4,6-Bis-((3R,5S)-3,5-diamino-piperidin-1-yl)-[1,3,5]triazain-2-yl)-1H-indole | + |
| 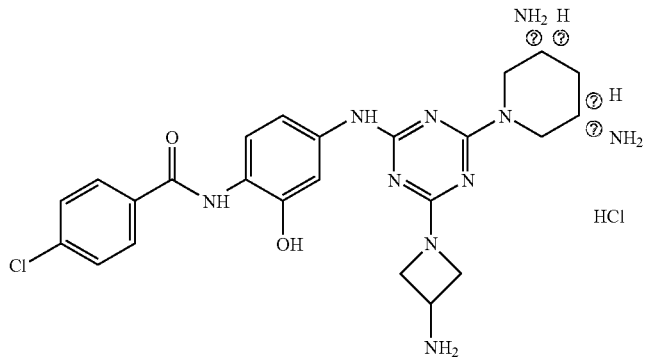 | N-{4-[4-(3-Amino-azetidin-1-yl)-6-((3R,5S)-3,5-diamino-piperidin-1-yl)-[1,3,5]triazin-2-ylamino]-2-hydroxy-phenyl}-4-chloro-benzamide | ++ |
⊘ indicates text missing or illegible when filed -continued

| Structure | Name | Potency |
|---|---|---|
| 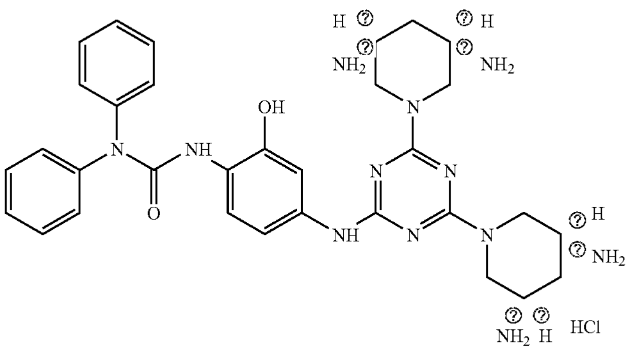 | N-[4-(3,3-diphenyl-ureido)-3-hydroxy-phenyl]-4,6-Bis-((3R,5S)-3,5-diamino-piperidin-1-yl)-[1,3,5]triazine-2-amine | |
| 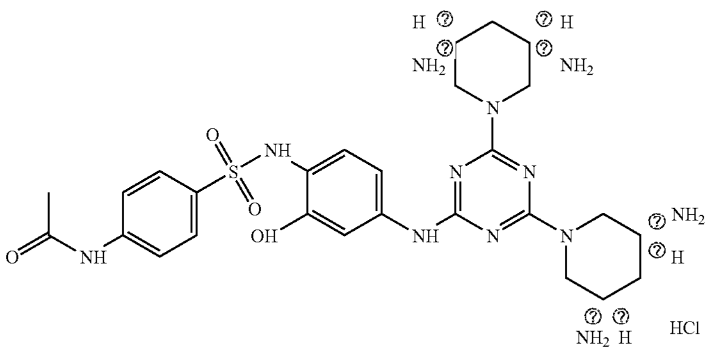 | N-[4-(4-acetylamino-benzenesulfonylamino)-3-hydroxy-phenyl]-4,6-Bis-((3R,5S)-3,5-diamino-piperidin-1-yl)-[1,3,5]triazine-2-amine | |
| 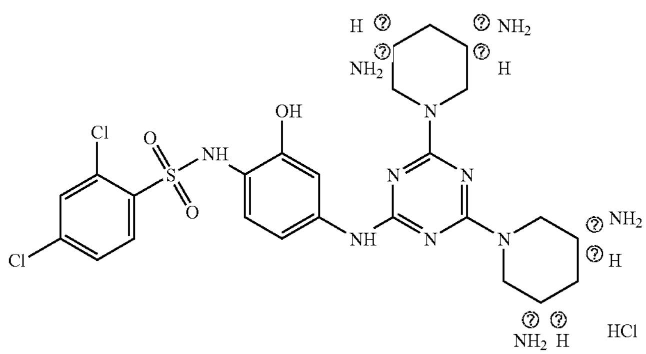 | N-[4-(2,4-dichloro-benzenesulfonylamino)-3-hydroxy-phenyl]-4,6-Bis-((3R,5S)-3,5-diamino-piperidin-1-yl)-[1,3,5]triazine-2-amine | |
| 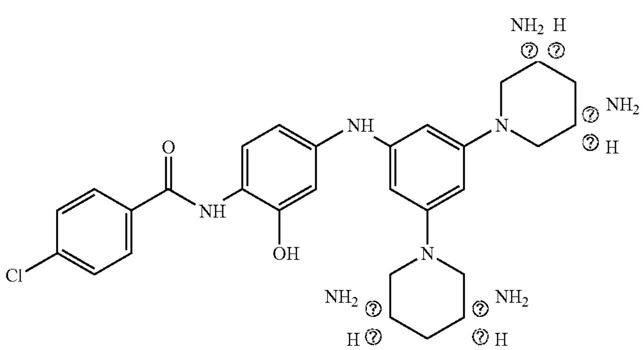 | N-[4-(4-chloro-benzoylamino)-3-hydroxy-phenyl]-4,6-Bis-((3R,5S)-3,5-diaamino-piperidin-1-yl)-[1,3,5]triazine-2-amine | |

⑦ indicates text missing or illegible when filed

-continued
| Structure | Name | Potency |
|---|---|---|
| 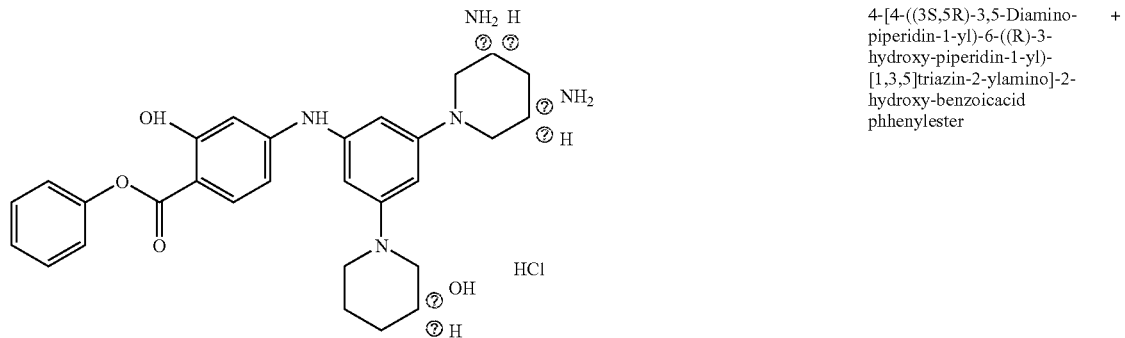 | 4-[4-((3S,5R)-3,5-Diamino-piperidin-1-yl)-6-((R)-3-hydroxy-piperidin-1-yl)-[1,3,5]triazin-2-ylamino]-2-hydroxy-benzoicacid phhenylester | + |
| 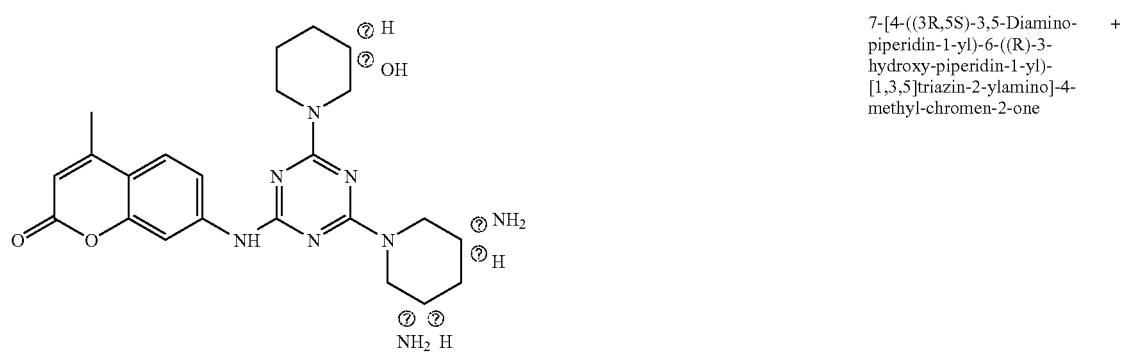 | 7-[4-((3R,5S)-3,5-Diamino-piperidin-1-yl)-6-((R)-3-hydroxy-piperidin-1-yl)-[1,3,5]triazin-2-ylamino]-4-methyl-chromen-2-one | + |
| 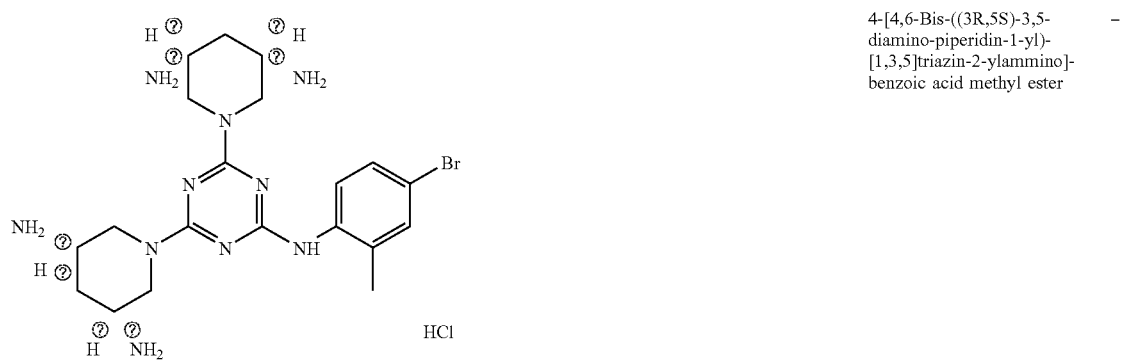 | 4-[4,6-Bis-((3R,5S)-3,5-diamino-piperidin-1-yl)-[1,3,5]triazin-2-ylammino]-benzoic acid methyl ester | – |
⁇ indicates text missing or illegible when filed -continued

| Structure | Name | Potency |
|---|---|---|
| 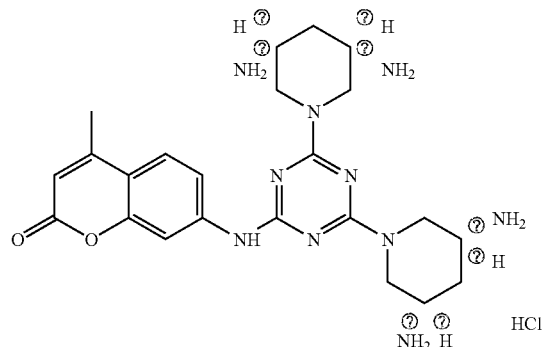 | N-(4-methyl-2-oxo-2H-chromen-7-yl)-4,6-Bis-((3R,5S)-3,5-diamino-piperidin-1-yl)-[1,3,5]triazine-2-amine | ++ |
| ⓘ indicates text missing or illegible when filed | | |
| 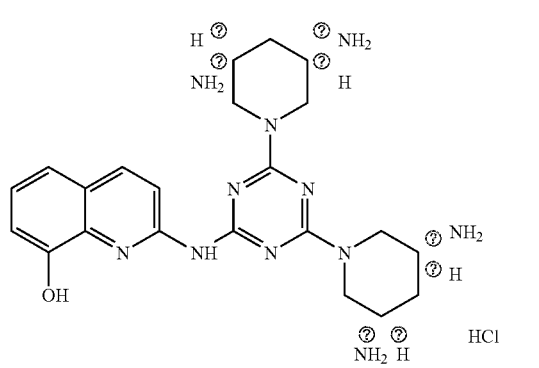 | N-(8-hydroxy-quinolin-2-yl)-4,6-Bis-((3R,5S)-3,5-diamino-piperidin-1-yl)-[1,3,5]triazine-2-ammine | − |
| ⓘ indicates text missing or illegible when filed | | |
| 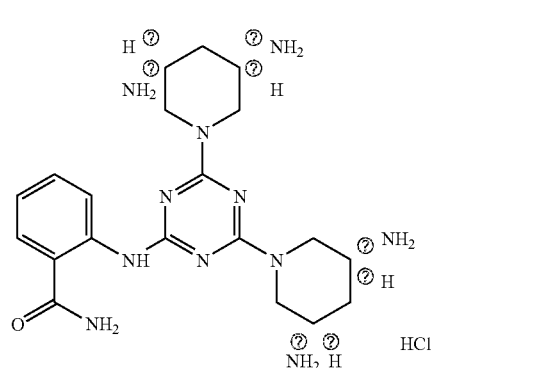 | N-(2-carbamoyl-phenyl)-4,6-Bis-((3R,5S)-3,5-diamino-piperidin-1-yl)-[1,3,5]triazine-2-amine | |
| ⓘ indicates text missing or illegible when filed | | |
| 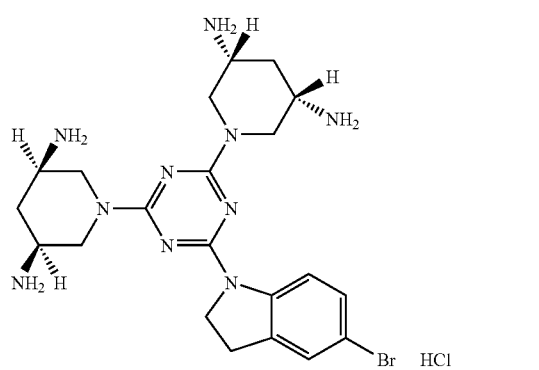 | 4-[4-(4,6-Bis-((3R,5S)-3,5-diamino-piperidin-1-yl)-[1,3,5]triazin-2-yl)-piperiazin-1-yl]-phenol | + |

-continued

| Structure | Name | Potency |
|---|---|---|
| 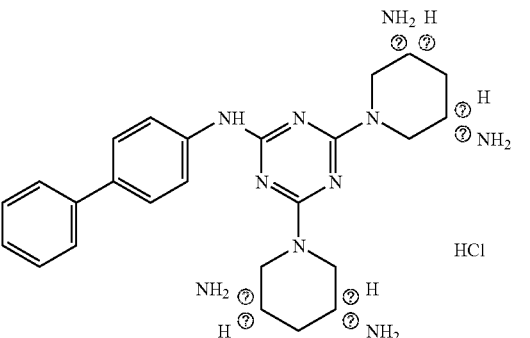 | N-biphenyl-4-yl-4,6-Bis-((3R,5S)-3,5-diamino-piperidin-1-yl)-[1,3,5]triazine-2-amine | + |
| ⓘ indicates text missing or illegible when filed | | |
| 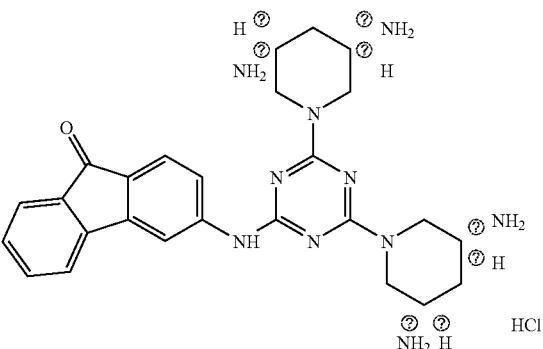 | N-(9-oxo-9H-fluoren-3-yl)-4,6-Bis-((3R,5S)-3,5-diamino-piperidin-1-yl)-[1,3,5]triazine-2-amine | ++ |
| ⓘ indicates text missing or illegible when filed | | |
| 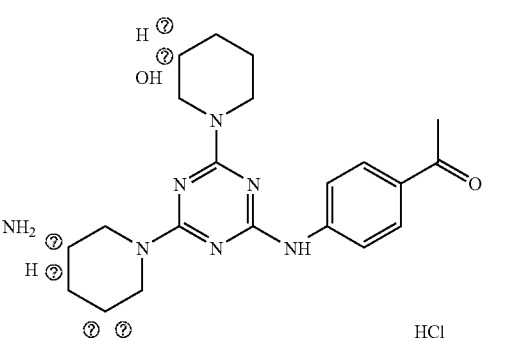 | 1-{4-[4-((3R,5S)-3,5-Diamino-piperidin-1-yl)-6-((R)-3-hydroxy-piperidin-1-yl)-[1,3,5]triazin-2-ylamino]-phenyl}-ethanone | − |
| ⓘ indicates text missing or illegible when filed | | |

-continued

| Structure | Name | Potency |
|---|---|---|
| 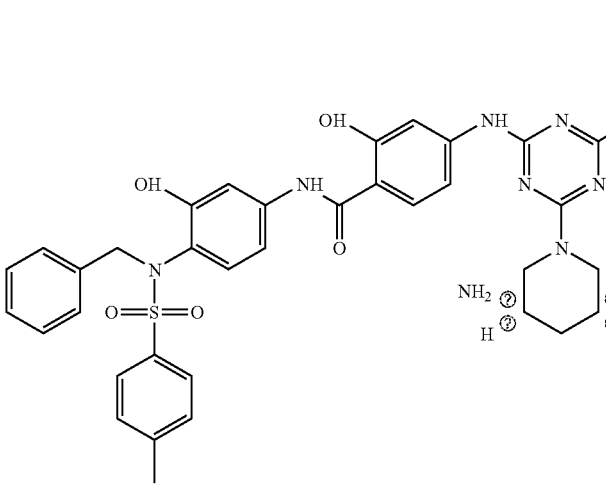 | N-{3-hydroxy-4-[4-(2-oxo-2,3-dihydro-benzoimidazol-1-yl)-piperidin-1-carbonyl]-phenyl}-4,6-Bis-((3R,5S)-3,5-diamino-piperidin-1-yl)-[1,3,5]triazine-2-amine | + |
| ⑦ indicates text missing or illegible when filed | | |
| 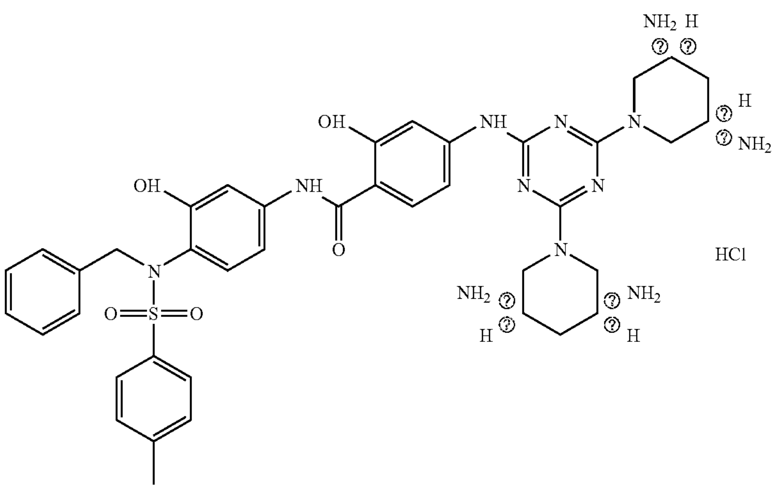 | N-(4-{4-[benzyl-(toluene-4-sulfonyl)-amino]-3-hydroxy-phenylcarbamoyl)-3-hydroxy-phenyl)-4,6-Bis-((3R,5S)-3,5-diamino-piperidin-1-yl)-[1,3,5]triazine-2-amine | ++ |
| ⑦ indicates text missing or illegible when filed | | |
| 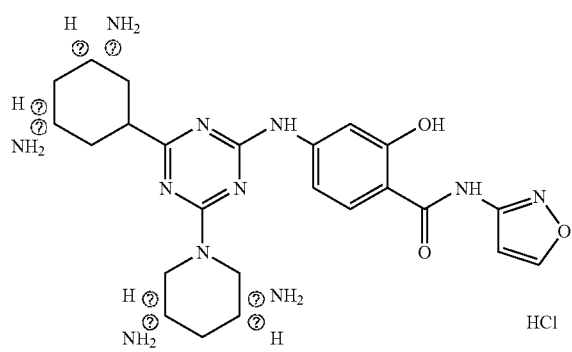 | N-[3-hydroxy-4-(isoxazol-3-ylcarbamoyl)-phenyl]-4,6-Bis-((3R,5S)-3,5-diamino-piperidin-1-yl)-[1,3,5]triazine-2-amine | + |
| ⑦ indicates text missing or illegible when filed | | |

| Structure | Name | Potency |
|---|---|---|
| | N-[3-hydroxy-4-(4-methoxy-phenylcarbamoyl)-phenyl]-4,6-Bis-((3R,5S)-3,5-diamino-piperidin-1-yl)-[1,3,5]triazine-2-amine · HCl | + |
| | N-[3-hydroxy-4-(6-methyl-pyridin-2-ylcarbamoyl)-phenyl]-4,6-Bis-((3R,5S)-3,5-diamino-piperidin-1-yl)-[1,3,5]triaazine-2-amine · HCl | + |
| | N-[3-hydroxy-4-(4-methyl-2-oxo-2H-chromen-7-ylcarbamoyl)-phenyl]-4,6-Bis-((3R,5S)-3,5-diamino-piperidin-1-yl)-[1,3,5]triazine-2-amine · HCl | ++ |
| | N-(4-phenylazo-phenyl)-4,6-Bis-((3R,5S)-3,5-0 diamino-piperidin-1-yl)-[1,3,5]triazine-2-amine · HCl | ++ |

-continued
| Structure | Name | Potency |
|---|---|---|
| 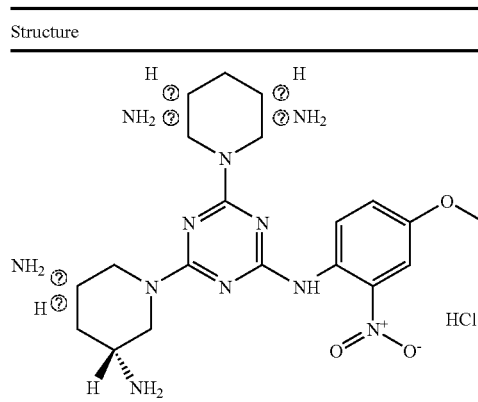 | N-(4-methoxy-2-nitro-phenyl)-4,6-Bis-((3R,5S)-3,5-diamino-piperidin-1-yl)-[1,3,5]triazine-2-amine | − |
| 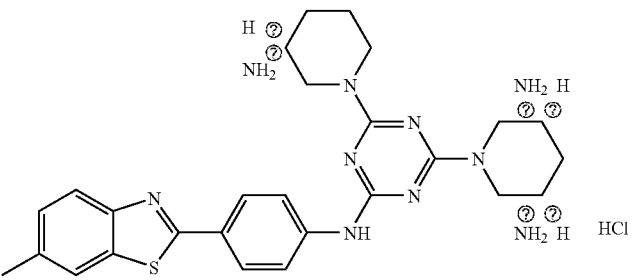 | N-[4-(6-methyl-benzothiazol-2-yl)-phenyl]-4,6-Bis-((3R,5S)-3,5-diamino-piperidin-1-yl)-[1,3,5]triazine-2-amine | ++ |
| 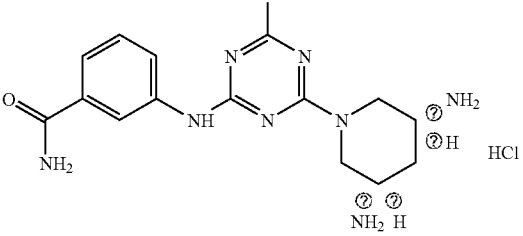 | N-(3-carbamoyl-phenyl)-4,6-Bis-((3R,5S)-3,5-diamino-piperidin-1-yl)-[1,3,5]triazine-2-amine | |
| 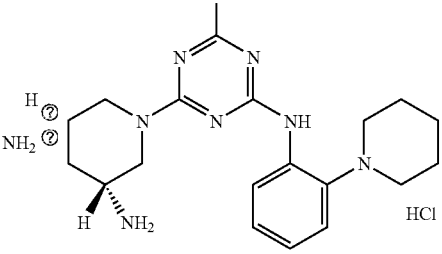 | N-(2-piperidin-1-yl-phenyl)-4,6-Bis-((3R,5S)-3,5-diamino-piperidin-1-yl)-[1,3,5]triazine-2-amine | − |
? indicates text missing or illegible when filed -continued
| Structure | Name | Potency |
|---|---|---|
| 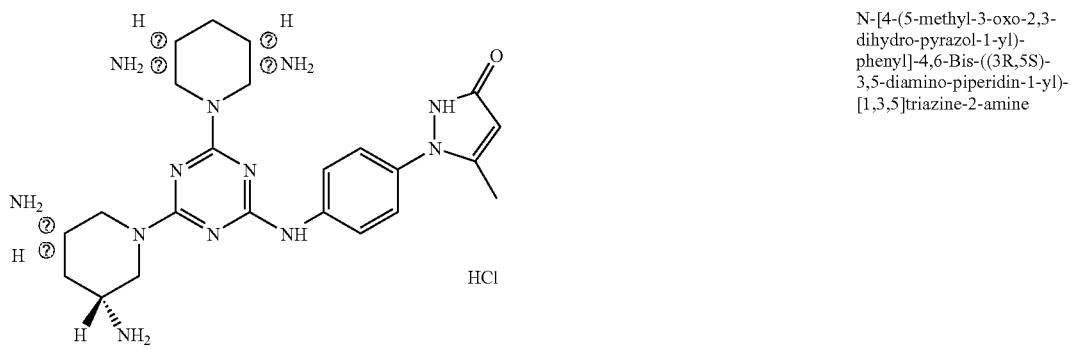 | N-[4-(5-methyl-3-oxo-2,3-dihydro-pyrazol-1-yl)-phenyl]-4,6-Bis-((3R,5S)-3,5-diamino-piperidin-1-yl)-[1,3,5]triazine-2-amine | |
| 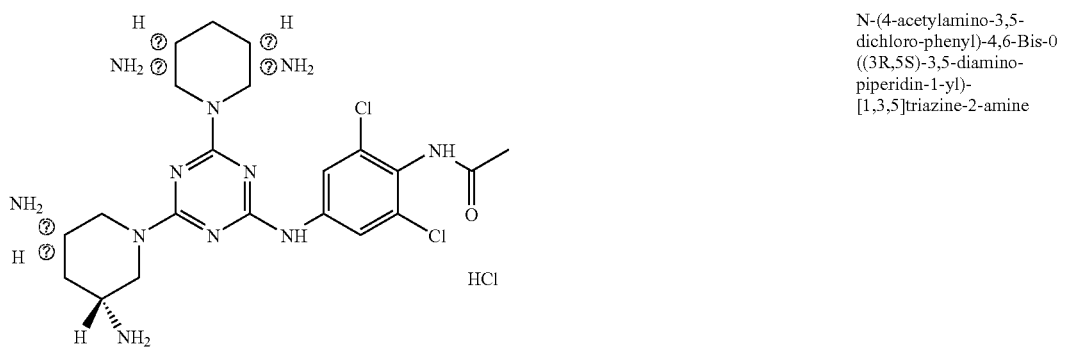 | N-(4-acetylamino-3,5-dichloro-phenyl)-4,6-Bis-0((3R,5S)-3,5-diamino-piperidin-1-yl)-[1,3,5]triazine-2-amine | – |
| 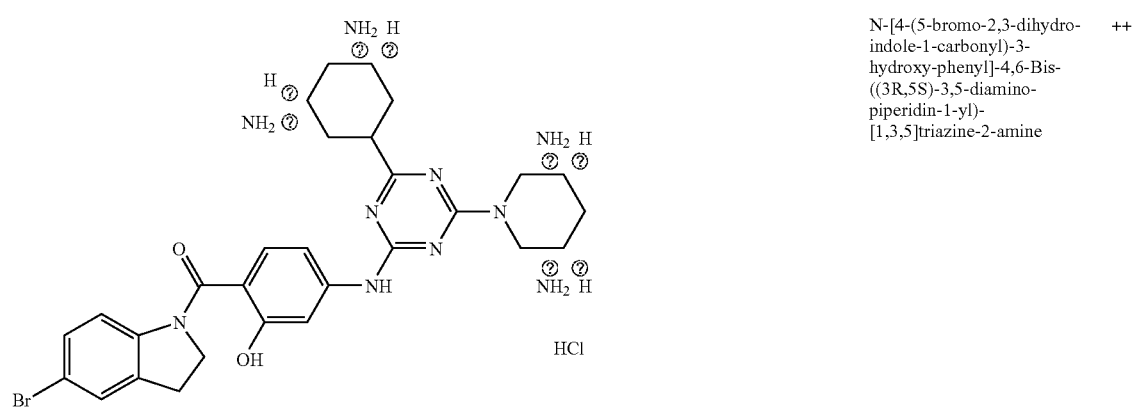 | N-[4-(5-bromo-2,3-dihydro-indole-1-carbonyl)-3-hydroxy-phenyl]-4,6-Bis-((3R,5S)-3,5-diamino-piperidin-1-yl)-[1,3,5]triazine-2-amine | ++ |
⑦ indicates text missing or illegible when filed

| Structure | Name | Potency |
|---|---|---|
| 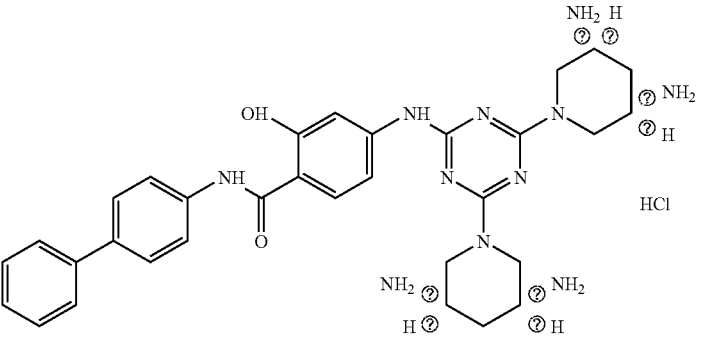 | N-[4-(biphenyl-4-ylcarbamoyl)-3-hydroxy-phenyl]-4,6-Bis-((3R,5S)-3,5-diamino-piperidin-1-yl)-[1,3,5]triazine-2-amine | ++ |
| 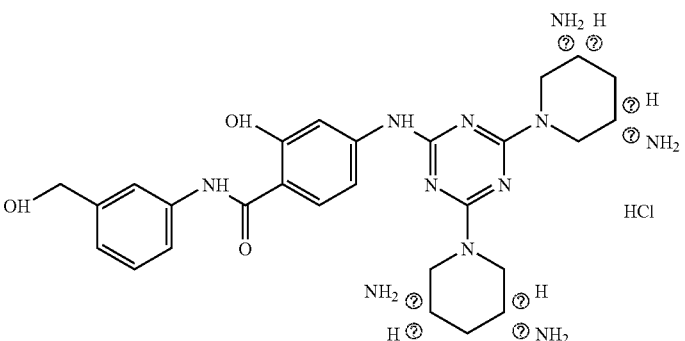 | N-[3-hydroxy-4-(3-hydroxymethyl-phenylcarbamoyl)-phenyl]-4,6-Bis-((3R,5S)-3,5-diamino-piperidin-1-yl)-[1,3,5]triazine-2-amine | + |
| 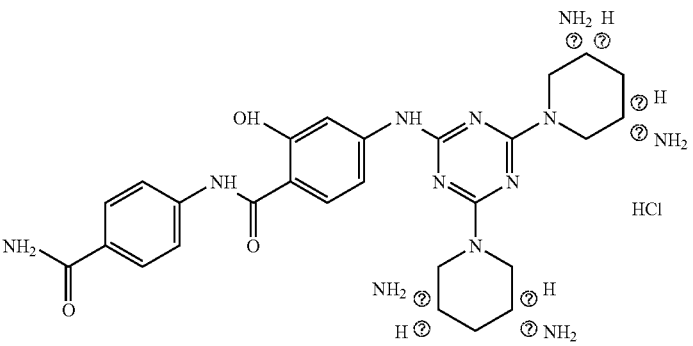 | N-[4-(4-carbamoyl-phenylcarbamoyl)-3-hydroxy-phenyl]-4,6-Bis-((3R,5S)-3,5-diamino-piperidin-1-yl)-[1,3,5]triazine-2-amine | − |
⑦ indicates text missing or illegible when filed -continued

| Structure | Name | Potency |
|---|---|---|
| 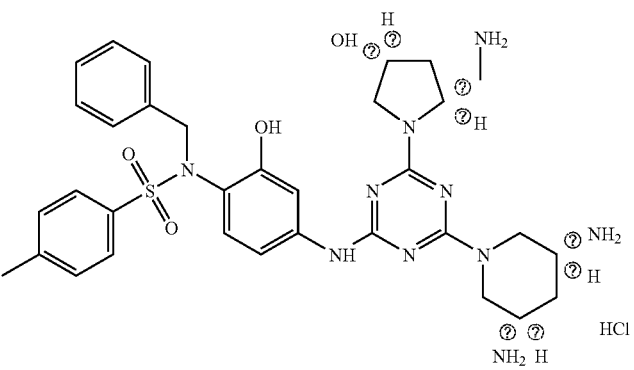 | 3-{4-[4-((2S,4R)-2-Aminomethyl-4-hydroxy-pyrrolidin-1-yl)-6-((3R,5S)-3,5-diamino-piperidin-1-yl)-[1,3,5]triazin-2-ylamino]-phenyl}-N-(2-chloro-phenyl)-3-oxo-propionamide | + |
| ⑦ indicates text missing or illegible when filed | | |
| 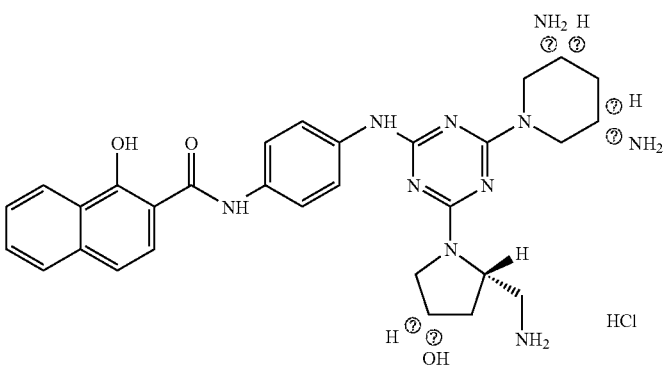 | N-{4-[4-((2S,4R)-2-Aminomethyl-4-hydroxy-pyrrolidin-1-yl)-6-((3R,5S)-3,5-diamino-piperidin-1-yl)-[1,3,5]triazin-2-ylamino]-2-hydroxy-phenyl}-N-benzyl-4-methyl-benzenesulfonamide | + |
| ⑦ indicates text missing or illegible when filed | | |
| 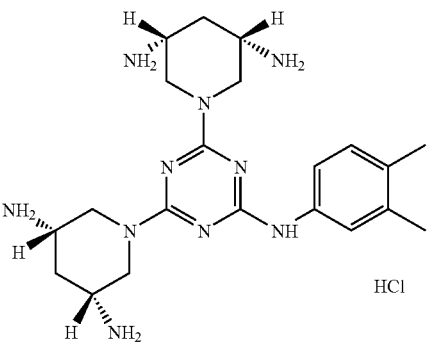 | 1-Hydroxy-naphthalene-2-carboxylicacid {4-[4-((2S,4R)-2-aminomethyl-4-hydroxy-pyrrolidin-1-yl)-6-((3R,5S)-3,5-diamino-piperidin-1-yl)-[1,3,5]triazin-2-ylamino]-phenyl}-amide | + |
| ⑦ indicates text missing or illegible when filed | | |
| 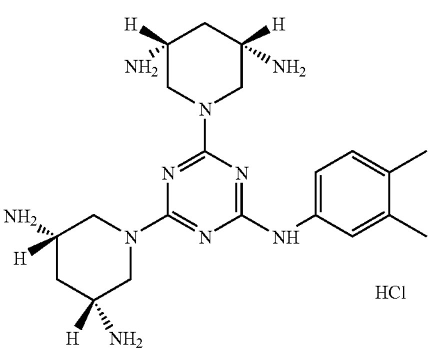 | N-(3,4-dimethyl-phenyl)-4,6-Bis-((3R,5S)-3,5-ddiamino-piperidin-1-yl)-[1,3,5]triazine-2-amine | + |

| Structure | Name | Potency |
|---|---|---|
| 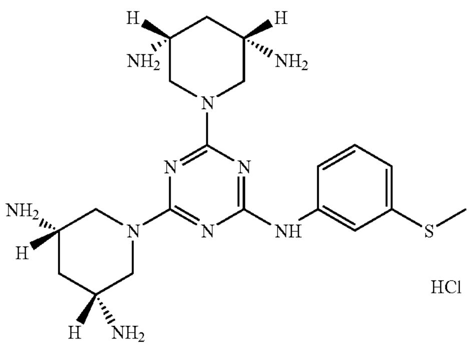 | N-(3-methyylsulfanyl-phenyl)-4,6-Bis-((3R,5S)-3,5-diamino-piperidin-1-yl)-[1,3,5]triazine-2-amine | + |
| 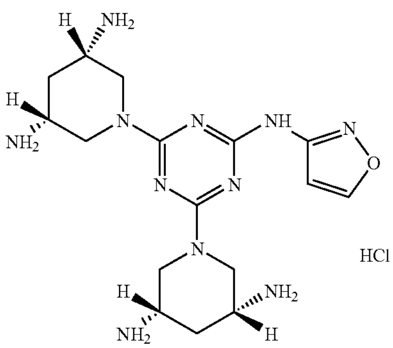 | N-isoxazol-3-yl-4,6-Bis-((3R,5S)-3,5-diamino-piperidin-1-yl)-[1,3,5]triazine-2-amine | − |
| 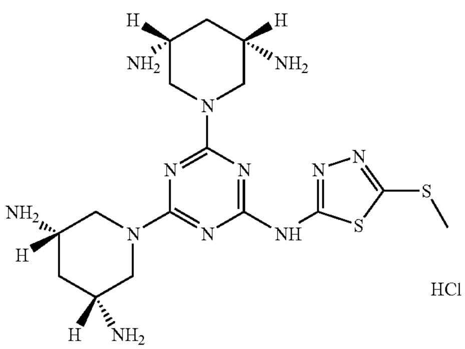 | N-(5-methylsulfanyl-[1,3,4]thiadiazol-2-yl)-4,6-Bis-((3R,5S)-3,5-diamino-piperidin-1-yl)-[1,3,5]triazine-2-amine | − |
| 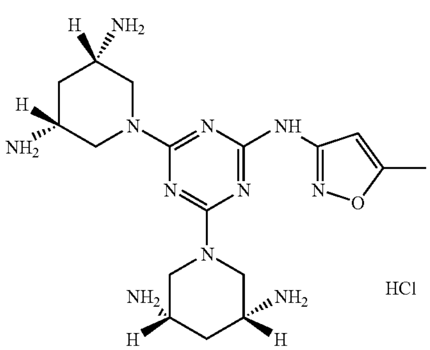 | N-(5-methyl-isoxazol-3-yl)-4,6-Bis-((3R,5S)-3,5-diamino-piperidin-1-yl)-[1,3,5]triazine-2-amine | − |

-continued

| Structure | Name | Potency |
|---|---|---|
| 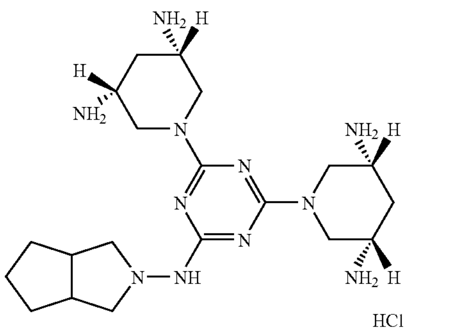 | N-(Occtahydro-cyclopenta[c]pyrrole-2-yl)-4,6-Bis-((3R,5S)-3,5-diamino-piperidin-1-yl)-[1,3,5]triazine-2-amine | |
| 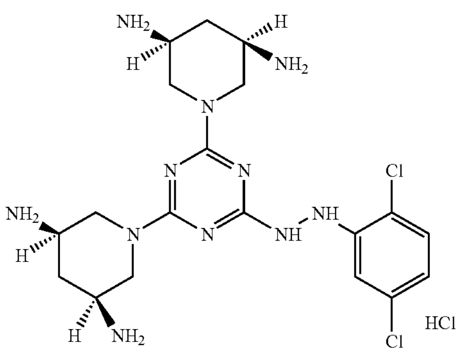 | N-(4,6-Bis-((3R,5S)-3,5-diamino-piperidin-1-yl)-[1,3,5]triazin-2-yl)-N'-(2,5-Dichloro-phenyl)-hydrazine | + |
| 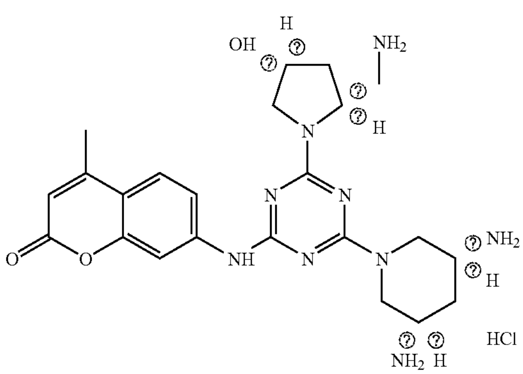 | 7-[4-((2S,4R)-2-Aminomethyl-4-hydroxy-pyrrolidin-1-yl)-6-((3R,5S)-3,5-diamino-piperidin-1-yl)-[1,3,5]triazin-2-ylamino]-4-methyl-chromen-2-one | − |

⑦ indicates text missing or illegible when filed

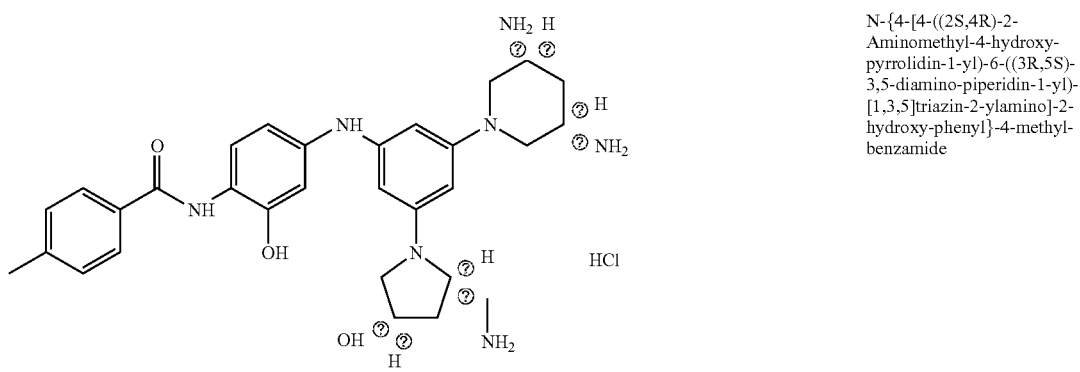

N-{4-[4-((2S,4R)-2-Aminomethyl-4-hydroxy-pyrrolidin-1-yl)-6-((3R,5S)-3,5-diamino-piperidin-1-yl)-[1,3,5]triazin-2-ylamino]-2-hydroxy-phenyl}-4-methyl-benzamide   −

⑦ indicates text missing or illegible when filed

-continued

| Structure | Name | Potency |
|---|---|---|
| (structure) | 3-{4-[4-((2S,4RE)-2-Aminomethyl-4-hydroxy-pyrrolidin-1-yl)-6-((3R,5S)-3,5-diamino-piperidin-1-yl)-[1,3,5]triazin-2-ylamino]-phenyl}-3-oxo-N-(4-trifluoromethylsulfanyl-phenyl)-propionamide | ++ |
| (structure) | 2-[4-((2S,4R)-2-Aminomethyl-4-hydroxy-pyrrolidin-1-yl)-6-((3R,5S)-3,5-diamino-piperidin-1-yl)-[1,3,5]triazin-2-ylamino]-fluoren-9-one | − |
| (structure) | 4-[4-((2S,4R)-2-Aminomethyl-4-hydroxy-pyrrolidin-1-yl)-6-((3R,5S)-3,5-diamino-piperidin-1-yl)-[1,3,56]triazin-2-ylamino]-N-(1H-indazol-6-yl)-benzenesulfonamide | − |

⊚ indicates text missing or illegible when filed

-continued

| Structure | Name | Potency |
|---|---|---|
| 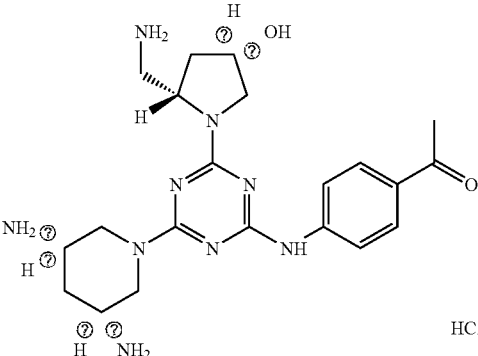 | 1-{4-[4-((2S,4R)-2-Aminomethyl-4-hydroxy-pyrrolidin-1-yl)-6-((3R,5S)-3,5-diamino-piperidin-1-yl)-[1,3,5]triazin-2-ylamino]-phenyl}-ethanone | − |
| 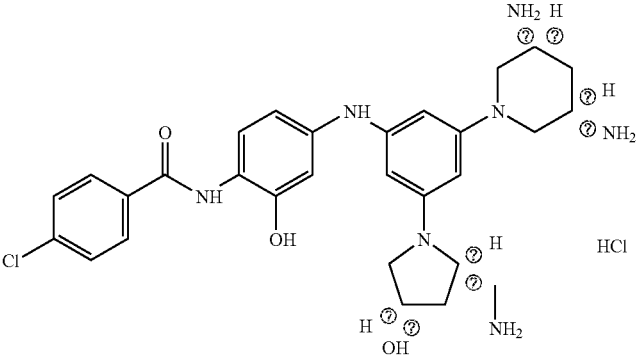 | N-{4-[4-((2S,4R)-2-Aminomethyl-4-hydroxy-pyrrolidin-1-yl)-6-((3R,5S)-3,5-diamino-piperidin-1-yl)-[1,3,5]triazin-2-ylamino]-2-hydroxy-phenyl}-4-chloro-benzamide | + |
| 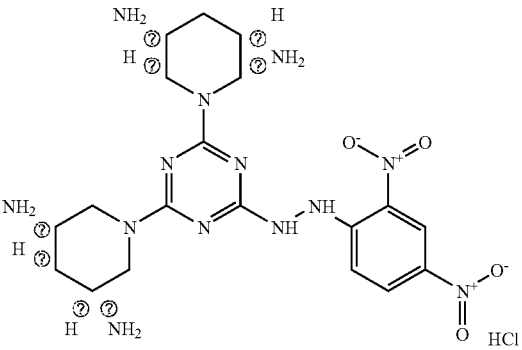 | N-(4,6-Bis-((3R,5S)-3,5-diamino-piperidin-1-yl)-[1,3,5]triazin-2-yl)-N'-(2,4-Dinitro-phenyl)-hydrazine | − |

⊙ indicates text missing or illegible when filed

-continued
| Structure | Name | Potency |
|---|---|---|
| 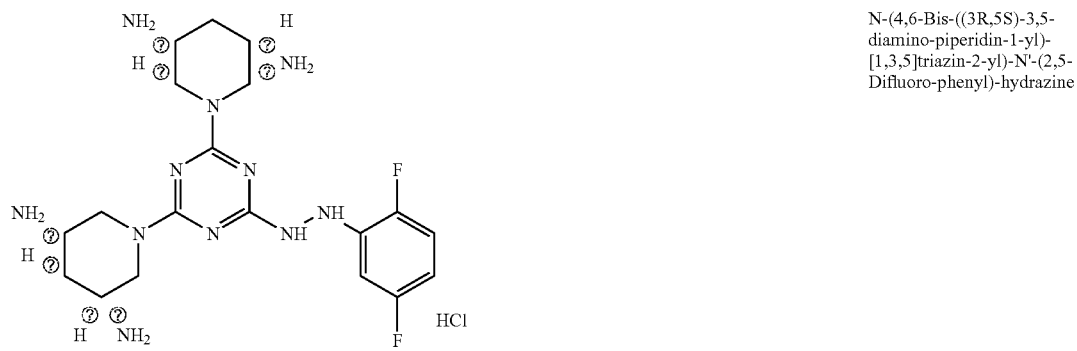 | N-(4,6-Bis-((3R,5S)-3,5-diamino-piperidin-1-yl)-[1,3,5]triazin-2-yl)-N'-(2,5-Difluoro-phenyl)-hydrazine | |
| 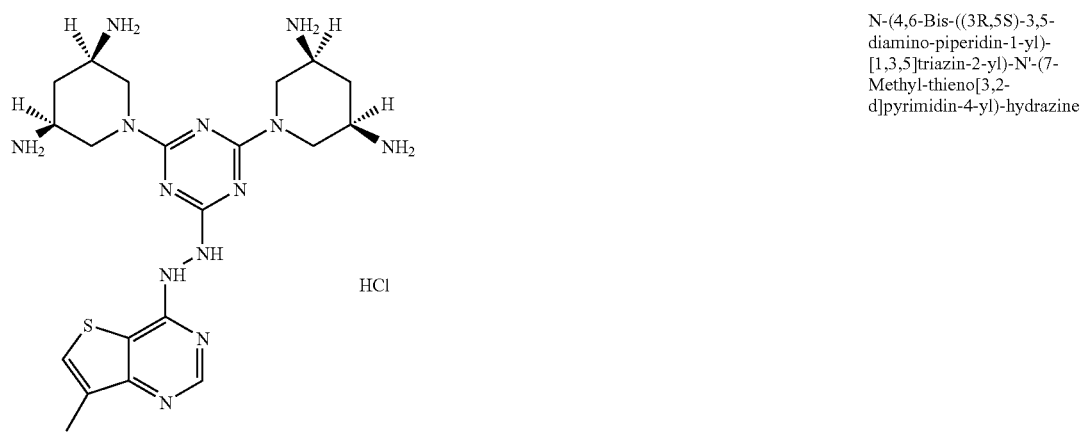 | N-(4,6-Bis-((3R,5S)-3,5-diamino-piperidin-1-yl)-[1,3,5]triazin-2-yl)-N'-(7-Methyl-thieno[3,2-d]pyrimidin-4-yl)-hydrazine | – |
| 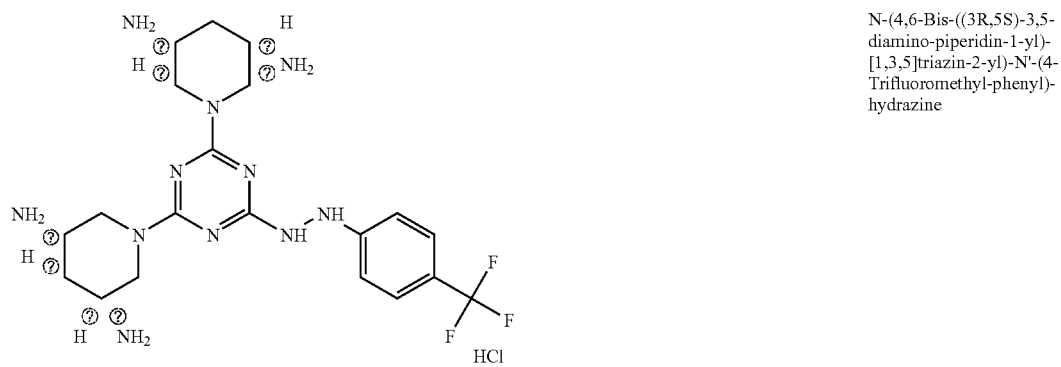 | N-(4,6-Bis-((3R,5S)-3,5-diamino-piperidin-1-yl)-[1,3,5]triazin-2-yl)-N'-(4-Trifluoromethyl-phenyl)-hydrazine | |
⊘ indicates text missing or illegible when filed -continued
| Structure | Name | Potency |
|---|---|---|
| 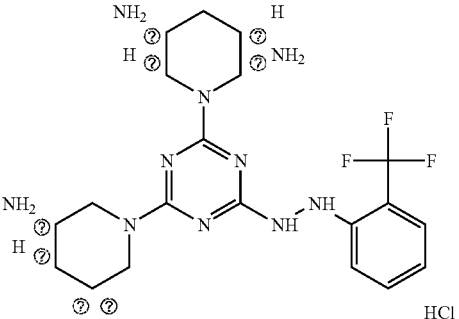 | N-(4,6-Bis-((3R,5S)-3,5-diamino-piperidin-1-yl)-[1,3,5]triazin-2-yl)-N'-(2-Trifluoromethyl-phenyl)-hydrazine | |
| 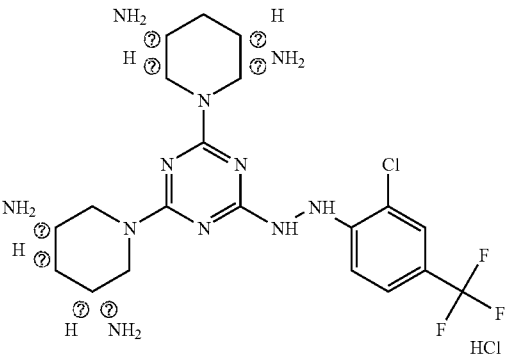 | N-(4,6-Bis-((3R,5S)-3,5-diamino-piperidin-1-yl)-[1,3,5]triazin-2-yl)-N'-(3-Chloro-5-trilfuoromethyl-pyridin-2-yl)-hydrazine | |
| 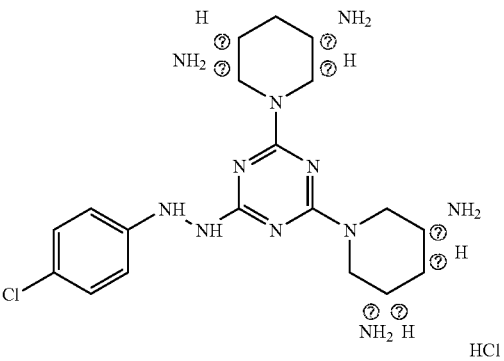 | N-(4,6-Bis-((3R,5S)-3,5-diamino-piperidin-1-yl)-[1,3,5]triazin-2-yl)-N'-(6-Chloro-pyridazin-2-yl)-hydrazine | |
⊙ indicates text missing or illegible when filed -continued

| Structure | Name | Potency |
|---|---|---|
| 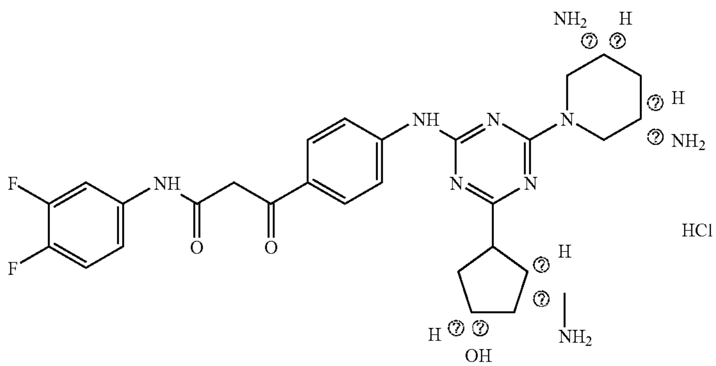 | 3-{4-[4-((2S,4R)-2-Aminomethyl-4-hydroxy-pyrrolidin-1-yl)-6-((3R,5S)-3,5-diamino-piperidin-1-yl)-[1,3,5]triazin-2-ylamino]-phenyl}-N-(3,4-difluoro-phenyl)-3-oxo-propionamide | + |
| 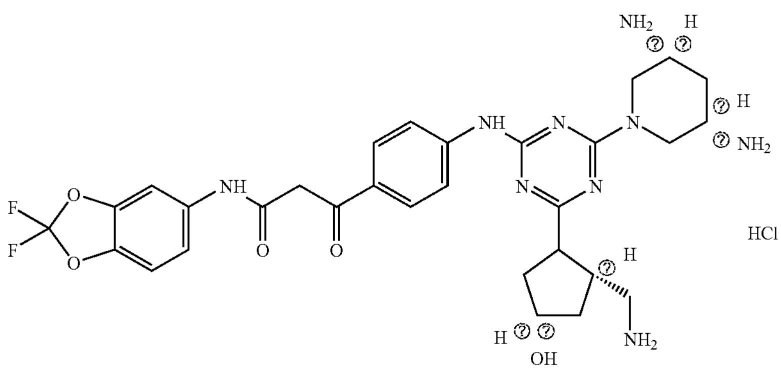 | 3-{4-[4-((2S,4R)-2-Aminomethyl-4-hydroxy-pyrrolidin-1-yl)-6-((3R,5S)-3,5-diamino-piperidin-1-yl)-[1,3,5]triazin-2-ylamino]-phenyl}-N-(2,2-difluoro-benzo[1,3]dioxol-5-yl)-3-oxo-propionamide | ++ |
| 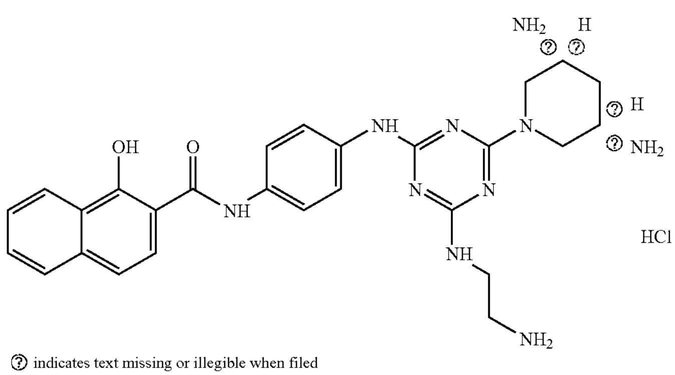 | 1-Hydroxy-naphthalene-2-carboxylicacid {4-[4-(2-amino-ethylamino)-6-((3R,5S)-3,5-diamino-piperidin-1-yl)-[1,3,5]triazin-2-ylamino]-phenyl}-amide | ++ |
| 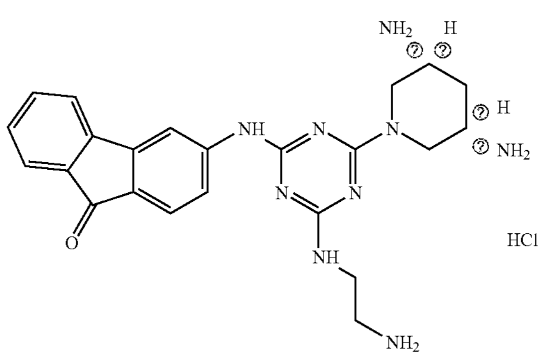 | 3-[4-(2-Amino-ethylamino)-6-((3R,5S)-3,5-diamino-piperidin-1-yl)-[1,3,5]triazin-2-ylamino]-fluoren-9-one | – |

⁇ indicates text missing or illegible when filed

-continued
| Structure | Name | Potency |
|---|---|---|
| 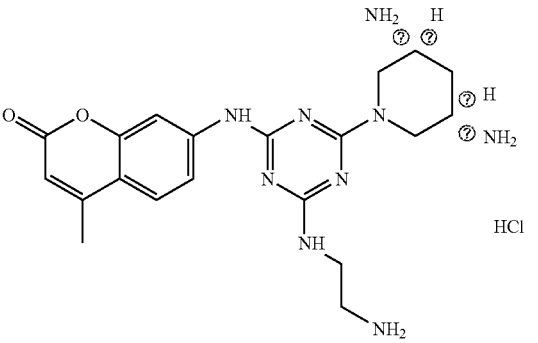 | 7-[4-(2-Amino-ethylamino)-6-((3R,5S)-3,5-diamino-piperidin-1-yl)-[1,3,5]triazin-2-ylamino]-4-methyl-chromen-2-one | – |
| 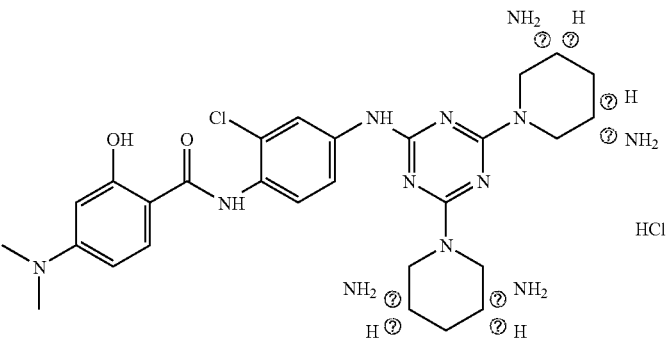 | N-[3-chloro-4-(4-dimethylamnino-2-hydroxy-benzoylamino)-phenyl]-4,6-Bis-(cis-3,5-Diamino-piperidin-1-yl)-[1,3,5]triazine-2-amine | |
| 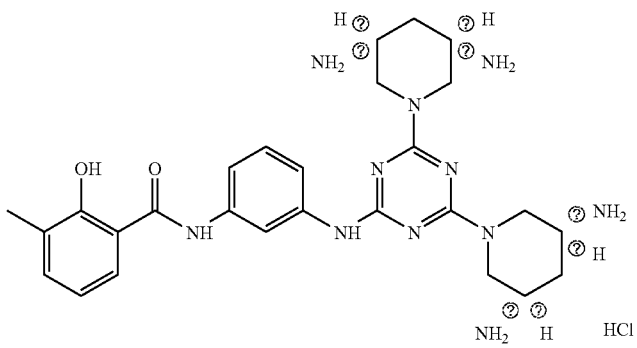 | N-[3-(2-hydroxy-3-methyl-benzoylamino)-phenyl]-4,6-Bis-((3R,5S)-3,5-diamino-piperidin-1-yl)-[1,3,5]triazine-2-amine | ++ |

-continued
| Structure | Name | Potency |
|---|---|---|
| 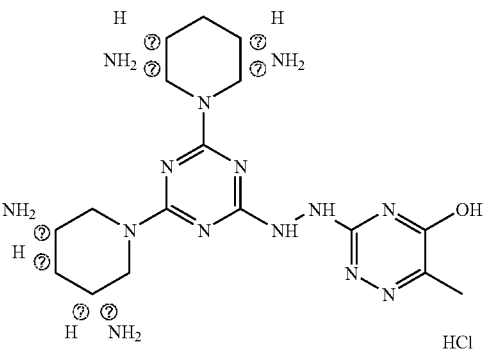 | 3-{N'-[4,6-Bis-((3R,5S)-3,5-diamino-piperidin-1-yl)-[1,3,5]triazin-2-yl]-hydrazino}-6-methyl-[1,2,4]triazin-5-ol | |
| 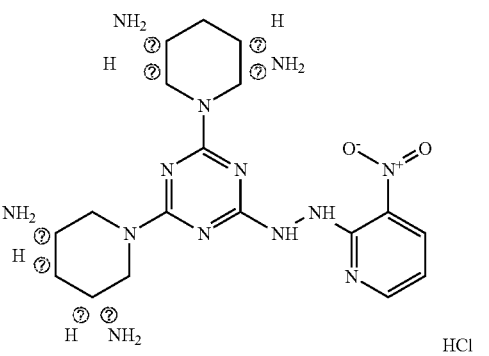 | N-(4,6-Bis-((3R,5S)-3,5-diamino-piperidin-1-yl)-[1,3,5]triazin-2-yl)-N'-(3-Nitro-pyridin-2-yl)-hydrazine | |
| 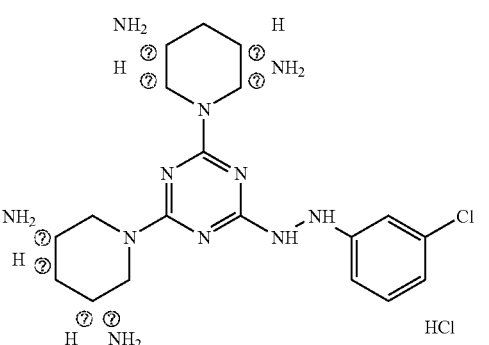 | N-(4,6-Biss-((3R,5S)-3,5-diamino-piperidin-1-yl)-[1,3,5]triazin-2-yl)-N'-(2-Chloro-4-methanesulfonyl-phenyl)-hydrazine | |
⊘ indicates text missing or illegible when filed -continued
| Structure | Name | Potency |
|---|---|---|
| 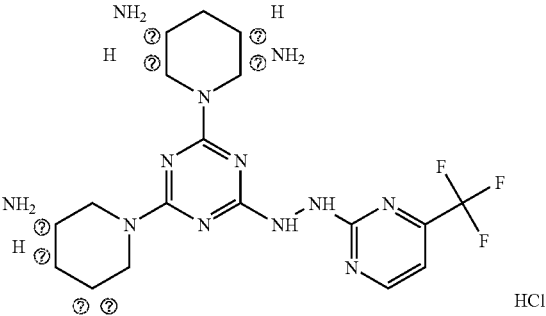 | N-(4,6-Bis-((3R,5S)-3,5-diamino-piperidin-1-yl)-[1,3,5]triazin-2-yl)-N'-(4-Trifluoromethyl-pyrimidin-2-yl)-hydrazine | |
| 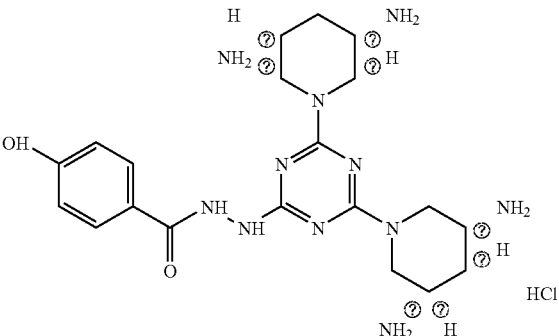 | 4-Hydroxy-benzoicacid N'-[4-((3R,5S)-3,5-diamino-piperidin-1-yl)-6-((3S,5R)-3,5-diamino-piperidin-1-yl)-[1,3,5]triazin-2-yl]-hydrazide | |
| 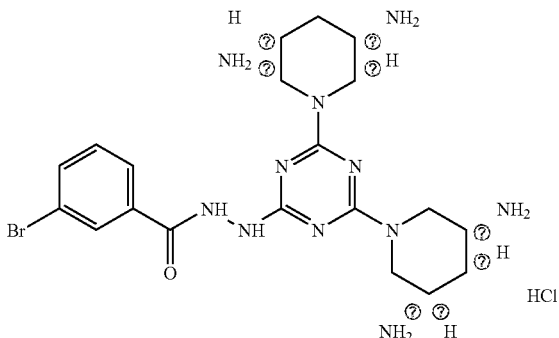 | 3-Bromo-benzoicacid N'-[4-((3R,5S)-3,5-diamino-piperidin-1-yl)-6-((3S,5R)-3,5-diamino-piperidin-1-yl)-[1,3,5]triazine-2-yl]-hydrazide | |
⑦ indicates text missing or illegible when filed -continued

| Structure | Name | Potency |
|---|---|---|
| 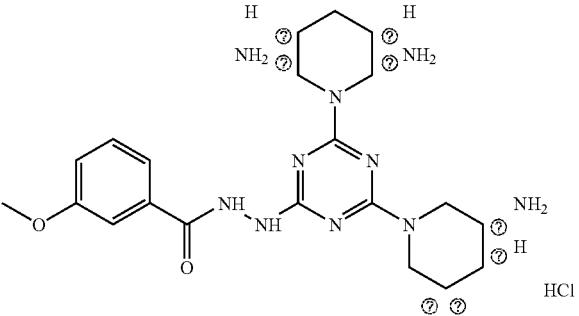 ⑦ indicates text missing or illegible when filed | 3-Methoxy-benzoicacid N'-[4,6-bis-((3R,5S)-3,5-diamino-piperidin-1-yl)-[1,3,5]triazin-2-yl]-hydrazide | |
| 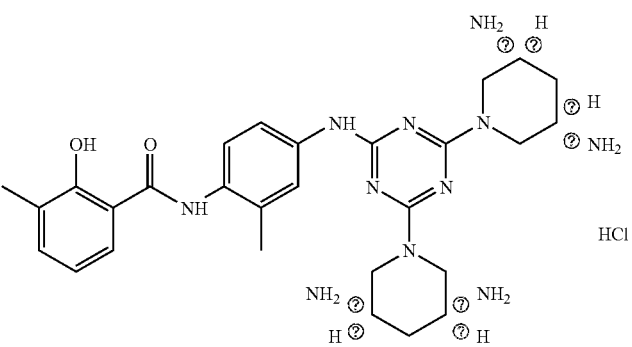 ⑦ indicates text missing or illegible when filed | N-[4-(2-hydroxy-3-methyl-benzoylamino)-3-methyl-phenyl]-4,6-Bis-((3R,5S)-3,5-diamino-piperidin-1-yl)-[1,3,5]triazine-2-amine | + |
| 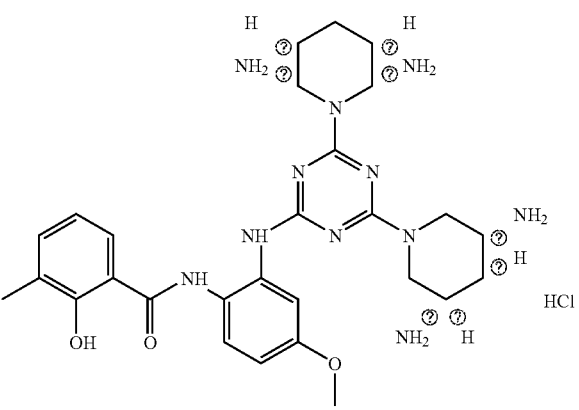 ⑦ indicates text missing or illegible when filed | N-[2-(2-hydroxy-3-methyl-benzoylamino)-5-methoxy-phenyl]-4,6-Bis-((3R,5S)-3,5-diamino-piperidin-1-yl)-[1,3,5]triazine-2-amine | – |

-continued

| Structure | Name | Potency |
|---|---|---|
| 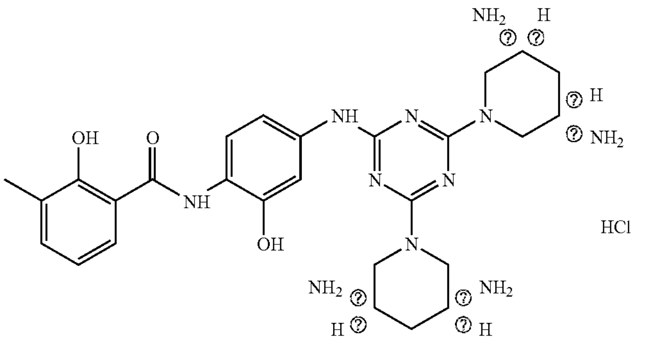 | N-[3-hydroxy-4-(2-hydroxy-3-methyl-benzoylamino)-phenyl]-4,6-Bis-((3R,5S)-3,5-diamino-piperidin-1-yl)-[1,3,5]triazine-2-amine | ++ |
| 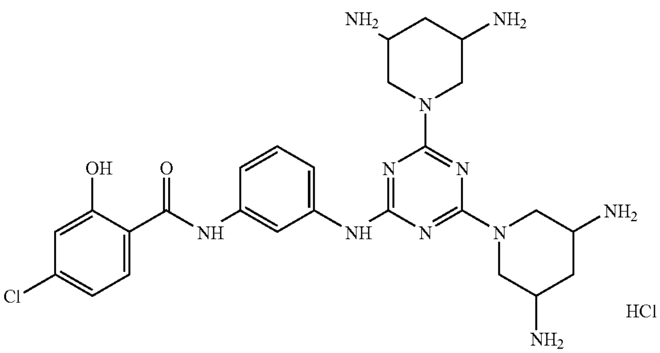 | N-[3-(4-chloro-2-hydroxy-benzoylamino)-phenyl]-4,6-Bis-((3R,5S)-3,5-diamino-piperidin-1-yl)-[1,3,5]triazine-2-amine | |
| 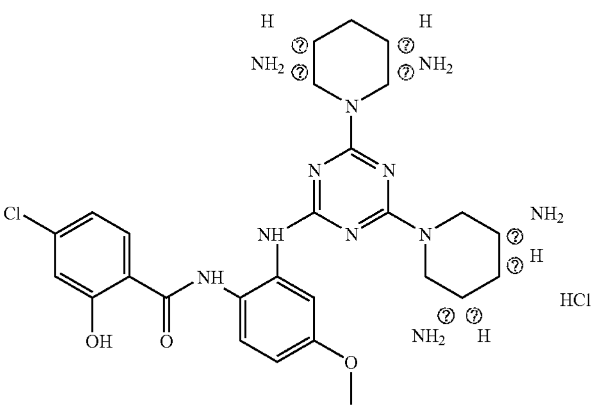 | BN-[2-(4-chloro-2-hydroxy-benzoylamino)-5-methoxy-phenyl]-4,6-Bis-((3R,5S)-3,5-diamino-piperidin-1-yl)-[1,3,5]triazine-2-amine | − |
| 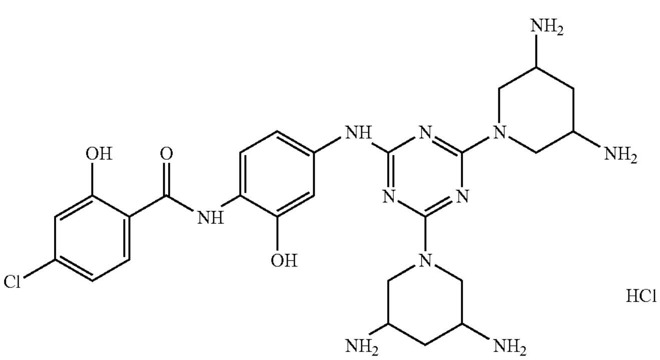 | N-[4-(4-chloro-2-hydroxy-benzoylamino)-3-hydroxy-phhenyl]-4,6-Bis-((3R,5S)-3,5-diamino-piperidin-1-yl)-[1,3,5]triazine-2-amine | |

⑦ indicates text missing or illegible when filed

-continued
| Structure | Name | Potency |
|---|---|---|
| 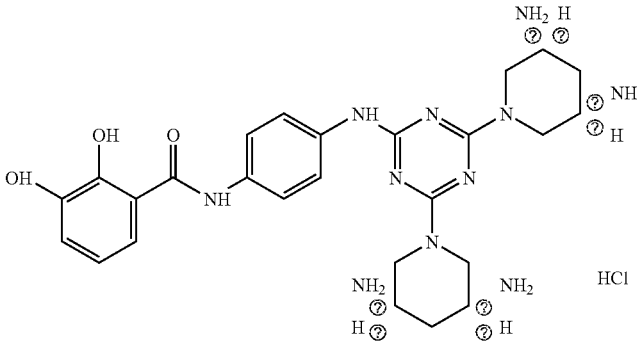 | N-[4-(2,3-dihydroxy-benzoylamino)-phenyl]-4,6-Bis-((3R,5S)-3,5-diamino-piperidin-1-yl)-[1,3,5]triazine-2-amine | ++ |
| 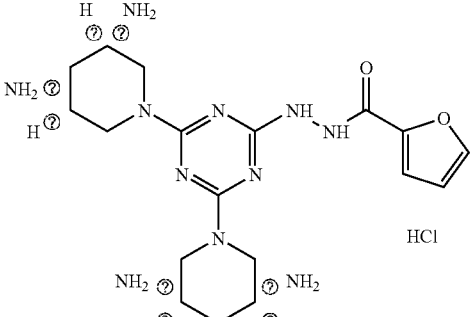 | Furan-2-carboxylicacid N'-[4-((3R,5S)-3,5-diamino-piperidin-1-yl)-6-((3S,5R)-3,5-diamino-piperidin-1-yl)-[1,3,5]triazin-2-yl]-hydrazide | |
| 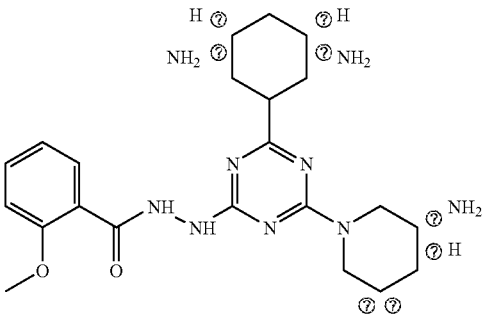 | 2-Methoxy-benzoicacid N'-[4,6-bis-((3R,5S)-3,5-diamino-piperidin-1-yl)-[1,3,5]triazin-2-yl]-hydrazide | |
⑦ indicates text missing or illegible when filed -continued
| Structure | Name | Potency |
|---|---|---|
| 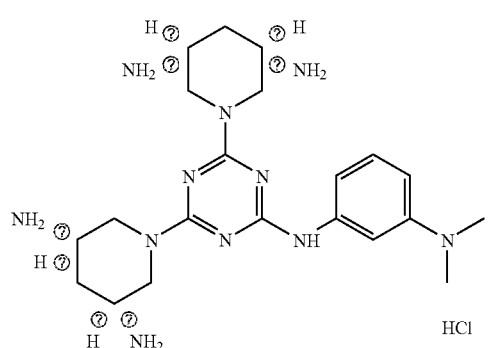 | N-(3-dimethylamino-phenyl)-4,6-Bis-((3R,5S)-3,5-diamino-piperidin-1-yl)-[1,3,5]triazine-2-amine | – |
| 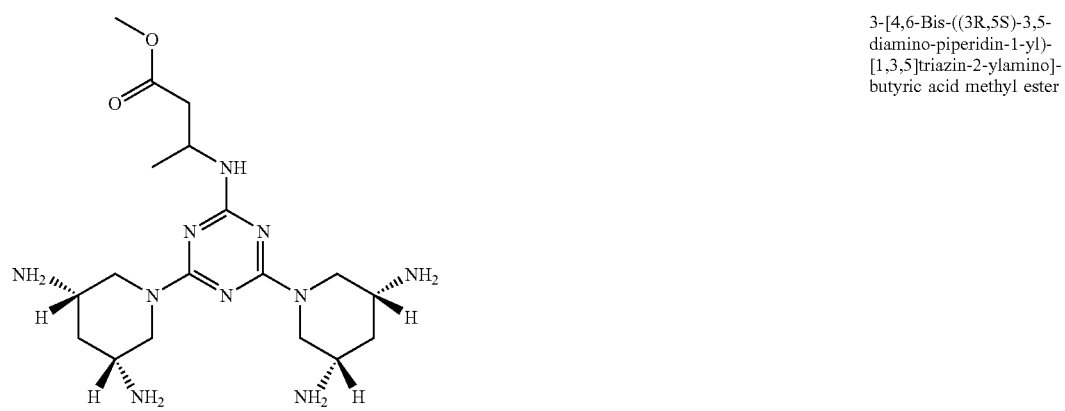 | 3-[4,6-Bis-((3R,5S)-3,5-diamino-piperidin-1-yl)-[1,3,5]triazin-2-ylamino]-butyric acid methyl ester | |
| 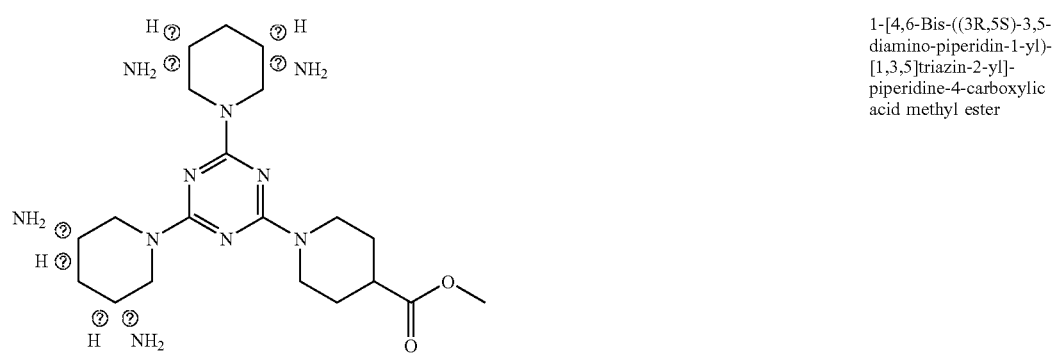 | 1-[4,6-Bis-((3R,5S)-3,5-diamino-piperidin-1-yl)-[1,3,5]triazin-2-yl]-piperidine-4-carboxylic acid methyl ester | |
⊘ indicates text missing or illegible when filed -continued

| Structure | Name | Potency |
|---|---|---|
| 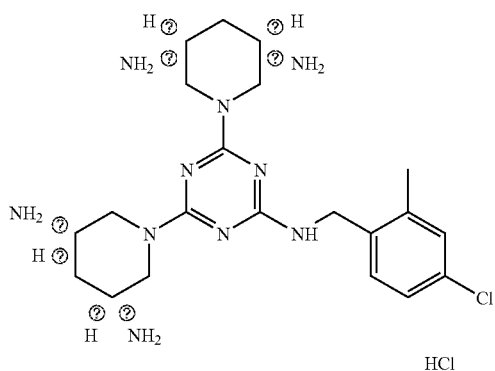 | N-(1,2,3,4-tetrahydro-quinolin-2-ylmethyl)-4,6-Bis-((3R,5S)-3,5-diamino-piperidin-1-yl)-]1,3,5]triazine-2-amine | |
| ⓘ indicates text missing or illegible when filed | | |
| 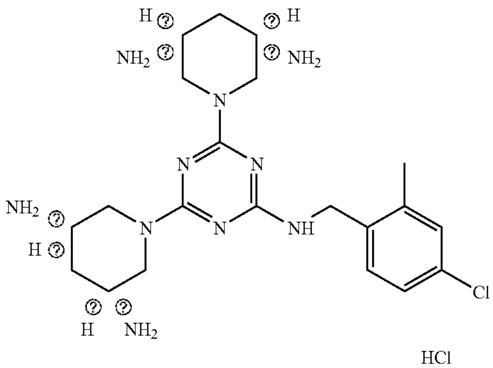 | N-(4-chloro-2-methyl-benzyl)-44,6-Bis-((3R,5S)-3,5-diamino-piperidin-1-yl)-[1,3,5]triazine-2-amine | − |
| ⓘ indicates text missing or illegible when filed | | |
| 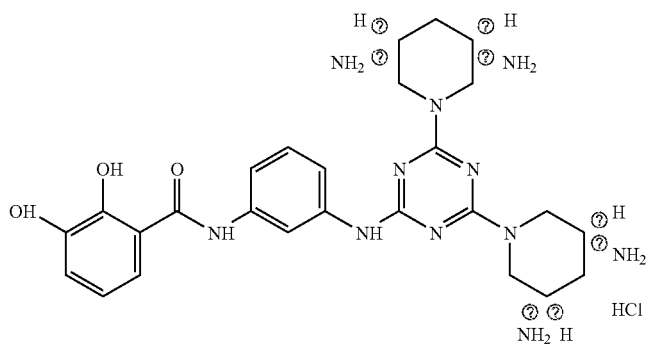 | N-[3-(2,3-dihydroxy-benzoylamino)-phenyl]-4,6-Bis-((3R,5S)-3,5-diamino-piperidin-1-yl)-[1,3,5]triazine-2-amine | ++ |
| ⓘ indicates text missing or illegible when filed | | |
| 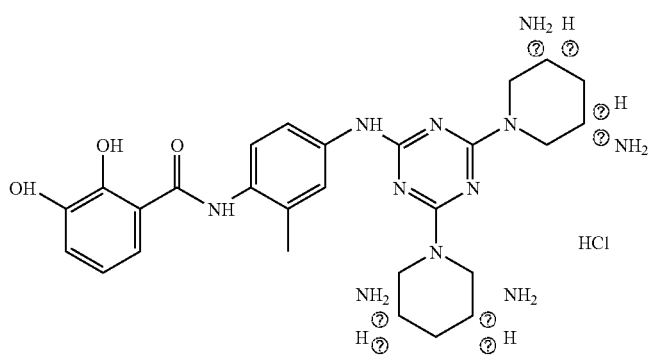 | N-[4-(2,3-dihydroxy-benzoylamino)-3-methyl-phenyl]-4,6-Bis-((3R,5S)-3,5-diamino-piperidin-1-yl)-[1,3,5]triazine-2-amine | ++ |
| ⓘ indicates text missing or illegible when filed | | |

-continued

| Structure | Name | Potency |
|---|---|---|
| 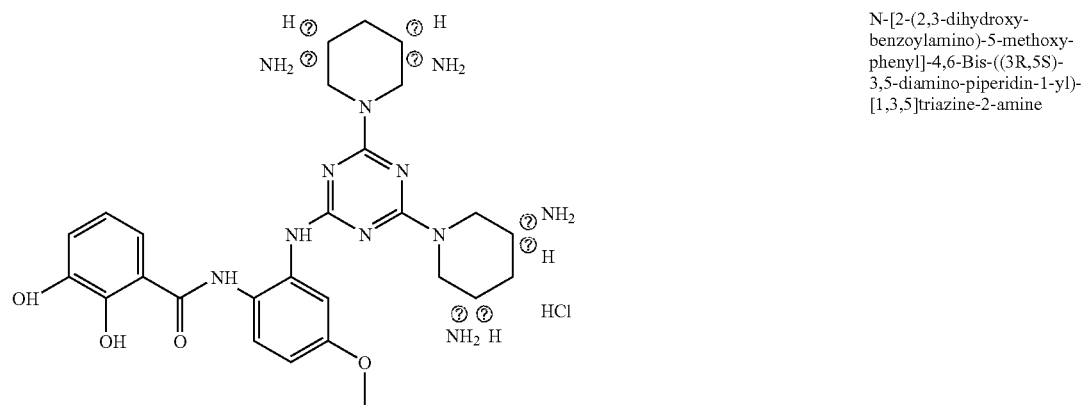 | N-[2-(2,3-dihydroxy-benzoylamino)-5-methoxy-phenyl]-4,6-Bis-((3R,5S)-3,5-diamino-piperidin-1-yl)-[1,3,5]triazine-2-amine | − |
| 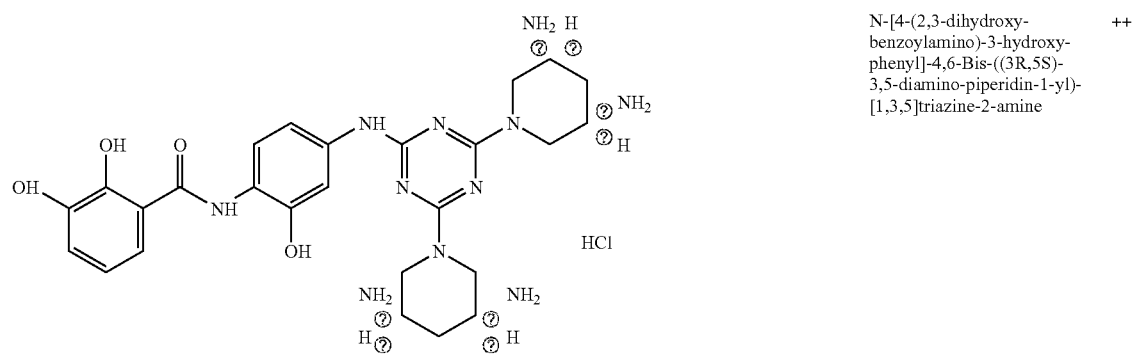 | N-[4-(2,3-dihydroxy-benzoylamino)-3-hydroxy-phenyl]-4,6-Bis-((3R,5S)-3,5-diamino-piperidin-1-yl)-[1,3,5]triazine-2-amine | ++ |
| 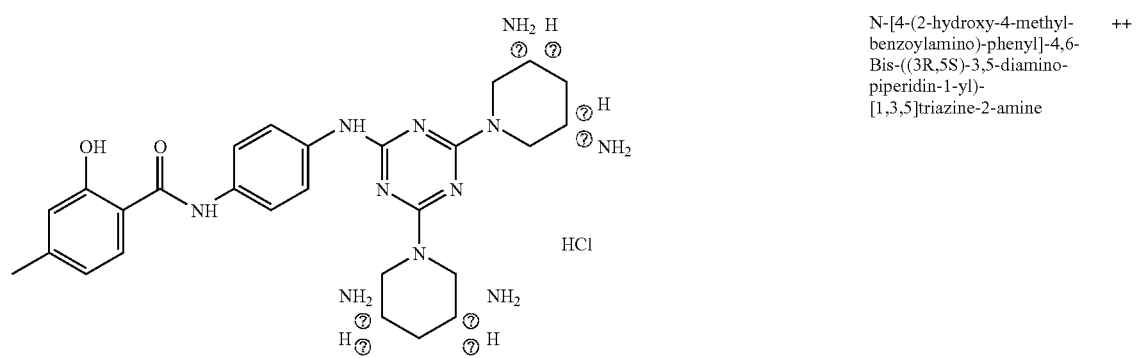 | N-[4-(2-hydroxy-4-methyl-benzoylamino)-phenyl]-4,6-Bis-((3R,5S)-3,5-diamino-piperidin-1-yl)-[1,3,5]triazine-2-amine | ++ |
| 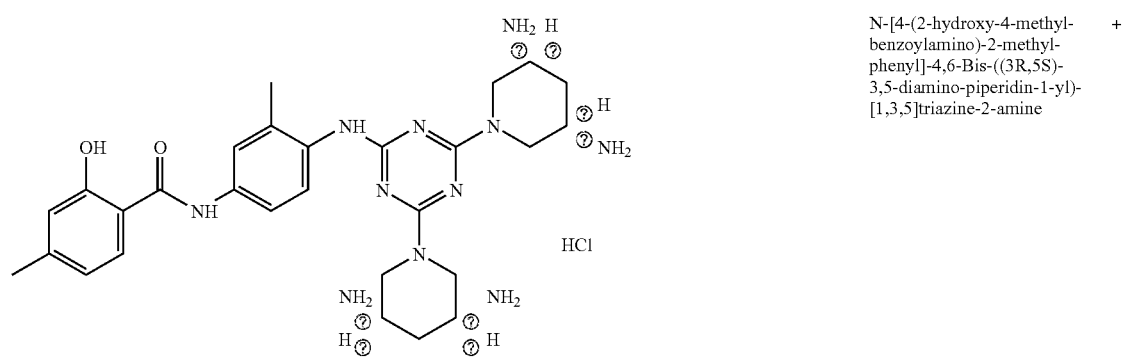 | N-[4-(2-hydroxy-4-methyl-benzoylamino)-2-methyl-phenyl]-4,6-Bis-((3R,5S)-3,5-diamino-piperidin-1-yl)-[1,3,5]triazine-2-amine | + |

-continued
| Structure | Name | Potency |
|---|---|---|
| 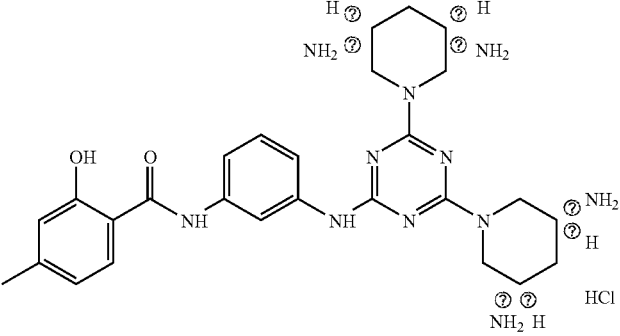 | N-[3-(2-hydroxy-4-methyl-benzoylamino)-phenyl]-4,6-Bis-((3R,5S)-3,5-diamino-piperidin-1-yl)-[1,3,5]triazine-2-amine | + |
| 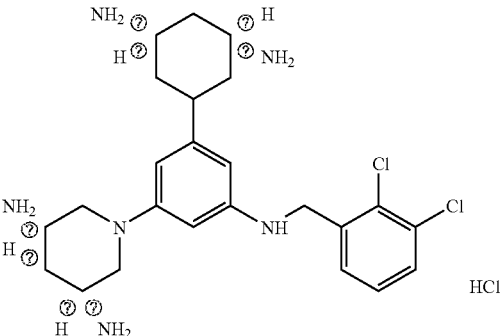 | N-(2,3-dichloro-benzyl)-4,6-Bis-((3R,5S)-3,5-diamino-piperidin-1-yl)-[1,3,5]triazine-2-amine | + |
| 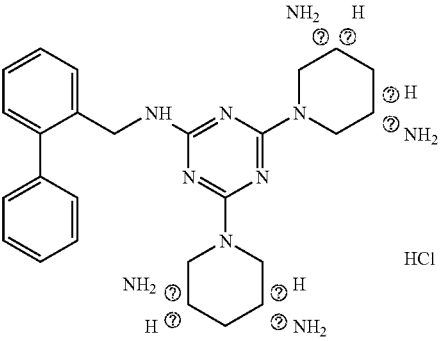 | N-biphenyl-2-ylmethyl-4,6-Bis-((3R,5S)-3,5-diamino-piperidin-1-yl)-[1,3,5]triazine-2-amine | |
| 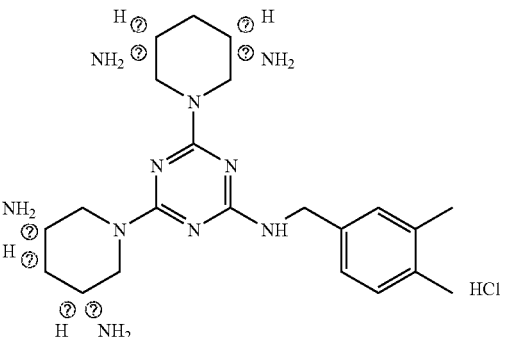 | N-(3,4-dimethyl-benzyl)-4,6-Bis-((3R,5S)-3,5-diamino-piperidin-1-yl)-[1,3,5]triazine-2-amine | |

-continued

| Structure | Name | Potency |
|---|---|---|
| 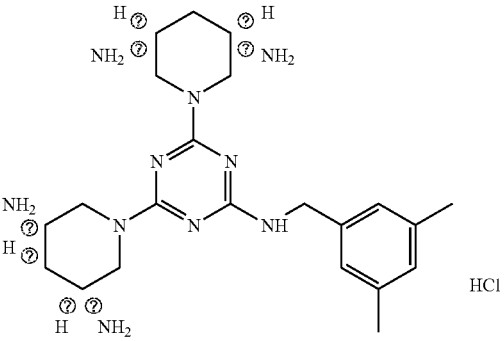 ⓘ indicates text missing or illegible when filed | N-(3,5-dimethyl-benzyl)-4,6-Bis-((3R,5S)-3,5-diamino-piperidin-1-yl)-[1,3,5]triazine-2-amine | |
| 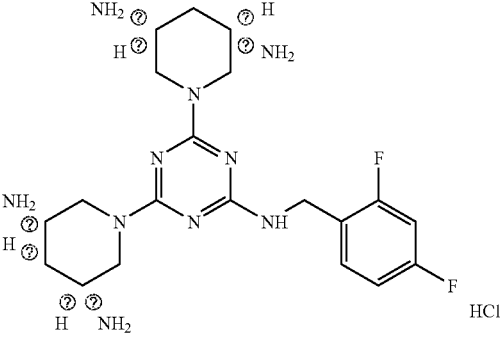 ⓘ indicates text missing or illegible when filed | N-(2,4-difluoro-benzyl)-4,6-Bis-((3R,5S)-3,5-diamino-piperidin-1-yl)-[1,3,5]triazine-2-amine | |
| 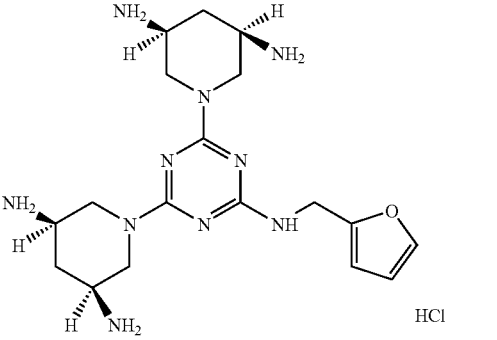 | N-furan-2-ylmethyl-4,6-Bis-((3R,5S)-3,5-diamino-piperidin-1-yl)-[1,3,5]triazine-2-amine | – |
| 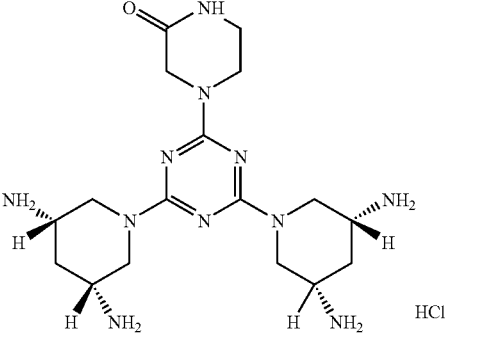 | 2,4-Bis-((3R,5S)-3,5-diamino-piperidin-1-yl)-6-(4-methyl-piperidin-1-yl)-[1,3,5]triazine | |

-continued

| Structure | Name | Potency |
|---|---|---|
| 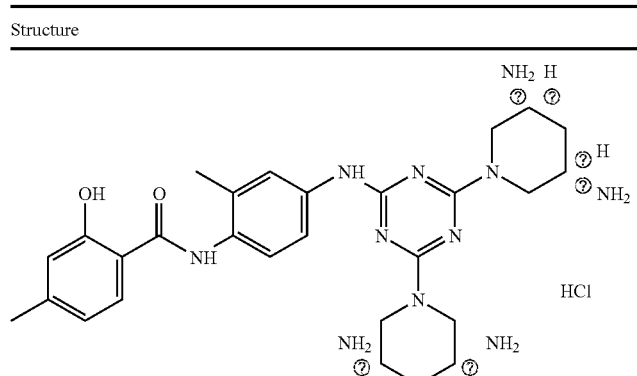 ⓘ indicates text missing or illegible when filed | N-[4-(2-hydroxy-4-methyl-benzoylamino)-3-methyl-phenyl]-4,6-Bis-((3R,5S)-3,5-diamino-piperidin-1-yl)-[1,3,5]triazine-2-amine | + |
| 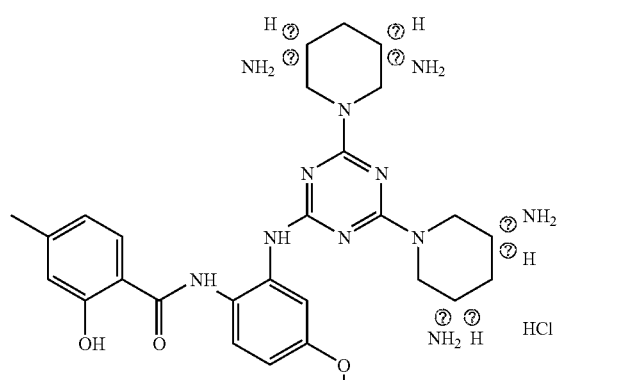 ⓘ indicates text missing or illegible when filed | N-[2-(2-hydroxy-4-methyl-benzoylamino)-5-methoxy-phenyl]-4,6-Bis-((3R,5S)-3,5-diamino-piperidin-1-yl)-[1,3,5]triazine-2-amine | − |
| 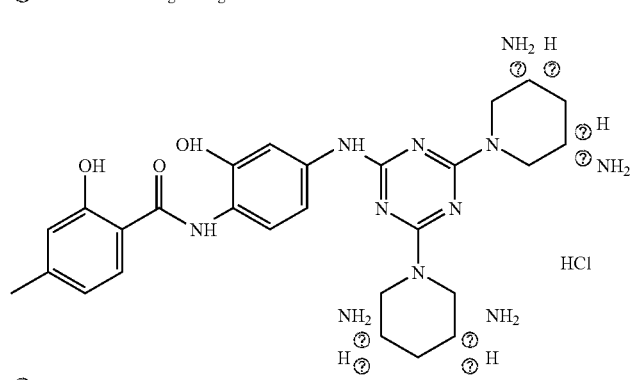 ⓘ indicates text missing or illegible when filed | N-[3-hydroxy-4-(2-hydroxy-4-methyl-benzoylamino)-phenyl]-4,6-Bis-((3R,5S)-3,5-diamino-piperidin-1-yl)-[1,3,5]triazine-2-amine | ++ |
| 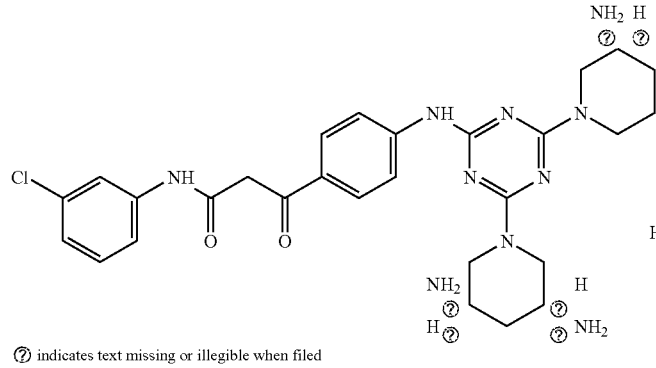 ⓘ indicates text missing or illegible when filed | N-{4-[2-(3-chloro-phenylcarbamoyl)-acetyl]-phenyl}-4,6-Bis-((3R,5S)-3,5-diamino-piperidin-1-yl)-[1,3,5]triazine-2-amine | ++ |

-continued

| Structure | Name | Potency |
|---|---|---|
| 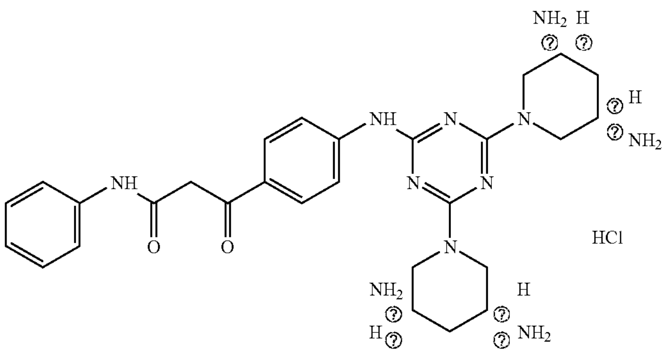 | N-[4-(2-phenylcarbamoyl-acetyl)-phenyl]-4,6-Bis-((3R,5S)-3,5-diamino-piperidin-1-yl)-[1,3,5]triazine-2-amine | ++ |
| 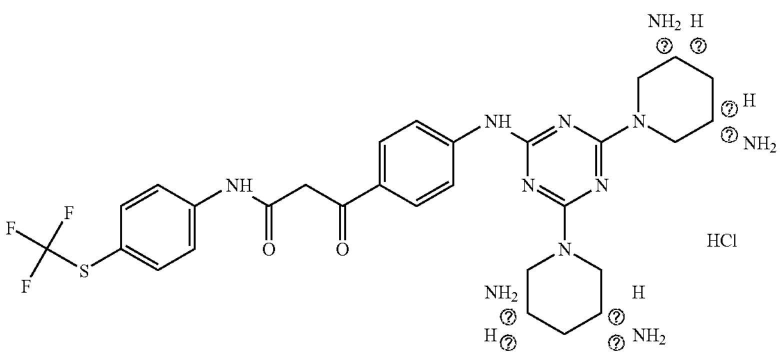 | N-{4-[2-(4-trifluoromethylsulfanyl-phenylcarbamoyl)-acetyl]-phenyl}-4,6-Bis-((3R,5S)-3,5-diamino-piperidin-1-yl)-[1,3,5]triazine-2-amine | ++ |
| 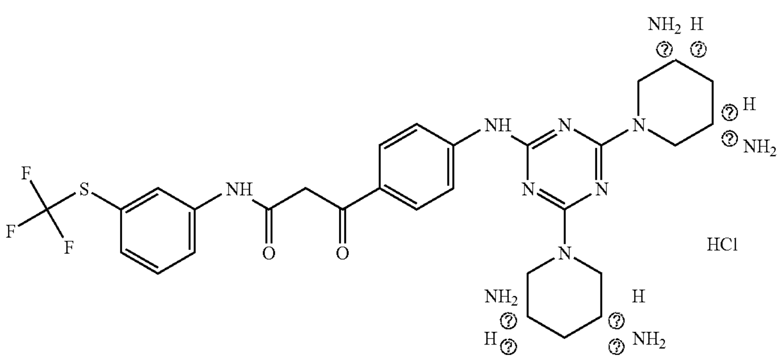 | N-{4-[2-(3-trifluoromethylsulfanyl-phenylcarbamoyl)-acetyl]-phenyl}-4,6-Bis-((3R,5S)-3,5-diamino-piperidin-1-yl)-[1,3,5]triazine-2-amine | ++ |
| 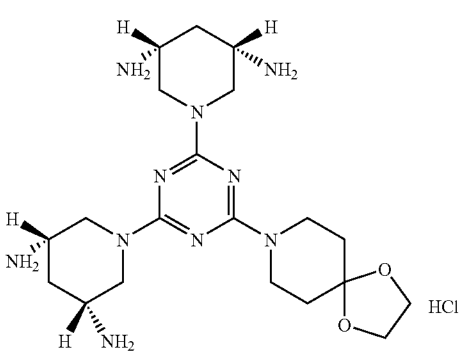 | 1-(4,6-Bis-((3R,5S)-3,5-diamino-piperidin-1-yl)-[1,3,5]triazine-2-yl)-pyrrolidin-3-ylamine | |

⑦ indicates text missing or illegible when filed

-continued

| Structure | Name | Potency |
|---|---|---|
| 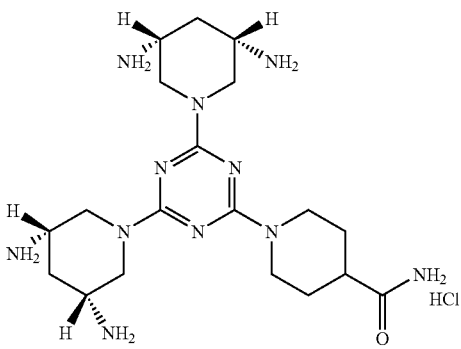 ⑦ indicates text missing or illegible when filed | 1-(4,6-Bis-((3R,5S)-33,5-diamino-piperidin-1-yl)-[1,3,5]triazin-2-yl)-4-(3-trifluoromethyl-phenyl)-piperidin-4-ol | |
| 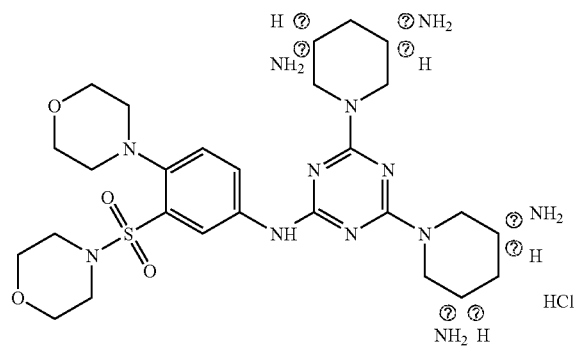 | 1-[1-(4,6-Bis-((3R,5S)-3,5-diamino-piperidin-1-yl)-[1,3,5]triazin-2-yl)-4-phenyl-piperidin-4-yl]-ethanone | |
| 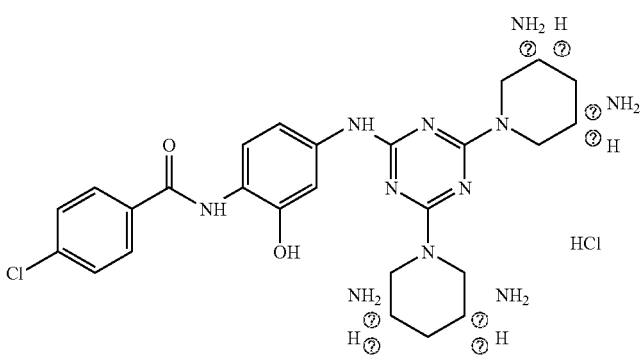 ⑦ indicates text missing or illegible when filed | N-[3-morpholine-4-sulfonyl)-4-morpholin-4-yl-phenyl]-4,6-Bis-((3R,5S)-3,5-diamino-piperidin-1-yl)-[1,3,5]triazine-2-amine | – |
| ⑦ indicates text missing or illegible when filed | N-[4-(4-chloro-benzoylamino)-3-hydroxy-phenyl]-4,6-Bis-((3R,5S)-3,5-diamino-piperidin-1-yl)-[1,3,5]triazine-2-amine | ++ |

-continued

| Structure | Name | Potency |
|---|---|---|
| 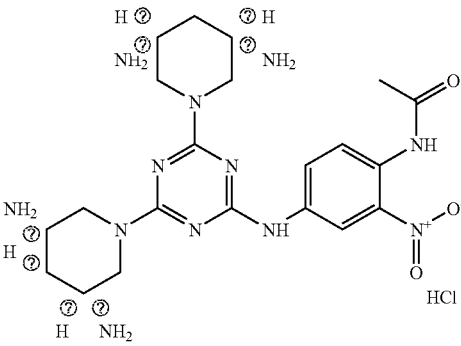 | N-(4-acetylamino-3-nitro-phenyl)-4,6-Bis-((3R,5S)-3,5-diamino-piperidin-1-yl)-[1,3,5]triazine-2-amine | |
| ⑦ indicates text missing or illegible when filed | | |
| 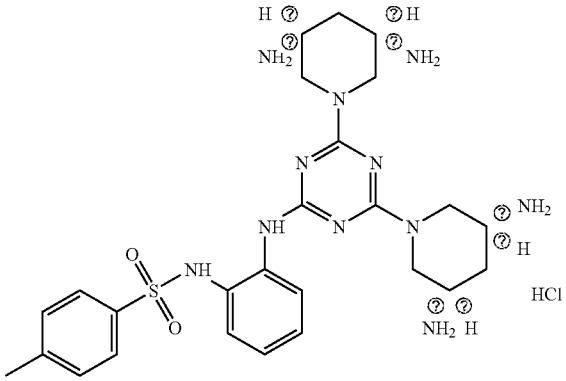 | N-[2-(toluene-4-sulfonylamino)-phenyl]-4,6-Bis-((3R,5S)-3,5-diamino-piperidin-1-yl)-[1,3,5]triazine-2-amine | − |
| ⑦ indicates text missing or illegible when filed | | |
| 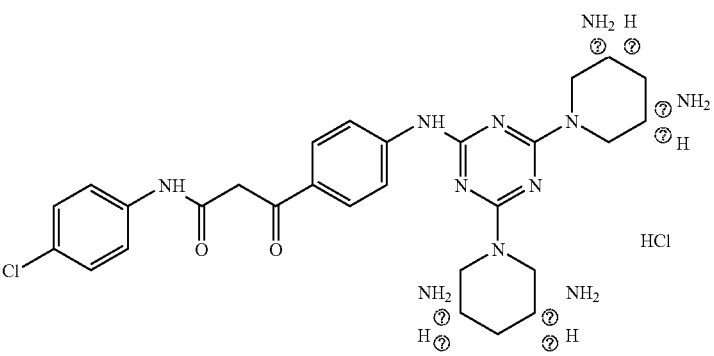 | N-{4-[2-(4-chloro-phenylcarbamoyl)-acetyl]-phenyl}-4,6-Bis-((3R,5S)-3,5-diamino-piperidin-1-yl)-[1,3,5]triazine-2-amine | ++ |
| ⑦ indicates text missing or illegible when filed | | |

-continued
| Structure | Name | Potency |
|---|---|---|
| 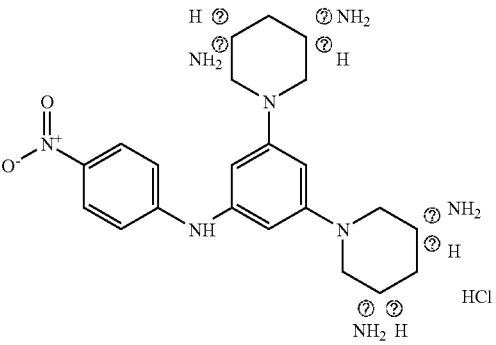 | (3,5-Bis-((3R,5S)-3,5-diamino-piperidin-1-yl)-phenyl)-(4-nitro-phenyl)-amine | − |
| 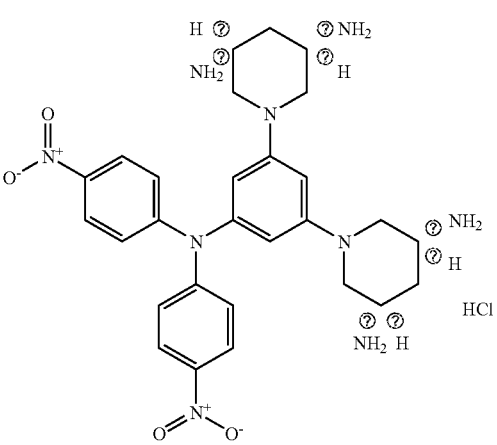 | (3,5-Bis-((3R,5S)-3,5-diamino-piperidin-1-yl)-phenyl)-bis-(4-nitro-phenyl)-amine | + |
| 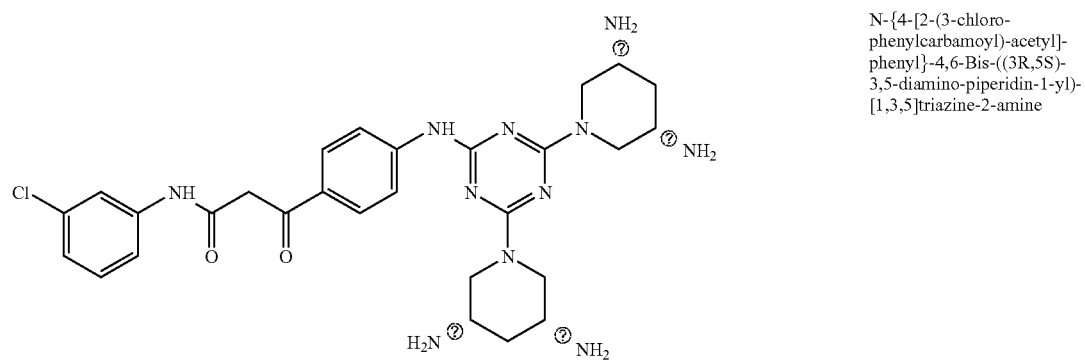 | N-{4-[2-(3-chloro-phenylcarbamoyl)-acetyl]-phenyl}-4,6-Bis-((3R,5S)-3,5-diamino-piperidin-1-yl)-[1,3,5]triazine-2-amine | |

| Structure | Name | Potency |
|---|---|---|
| (structure) | N-[4-(2-hydroxy-3-nitro-benzoylamino)-phenyl]-4,6-Bis-((3R,5S)-3,5-diamino-piperidin-1-yl)-[1,3,5]triazine-2-amine | − |
| (structure) | N-[4-(2-hydroxy-3-nitro-benzoylamino)-3-methyl-phenyl]-4,6-Bis-((3R,5S)-3,5-diamino-piperidin-1-yl)-[1,3,5]triazine-2-amine | + |
| (structure) | N-[3-(2-hydroxy-3-nitro-benzoylamino)-phenyl]-4,6-Bis-((3R,5S)-3,5-diamino-piperidin-1-yl)-[1,3,5]triazine-2-amine | ++ |
| (structure) | 2-[4,6-Bis-((3R,5S)-3,5-diamino-piperidin-1-yl)-[1,3,5]triazin-2-ylamino]-3-methoxy-benzoic acid | |

-continued
| Structure | Name | Potency |
|---|---|---|
| 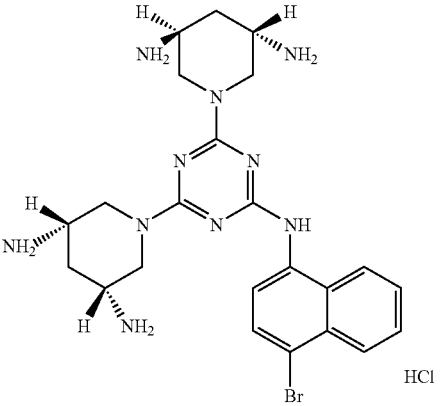 | N-(4-bromo-naphthalen-1-yl)-4,6-Bis-((3R,5S)-3,5-diamino-piperidin-1-yl)-[1,3,5]triazine-2-amine | + |
| 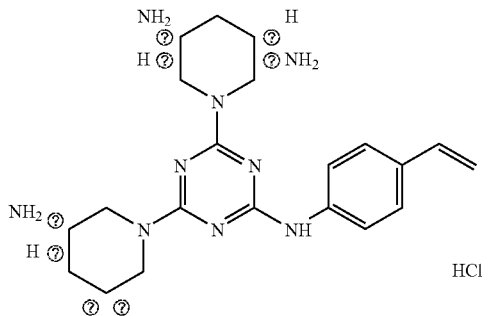<br>⊘ indicates text missing or illegible when filed | N-(4-vinyl-phenyl)-4,6-Bis-((3R,5S)-3,5-diamino-piperidin-1-yl)-[1,3,5]triazine-2-amine | + |
| 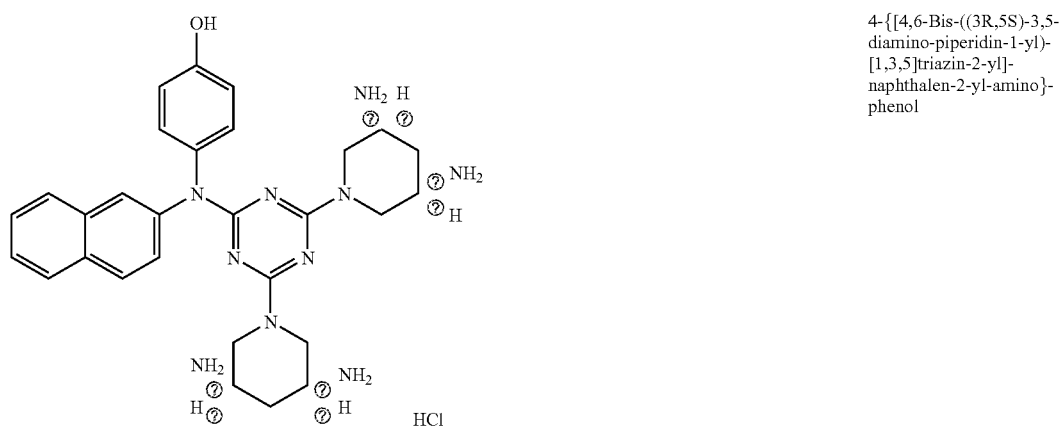<br>⊘ indicates text missing or illegible when filed | 4-{[4,6-Bis-((3R,5S)-3,5-diamino-piperidin-1-yl)-[1,3,5]triazin-2-yl]-naphthalen-2-yl-amino}-phenol | |

-continued

| Structure | Name | Potency |
|---|---|---|
| 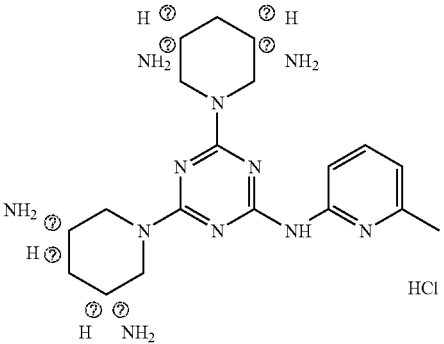 | N-(6-methyl-pyridin-2-yl)-4,6-Bis-((3R,5S)-3,5-diamino-piperidin-1-yl)-[1,3,5]triazine-2-amine | − |
| ⑦ indicates text missing or illegible when filed | | |
| 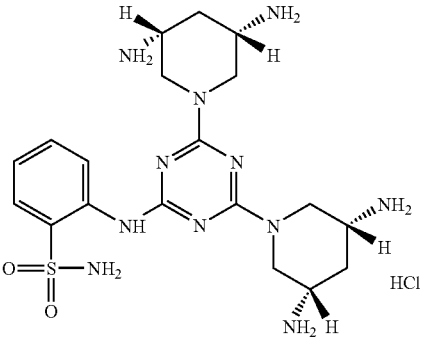 | N-(2-sulfamoyl-phenyl)-4,6-Bis-((3R,5S)-3,5-diamino-piperidin-1-yl)-[1,3,5]triazine-2-amine | − |
| 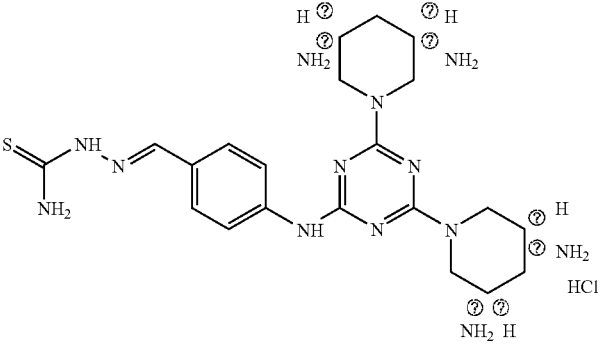 | N-(4-thioureido-iminomethyl-phenyl)-4,6-Bis-((3R,5S)-3,5-diamino-piperidin-1-yl)-[1,3,5]triazine-2-amine | + |
| ⑦ indicates text missing or illegible when filed | | |
| 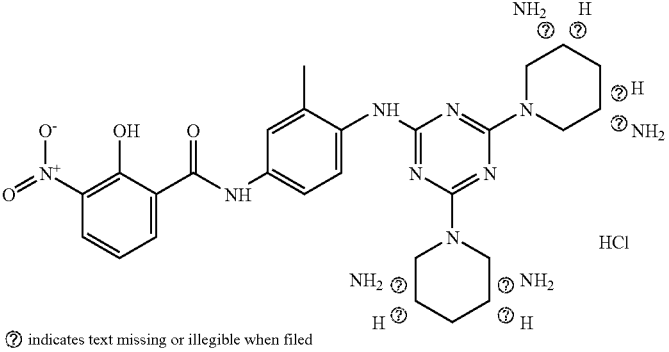 | N-[4-(2-hydroxy-3-nitro-benzoylamino)-2-methyl-pphenyl]-4,6-Bis-((3R,5S)-3,5-diamino-piperidin-1-yl)-[1,3,5]triazine-2-amine | − |
| ⑦ indicates text missing or illegible when filed | | |

-continued

| Structure | Name | Potency |
|---|---|---|
| 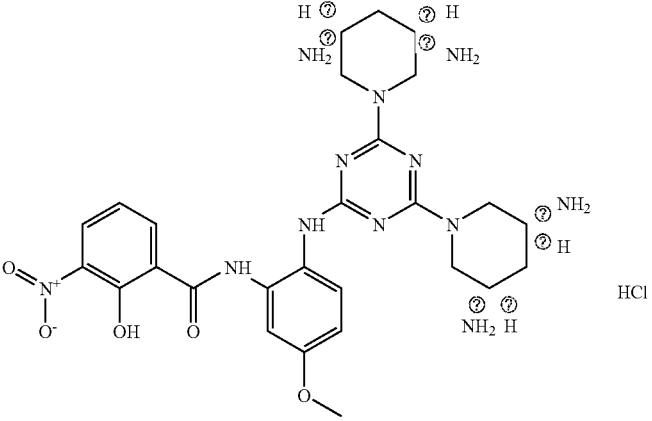 ⑦ indicates text missing or illegible when filed | N-[2-(2-hydroxy-3-nitro-benzoylamino)-4-methoxy-phenyl]-4,6-Bis-((3R,5S)-3,5-diamino-piperidin-1-yl)-[1,3,5]triazine-2-amine | − |
| 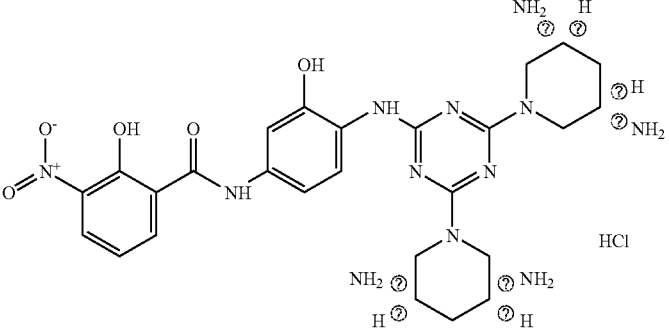 ⑦ indicates text missing or illegible when filed | N-[2-hydroxy-4-(2-hydroxy-3-nitro-benzoylamino)-phenyl]-4,6-Bis-((3R,5S)-3,5-diamino-piperidin-1-yl)-[1,3,5]triazine-2-amine | + |
| 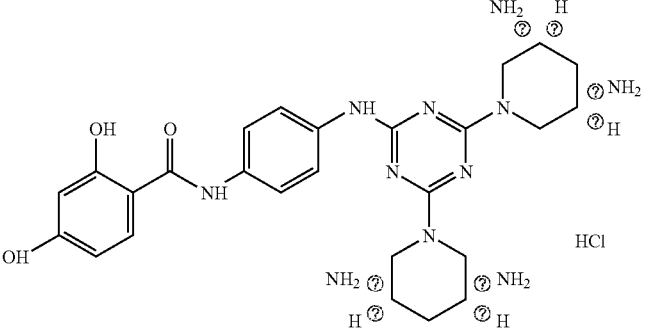 ⑦ indicates text missing or illegible when filed | N-[4-(2,4-dihydroxy-benzoylamino)-phenyl]-4,6-Bis-((3R,5S)-3,5-diamino-piperidin-1-yl)-[1,3,5]triazine-2-amine | ++ |
| 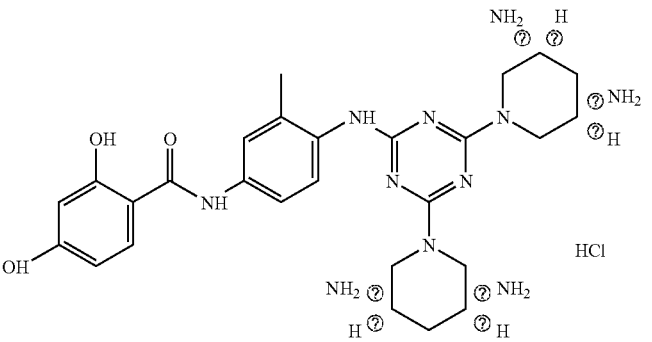 ⑦ indicates text missing or illegible when filed | N-[4-(2,4-dihydroxy-benzoylamino)-2-methyl-phenyl]-4,6-Bis-((3R,5S)-3,5-diamino-piperidin-1-yl)-[1,3,5]triazine-2-amine | + |

-continued

| Structure | Name | Potency |
|---|---|---|
| 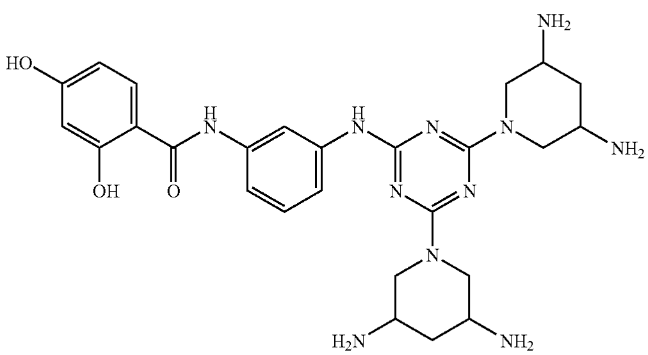 | N-[3-(2,4-dihydroxy-benzoylamino)-phenyl]-4,6-Bis-((3R,5S)-3,5-diamino-piperidin-1-yl)-[1,3,5]triazine-2-amine | |
| 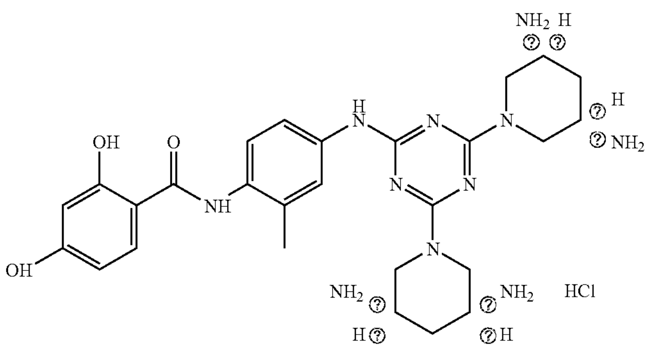 | N-[4-(2,4-dihydroxy-benzoylamino)-3-methyl-phenyl]-4,6-Bis-((3R,5S)-3,5-diamino-piperidin-1-yl)-[1,3,5]triazine-2-amine | ++ |

⑦ indicates text missing or illegible when filed

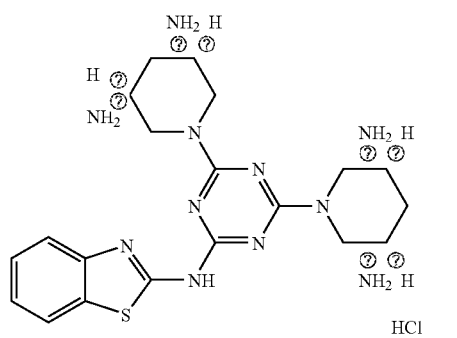

N-benzothiazol-2-yl-4,6-Bis-((3R,5S)-3,5-diamino-piperidin-1-yl)-[1,3,5]triazine-2-amine    +

⑦ indicates text missing or illegible when filed

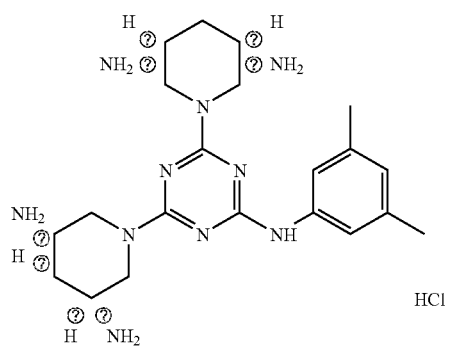

N-(3,5-dimethyl-phenyl)-4,6-Bis-((3R,5S)-3,5-diamino-piperidin-1-yl)-[1,3,5]triazine-2-amine    +

⑦ indicates text missing or illegible when filed

-continued
| Structure | Name | Potency |
|---|---|---|
| 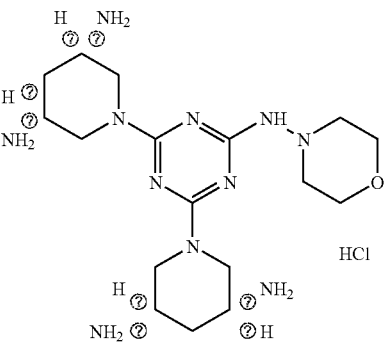 | N-[2-chloro-5-(2-cyano-ethylsulfamoyl)-phenyl]-4,6-Bis-((3R,5S)-3,5-diamino-piperidin-1-yl)-[1,3,5]triazine-2-amine | – |
| 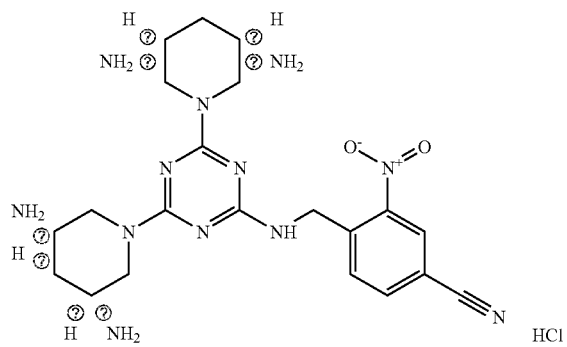 | N-(Morpholino)-4,6-Bis-((3R,5S)-3,5-diamino-piperidin-1-yl)-[1,3,5]triazine-2-amine | |
| 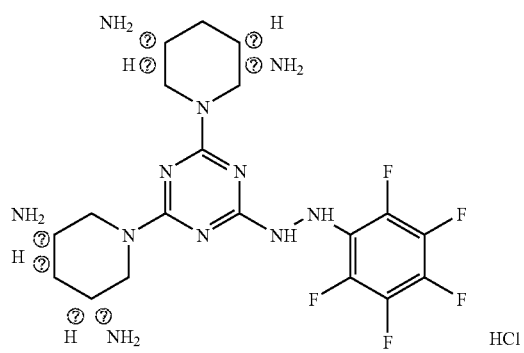 | 4-{N'-[4-((3R,5S)-3,5-Diamino-piperidin-1-yl)-6-((3S,5R)-3,5-diamino-piperidin-1-yl)-[1,3,5]triazin-2-yl]-hydrazino}-3-nitro-benzonitrile | – |
| 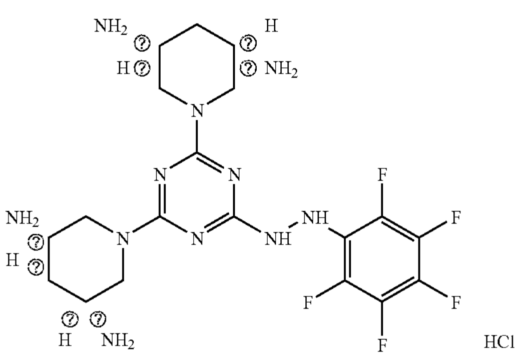 | N-(4,6-Bis-((3R,5S)-3,5-diamino-piperidin-1-yl)-[1,3,5]triazin-2-yl)-N'-Pentafluorophenyl-hydrazine | |

-continued

| Structure | Name | Potency |
|---|---|---|
| 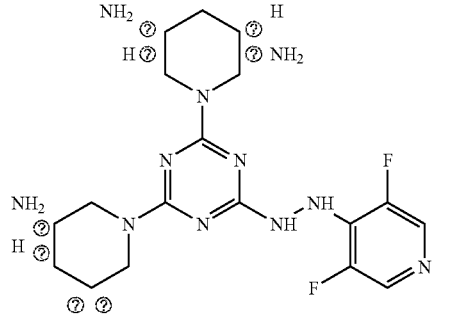 ⑦ indicates text missing or illegible when filed | N-(4,6-Bis-((3R,5S)-3,5-diamino-piperidin-1-yl)-[1,3,5]triazin-2-yl)-N'-(3,5-Dichloro-pyridin-4-yl)-hydrazine | + |
| 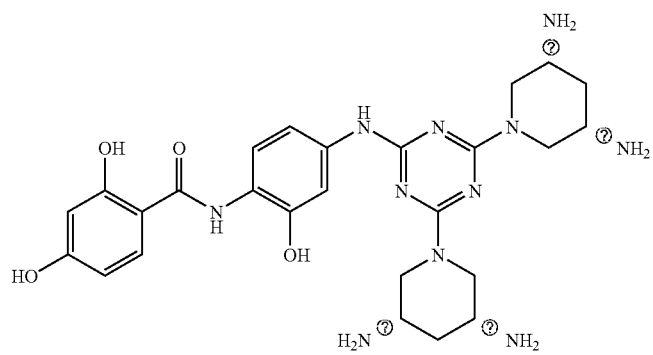 ⑦ indicates text missing or illegible when filed | N-[4-(2,4-dihydroxy-benzoylamino)-3-hydroxy-phenyl]-4,6-Bis-((3R,5S)-3,5-diamino-piperidin-1-yl)-[1,3,5]triazine-2-amine | |
| 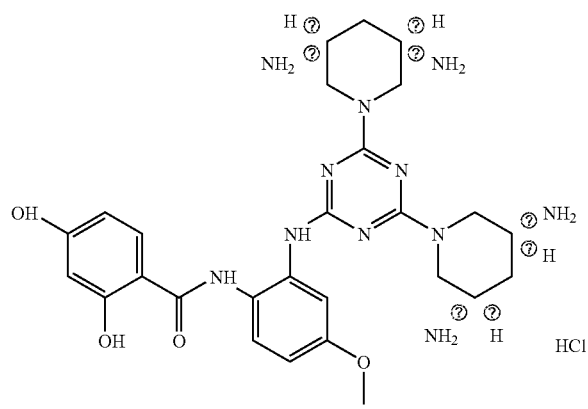 ⑦ indicates text missing or illegible when filed | N-[2-(2,4-dihydroxy-benzoylamino)-5-methoxy-phenyl]-4,6-Bis-((3R,5S)-3,5-diamino-piperidin-1-yl)-[1,3,5]triazine-2-amine | − |

-continued
| Structure | Name | Potency |
|---|---|---|
| 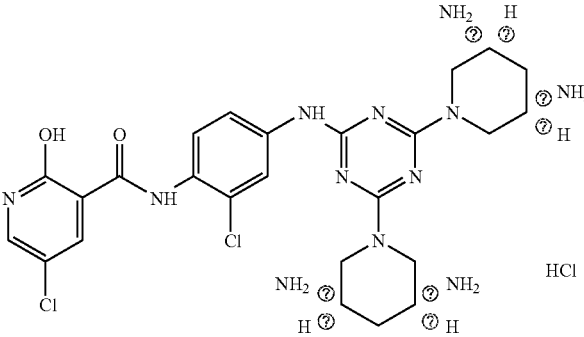 | N-{3-chloro-4-[(5-chloro-2-hydroxy-pyridine-3-carbonyl)-amino]-phenyl}-4,6-Biss-(cis-3,5-Diamino-piperidin-1-yl)-[1,3,5]triazine-2-amine | |
| 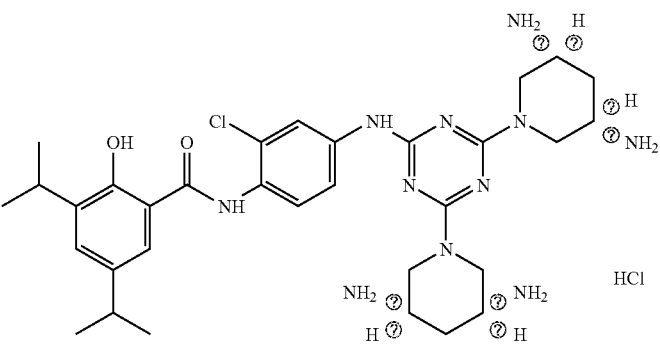 | N-[3-chloro-4-(2-hydroxy-3,5-diisopropyl-benzoylamino)-phenyl]-4,6-Bis-(cis-3,5-Diamino-piperidin-1-yl)-[1,3,5]triazine-2-amine | |
| 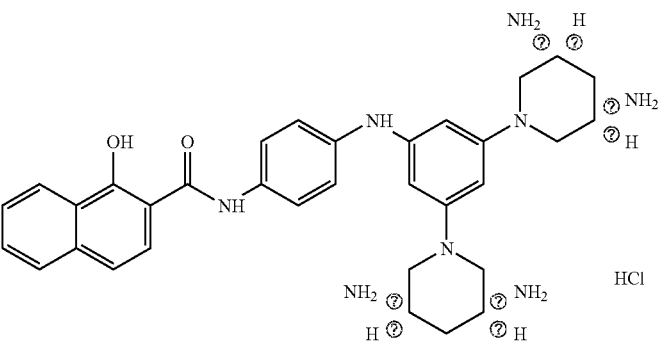 | 1-Hydroxy-naphthalene-2-cxarboxylicacid {4-[3-((3R,5S)-3,5-diamino-piperidin-1-yl)-5-((3S,5R)-3,5-diamino-piperidin-1-yl)-phenylamino]-phenyl}-amide | ++ |

-continued

| Structure | Name | Potency |
|---|---|---|
| 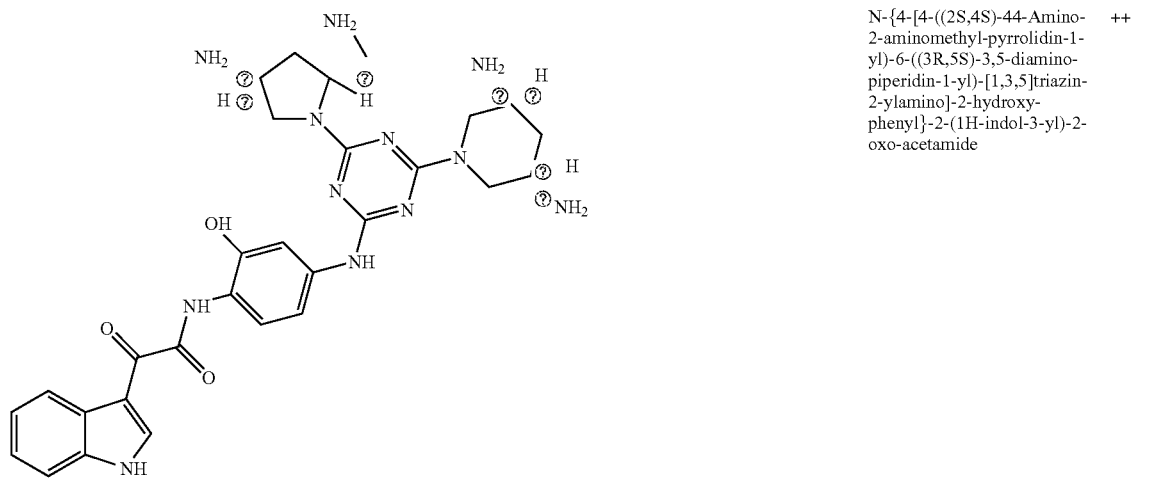 | N-{4-[4-((2S,4S)-44-Amino-2-aminomethyl-pyrrolidin-1-yl)-6-((3R,5S)-3,5-diamino-piperidin-1-yl)-[1,3,5]triazin-2-ylamino]-2-hydroxy-phenyl}-2-(1H-indol-3-yl)-2-oxo-acetamide | ++ |
| ⑦ indicates text missing or illegible when filed | | |
| 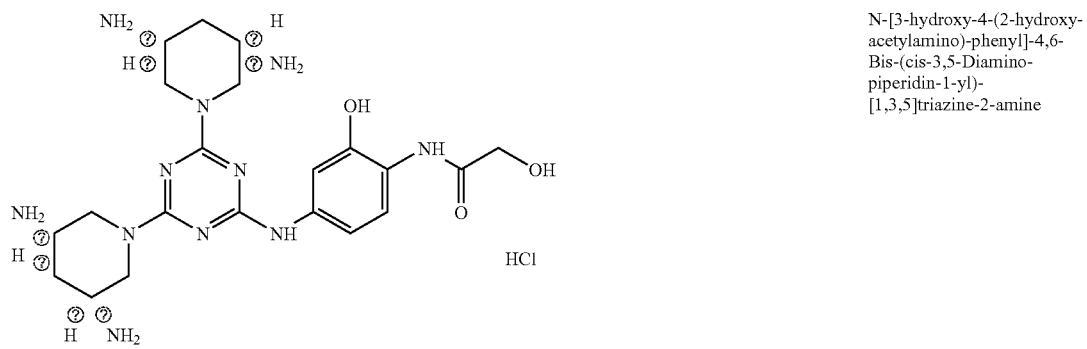 | N-[3-hydroxy-4-(2-hydroxy-acetylamino)-phenyl]-4,6-Bis-(cis-3,5-Diamino-piperidin-1-yl)-[1,3,5]triazine-2-amine | |
| ⑦ indicates text missing or illegible when filed | | |
| 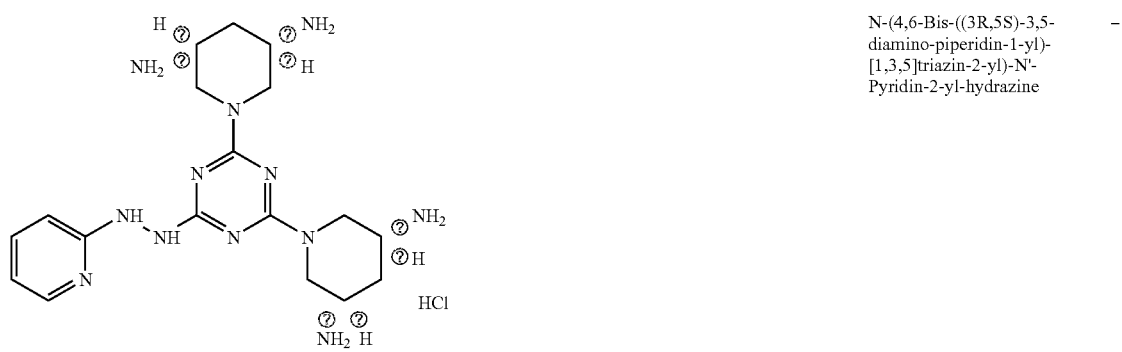 | N-(4,6-Bis-((3R,5S)-3,5-diamino-piperidin-1-yl)-[1,3,5]triazin-2-yl)-N'-Pyridin-2-yl-hydrazine | − |
| ⑦ indicates text missing or illegible when filed | | |

-continued
| Structure | Name | Potency |
|---|---|---|
| 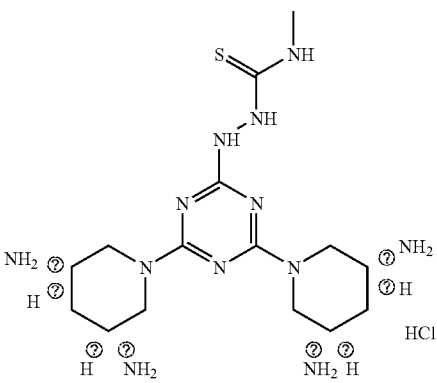 | N-(4,6-Bis-((3R,5S)-3,5-diamino-piperidin-1-yl)-[1,3,5]triazin-2-yl)-N'-(2,6-Dimethyl-pyrimidin-4-yl)-hydrazine | |
| 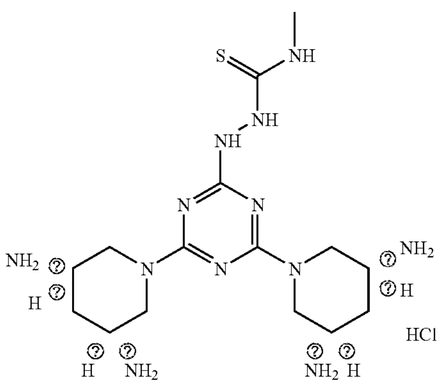 | N-(3-methyl-thioureido)-4,6-Bis-((3R,5S)-3,5-diamino-piperidin-1-yl)-[1,3,5]triazine-2-amine | − |
| 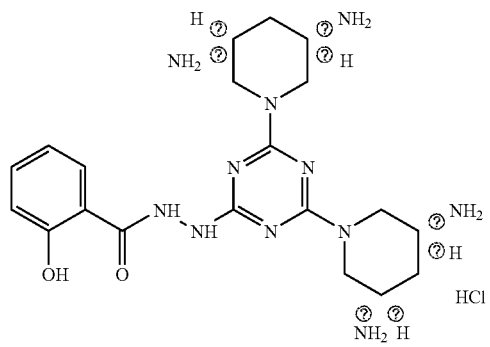 | 2-Hydroxy-benzoicacid N'-[4-((3R,5S)-3,5-diamino-piperidin-1-yl)-6-((3S,5R)-3,5-diamino-piperidin-1-yl)-[1,3,5]triazin-2-yl]-hydrazide | + |
| 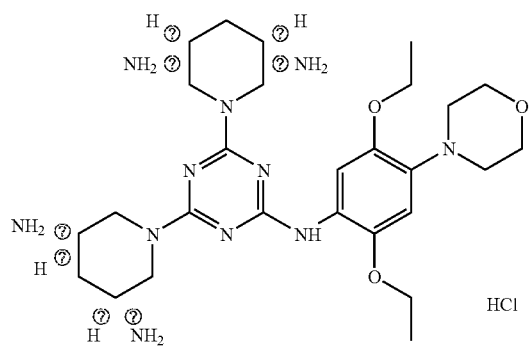 | N-(2,5-diethoxy-4-morpholin-4-yl-phenyl)-4,6-Bis-((3R,5S)-3,5-diamino-piperidin-1-yl)-[1,3,5]triazine-2-amine | |

-continued

| Structure | Name | Potency |
|---|---|---|
| 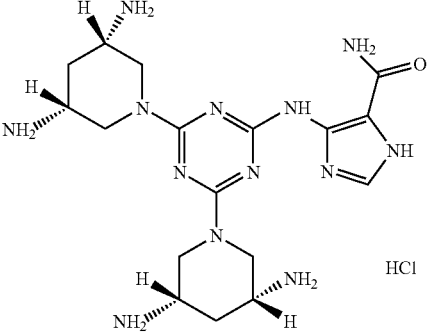 | N-(5-carbamoyl-1H-imidazol-4-yl)-4,6-Bis-((3R,5S)-3,5-diamino-piperidin-1-yl)-[1,3,5]triazine-2-amine | – |
| 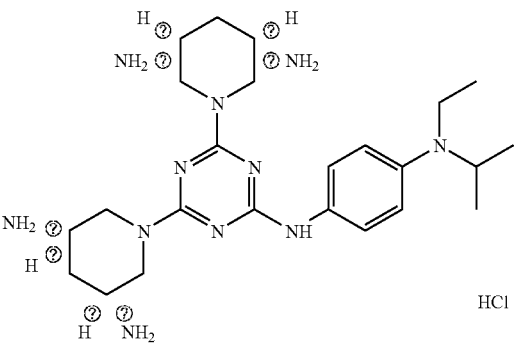 | N-[4-(ethyl-isopropyl-amino)-phenyl]-4,6-Bis-((3R,5S)-3,5-diamino-piperidin-1-yl)-[1,3,5]triazine-2-amine | – |

⑦ indicates text missing or illegible when filed

| | | |
|---|---|---|
| 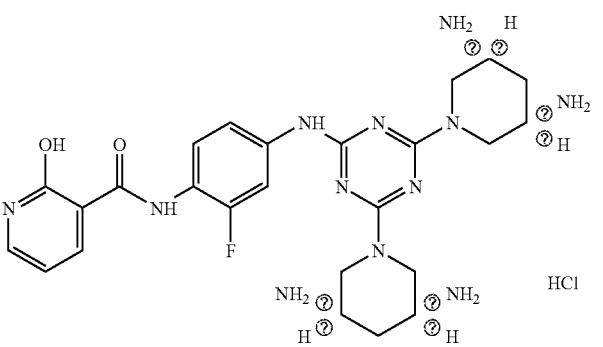 | N-(3-fluoro-3-[(2-hydroxy-pyridine-3-carbonyl)-amino]-phenyl}-4,6-Bis-(cis-3,5-Diamino-piperidin-1-yl)-[1,3,5]triazine-2-amine | |

⑦ indicates text missing or illegible when filed

| | | |
|---|---|---|
| 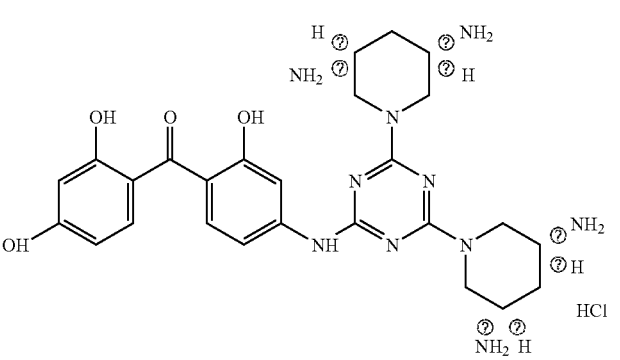 | N-[4-(2,4-ddihydroxy-benzoyl)-3-hydroxy-phenyl]-4,6-Bis-(cis-3,5-Diamino-piperidin-1-yl)-[1,3,5]triazine-2-amine | |

⑦ indicates text missing or illegible when filed

-continued

| Structure | Name | Potency |
|---|---|---|
| 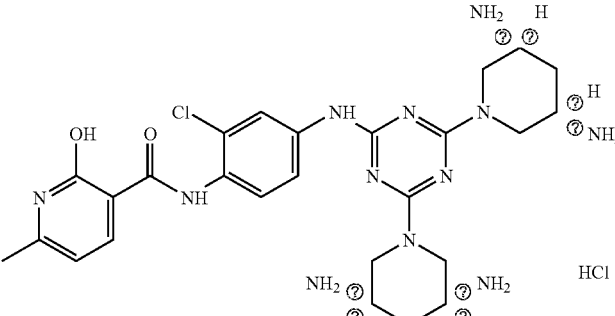 | N-{3-chloro-4-[(2-hydrooxy-6-methyl-pyridine-3-carbonyl)-amino]-phenyl}-4,6-Bis-(cis-3,5-Diamino-piperidin-1-yl)-[1,3,5]triazine-2-amine | |
| ⑦ indicates text missing or illegible when filed | | |
| 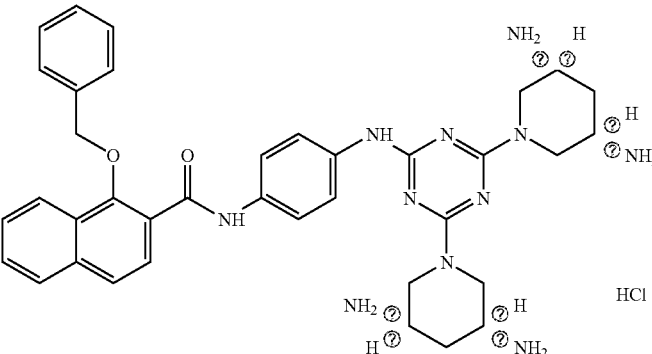 | 1-Benzyloxy-naphthalene-2-carboxylicacid {4-[3-((3R,5S)-3,5-diamino-piperidin-1-yl)-5-((3S,5RE)-3,5-diamino-piperidin-1-yl)-phenylamino]-phenyl}-amide | ++ |
| ⑦ indicates text missing or illegible when filed | | |
| 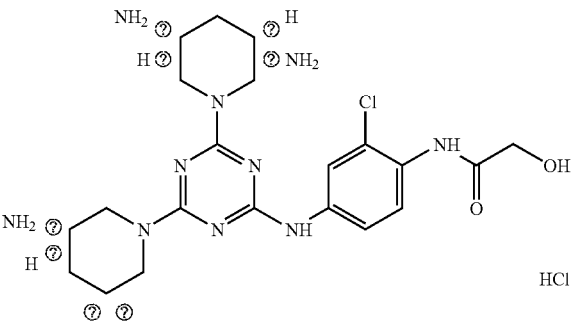 | N-[3-chloro-4-(2-hydroxy-acetylamino)-phenyl]-4,6-Bis-(cis-3,5-Diamino-piperidin-1-yl)-[1,3,5]triazine-2-amine | |
| ⑦ indicates text missing or illegible when filed | | |

-continued

| Structure | Name | Potency |
|---|---|---|
| 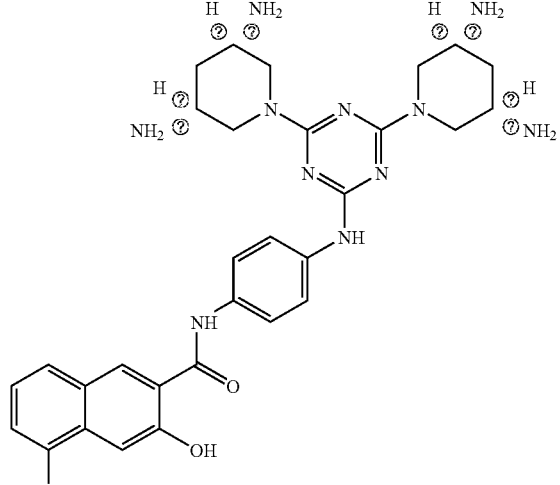 ⓘ indicates text missing or illegible when filed | N-{4-[(3,5-dihydroxy-naphthalene-2-carbonyl)-amino]-phenyl}-4,6-Bis-((3R,5S)-3,5-diamino-piperidin-1-yl)-[1,3,5]triazine-2-amine | + |
| 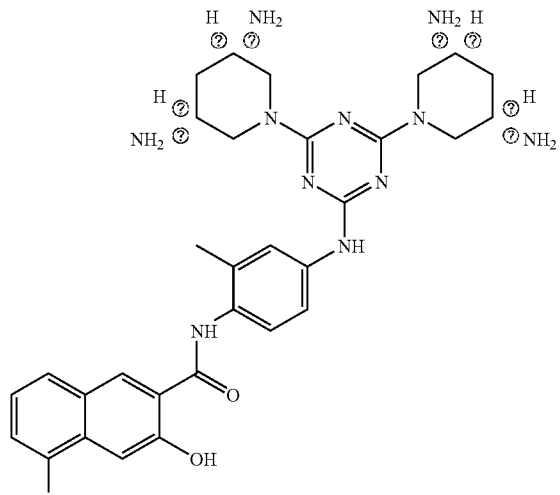 ⓘ indicates text missing or illegible when filed | N-{4-[(3,5-dihydroxy-naphthalene-2-carbonyl)-amino]-3-methyl-phenyl]-4,6-Bis-((3R,5S)-3,5-diamino-piperidin-1-yl)-[1,3,5]triazine-2-amine | + |
| 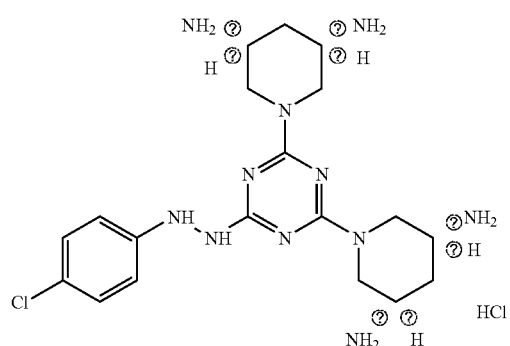 ⓘ indicates text missing or illegible when filed | N-(4,6-Bis-((3R,5S)-3,5-diamino-piperidin-1-yl)-[1,3,5]triazin-2-yl)-N'-(4-Chloro-phenyl)-hydrazine | |

-continued
| Structure | Name | Potency |
|---|---|---|
| 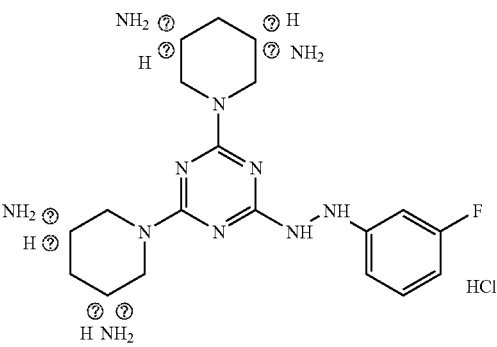 ⑦ indicates text missing or illegible when filed | N-(4,6-Bis-((3R,5S)-3,5-diamino-piperidin-1-yl)-[1,3,5]triazin-2-yl)-N'-(3-Fluoro-phenyl)-hydrazine | – |
| 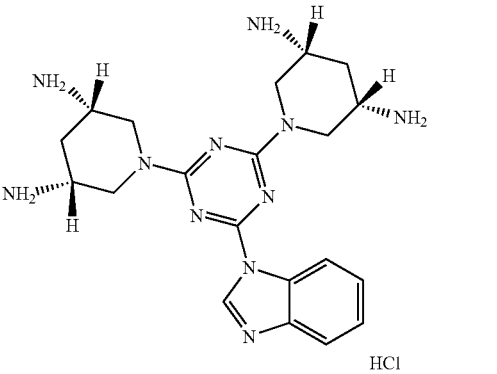 | 1-(4,6-Bis-((3R,5S)-3,5-diamino-piperidin-1-yl)-[1,3,5]triazin-2-yl)-1H-benzoimidazole | – |
| 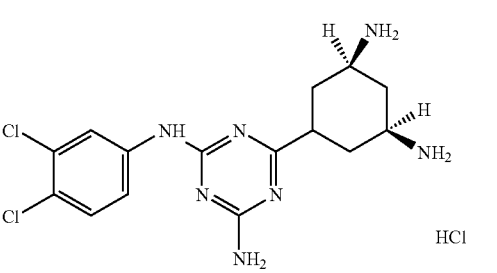 | 6-((3S,5R)-3,5-Diamino-piperidin-1-yl)-N-(3,4-dichlorro-phenyl)-[1,3,5]triazine-2,4-diamine | – |
| 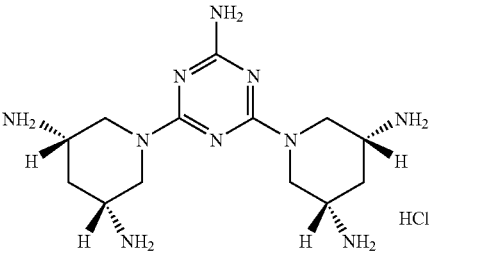 | 4,6-Bis-((3R,5S)-3,5-diamino-piperidin-1-yl)-[1,3,5]triazin-2-ylamine | – |

-continued

| Structure | Name | Potency |
|---|---|---|
| (structure) | N-{4-[2-(2-chloro-phenylcarbamoyl)-acetyl]-phenyl}-4,6-Bis-((3R,5S)-3,5-diamino-piperidin-1-yl)-[1,3,5]triazine-2-amine | ++ |
| (structure) | N-pyrrolidin-3-ylmethyl-4,6-Bis-((3R,5S)-3,5-diamino-piperidin-1-yl)-[1,3,5]triazine-2-amine | |
| (structure) | N-{4-[(3,5-dihydroxy-naphthalene-2-carbonyl)-amino]-2-methyl-phenyl}-4,6-Bis-((3R,5S)-3,5-diamino-piperidin-1-yl)-[1,3,5]triazine-2-amine | + |

? indicates text missing or illegible when filed

| Structure | Name | Potency |
|---|---|---|
| 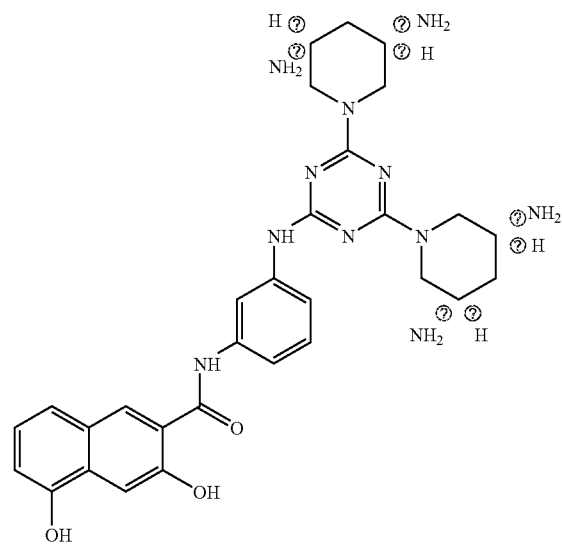 | N-{3-[(3,5-dihydroxy-naphthalene-2-carbonyl)-amino]-phenyl}-4,6-Bis-((3R,5S)-3,5-diamino-piperidin-1-yl)-[1,3,5]triazine-2-amine | + |
| ⑦ indicates text missing or illegible when filed | | |
| 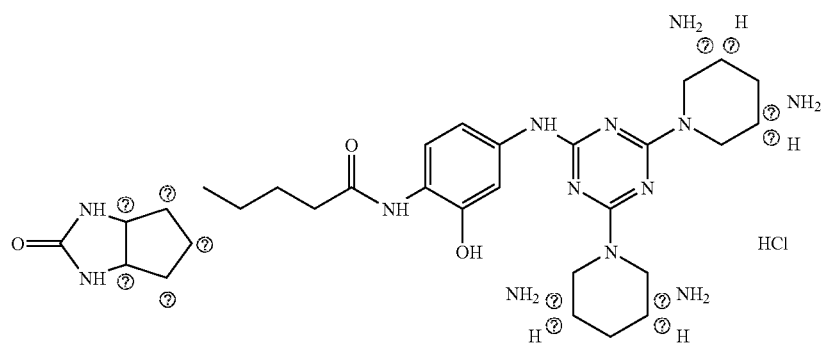 | 5-((3aR,4S,6aS)-2-Oxo-hexahydro-thieno[3,4-d]imidazol-4-yl)-pentanoicacid {4-[4-((3R,5S)-3,5-diamino-piperidin-1-yl)-6-((3S,5R)-3,5-diamino-piperidin-1-yl)-[1,3,5]triazin-2-ylamino]-2-hydroxy-phenyl}-amide | – |
| ⑦ indicates text missing or illegible when filed | | |
| 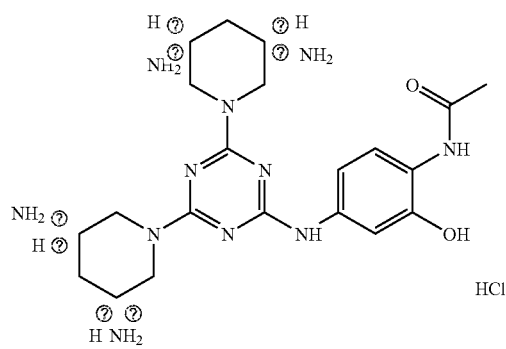 | N-(4-acetylamino-3-hydroxy-phenyl)-4,6-Bis-((3R,5S)-3,5-diamino-piperidin-1-yl)-[1,3,5]triazine-2-amine | – |
| ⑦ indicates text missing or illegible when filed | | |

-continued
| Structure | Name | Potency |
|---|---|---|
| 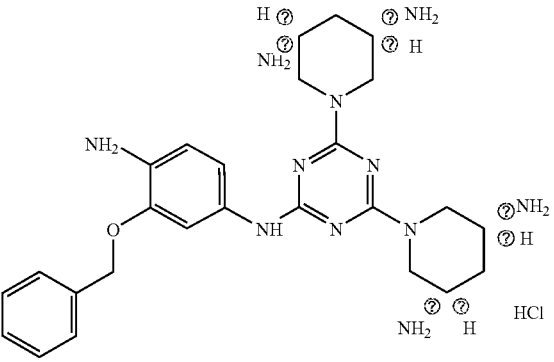 | N-(4-amino-3-benzyloxy-phenyl)-4,6-Bis-((3R,5S)-3,5-diamino-piperidin-1-yl)-[1,3,5]triazine-2-amine | − |
| 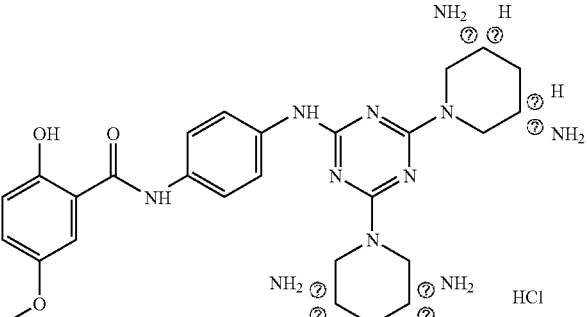 | N-[4-(2-hydroxy-5-methoxy-benzoylamino)-phenyl]-4,6-Bis-((3R,5S)-3,5-diamino-piperidin-1-yl)-[1,3,5]triazine-2-amine | + |
| 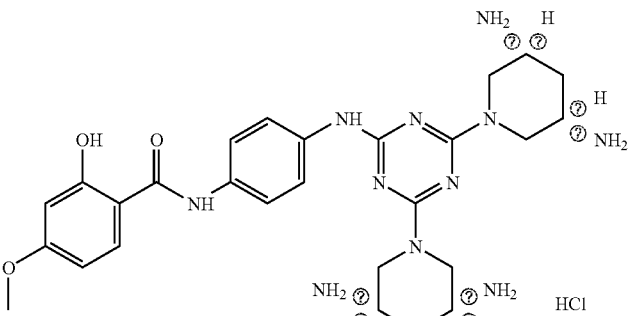 | N-[4-(2-hydroxy-4-methoxy-benzoylamino)-phenyl]-4,6-Bis-((3R,5S)-3,5-diamino-piperidin-1-yl)-[1,3,5]triazine-2-amine | − |
⑦ indicates text missing or illegible when filed -continued
| Structure | Name | Potency |
|---|---|---|
| 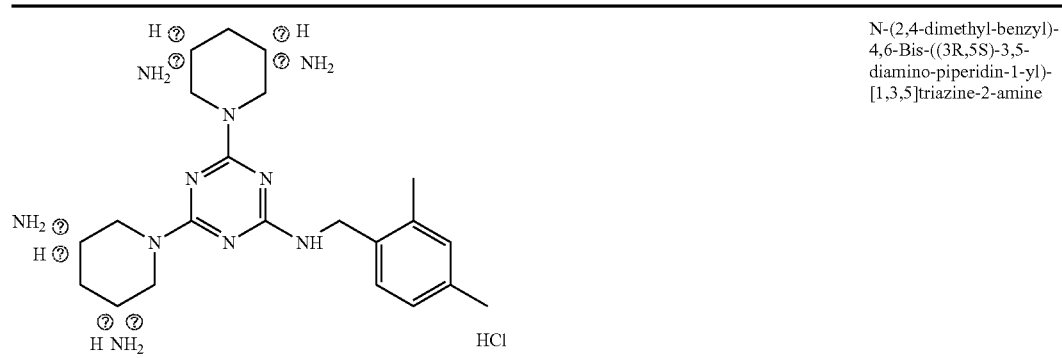 | N-(2,4-dimethyl-benzyl)-4,6-Bis-((3R,5S)-3,5-diamino-piperidin-1-yl)-[1,3,5]triazine-2-amine | |
| 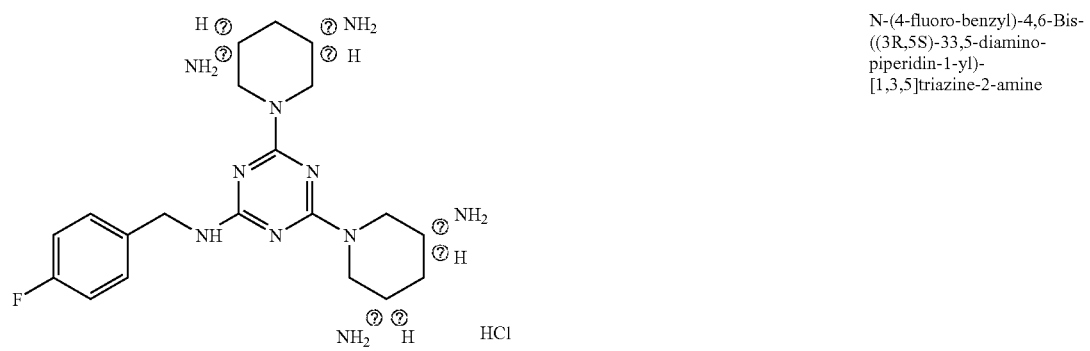 | N-(4-fluoro-benzyl)-4,6-Bis-((3R,5S)-33,5-diamino-piperidin-1-yl)-[1,3,5]triazine-2-amine | |
| 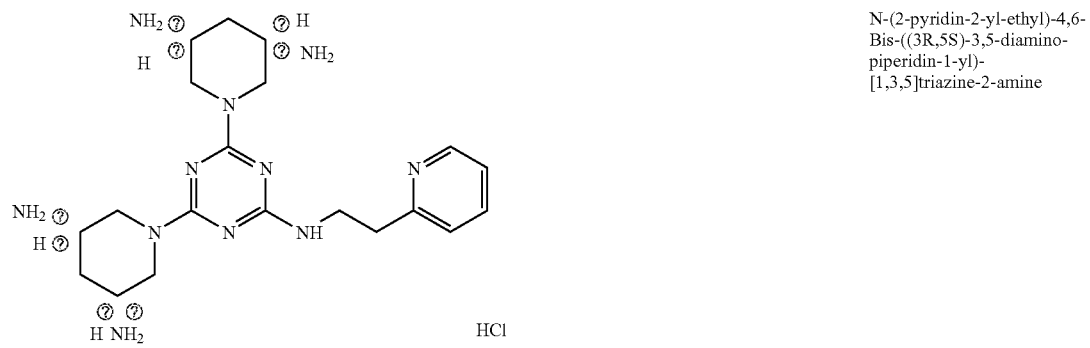 | N-(2-pyridin-2-yl-ethyl)-4,6-Bis-((3R,5S)-3,5-diamino-piperidin-1-yl)-[1,3,5]triazine-2-amine | |
| 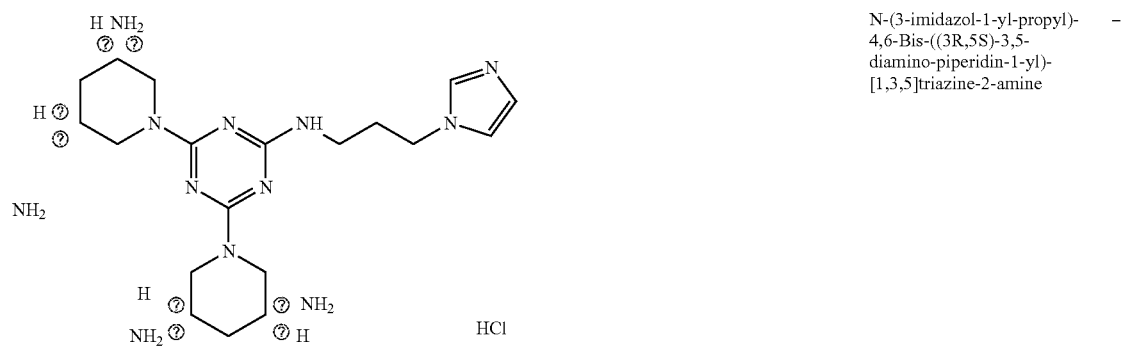 | N-(3-imidazol-1-yl-propyl)-4,6-Bis-((3R,5S)-3,5-diamino-piperidin-1-yl)-[1,3,5]triazine-2-amine | – |

-continued
| Structure | Name | Potency |
|---|---|---|
| 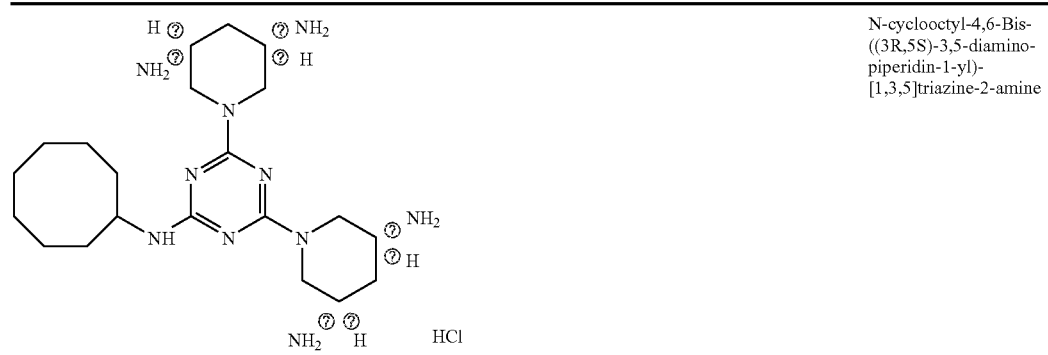 | N-cyclooctyl-4,6-Bis-((3R,5S)-3,5-diamino-piperidin-1-yl)-[1,3,5]triazine-2-amine | |
| 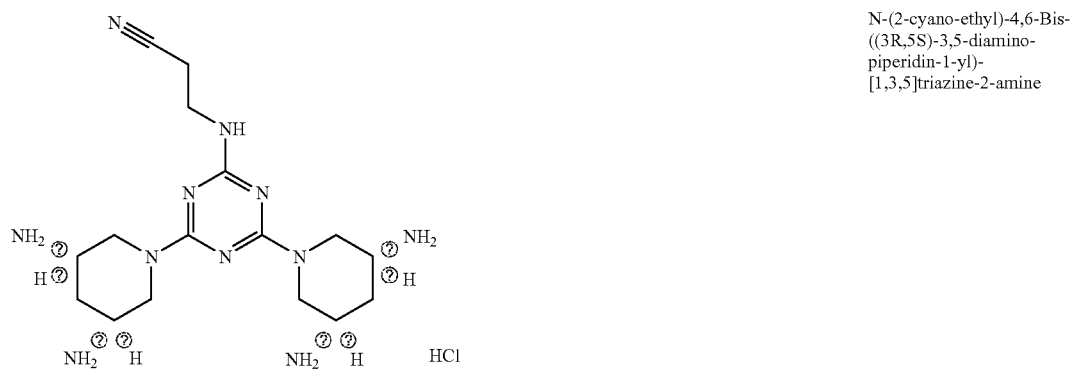 | N-(2-cyano-ethyl)-4,6-Bis-((3R,5S)-3,5-diamino-piperidin-1-yl)-[1,3,5]triazine-2-amine | |
| 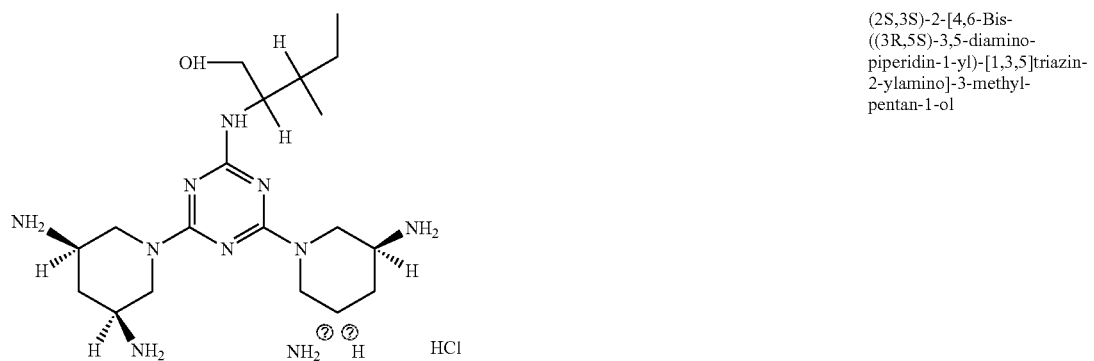 | (2S,3S)-2-[4,6-Bis-((3R,5S)-3,5-diamino-piperidin-1-yl)-[1,3,5]triazin-2-ylamino]-3-methyl-pentan-1-ol | |
| 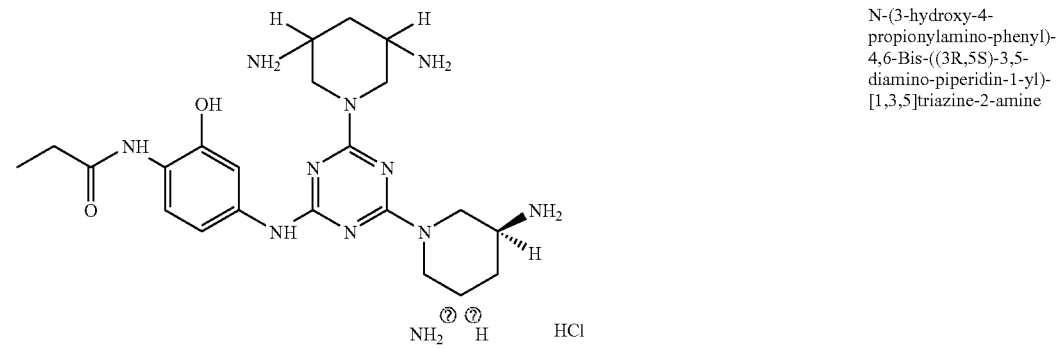 | N-(3-hydroxy-4-propionylamino-phenyl)-4,6-Bis-((3R,5S)-3,5-diamino-piperidin-1-yl)-[1,3,5]triazine-2-amine | |

-continued

| Structure | Name | Potency |
|---|---|---|
| 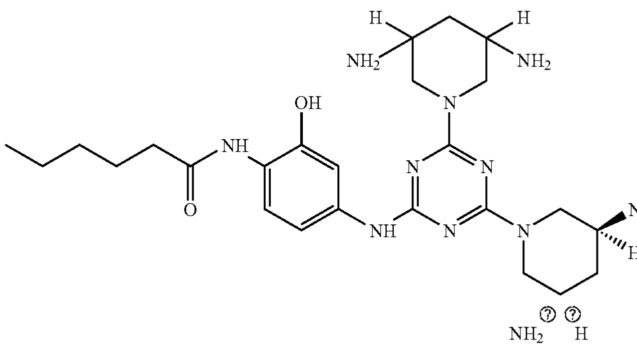 | N-(4-hexanoylamino-3-hydroxy-phenyl)-4,6-Bis-((3R,5S)-3,5-diamino-piperidin-1-yl)-[1,3,5]triazine-2-amine | ++ |
| 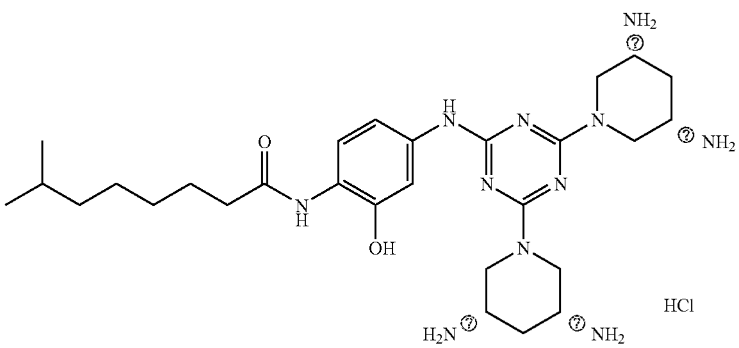 | N-[3-hydroxy-4-(7-methyl-octanoylamino)-phenyl]-4,6-Bis-((3R,5S)-3,5-diamino-piperidin-1-yl)-[1,3,5]triazine-2-amine | ++ |
| 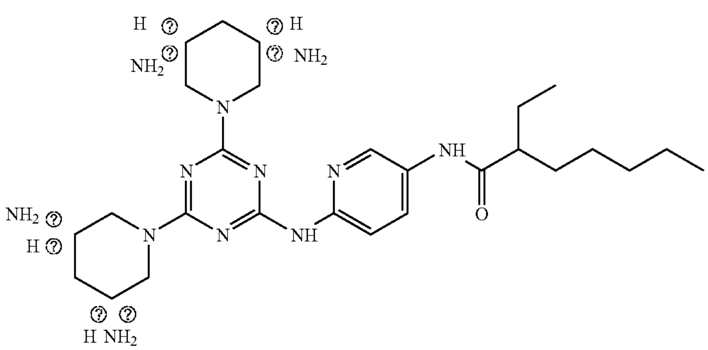 | N-[4-(2-ethyl-heptanoylamino)-3-hydroxy-phenyl]-4,6-Bis-((3R,5S)-3,5-diamino-piperidin-1-yl)-[1,3,5]triazine-2-amine | ++ |
| 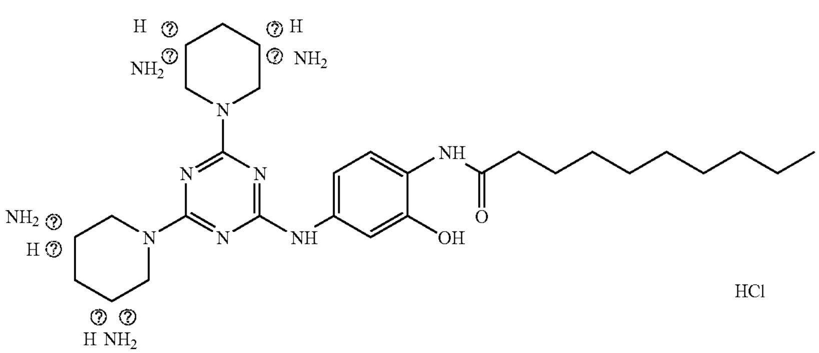 | N-(4-decanoylamino-3-hydroxy-phenyl)-4,6-Bis-((3R,5S)-3,5-diamino-piperidin-1-yl)-[1,3,5]triazine-2-amine | ++ |

-continued

| Structure | Name | Potency |
|---|---|---|
| 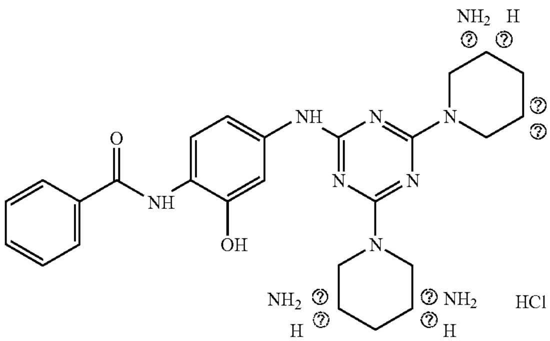 | N-(4-benzoylamino-3-hydroxy-phenyl)-4,6-Bis-((3R,5S)-3,5-diamino-piperidin-1-yl)-[1,3,5]triazine-2-amine | ++ |
| 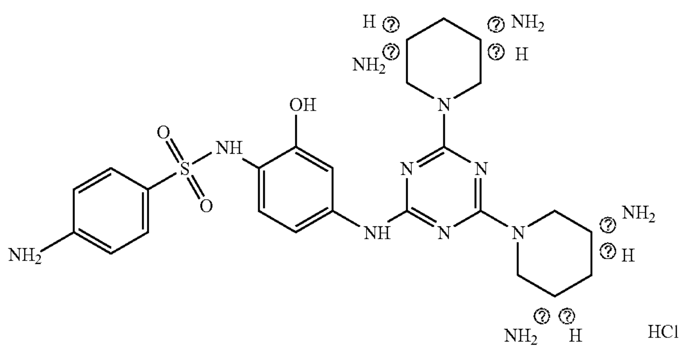 | N-[4-(4-amino-benzenesulfonylamino)-3-hydroxy-phenyl]-4,6-Bis-((3R,5S)-33,5-diamino-piperidin-1-yl)-[1,3,5]triazine-2-amine | + |
| 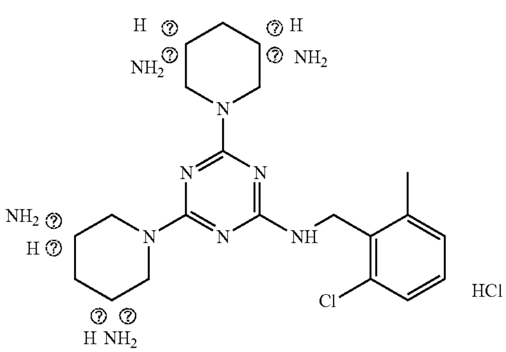 | N-(2-chloro-6-methyl-benzyl)-4,6-Bis-((3R,5S)-3,5-diamino-piperidin-1-yl)-[1,3,5]triazine-2-amine | |

-continued
| Structure | Name | Potency |
|---|---|---|
| 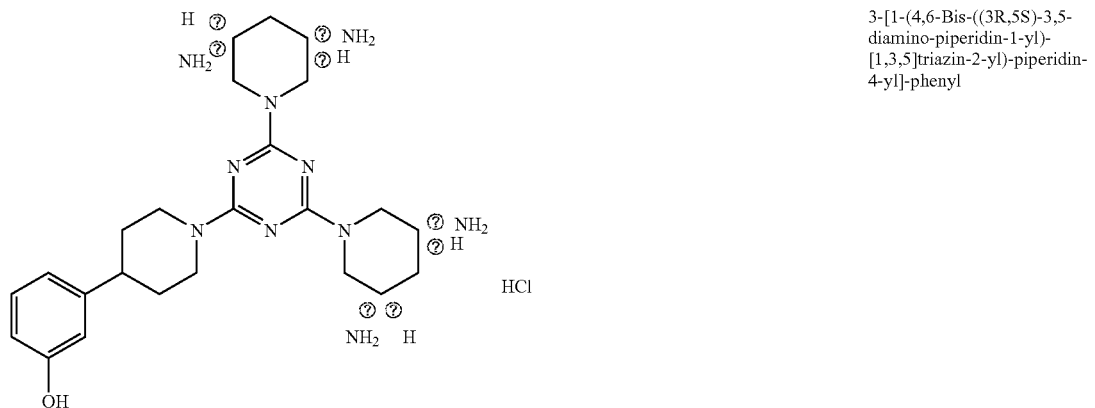 | 3-[1-(4,6-Bis-((3R,5S)-3,5-diamino-piperidin-1-yl)-[1,3,5]triazin-2-yl)-piperidin-4-yl]-phenyl | – |
| 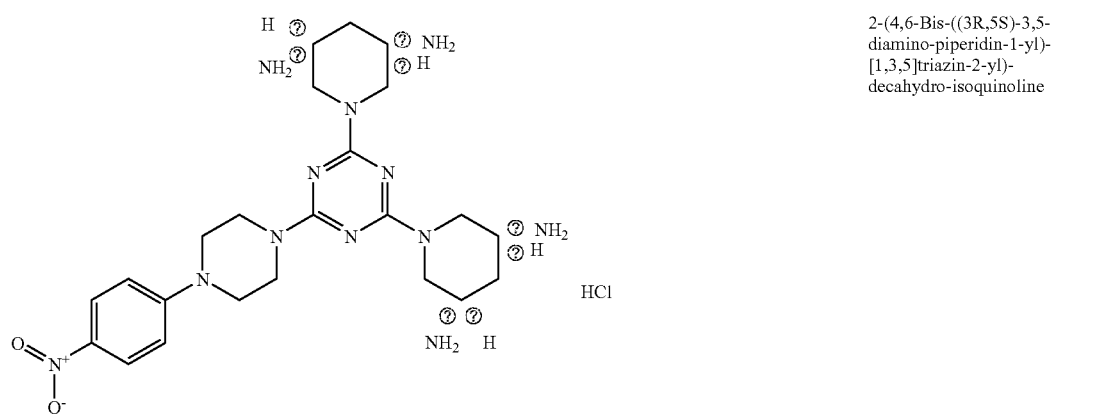 | 2-(4,6-Bis-((3R,5S)-3,5-diamino-piperidin-1-yl)-[1,3,5]triazin-2-yl)-decahydro-isoquinoline | – |
| 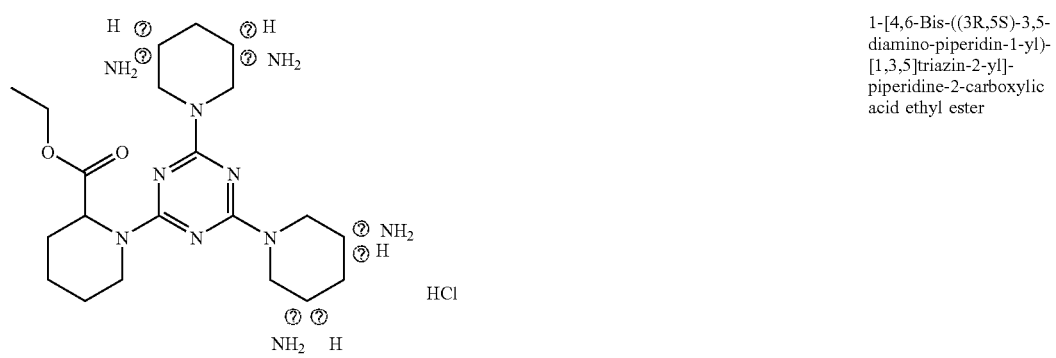 | 1-[4,6-Bis-((3R,5S)-3,5-diamino-piperidin-1-yl)-[1,3,5]triazin-2-yl]-piperidine-2-carboxylic acid ethyl ester | |
? indicates text missing or illegible when filed -continued

| Structure | Name | Potency |
|---|---|---|
| 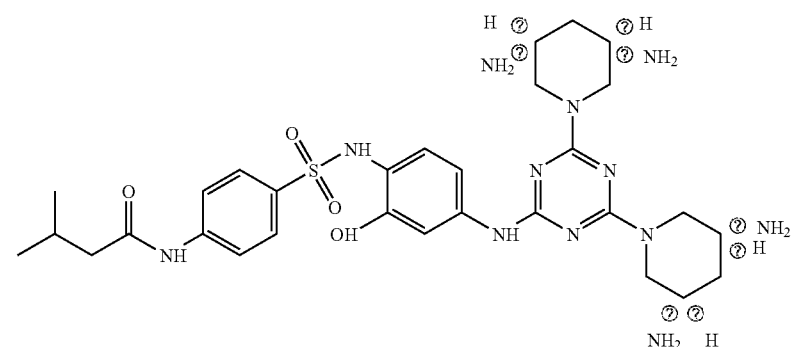 ⓘ indicates text missing or illegible when filed | N-{3-hydroxy-4-[4-(3-methyl-butylamino)-benzenesulfonylamino]-phenyl}-4,6-Bis-((3R,5S)-3,5-diamino-piperidin-1-yl)-[1,3,5]triazine-2-amine | ++ |
| 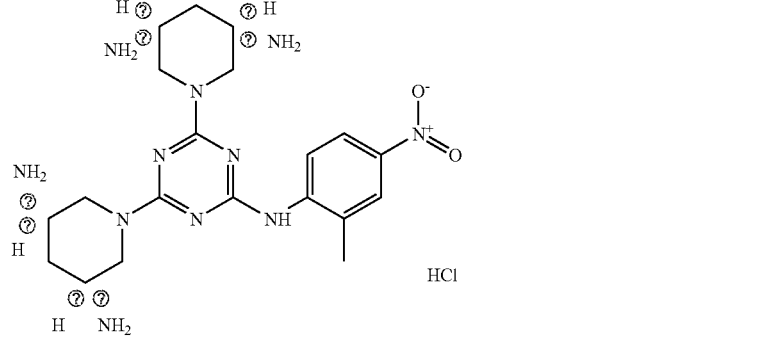 ⓘ indicates text missing or illegible when filed | N-(2-methyl-4-nitro-phenyl)-4,6-Bis-((3R,5S)-3,5-diamino-piperidin-1-yl)-[1,3,5]triazine-2-amine | |
| 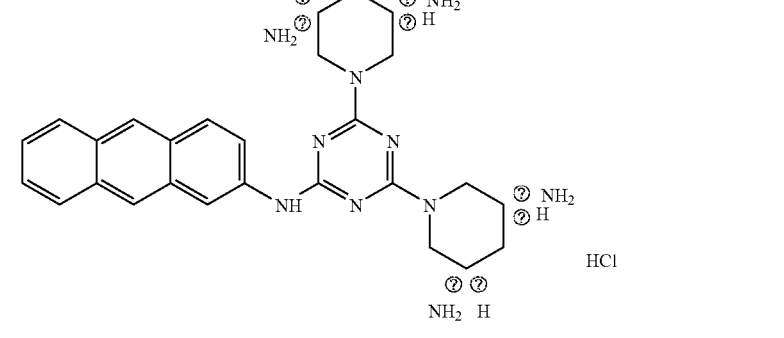 ⓘ indicates text missing or illegible when filed | N-anthracen-2-yl-4,6-Bis-((3R,5S)-3,5-diamino-piperidin-1-yl)-[1,3,5]triazine-2-amine | |
| 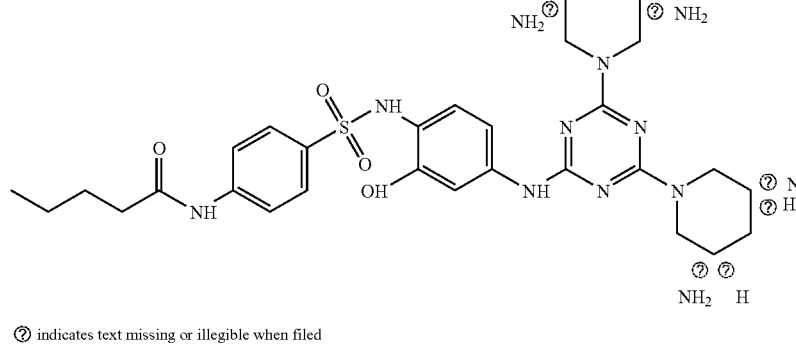 ⓘ indicates text missing or illegible when filed | N-[3-hydroxy-4-(4-pentanoylamino-benzenesulfonylamino)-phenyl]-4,6-Bis-((3R,5S)-3,5-diamino-piperidin-1-yl)-[1,3,5]triazine-2-amine | + |

-continued

| Structure | Name | Potency |
|---|---|---|
| 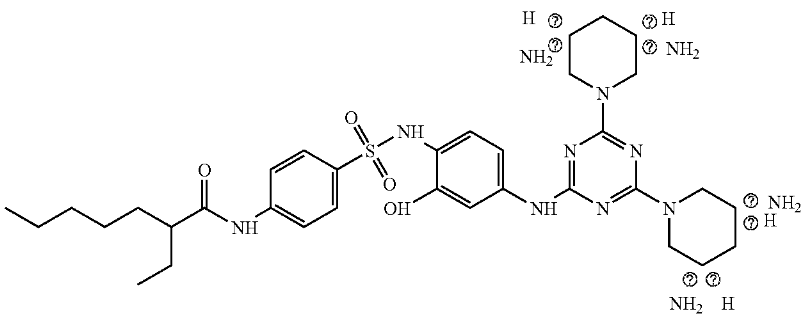 | N-{4-[4-(2-ethyl-heptanoylamino)-benzenesulfonylamino]-3-hydroxy-phenyl}-4,6-Bis-((3R,5S)-3,5-diamino-piperidin-1-yl)-[1,3,5]triazine-2-amine | ++ |
| 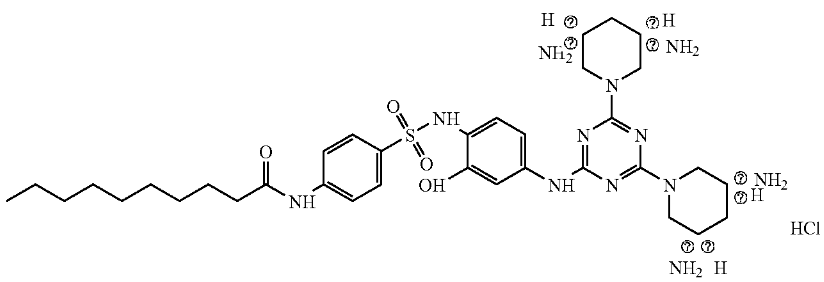 | N-[4-(4-decanoylamino-benzenesulfonylamino)-3-hydroxy-phenyl]-4,6-Bis-((3R,5S)-3,5-diamino-piperidin-1-yl)-[1,3,5]triazine-2-amine | ++ |
| 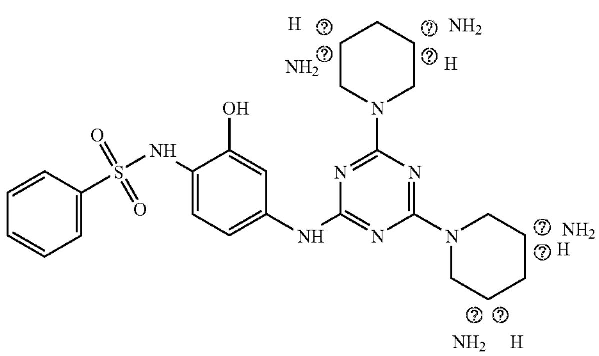 | N-(4-benzenesulfonylamino-3-hydroxy-phenyl)-4,6-Bis-((3R,5S)-3,5-diamino-piperidin-1-yl)-[1,3,5]triazine-2-amine | + |
| 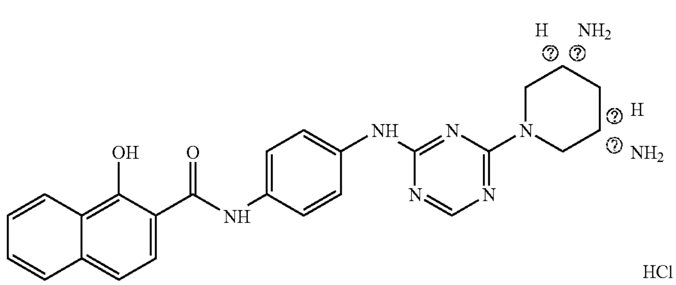 | 1-Hydroxy-naphthalene-2-carboxylicacid {4-[4-((3S,5R)-3,5-diamino-piperidin-1-yl)-[1,3,5]triazin-2-ylamino]-phenyl}-amide | ++ |

-continued

| Structure | Name | Potency |
|---|---|---|
| 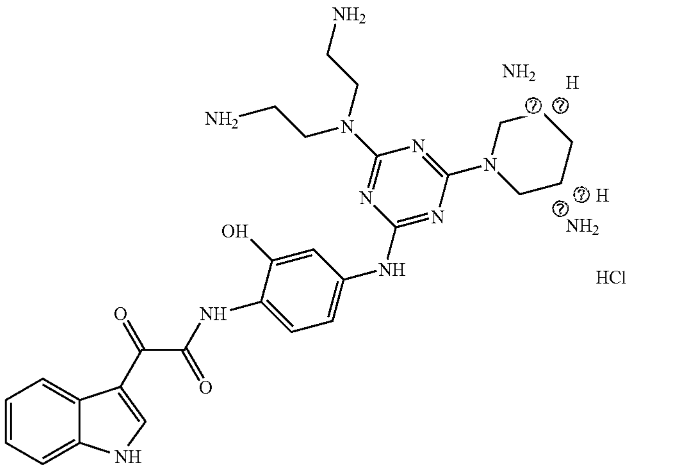 | N-{4-[4-[Bis-(2-amino-ethyl)-amino]-6-((3R,5S)-3,5-diamino-piperidin-1-yl)-[1,3,5]triazin-2-ylamino]-2-hydroxy-phenyl}-2-(1H-indol-3-yl)-2-oxo-acetamide | ++ |
| 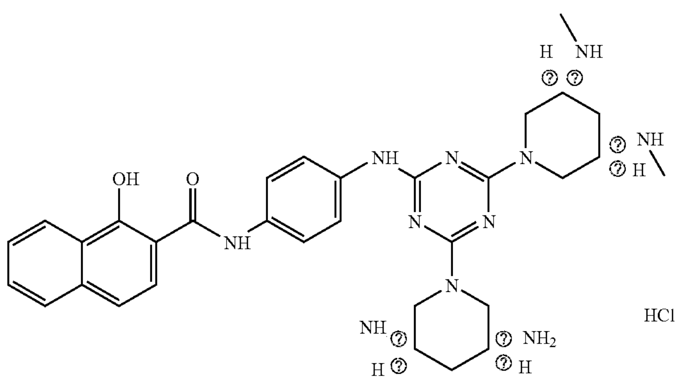 | N-{4-[(1-hydroxy-naaphthalene-2-carbonyl)-amino]-phenyl}-44,6-Bis-((3R,5S)-3,5-diamino-piperidin-1-yl)-[1,3,5]triazine-2-amine | ++ |
| 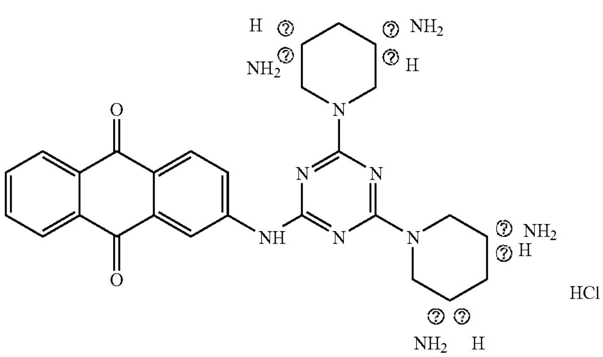 | N-(9,10-dioxo-9,10-dihydro-anthracen-2-yl)-4,6-Bis-((3R,5S)-3,5-diamino-piperidin-1-yl)-[1,3,5]triazine-2-amine | |

⊘ indicates text missing or illegible when filed

-continued

| Structure | Name | Potency |
|---|---|---|
| 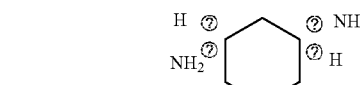<br>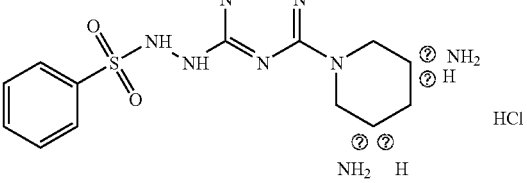 | N-(3-ethylnyl-phenyl)-4,6-Bis-((3R,5S)-3,5-diamino-piperidin-1-yl)-[1,3,5]triazine-2-amine | – |
| 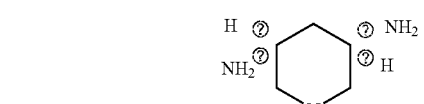<br>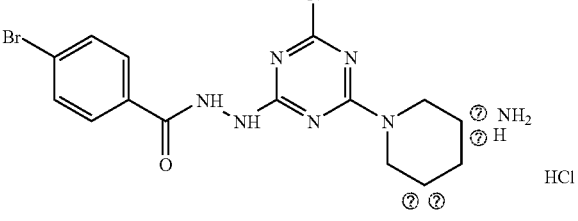 | N-(benzenesulfonylamino)-4,6-Bis-((3R,5S)-3,5-diamino-piperidin-1-yl)-[1,3,5]triazine-2-amine | |
| 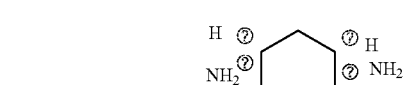<br>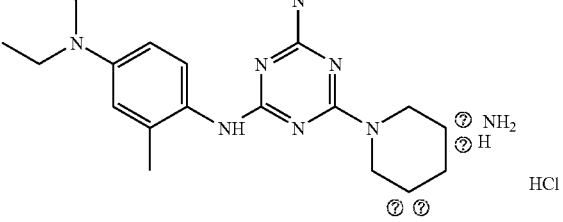 | 4-Bromo-benzoicacid N'-[4-((3R,5S)-3,5-diamino-piperidin-1-yl)-6-((3S,5R)-3,5-diamino-piperidin-1-yl)-[1,3,5]triazine-2-yl]-hydrazide | |
| 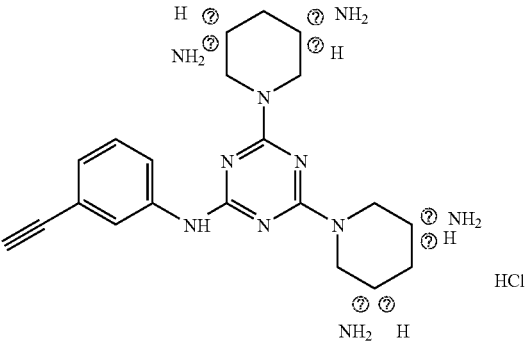<br>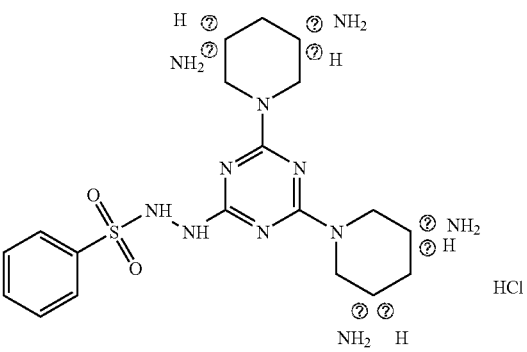 | N-(4-diethylamino-2-methyl-phenyl)-4,6-Bis-((3R,5S)-3,5-diamino-piperidin-1-yl)-[1,3,5]triazine-2-amine | |

⓶ indicates text missing or illegible when filed

-continued
| Structure | Name | Potency |
|---|---|---|
| 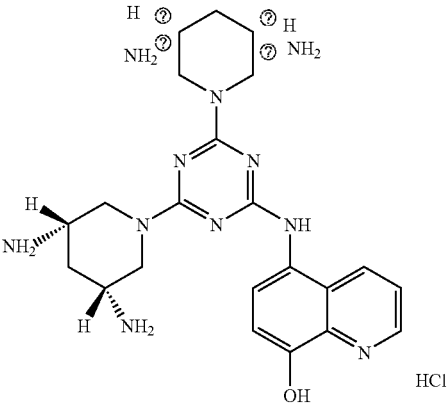 | N-(8-hydroxy-quinolin-5-yl)-4,6-Bis-((3R,5S)-3,5-diamino-piperidin-1-yl)-[1,3,5]triazine-2-amine | ++ |
| 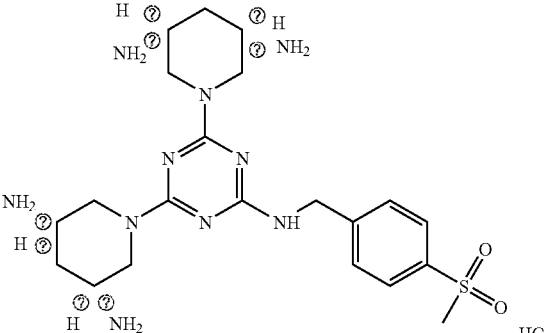 | N-(4-methanesulfonyl-benzyl)-4,6-Bis-((3R,5S)-3,5-diamino-piperidin-1-yl)-[1,3,5]triazine-2-amine | |
| 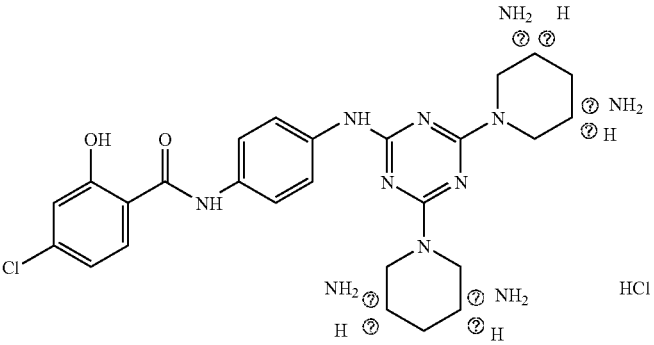 | N-[4-(4-chloro-2-hydroxy-benzoylamino)-phenyl]-4,6-Bis-((3R,5S)-3,5-diamino-piperidin-1-yl)-[1,3,5]triazine-2-amine | ++ |

-continued

| Structure | Name | Potency |
|---|---|---|
| 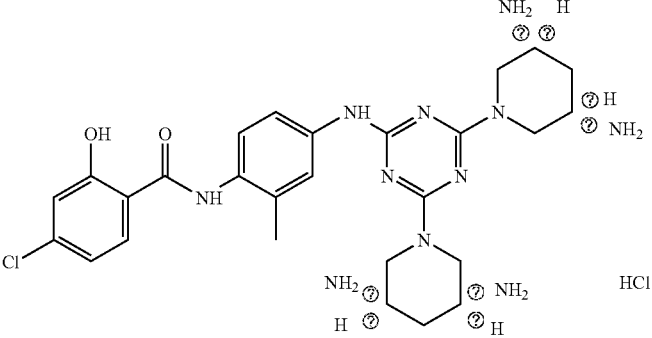 | N-[4-(4-chloro-2-hydroxy-benzoylamino)-3-methyl-phenyl]-4,6-Bis-((3R,5S)-3,5-diamino-piperidin-1-yl)-[1,3,5]triazine-2-amine | ++ |
| 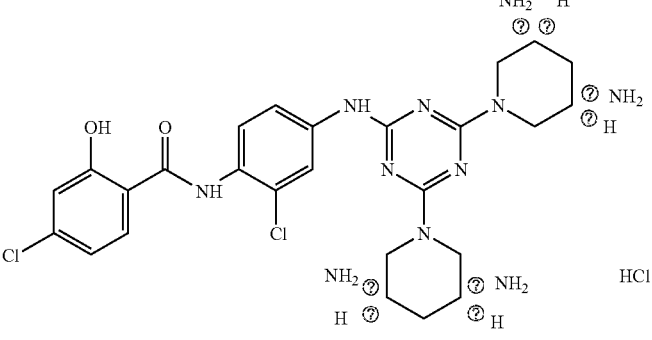 | N-[3-chloro-4-(4-chloro-2-hydroxy-benzoylamino)-phenyl]-4,6-Bis-((3R,5S)-3,5-diamino-piperidin-1-yl)-[1,3,5]triazine-2-amine | ++ |
| 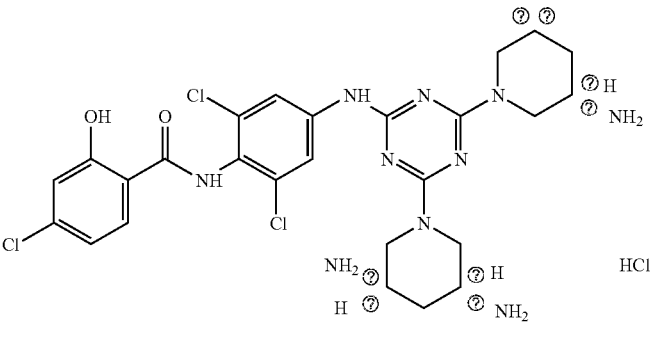 | N-[3,5-dichloro-4-(4-chloro-2-hydroxy-benzoylamino)-phenyl]-4,6-Bis-((3R,5S)-3,5-diamino-piperidin-1-yl)-[1,3,5]triazine-2-amine | ++ |
| 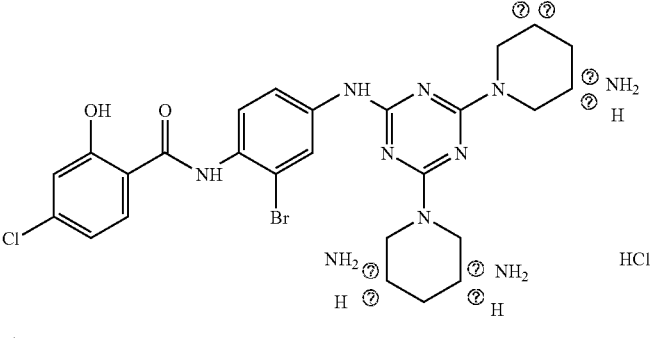 | N-[3-bromo-4-(4-chloro-2-hydroxy-benzoylamino)-phenyl]-4,6-Bis-((3R,5S)-3,5-diamino-piperidin-1-yl)-[1,3,5]triazine-2-amine | ++ |

⊘ indicates text missing or illegible when filed

-continued

| Structure | Name | Potency |
|---|---|---|
| 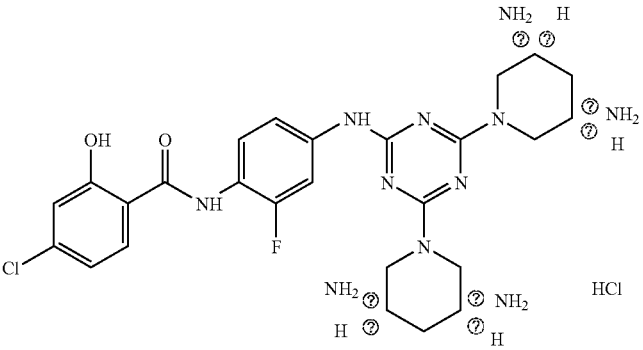 | N-[4-(4-chloro-2-hydroxy-benzoylamino)-3-fluoro-phenyl]-4,6-Bis-((3R,5S)-3,5-diamino-piperidin-1-yl)-[1,3,5]triazine-2-amine | ++ |
| ⑦ indicates text missing or illegible when filed | | |
| 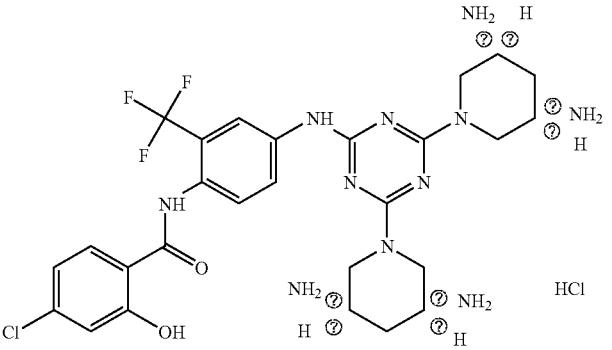 | N-[4-(4-chloro-2-hydroxy-benzoylamino)-3-trifluoromethyl-phenyl]-4,6-Bis-((3R,5S)-3,5-diamino-piperidin-1-yl)-[1,3,5]triazine-2-amine | ++ |
| ⑦ indicates text missing or illegible when filed | | |
| 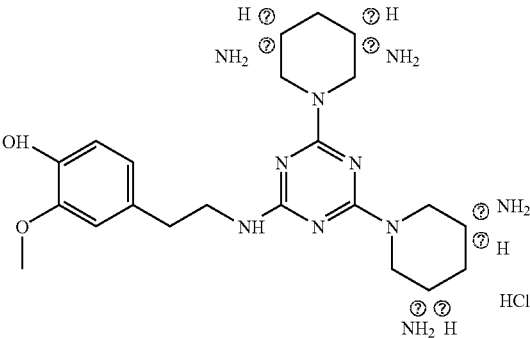 | N-[2-(4-hydroxy-3-methoxy-phenyl)-ethyl]-4,6-Bis-((3R,5S)-3,5-diamino-piperidin-1-yl)-[1,3,5]triazine-2-amine | |
| ⑦ indicates text missing or illegible when filed | | |

| Structure | Name | Potency |
|---|---|---|
| 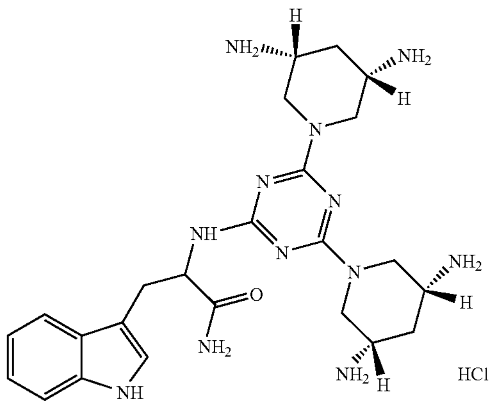 | N-[1-carbamoyl-2-(1H-indol-3-yl)-ethyl]-4,6-Bis-((3R,5S)-3,5-diamino-piperidin-1-yl)-[1,3,5]triazine-2-amine | |
| 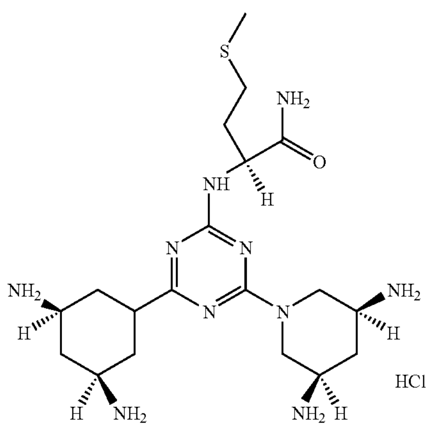 | (S)-2-[4,6-Bis-((3R,5S)-3,5-diamino-piperidin-1-yl)-[1,3,5]triazin-2-ylamino]-4-methylsulfanyl-butyramide | |
| 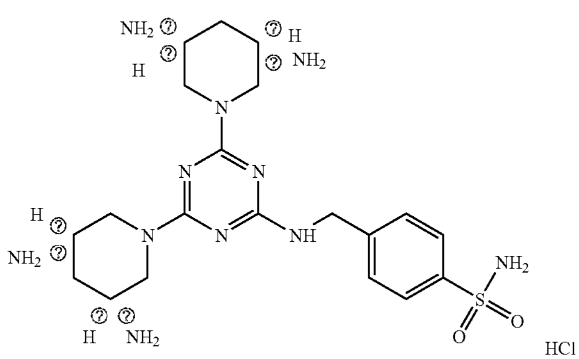 | N-(4-sulfamoyl-benzyl)-4,6-Bis-((3R,5S)-3,5-diamino-piperidin-1-yl)-[1,3,5]triazine-2-amine | |

⊘ indicates text missing or illegible when filed

-continued
| Structure | Name | Potency |
|---|---|---|
| 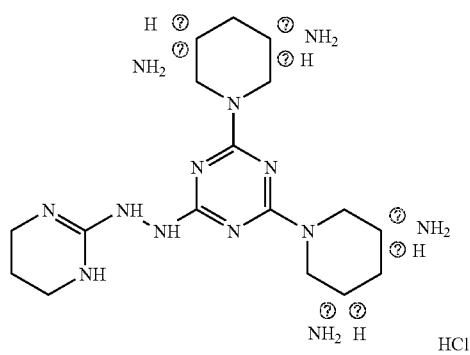 | N-(4,6-Bis-((3R,5S)-3,5-diamino-piperidin-1-yl)-[1,3,5]triazin-2-yl)-N'-(1,4,5,6-tetrahydro-pyrimidin-2-yl)-hydrazine | − |
| 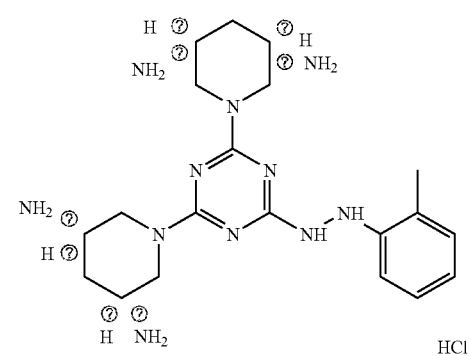 | N-(4,6-Bis-((3R,5S)-3,5-diamino-piperidin-1-yl)-[1,3,5]triazin-2-yl)-N'-o-Tolyl-hydrazine | + |
| 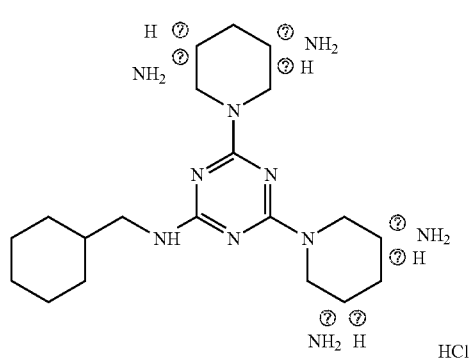 | N-cyclohexamethyl-4,6-Bis-((3R,5S)-3,5-diamino-piperidin-1-yl)-[1,3,5]triazine-2-amine | |
| 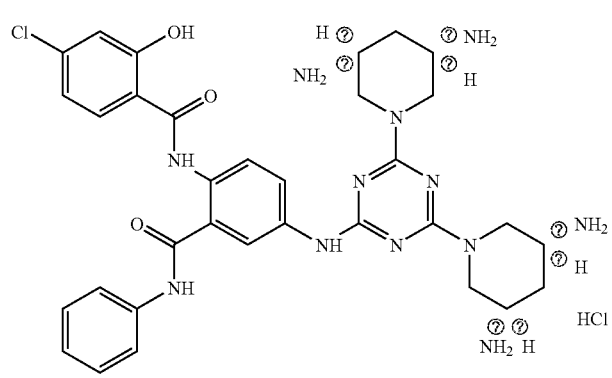 | N-[4-(4-chloro-2-hydroxy-benzoylamino)-3-phenylcarbamoyl-phenyl]-4,6-Bis-((3R,5S)-3,5-diamino-piperidin-1-yl)-[1,3,5]triazine-2-amine | ++ |

-continued

| Structure | Name | Potency |
|---|---|---|
| 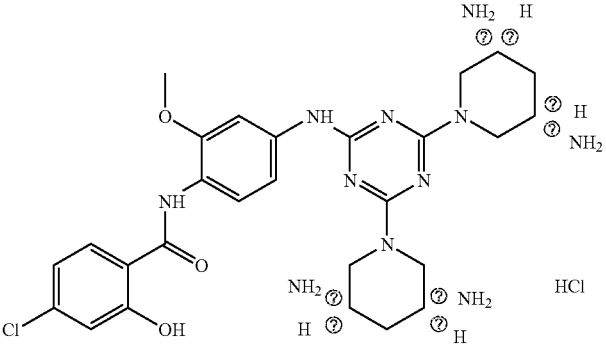 | N-[4-(4-chlorro-2-hydroxy-benzoylamino)-3-methoxy-phenyl]-4,6-Bis-((3R,5S)-3,5-diamino-piperidin-1-yl)-[1,3,5]triazine-2-amine | ++ |
| ⑦ indicates text missing or illegible when filed | | |
| 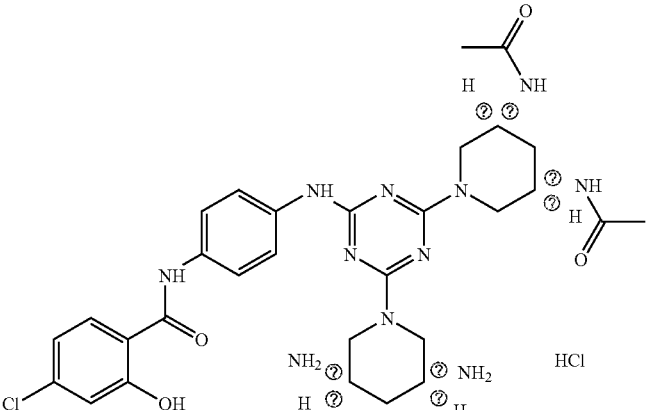 | N-{4-[(1-hydroxy-naphthalene-2-carbonyl)-amino]-phenyl}-4,6-Bis-((3R,5S)-3,5-diamino-piperidin-1-yl)-[1,3,5]triazine-2-amine | |
| ⑦ indicates text missing or illegible when filed | | |
| 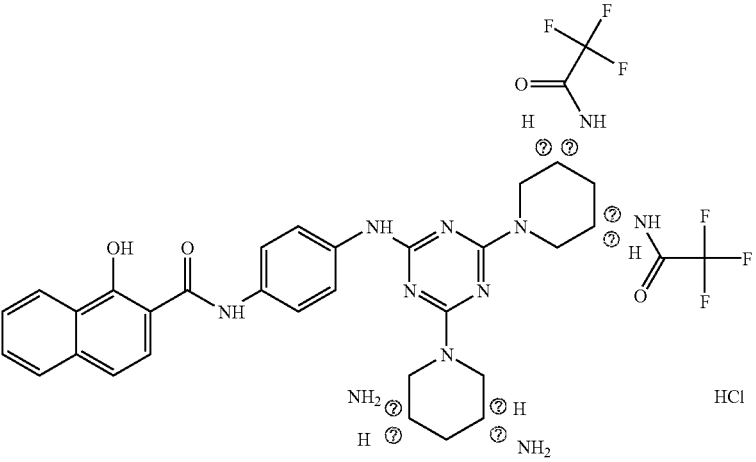 | N-{4-[(1-hydroxy-naphthalene-2-carbonyl)-amino]-phenyl}-4,6-Bis-((3R,5S)-3,5-diamino-piperidin-1-yl)-[1,3,5]triazine-2-amine | ++ |
| ⑦ indicates text missing or illegible when filed | | |

-continued

| Structure | Name | Potency |
|---|---|---|
| 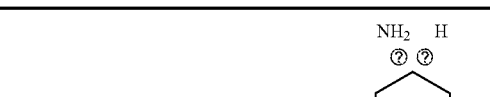 ⓘ indicates text missing or illegible when filed | N-[3-chloro-4-(4-chloro-2-hydroxy-benzoylamino)-5-methyl-phenyl]-4,6-Bis-((3R,5S)-3,5-diamino-piperidin-1-yl)-[1,3,5]triazine-2-amine | ++ |
| 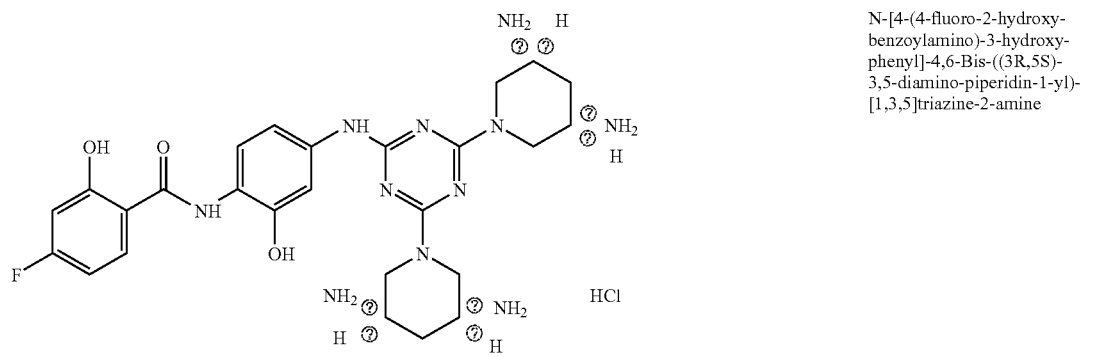 ⓘ indicates text missing or illegible when filed | N-[4-(4-fluoro-2-hydroxy-benzoylamino)-3-hydroxy-phenyl]-4,6-Bis-((3R,5S)-3,5-diamino-piperidin-1-yl)-[1,3,5]triazine-2-amine | ++ |
| 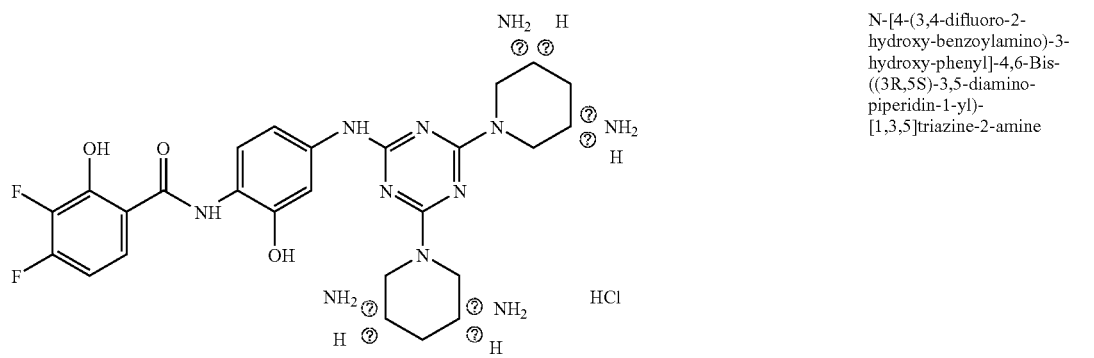 ⓘ indicates text missing or illegible when filed | N-[4-(3,4-difluoro-2-hydroxy-benzoylamino)-3-hydroxy-phenyl]-4,6-Bis-((3R,5S)-3,5-diamino-piperidin-1-yl)-[1,3,5]triazine-2-amine | + |
| 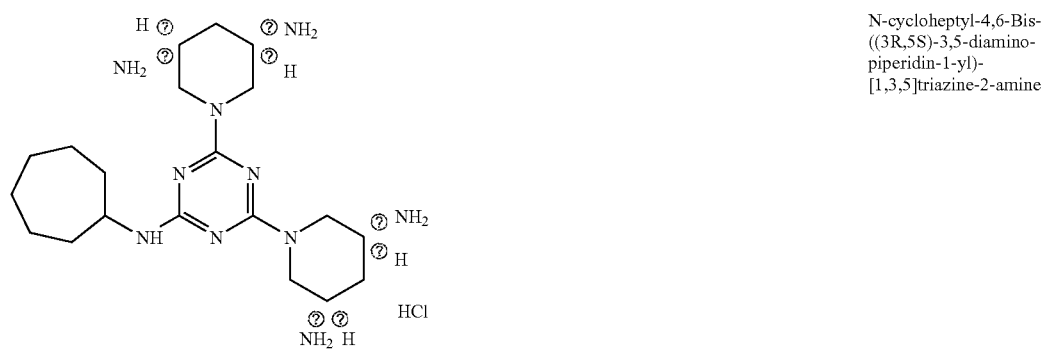 ⓘ indicates text missing or illegible when filed | N-cycloheptyl-4,6-Bis-((3R,5S)-3,5-diamino-piperidin-1-yl)-[1,3,5]triazine-2-amine | |

-continued
| Structure | Name | Potency |
|---|---|---|
| 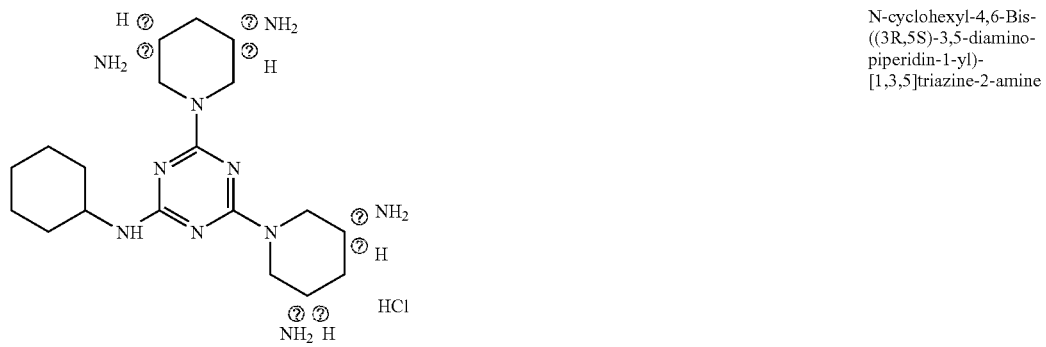 | N-cyclohexyl-4,6-Bis-((3R,5S)-3,5-diamino-piperidin-1-yl)-[1,3,5]triazine-2-amine | |
| 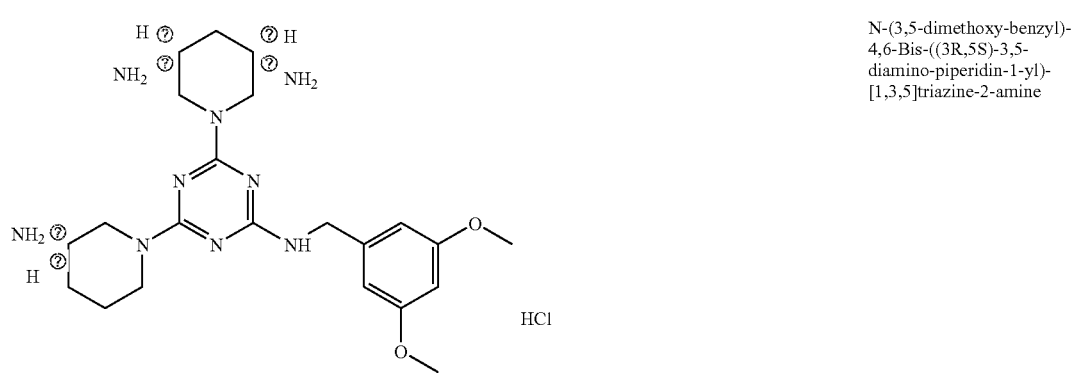 | N-(3,5-dimethoxy-benzyl)-4,6-Bis-((3R,5S)-3,5-diamino-piperidin-1-yl)-[1,3,5]triazine-2-amine | |
| 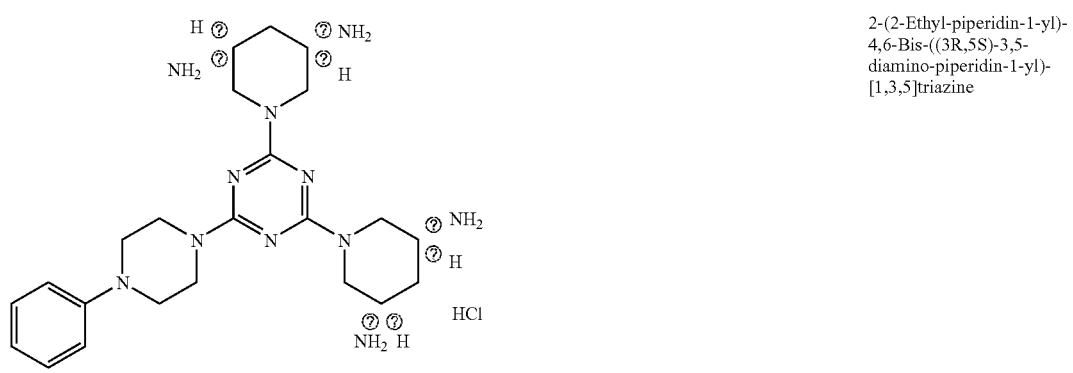 | 2-(2-Ethyl-piperidin-1-yl)-4,6-Bis-((3R,5S)-3,5-diamino-piperidin-1-yl)-[1,3,5]triazine | |
| 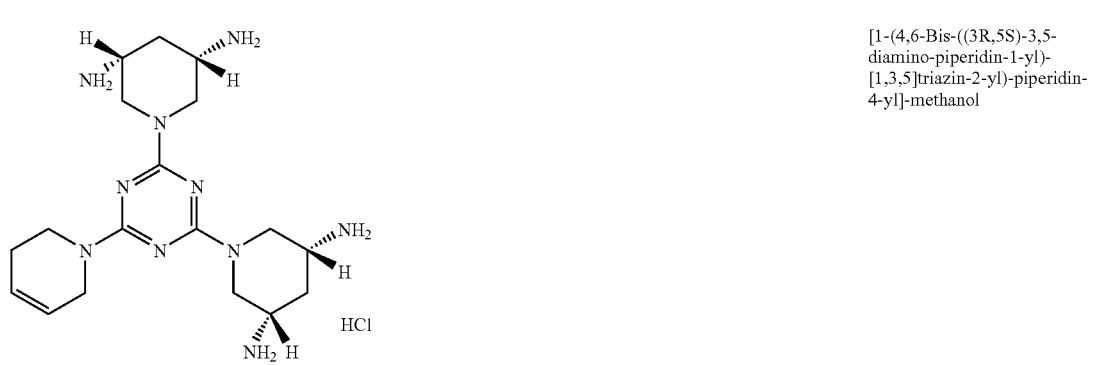 | [1-(4,6-Bis-((3R,5S)-3,5-diamino-piperidin-1-yl)-[1,3,5]triazin-2-yl)-piperidin-4-yl]-methanol | |
⑦ indicates text missing or illegible when filed -continued

| Structure | Name | Potency |
|---|---|---|
| 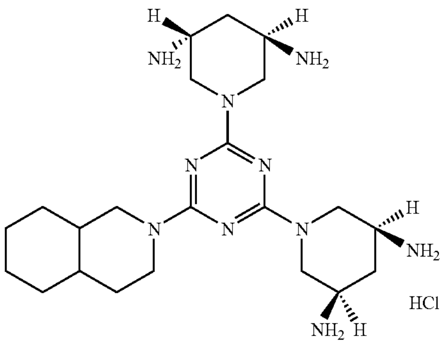 | 2,4-Biss-((3R,5S)-3,5-diamino-piperidin-1-yl)-6-(4-p-tolyl-piperazin-1-yl)-[1,3,5]triazine | − |
| 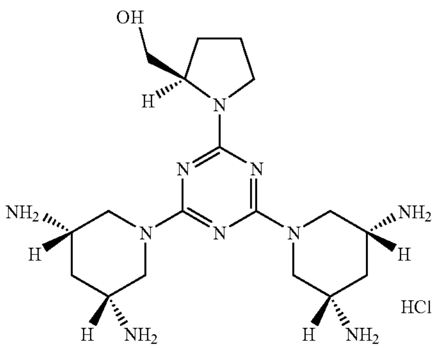 | 1-(4,6-Bis-((3R,5S)-3,5-diamino-piperidin-1-yl)-[1,3,5]triazin-2-yl)-piperidin-4-ylamine | |
| 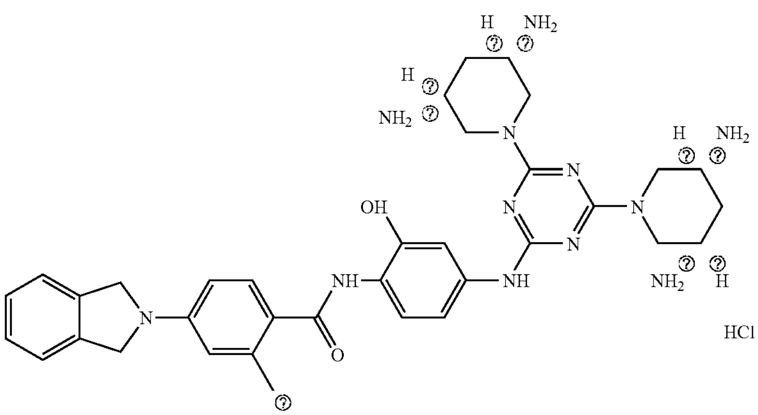 | N-{4-[4-(1,3-dihydro-isoindol-2-yl)-2-hydroxy-benzoylamino]-3-hydroxy-phenyl}-4,6-Bis-((3R,5S)-3,5-diamino-piperidin-1-yl)-[1,3,5]triazine-2-amine | + |
| 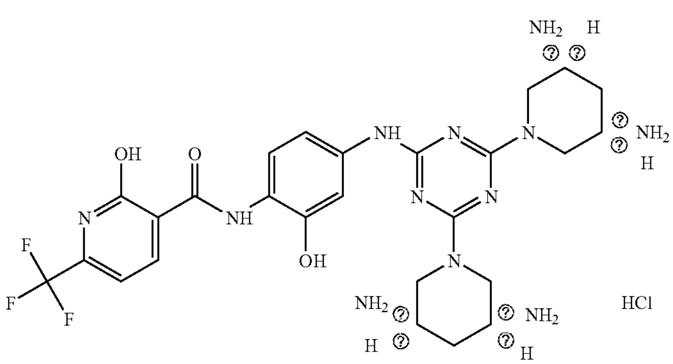 | N-{3-hydroxy-4-[(2-hydroxy-6-trifluoromethyl-pyridine-3-carbonyl)-amino]-phenyl}-4,6-Bis-((3R,5S)-3,5-diamino-piperidin-1-yl)-[1,3,5]triazine-2-amine | + |

② indicates text missing or illegible when filed

-continued

| Structure | Name | Potency |
|---|---|---|
| 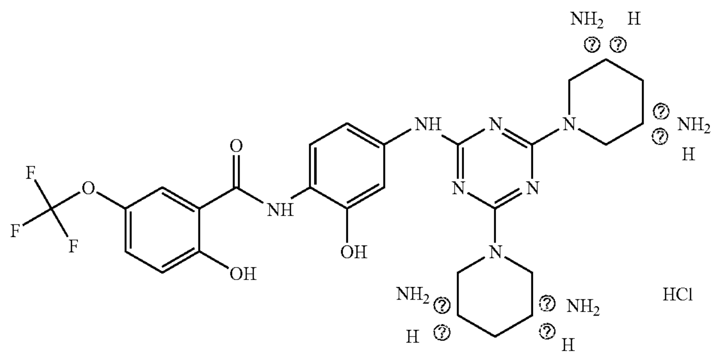 | N-[3-hydroxy-4-(2-hydroxy-5-trifluoromethoxy-benzoylamino)-phenyl]-4,6-Bis-((3R,5S)-3,5-diamino-piperidin-1-yl)-[1,3,5]triazine-2-amine | ++ |
| 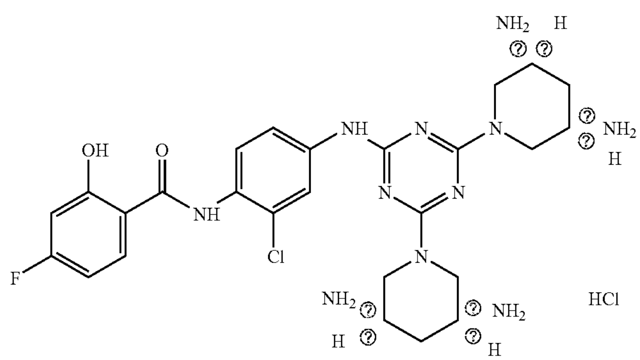 | N-[3-chloro-4-(4-fluoro-2-hydroxy-benzoylamino)-phenyl]-4,6-Bis-((3R,5S)-3,5-diamino-piperidin-1-yl)-[1,3,5]triazine-2-amine | – |
| 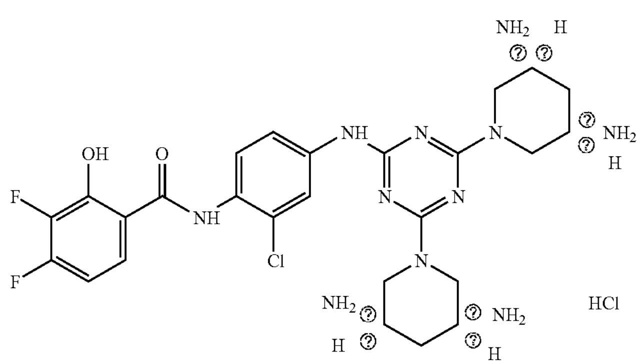 | N-[3-chloro-4-(3,4-difluoro-2-hydroxy-benzoylamino)-pheny]-4,6-Bis-((3R,5S)-3,5-diamino-piperidin-1-yl)-[1,3,5]triazine-2-ammine | ++ |

⊘ indicates text missing or illegible when filed

-continued
| Structure | Name | Potency |
|---|---|---|
| 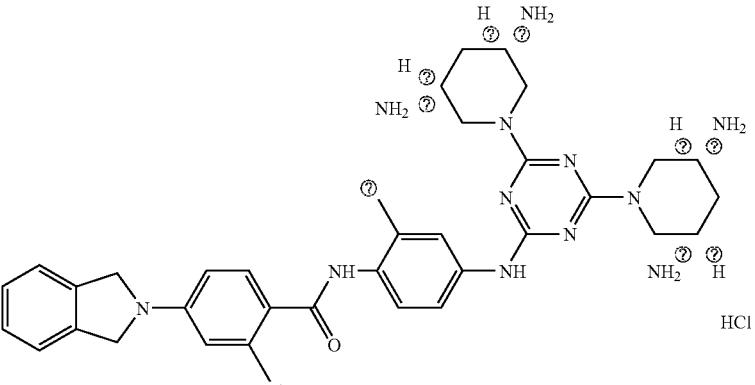 | N-{3-chloro-4-[4-(1,3-dihydro-isoindol-2-yl)-2-hydroxy-benzoylamino]-phenyl}-4,6-Bis-((3R,5S)-3,5-diamino-piperidin-1-yl)-[1,3,5]triazine-2-amine | ++ |
| 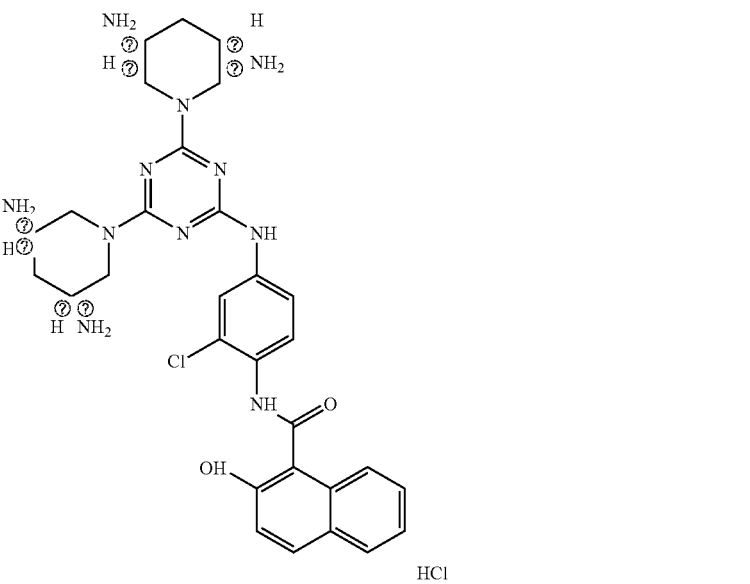 | N-{3-chloro-4-[(2-hydroxy-naphthalene-1-carbonyl)-amino]-phenyl}-4,6-Bis-((3R,5S)-3,5-diamino-piperidin-1-yl)-[1,3,5]triazine-2-amine | ++ |
| 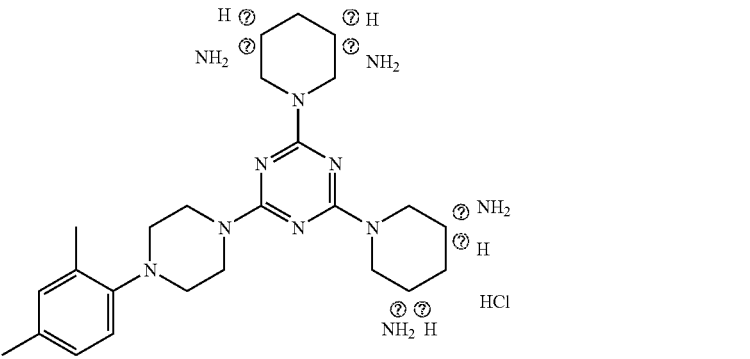 | 8-(4,6-Bis-((3R,5S)-3,5-diamino-piperidin-1-yl)-[1,3,5]triazin-2-yl)-1,4-dioxa-8-aza-spiro[4,5]decane | |
⓿ indicates text missing or illegible when filed -continued

| Structure | Name | Potency |
|---|---|---|
| 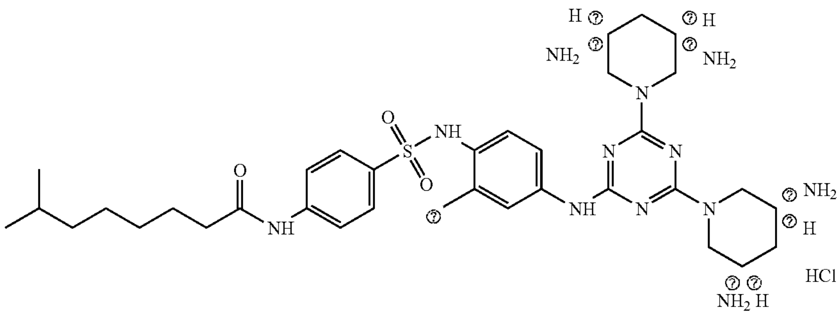 | N-{3-hydroxy-4-[4-(7-methyl-octanoylamino)-benzenesulfonylamino]-phenyl}-4,6-Bis-((3R,5S)-3,5-diamino-piperidin-1-yl)-[1,3,5]triazine-2-amine | ++ |
| 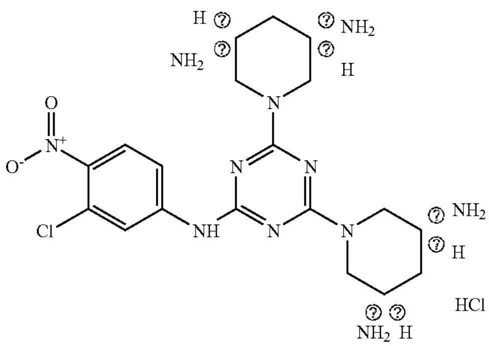 | N-(3-chloro-4-nitro-phenyl)-4,6-Bis-((3R,5S)-3,5-diamino-piperidin-1-yl)-[1,3,5]triazine-2-amine | ++ |
| 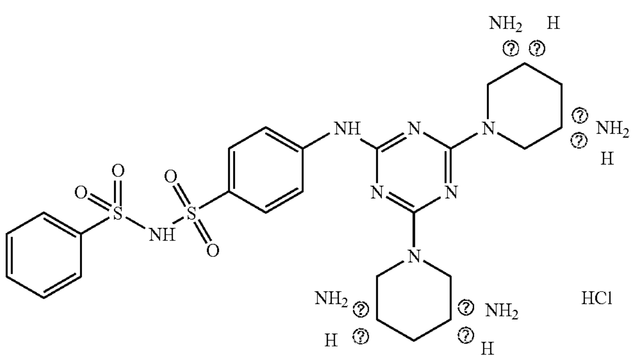 | N-(4-benzenesulfonyl-sulfamoyl-phenyl)-4,6-Bis-((3R,5S)-3,5-diamino-piperidin-1-yl)-[1,3,5]triazine-2-amine | |
| 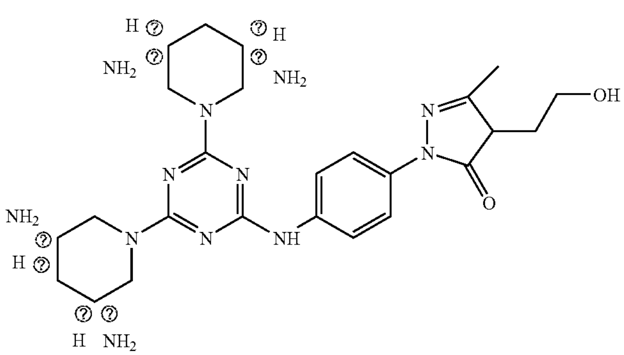 | N-{4-[4-(2-hydroxy-ethyl)-3-methyl-5-oxo-4,5-dihydro-pyrazol-1-yl]-phenyl}-4,6-Bis-((3R,5S)-3,5-diamino-piperidin-1-yl)-[1,3,5]triazine-2-amine | – |

⁇ indicates text missing or illegible when filed

-continued

| Structure | Name | Potency |
|---|---|---|
| (structure) | N-(6-nitro-benzothiazol-2-yl)-4,6-Bis-((3R,5S)-3,5-diamino-piperidin-1-yl)-[1,3,5]triazine-2-amine | ++ |

⑦ indicates text missing or illegible when filed

| | N-(4-benzoyl-phenyl)-4,6-Bis-((3R,5S)-3,5-diamino-piperidin-1-yl)-[1,3,5]triazine-2-amine | + |

⑦ indicates text missing or illegible when filed

| | N-{3-chlorro-4-[(2-hydroxy-6-trifluoromethyl-pyridine-3-carbonyl)-amino]-phenyl}-4,6-Bis-((3R,5S)-3,5-diamino-piperidin-1-yl)-[1,3,5]triazine-2-amine | ++ |

⑦ indicates text missing or illegible when filed

| | N-[4-(4-fluoro-2-hydroxy-benzoylamino)-phenyl]-4,6-Bis-((3R,5S)-3,5-diamino-piperidin-1-yl)-[1,3,5]triazine-2-amine | ++ |

⑦ indicates text missing or illegible when filed

-continued

| Structure | Name | Potency |
|---|---|---|
| 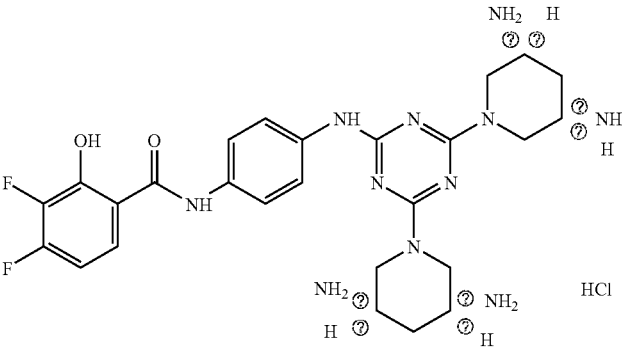 | N-[4-(3,4-difluoro-2-hydroxy-benzoylamino)-phenyl]-4,6-Bis-((3R,5S)-3,5-diamino-piperidin-1-yl)-[1,3,5]triazine-2-amine | + |
| ⓘ indicates text missing or illegible when filed | | |
| 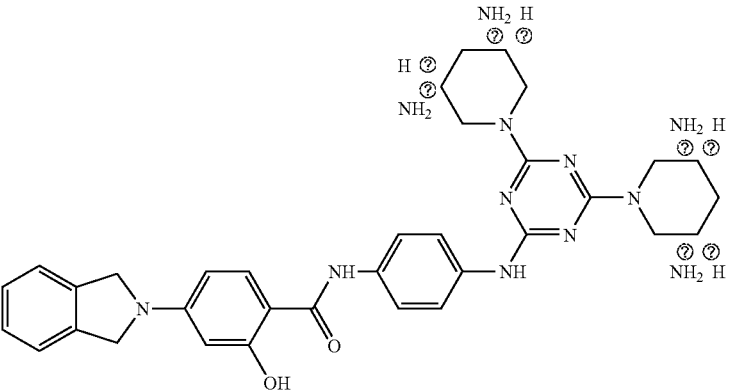 | N-{4-[4-(1,3-dihydro-isoindol-2-yl)-2-hydroxy-benzoylamino]-phenyl}-4,6-Bis-((3R,5S)-3,5-diamino-piperidin-1-yl)-[1,3,5]triazine-2-amine | ++ |
| ⓘ indicates text missing or illegible when filed | | |
| 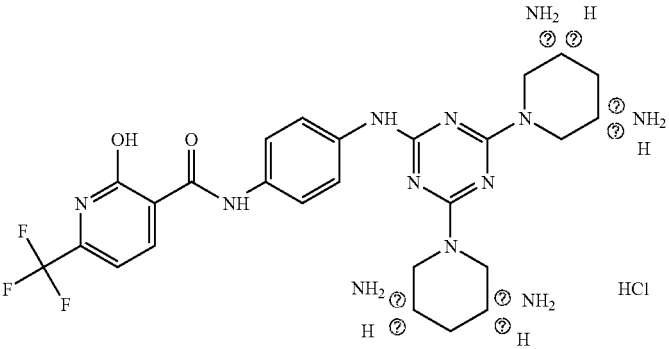 | N-{4-[(2-hydroxy-6-trifluoromethyl-pyridine-3-carbonyl)-amino]-phenyl}-4,6-Bis-((3R,5S)-3,5-diamino-piperidin-1-yl)-[1,3,5]triazine-2-amine | ++ |
| ⓘ indicates text missing or illegible when filed | | |

-continued

| Structure | Name | Potency |
|---|---|---|
| 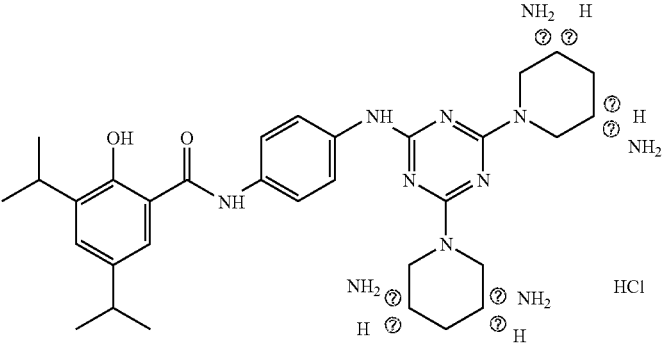 ⓘ indicates text missing or illegible when filed | N-[4-(2-hydroxy-3,5-diisopropyl-benzoylamino)-phenyl]-4,6-Bis-((3R,5S)-3,5-diamino-piperidin-1-yl)-[1,3,5]triazine-2-amine | ++ |
| 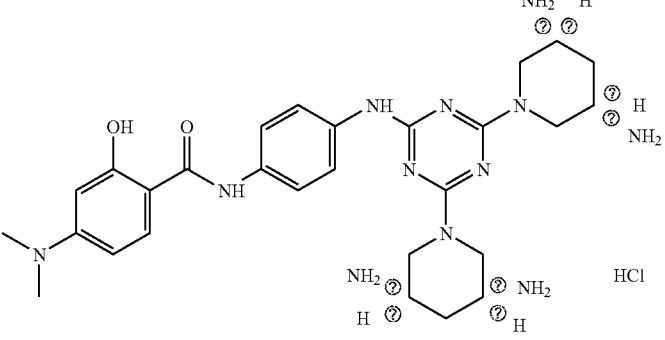 ⓘ indicates text missing or illegible when filed | N-[4-(4-dimethylamino-2-hydroxy-benzoylamino)-phenyl]-4,6-Bis-((3R,5S)-3,5-diamino-piperidin-1-yl)-[1,3,5]triazine-2-amine | ++ |
| 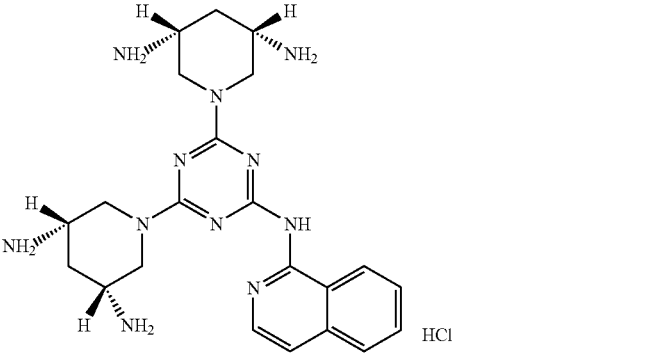 | N-isoquinolin-1-yl-4,6-Bis-((3R,5S)-3,5-diamino-piperidin-1-yl)-[1,3,5]triazine-2-amine | |
| 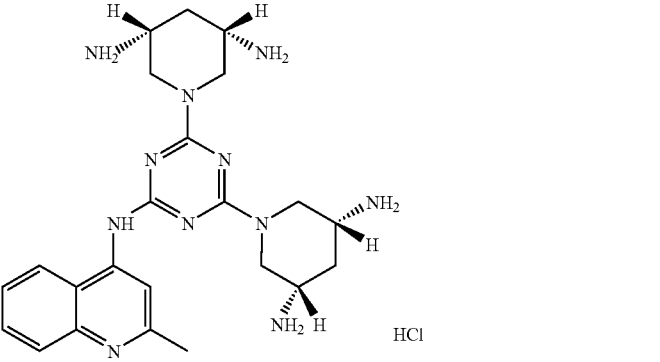 | N-(2-methyl-quinolin-4-yl)-4,6-Bis-((3R,5S)-3,5-diamino-piperidin-1-yl)-[1,3,5]triazine-2-amine | |

-continued

| Structure | Name | Potency |
|---|---|---|
| 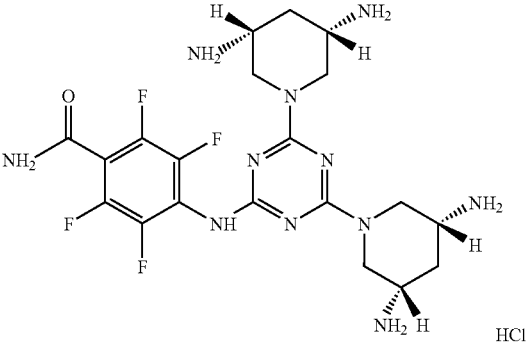 | N-(4-carbamoyl-2,3,5,6-tetrafluoro-phenyl)-4,6-Bis-((3R,5S)-3,5-diamino-piperidin-1-yl)-[1,3,5]triazine-2-amine | |
| 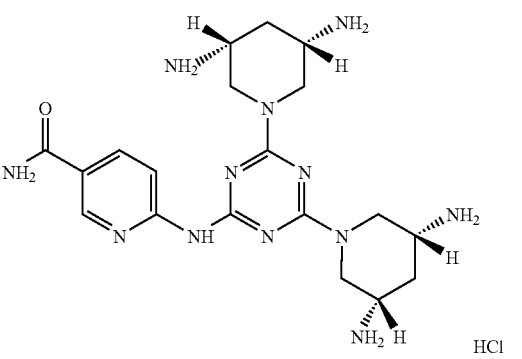 | N-(5-carbamoyl-pyridin-2-yl)-4,6-Bis-((3R,5S)-3,5-diamino-piperidin-1-yl)-[1,3,5]triazine-2-amine | – |
| 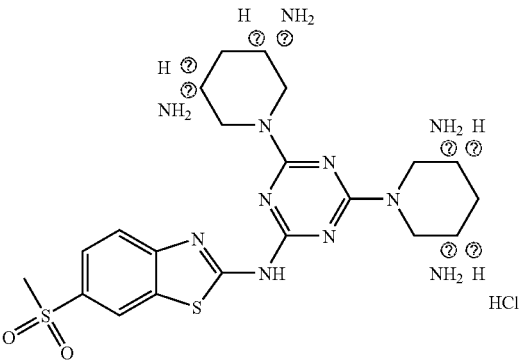 | N-(6-methanesulfonyl-benzothiazol-2-yl)-4,6-Bis-((3R,5S)-3,5-diamino-piperidin-1-yl)-[1,3,5]triazine-2-amine | |

⟨?⟩ indicates text missing or illegible when filed

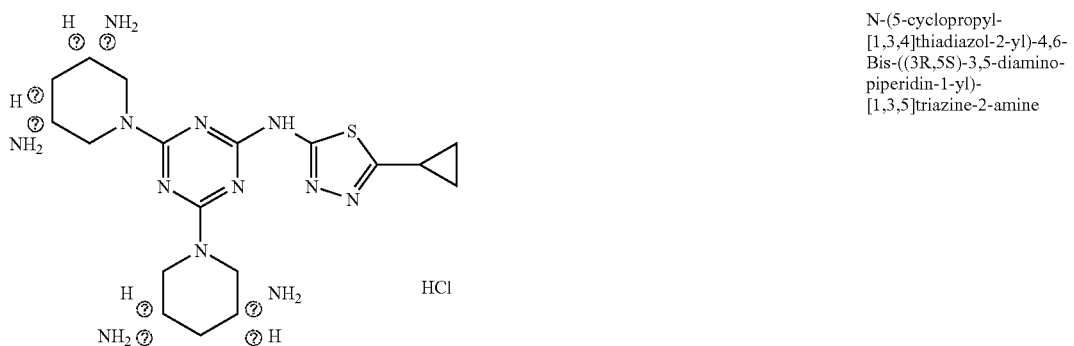

N-(5-cyclopropyl-[1,3,4]thiadiazol-2-yl)-4,6-Bis-((3R,5S)-3,5-diamino-piperidin-1-yl)-[1,3,5]triazine-2-amine ⟨?⟩ indicates text missing or illegible when filed -continued

| Structure | Name | Potency |
|---|---|---|
| 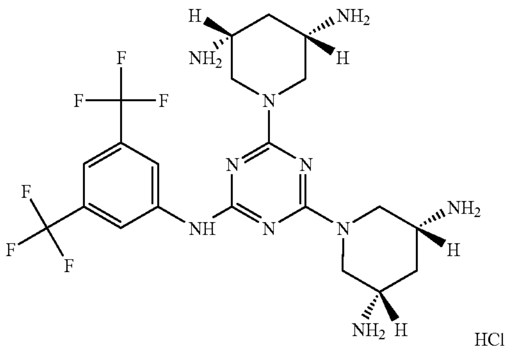 | N-(3,5-bis-trifluoromethyl-phenyl)-4,6-Bis-((3R,5S)-3,5-diamino-piperidin-1-yl)-[1,3,5]triazine-2-amine | |
| 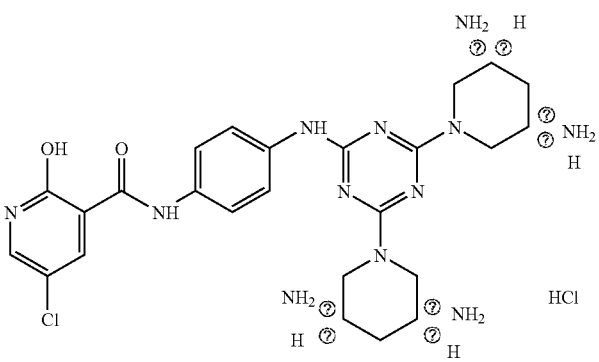 | N-{4-[(3-hydroxy-pyridine-2-carbonyl)-amino]-phenyl}-4,6-Bis-((3R,5S)-3,5-diamino-piperidin-1-yl)-[1,3,5]triazine-2-amine | + |
| 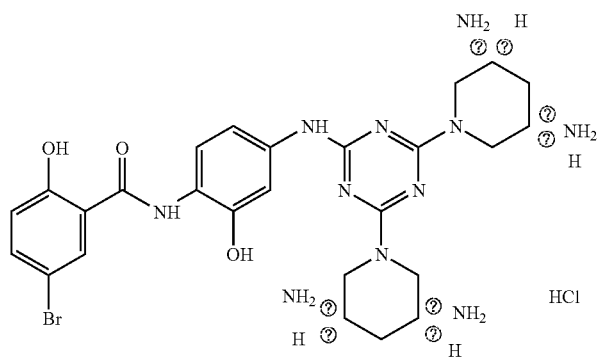 | N-{4-[(5-chloro-2-hydroxy-pyridine-3-carbonyl)-amino]-phenyl}-4,6-Bis-((3R,5S)-3,5-diamino-piperidin-1-yl)-[1,3,5]triazine-2-amine | + |
| 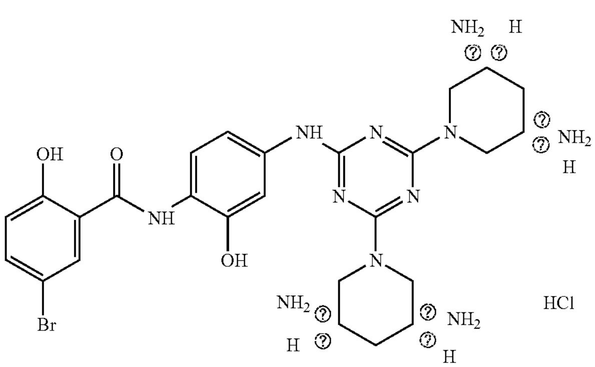 | N-[4-(5-bromo-2-hydroxy-benzoylamino)-3-hydroxy-phenyl]-4,6-Bis-((3R,5S)-3,5-diamino-piperidin-1-yl)-[1,3,5]triazine-2-amine | ++ |

⑦ indicates text missing or illegible when filed

| Structure | Name | Potency |
|---|---|---|
| (structure) | N-[3-hydroxy-4-(2-hydroxy-3,5-diisopropyl-benzoylamino)-phenyl]-4,6-Bis-((3R,5S)-3,5-diamino-piperidin-1-yl)-[1,3,5]triazine-2-amine | ++ |
| (structure) | N-[3-hydroxy-4-(2-hydroxy-3,4-dimethoxy-benzoylamino)-phenyl]-4,6-Bis-((3R,5S)-3,5-diamino-piperidin-1-yl)-[1,3,5]triazine-2-amine | + |
| (structure) | N-{3-hydroxy-4-[(2-hydroxy-6-methyl-pyridine-3-carbonyl)-amino]-phenyl}-4,6-Bis-((3R,5S)-3,5-diamino-piperidin-1-yl)-[1,3,5]triazine-2-amine | + |
| (structure) | N-[4-(4-dimethylamino-2-hydroxy-benzoylamino)-3-hydroxy-phenyl]-4,6-Bis-((3R,5S)-3,5-diamino-piperidin-1-yl)-[1,3,5]triazine-2-amine | ++ |

-continued

| Structure | Name | Potency |
|---|---|---|
| 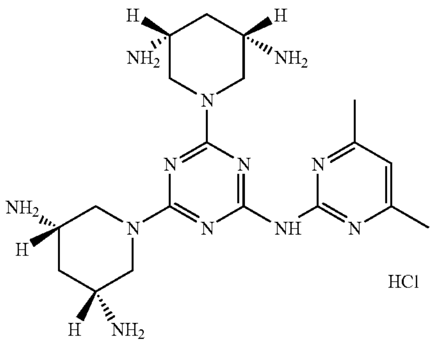 | N-(4,6-dimethyl-pyrimidin-2-yl)-4,6-Bis-((3R,5S)-3,5-diamino-piperidin-1-yl)-[1,3,5]triazine-2-amine | |
| 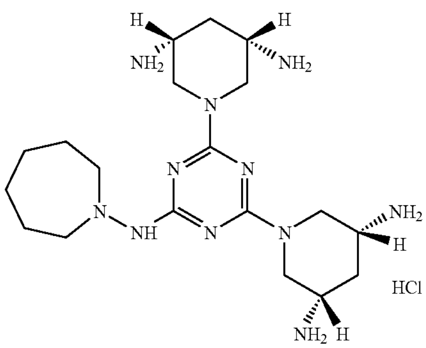 | N-(azepan-1-yl)-4,6-Bis-((3R,5S)-3,5-diamino-piperidin-1-yl)-[1,3,5]triazine-2-amine | |
| 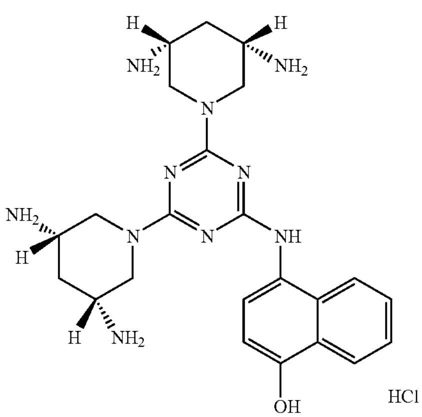 | N-(4-hydroxy-naphthalen-1-yl)-4,6-Bis-((3R,5S)-3,5-diamino-piperidin-1-yl)-[1,3,5]triazine-2-amine | ++ |
| 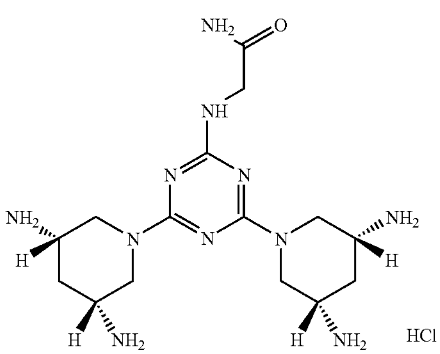 | N-carbamoylmethyl-4,6-Bis-((3R,5S)-3,5-diamino-piperidin-1-yl)-[1,3,5]triazine-2-amine | – |

| Structure | Name | Potency |
|---|---|---|
| 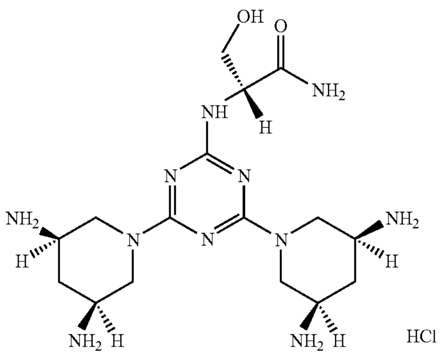 | (S)-2-[4-((3R,5S)-3,5-Diamino-piperidin-1-yl)-6-((3S,5R)-3,5-diamino-piperidin-1-yl)-[1,3,5]triazin-2-ylamino]-3-hydroxy-propionamide | − |
| 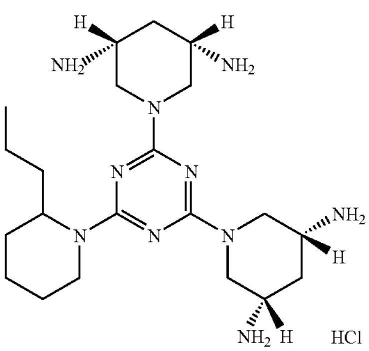 | 2,4-Bis-((3R,5S)-3,5-diamino-piperidin-1-yl)-6-(4-pyrimidin-2-yl-piperazin-1-yl)-[1,3,5]triazine | |
| 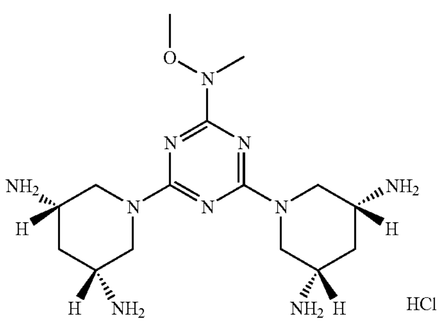 | N-[4,6-Bis-((3R,5S)-3,5-diamino-piperidin-1-yl)-[1,3,5]triazin-2-yl]-O,N-dimethyl-hydroxylamine | |
| 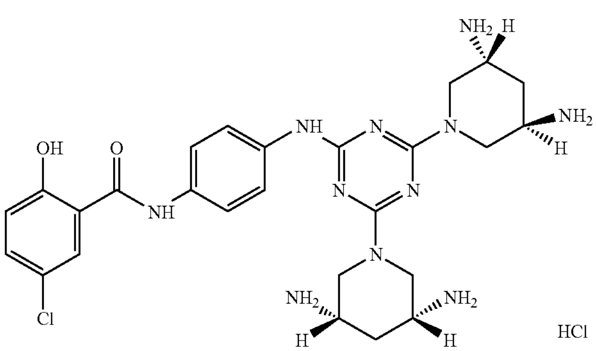 | N-[4-(5-chloro-2-hydroxy-benzoylamino)-phenyl]-4,6-Bis-((3R,5S)-3,5-diamino-piperidin-1-yl)-[1,3,5]triazine-2-amine | ++ |

| Structure | Name | Potency |
|---|---|---|
| (structure) | N-[4-(5-bromo-2-hydroxy-benzoylamino)-phenyl]-4,6-Bis-((3R,5S)-3,5-diamino-piperidin-1-yl)-[1,3,5]triazine-2-amine · HCl | ++ |
| (structure) | N-[3-hydroxy-4-(2-hydroxy-4-methoxy-benzoylamino)-phenyl]-4,6-Bis-((3R,5S)-3,5-diamino-piperidin-1-yl)-[1,3,5]triazine-2-amine · HCl | ++ |
| (structure) | N-[3-hydroxy-4-(2-hydroxy-5-methoxy-benzoylamino)-phenyl]-4,6-Bis-((3R,5S)-3,5-diamino-piperidin-1-yl)-[1,3,5]triazine-2-amine · HCl | ++ |
| (structure) | N-[3-hydroxy-4-(2-hydroxy-4-methyl-benzoylamino)-phenyl]-4,6-Bis-((3R,5S)-3,5-diamino-piperidin-1-yl)-[1,3,5]triazine-2-amine · HCl H₂C | ++ |

⑦ indicates text missing or illegible when filed

-continued

| Structure | Name | Potency |
|---|---|---|
| 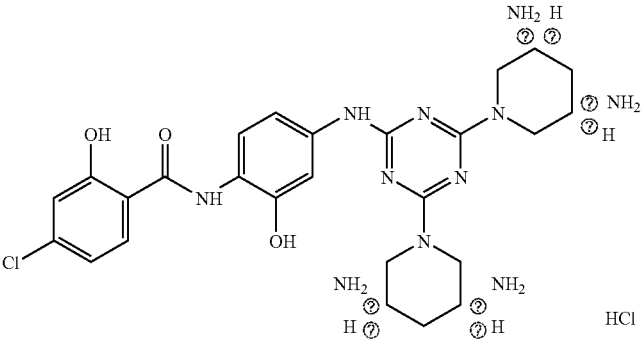 ⑦ indicates text missing or illegible when filed | N-[4-(4-chloro-2-hydroxy-benzoylamino)-3-hydroxy-phenyl]-4,6-Bis-((3R,5S)-3,5-diamino-piperidin-1-yl)-[1,3,5]triazine-2-amine | ++ |
| 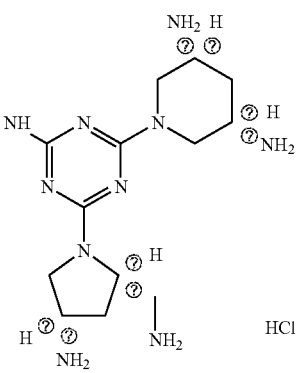 ⑦ indicates text missing or illegible when filed | N-{4-[4-((2S,4S)-4-Amino-2-aminomethyl-pyrrolidin-1-yl)-6-((3R,5S)-3,5-diamino-piperidin-1-yl)-[1,3,5]triazin-2-ylamino]-2-hydroxy-phenyl}-4-chloro-2-hydroxy-benzamide | ++ |
| 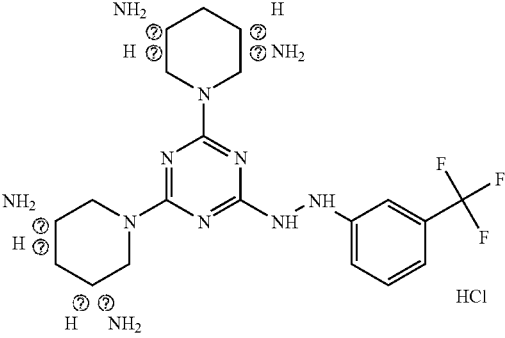 ⑦ indicates text missing or illegible when filed | N-(4,6-Bis-((3R,5S)-3,5-diamino-piperidin-1-yl)-[1,3,5]triazin-2-yl)-N'-(3-Trifluoromethyl-phenyl)-hydrazine | + |
| 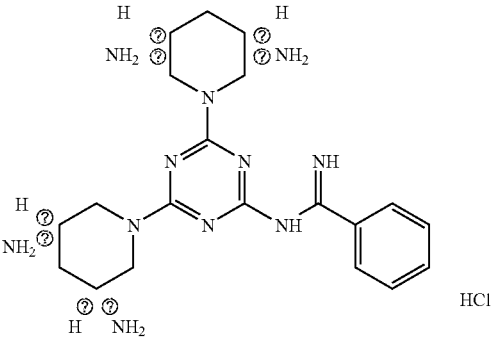 ⑦ indicates text missing or illegible when filed | N-[4,6-Bis-((3R,5S)-3,5-diamino-piperidin-1-yl)-[1,3,5]triazin-2-yl]-benzamide | |

-continued
| Structure | Name | Potency |
|---|---|---|
| 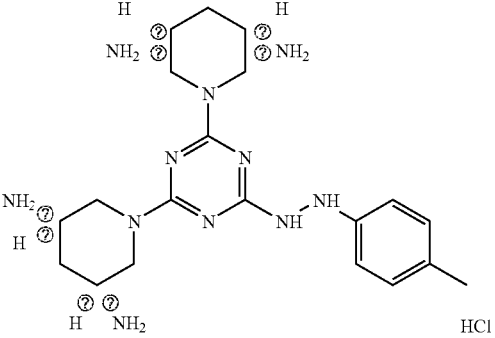 | N-(4,6-Bis-((3R,5S)-3,5-diamino-piperidin-1-yl)-[1,3,5]triazin-2-yl)-N'-p-Tolyl-hydrazine | + |
| 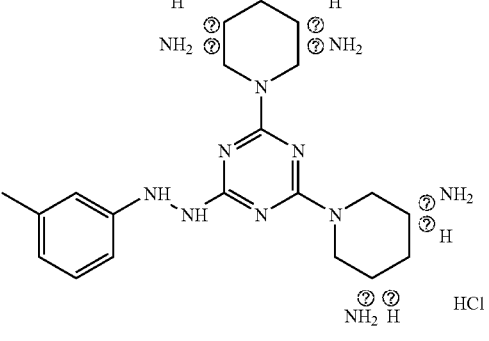 | N-(4,6-Bis-((3R,5S)-3,5-diamino-piperidin-1-yl)-[1,3,5]triazin-2-yl)-N'-m-Tolyl-hydrazine | + |
| 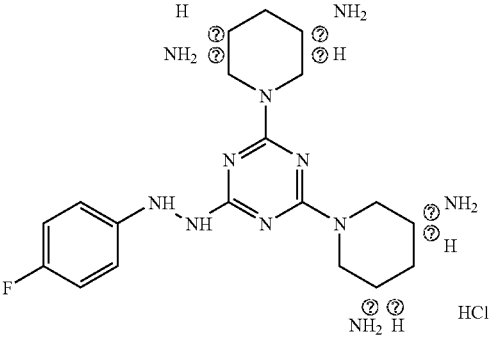 | N-(4,6-Bis-((3R,5S)-3,5-diamino-piperidin-1-yl)-[1,3,5]triazin-2-yl)-N'-(4-Fluoro-phenyl)-hydrazine | + |
| 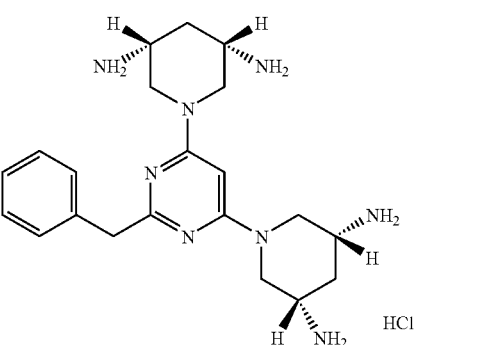 | 2-Benzyl-4,6-Bis-((3R,5S)-3,5-diamino-piperidin-1-yl)-pyrimidine | |

-continued

| Structure | Name | Potency |
|---|---|---|
| 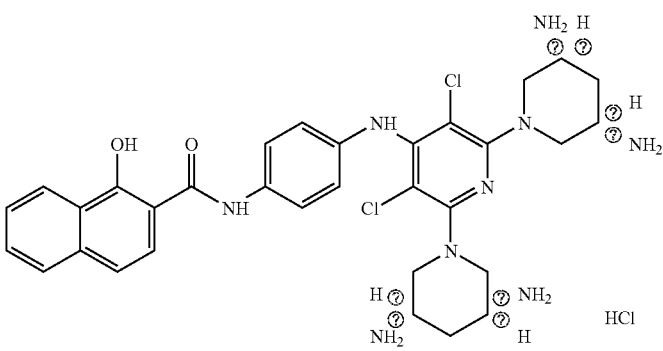 | (3,4-Dichloro-phenyl)-(2,6-Bis-((3R,5S)-3,5-diamino-piperidin-1-yl)-pyrimidin-4-yl)-amine | |
| 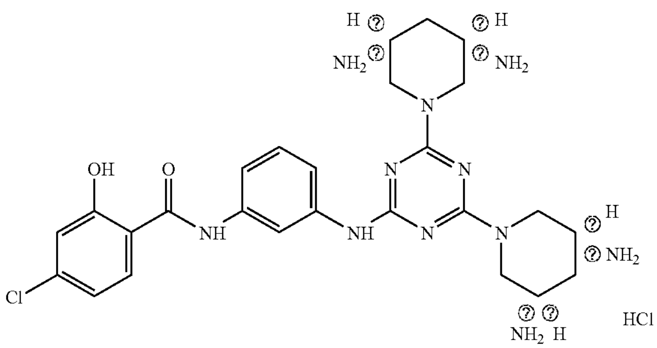 | N-[3-(4-chloro-2-hydroxy-benzoylamino)-phenyl]-4,6-Bis-((3R,5S)-3,5-diamino-piperidin-1-yl)-[1,3,5]triazine-2-amine | ++ |

⑦ indicates text missing or illegible when filed

| | 1-Hydroxy-naphthalene-2-carboxylic acid [4-(3,5-dichloro-2,6-Bis-((3R,5S)-3,5-diamino-piperidin-1-yl)-pyridin-4-ylamino)-phenyl]-amide | ++ |
|---|---|---|

⑦ indicates text missing or illegible when filed

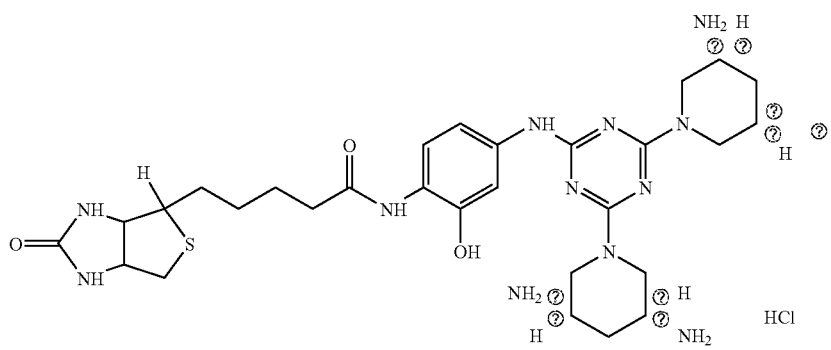

| | 5-((S)-2-Oxo-hexahydro-thieno[3,4-d]imidazol-2-yl)-penanoicacid {4-[4-((3S,5S)-3-amino-5-azido-piperidin-1-yl)-6-((3S,5R)-3,5-diamino-piperidin-1-yl)-[1,3,5]triazin-2-ylamino]-2-hydroxy-phenyl}-amide | – |
|---|---|---|

⑦ indicates text missing or illegible when filed

-continued

| Structure | Name | Potency |
|---|---|---|
| 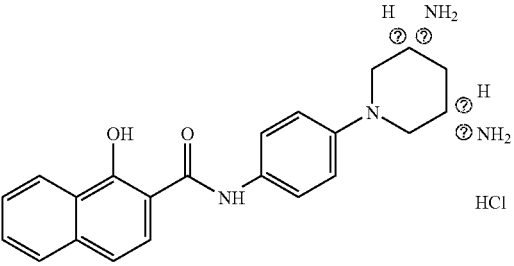 ⊙ indicates text missing or illegible when filed | 1-Hydroxy-naphthalene-2-carboxylicacid [4-((3S,5R)-3,5-diamino-piperidin-1-yl)-phenyl]-amide | – |
| 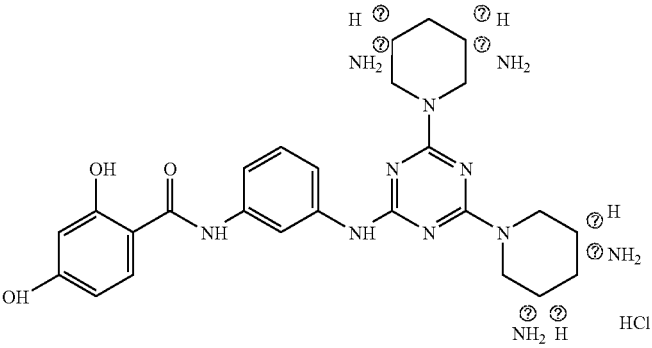 ⊙ indicates text missing or illegible when filed | N-[3-(2,4-dihydroxy-benzoylamino)-phenyl]-4,6-Bis-((3R,5S)-3,5-diamino-piperidin-1-yl)-[1,3,5]triazine-2-amine | ++ |
| 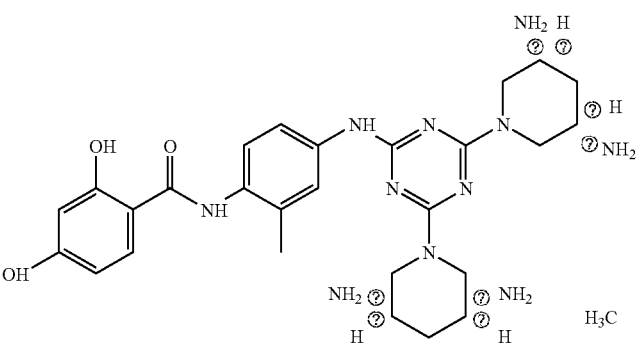 ⊙ indicates text missing or illegible when filed | N-[4-(2,4-dihydroxy-benzoylamino)-3-methyl-phenyl]-4,6-Bis-((3R,5S)-3,5-diamino-piperidin-1-yl)-[1,3,5]triazine-2-amine | ++ |
| 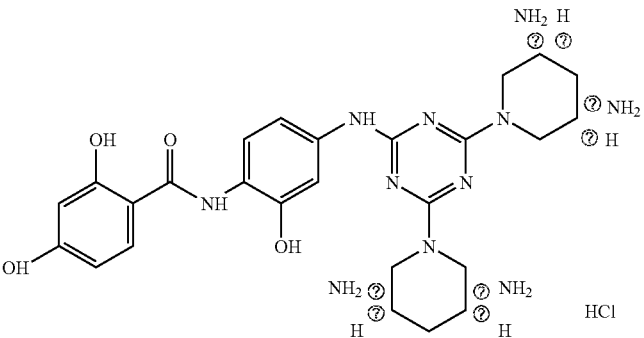 ⊙ indicates text missing or illegible when filed | N-[4-(2,4-dihydroxy-benzoylamino)-3-hydroxy-phenyl]-4,6-Bis-((3R,5S)-3,5-diamino-piperidin-1-yl)-[1,3,5]triazine-2-amine | ++ |

-continued

| Structure | Name | Potency |
|---|---|---|
| 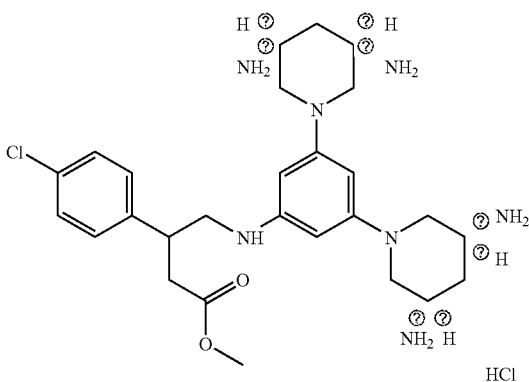 | 4,6-Bis-((3R,5S)-3,5-diamino-piperidin-1-yl)-pyrimidine | |
| 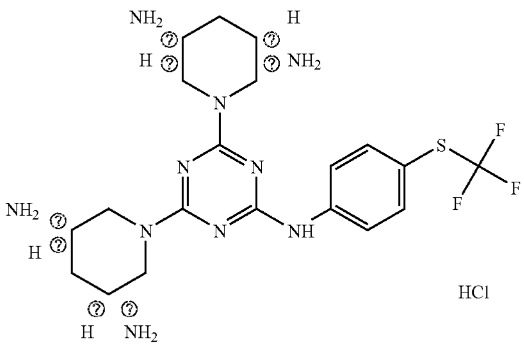 | N-(4-trifluoromethylsulfanyl-phenyl)-4,6-Bis-((3R,5S)-3,5-diamino-piperidin-1-yl)-[1,3,5]triazine-2-amine | |
| 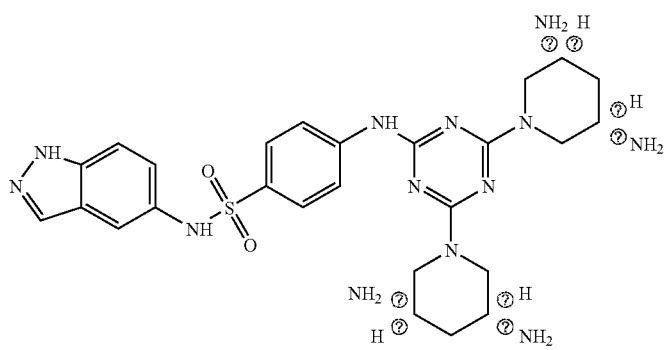 | 4-[4,6-Bis-((3R,5S)-33,5-diamino-piperidin-1-yl)-[1,3,5]triazin-2-ylamino]-3-(4-chloro-phenyl)-butyric acid methyl ester | |
| 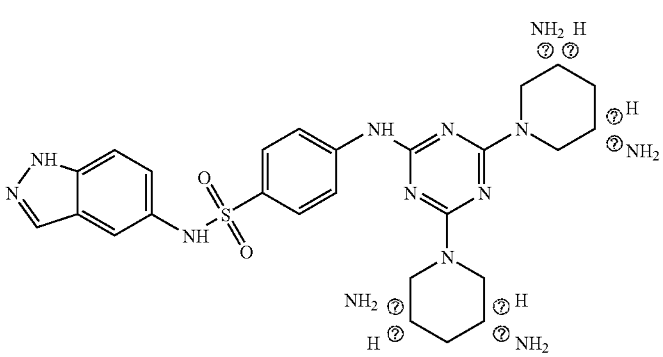 | N-[4-(1H-indazol-5-ylsulfamoyl)-phenyl]-4,6-Bis-((3R,5S)-3,5-diamino-piperidin-1-yl)-[1,3,5]triazine-2-amine | |

⑦ indicates text missing or illegible when filed

-continued

| Structure | Name | Potency |
|---|---|---|
| 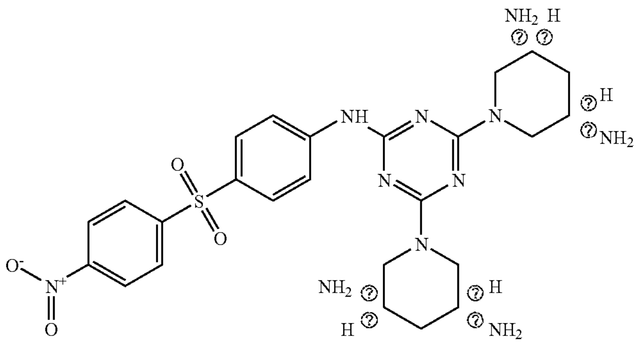 | N-[4-(4-nitro-benzenesulfonyl)-phenyl]-4,6-Bis-((3R,5S)-3,5-diamino-piperidin-1-yl)-[1,3,5]triazine-2-amine | |
| 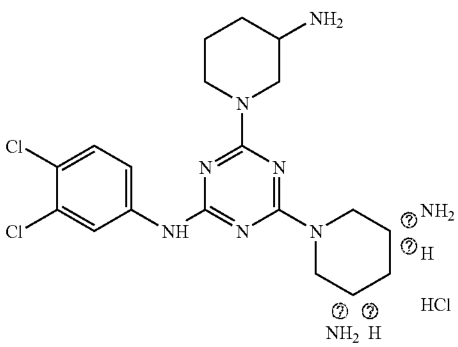 | (3R,5S)-1-[4-(3-Amino-piperidin-1-yl)-6-(3,4-dichloro-phenylammino)-[1,3,5]triazin-22-yl]-piperidine-3,5-diamine | + |
| 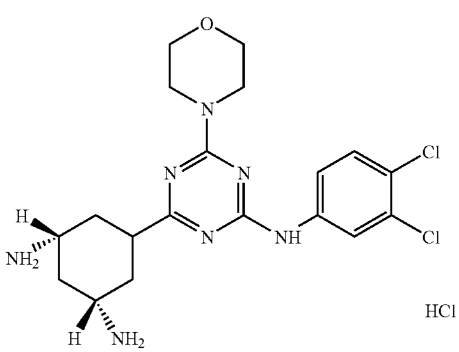 | (3S,5R)-1-[4-(3,4-Dichloro-phenylamino)-6-morpholin-4-yl-[1,3,5]triazin-2-yl]-piperidine-3,5-diamine | |
| 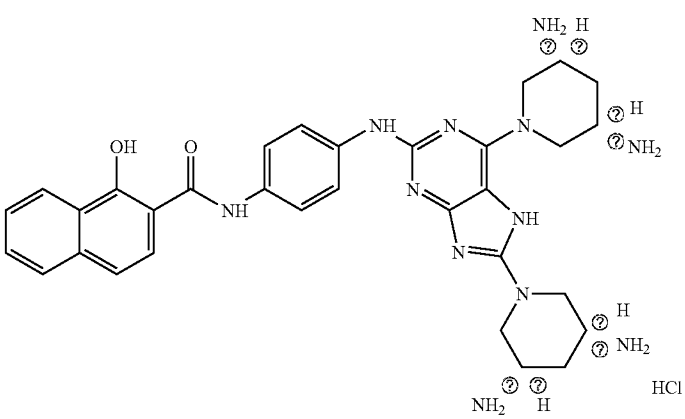 | 1-Hydroxy-naphthalene-2-carboxylicacid {4-[6-((3R,5S)-3,5-diamino-piperidin-1-yl)-8-((3S,5R)-3,5-diamino-piperidin-1-yl)-7H-purin-2-ylamino]-phenyl}-amide | ++ |

| Structure | Name | Potency |
|---|---|---|
| 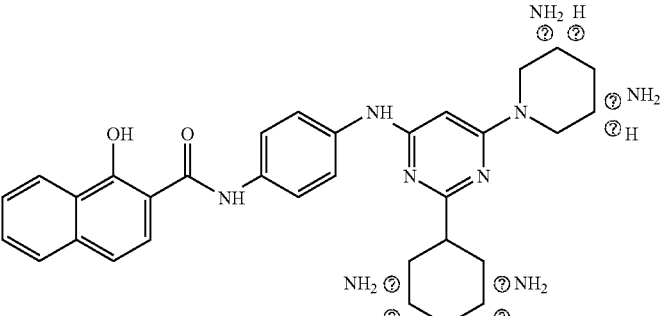 | 1-Hydroxy-naphthalene-2-carboxylicacid {4-[2-((3R,5S)-3,5-diamino-piperidin-1-yl)-6-((3S,5R)-3,5-diamino-piperidin-1-yl)-pyrimidin-4-ylamino]-phenyl}-amide | ++ |
| 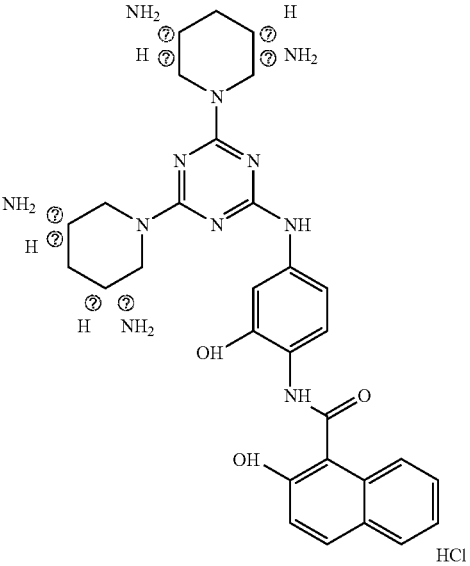 | N-{3-hydroxy-4-[(2-hydroxy-naphthalene-1-carbonyl)-amino]-phenyl}-4,6-Bis-((3R,5S)-3,5-diamino-piperidin-1-yl)-[1,3,5]triazine-2-amine | ++ |
⊘ indicates text missing or illegible when filed -continued

| Structure | Name | Potency |
|---|---|---|
| 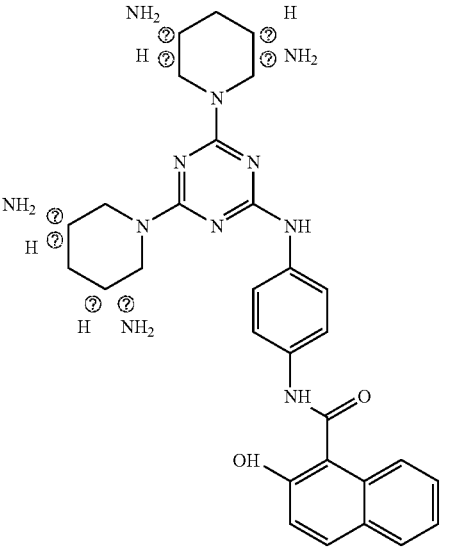 | N-{4-[(2-hydroxy-naphthalene-1-carbonyl)-amino]-phenyl}-4,6-Bis-((3R,5S)-3,5-diamino-piperidin-1-yl)-[1,3,5]triazine-2-amine | ++ |
| ⓘ indicates text missing or illegible when filed | | |
| 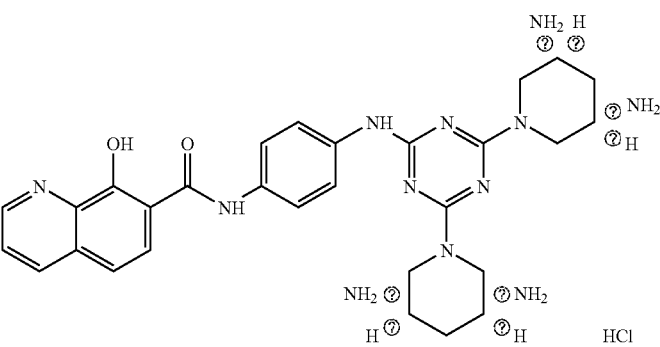 | N-{4-[(8-hydroxy-quinoline-7-carbonyl)-amino]-phenyl}-4,6-Bis-((3R,5S)-3,5-diamino-piperidin-1-yl)-[1,3,5]triazine-2-amine | ++ |
| ⓘ indicates text missing or illegible when filed | | |
| 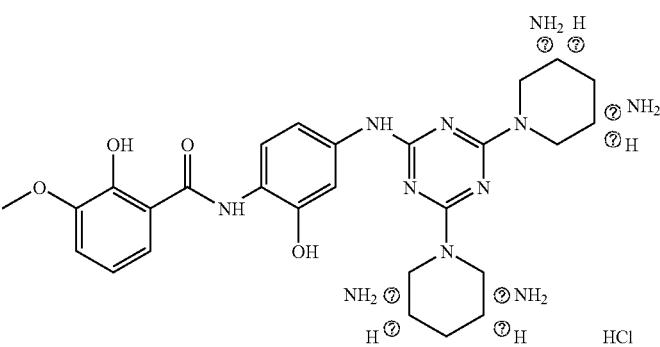 | N-[3-hydroxy-4-(2-hydroxy-3-methoxy-benzoylamino)-phenyl]-4,6-Bis-((3R,5S)-3,5-diamino-piperidin-1-yl)-[1,3,5]triazine-2-amine | ++ |
| ⓘ indicates text missing or illegible when filed | | |

| Structure | Name | Potency |
|---|---|---|
| | N-[3-chloro-4-(2-hydroxy-3-methoxy-benzoylamino)-phenyl]-4,6-Bis-((3R,5S)-3,5-diamino-piperidin-1-yl)-[1,3,5]triazine-2-amine | ++ |
| 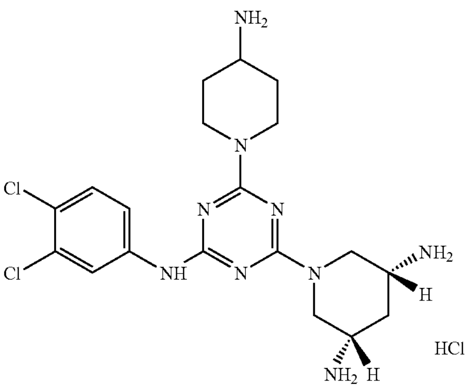 | (3R,5S)-1-[4-(4-Amino-piperidin-1-yl)-6-(3,4-dichloro-phenylamino)-[1,3,5]triazin-2-yl]-piperidine-3,5-diamine | + |
| 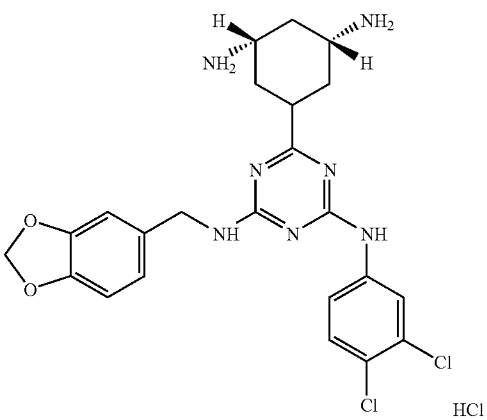 | N-Benzo[1,3]dioxol-5-ylmethyl-6-((3R,5R)-3,5-diamino-piperidin-1-yl)-N'-(3,4-dichloro-phenyl)-[1,3,5]triazine-2,4-diamine | |
| 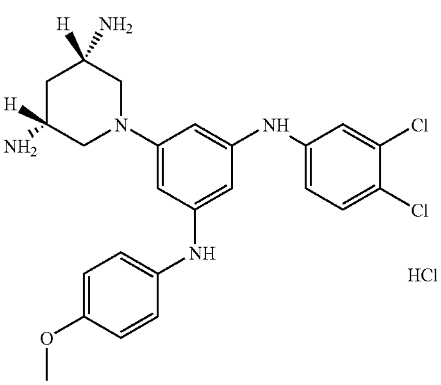 | 6-((3R,5S)-3,5-Diamino-piperidin-1-yl)-N-(3,4-dichloro-phenyl)-N'-(4-methoxy-phenyl)-[1,3,5]triazine-2,4-diamine | |

-continued

| Structure | Name | Potency |
|---|---|---|
| | N-{4-[2-(2-morpholin-4-yl-phenylcarbamoyl)-acetyl]-phenytl}-4,6-Bis-((3R,5S)-3,5-diamino-piperidin-1-yl)-[1,3,5]triazine-2-amnine | ++ |
| 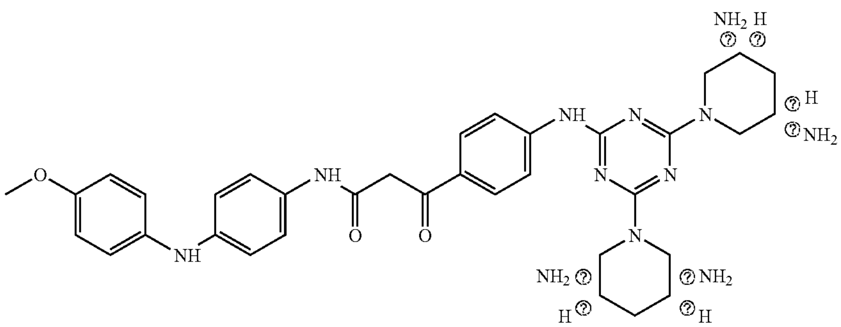 | N-(4-{2-[4-(4-methoxy-phenylamino)-phenylcarbamoyl]-acetyl}-phenyl)-4,6-Bis-((3R,5S)-3,5-diamino-piperidin-1-yl)-[1,3,5]triazine-2-amine | ++ |
| 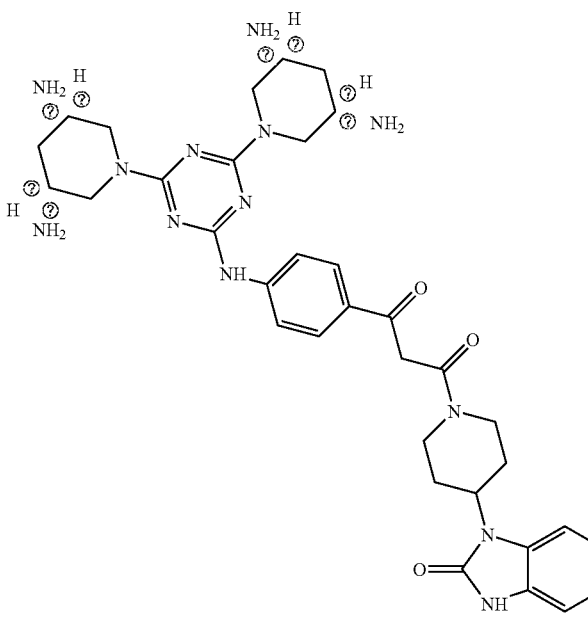 | N-(4-{3-oxo-3-[4-(2-oxo-2,3-dihydro-benzoimidazol-1-yl)-piperidin-1-yl]-propionly}-phenyl)-4,6-Bis-((3R,5S)-3,5-diamino-piperidin-1-yl)-[1,3,5]triazine-2-amine | – |

⟨?⟩ indicates text missing or illegible when filed

| Structure | Name | Potency |
|---|---|---|
| (structure) | N-{4-[2-(4-methoxy-phenylcarbamoyl)-acetyl]-phenyl}-4,6-Bis-((3R,5S)-3,5-diamino-piperidin-1-yl)-[1,3,5]triazine-2-amine | ++ |
| (structure) HCl | N-[4-(2-hydroxy-3-methoxy-benzoylamino)-phenyl]-4,6-Bis-((3R,5S)-3,5-diamino-piperidin-1-yl)-[1,3,5]triazine-2-amine | + |
| (structure) HCl | N-[4-(2-hydroxy-5-trifluoromethoxy-benzoylamino)-phenyl]-4,6-Bis-((3R,5S)-3,5-diamino-piperidin-1-yl)-[1,3,5]triazine-2-amine | ++ |
| (structure) HCl | N-[4-(2,4-dihydroxy-3,6-dimethyl-benzoylamino)-phenyl]-4,6-Bis-((3R,5S)-3,5-diamino-piperidin-1-yl)-[1,3,5]triazine-2-amine | ++ |

| Structure | Name | Potency |
|---|---|---|
| 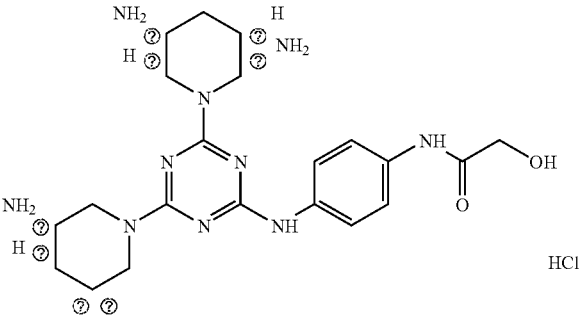 HCl | N-[4-(2-hydroxy-acetylamino)-phenyl]-4,6-Bis-((3R,5S)-3,5-diamino-piperidin-1-yl)-[1,3,5]triazine-2-amine | – |
| 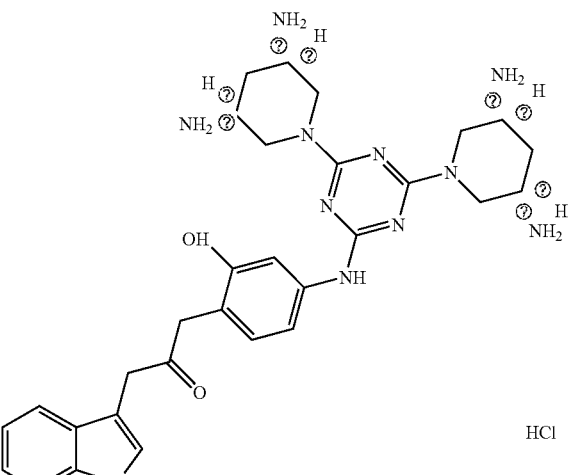 HCl | N-[3-hydroxy-4-(2-1H-indol-3-yl-acetylamino)-phenyl]-4,6-Bis-((3R,5S)-3,5-diamino-piperidin-1-yl)-[1,3,5]triazine-2-amine | ++ |
| 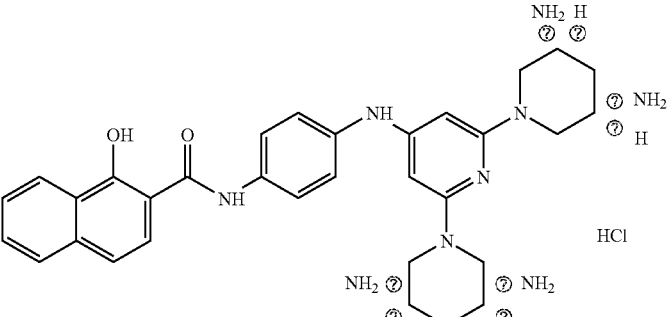 HCl | 1-Hydroxy-naphthalene-2-carboxylic acid [4-(2,6-Bis-((3R,5S)-3,5-diamino-piperidin-1-yl)-pyridin-4-ylamino)-phenyl]-amide | ++ |

-continued

| Structure | Name | Potency |
|---|---|---|
| (structure) | 1-Hydroxy-naphthalene-2-carboxylic acid [4-(4,6-Bis-((3R,5S)-3,5-diamino-piperidin-1-yl)-pyridin-2-ylamino)-phenyl]-amide · HCl | ++ |
| (structure) | N-{4-[2-(6-methyl-pyridin-2-ylcarbamoyl)-acetyl]-phenyl}-4,6-Bis-((3R,5S)-3,5-diamino-piperidin-1-yl)-[1,3,5]triazine-2-amine · HCl | + |
| (structure) | N-{4-[2-(3-bromo-phenylcarbamoyl)-acetyl]-phenyl}-4,6-Biss-((3R,5S)-3,5-diamino-piperidin-1-yl)-[1,3,5]triazine-2-amine · HCl | ++ |
| (structure) | N-{4-[2-(biphenyl-44-ylcarbamoyl)-acetyl]-phenyl}-44,6-Bis-((3R,5S)-3,5-diamino-piperidin-1-yl)-[1,3,5]triazine-2-amine · HCl | ++ |

-continued

| Structure | Name | Potency |
|---|---|---|
| 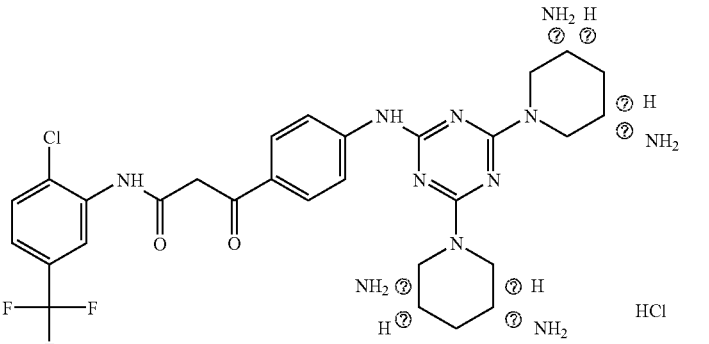 | N-{4-[2-(2-chloro-5-trifluoromethyl-phenylcarbamoyl)-acetyl]-phenyl}-4,6-Bis-((3R,5S)-3,5-diamino-piperidin-1-yl)-[1,3,5]triazine-2-amine | ++ |
| ⑦ indicates text missing or illegible when filed | | |
| 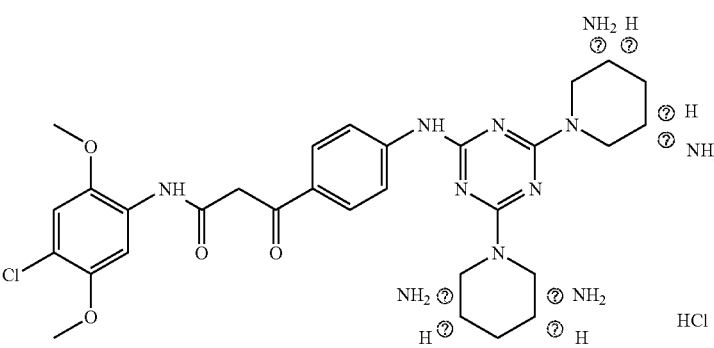 | N-{4-[2-(4-chloro-2,5-dimethoxy-phenylcarbamoyl)-acetyl]-phenyl}-4,6-Bis-((3R,5S)-3,5-diamino-piperidin-1-yl)-[1,3,5]triazine-2-amine | ++ |
| ⑦ indicates text missing or illegible when filed | | |
| 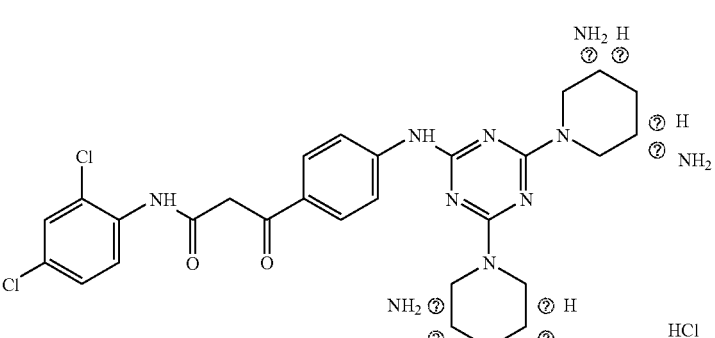 | N-{4-[2-(2,4-dichloro-phenylcarbamoyl)-acetyl]-phenyl}-4,6-Bis-((3R,5S)-3,5-diamino-piperidin-1-yl)-[1,3,5]triazine-2-amine | + |
| ⑦ indicates text missing or illegible when filed | | |
| 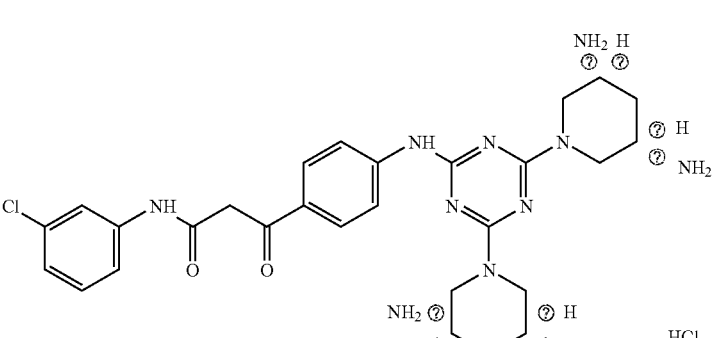 | N-{4-[2-(3-chloro-phenylcarbamoyl)-acetyl]-phenyl}-4,6-Bis-((3R,5S)-3,5-diamino-piperidin-1-yl)-[1,3,5]triazine-2-amine | |
| ⑦ indicates text missing or illegible when filed | | |

-continued

| Structure | Name | Potency |
|---|---|---|
| 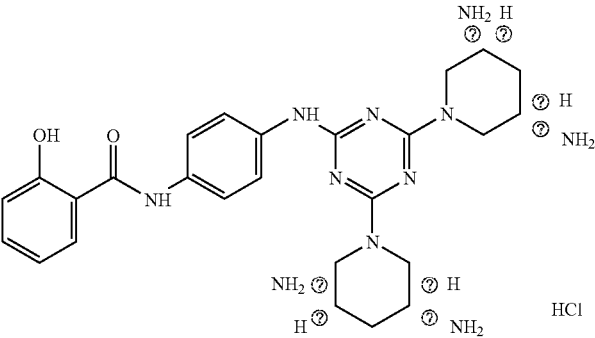 HCl | N-[4-(2-hydroxy-benzoylamino)-phenyl]-4,6-Bis-((3R,5S)-3,5-diamino-piperidin-1-yl)-[1,3,5]triazine-2-amine | |
| 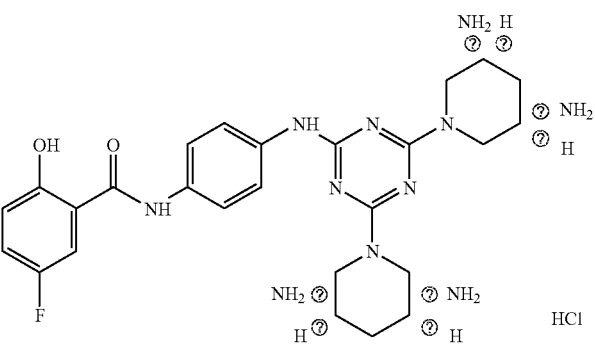 HCl | N-[4-(5-fluoro-2-hydroxy-benzoylamino)-phenyl]-4,6-Bis-((3R,5S)-3,5-diamino-piperidin-1-yl)-[1,3,5]triazine-2-amine | |
| 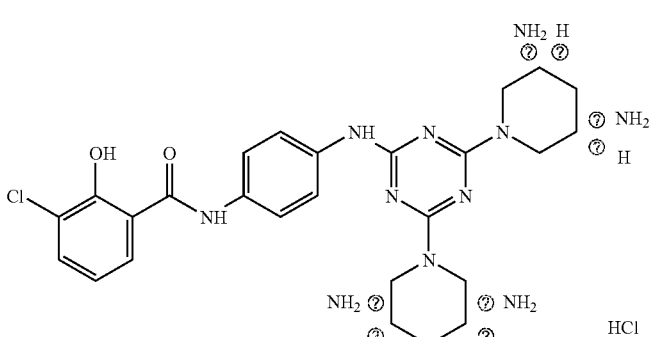 HCl | N-[4-(3-chloro-2-hydroxy-benzoylamino)-phenyl]-4,6-Bis-((3R,5S)-3,5-diamino-piperidin-1-yl)-[1,3,5]triazine-2-amine | |
| 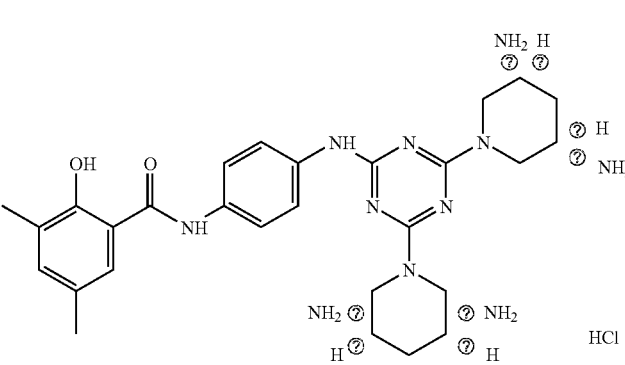 HCl | N-0[4-(2-hydroxy-3,5-dimethyl-benzoylamino)-phenyl]-4,6-Bis-((3R,5S)-3,5-diamino-piperidin-1-yl)-[1,3,5]triazine-2-amine | |

⓵ indicates text missing or illegible when filed

-continued

| Structure | Name | Potency |
|---|---|---|
| 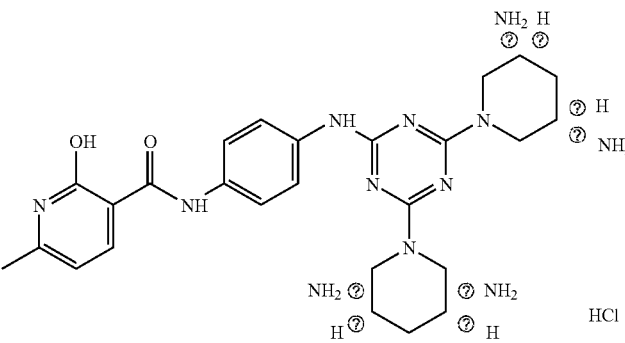 | N-{4-[(2-hydroxy-6-methyl-pyridine-3-carbonyl)-amino]-phenyl}-4,6-Bis-((3R,5S)-3,5-diamino-piperidin-1-yl)-[1,3,5]triazine-2-amine | |
| 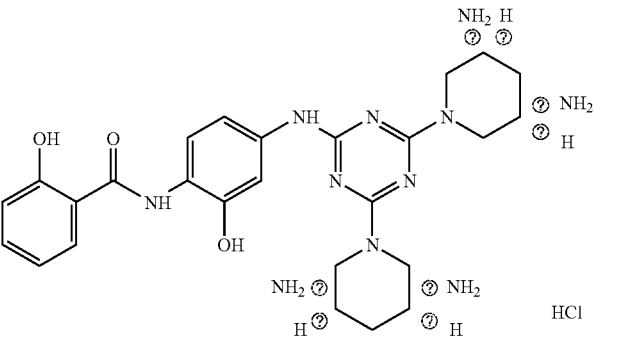 | N-[3-hydroxy-4-(2-hydroxy-benzoylamino)-phenyl]-4,6-Bis-((3R,5S)-3,5-diamino-piperidin-1-yl)-[1,3,5]triazine-2-amine | |
| 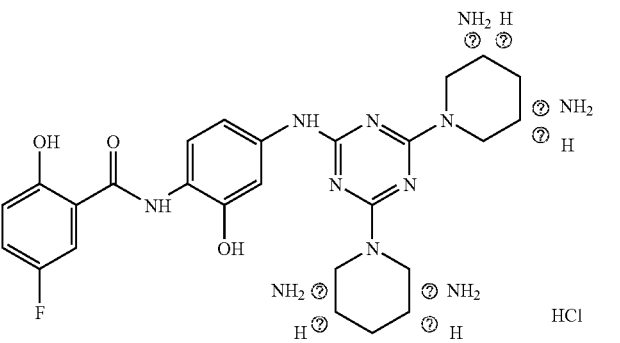 | N-[4-(5-fluoro-2-hydroxy-benzoylamino)-3-hydroxy-phhenyl]-4,6-Bis-((3R,5S)-3,5-diamino-piperidin-1-yl)-[1,3,5]triazine-2-amine | |
| 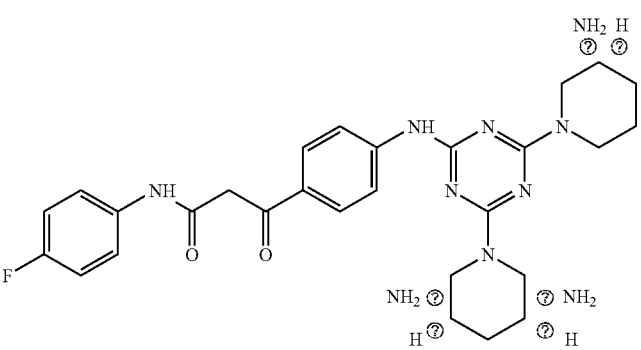 | N-{4-[2-(4-fluoro-phenylcarbamoyl)-acetyl]-phenyl}-4,6-Bis-((3R,5S)-3,5-diamino-piperidin-1-yl)-[1,3,5]triazine-2-amine | ++ |

-continued

| Structure | Name | Potency |
|---|---|---|
| 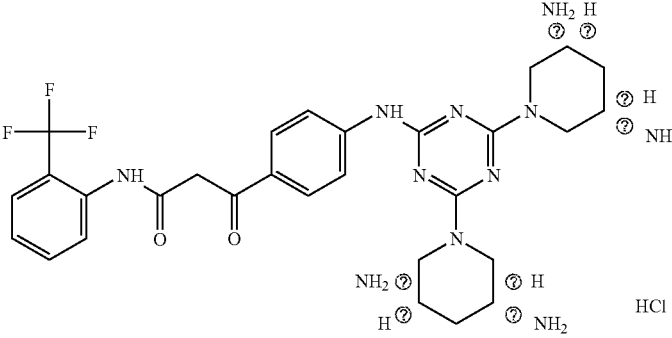 | N-{4-[2-(2-trifluoromethyl-phenylcarbamoyl)-acetyl]-phenyl}-4,6-Bis-((3R,5S)-3,5-diamino-piperidin-1-yl)-[1,3,5]triazine-2-amine | + |
| 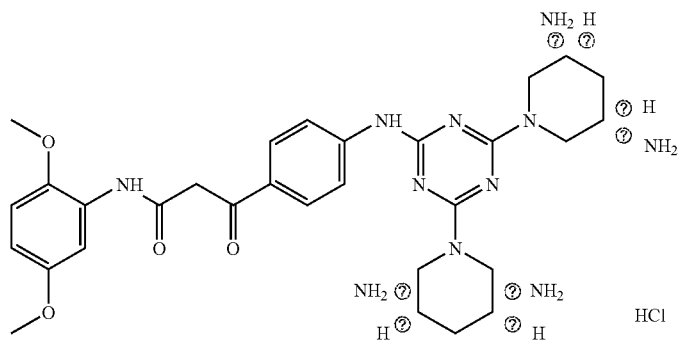 | N-{4-[2-(2,5-dimethoxy-phenylcarbamoyl)-acetyl]-phenyl}-4,6-Bis-((3R,5S)-3,5-diamino-piperidin-1-yl)-[1,3,5]triazine-2-amine | + |
| 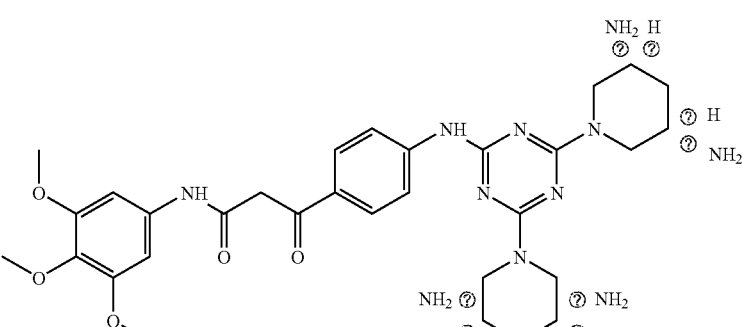 | N-{4-[2-(3,4,5-trimethoxy-phenylcarbamoyl)-acetyl]-phenyl}-4,6-Bis-((3R,5S)-3,5-diamino-piperidin-1-yl)-[1,3,5]triazine-2-amine | − |
| 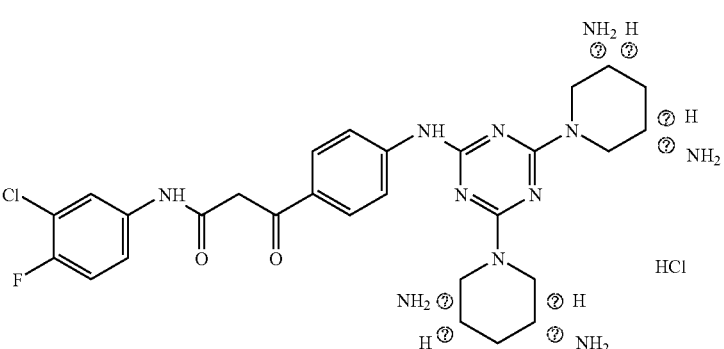 | N-{4-[2-(3-chloro-4-fluoro-phenylcarbamoyl)-acetyl]-phenyl}-4,6-Bis-((3R,5S)-3,5-diamino-piperidin-1-yl)-[1,3,5]triazine-2-amine | ++ |

| Structure | Name | Potency |
|---|---|---|
| (structure) | N-{4-[2-(3-trifluoromethoxy-phenylcarbamoyl)-acetyl]-phenyl}-4,6-Bis-((3R,5S)-3,5-diamino-piperidin-1-yl)-[1,3,5]triazine-2-amine | ++ |
| (structure) | N-{4-[2-(3,4-difluoro-phenylcarbamoyl)-acetyl]-phenyl}-4,6-Bis-((3R,5S)-3,5-diamino-piperidin-1-yl)-[1,3,5]triazine-2-amine | |
| (structure) | N-[4-(5-chloro-2-hydroxy-benzoylamino)-3-hydroxy-phenyl]-4,6-Bis-((3R,5S)-3,5-diamino-piperidin-1-yl)-[1,3,5]triazine-2-amine | |
| (structure) | N-{3-hydroxy-4-[(3-hydroxy-pyridine-2-carbonyl)-amino]-phenyl}-4,6-Bis-((3R,5S)-3,5-diamino-piperidin-1-yl)-[1,3,5]triazine-2-amine | |

⁇ indicates text missing or illegible when filed

-continued
| Structure | Name | Potency |
|---|---|---|
| 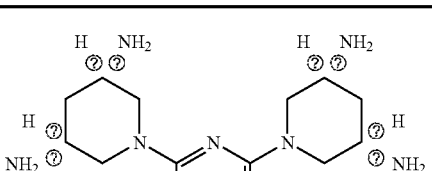 HCl | NM-{4-[(3-hydroxy-quinoxaline-2-carbonyl)-amino]-phenyl}-4,6-Bis-((3R,5S)-3,5-diamino-piperidin-1-yl)-[1,3,5]triazine-2-amine | |
| 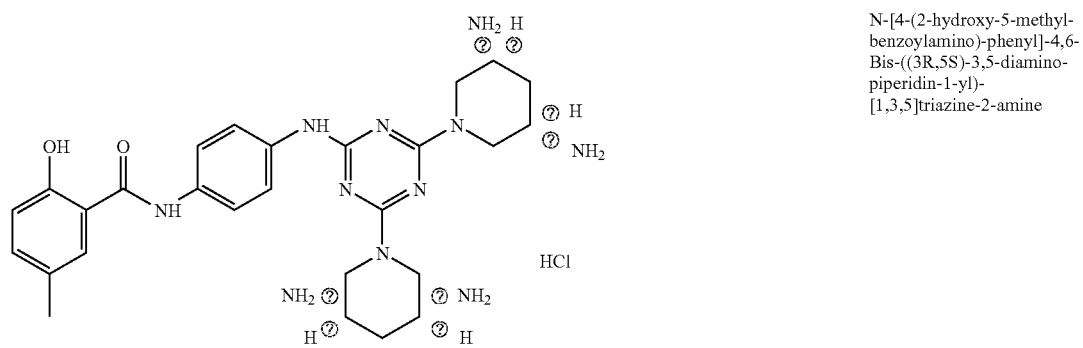 HCl | N-[4-(2-hydroxy-5-methyl-benzoylamino)-phenyl]-4,6-Bis-((3R,5S)-3,5-diamino-piperidin-1-yl)-[1,3,5]triazine-2-amine | |
| 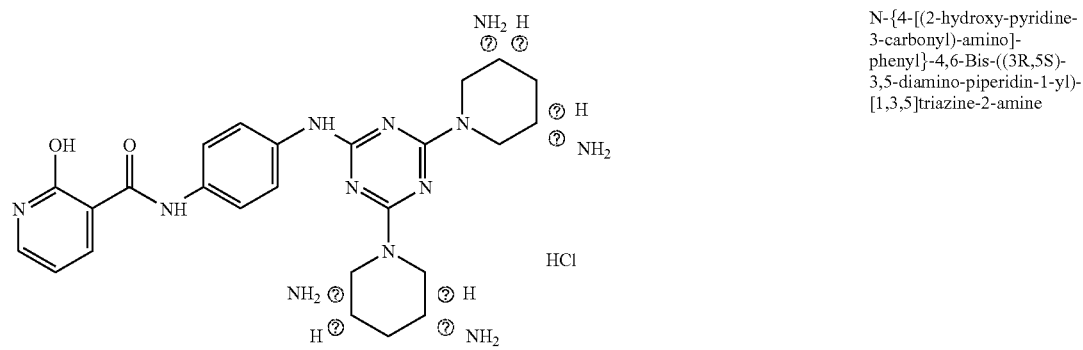 HCl | N-{4-[(2-hydroxy-pyridine-3-carbonyl)-amino]-phenyl}-4,6-Bis-((3R,5S)-3,5-diamino-piperidin-1-yl)-[1,3,5]triazine-2-amine | |
⑦ indicates text missing or illegible when filed -continued

| Structure | Name | Potency |
|---|---|---|
| 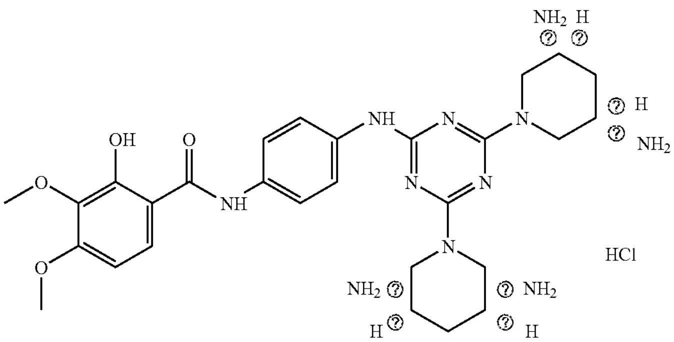 | N-[4-(2-hydroxy-3,4-dimethoxy-benzoylamino)-phenyl]-4,6-Bis-((3R,5S)-3,5-diamino-piperidin-1-yl)-[1,3,5]triazine-2-amine | |
| 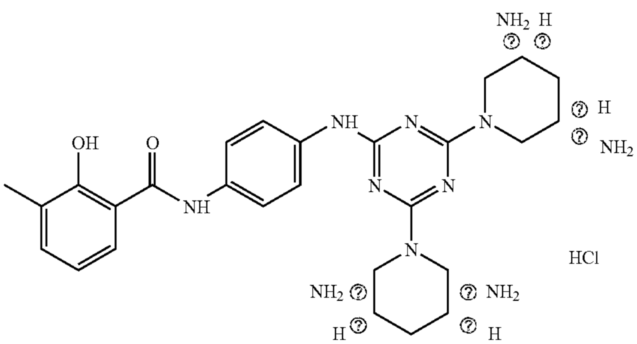 | N-[4-(2-hydroxy-3-methyl-benzoylamino)-phenyl]-4,6-Bis-((3R,5S)-3,5-diamino-piperidin-1-yl)-[1,3,5]triazine-2-amine | |
| 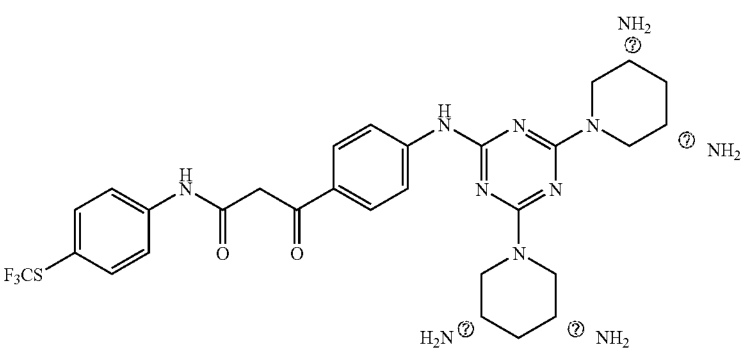 | N-{4-[2-(4-trifluoromethylsulfanyl-phenylcarbamoyl)-acetyl]-phenyl}-4,6-Bis-((3R,5S)-3,5-diamino-piperidin-1-yl)-[1,3,5]triazine-2-amine | |
| 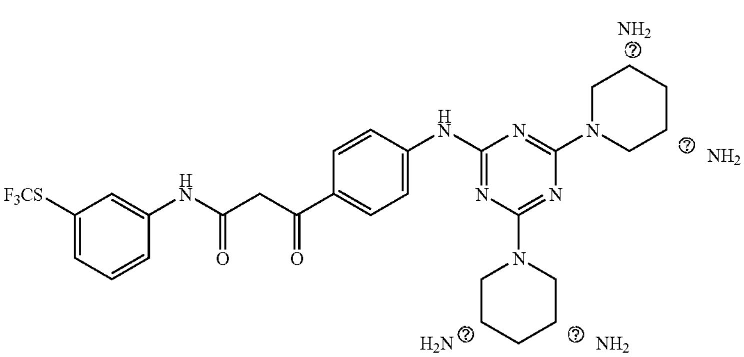 | N-{4-[2-(3-trifluoromethylsulfanyl-phenylcarbamoyl)-acetyl]-phenyl}-4,6-Bis-((3R,5S)-3,5-diamino-piperidin-1-yl)-[1,3,5]triazine-2-amine | |

-continued

| Structure | Name | Potency |
|---|---|---|
| 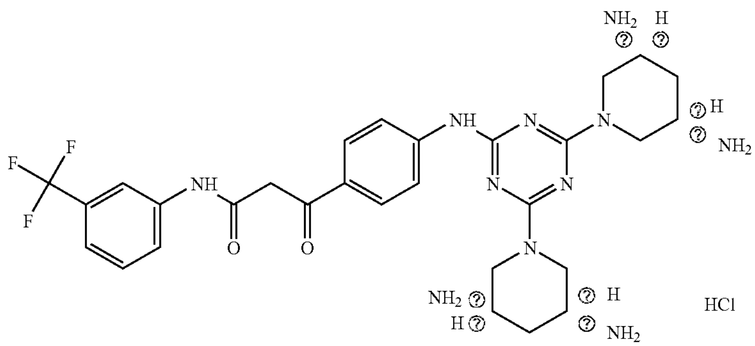 | N-{4-[2-(3-trifluoromethyl-phenylcarbamoyl)-acetyl]-phenyl}-4,6-Bis-((3R,5S)-3,5-diamino-piperidin-1-yl)-[1,3,5]triazine-2-amine | ++ |
| 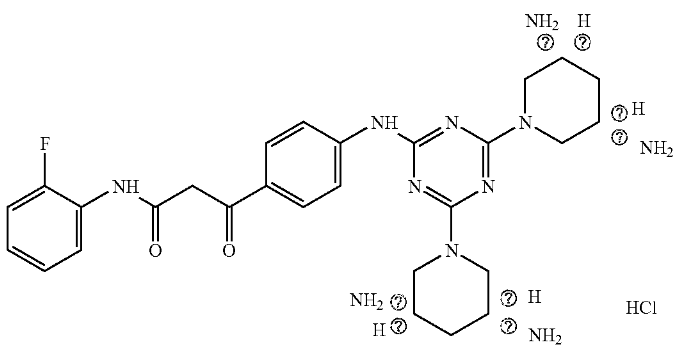 | N-{4-[2-(2-fluoro-phenylcarbamoyl)-acetyl]-phenyl}-4,6-Bis-((3R,5S)-3,5-diamino-piperidin-1-yl)-[1,3,5]triazine-2-amine | + |
| 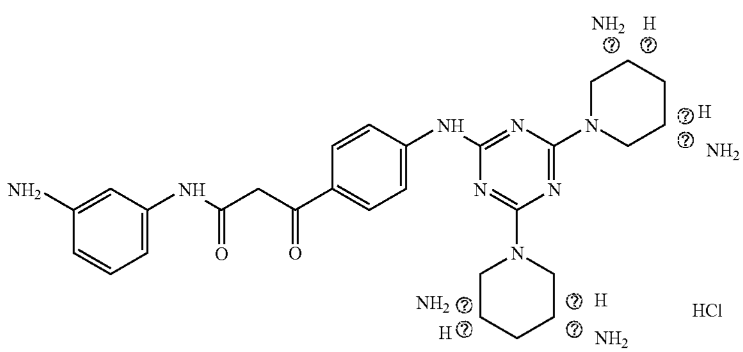 | N-{4-[2-(3-amino-phenylcarbamoyl)-acetyl]-phenyl}-4,6-Bis-((3R,5S)-3,5-diamino-piperidin-1-yl)-[1,3,5]triazine-2-amine | − |
| 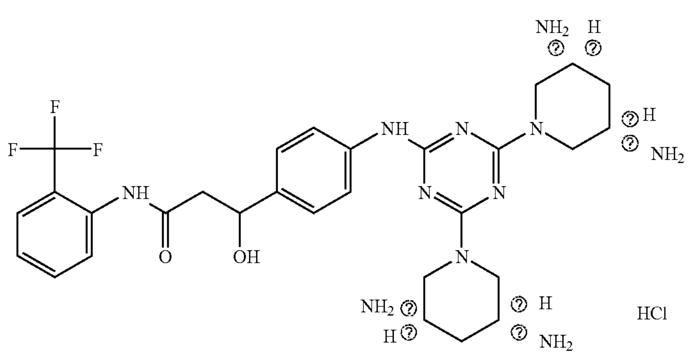 | N-{4-[1-hydroxy-2-(2-trifluoromethyl-phenylcarbazmoyl)-ethyl]-phenyl}-4,6-Bis-((3R,5S)-3,5-diamino-piperidin-1-yl)-[1,3,5]triazine-2-amine | + |

-continued
| Structure | Name | Potency |
|---|---|---|
| 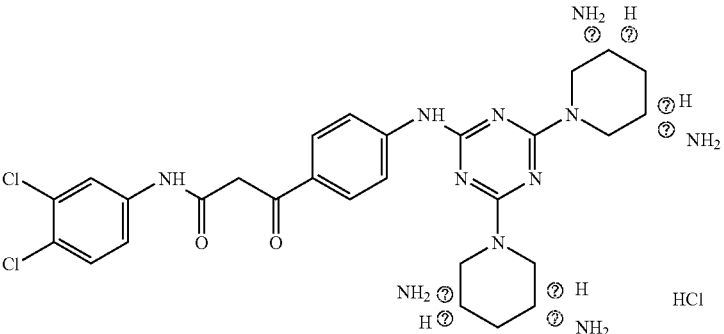 | N-{4-[2-(3,4-dichloro-phenylcarbamoyl)-acetyl]-phenyl}-4,6-Bis-((3R,5S)-3,5-diamino-piperidin-1-yl)-[1,3,5]triazine-2-amine | |
| 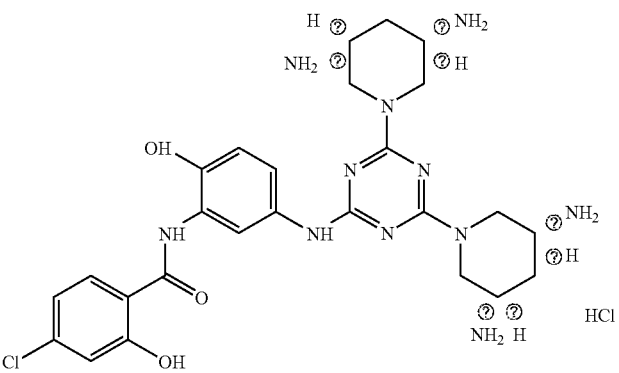 | N-[3-(4-chloro-2-hydroxy-benzoylamino)-4-hydroxy-phenyl]-4,6-Bis-((3R,5S)-3,5-diamino-piperidin-1-yl)-[1,3,5]triazine-2-amine | |
| 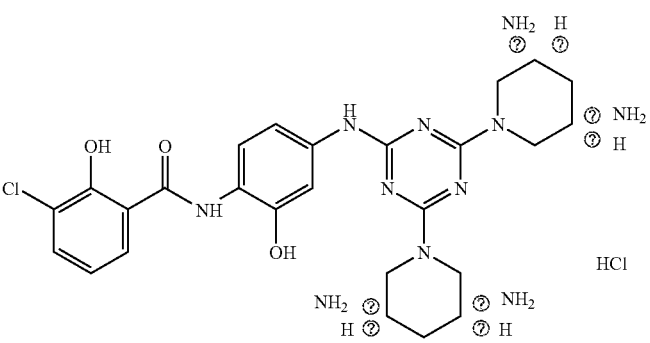 | N-[4-(3-chloro-2-hydroxy-benzoylamino)-3-hydroxy-phenyl]-4,6-Bis-((3R,5S)-3,5-diamino-piperidin-1-yl)-[1,3,5]triazine-2-amine | |

| Structure | Name | Potency |
|---|---|---|
| 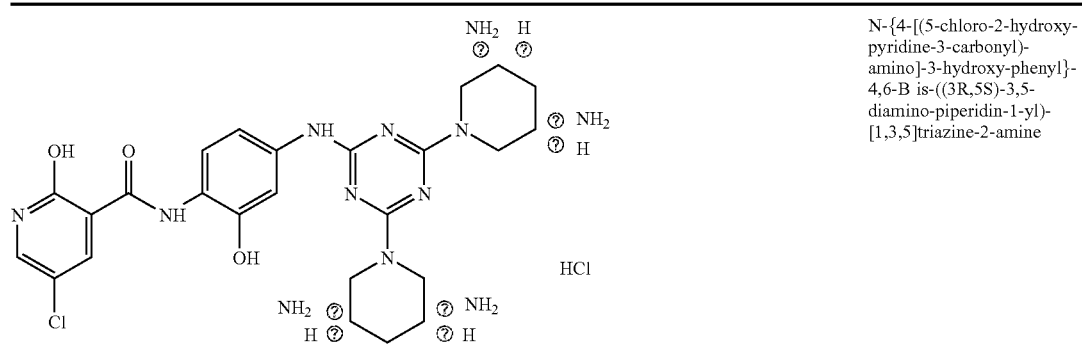 | N-{4-[(5-chloro-2-hydroxy-pyridine-3-carbonyl)-amino]-3-hydroxy-phenyl}-4,6-Bis-((3R,5S)-3,5-diamino-piperidin-1-yl)-[1,3,5]triazine-2-amine | |
| 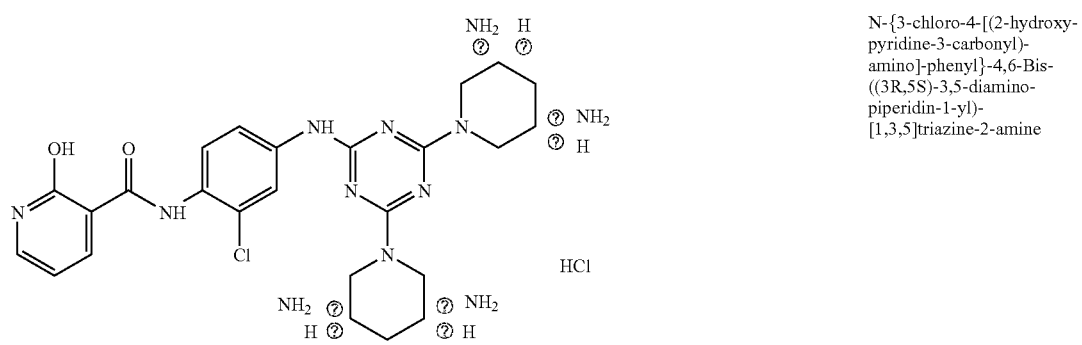 | N-{3-chloro-4-[(2-hydroxy-pyridine-3-carbonyl)-amino]-phenyl}-4,6-Bis-((3R,5S)-3,5-diamino-piperidin-1-yl)-[1,3,5]triazine-2-amine | |
| 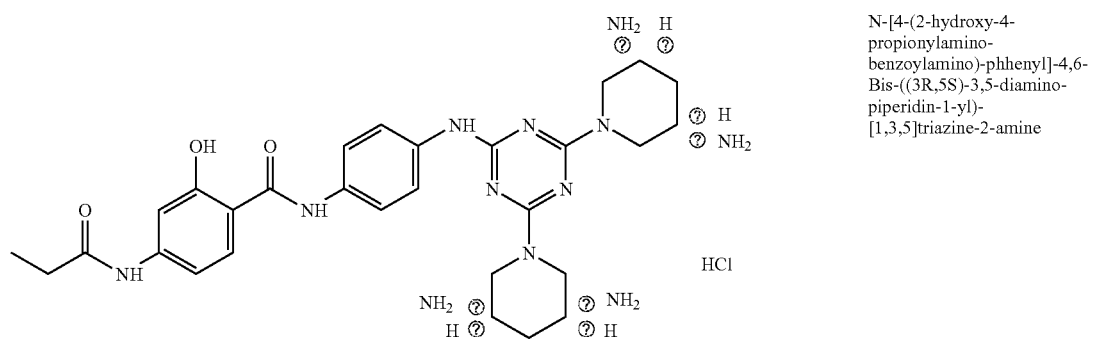 | N-[4-(2-hydroxy-4-propionylamino-benzoylamino)-phhenyl]-4,6-Bis-((3R,5S)-3,5-diamino-piperidin-1-yl)-[1,3,5]triazine-2-amine | |
| 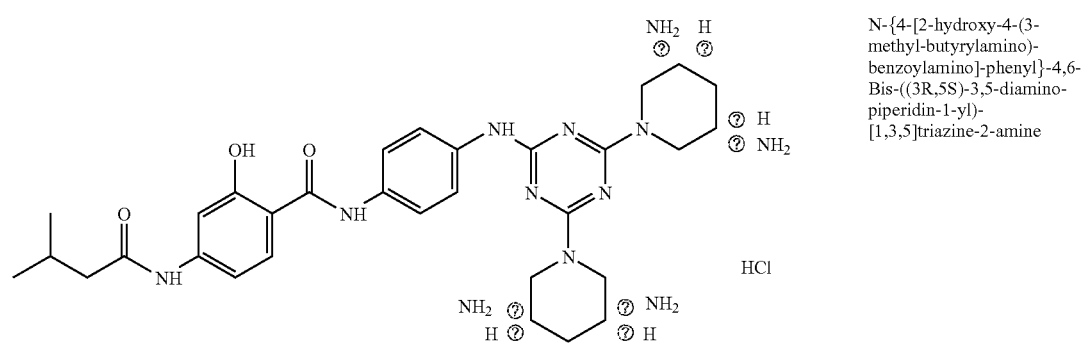 | N-{4-[2-hydroxy-4-(3-methyl-butyrylamino)-benzoylamino]-phenyl}-4,6-Bis-((3R,5S)-3,5-diamino-piperidin-1-yl)-[1,3,5]triazine-2-amine | |

-continued

| Structure | Name | Potency |
|---|---|---|
| 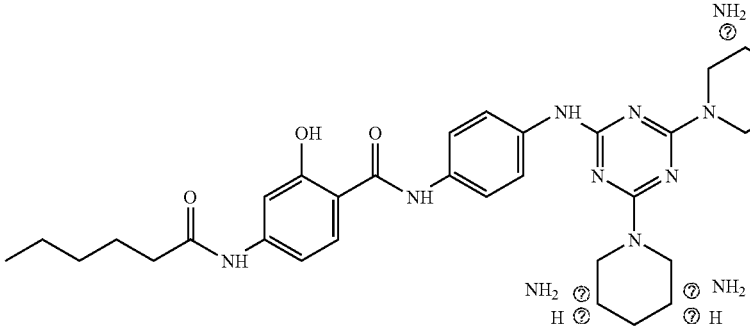 | N-[4-(4-hexanoylamino-2-hydroxy-benzoylamino)-phenyl]-4,6-Bis-((3R,5S)-3,5-diamino-piperidin-1-yl)-[1,3,5]triazine-2-amine | |
| 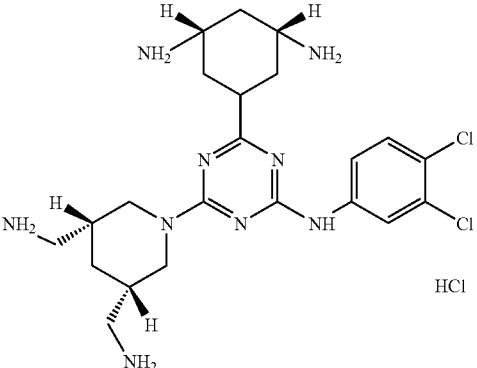 | (3R,5S)-1-[4-((3R,5S)-3,5-Bis-(aminomethyl)-piperidin-1-yl)-6-(3,4-dichloro-phenylamino)-[1,3,5]triazin-2-yl]-piperidine-3,5-diamine | + |
| 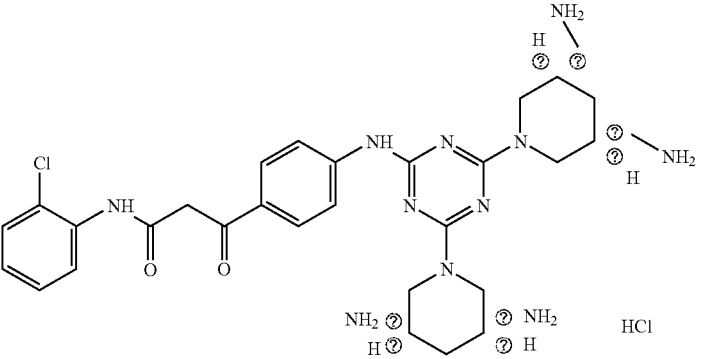 | 3-{4-[4-((3R,5S)-3,5-Bis-(aminomethyl)-piperidin-1-yl)-6-((3R,5S)-3,5-diamino-piperidin-1-yl)-[1,3,5]triazin-2-ylamino]-phenyl}-N-(2-chloro-phenyl)-3-oxo-propionamide | + |
| 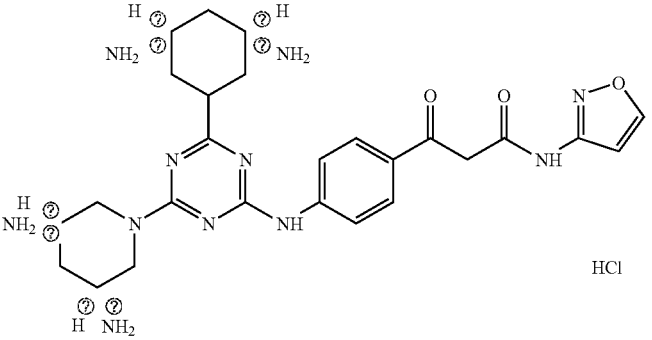 | N-{4-[2-(isoxazol-3-ylcarbamoyl)-acetyl]-phenyl}-4,6-Bis-((3R,5S)-3,5-diamino-piperidin-1-yl)-[1,3,5]triazine-2-amine | + |

-continued

| Structure | Name | Potency |
|---|---|---|
| 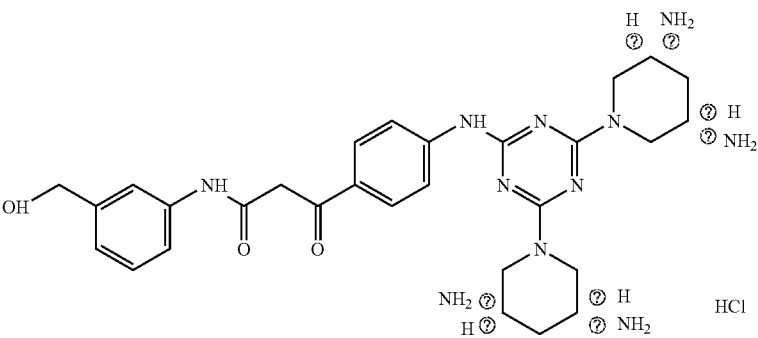 | N-{4-[2-(3-hydroxymethyl-phenylcarbamoyl)-acetyl]-phenyl}-4,6-Bis-((3R,5S)-3,5-diamino-piperidin-1-yl)-[1,3,5]triazine-2-amine | − |
| ⑦ indicates text missing or illegible when filed | | |
| 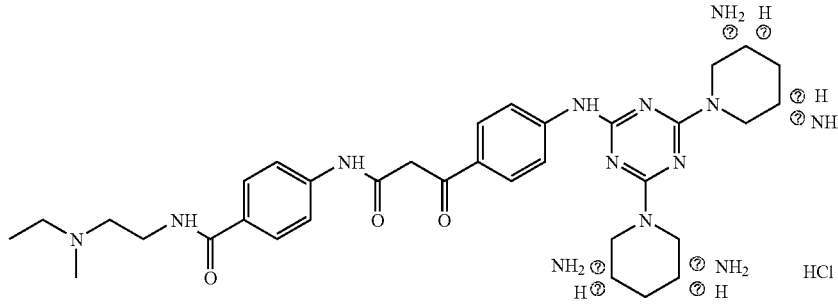 | N-(4-{2-[4-(2-diethylamino-ethylcarbamoyl)-phhenylcxarbamoyl]-acetyl}-phenyl)-4,6-Bis-((3R,5S)-3,5-diamino-piperidin-1-yl)-[1,3,5]triazine-2-amine | − |
| ⑦ indicates text missing or illegible when filed | | |
| 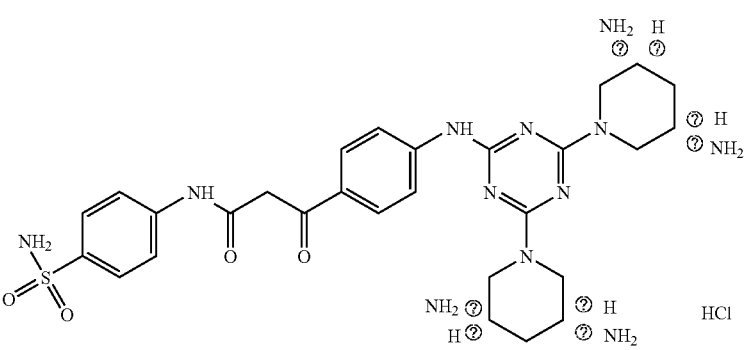 | N-{4-[2-(4-sulfamoyl-phenylcarbamoyl)-acetyl]-phenyl}-44,6-Bis-((3R,5S)-3,5-diamino-piperidin-1-yl)-[1,3,5]triazine-2-amine | + |
| ⑦ indicates text missing or illegible when filed | | |
| 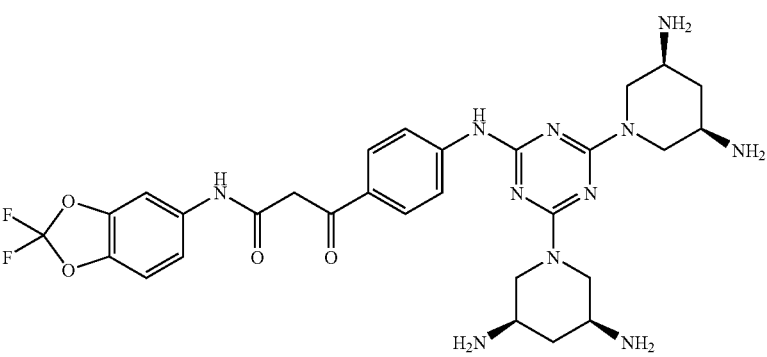 | N-{4-[2-(2,2-difluoro-benzo[1,3]dioxol-5-ylcarbamoyl)-acetyl]-phenyl}-4,6-Bis-((3R,5S)-3,5-diamino-piperidin-1-yl)-[1,3,5]triazine-2-amine | |

-continued

| Structure | Name | Potency |
|---|---|---|
| 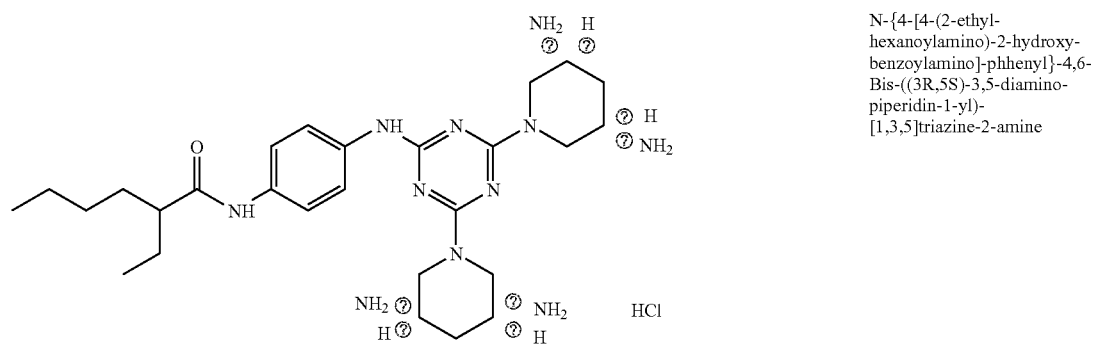 | N-{4-[4-(2-ethyl-hexanoylamino)-2-hydroxy-benzoylamino]-phhenyl}-4,6-Bis-((3R,5S)-3,5-diamino-piperidin-1-yl)-[1,3,5]triazine-2-amine | |
| 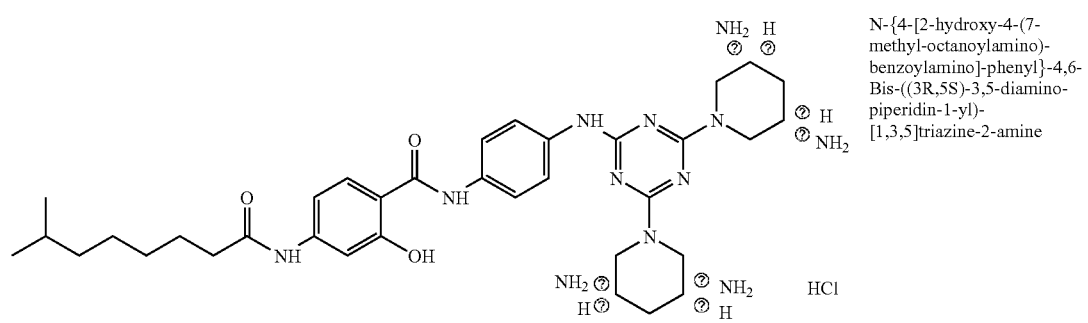 | N-{4-[2-hydroxy-4-(7-methyl-octanoylamino)-benzoylamino]-phenyl}-4,6-Bis-((3R,5S)-3,5-diamino-piperidin-1-yl)-[1,3,5]triazine-2-amine | |
| 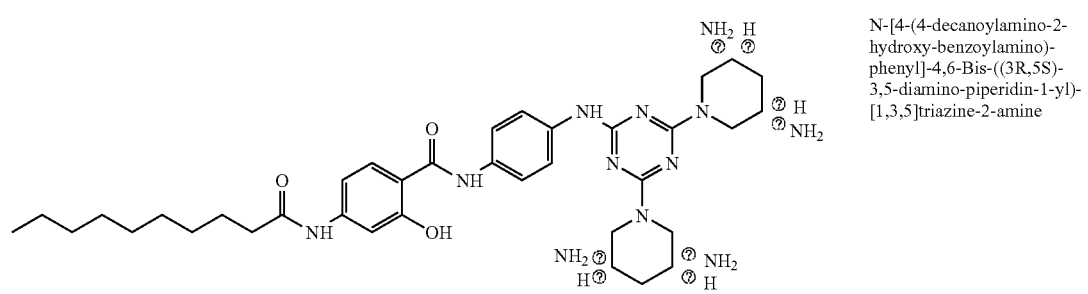 | N-[4-(4-decanoylamino-2-hydroxy-benzoylamino)-phenyl]-4,6-Bis-((3R,5S)-3,5-diamino-piperidin-1-yl)-[1,3,5]triazine-2-amine | |
| 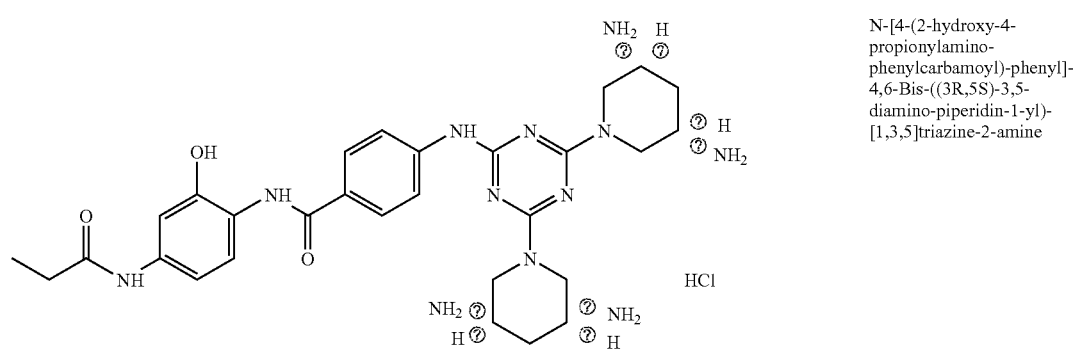 | N-[4-(2-hydroxy-4-propionylamino-phenylcarbamoyl)-phenyl]-4,6-Bis-((3R,5S)-3,5-diamino-piperidin-1-yl)-[1,3,5]triazine-2-amine | |

-continued

| Structure | Name | Potency |
|---|---|---|
| 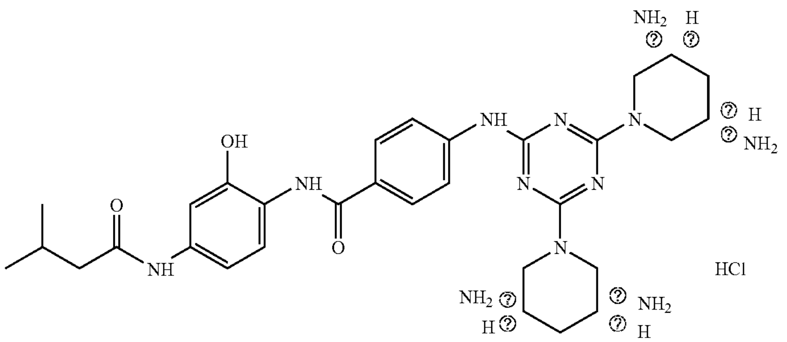 | N-{4-[2-hydroxy-4-(3-methyl-butyrylamino)-phenylcarbamoyl]-phenyl}-4,6-Bis-((3R,5S)-3,5-diamino-piperidin-1-yl)-[1,3,5]triazine-2-amine | |
| 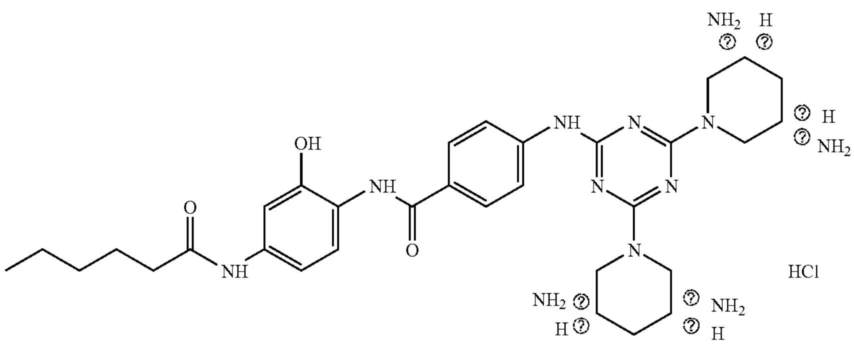 | N-[4-(4-hexanoylamino-2-hydroxy-phenylcarbamoyl)-phenyl]-4,6-Bis-((3R,5S)-3,5-diamino-piperidin-1-yl)-[1,3,5]triazine-2-amine | |
| 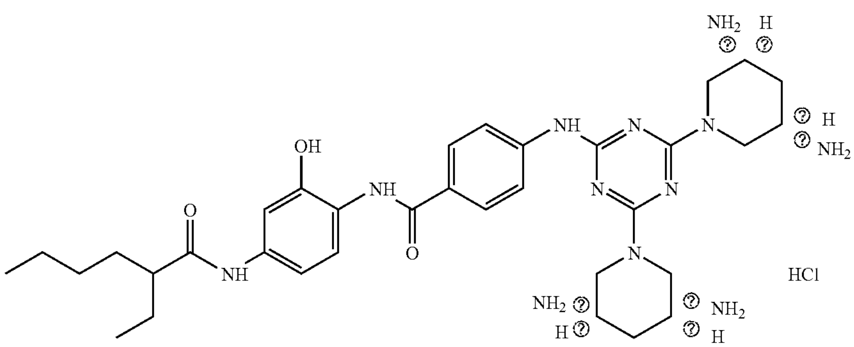 | N-{4-[4-(2-ethyl-hexanoylamino)-2-hydroxy-phenylcarbamoyl]-phenyl}-4,6-Bis-((3R,5S)-3,5-diamino-piperidin-1-yl)-[1,3,5]triazine-2-amine | |
| 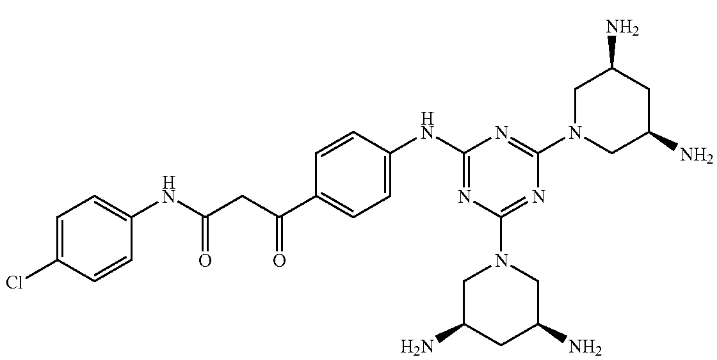 | N-{4-[2-(4-chloro-phenylcarbamoyl)-acetyl]-phenyl}-4,6-Bis-((3R,5S)-3,5-diamino-piperidin-1-yl)-[1,3,5]triazine-2-amine | |

⑦ indicates text missing or illegible when filed

-continued

| Structure | Name | Potency |
|---|---|---|
| (structure) | N-{4-[2-(4-chloro-2-fluoro-phenylcarbamoyl)-acetyl]-phenyl}-4,6-Bis-((3R,5S)-3,5-diamino-piperidin-1-yl)-[1,3,5]triazine-2-amine · HCl | ++ |
| (structure) | N-(4-{2-[4-(1H-indazol-6-ylsulfamoyl)-phenylcarbamoyl]-acetyl}-phenyl)-4,6-Bis-((3R,5S)-3,5-diamino-piperidin-1-yl)-[1,3,5]triazine-2-amine · HCl | + |
| (structure) | N-(4-{2-[(benzo[1,3]dioxol-5-ylmethyl)-carbamoyl]-acetyl}-phenyl)-4,6-Bis-((3R,5S)-3,5-diamino-piperidin-1-yl)-[1,3,5]triazine-2-amine · HCl | − |
| (structure) | N-{4-[2-(4-aminomethyl-phenylcarbamoyl)-acetyl]-phenyl}-4,6-Bis-((3R,5S)-3,5-diamino-piperidin-1-yl)-[1,3,5]triazine-2-amine · HCl | − |

⑦ indicates text missing or illegible when filed

-continued

| Structure | Name | Potency |
|---|---|---|
| 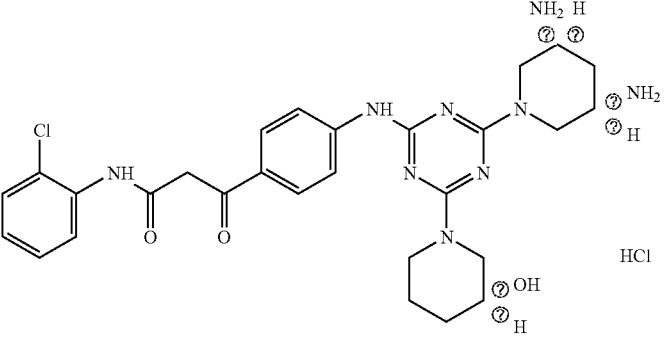 | N-(2-Chloro-phenyl)-3-{4-[4-(3S,5R)-3,5-diamino-piperidin-1-yl)-6-((R)-3-hydroxy-piperidin-1-yl)-[1,3,5]triazin-2-ylamino]-phenyl}-3-oxo-propionamide | + |
| ⑦ indicates text missing or illegible when filed | | |
| 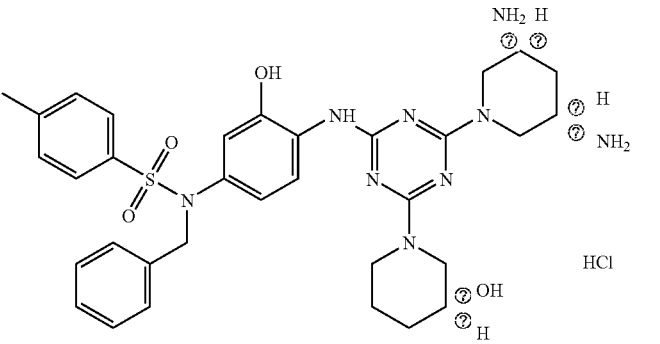 | N-Benzyl-N-{4-[4-((3R,5S)-3,5-diamino-piperidin-1-yl)-6-((R)-3-hydroxy-piperidin-1-yl)-[1,3,5]triazin-2-ylamino]-3-hydroxy-phenyl}-4-methyl-benzenesulfonamide | + |
| ⑦ indicates text missing or illegible when filed | | |
| 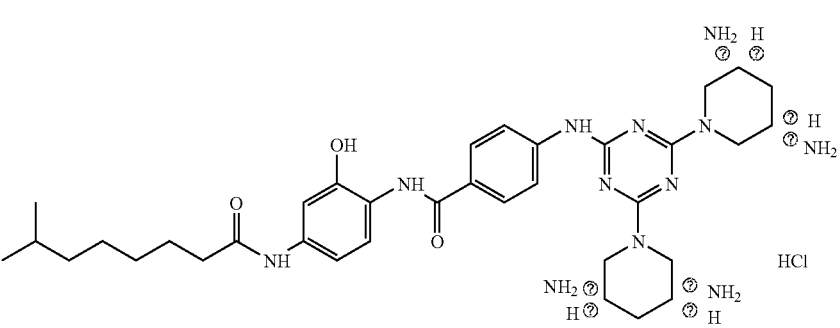 | N-{4-[2-hydroxy-4-(7-methyl-octanoylamino)-phenylcarbamoyl]-phenyl}-4,6-Bis-((3R,5S)-3,5-ddiamino-piperidin-1-yl)-[1,3,5]triazine-2-amine | |
| ⑦ indicates text missing or illegible when filed | | |
| 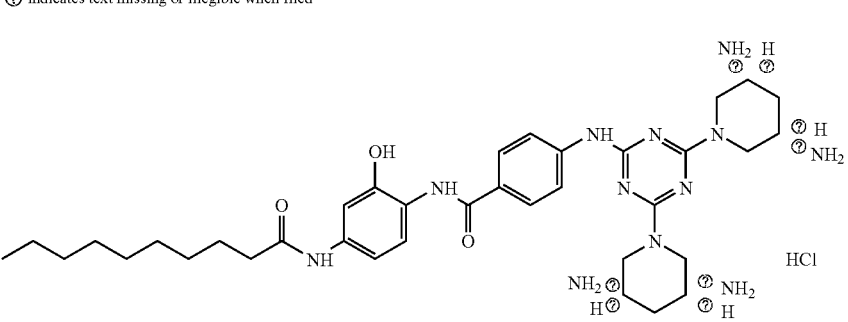 | N-[4-(4-decanoylamino-2-hydroxy-phenylcarbamoyl)-phenyl]-4,6-Bis-((3R,5S)-3,5-diamino-piperidin-1-yl)-[1,3,5]triazine-2-amine | |
| ⑦ indicates text missing or illegible when filed | | |

-continued

| Structure | Name | Potency |
|---|---|---|
| 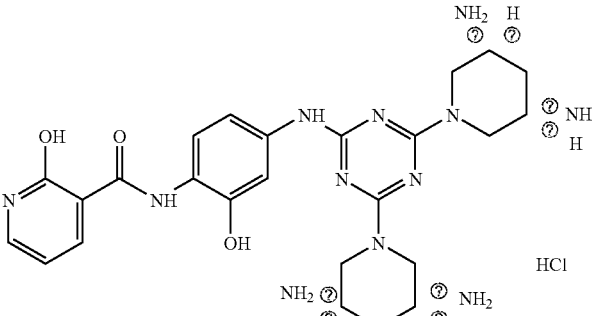 | N-{3-hydroxy-4-[(2-hydroxy-pyridine-3-carbonyl)-amino]-phenyl}-4,6-Bis-((3R,5S)-3,5-diamino-piperidin-1-yl)-[1,3,5]triazine-2-amine | ++ |
| 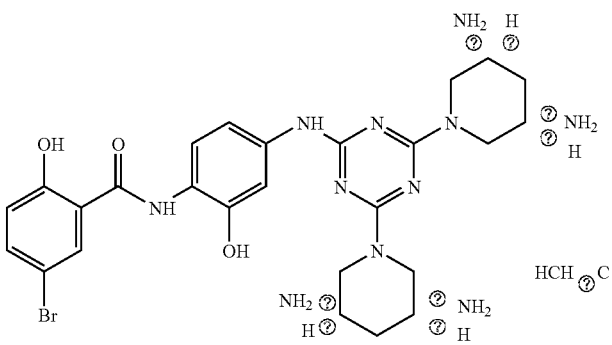 | N-[4-(5-bromo-2-hydroxy-benzoylamino)-3-hydroxy-phhenyl]-4,6-Bis-((3R,5S)-3,5-diamino-piperidin-1-yl)-[1,3,5]triazine-2-amine | |
| 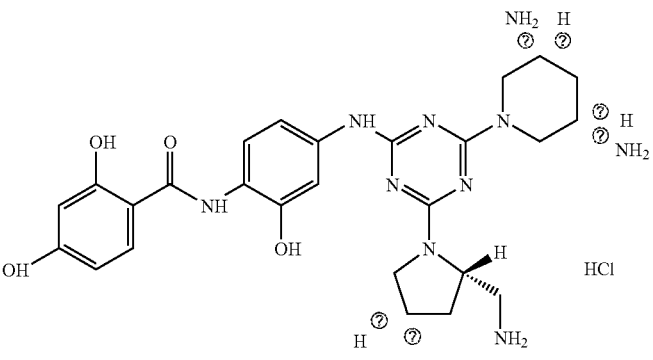 | N-{4-[4-((2S,4S)-4-Amino-2-aminomethyl-pyrrolidin-1-yl)-6-((3R,5S)-3,5-diamino-piperidin-1-yl)-[1,3,5]triazin-2-ylamino]-2-hydroxy-phenyl}-2,4-dihydroxy-benzamide | ++ |

⑦ indicates text missing or illegible when filed

-continued

| Structure | Name | Potency |
|---|---|---|
| 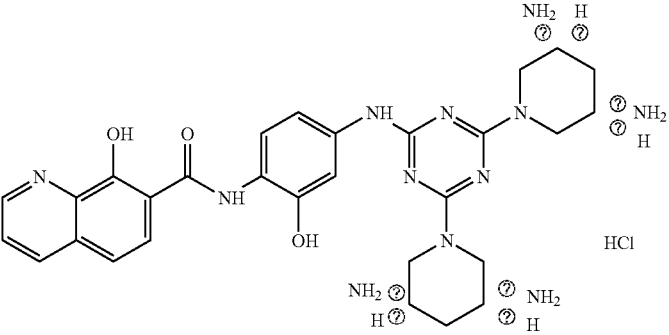 | N-{3-hydroxy-4-[(8-hydroxy-quinoline-7-carbonyl)-amino]-phenyl}-4,6-Bis-(cis-3,5-Diamino-piperidin-1-yl)-[1,3,5]triazine-2-amine | |
| ⑦ indicates text missing or illegible when filed | | |
| 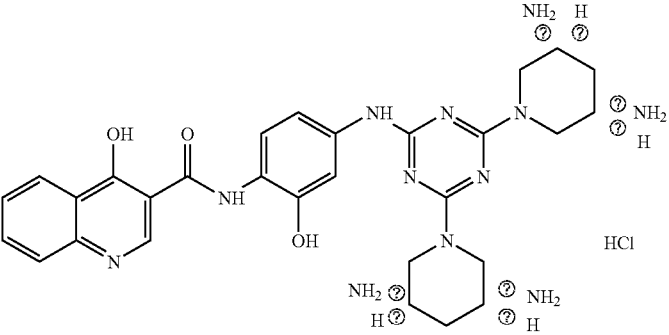 | N-{3-hydroxy-4-[(4-hydroxy-quinoline-3-carbonyl)-amino]-phenyl}-4,6-Bis-(cis-3,5-Diamino-piperidin-1-yl)-[1,3,5]triazine-2-amine | |
| ⑦ indicates text missing or illegible when filed | | |
| 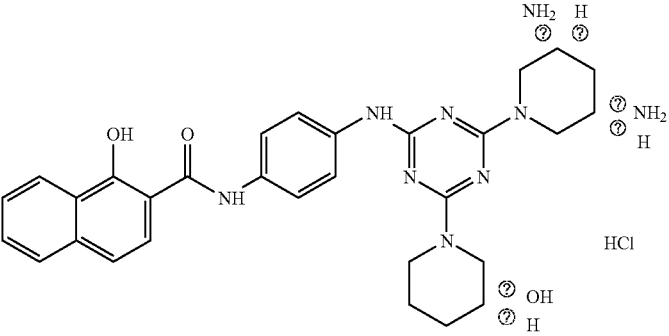 | 1-Hydroxy-naphthalene-2-carboxylicacid {4-[4-((3S,5R)-3,5-diamino-piperidin-1-yl)-6-((R)-3-hydroxy-piperidin-1-yl)-[1,3,5]triazin-2-ylamino]-phenyl}-amide | + |
| ⑦ indicates text missing or illegible when filed | | |
| 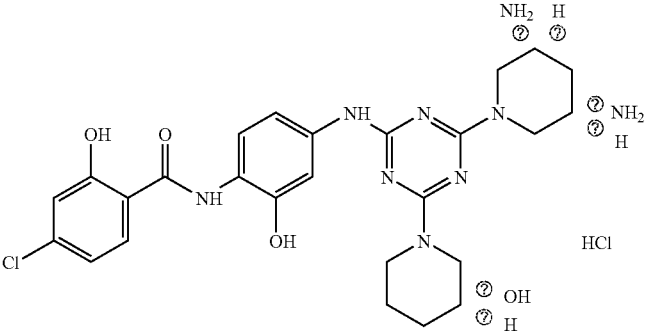 | 4-Chloro-N-{4-[4-((3S,5R)-3,5-diamino-piperidin-1-yl)-6-((R)-3-hydroxy-piperidin-1-yl)-[1,3,5]triazin-2-ylamino]-2-hydroxy-phenyl}-benzamide | + |
| ⑦ indicates text missing or illegible when filed | | |

-continued

| Structure | Name | Potency |
|---|---|---|
| 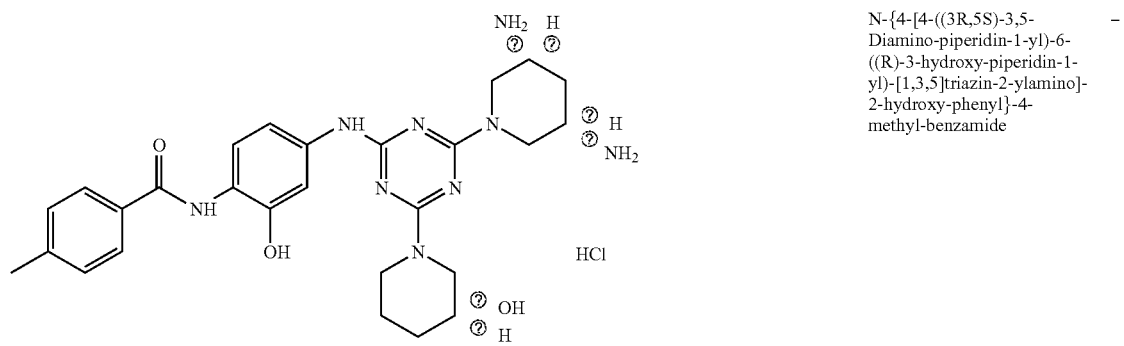 | N-{4-[4-((3R,5S)-3,5-Diamino-piperidin-1-yl)-6-((R)-3-hydroxy-piperidin-1-yl)-[1,3,5]triazin-2-ylamino]-2-hydroxy-phenyl}-4-methyl-benzamide | − |
| 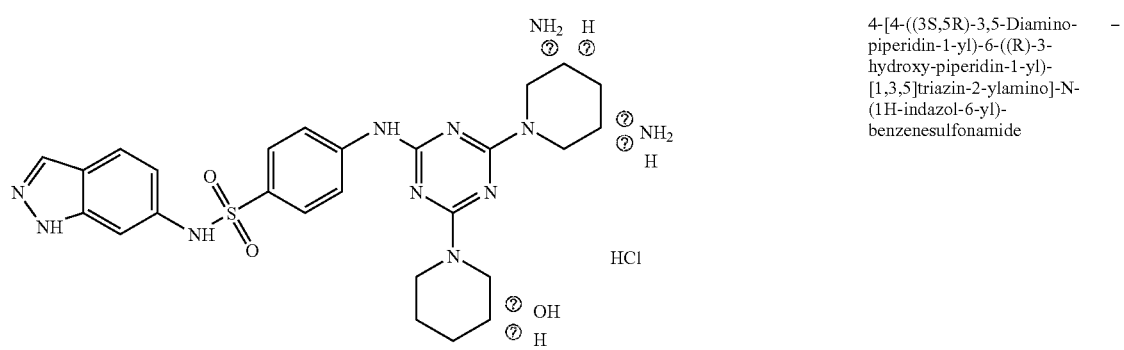 | 4-[4-((3S,5R)-3,5-Diamino-piperidin-1-yl)-6-((R)-3-hydroxy-piperidin-1-yl)-[1,3,5]triazin-2-ylamino]-N-(1H-indazol-6-yl)-benzenesulfonamide | − |
| 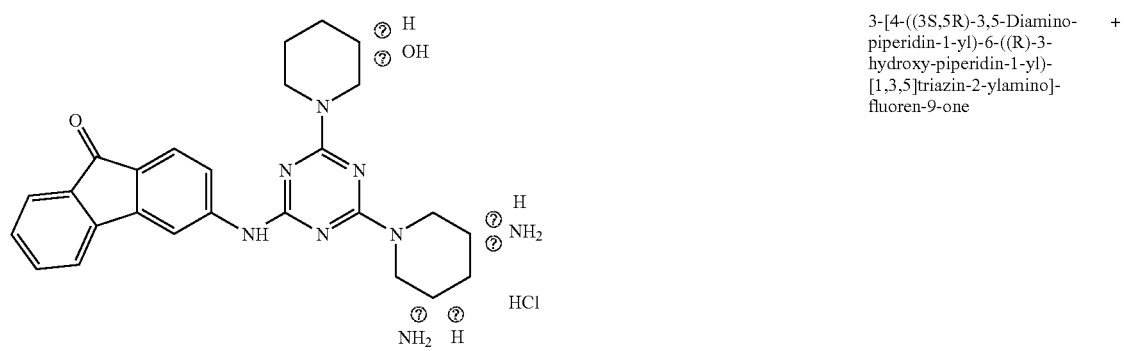 | 3-[4-((3S,5R)-3,5-Diamino-piperidin-1-yl)-6-((R)-3-hydroxy-piperidin-1-yl)-[1,3,5]triazin-2-ylamino]-fluoren-9-one | + |
| 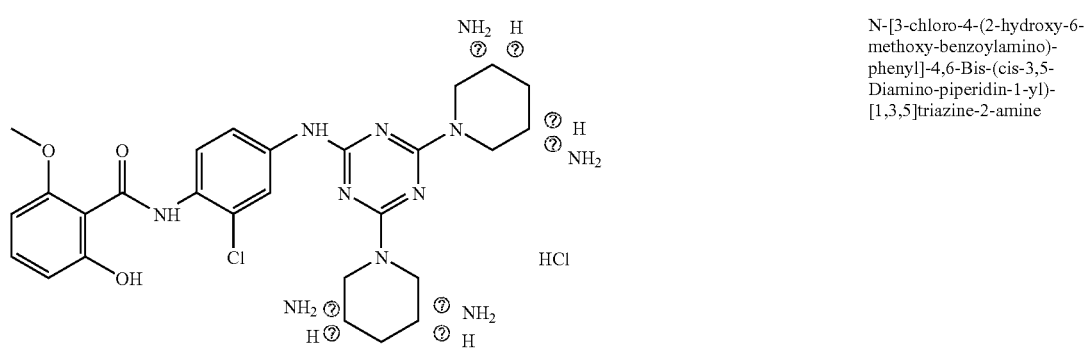 | N-[3-chloro-4-(2-hydroxy-6-methoxy-benzoylamino)-phenyl]-4,6-Bis-(cis-3,5-Diamino-piperidin-1-yl)-[1,3,5]triazine-2-amine | |

⑦ indicates text missing or illegible when filed

-continued

| Structure | Name | Potency |
|---|---|---|
| 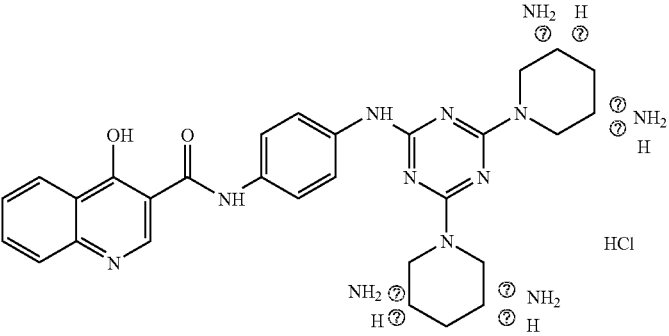 ⓘ indicates text missing or illegible when filed | N-{4-[(4-hydroxy-quinoline-3-carbonyl)-amino]-phenyl}-4,6-Bis-(cis-3,5-Diamino-piperidin-1-yl)-[1,3,5]triazine-2-amine | |
| 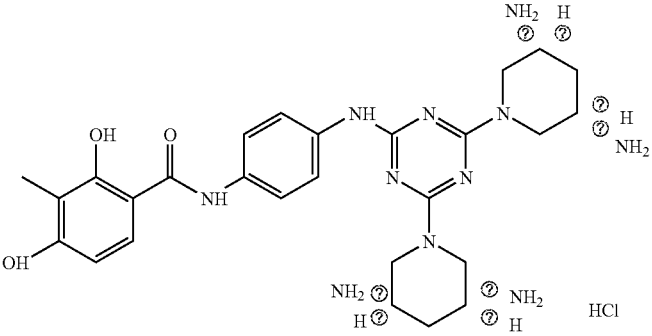 ⓘ indicates text missing or illegible when filed | N-[4-(2,4-dihydroxy-3-methyl-benzoylamino)-phenyl]-4,6-Bis-(cis-3,5-Diamino-piperidin-1-yl)-[1,3,5]triazie-2-amine | |
| 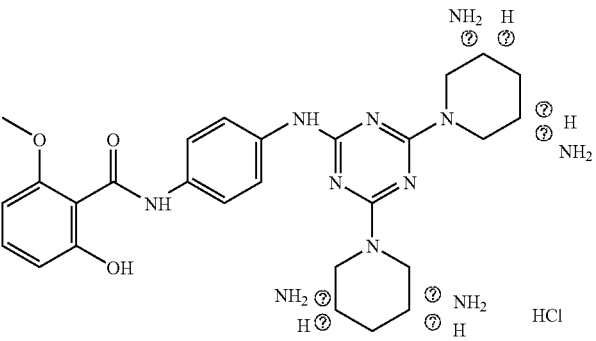 ⓘ indicates text missing or illegible when filed | N-[4-(2-hydroxy-6-methoxy-benzoylamino)-phenyl]-4,6-Bis-(cis-3,5-Diamino-piperidin-1-yl)-[1,3,5]triazine-2-amine | |

-continued

| Structure | Name | Potency |
|---|---|---|
| 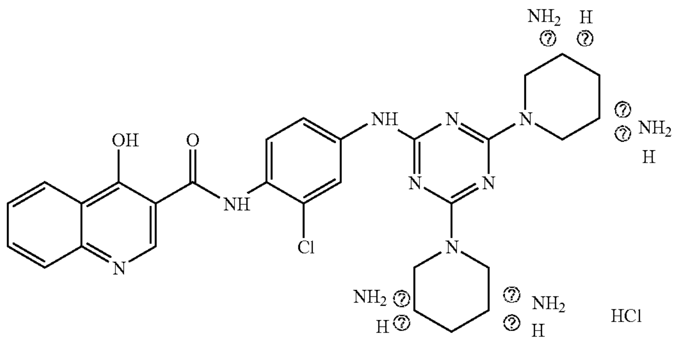 | N-{3-chloro-4-[(4-hydroxy-quinoline-3-carbonyl)-amino]-phenyl}-4,6-Bis-(cis-3,5-Diamino-piperidin-1-yl)-[1,3,5]triazine-2-amine | |
| 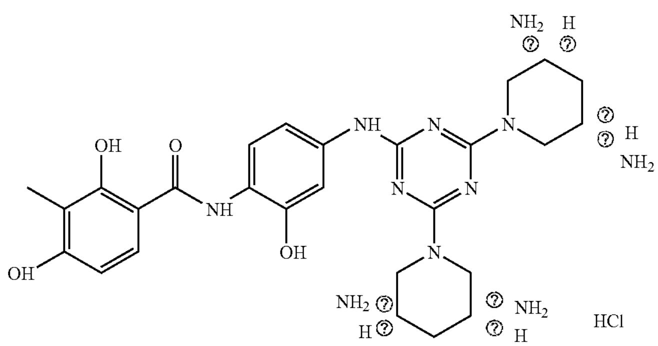 | N-[4-(2,4-dihydroxy-3-methyl-benzoylamino)-3-hydroxy-phenyl]-4,6-Bis-(cis-3,5-Diamino-piperidin-1-yl)-[1,3,5]triazine-2-amine | |
| 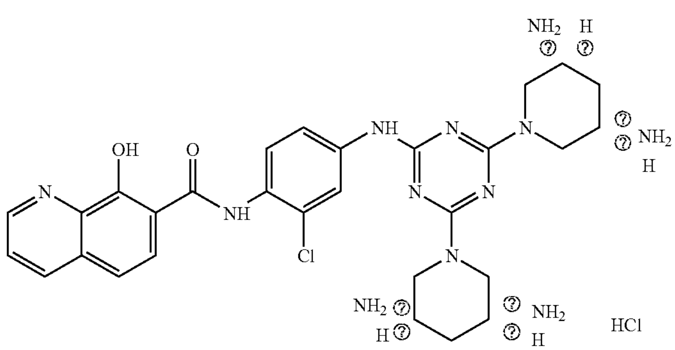 | N-{3-chloro-4-[*8-hydroxy-quinoline-7-carbonyl)-amino]-phenyl}-4,6-Bis-(cis-3,5-Diamino-piperidin-1-yl)-[1,3,5]triazine-2-amine | |

⍰ indicates text missing or illegible when filed

-continued

| Structure | Name | Potency |
|---|---|---|
| 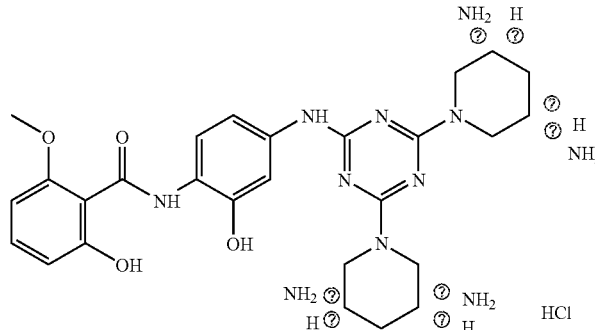 | N-[3-hydroxy-4-(2-hydroxy-6-methoxy-benzoylamino)-phenyl]-4,6-Bis-(cis-3,5-Diamino-piperidin-1-yl)-[1,3,5]triazine-2-amine | |

⑦ indicates text missing or illegible when filed

It is claimed:

1. A compound of Formula I:

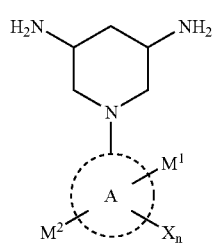

(I)

wherein:

Ring A is a 5- or 6-membered mono- or bicyclic aryl or heteroaryl;

$M^1$ and $M^2$ are independently —H, halo, —CF$_3$, —CN, —NO$_2$, —CONH$_2$, —COOH, —OH, or —NHNH$_2$, or an unsubstituted or substituted —(C$_1$–C$_6$)alkyl, aryl, heteroaryl, —(CH$_2$)$_n$-aryl, —(CH$_2$)$_n$-heteroaryl, —(CH$_2$)$_n$-heterocycloalkyl, —(CH═CH)$_n$-aryl, —(CH═CH)$_n$-heteroaryl, —(C$_2$–C$_6$)alkenylaryl, —(C$_2$–C$_6$)alkenyl-heteroaryl, —(C≡C)$_n$-aryl, —(C≡C)$_n$-heteroaryl, —O—(C$_1$–C$_6$)alkyl, —O-aryl, —O-heteroaryl, —O-cycloalkyl, —O-heterocycloalkyl, —S—(C$_1$–C$_6$)alkyl, —S-aryl, —S-heteroaryl, —S-cycloalkyl, —S-heterocycloalkyl, —(C═O)(C$_1$–C$_6$)alkyl, —(C═O)aryl, —(C═O)heterocycloalkyl, —O(C═O)—(C$_1$–C$_6$)alkyl, —(C═O)O—(C$_1$–C$_6$)alkyl, —(S═O)aryl, —(S═O)heteroeycloalkyl, —S(O)$_2$aryl, —S(O)$_2$heterocycloalkyl, —NHC(NH)-axyl, —NHNH-aryl, —NHNHC(O)-aryl, —NHNH-cycloheteroalkyl, —NHNHS(O)$_2$-aryl, —NHOH, —NHO—(C$_1$–C$_6$)alkyl, —N(OH)—(C$_1$–C$_6$)alkyl, —N((C$_1$–C$_6$)alkyl)O—(C$_1$–C$_6$)alkyl, —NHNHC(S)NH—(C$_1$–C$_6$)alkyl, —NHNH-heteroaryl, or —N(R$^1$)R$^2$, wherein R$^1$ and R$^2$ are independently selected from —H, a substituted or unsubstituted alkyl, aryl, heteroaryl, cycloalkyl, or heterocycloalkyl, or R$^1$ and R$^2$ together with the N atom form a 4-, 5, or 6-membered substituted or unsubstituted heterocycloalkyl, wherein n is an integer from 1–4;

X$_n$ is independently selected from —H, halo, —CF$_3$, —CN, —COOH, —OH, —NH$_2$, —NO$_2$, —C(O)N(R$^3$) R$^4$ wherein R$^3$ and R$^4$ are independently —(C$_1$–C$_6$) alkyl or —H, and optionally substituted —O—(C$_1$–C$_6$) alkyl or —(C$_1$–C$_6$)alkyl;

or a pharmaceutically acceptable salt, hydrate, or solvate thereof.

2. The compound of claim 1 wherein Ring A is selected from the group consisting of:

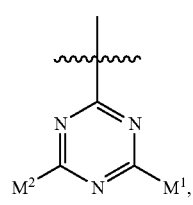

Ia

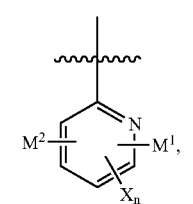

Ib

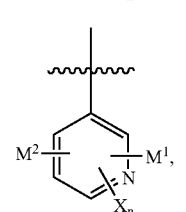

Ic

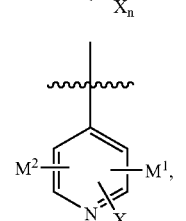

Id

Ie 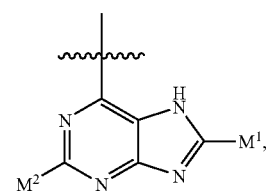
If 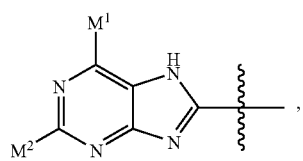
Ig 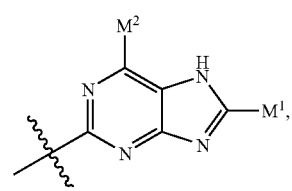
Ih 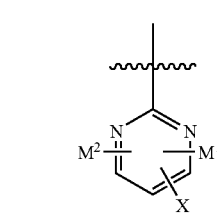
Ii 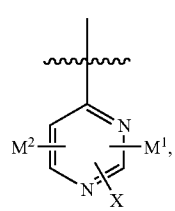
Ij 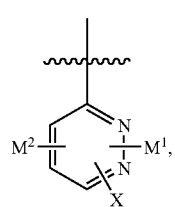
Ik 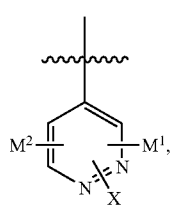
Il 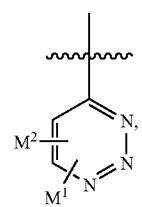
Im 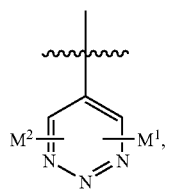
In 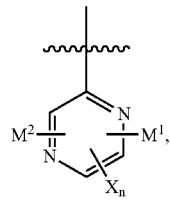
Io 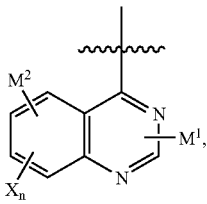
Ip 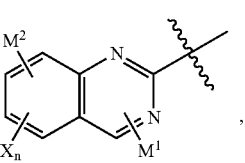
Iq 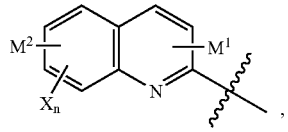
Ir 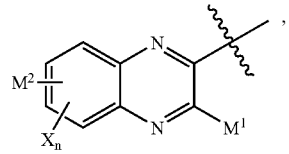
Is 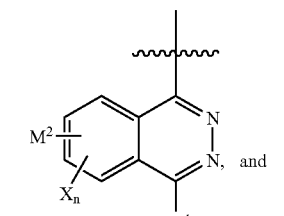, and
It 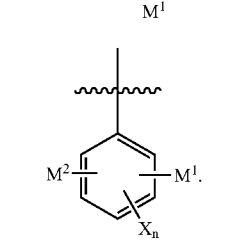.
3. The compound of claim 1 wherein Ring A is selected from the group consisting of:

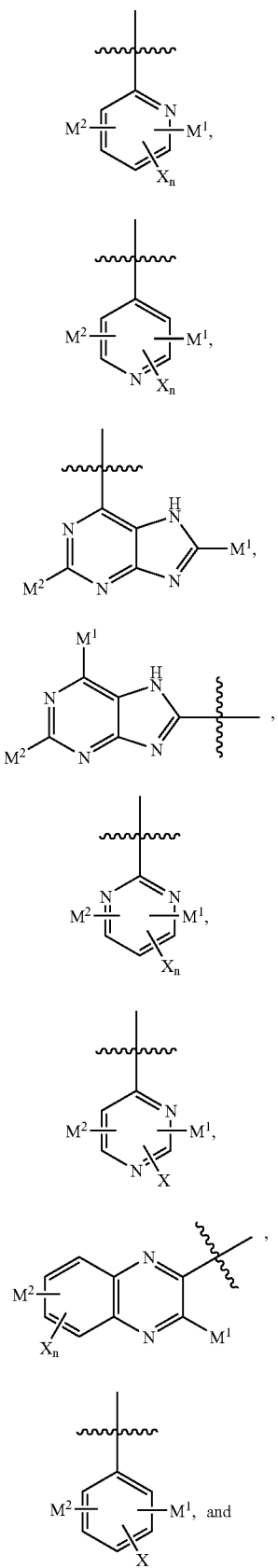
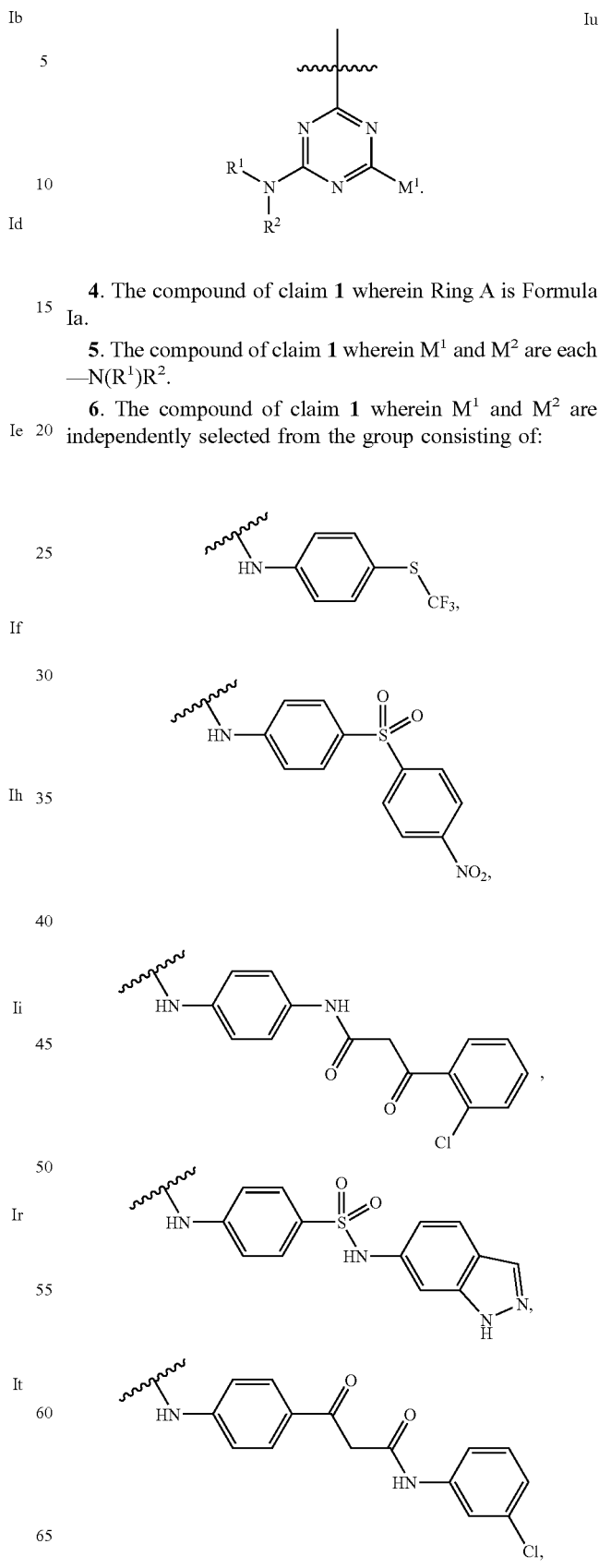
4. The compound of claim 1 wherein Ring A is Formula Ia.
5. The compound of claim 1 wherein $M^1$ and $M^2$ are each $-N(R^1)R^2$.
6. The compound of claim 1 wherein $M^1$ and $M^2$ are independently selected from the group consisting of:

723
-continued
724
-continued
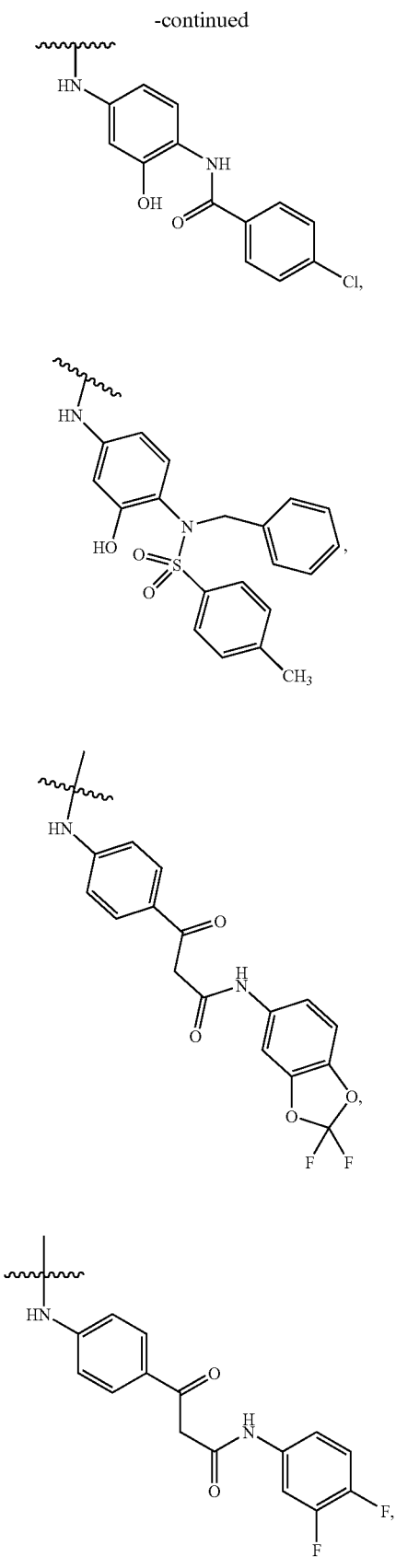
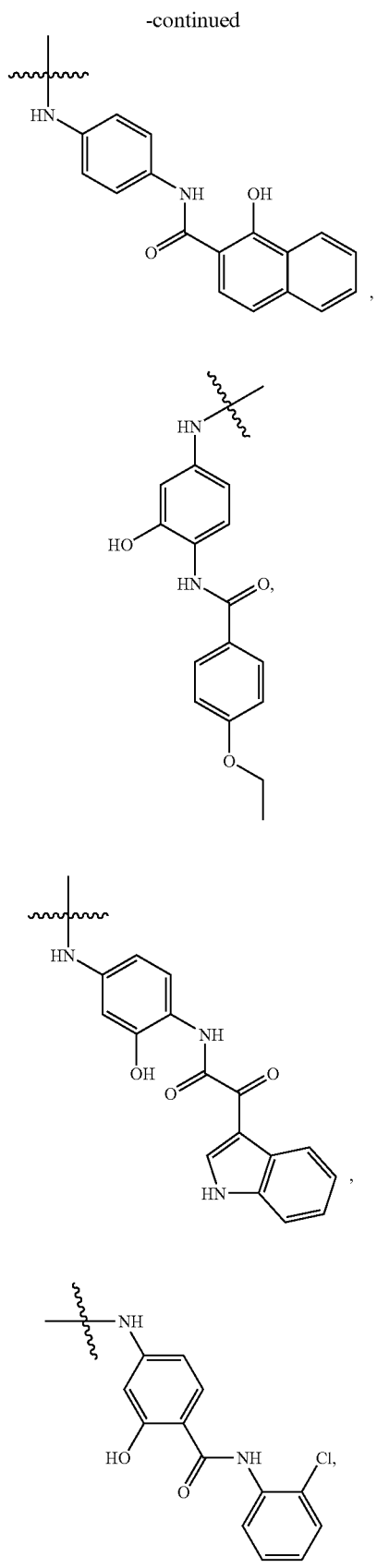

725
-continued
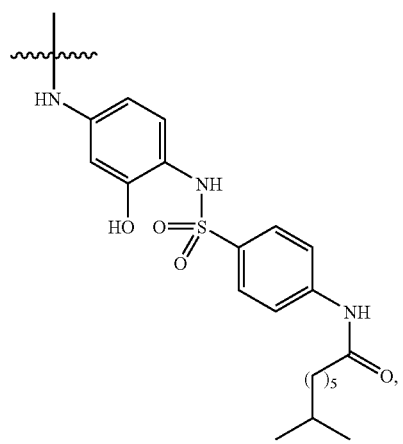
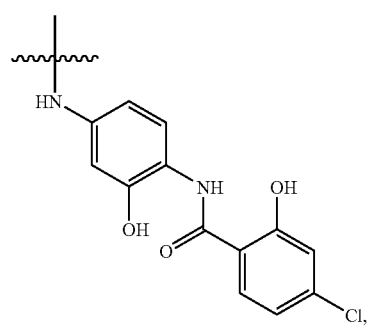
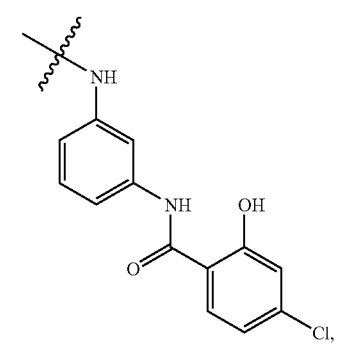
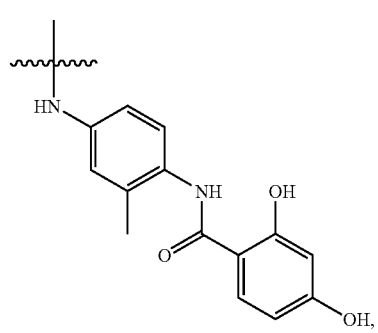
726
-continued
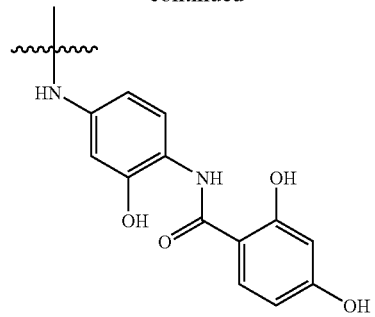
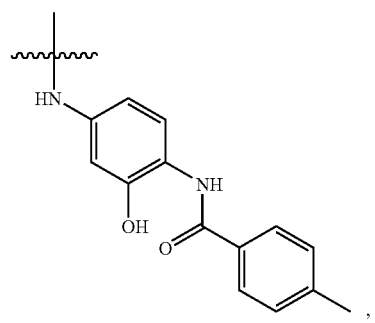
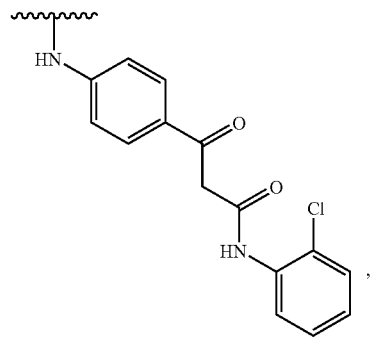
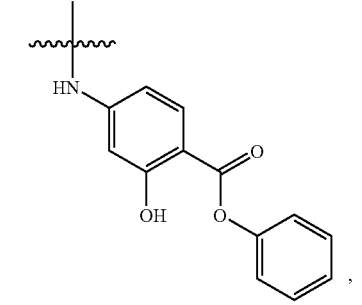
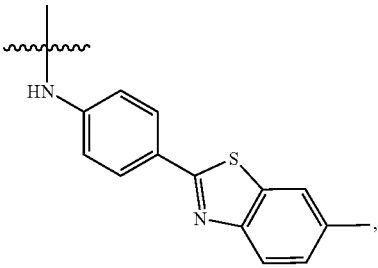

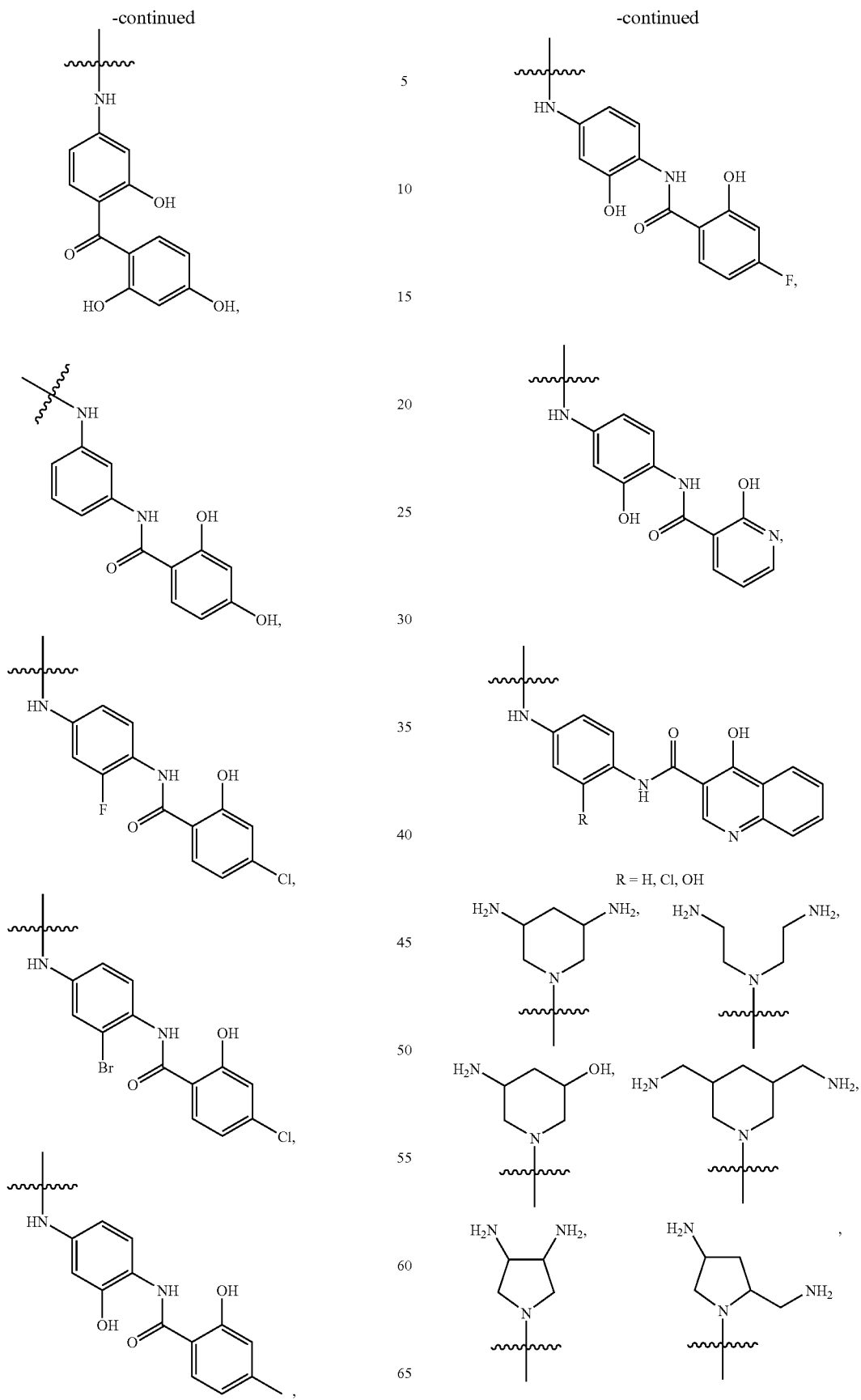

-continued
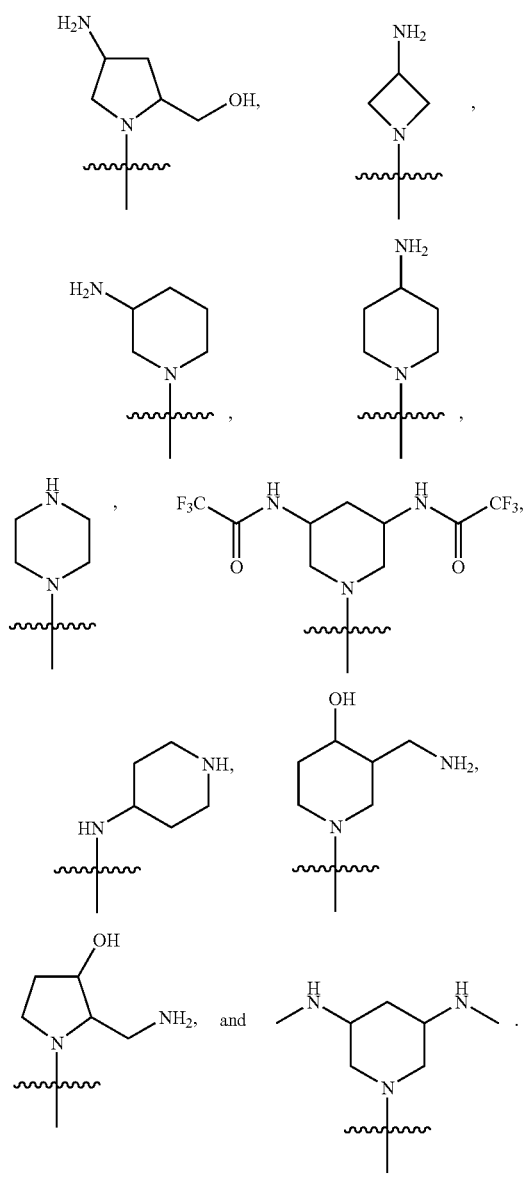
7. The compound of claim 6 wherein $M^2$ is selected from the group consisting of:
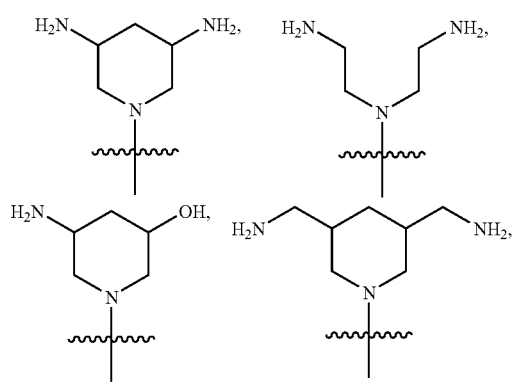
-continued
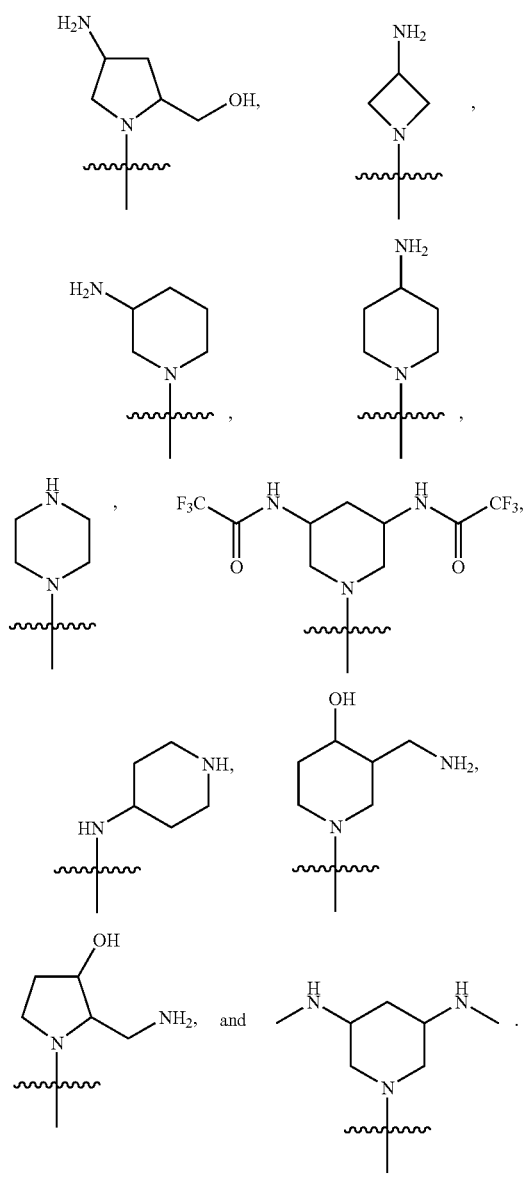
8. The compound of claim 6 wherein Ring A is selected from the group consisting of:
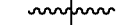
Ib

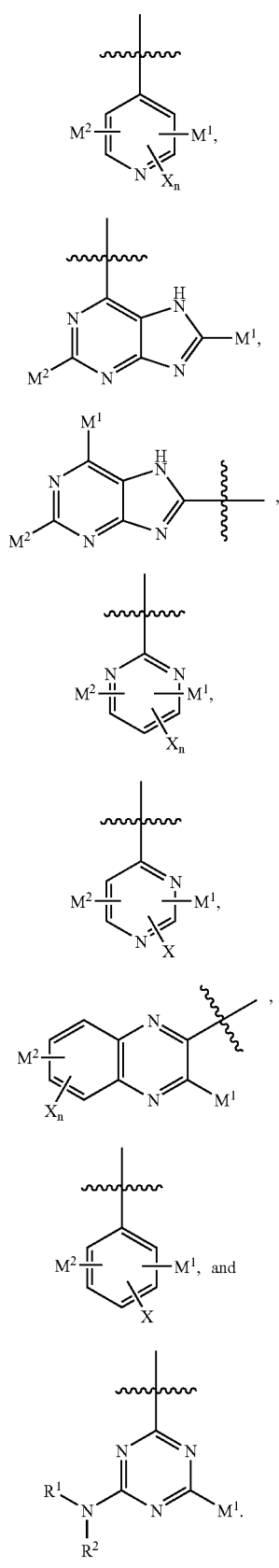

9. The compound of claim 6 wherein Ring A is Formula Ia.

10. A pharmaceutically acceptable composition comprising a therapeutically effect amount of the compound of Formula I, or a salt or solvate thereof and a pharmaceutically acceptable carrier.

11. A compound selected from the group consisting of:

N-[4-(2,2-difluoro-benzo[1,3]dioxol-5-ylcarbamoyl)-3-hydroxy-phenyl]-4,6-Bis-((3R,5S)-3,5-diamino-piperidin-1-yl)-[1,3,5]triazine-2-amine;

N-[4-(4-chloro-2,5-dimethoxy-phenylcarbamoyl)-3-hydroxy-phenyl]-4,6-Bis-((3R,5S)-3,5-diamino-piperidin-1-yl)-[1,3,5]triazine-2-amine;

N-[4-(2,4-dichloro-phenylcarbamoyl)-3-hydroxy-phenyl]-4,6-Bis-((3R,5S)-3,5-diamino-piperidin-1-yl)-[1,3,5]triazine-2-amine;

N-[4-(3-chloro-phenylcarbamoyl)-3-hydroxy-phenyl]-4,6-Bis-((3R,5S)-3,5-diamino-piperidin-1-yl)-[1,3,5]triazine-2-amine;

N-[4-(4-fluoro-phenylcarbamoyl)-3-hydroxy-phenyl]-4,6-Bis-((3R,5S)-3,5-diamino-piperidin-1-yl)-[1,3,5]triazine-2-amine;

N-[4-(2,5-dimethoxy-phenylcarbamoyl)-3-hydroxy-phenyl]-4,6-Bis-((3R,5S)-3,5-diamino-piperidin-1-yl)-[1,3,5]triazine-2-amine;

N-[4-(3-chloro-4-fluoro-phenylcarbamoyl)-3-hydroxy-phenyl]-4,6-Bis-((3R,5S)-3,5-diamino-piperidin-1-yl)-[1,3,5]triazine-2-amine;

N-[3-hydroxy-4-(3-trifluoromethoxy-phenylcarbamoyl)-phenyl]-4,6-Bis-((3R,5S)-3,5-diamino-piperidin-1-yl)-[1,3,5]triazine-2-amine;

N-[4-(3,4-difluoro-phenylcarbamoyl)-3-hydroxy-phenyl]-4,6-Bis-((3R,5S)-3,5-diamino-piperidin-1-yl)-[1,3,5]triazine-2-amine;

N-[4-(4-chloro-2-fluoro-phenylcarbamoyl)-3-hydroxy-phenyl]-4,6-Bis-((3R,5S)-3,5-diamino-piperidin-1-yl)-[1,3,5]triazine-2-amine;

N-[4-(benzo[1,3]dioxol-5-ylcarbamoyl)-3-hydroxy-phenyl]-4,6-Bis-((3R,5S)-3,5-diamino-piperidin-1-yl)-[1,3,5]triazine-2-amine;

N-[3-hydroxy-4-(3-trifluoromethylsulfanyl-phenylcarbamoyl)-phenyl]-4,6-Bis-((3R,5S)-3,5-diamino-piperidin-1-yl)-[1,3,5]triazine-2-amine;

N-[3-hydroxy-4-(3-trifluoromethyl-phenylcarbamoyl)-phenyl]-4,6-Bis-((3R,5S)-3,5-diamino-piperidin-1-yl)-[1,3,5]triazine-2-amine;

N-[4-(3,4-dichloro-phenylcarbamoyl)-3-hydroxy-phenyl]-4,6-Bis-((3R,5S)-3,5-diamino-piperidin-1-yl)-[1,3,5]triazine-2-amine;

N-[3-hydroxy-4-(4-hydroxy-phenylcarbamoyl)-phenyl]-4,6-Bis-((3R,5S)-3,5-diamino-piperidin-1-yl)-[1,3,5]triazine-2-amine;

N-[4-(1H-benzoimidazol-5-ylcarbamoyl)-3-hydroxy-phenyl]-4,6-Bis-((3R,5S)-3,5-diamino-piperidin-1-yl)-[1,3,5]triazine-2-amine;

1-Hydroxy-naphthalene-2-carboxylic acid {4-[4-[bis-(2-amino-ethyl)-amino]-6-((3R,5S)-3,5-diamino-piperidin-1-yl)-[1,3,5]triazin-2-ylamino]-phenyl}-amide;

N-{4-[2-(2-chloro-phenylcarbamoyl)-acetyl]-phenyl}-4,6-Bis-((3R,5S)-3,5-diamino-piperidin-1-yl)-[1,3,5]triazine-2-amine;

3-{4-[4-((3S,5R)-3-Amino-5-hydroxy-piperidin-1-yl)-6-((3S,5R)-3,5-diamino-piperidin-1-yl)-[1,3,5]triazin-2-ylamino]-phenyl}-N-(2-chloro-phenyl)-3-oxo-propionamide;

1-Hydroxy-naphthalene-2-carboxylic acid {4-[4-((3S,5R)-3-amino-5-hydroxy-piperidin-1-yl)-6-((3S,5R)-3,5-diamino-piperidin-1-yl)-[1,3,5]triazin-2-ylamino]-phenyl}-amide;

3-[4-((3S,5R)-3-Amino-5-hydroxy-piperidin-1-yl)-6-((3S,5R)-3,5-diamino-piperidin-1-yl)-[1,3,5]triazin-2-ylamino]-fluoren-9-one;

4-[4-((3S,5R)-3-Amino-5-hydroxy-piperidin-1-yl)-6-((3S,5R)-3,5-diamino-piperidin-1-yl)-[1,3,5]triazin-2-ylamino]-2-hydroxy-benzoic acid phenyl ester;

N-{4-[4-((3S,5R)-3-Amino-5-hydroxy-piperidin-1-yl)-6-((3S,5R)-3,5-diamino-piperidin-1-yl)-[1,3,5]triazin-2-ylamino]-2-hydroxy-phenyl}-4-chloro-benzamide;

N-Benzyl-N-{4-[4-((3R,5S)-3,5-diamino-piperidin-1-yl)-6-((3R,4S)-3,4-diamino-pyrrolidin-1-yl)-[1,3,5]triazin-2-ylamino]-2-hydroxy-phenyl}-4-methyl-benzenesulfonamide;

1-Hydroxy-naphthalene-2-carboxylic acid {4-[4-((3R,5S)-3,5-diamino-piperidin-1-yl)-6-((3R,4S)-3,4-diamino-pyrrolidin-1-yl)-[1,3,5]triazin-2-ylamino]-phenyl}-amide;

N-[4-(3,5-dichloro-2-hydroxy-benzenesulfonylamino)-3-hydroxy-phenyl]-4,6-Bis-((3R,5S)-3,5-diamino-piperidin-1-yl)-[1,3,5]triazine-2-amine;

N-[4-(4-ethoxy-benzoylamino)-3-hydroxy-phenyl]-4,6-Bis-((3R,5S)-3,5-diamino-piperidin-1-yl)-[1,3,5]triazine-2-amine;

N-{4-[4-((3R,5S)-3,5-Bis-(aminomethyl)-piperidin-1-yl)-6-((3R,5S)-3,5-diamino-piperidin-1-yl)-[1,3,5]triazin-2-ylamino]-2-hydroxy-phenyl}-4-chloro-benzamide;

1-Hydroxy-naphthalene-2-carboxylic acid {4-[4-((3R,5S)-3,5-bis-(aminomethyl)-piperidin-1-yl)-6-((3R,5S)-3,5-diamino-piperidin-1-yl)-[1,3,5]triazin-2-ylamino]-phenyl}-amide;

N-{4-[2-(3,4-difluoro-phenylcarbamoyl)-acetyl]-phenyl}-4,6-Bis-((3R,5S)-3,5-diamino-piperidin-1-yl)-[1,3,5]triazine-2-amine;

N-{4-[2-(2,2-difluoro-benzo[1,3]dioxol-5-ylcarbamoyl)-acetyl]-phenyl}-4,6-Bis-((3R,5S)-3,5-diamino-piperidin-1-yl)-[1,3,5]triazine-2-amine;

N-[4-(3-bromo-benzoylamino)-3-hydroxy-phenyl]-4,6-Bis-((3R,5S)-3,5-diamino-piperidin-1-yl)-[1,3,5]triazine-2-amine;

N-[3-hydroxy-4-(3-phenyl-acryloylamino)-phenyl]-4,6-Bis-((3R,5S)-3,5-diamino-piperidin-1-yl)-[1,3,5]triazine-2-amine;

1-Hydroxy-naphthalene-2-carboxylic acid {4-[4-((2S,4S)-4-amino-2-aminomethyl-pyrrolidin-1-yl)-6-((3R,5S)-3,5-diamino-piperidin-1-yl)-[1,3,5]triazin-2-ylamino]-phenyl}-amide;

3-{4-[4-((2S,4S)-4-Amino-2-aminomethyl-pyrrolidin-1-yl)-6-((3R,5S)-3,5-diamino-piperidin-1-yl)-[1,3,5]triazin-2-ylamino]-phenyl}-3-oxo-N-(4-trifluoromethylsulfanyl-phenyl)-propionamide;

4-[4-((2S,4S)-4-Amino-2-aminomethyl-pyrrolidin-1-yl)-6-((3R,5S)-3,5-diamino-piperidin-1-yl)-[1,3,5]triazin-2-ylamino]-2-hydroxy-benzoic acid phenyl ester;

N-{4-[4-((2S,4S)-4-Amino-2-aminomethyl-pyrrolidin-1-yl)-6-((3R,5S)-3,5-diamino-piperidin-1-yl)-[1,3,5]triazin-2-ylamino]-2-hydroxy-phenyl}-4-chloro-benzamide;

3-{4-[4-((2S,4S)-4-Amino-2-aminomethyl-pyrrolidin-1-yl)-6-((3R,5S)-3,5-diamino-piperidin-1-yl)-[1,3,5]triazin-2-ylamino]-phenyl}-N-(2,2-difluoro-benzo[1,3]dioxol-5-yl)-3-oxo-propionamide;

1-Hydroxy-naphthalene-2-carboxylic acid {4-[4-((2S,4S)-4-amino-2-hydroxymethyl-pyrrolidin-1-yl)-6-((3R,5S)-3,5-diamino-piperidin-1-yl)-[1,3,5]triazin-2-ylamino]-phenyl}-amide;

3-{4-[4-((2S,4S)-4-Amino-2-hydroxymethyl-pyrrolidin-1-yl)-6-((3R,5S)-3,5-diamino-piperidin-1-yl)-[1,3,5]triazin-2-ylamino]-phenyl}-3-oxo-N-(4-trifluoromethylsulfanyl-phenyl)-propionamide;

3-{4-[4-((2S,4S)-4-Amino-2-hydroxymethyl-pyrrolidin-1-yl)-6-((3R,5S)-3,5-diamino-piperidin-1-yl)-[1,3,5]triazin-2-ylamino]-phenyl}-N-(2,2-difluoro-benzo[1,3]dioxol-5-yl)-3-oxo-propionamide;

N-(2-Chloro-phenyl)-3-{4-[4-((3R,5S)-3,5-diamino-piperidin-1-yl)-6-methoxy-[1,3,5]triazin-2-ylamino]-phenyl}-3-oxo-propionamide;

N-Benzyl-N-{4-[4-((3R,5S)-3,5-diamino-piperidin-1-yl)-6-methoxy-[1,3,5]triazin-2-ylamino]-2-hydroxy-phenyl}-4-methyl-benzenesulfonamide;

1-Hydroxy-naphthalene-2-carboxylic acid {4-[4-((3R,5S)-3,5-diamino-piperidin-1-yl)-6-methoxy-[1,3,5]triazin-2-ylamino]-phenyl}-amide;

3-{4-[4-((3R,5S)-3,5-Diamino-piperidin-1-yl)-6-methoxy-[1,3,5]triazin-2-ylamino]-phenyl}-3-oxo-N-(4-trifluoromethylsulfanyl-phenyl)-propionamide;

4-[4-((3R,5S)-3,5-Diamino-piperidin-1-yl)-6-methoxy-[1,3,5]triazin-2-ylamino]-2-hydroxy-benzoic acid phenyl ester;

4-Chloro-N-{4-[4-((3R,5S)-3,5-diamino-piperidin-1-yl)-6-methoxy-[1,3,5]triazin-2-ylamino]-2-hydroxy-phenyl}-benzamide;

3-{4-[4-((3R,5S)-3,5-Diamino-piperidin-1-yl)-6-methoxy-[1,3,5]triazin-2-ylamino]-phenyl}-N-(3,4-difluoro-phenyl)-3-oxo-propionamide;

3-{4-[4-((3R,5S)-3,5-Diamino-piperidin-1-yl)-6-methoxy-[1,3,5]triazin-2-ylamino]-phenyl}-N-(2,2-difluoro-benzo[1,3]dioxol-5-yl)-3-oxo-propionamide;

N-{4-[(adamantane-1-carbonyl)-amino]-3-hydroxy-phenyl}-4,6-Bis-((3R,5S)-3,5-diamino-piperidin-1-yl)-[1,3,5]triazine-2-amine;

N-[4-(3-chloro-benzoylamino)-3-hydroxy-phenyl]-4,6-Bis-((3R,5S)-3,5-diamino-piperidin-1-yl)-[1,3,5]triazine-2-amine;

1-Hydroxy-naphthalene-2-carboxylic acid {4-[4-((3R,4S)-3-aminomethyl-4-hydroxy-piperidin-1-yl)-6-((3R,5S)-3,5-diamino-piperidin-1-yl)-[1,3,5]triazin-2-ylamino]-phenyl}-amide;

1-Hydroxy-naphthalene-2-carboxylic acid {4-[4-((2S,3S)-2-aminomethyl-3-hydroxy-pyrrolidin-1-yl)-6-((3R,5S)-3,5-diamino-piperidin-1-yl)-[1,3,5]triazin-2-ylamino]-phenyl}-amide;

N-{4-[4-((2S,3S)-2-Aminomethyl-3-hydroxy-pyrrolidin-1-yl)-6-((3R,5S)-3,5-diamino-piperidin-1-yl)-[1,3,5]triazin-2-ylamino]-2-hydroxy-phenyl}-4-methyl-benzamide;

N-{3-hydroxy-4-[2-(1H-indol-3-yl)-2-oxo-acetylamino]-phenyl}-4,6-Bis-((3R,5S)-3,5-diamino-piperidin-1-yl)-[1,3,5]triazine-2-amine;

N-{3-hydroxy-4-[3-phenyl-2-(toluene-4-sulfonylamino)-propionylamino]-phenyl}-4,6-Bis-((3R,5S)-3,5-diamino-piperidin-1-yl)-[1,3,5]triazine-2-amine;

N-[4-(3-oxo-3-phenyl-propionylamino)-phenyl]-4,6-Bis-((3R,5S)-3,5-diamino-piperidin-1-yl)-[1,3,5]triazine-2-amine;

N-[3-hydroxy-4-(4-methoxy-benzoylamino)-phenyl]-4,6-Bis-((3R,5S)-3,5-diamino-piperidin-1-yl)-[1,3,5]triazine-2-amine;

N-[4-(2,4-dimethoxy-benzoylamino)-3-hydroxy-phenyl]-4,6-Bis-((3R,5S)-3,5-diamino-piperidin-1-yl)-[1,3,5]triazine-2-amine;

N-[3-hydroxy-4-(2-methoxy-benzoylamino)-phenyl]-4,6-Bis-((3R,5S)-3,5-diamino-piperidin-1-yl)-[1,3,5]triazine-2-amine;

N-Benzyl-N-{4-[4-((3R,5S)-3,5-diamino-piperidin-1-yl)-6-(4-pyridin-4-yl-piperazin-1-yl)-[1,3,5]triazin-2-ylamino]-2-hydroxy-phenyl}-4-methyl-benzenesulfonamide;

4-Chloro-N-{4-[4-((3S,5R)-3,5-diamino-piperidin-1-yl)-6-piperazin-1-yl-[1,3,5]triazin-2-ylamino]-2-hydroxy-phenyl}-benzamide;

N-{4-[4-((3R,5S)-3,5-Diamino-piperidin-1-yl)-6-(piperidin-4-ylamino)-[1,3,5]triazin-2-ylamino]-2-hydroxy-phenyl}-4-methyl-benzamide;

4-Chloro-N-{4-[4-((3S,5R)-3,5-diamino-piperidin-1-yl)-6-(piperidin-4-ylamino)-[1,3,5]triazin-2-ylamino]-2-hydroxy-phenyl}-benzamide;

4-Chloro-N-{4-[4-((3S,5R)-3,5-diamino-piperidin-1-yl)-6-(piperidin-3-ylamino)-[1,3,5]triazin-2-ylamino]-2-hydroxy-phenyl}-benzamide;

N-{4-[(1-hydroxy-naphthalene-2-carbonyl)-amino]-phenyl}-4,6-Bis-((3R,5S)-3,5-diamino-piperidin-1-yl)-[1,3,5]triazine-2-amine;

N-[3-hydroxy-4-(4-methyl-benzoylamino)-phenyl]-4,6-Bis-((3R,5S)-3,5-diamino-piperidin-1-yl)-[1,3,5]triazine-2-amine;

4-[4,6-Bis-((3R,5S)-3,5-diamino-piperidin-1-yl)-[1,3,5]triazin-2-ylamino]-2-hydroxy-benzoic acid phenyl ester;

N-(9H-fluoren-2-yl)-4,6-Bis-((3R,5S)-3,5-diamino-piperidin-1-yl)-[1,3,5]triazine-2-amine;

N-{4-[4-(3-Amino-azetidin-1-yl)-6-((3R,5S)-3,5-diamino-piperidin-1-yl)-[1,3,5]triazin-2-ylamino]-2-hydroxy-phenyl}-4-chloro-benzamide;

N-pyren-1-yl-4,6-Bis-((3R,5S)-3,5-diamino-piperidin-1-yl)-[1,3,5]triazine-2-amine;

N-(4-methyl-2-oxo-2H-chromen-7-yl)-4,6-Bis-((3R,5S)-3,5-diamino-piperidin-1-yl)-[1,3,5]triazine-2-amine;

N-(9-oxo-9H-fluoren-3-yl)-4,6-Bis-((3R,5S)-3,5-diamino-piperidin-1-yl)-[1,3,5]triazine-2-amine;

N-(4-phenylazo-phenyl)-4,6-Bis-((3R,5S)-3,5-diamino-piperidin-1-yl)-[1,3,5]triazine-2-amine;

N-[4-(6-methyl-benzothiazol-2-yl)-phenyl]-4,6-Bis-((3R,5S)-3,5-diamino-piperidin-1-yl)-[1,3,5]triazine-2-amine;

3-{4-[4-((2S,4R)-2-Aminomethyl-4-hydroxy-pyrrolidin-1-yl)-6-((3R,5S)-3,5-diamino-piperidin-1-yl)-[1,3,5]triazin-2-ylamino]-phenyl}-3-oxo-N-(4-trifluoromethylsulfanyl-phenyl)-propionamide;

3-{4-[4-((2S,4R)-2-Aminomethyl-4-hydroxy-pyrrolidin-1-yl)-6-((3R,5S)-3,5-diamino-piperidin-1-yl)-[1,3,5]triazin-2-ylamino]-phenyl}-N-(2,2-difluoro-benzo[1,3]dioxol-5-yl)-3-oxo-propionamide;

1-Hydroxy-naphthalene-2-carboxylic acid {4-[4-(2-amino-ethylamino)-6-((3R,5S)-3,5-diamino-piperidin-1-yl)-[1,3,5]triazin-2-ylamino]-phenyl}-amide;

N-[3-(2-hydroxy-3-methyl-benzoylamino)-phenyl]-4,6-Bis-((3R,5S)-3,5-diamino-piperidin-1-yl)-[1,3,5]triazine-2-amine;

N-[3-hydroxy-4-(2-hydroxy-3-methyl-benzoylamino)-phenyl]-4,6-Bis-((3R,5S)-3,5-diamino-piperidin-1-yl)-[1,3,5]triazine-2-amine;

N-[4-(2,3-dihydroxy-benzoylamino)-phenyl]-4,6-Bis-((3R,5S)-3,5-diamino-piperidin-1-yl)-[1,3,5]triazine-2-amine;

N-[3-(2,3-dihydroxy-benzoylamino)-phenyl]-4,6-Bis-((3R,5S)-3,5-diamino-piperidin-1-yl)-[1,3,5]triazine-2-amine;

N-[4-(2,3-dihydroxy-benzoylamino)-3-methyl-phenyl]-4,6-Bis-((3R,5S)-3,5-diamino-piperidin-1-yl)-[1,3,5]triazine-2-amine;

N-[4-(2,3-dihydroxy-benzoylamino)-3-hydroxy-phenyl]-4,6-Bis-((3R,5S)-3,5-diamino-piperidin-1-yl)-[1,3,5]triazine-2-amine;

N-[4-(2-hydroxy-4-methyl-benzoylamino)-phenyl]-4,6-Bis-((3R,5S)-3,5-diamino-piperidin-1-yl)-[1,3,5]triazine-2-amine;

N-[3-hydroxy-4-(2-hydroxy-4-methyl-benzoylamino)-phenyl]-4,6-Bis-((3R,5S)-3,5-diamino-piperidin-1-yl)-[1,3,5]triazine-2-amine;

N-{4-[2-(3-chloro-phenylcarbamoyl)-acetyl]-phenyl}-4,6-Bis-((3R,5S)-3,5-diamino-piperidin-1-yl)-[1,3,5]triazine-2-amine;

N-[4-(2-phenylcarbamoyl-acetyl)-phenyl]-4,6-Bis-((3R,5S)-3,5-diamino-piperidin-1-yl)-[1,3,5]triazine-2-amine;

N-{4-[2-(4-trifluoromethylsulfanyl-phenylcarbamoyl)-acetyl]-phenyl}-4,6-Bis-((3R,5S)-3,5-diamino-piperidin-1-yl)-[1,3,5]triazine-2-amine;

N-{4-[2-(3-trifluoromethylsulfanyl-phenylcarbamoyl)-acetyl]-phenyl}-4,6-Bis-((3R,5S)-3,5-diamino-piperidin-1-yl)-[1,3,5]triazine-2-amine;

N-{4-[2-(4-chloro-phenylcarbamoyl)-acetyl]-phenyl}-4,6-Bis-((3R,5S)-3,5-diamino-piperidin-1-yl)-[1,3,5]triazine-2-amine;

N-[4-(4-chloro-benzoylamino)-3-hydroxy-phenyl]-4,6-Bis-((3R,5S)-3,5-diamino-piperidin-1-yl)-[1,3,5]triazine-2-amine;

N-[3-(2-hydroxy-3-nitro-benzoylamino)-phenyl]-4,6-Bis-((3R,5S)-3,5-diamino-piperidin-1-yl)-[1,3,5]triazine-2-amine;

N-[4-(2,4-dihydroxy-benzoylamino)-phenyl]-4,6-Bis-((3R,5S)-3,5-diamino-piperidin-1-yl)-[1,3,5]triazine-2-amine;

N-[4-(2,4-dihydroxy-benzoylamino)-3-methyl-phenyl]-4,6-Bis-((3R,5S)-3,5-diamino-piperidin-1-yl)-[1,3,5]triazine-2-amine;

1-Hydroxy-naphthalene-2-carboxylic acid {4-[3-((3R,5S)-3,5-diamino-piperidin-1-yl)-5-((3S,5R)-3,5-diamino-piperidin-1-yl)-phenylamino]-phenyl}-amide;

N-{4-[4-((2S,4S)-4-Amino-2-aminomethyl-pyrrolidin-1-yl)-6-((3R,5S)-3,5-diamino-piperidin-1-yl)-[1,3,5]triazin-2-ylamino]-2-hydroxy-phenyl}-2-(1H-indol-3-yl)-2-oxo-acetamide;

1-Benzyloxy-naphthalene-2-carboxylic acid {4-[3-((3R,5S)-3,5-diamino-piperidin-1-yl)-5-((3S,5R)-3,5-diamino-piperidin-1-yl)-phenylamino]-phenyl}-amide;

1-Hydroxy-naphthalene-2-carboxylic acid {4-[4,6-bis-((2S,4S)-4-amino-2-aminomethyl-pyrrolidin-1-yl)-[1,3,5]triazin-2-ylamino]-phenyl}-amide;

N-(4-hexanoylamino-3-hydroxy-phenyl)-4,6-Bis-((3R,5S)-3,5-diamino-piperidin-1-yl)-[1,3,5]triazine-2-amine;

N-[3-hydroxy-4-(7-methyl-octanoylamino)-phenyl]-4,6-Bis-((3R,5S)-3,5-diamino-piperidin-1-yl)-[1,3,5]triazine-2-amine;

N-[4-(2-ethyl-heptanoylamino)-3-hydroxy-phenyl]-4,6-Bis-((3R,5S)-3,5-diamino-piperidin-1-yl)-[1,3,5]triazine-2-amine;

N-(4-decanoylamino-3-hydroxy-phenyl)-4,6-Bis-((3R,5S)-3,5-diamino-piperidin-1-yl)-[1,3,5]triazine-2-amine;

N-(4-benzoylamino-3-hydroxy-phenyl)-4,6-Bis-((3R,5S)-3,5-diamino-piperidin-1-yl)-[1,3,5]triazine-2-amine;

N-{4-[4-(2-ethyl-heptanoylamino)-benzene sulfonylamino]-3-hydroxy-phenyl}-4,6-Bis-((3R,5S)-3,5-diamino-piperidin-1-yl)-[1,3,5]triazine-2-amine;

N-[4-(4-decanoylamino-benzenesulfonylamino)-3-hydroxy-phenyl]-4,6-Bis-((3R,5S)-3,5-diamino-piperidin-1-yl)-[1,3,5]triazine-2-amine;

N-{3-hydroxy-4-[4-(3-methyl-butyrylamino)-benzene sulfonylamino]-phenyl}-4,6-Bis-((3R,5S)-3,5-diamino-piperidin-1-yl)-[1,3,5]triazine-2-amine;

1-Hydroxy-naphthalene-2-carboxylicacid {4-[4-((3S,5R)-3,5-diamino-piperidin-1-yl)-[1,3,5]triazin-2-ylamino]-phenyl}-amide;

N-{4-[4-[Bis-(2-amino-ethyl)-amino]-6-((3R,5S)-3,5-diamino-piperidin-1-yl)-[1,3,5]triazin-2-ylamino]-2-hydroxy-phenyl}-2-(1H-indol-3-yl)-2-oxo-acetamide;

N-{4-[(1-hydroxy-naphthalene-2-carbonyl)-amino]-phenyl}-4,6-Bis-((3R,5S)-3,5-diamino-piperidin-1-yl)-[1,3,5]triazine-2-amine;

N-[4-(4-chloro-2-hydroxy-benzoylamino)-phenyl]-4,6-Bis-((3R,5S)-3,5-diamino-piperidin-1-yl)-[1,3,5]triazine-2-amine;

N-[4-(4-chloro-2-hydroxy-benzoylamino)-3-methyl-phenyl]-4,6-Bis-((3R,5S)-3,5-diamino-piperidin-1-yl)-[1,3,5]triazine-2-amine;

N-[3-chloro-4-(4-chloro-2-hydroxy-benzoylamino)-phenyl]-4,6-Bis-((3R,5S)-3,5-diamino-piperidin-1-yl)-[1,3,5]triazine-2-amine;

N-[3,5-dichloro-4-(4-chloro-2-hydroxy-benzoylamino)-phenyl]-4,6-Bis-((3R,5S)-3,5-diamino-piperidin-1-yl)-[1,3,5]triazine-2-amine;

N-[3-bromo-4-(4-chloro-2-hydroxy-benzoylamino)-phenyl]-4,6-Bis-((3R,5S)-3,5-diamino-piperidin-1-yl)-[1,3,5]triazine-2-amine;

N-[4-(4-chloro-2-hydroxy-benzoylamino)-3-fluoro-phenyl]-4,6-Bis-((3R,5S)-3,5-diamino-piperidin-1-yl)-[1,3,5]triazine-2-amine;

N-(8-hydroxy-quinolin-5-yl)-4,6-Bis-((3R,5S)-3,5-diamino-piperidin-1-yl)-[1,3,5]triazine-2-amine;

N-[4-(4-chloro-2-hydroxy-benzoylamino)-3-trifluoromethyl-phenyl]-4,6-Bis-((3R,5S)-3,5-diamino-piperidin-1-yl)-[1,3,5]triazine-2-amine;

N-[4-(4-chloro-2-hydroxy-benzoylamino)-3-phenylcarbamoyl-phenyl]-4,6-Bis-((3R,5S)-3,5-diamino-piperidin-1-yl)-[1,3,5]triazine-2-amine;

N-[4-(4-chloro-2-hydroxy-benzoylamino)-3-methoxy-phenyl]-4,6-Bis-((3R,5S)-3,5-diamino-piperidin-1-yl)-[1,3,5]triazine-2-amine;

N-{4-[(1-hydroxy-naphthalene-2-carbonyl)-amino]-phenyl}-4,6-Bis-((3R,5S)-3,5-diamino-piperidin-1-yl)-[1,3,5]triazine-2-amine;

N-[3-chloro-4-(4-chloro-2-hydroxy-benzoylamino)-5-methyl-phenyl]-4,6-Bis-((3R,5S)-3,5-diamino-piperidin-1-yl)-[1,3,5]triazine-2-amine;

N-[4-(4-fluoro-2-hydroxy-benzoylamino)-3-hydroxy-phenyl]-4,6-Bis-((3R,5S)-3,5-diamino-piperidin-1-yl)-[1,3,5]triazine-2-amine;

N-[3-hydroxy-4-(2-hydroxy-5-trifluoromethoxy-benzoylamino)-phenyl]-4,6-Bis-((3R,5S)-3,5-diamino-piperidin-1-yl)-[1,3,5]triazine-2-amine;

N-[3-chloro-4-(3,4-difluoro-2-hydroxy-benzoylamino)-phenyl]-4,6-Bis-((3R,5S)-3,5-diamino-piperidin-1-yl)-[1,3,5]triazine-2-amine;

N-{3-chloro-4-[4-(1,3-dihydro-isoindol-2-yl)-2-hydroxy-benzoylamino]-phenyl}-4,6-Bis-((3R,5S)-3,5-diamino-piperidin-1-yl)-[1,3,5]triazine-2-amine;

N-{3-chloro-4-[(2-hydroxy-naphthalene-1-carbonyl)-amino]-phenyl}-4,6-Bis-((3R,5S)-3,5-diamino-piperidin-1-yl)-[1,3,5]triazine-2-amine;

N-{3-chloro-4-[(2-hydroxy-6-trifluoromethyl-pyridine-3-carbonyl)-amino]-phenyl}-4,6-Bis-((3R,5S)-3,5-diamino-piperidin-1-yl)-[1,3,5]triazine-2-amine;

N-{3-hydroxy-4-[4-(7-methyl-octanoylamino)-benzene sulfonylamino]-phenyl}-4,6-Bis-((3R,5S)-3,5-diamino-piperidin-1-yl)-[1,3,5]triazine-2-amine;

N-[4-(4-fluoro-2-hydroxy-benzoylamino)-phenyl]-4,6-Bis-((3R,5S)-3,5-diamino-piperidin-1-yl)-[1,3,5]triazine-2-amine;

N-(3-chloro-4-nitro-phenyl)-4,6-Bis-((3R,5S)-3,5-diamino-piperidin-1-yl)-[1,3,5]triazine-2-amine;

N-{4-[4-(1,3-dihydro-isoindol-2-yl)-2-hydroxy-benzoylamino]-phenyl}-4,6-Bis-((3R,5S)-3,5-diamino-piperidin-1-yl)-[1,3,5]triazine-2-amine;

N-{4-[(2-hydroxy-6-trifluoromethyl-pyridine-3-carbonyl)-amino]-phenyl}-4,6-Bis-((3R,5S)-3,5-diamino-piperidin-1-yl)-[1,3,5]triazine-2-amine;

N-(6-nitro-benzothiazol-2-yl)-4,6-Bis-((3R,5S)-3,5-diamino-piperidin-1-yl)-[1,3,5]triazine-2-amine;

N-[4-(2-hydroxy-3,5-diisopropyl-benzoylamino)-phenyl]-4,6-Bis-((3R,5S)-3,5-diamino-piperidin-1-yl)-[1,3,5]triazine-2-amine;

N-[4-(4-dimethylamino-2-hydroxy-benzoylamino)-phenyl]-4,6-Bis-((3R,5S)-3,5-diamino-piperidin-1-yl)-[1,3,5]triazine-2-amine;

N-[4-(5-bromo-2-hydroxy-benzoylamino)-3-hydroxy-phenyl]-4,6-Bis-((3R,5S)-3,5-diamino-piperidin-1-yl)-[1,3,5]triazine-2-amine;

N-[3-hydroxy-4-(2-hydroxy-3,5-diisopropyl-benzoylamino)-phenyl]-4,6-Bis-((3R,5S)-3,5-diamino-piperidin-1-yl)-[1,3,5]triazine-2-amine;

N-[4-(4-dimethylamino-2-hydroxy-benzoylamino)-3-hydroxy-phenyl]-4,6-Bis-((3R,5S)-3,5-diamino-piperidin-1-yl)-[1,3,5]triazine-2-amine;

N-[4-(5-chloro-2-hydroxy-benzoylamino)-phenyl]-4,6-Bis-((3R,5S)-3,5-diamino-piperidin-1-yl)-[1,3,5]triazine-2-amine;

N-[4-(5-bromo-2-hydroxy-benzoylamino)-phenyl]-4,6-Bis-((3R,5S)-3,5-diamino-piperidin-1-yl)-[1,3,5]triazine-2-amine;

N-(4-hydroxy-naphthalen-1-yl)-4,6-Bis-((3R,5S)-3,5-diamino-piperidin-1-yl)-[1,3,5]triazine-2-amine;

N-[3-hydroxy-4-(2-hydroxy-4-methoxy-benzoylamino)-phenyl]-4,6-Bis-((3R,5S)-3,5-diamino-piperidin-1-yl)-[1,3,5]triazine-2-amine;

N-[3-hydroxy-4-(2-hydroxy-5-methoxy-benzoylamino)-phenyl]-4,6-Bis-((3R,5S)-3,5-diamino-piperidin-1-yl)-[1,3,5]triazine-2-amine;

N-[3-hydroxy-4-(2-hydroxy-4-methyl-benzoylamino)-phenyl]-4,6-Bis-((3R,5S)-3,5-diamino-piperidin-1-yl)-[1,3,5]triazine-2-amine;

N-[4-(4-chloro-2-hydroxy-benzoylamino)-3-hydroxy-phenyl]-4,6-Bis-((3R,5S)-3,5-diamino-piperidin-1-yl)-[1,3,5]triazine-2-amine;

N-{4-[4-((2S,4S)-4-Amino-2-aminomethyl-pyrrolidin-1-yl)-6-((3R,5S)-3,5-diamino-piperidin-1-yl)-[1,3,5]triazin-2-ylamino]-2-hydroxy-phenyl}-4-chloro-2-hydroxy-benzamide;

N-[3-(4-chloro-2-hydroxy-benzoylamino)-phenyl]-4,6-Bis-((3R,5S)-3,5-diamino-piperidin-1-yl)-[1,3,5]triazine-2-amine;

1-Hydroxy-naphthalene-2-carboxylic acid [4-(3,5-dichloro-2,6-Bis-((3R,5S)-3,5-diamino-piperidin-1-yl)-pyridin-4-ylamino)-phenyl]-amide;

N-[3-(2,4-dihydroxy-benzoylamino)-phenyl]-4,6-Bis-((3R,5S)-3,5-diamino-piperidin-1-yl)-[1,3,5]triazine-2-amine;

N-[4-(2,4-dihydroxy-benzoylamino)-3-methyl-phenyl]-4,6-Bis-((3R,5S)-3,5-diamino-piperidin-1-yl)-[1,3,5]triazine-2-amine;

N-[4-(2,4-dihydroxy-benzoylamino)-3-hydroxy-phenyl]-4,6-Bis-((3R,5S)-3,5-diamino-piperidin-1-yl)-[1,3,5]triazine-2-amine;

1-Hydroxy-naphthalene-2-carboxylic acid {4-[6-((3R,5S)-3,5-diamino-piperidin-1-yl)-8-((3S,5R)-3,5-diamino-piperidin-1-yl)-7H-purin-2-ylamino]-phenyl}-amide;

1-Hydroxy-naphthalene-2-carboxylic acid {4-[2-((3R,5S)-3,5-diamino-piperidin-1-yl)-6-((3S,5R)-3,5-diamino-piperidin-1-yl)-pyrimidin-4-ylamino]-phenyl}-amide;

N-{3-hydroxy-4-[(2-hydroxy-naphthalene-1-carbonyl)-amino]-phenyl}-4,6-Bis-((3R,5S)-3,5-diamino-piperidin-1-yl)-[1,3,5]triazine-2-amine;

N-{4-[(2-hydroxy-naphthalene-1-carbonyl)-amino]-phenyl}-4,6-Bis-((3R,5S)-3,5-diamino-piperidin-1-yl)-[1,3,5]triazine-2-amine;

1-Hydroxy-naphthalene-2-carboxylic acid [4-(2,6-Bis-((3R,5S)-3,5-diamino-piperidin-1-yl)-pyridin-4-ylamino)-phenyl]-amide;

N-{4-[2-(4-methoxy-phenylcarbamoyl)-acetyl]-phenyl}-4,6-Bis-((3R,5S)-3,5-diamino-piperidin-1-yl)-[1,3,5]triazine-2-amine;

1-Hydroxy-naphthalene-2-carboxylic acid [4-(4,6-Bis-((3R,5S)-3,5-diamino-piperidin-1-yl)-pyridin-2-ylamino)-phenyl]-amide;

N-{4-[2-(3-bromo-phenylcarbamoyl)-acetyl]-phenyl}-4,6-Bis-((3R,5S)-3,5-diamino-piperidin-1-yl)-[1,3,5]triazine-2-amine;

N-{4-[2-(biphenyl-4-ylcarbamoyl)-acetyl]-phenyl}-4,6-Bis-((3R,5S)-3,5-diamino-piperidin-1-yl)-[1,3,5]triazine-2-amine;

N-{4-[2-(2-chloro-5-trifluoromethyl-phenylcarbamoyl)-acetyl]-phenyl}-4,6-Bis-((3R,5S)-3,5-diamino-piperidin-1-yl)-[1,3,5]triazine-2-amine;

N-{4-[2-(4-chloro-2,5-dimethoxy-phenylcarbamoyl)-acetyl]-phenyl}-4,6-Bis-((3R,5S)-3,5-diamino-piperidin-1-yl)-[1,3,5]triazine-2-amine;

N-{4-[2-(4-fluoro-phenylcarbamoyl)-acetyl]-phenyl}-4,6-Bis-((3R,5S)-3,5-diamino-piperidin-1-yl)-[1,3,5]triazine-2-amine;

N-{4-[2-(3-trifluoromethyl-phenylcarbamoyl)-acetyl]-phenyl}-4,6-Bis-((3R,5S)-3,5-diamino-piperidin-1-yl)-[1,3,5]triazine-2-amine;

N-{4-[2-(4-chloro-2-fluoro-phenylcarbamoyl)-acetyl]-phenyl}-4,6-Bis-((3R,5S)-3,5-diamino-piperidin-1-yl)-[1,3,5]triazine-2-amine;

N-{3-hydroxy-4-[(2-hydroxy-pyridine-3-carbonyl)-amino]-phenyl}-4,6-Bis-((3R,5S)-3,5-diamino-piperidin-1-yl)-[1,3,5]triazine-2-amine;

N-{4-[4-((2S,4S)-4-Amino-2-aminomethyl-pyrrolidin-1-yl)-6-((3R,5S)-3,5-diamino-piperidin-1-yl)-[1,3,5]triazin-2-ylamino]-2-hydroxy-phenyl}-2,4-dihydroxy-benzamide;

N-(4-{4-[benzyl-(toluene-4-sulfonyl)-amino]-3-hydroxy-phenylcarbamoyl}-3-hydroxy-phenyl)-4,6-Bis-((3R,5S)-3,5-diamino-piperidin-1-yl)-[1,3,5]triazine-2-amine;

N-[3-hydroxy-4-(4-methyl-2-oxo-2H-chromen-7-ylcarbamoyl)-phenyl]-4,6-Bis-((3R,5S)-3,5-diamino-piperidin-1-yl)-[1,3,5]triazine-2-amine;

N-[4-(5-bromo-2,3-dihydro-indole-1-carbonyl)-3-hydroxy-phenyl]-4,6-Bis-((3R,5S)-3,5-diamino-piperidin-1-yl)-[1,3,5]triazine-2-amine; and N-[4-(biphenyl-4-ylcarbamoyl)-3-hydroxy-phenyl]-4,6-Bis-((3R,5S)-3,5-diamino-piperidin-1-yl)-[1,3,5]triazine-2-amine.

\* \* \* \* \*